(12) United States Patent
Kim et al.

(10) Patent No.: US 10,038,146 B2
(45) Date of Patent: *Jul. 31, 2018

(54) ORGANIC LIGHT-EMITTING COMPOUND AND ORGANIC ELECTROLUMINESCENT DEVICE USING SAME

(71) Applicant: DOOSAN CORPORATION, Seoul (KR)

(72) Inventors: Hoe Moon Kim, Suwon-si (KR); Sung Moo Kim, Yongin-si (KR); Young Bae Kim, Hwaseong-si (KR); Tae Hyung Kim, Yongin-si (KR); Ho Cheol Park, Suwon-si (KR); Chang Jun Lee, Ansan-si (KR); Young Mi Baek, Yongin-si (KR); Jin Yong Shin, Yongin-si (KR)

(73) Assignee: DOOSAN CORPORATION, Seoul (KR)

( * ) Notice: Subject to any disclaimer, the term of this patent is extended or adjusted under 35 U.S.C. 154(b) by 483 days.

This patent is subject to a terminal disclaimer.

(21) Appl. No.: 14/363,372

(22) PCT Filed: Dec. 7, 2012

(86) PCT No.: PCT/KR2012/010627
§ 371 (c)(1),
(2) Date: Jun. 6, 2014

(87) PCT Pub. No.: WO2013/085339
PCT Pub. Date: Jun. 13, 2013

(65) Prior Publication Data
US 2014/0374724 A1    Dec. 25, 2014

(30) Foreign Application Priority Data

Dec. 7, 2011    (KR) .................. 10-2011-0130547
Sep. 21, 2012    (KR) .................. 10-2012-0105048

(51) Int. Cl.
| | |
|---|---|
| *H01L 51/50* | (2006.01) |
| *H01L 51/00* | (2006.01) |
| *C09K 11/06* | (2006.01) |
| *C07D 471/04* | (2006.01) |
| *C07D 487/04* | (2006.01) |

(52) U.S. Cl.
CPC ........ *H01L 51/0071* (2013.01); *C07D 471/04* (2013.01); *C07D 487/04* (2013.01); *C09K 11/06* (2013.01); *H01L 51/0067* (2013.01); *H01L 51/0072* (2013.01); *H01L 51/0074* (2013.01); *H01L 51/0094* (2013.01); *H01L 51/0052* (2013.01); *H01L 51/0081* (2013.01); *H01L 51/0085* (2013.01); *H01L 51/5016* (2013.01); *H01L 2251/308* (2013.01)

(58) Field of Classification Search
None
See application file for complete search history.

(56) References Cited

FOREIGN PATENT DOCUMENTS

| | | | | |
|---|---|---|---|---|
| CA | 2012626 A1 | | 9/1991 | |
| JP | 11-144867 | | 5/1999 | |
| JP | 11144767 | * | 5/1999 | ............. H01L 51/50 |
| JP | 11144867 | * | 5/1999 | ............. C09K 11/06 |
| JP | 2010-205982 | | 9/2010 | |
| JP | 2011526610 A | | 10/2011 | |
| KR | 10-2010-0131271 A | | 12/2010 | |
| KR | 10-2011-0002156 | * | 1/2011 | ............. C09K 11/06 |
| KR | 10-2011-0083442 | | 7/2011 | |
| KR | 10-2011-0117549 A | | 10/2011 | |
| WO | 2007/022845 A1 | | 3/2007 | |

OTHER PUBLICATIONS

Bosch, Joan et al., Rearrangement under alkaline conditions of compounds related to tetracyclic Strychnos indole alkaloids Heterocycles (1984), 22(3), 561-4 (STN Abstract Only).*
Joseph, Delphine et al.,"Tetracyclic compounds from tetrahydrocarbazolones. Part 1. Synthesis from 2,3,4,9-tetrahydrocarbazol-1-ones", Journal of Chemical Research, Synopses, 1995, No. 9, p. 350-351.
Japanese Patent Office, Communication dated Apr. 7, 2015 issued in counterpart application No. 2014-545825.
Isabel C.F.R. Ferreira, et al., "Synthesis of New Methylated thieno[2,3-a] and [3,2-b]carbazoles by Reductive Cyclization of 6-(2'-Nitrophenyl)Benzo[b]thiophenes Obtained by Palladium-catalyzed Cross-coupling", J. Heterocyclic Chem., May-Jun. 2001, pp. 749-754, vol. 38.
Communication dated Nov. 28, 2016 by the Japanese Patent Office in counterpart Japanese Application No. 2015-199547.
Dager et al., "Khimiya Geterotsiklicheskikh Soedinenii", 1986, pp. 217-221.
Zhang et al., "New Progress of Research in Carbazole Compounds", Chinese Journal of Organic Chemistry, vol. 30, No. 6, 2010, pp. 783-796.

* cited by examiner

*Primary Examiner* — Gregory D Clark
(74) *Attorney, Agent, or Firm* — Sughrue Mion, PLLC

(57) ABSTRACT

The present invention relates to a novel indole-based compound having superior hole injection and transport capabilities, light-emitting capabilities, and the like, and an organic electroluminescent device which comprises the indole-based compound in one or more organic layers thereof so as to thereby achieve improved characteristics, such as light-emitting efficiency, driving voltage, and lifespan characteristics.

9 Claims, No Drawings

ORGANIC LIGHT-EMITTING COMPOUND AND ORGANIC ELECTROLUMINESCENT DEVICE USING SAME

CROSS REFERENCE TO RELATED APPLICATIONS

This application is a National Stage of International Application No. PCT/KR2012/010627, filed on Dec. 7, 2012, which claims priority from Korean Patent Application Nos. 10-2011-0130547, filed on Dec. 7, 2011, and 10-2012-0105048, filed on Sep. 21, 2012, the contents of all of which are incorporated herein by reference in their entirety.

TECHNICAL FIELD

The present invention relates to a novel organic light-emitting compound and an organic electroluminescent device using the same, and more particularly, to a novel indole-based compound having superior hole injection and transport capabilities, light-emitting capabilities, and the like, and an organic electroluminescent device which comprises the indole-based compound in one or more organic layers thereof so as to thereby achieve improved characteristics, such as light-emitting efficiency, driving voltage, and lifespan characteristics.

BACKGROUND ART

In a study on an organic electroluminescent (EL) device (hereinafter, simply referred to as 'organic EL device'), which has continued from the start point of observation of an organic thin film light emission by Bernanose in the 1950s to blue electric light emission using an anthracene single crystal in 1965, an organic EL device having a lamination structure, which is divided into functional layers of a hole layer and a light emitting layer, was proposed by Tang in 1987, and the organic EL device has been developed in the form of introducing each characteristic organic layer into a device in order to manufacture the organic EL device having high efficiency and long lifespan, thereby leading to the development of specialized materials used therein.

When voltage is applied between two electrodes of the organic EL device, holes are injected into the organic layer at the anode and electrons are injected into the organic layer at the cathode. When the injected holes and electrons meet each other, an exciton is formed, and the exciton falls down to a bottom state to emit light. Materials used as the organic layer may be classified into a light-emitting material, a hole injection material, a hole transporting material, an electron transporting material, an electron injection material, and the like according to the function.

Materials for forming the light-emitting layer of the organic EL device may be divided into blue, green, and red light-emitting materials according to the light-emitting color. In addition, yellow and orange light-emitting materials are also used as a light-emitting material for implementing a much better natural color. Further, a host/dopant system may be used as a light-emitting material for the purpose of enhancing color purity and light-emitting efficiency through an energy transfer. Dopant materials may be divided into a fluorescent dopant using an organic material and a phosphorescent dopant in which a metal complex compound including heavy atoms such as Ir and Pt is used. Since the development of the phosphorescent material may theoretically enhance light-emitting efficiency by up to 4 times compared to the development of the fluorescent material, interests in not only phosphorescent dopant, but also phosphorescent host materials have been focused.

As the hole transporting layer, the hole blocking layer and the electron transporting layer, NPB, BCP, $Alg_a$ and the like represented by the following Formulae have been widely known until now, and for the light-emitting material, anthracene derivatives have been reported as a phosphorescent dopant/host material. In particular, for the phosphorescent material having a great advantage in terms of enhancing the efficiency, metal complex compounds including Ir, such as Firpic, $Ir(ppy)_3$ and $(acac)Ir(btp)_2$ are used as blue, green and red dopant materials. Until now, CBP exhibits excellent characteristics as a phosphorescent host material.

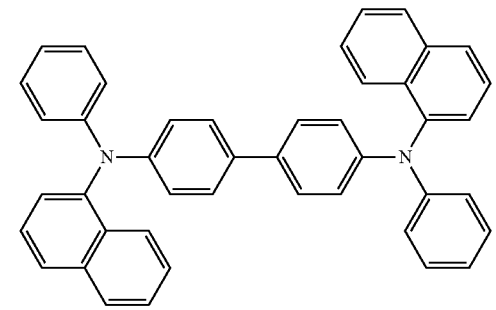

NPB

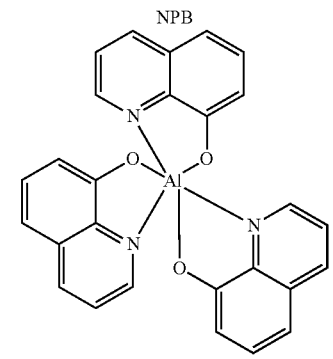

Alq3

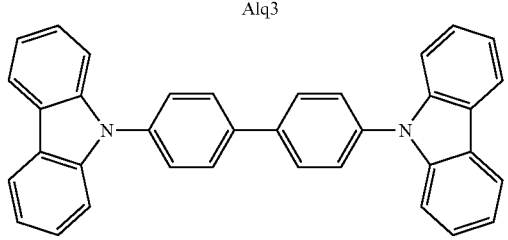

CBP

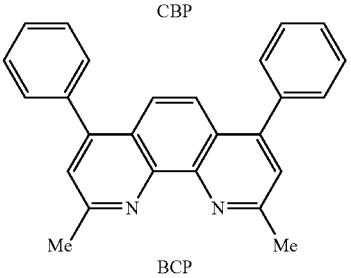

BCP

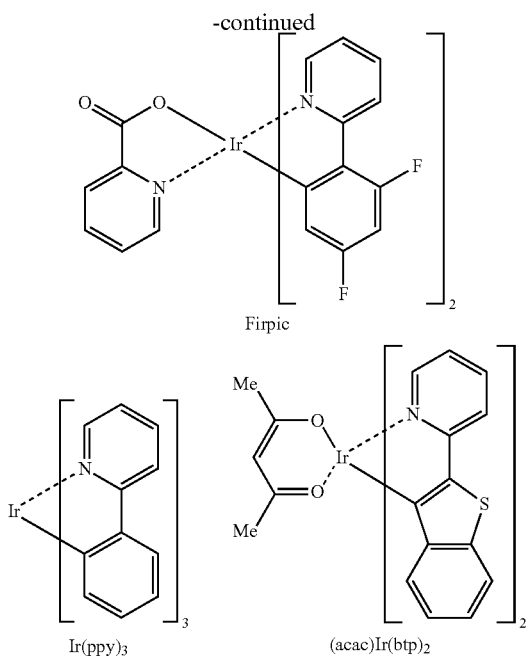

Firpic

Ir(ppy)₃   (acac)Ir(btp)₂

However, the existing materials are advantageous in terms of light emitting characteristics, but fall short of a level that sufficiently satisfies the lifespan in the organic EL device caused by the low glass transition temperature and very poor thermal stability.

DISCLOSURE

Technical Problem

An object of the present invention is to provide an indole-based compound which may enhance driving voltage, light-emitting efficiency, and the like, and an organic EL device using the same.

Technical Solution

In order to achieve the above described object, the present invention provides a compound represented by the following Formula 1.

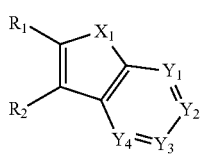

[Formula 1]

In the formula, $R_1$ and $R_2$ are each independently selected from the group consisting of hydrogen, deuterium, halogen, a cyano group, a nitro group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_2$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, $Y_1$ to $Y_4$ are each independently N or $CR_3$, and one of $Y_1$ and $Y_2$, $Y_2$ and $Y_3$, and $Y_3$ and $Y_4$ forms a fused ring represented by the following Formula 2,

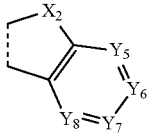

[Formula 2]

in the formula, $Y_5$ to $Y_8$ are each independently N or $CR_4$, and the dotted line means a site where fusion with the compound of Formula 1 occurs, $X_1$ and $X_2$ are each independently selected from the group consisting of O, S, Se, $N(Ar_1)$, $C(Ar_2)(Ar_3)$ and $Si(Ar_4)(Ar_5)$, and at least one of $X_1$ and $X_2$ is $N(Ar_1)$, $R_3$ and $R_4$ are each independently selected from the group consisting of hydrogen, deuterium, halogen, a cyano group, a nitro group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_2$ to $C_{40}$ alkylboron group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group, $Ar_1$ to $Ar_5$ are each independently selected from the group consisting of a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_2$ to $C_{40}$ alkylboron group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group, and the $C_1$ to $C_{40}$ alkyl group, the $C_3$ to $C_{40}$ cycloalkyl group, the heterocycloalkyl group having 3 to 40 nuclear atoms, the $C_6$ to $C_{60}$ aryl group, the heteroaryl group having 5 to 60 nuclear atoms, the $C_1$ to $C_{40}$ alkyloxy group, the $C_6$ to $C_{60}$ aryloxy group, the $C_3$ to $C_{40}$ alkylsilyl group, the $C_6$ to $C_{60}$ arylsilyl group, the $C_2$ to $C_{40}$ alkylboron group, the $C_6$ to $C_{60}$ aryl boron group, the $C_6$ to $C_{60}$ arylphosphine group, the $C_6$ to $C_{60}$ arylphosphine oxide group and the $C_6$ to $C_{60}$ arylamine group of $R_1$ to $R_4$ and $Ar_1$ to $Ar_5$ may be each independently substituted with one or more substituents selected from the group consisting of deuterium, halogen, a cyano group, a nitro group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_2$ to $C_{40}$ alkylboron group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group.

Herein, when $Y_1$ to $Y_4$ are all $CR_3$, $R_3$ may be the same as or different from each other, and adjacent $R_3$'s may combine with each other to form a fused ring. Further, when $Y_5$ to $Y_8$ are all $CR_4$, $R_4$ may also be the same as or different from each other, and adjacent $R_4$'s may combine with each other to form a fused ring.

In addition, when $R_1$ to $R_4$ and $Ar_1$ to $Ar_5$ are substituted with a plurality of substituents, the plurality of substituents may be the same as or different from each other.

The alkyl used in the present invention is a straight or branched saturated hydrocarbon having 1 to 40 carbon atoms, and examples thereof include methyl, ethyl, propyl, isobutyl, sec-butyl, pentyl, iso-amyl, hexyl, and the like.

Furthermore, the aryl used in the present invention means an aromatic part having 6 to 60 carbon atoms of a single ring or a combination of two or more rings, and the two or more rings may be simply pendant to each other or pendant to each other in a fused form. Examples of the aryl include phenyl, indenyl, naphthyl, anthracenyl, fluorenyl, phenanthryl, pyrenyl, chrysenyl, and the like.

Further, the heteroaryl used in the present invention means a monoheterocyclic or polyheterocyclic aromatic part having 5 to 60 nuclear atoms, and one or more carbons in the ring, preferably 1 to 3 carbons, are substituted with a hetero atom such as N, O, S, Si or Se. For the heteroaryl, it is interpreted that two or more rings may be simply pendant to each other or pendant to each other in a fused form, and furthermore, a form that is fused with an aryl group is also included. Examples of the heteroaryl include pyrazolyl, imidazolyl, oxazolyl, thiazolyl, triazolyl, tetrazolyl, oxadiazolyl, pyridinyl, pyrimidinyl, triazinyl, carbazolyl, indolyl, quinolinyl, isoquinolinyl, and the like.

The fused ring used in the present invention means a fused aliphatic ring, a fused aromatic ring, a fused heteroaliphatic ring, a fused heteroaromatic ring, or a combined form thereof.

Meanwhile, the present invention provides an organic electroluminescent device including (i) an anode, (ii) a cathode, and (iii) an organic layer having one or more layers interposed between the anode and the cathode, in which at least one in the organic layer having one or more layers includes the compound represented by Formula 1.

In this case, the organic layer including the compound represented by Formula 1 may be selected from the group consisting of a hole injection layer, a hole transporting layer, an electron transporting layer, an electron injection layer and a light-emitting layer.

Specifically, the organic layer including the compound represented by Formula 1 is a light-emitting layer, and the compound may be used as a phosphorescent host of the light-emitting layer.

BEST MODE

The present invention provides a novel indole-based compound having a molecular weight larger than that of a material for an organic electroluminescent device [for example: 4,4-dicarbazolybiphenyl (hereinafter, represented as CBP)] in the related art, and excellent driving voltage characteristics and efficiency. The indole-based compound of the present invention has a structure of a compound represented by the above Formula 1. In the organic electroluminescent device, a host molecule needs to have an energy level larger than that of a dopant molecule in order to have high light-emitting efficiency, and the compound of the present invention has a wide band gap (sky blue to red) because a fused carbon ring or a fused heterocyclic moiety, preferably a fused heterocyclic moiety is connected to an indole-based basic structure, and the energy level is controlled by various substituents. Accordingly, the compound of Formula 1 may minimize energy loss during the light-emitting process, thereby exhibiting an effect of improving light-emitting efficiency. Furthermore, these characteristics of the compound may improve hole injection and transport capabilities, light-emitting efficiency, driving voltage, lifespan characteristics, and the like as well as phosphorescent characteristics of the device. Further, the compound of Formula 1 may be applied to the hole transporting layer, the electron transporting layer, and the like as well as the light-emitting layer according to the type of substituent to be introduced.

In particular, due to the indole-based moiety, the compound of Formula 1 may exhibit excellent characteristics as a material for a light-emitting host (a material for a blue, green and/or red phosphorescent host, or a material for a fluorescent dopant) compared to the CBP in the related art. Further, the molecular weight of the compound is significantly increased in the indole-based basic structure due to various aromatic ring substituents, so that the glass transition temperature is enhanced, and accordingly, the compound of Formula 1 may have higher thermal stability than that of the CBP in the related art. Therefore, a device including the compound of the present invention may greatly enhance durability and lifespan characteristics.

Herein, when a broad band-gap and thermal stability are considered, it is preferred that $R_1$ to $R_4$ of Formula 1 are each independently selected from the group consisting of hydrogen, a $C_6$ to $C_{60}$ aryl group (for example: phenyl, naphthyl, and bisphenyl), a heteroaryl group having 5 to 60 nuclear atoms (for example: pyridine), and a $C_6$ to $C_{60}$ arylamine group, and the $C_6$ to $C_{60}$ aryl group, the heteroaryl group having 5 to 60 nuclear atoms, and the $C_6$ to $C_{60}$ arylamine group of $R_1$ and $R_2$ may be substituted with one or more substituents selected from the group consisting of a $C_1$ to $C_{40}$ alkyl group, a $C_6$ to $C_{60}$ aryl group, and a heteroaryl group having 5 to 60 nuclear atoms.

In addition, when $X_1$ and/or $X_2$ of Formula 1 are(is) $N(Ar_1)$, $C(Ar_2)(Ar_3)$, or $Si(Ar_4)(Ar_5)$, it is preferred that $Ar_1$ to $Ar_5$ are each independently selected from the group consisting of a $C_6$ to $C_{60}$ aryl group, a heteroaryl group having 5 to 60 nuclear atoms, and a $C_6$ to $C_{60}$ arylamine group.

More preferably, $R_1$ to $R_4$ and $Ar_1$ to $Ar_5$ may be each independently selected from the group of the following substituents (Functional Groups S1 to S192).

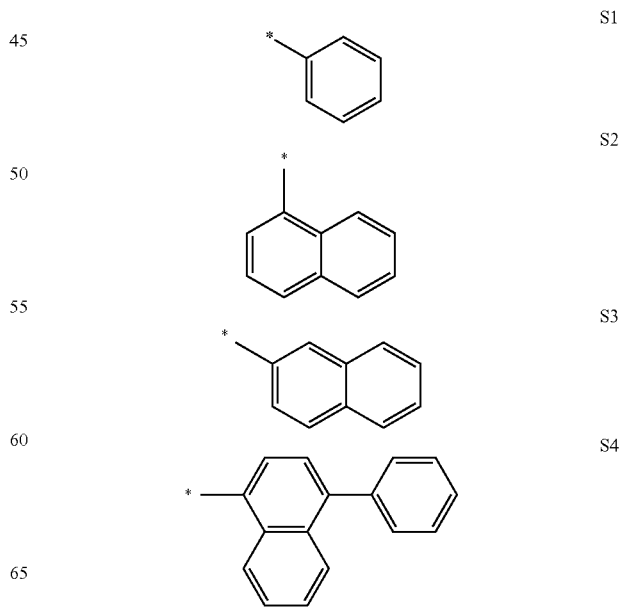

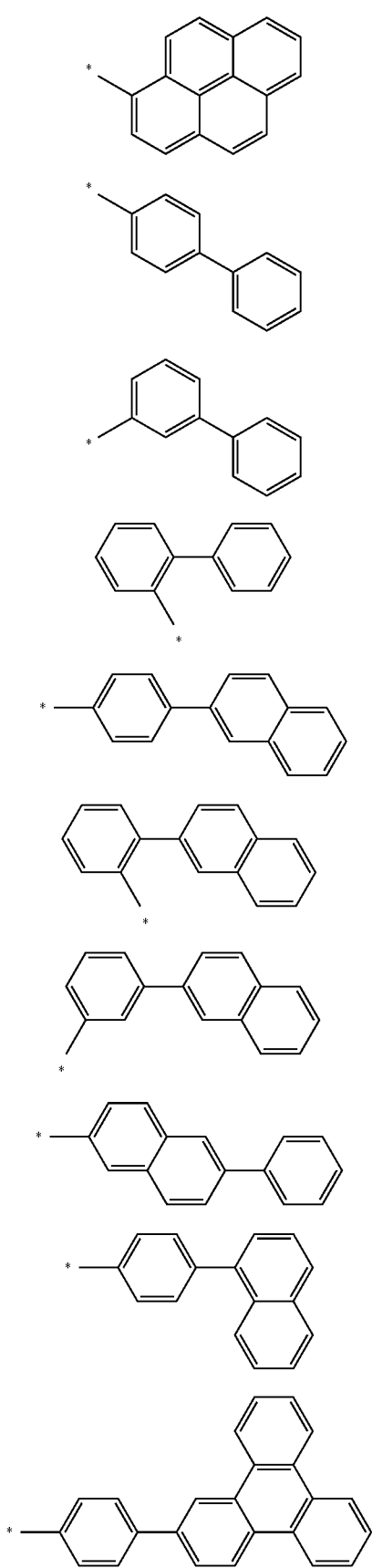
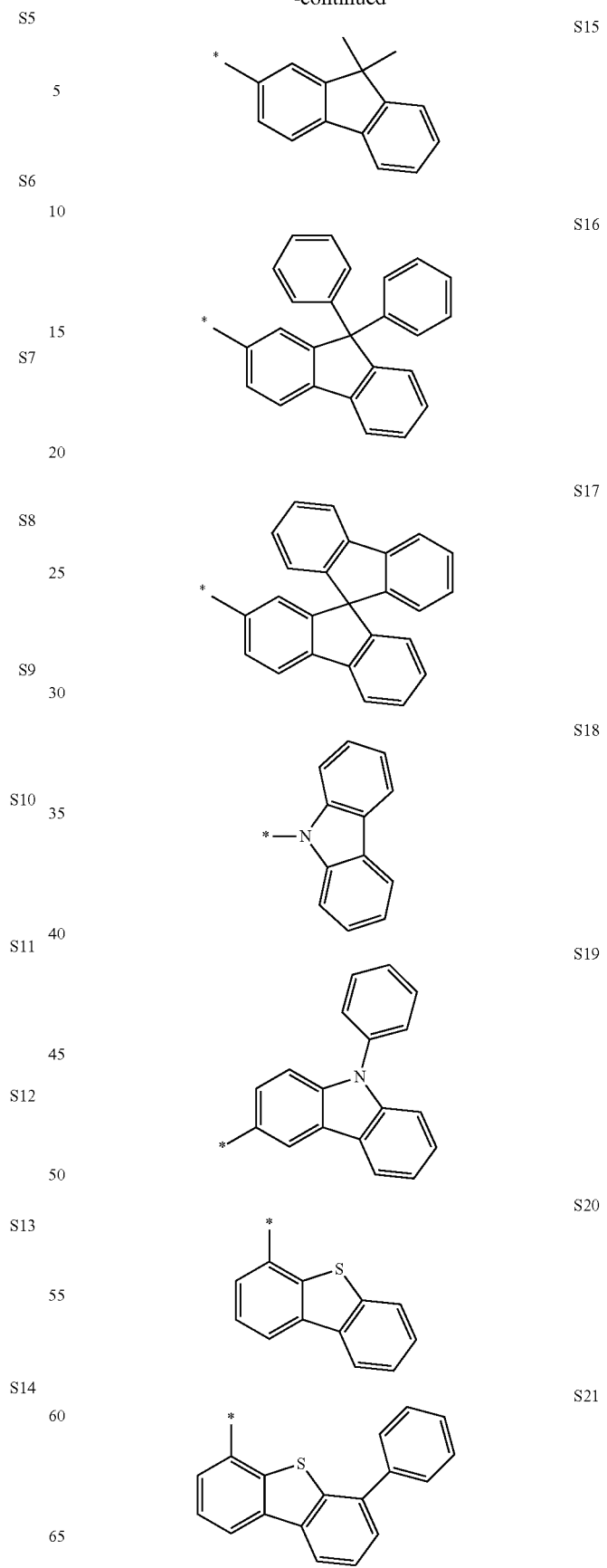

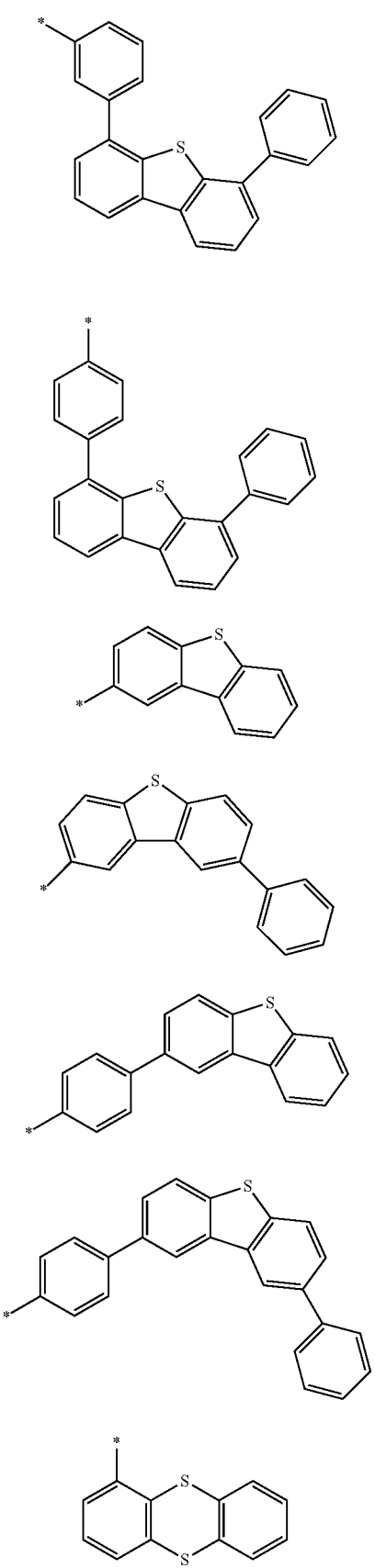
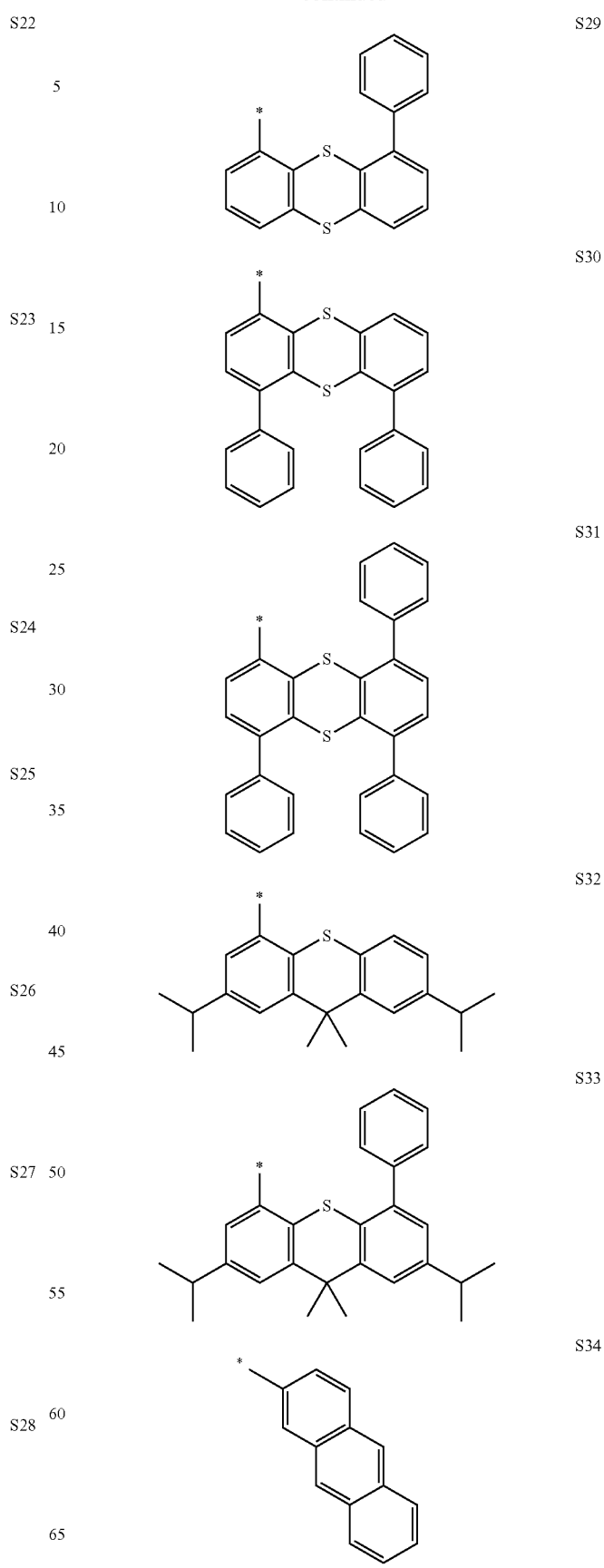

| | |
|---|---|
| S35 | S43 |
| S36 | S44 |
| S37 | S45 |
| S38 | S46 |
| S39 | S47 |
| S40 | S48 |
| S41 | S49 |
| S42 | S50 |

-continued

| | |
|---|---|
| S51 | S61 |
| S52 | S62 |
| S53 | S63 |
| S54 | S64 |
| S55 | S65 |
| S56 | S66 |
| S57 | S67 |
| S58 | S68 |
| S59 | S69 |
| S60 | |

-continued
S70 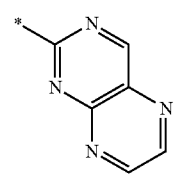
S71 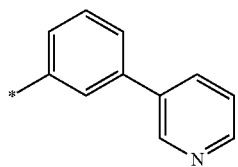
S72 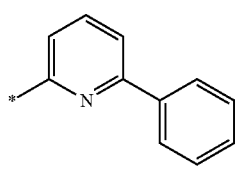
S73 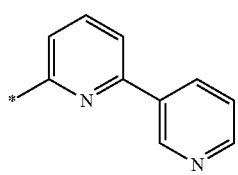
S74 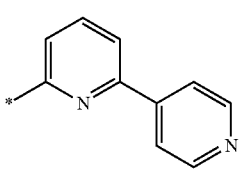
S75 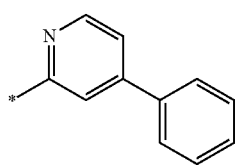
S76 
S77 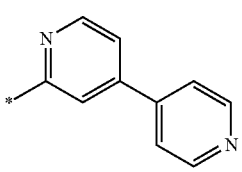
S78 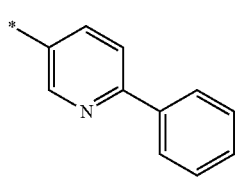
-continued
S79 
S80 
S81 
S82 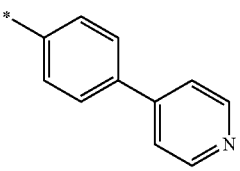
S83 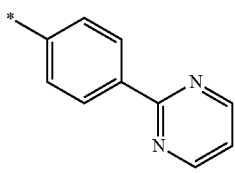
S84 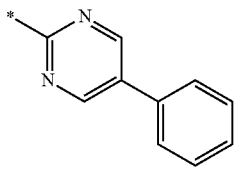
S85 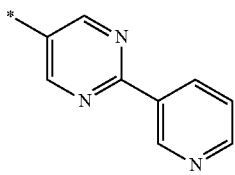
S86 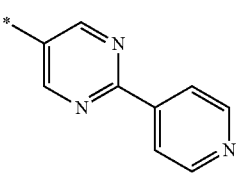
S87 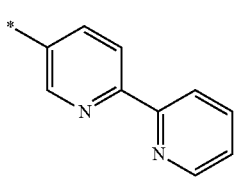

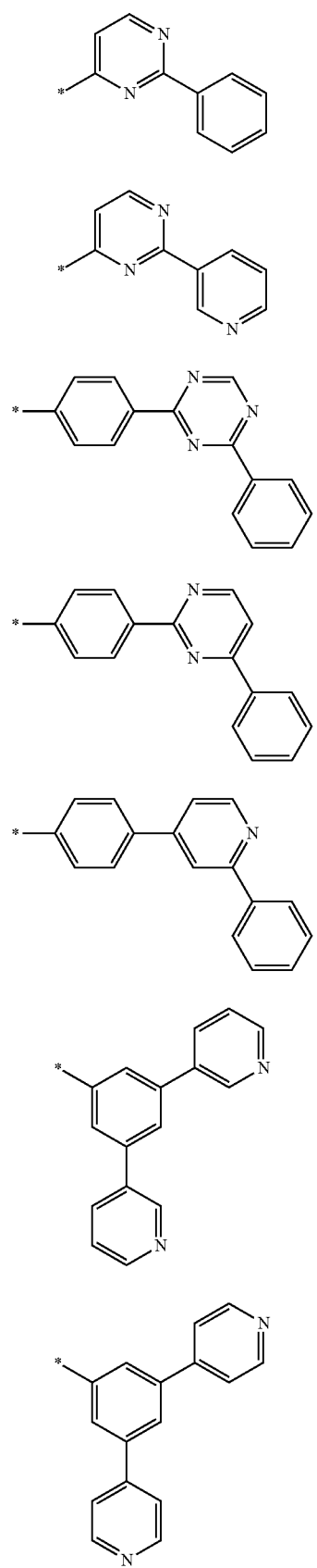
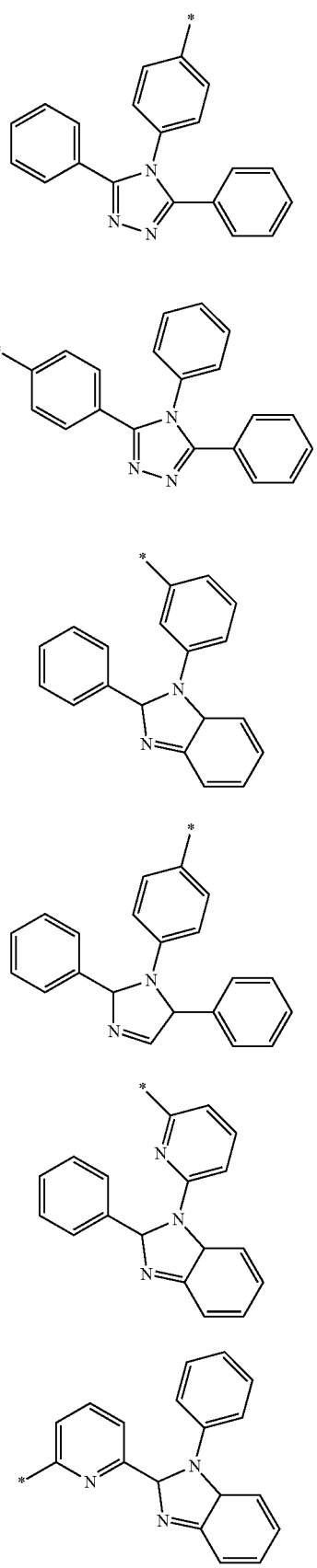

S101 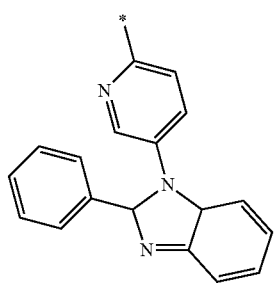
S102 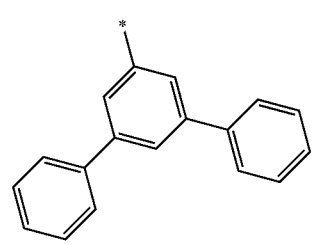
S103 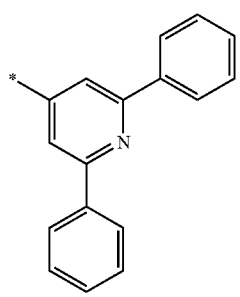
S104 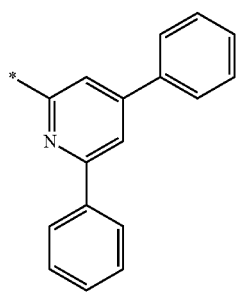
S105 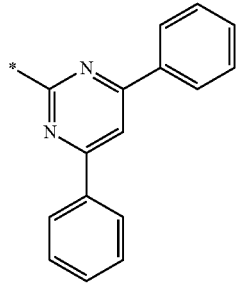
S106 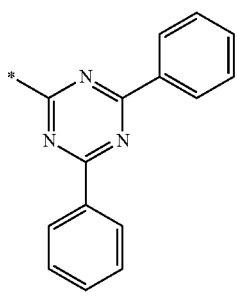
S107 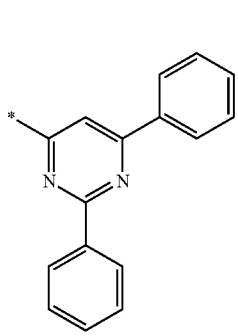
S108 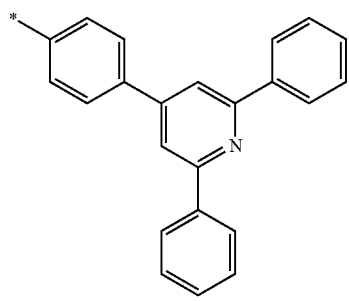
S109 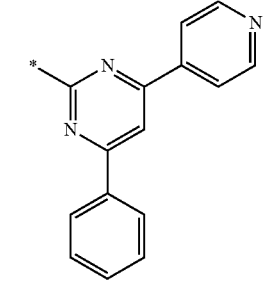
S110 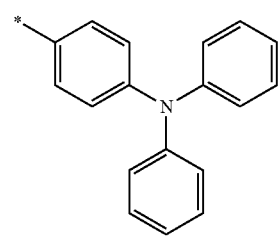

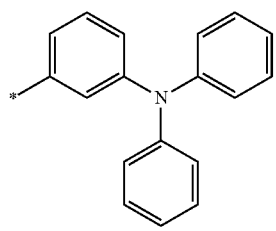
S111
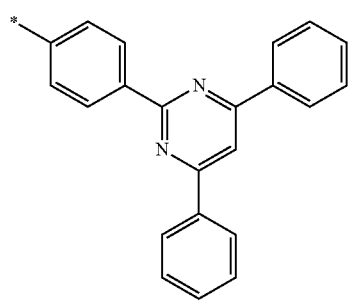
S112
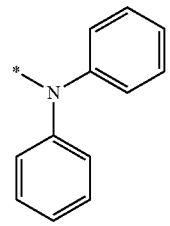
S113
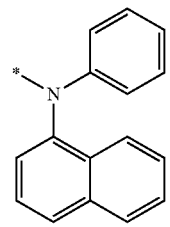
S114
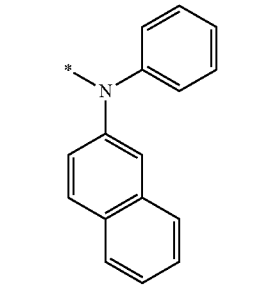
S115
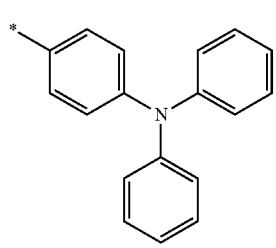
S116
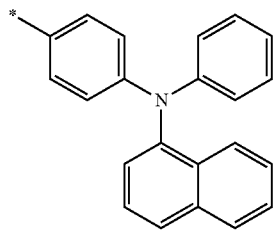
S117
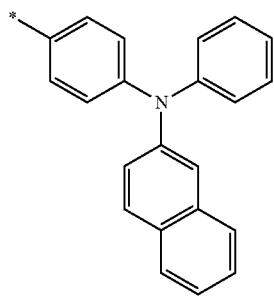
S118
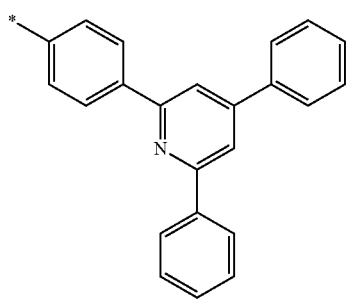
S119
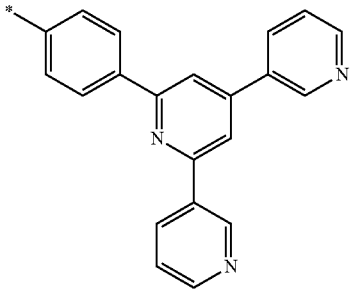
S120
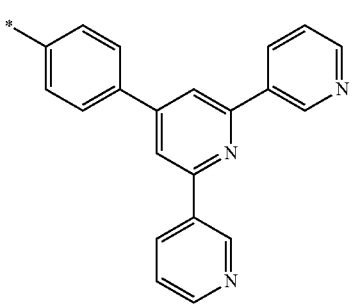
S121

S122 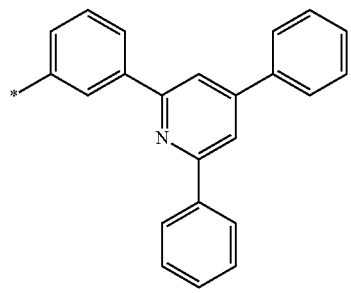
S123 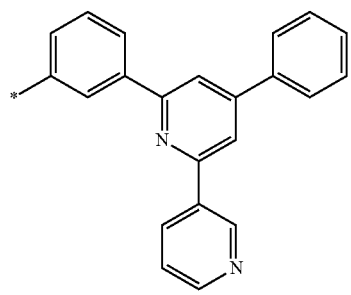
S124 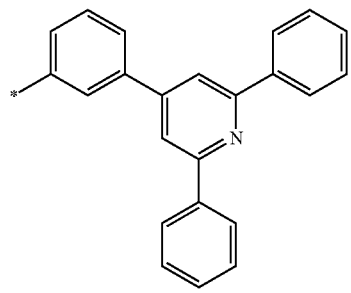
S125 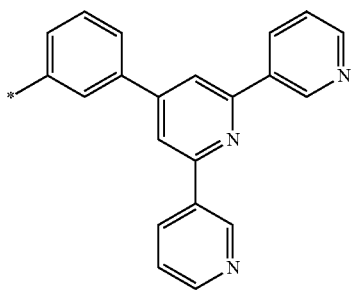
S126 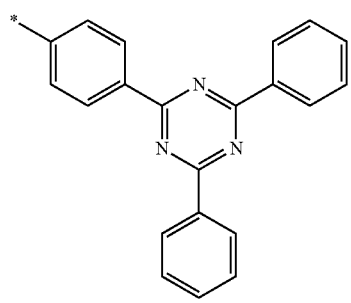
S127 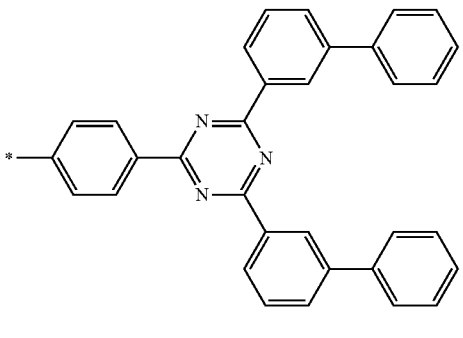
S128 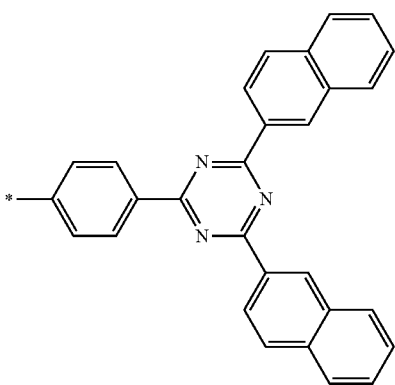
S129 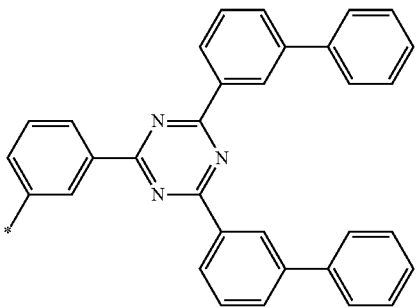
S130 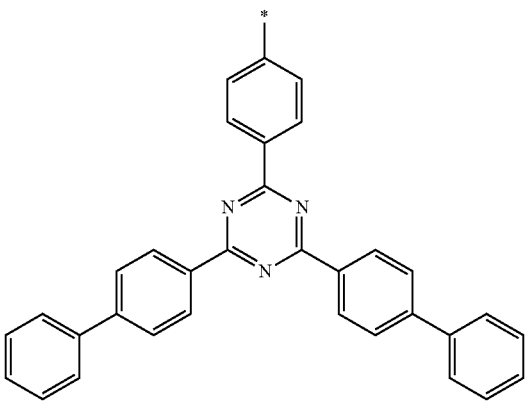

-continued
S131
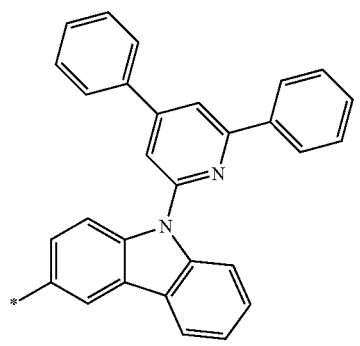
S132
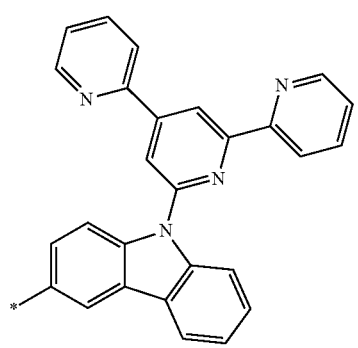
S133
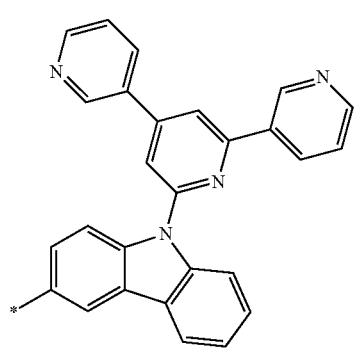
S134
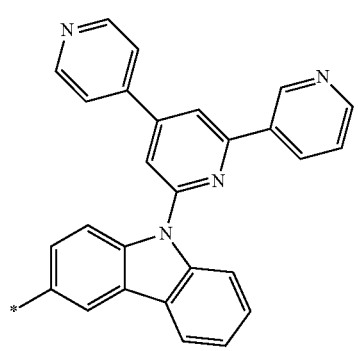
-continued
S135
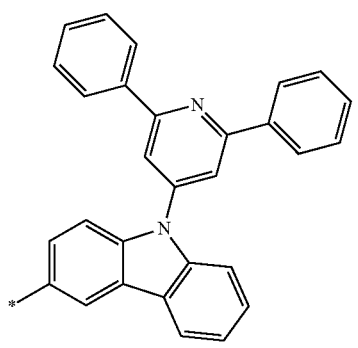
S136
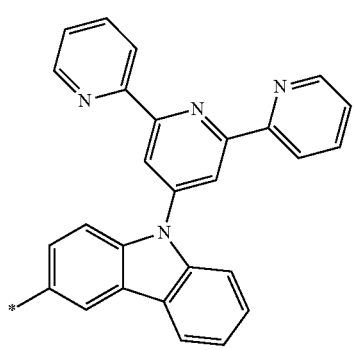
S137
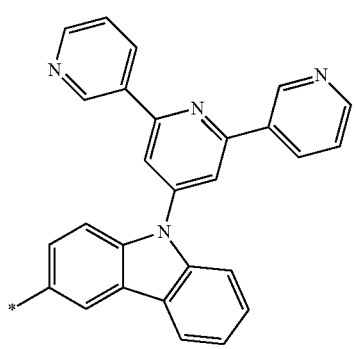
S138
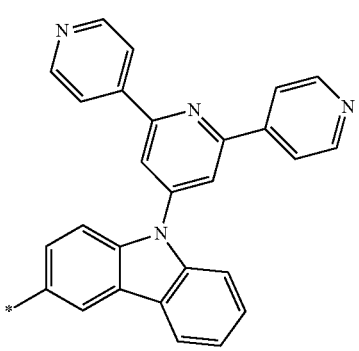

S139
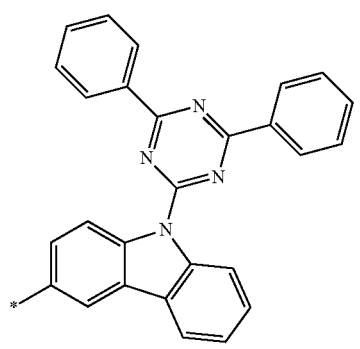
S140
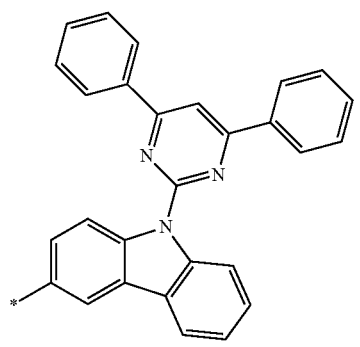
S141
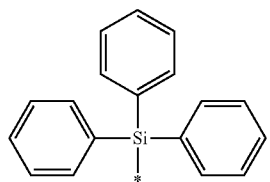
S142
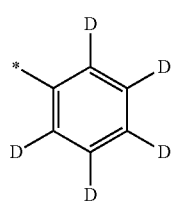
S143
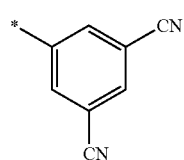
S144
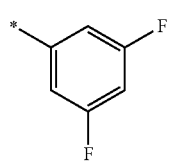
S145
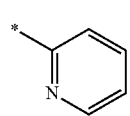
S146
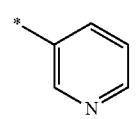
S147
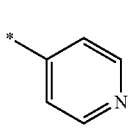
S148
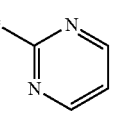
S149
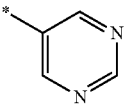
S150
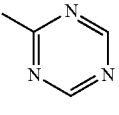
S151
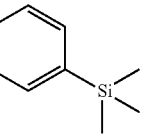
S152
S153
S154
S155
S156
S157

-continued
S158
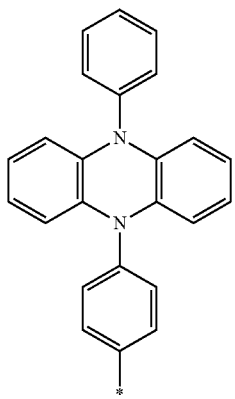
S159
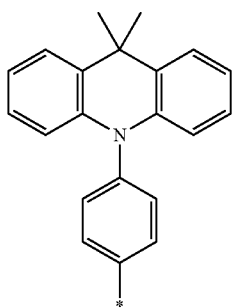
S160
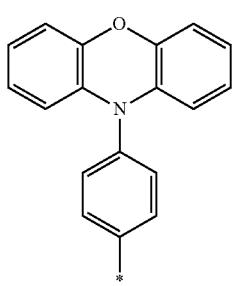
S161
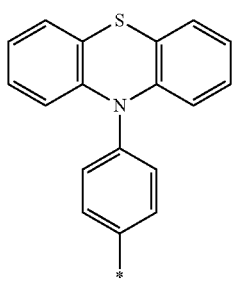
S162
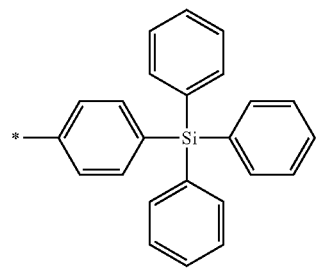
-continued
S163
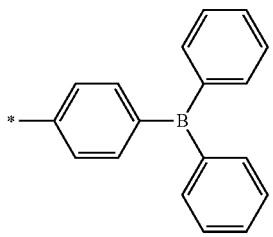
S164
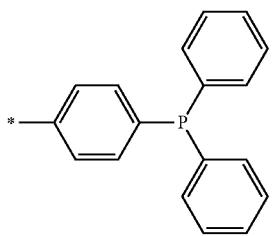
S165
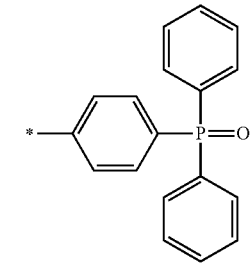
S166
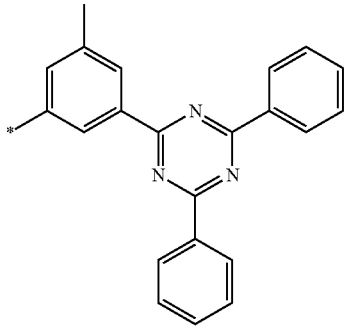
S167
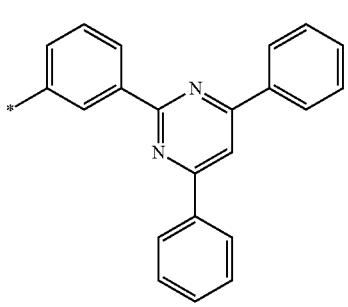

-continued
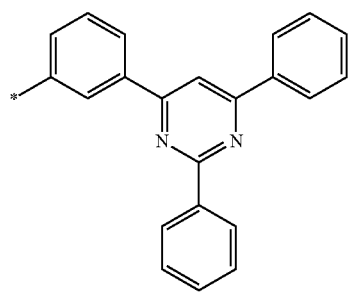 S168
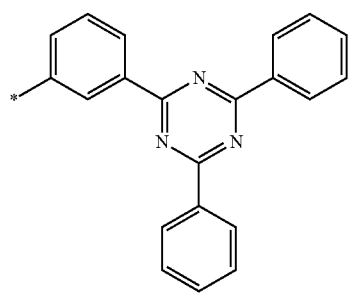 S169
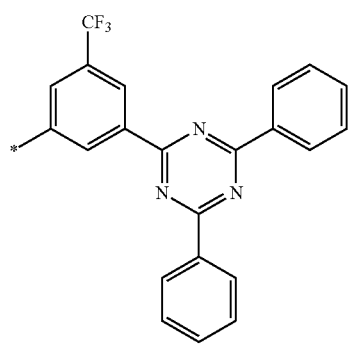 S170
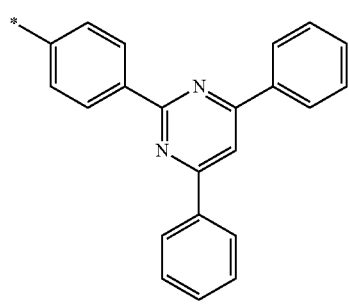 S171
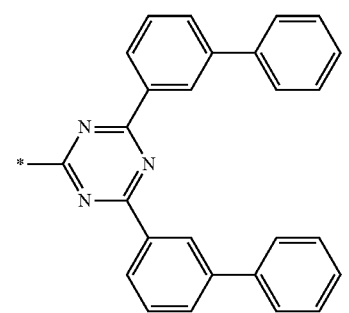 S172
-continued
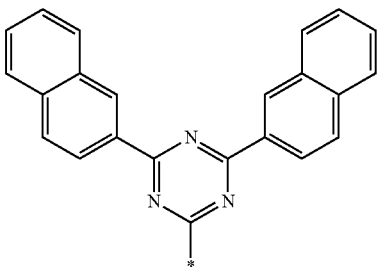 S173
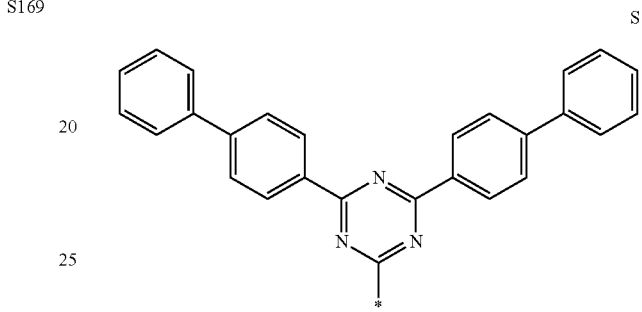 S174
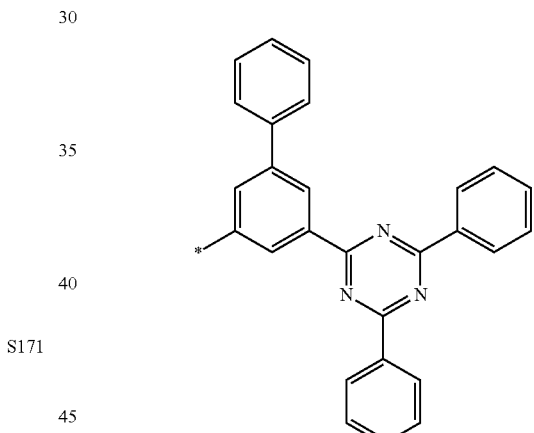 S175
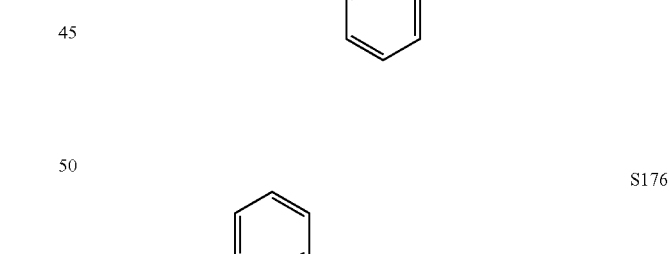 S176
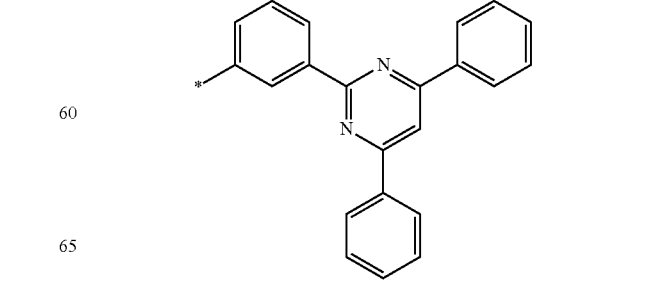

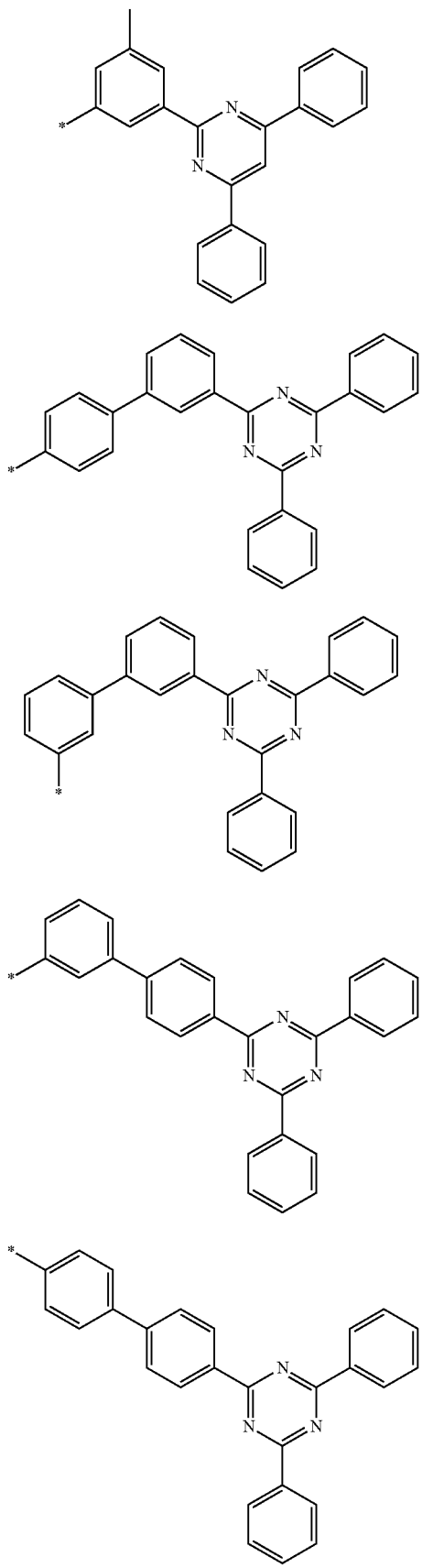
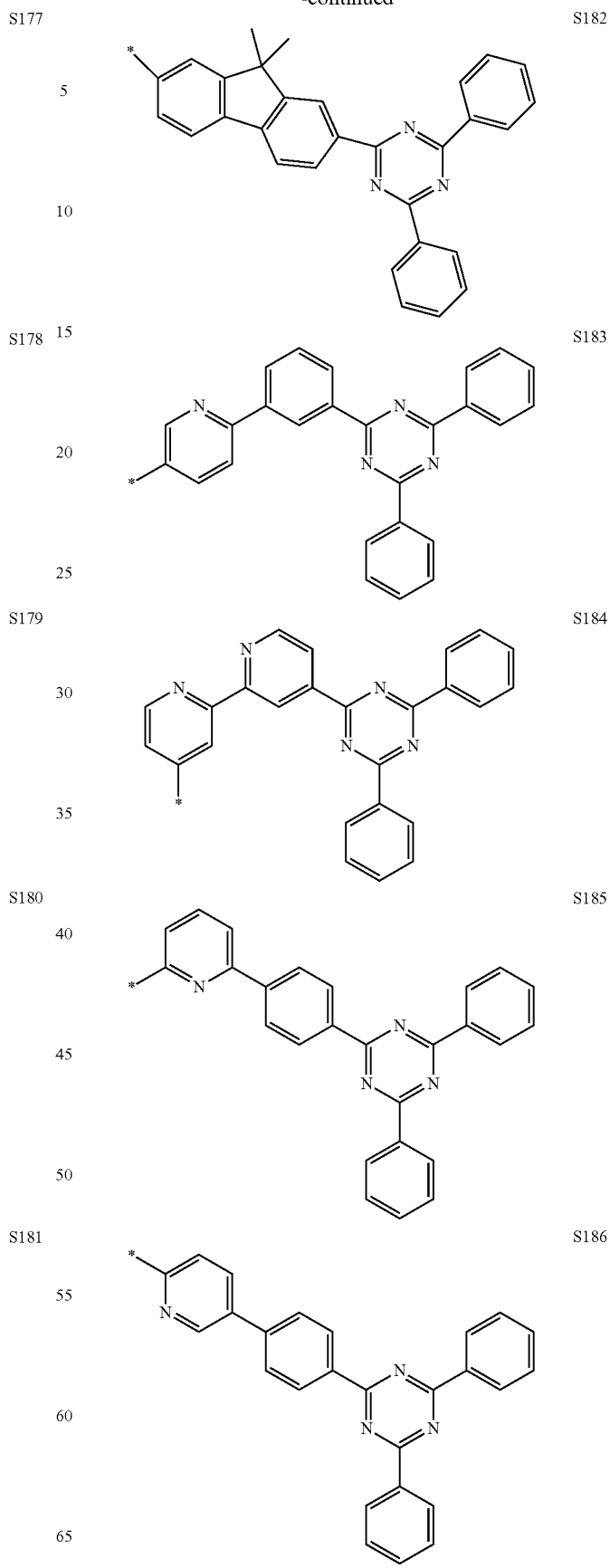

S187
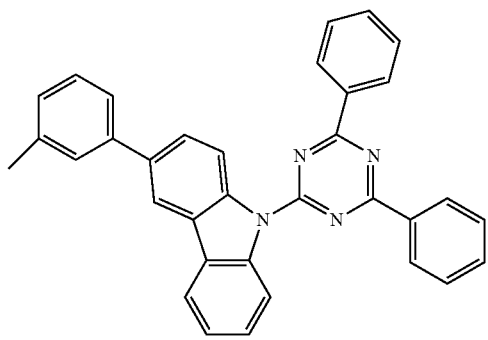
S188
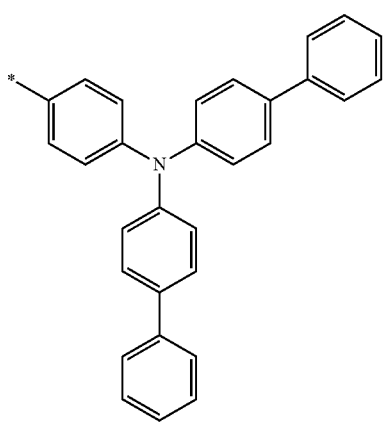
S189
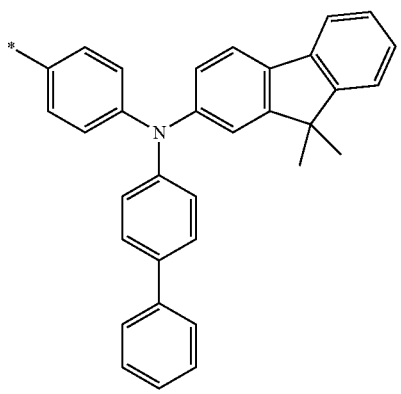
S190
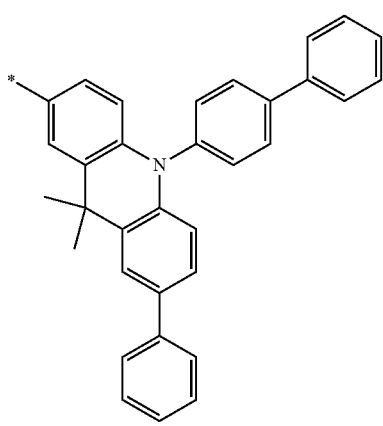
S191
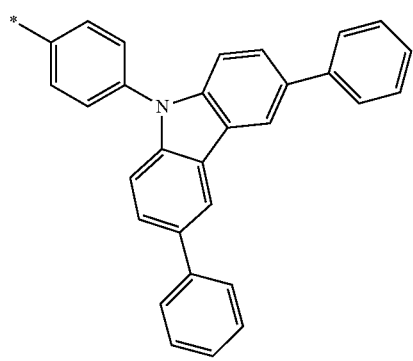
S192
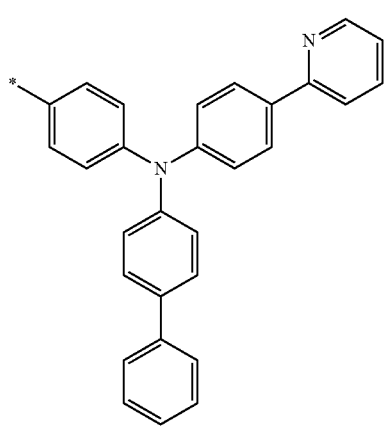
It is preferred that these compounds represented by Formula 1 according to the present invention are selected from the group consisting of the compounds represented by the following Formulae 1a to 1f.
[Formula 1a]
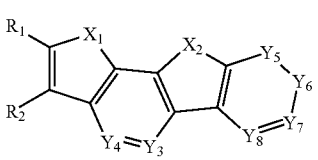
[Formula 1b]
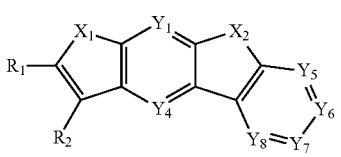
[Formula 1c]
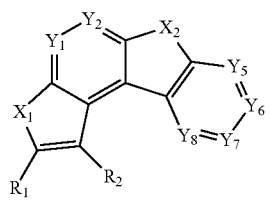

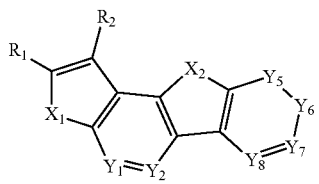
[Formula 1d]

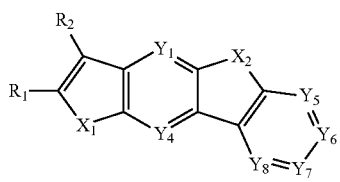
[Formula 1e]

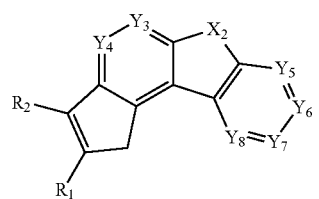
[Formula 1f]

In Formulae 1a to 1f, $R_1$, $R_2$, $X_1$, $X_2$ and $Y_1$ to $Y_8$ are the same as those defined above.

Furthermore, when the driving voltage and the current efficiency of the organic electroluminescent device are considered, it is preferred that in the compound represented by Formula 1 according to the present invention, both $X_1$ and $X_2$ are $N(Ar_1)$. Specifically, the compound represented by Formula 1 according to the present invention may be a compound represented by the following Formula 3.

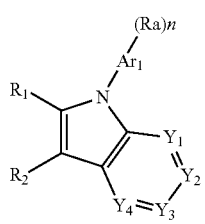
[Formula 3]

In Formula 3, $R_1$, $R_2$, and $Y_1$ to $Y_4$ are the same as those defined above, and one of $Y_1$ and $Y_2$, $Y_2$ and $Y_3$, and $Y_3$ and $Y_4$ forms a fused ring represented by the following Formula 4,

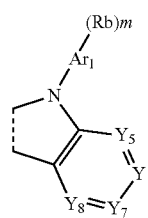
[Formula 4]

in Formula 4, $Y_5$ to $Y_8$ are the same as those defined above, the dotted line means a site where fusion with the compound of Formula 3 occurs, $Ar_1$ is a $C_6$ to $C_{60}$ aryl group, or a heteroaryl group having 5 to 60 nuclear atoms, and $R_a$ and $R_b$ are each independently selected from the group consisting of hydrogen, deuterium, halogen, a cyano group, a nitro group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_2$ to $C_{40}$ alkylboron group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group, and the $C_1$ to $C_{40}$ alkyl group, the $C_3$ to $C_{40}$ cycloalkyl group, the heterocycloalkyl group having 3 to 40 nuclear atoms, the $C_6$ to $C_{60}$ aryl group, the heteroaryl group having 5 to 60 nuclear atoms, the $C_1$ to $C_{40}$ alkyloxy group, the $C_6$ to $C_{60}$ aryloxy group, the $C_3$ to $C_{40}$ alkylsilyl group, the $C_6$ to $C_{60}$ arylsilyl group, the $C_2$ to $C_{40}$ alkylboron group, the $C_6$ to $C_{60}$ aryl boron group, the $C_6$ to $C_{60}$ arylphosphine group, the $C_6$ to $C_{60}$ arylphosphine oxide group and the $C_6$ to $C_{60}$ arylamine group of $R_a$ and $R_b$ may be each independently substituted with one or more substituents selected from the group consisting of deuterium, halogen, a cyano group, a nitro group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_2$ to $C_{40}$ alkylboron group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group, and n and m are each independently an integer of 0 to 5, provided that n+m is at least 1 or more. Herein, when the structure of Formula 3 is reviewed, $Ar_1$ may also be interpreted to be a divalent functional group, such as a $C_6$ to $C_{60}$ arylene group, or a heteroarylene group having 5 to 60 nuclear atoms.

More preferably, the compound represented by Formula 1 according to the present invention may be a compound represented by the following Formula 5.

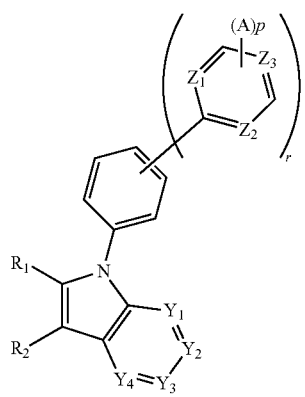
[Formula 5]

in Formula 5, $R_1$, $R_2$, and $Y_1$ to $Y_4$ are the same as those defined above, and one of $Y_1$ and $Y_2$, $Y_2$ and $Y_3$, and $Y_3$ and $Y_4$ forms a fused ring represented by the following Formula 6,

[Formula 6]

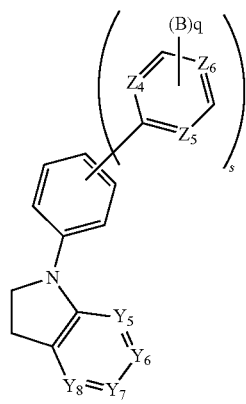

in Formula 6, $Y_5$ to $Y_8$ are the same as those defined above, the dotted line means a site where fusion with the compound of Formula 5 occurs, $Z_1$ to $Z_6$ are each independently N or $CAr_6$, and $Ar_6$, A and B are each independently selected from the group consisting of a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_2$ to $C_{40}$ alkylboron group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group, r and s are each an integer of 0 to 5, provided that r+s is at least 1 or more, and p and q are each an integer of 0 to 3.

In this case, the compound represented by Formula 5 may be selected from the group consisting of the compounds represented by the following Formulae 5a to 5f.

[Formula 5a]

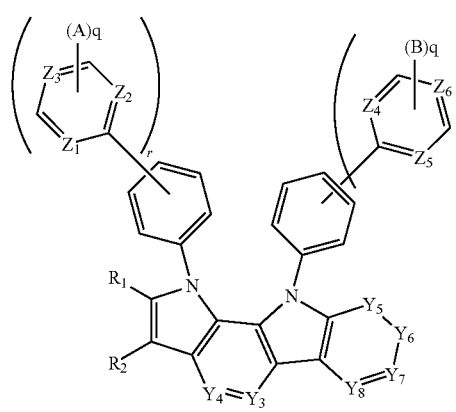

[Formula 5b]

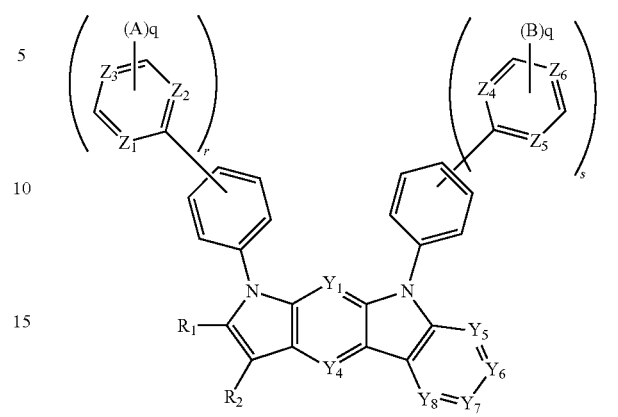

[Formula 5c]

[Formula 5d]

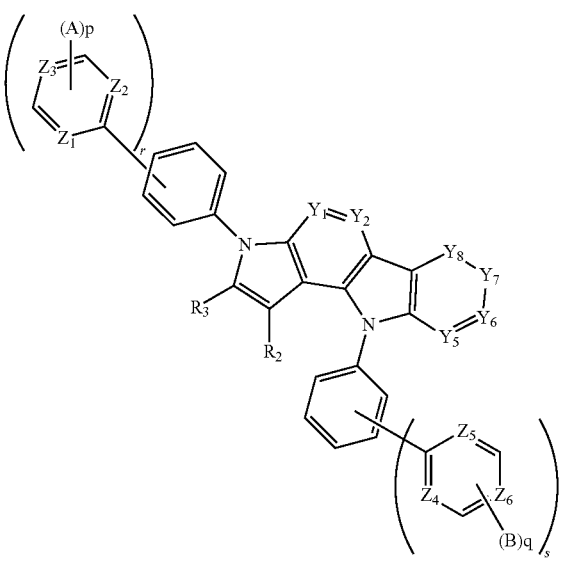

[Formula 5e]

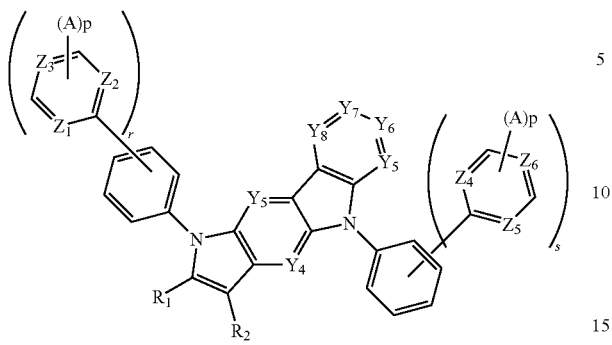

[Formula 5f]

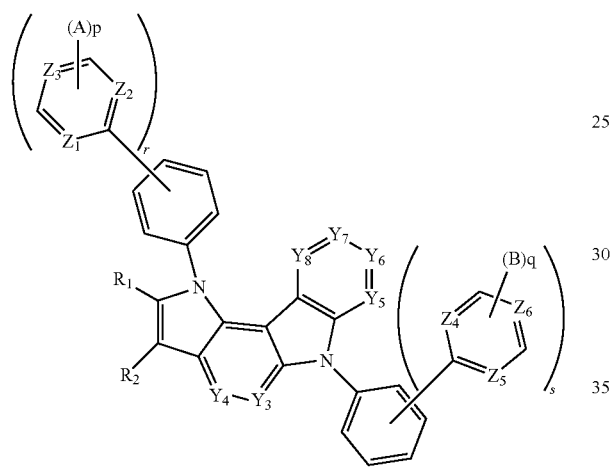

In Formulae 5a to 5f, $R_1$, $R_2$, $Y_1$ to $Y_8$, $Z_1$ to $Z_6$, A, B, r, s, p and q are the same as those defined above.

Further, it is preferred that $Ar_6$, A, and B of the compound represented by Formula 5 are each independently selected from the group consisting of a $C_6$ to $C_{60}$ aryl group, a heteroaryl group having 5 to 60 nuclear atoms and a $C_6$ to $C_{60}$ arylamine group.

Meanwhile, when the driving voltage and the current efficiency of the organic electroluminescent device are considered, it is preferred that in the compound represented by Formula 1 according to the present invention, $X_2$ is $N(Ar_1)$ when $X_1$ is S, and $X_1$ is $N(Ar_1)$ when $X_2$ is S. Specifically, the compound represented by Formula 1 according to the present invention may be selected from the group consisting of the compounds represented by the following Formulae 6a to 6l.

[Formula 6a]

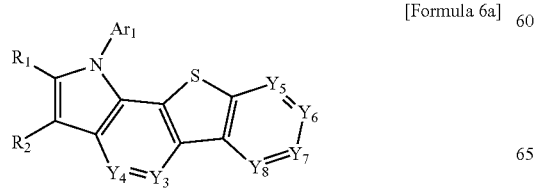

[Formula 6b]

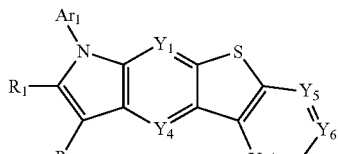

[Formula 6c]

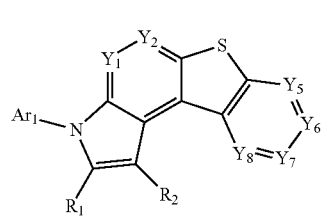

[Formula 6d]

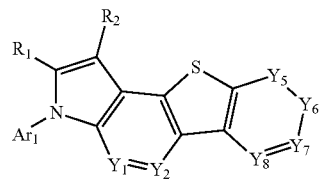

[Formula 6e]

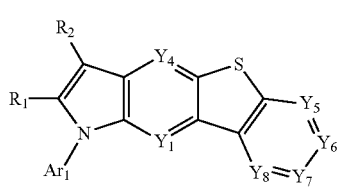

[Formula 6f]

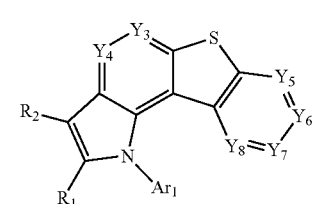

[Formula 6g]

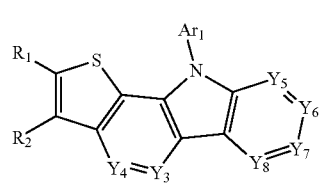

[Formula 6h]

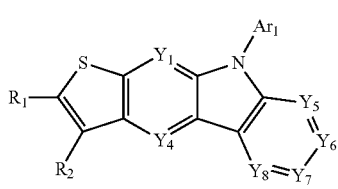

[Formula 6i]

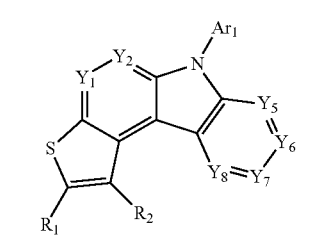

[Formula 6j]
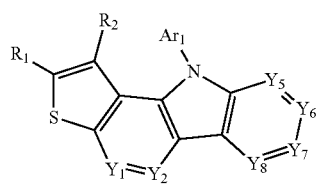
[Formula 6k]
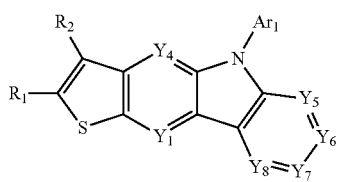
[Formula 6l]
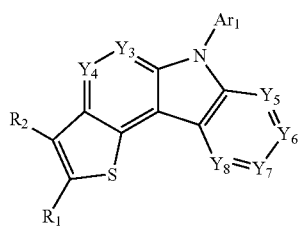
In the formulae, $R_1$, $R_2$, $Y_1$ to $Y_8$, and $Ar_1$ are the same as those defined above. Specific examples of the aforementioned compound represented by Formula 1 according to the present invention include the following compounds (1 to 1583), but the compound of the present invention is not limited to the following compounds.
1
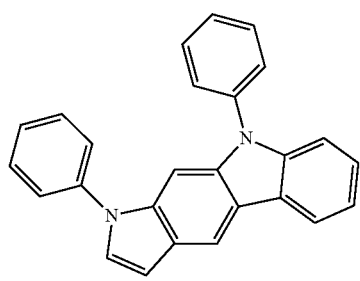
2
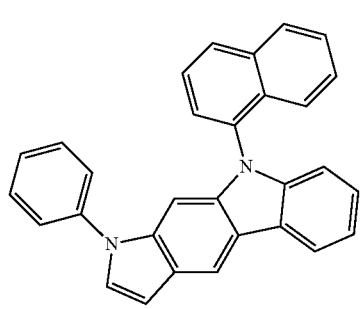
3
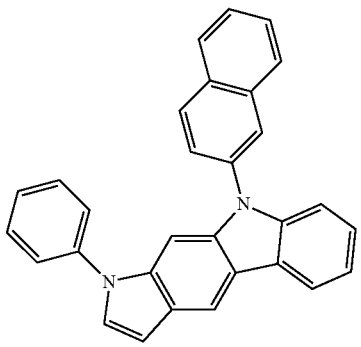
4
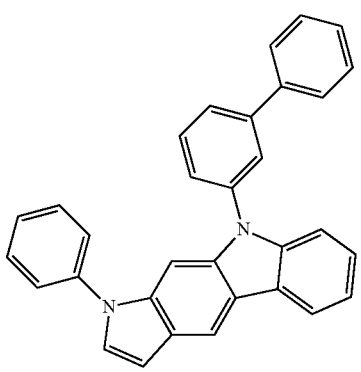
5
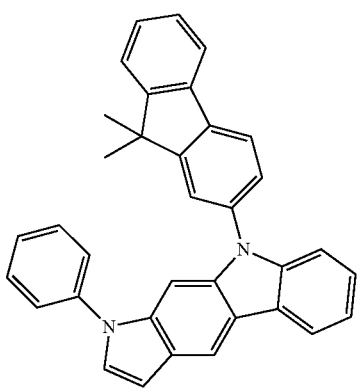
6
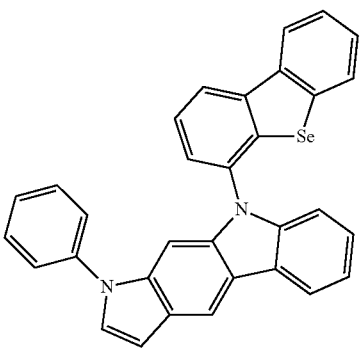

45
-continued
7
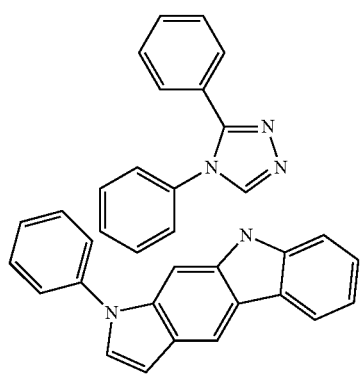
8
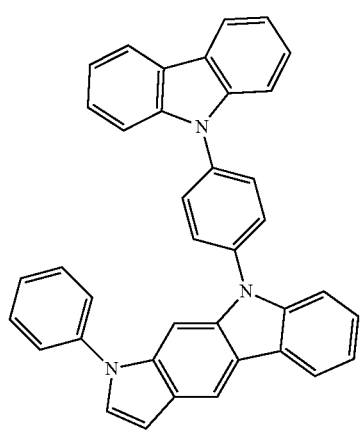
9
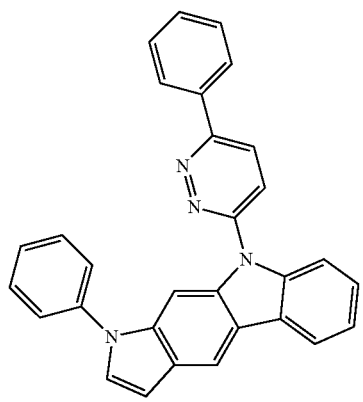
10
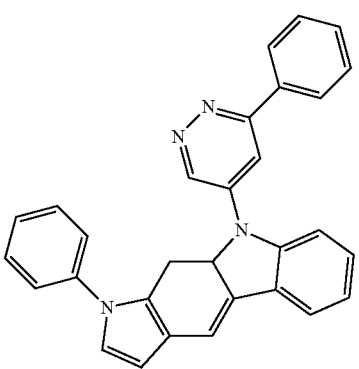
46
-continued
11
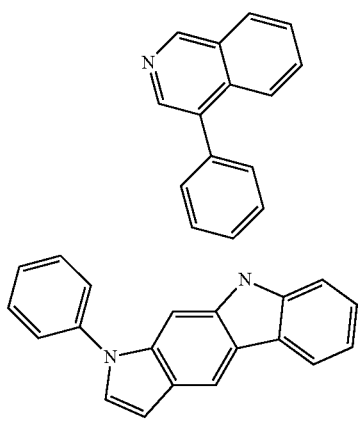
12
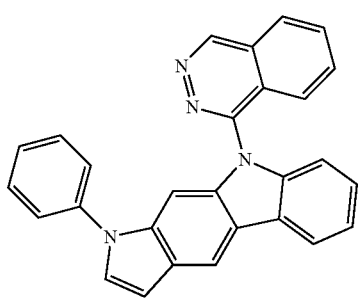
13
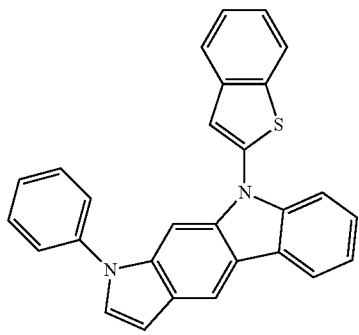
14
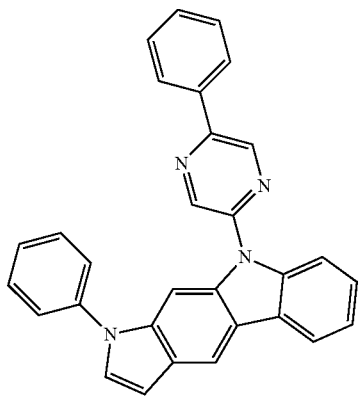

15
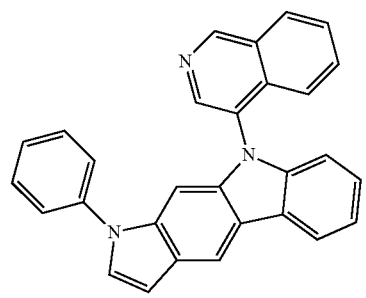
16
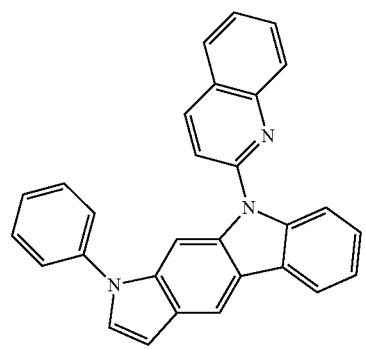
17
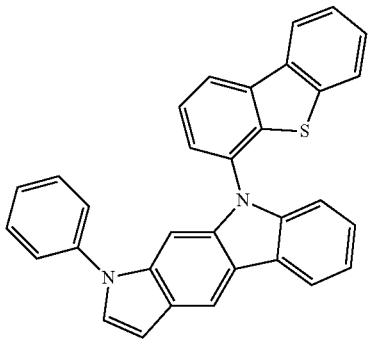
18
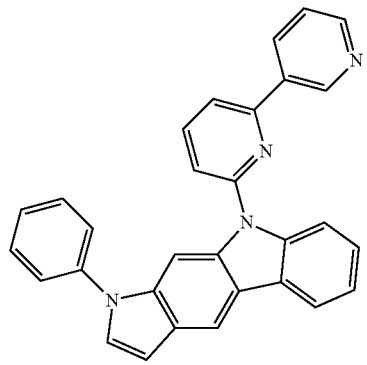
19
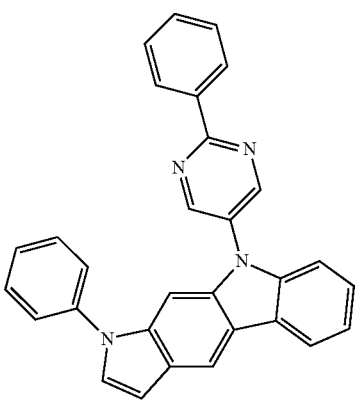
20
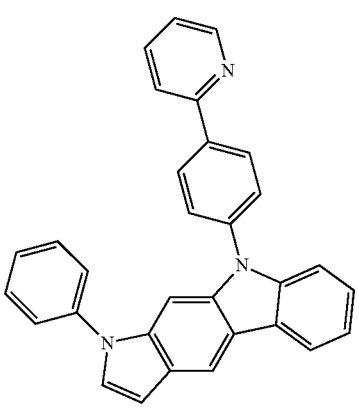
21
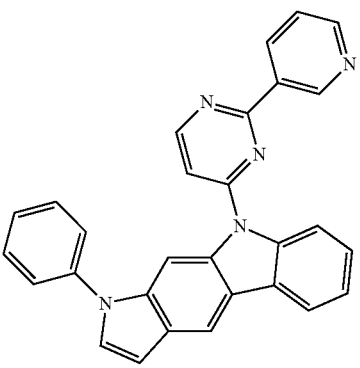
22
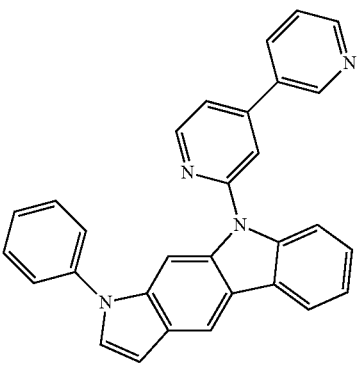

23
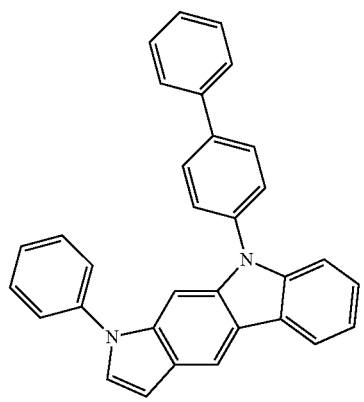
24
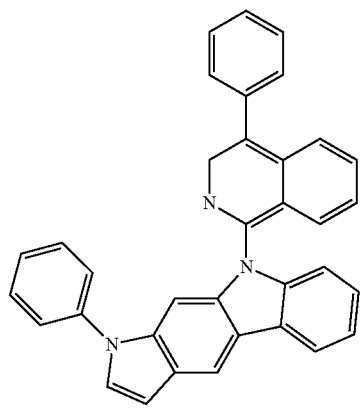
25
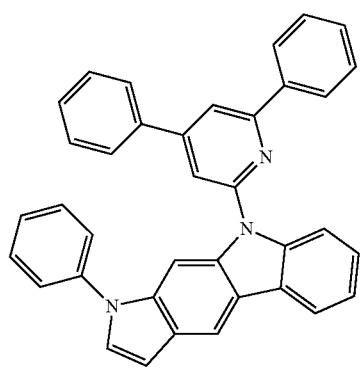
26
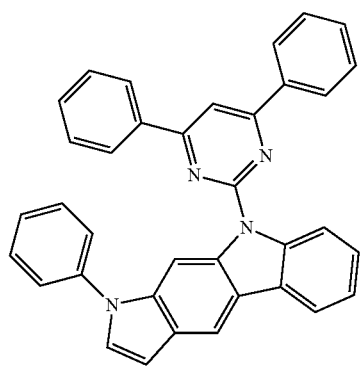
27
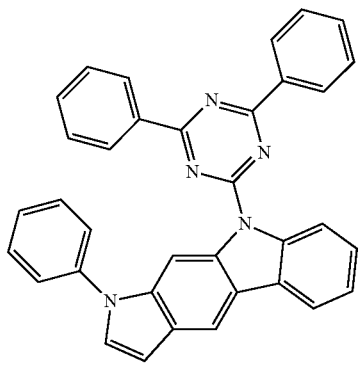
28
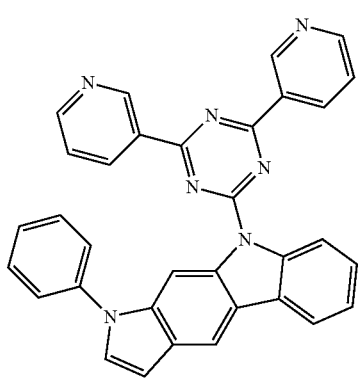
29
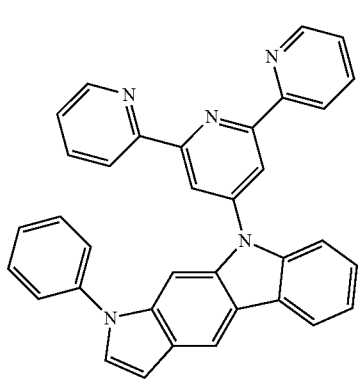
30
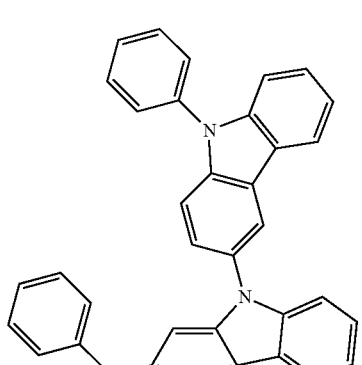

31
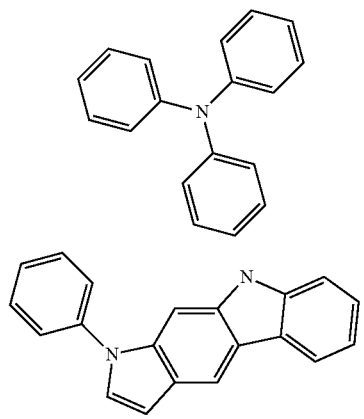
32
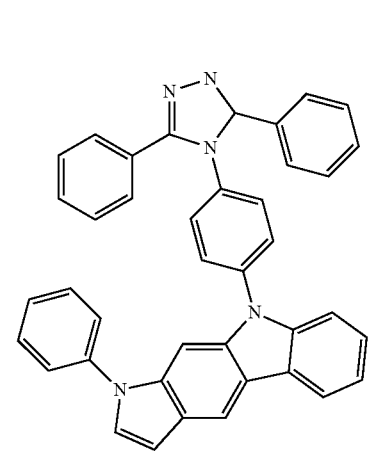
33
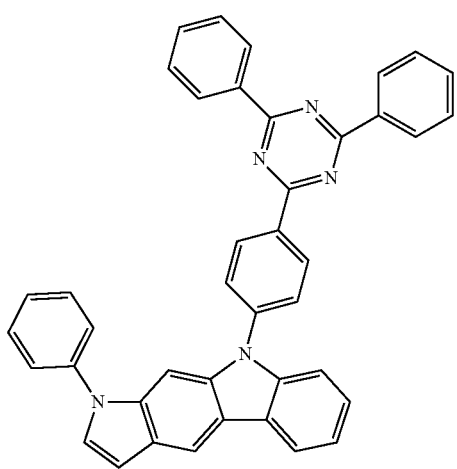
34
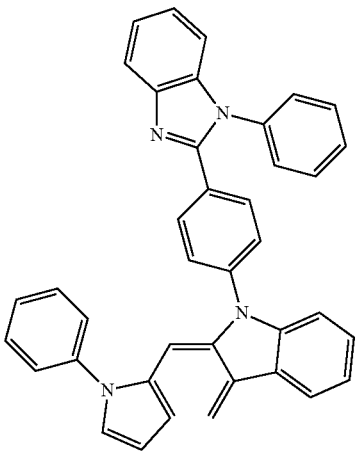
35
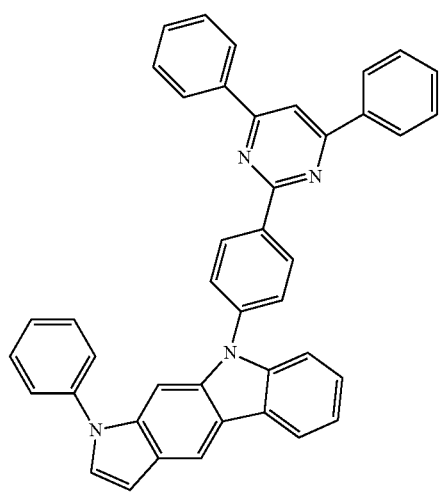
36
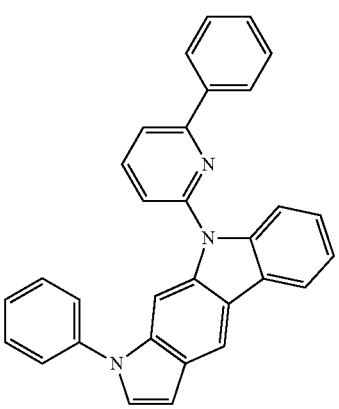

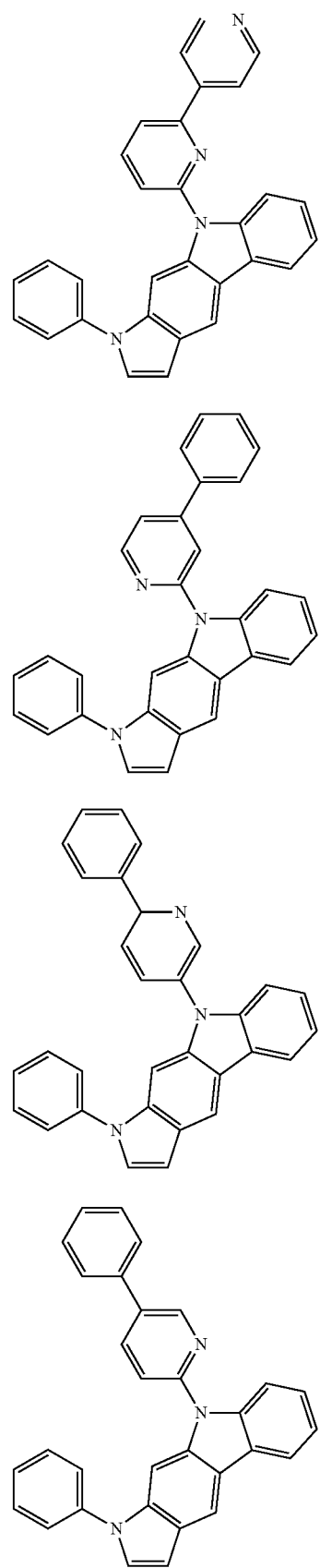
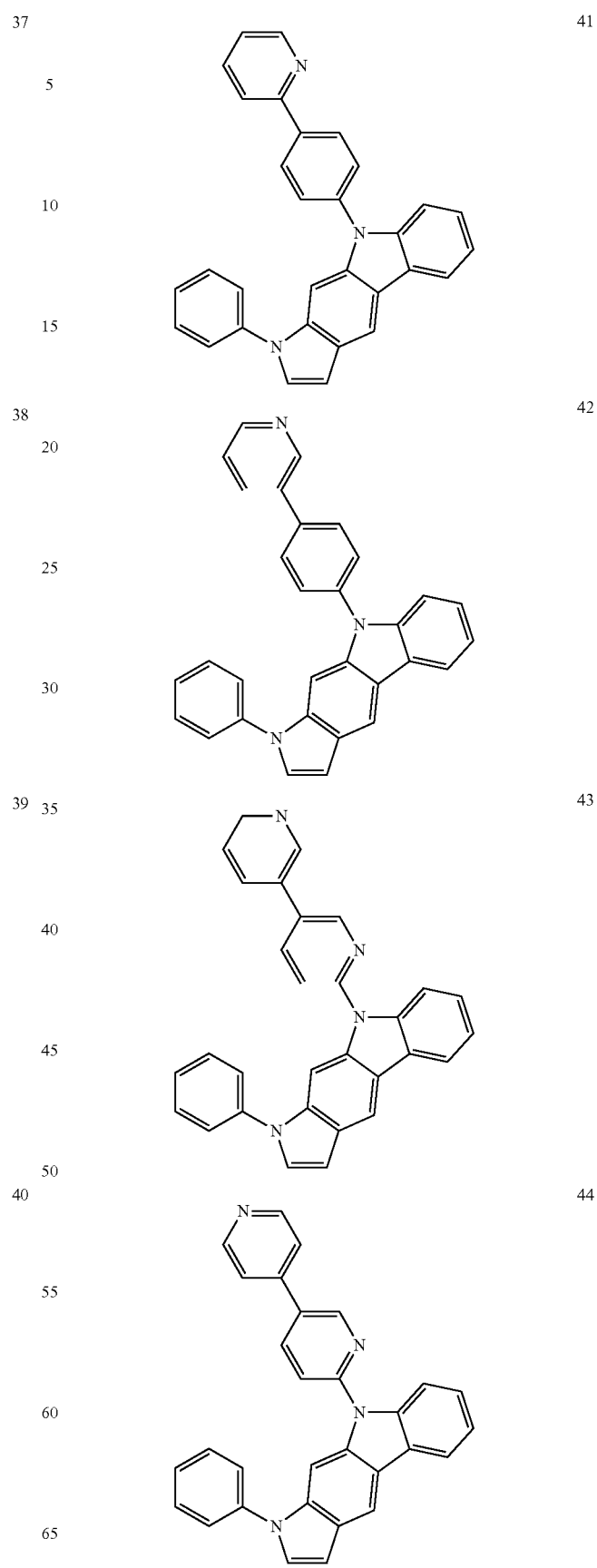

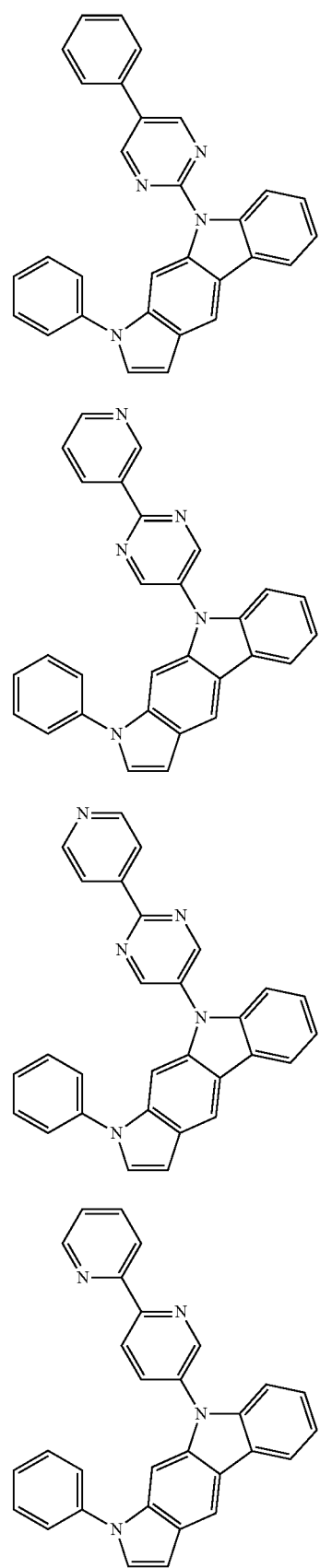
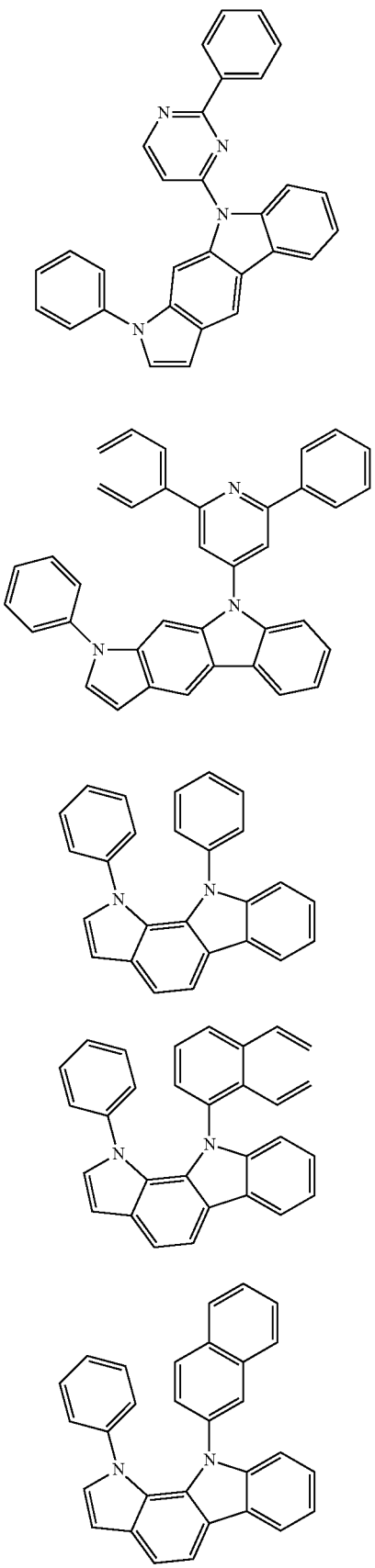

54
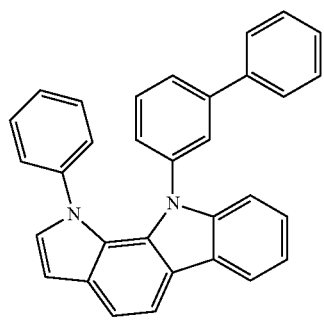
55
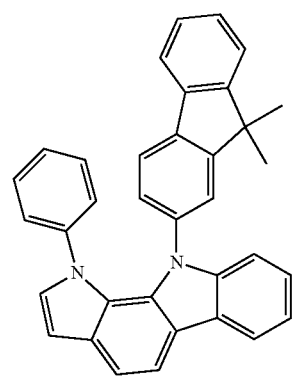
56
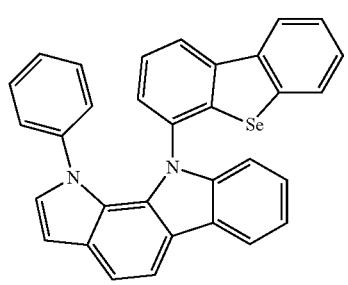
57
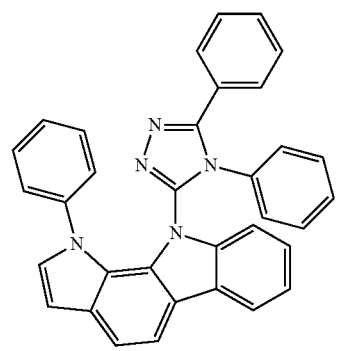
58
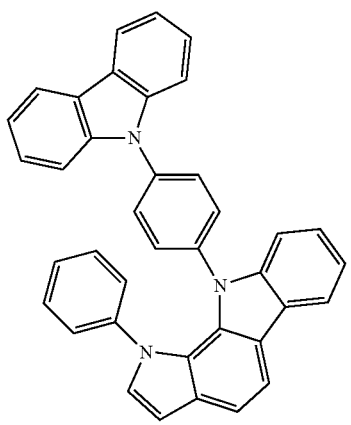
59
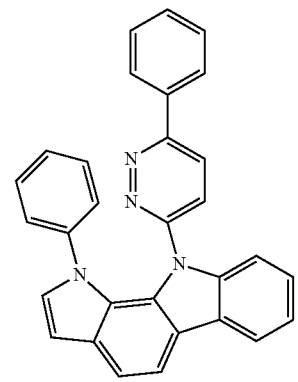
60
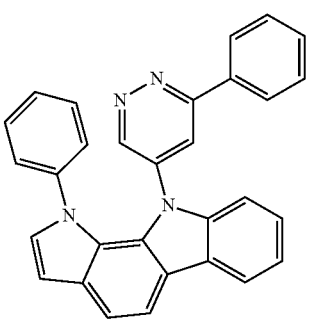
61
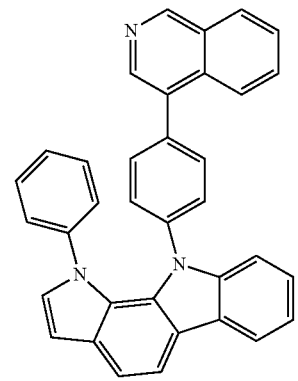

59
-continued
62
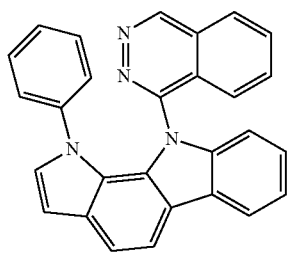
63
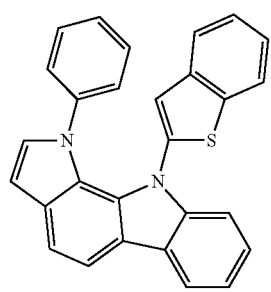
64
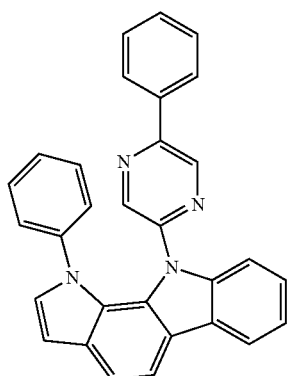
65
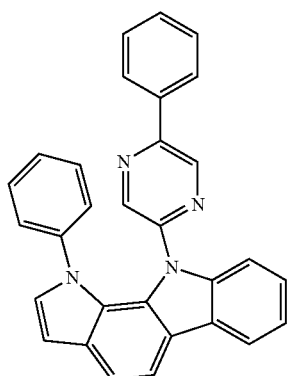
66
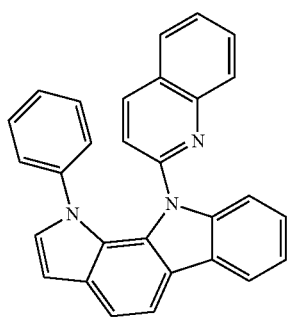
60
-continued
67
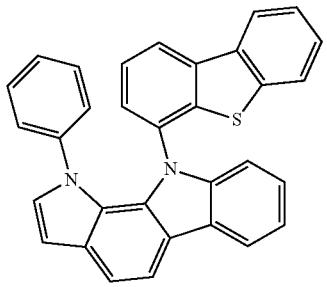
68
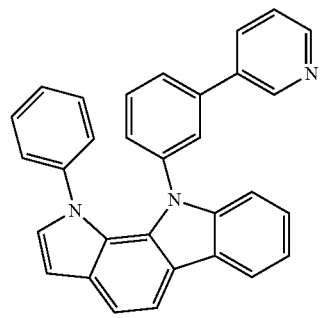
69
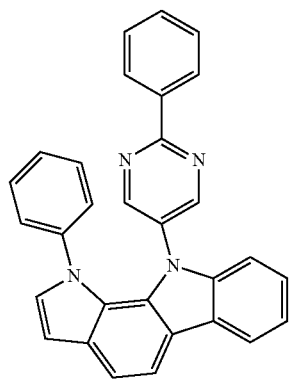
70
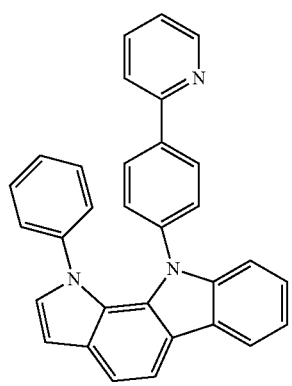

71
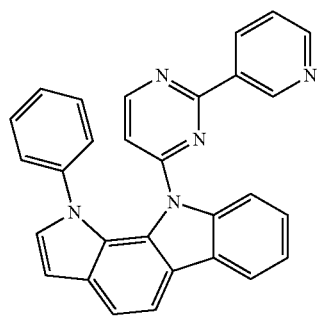
72
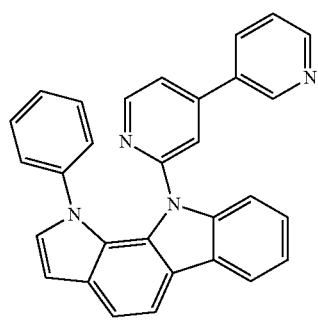
73
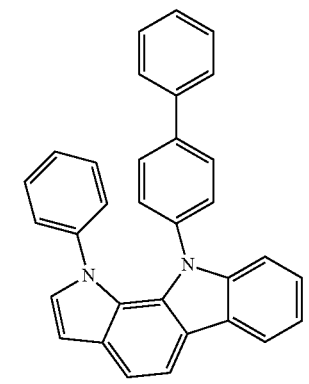
74
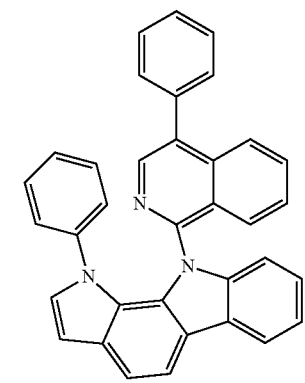
75
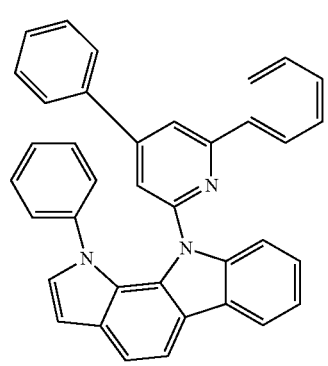
76
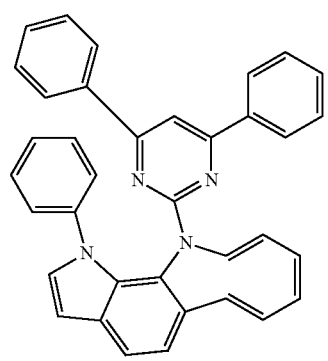
77
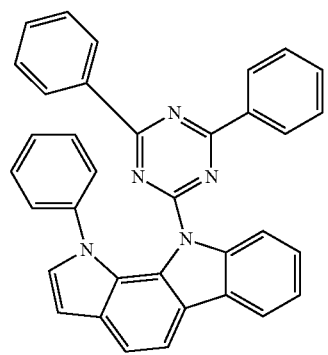
78
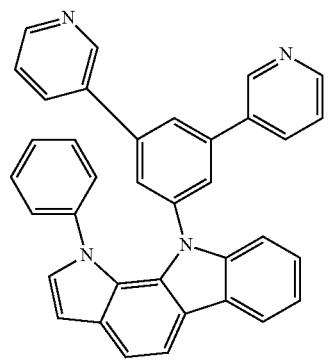

79
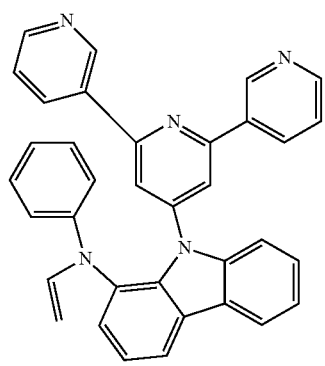
80
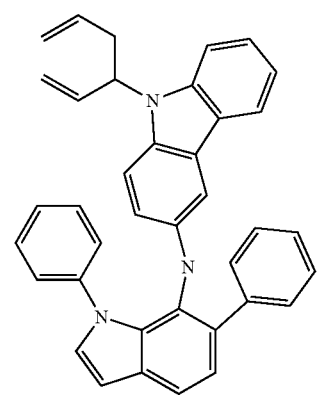
81
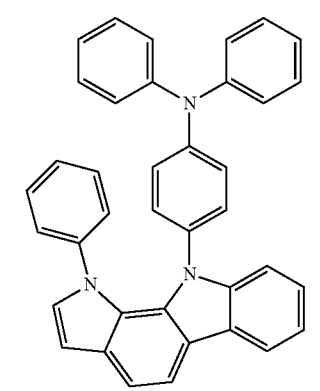
82
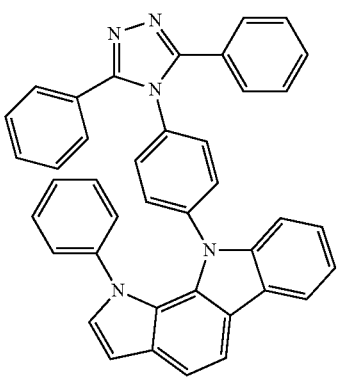
83
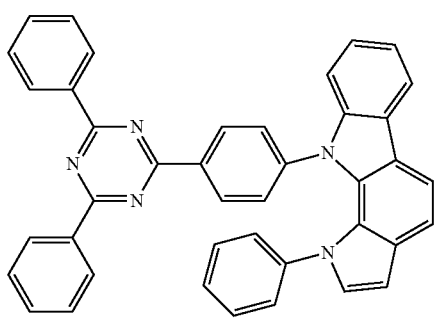
84
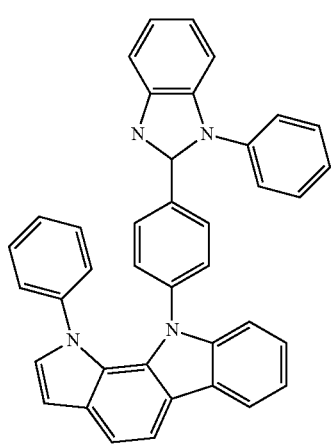
85
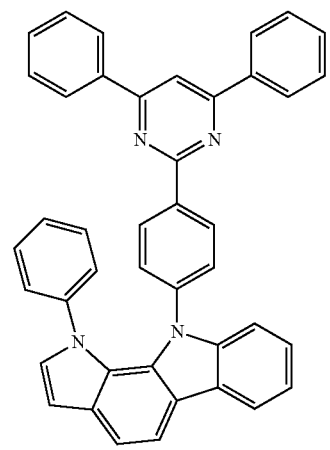
86
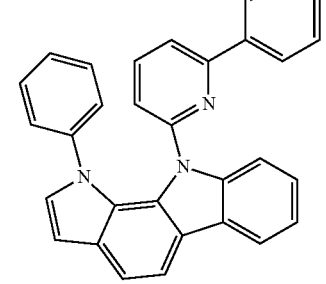

87
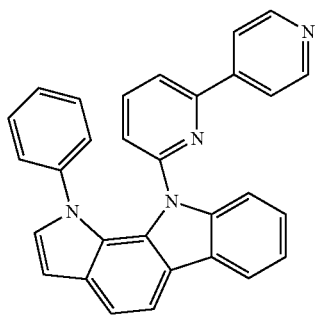
88
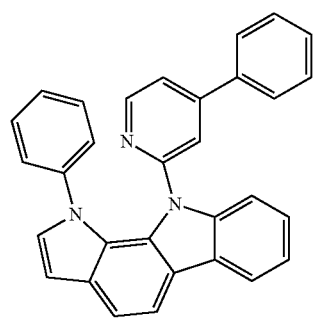
89
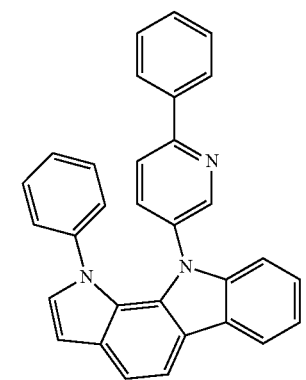
90
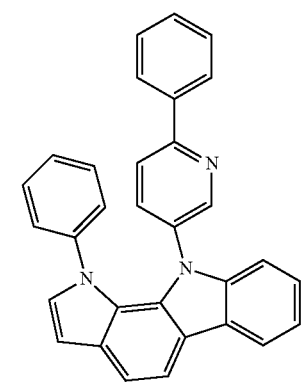
91
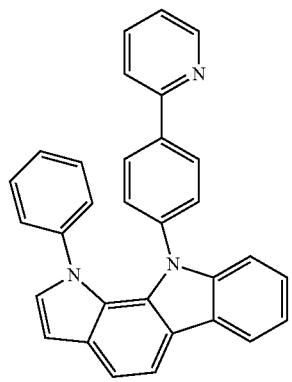
92
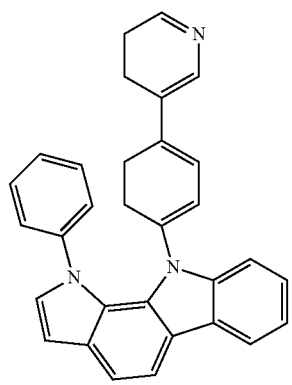
93
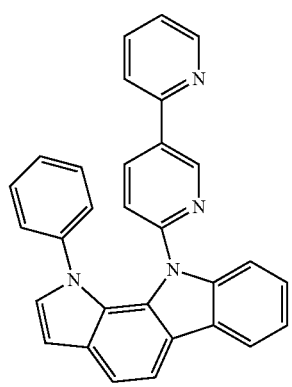
94
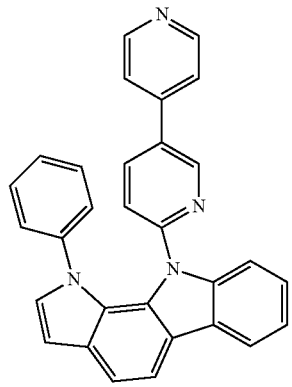

95 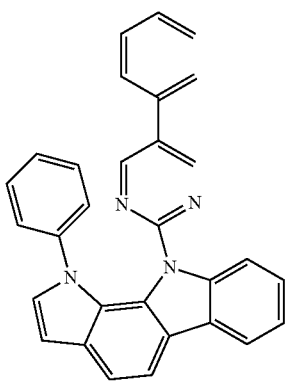
96 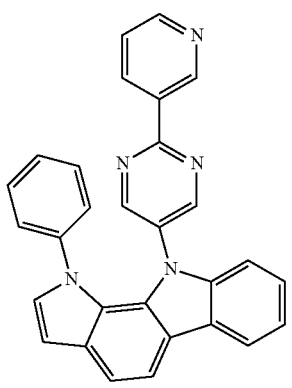
97 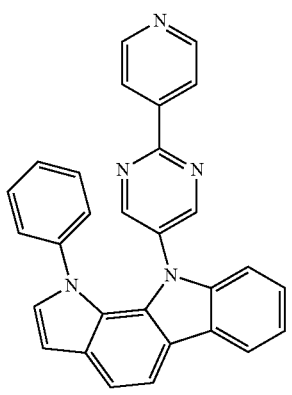
98 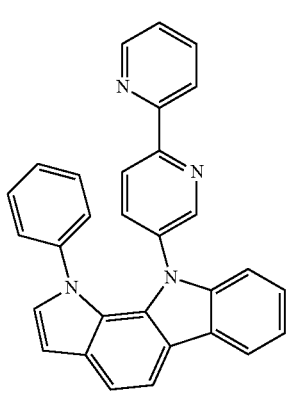
99 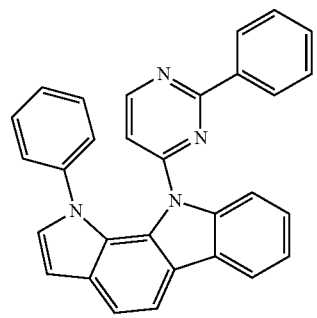
100 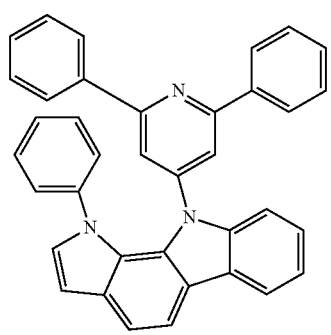
101 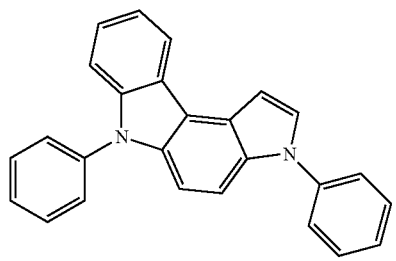
102 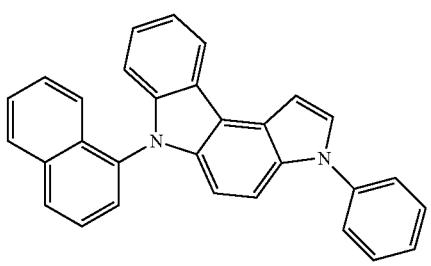
103 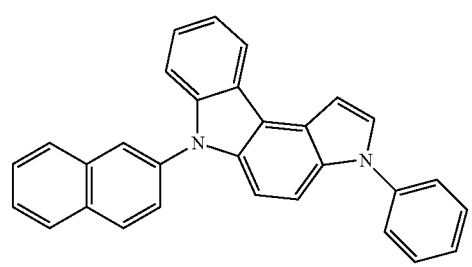

104
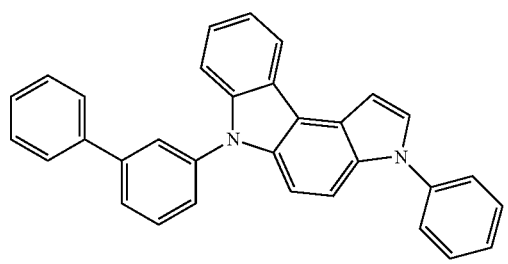
105
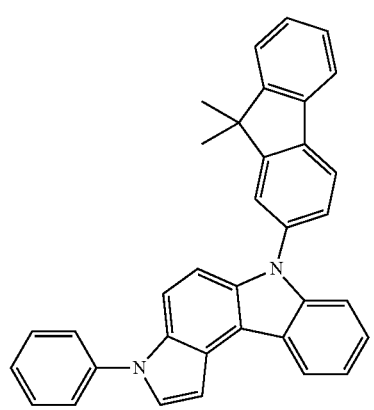
106
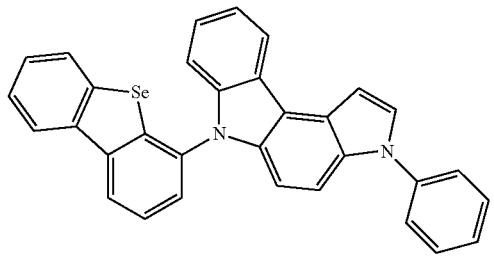
107
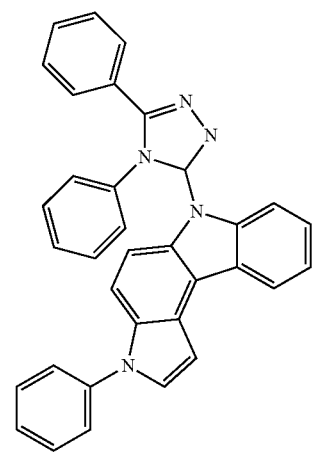
108
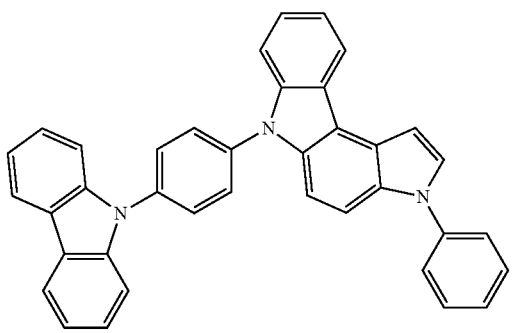
109
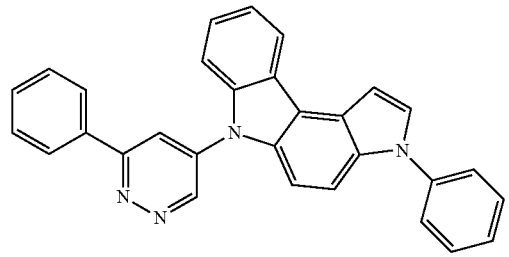
110
111
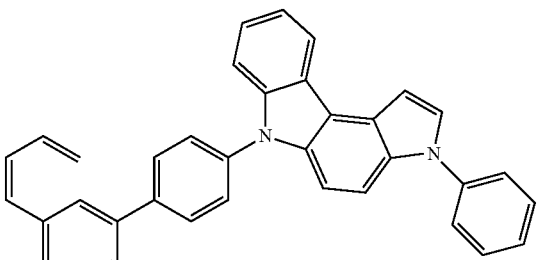
112
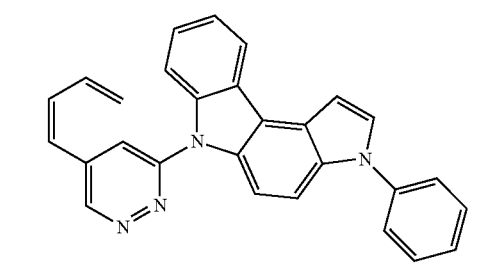

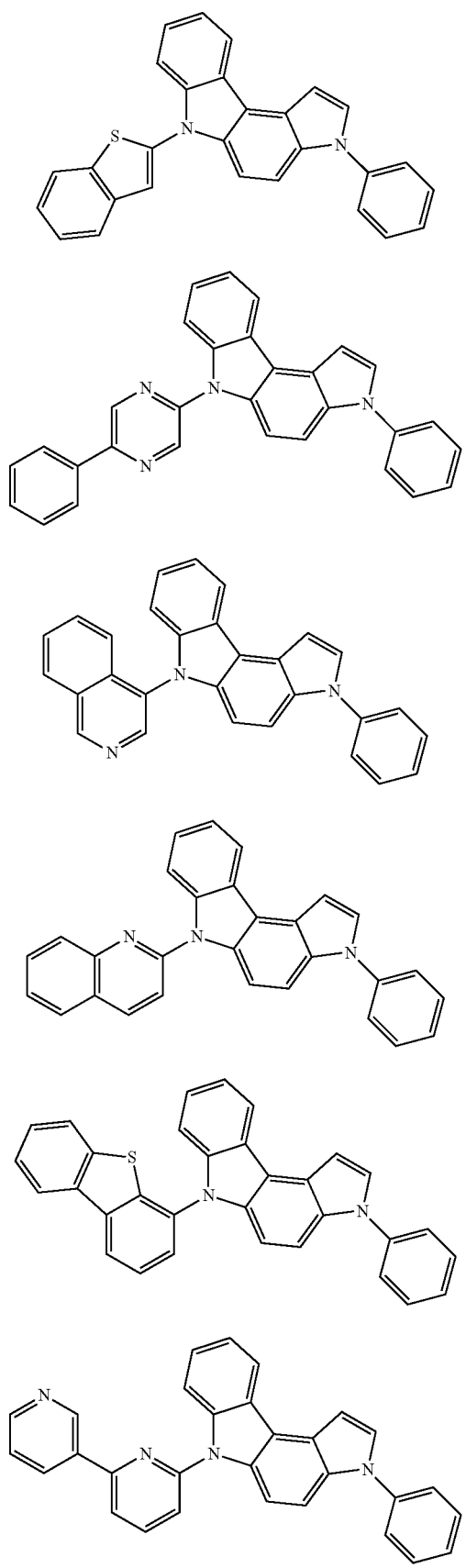

124
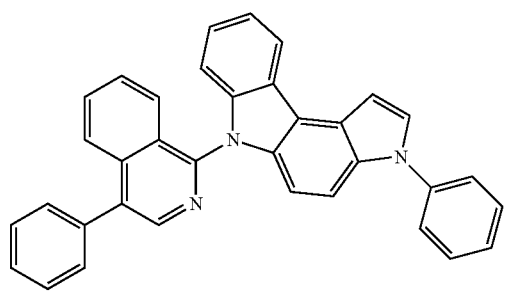
125
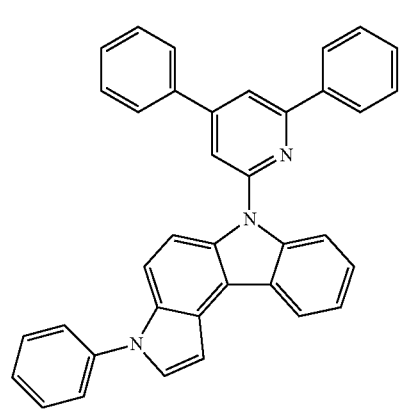
126
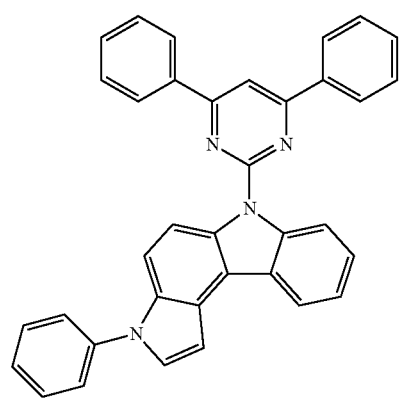
127

128
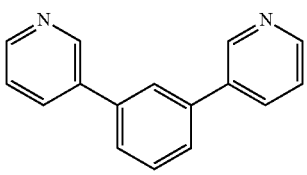
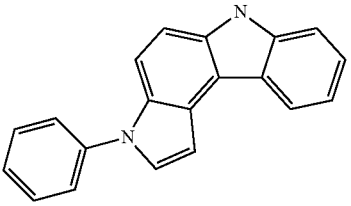
129
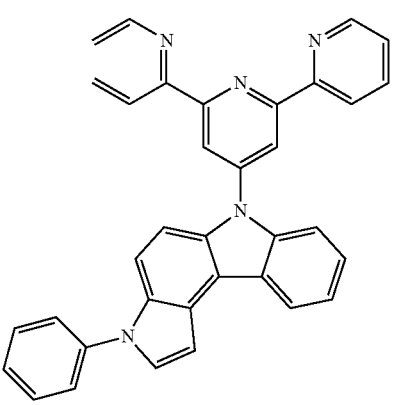
130
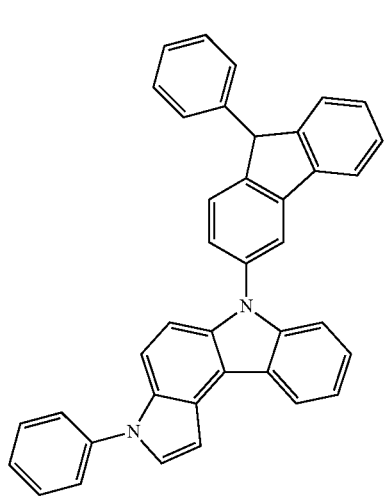

131
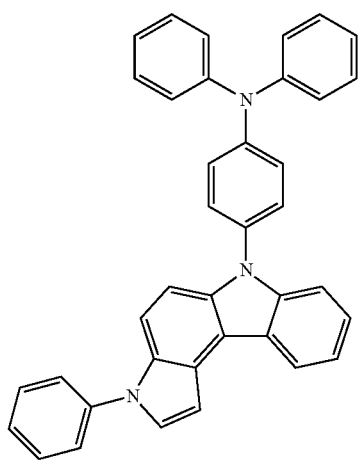
132
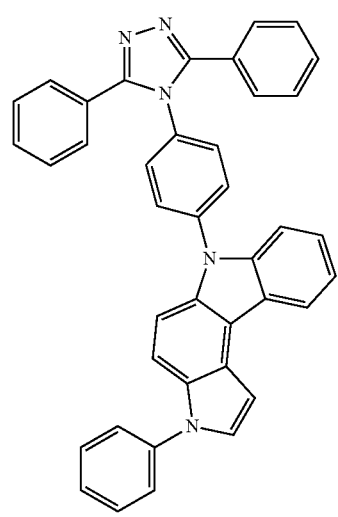
133
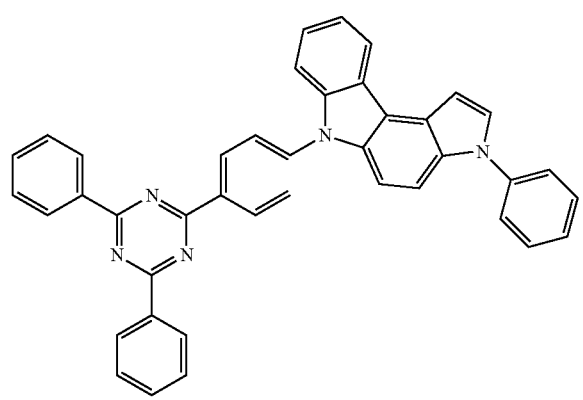
134
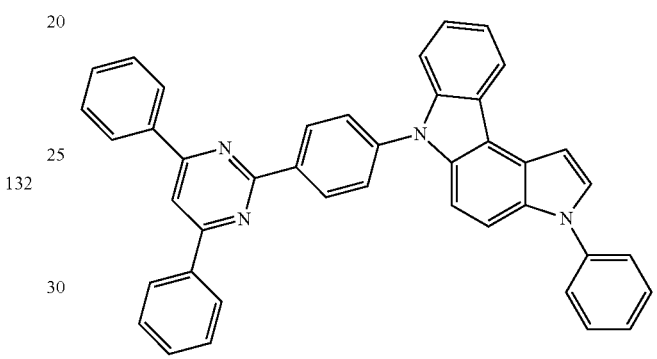
135
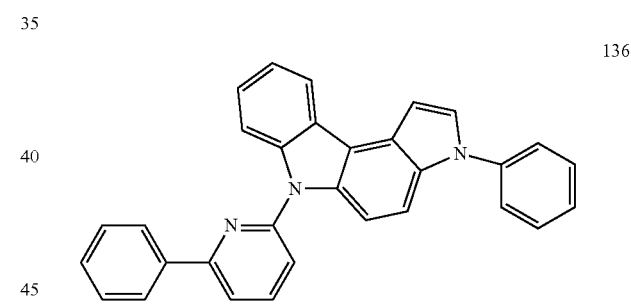
136
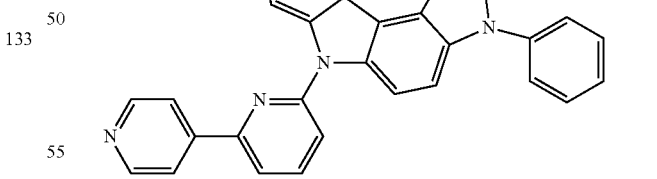
137
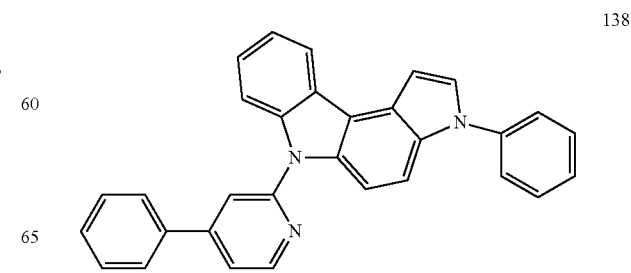
138

139
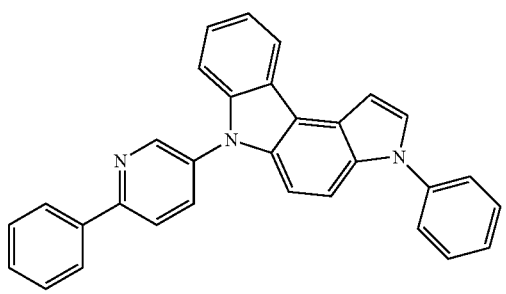
140
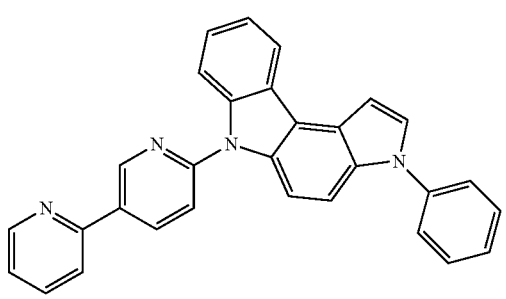
141
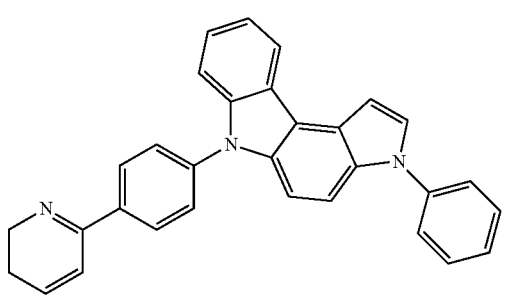
142
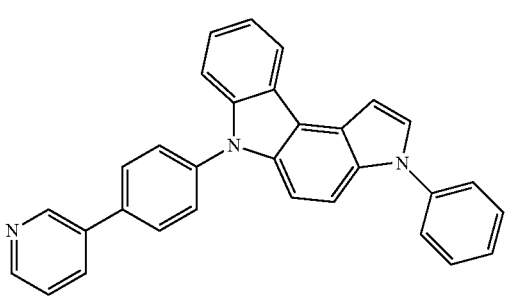
143
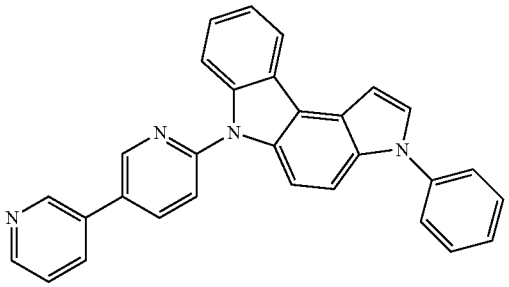
144
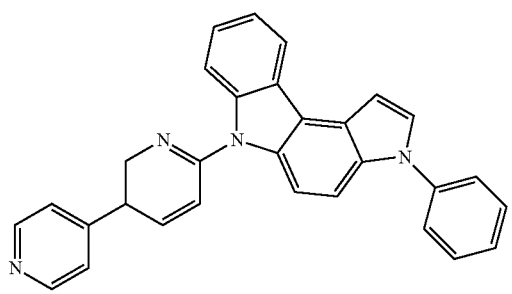
145
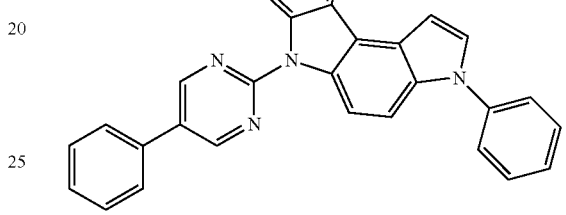
145
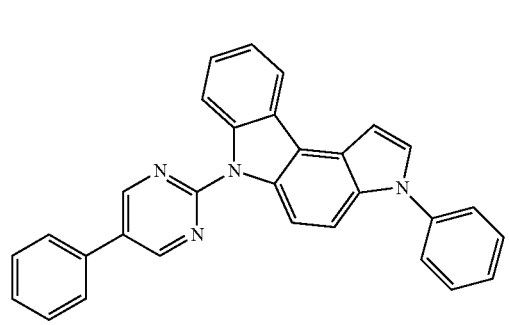
146
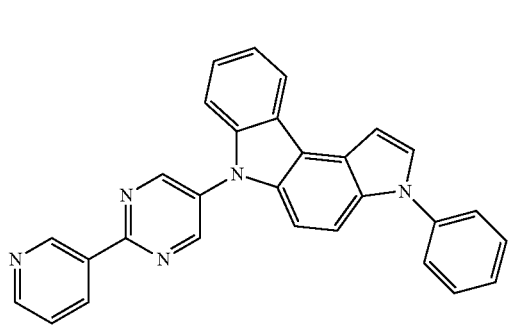
147
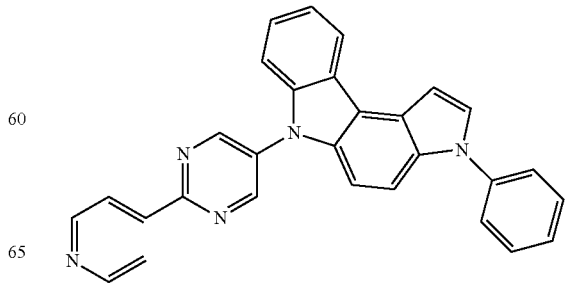

148
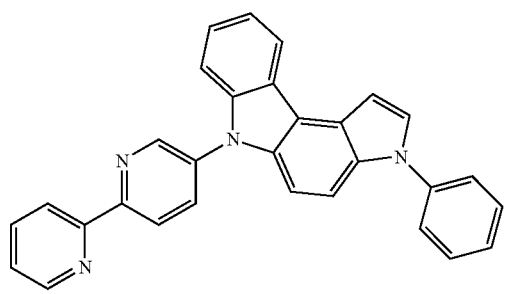
149
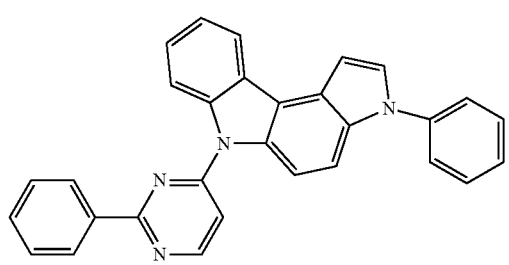
150
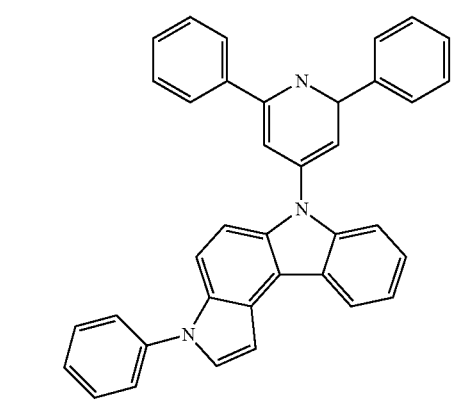
151
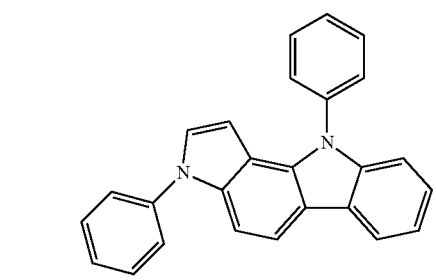
152
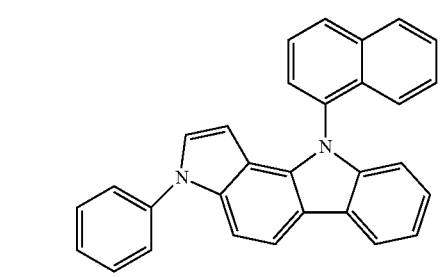
153
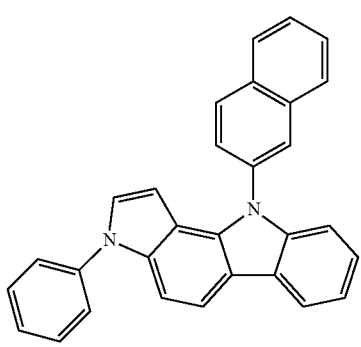
154
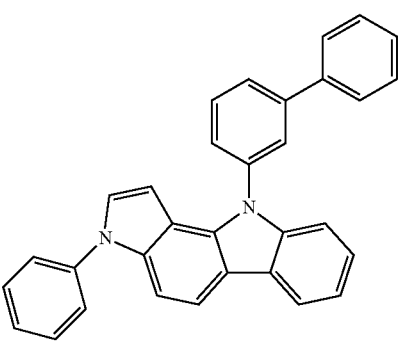
155
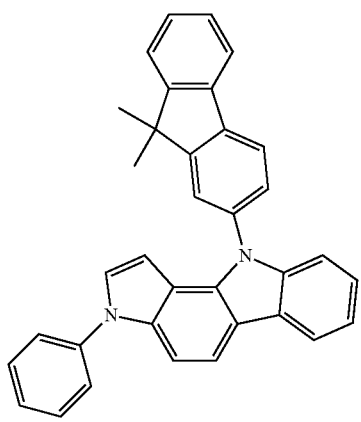
156
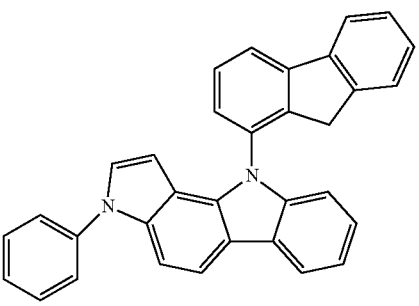

157
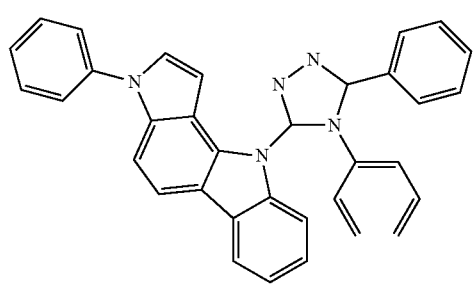
158
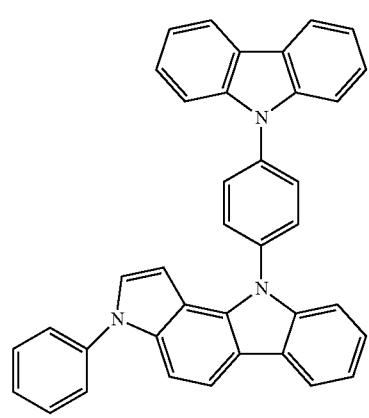
159
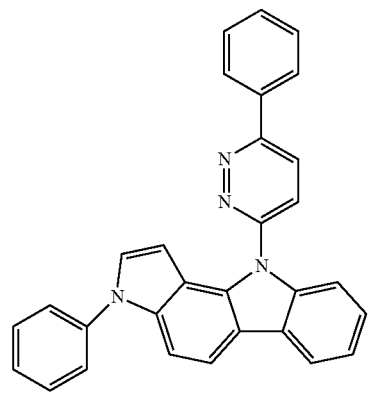
160
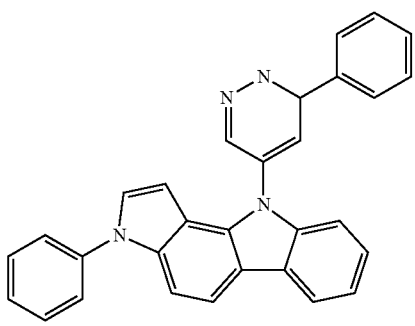
161
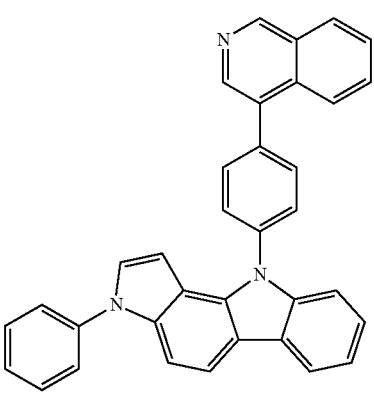
162
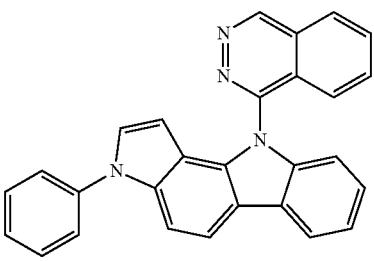
163
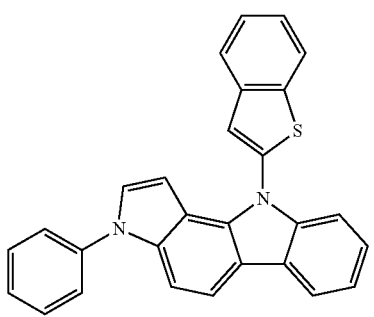
164
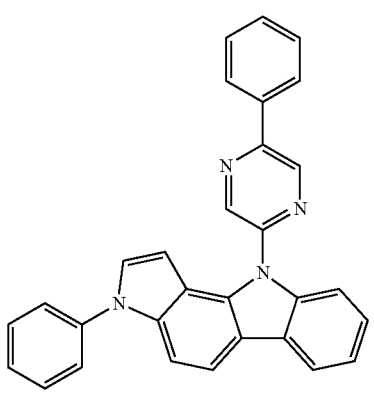
165
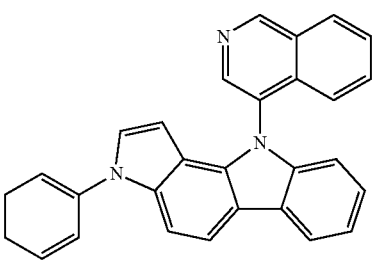

166
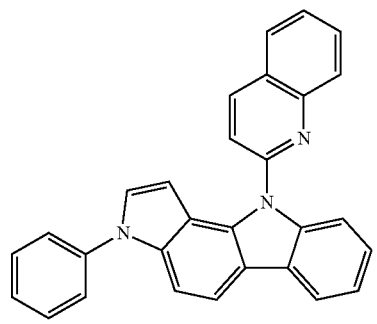
167
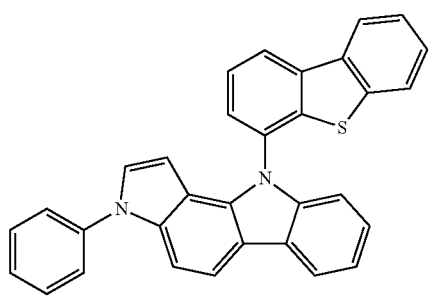
168
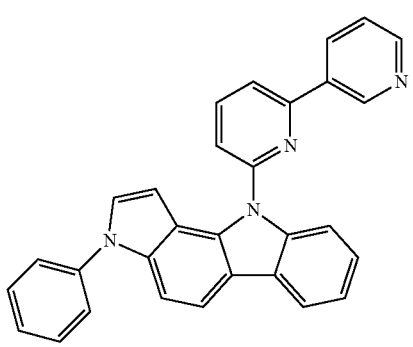
169
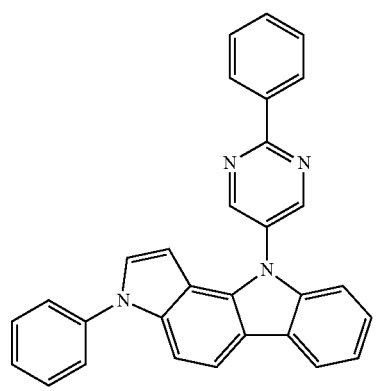
170
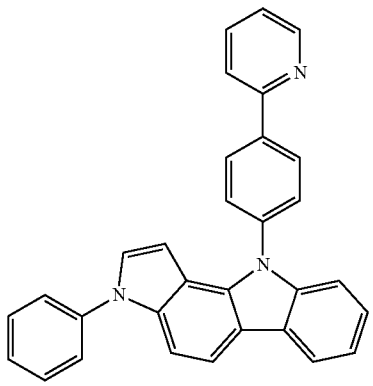
171
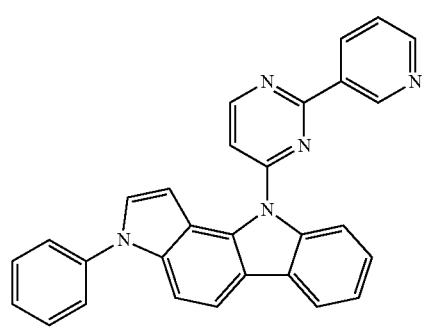
172
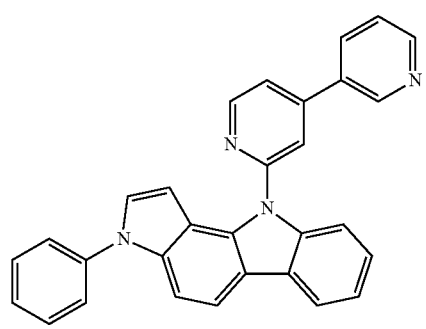
173
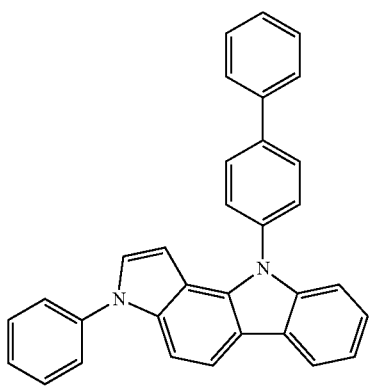

174 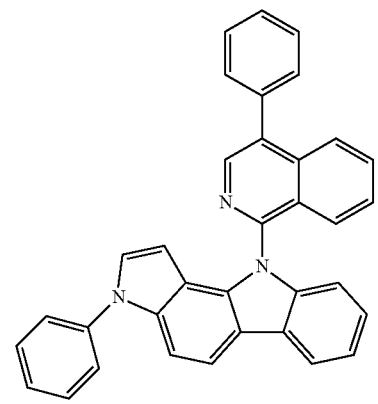
175 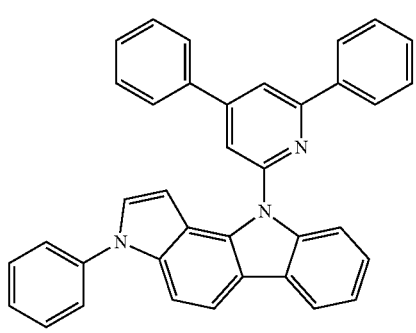
176 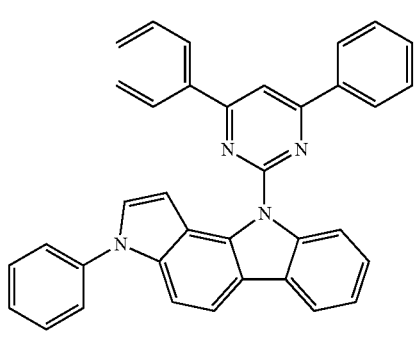
177 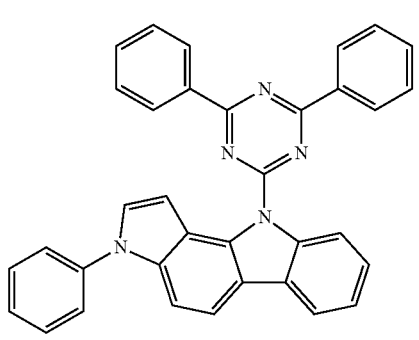
178 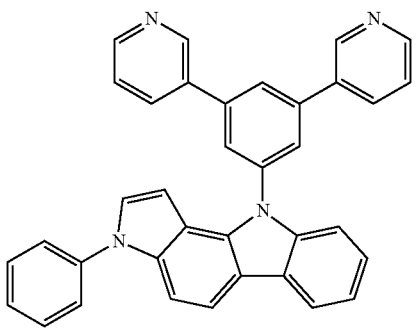
179 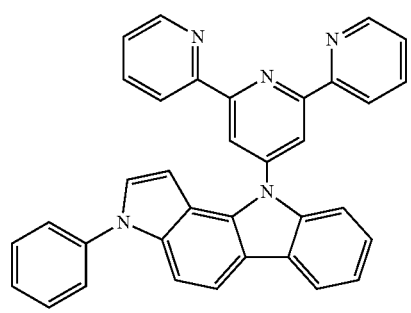
180 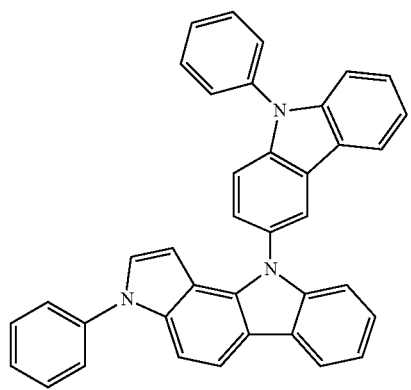
181 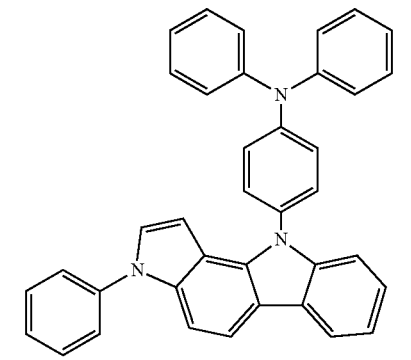

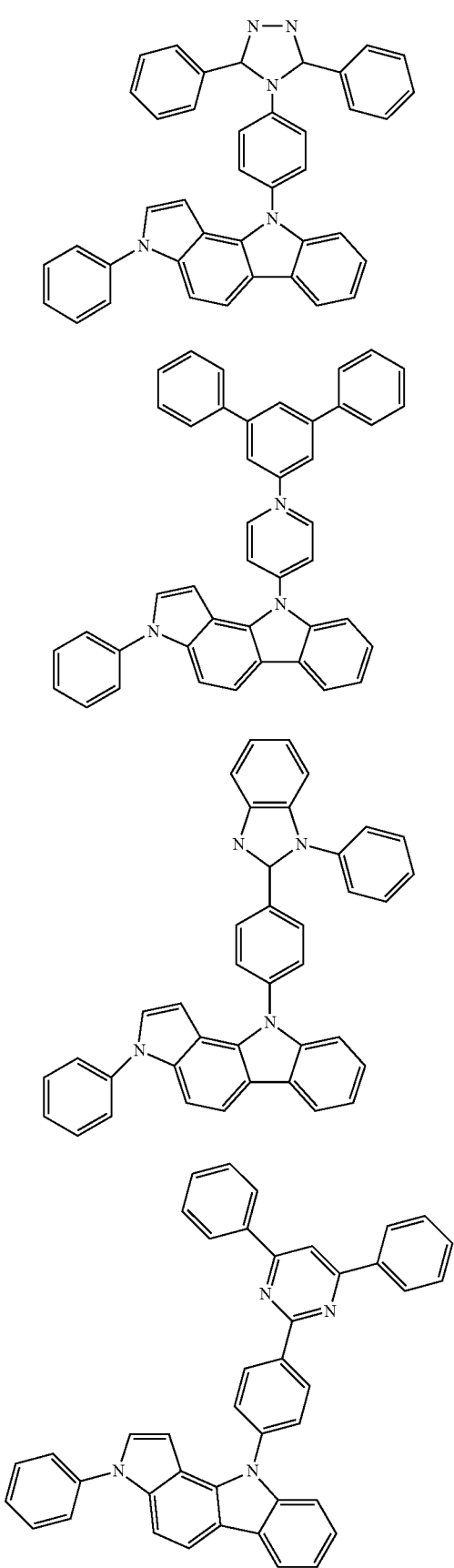
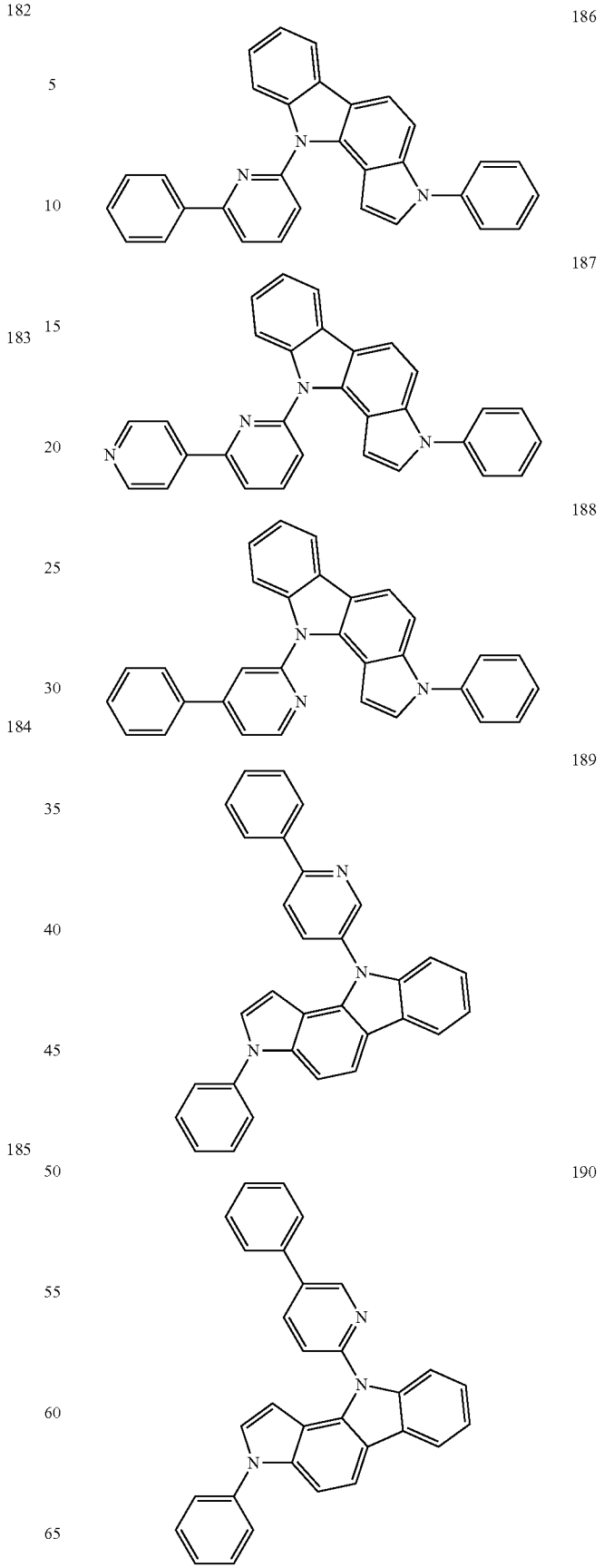

191
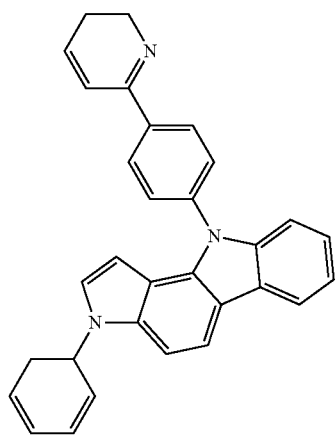
192
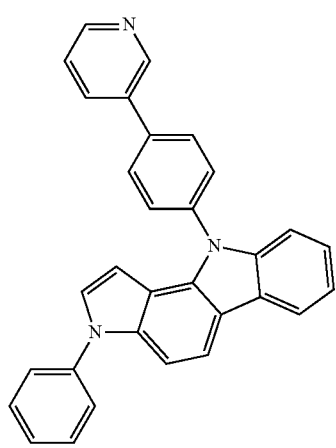
193
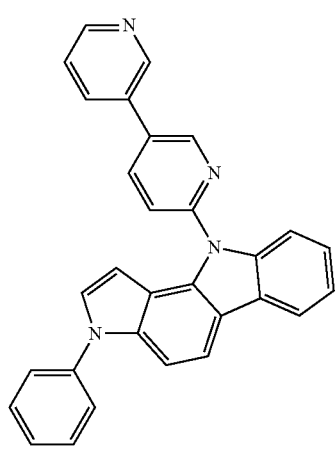
194
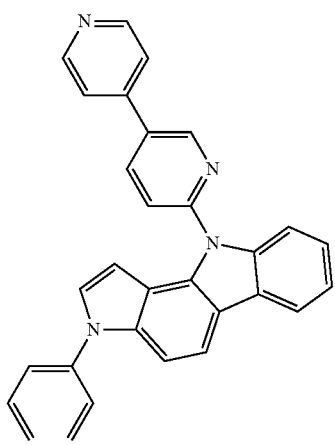
195
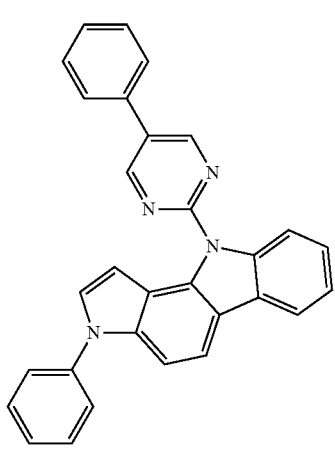
196
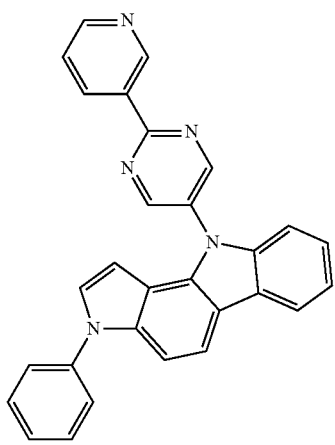

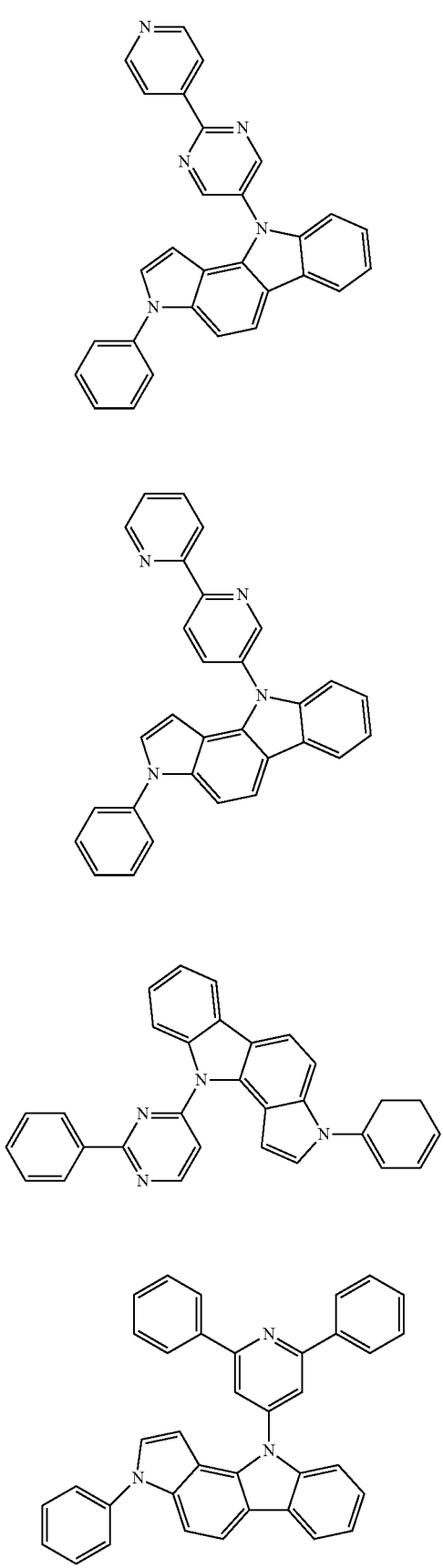

-continued
207
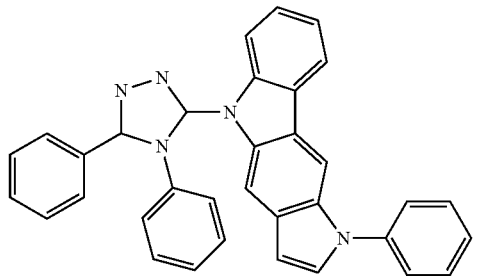
208
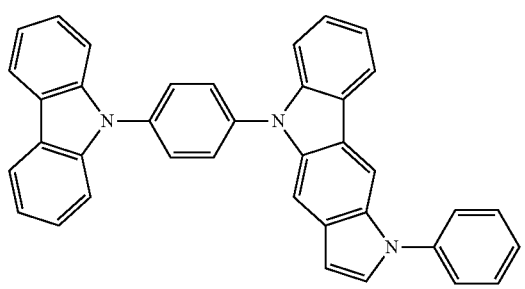
209
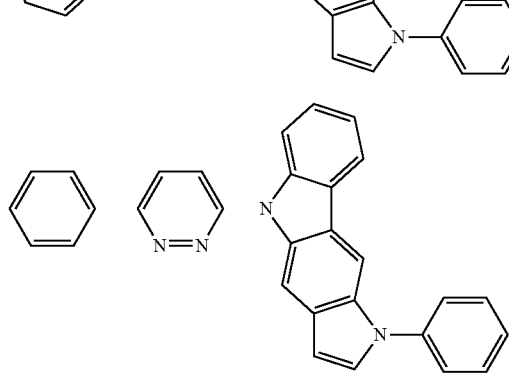
210
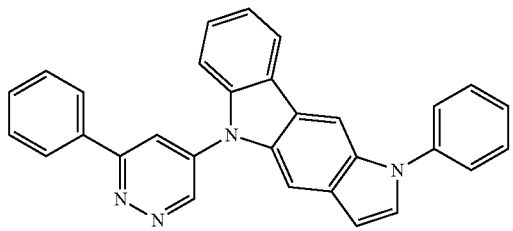
211
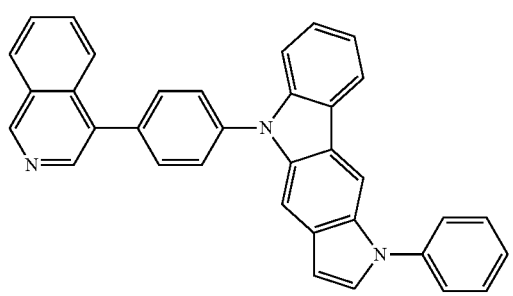
212
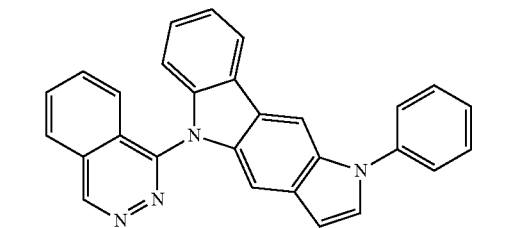
-continued
213
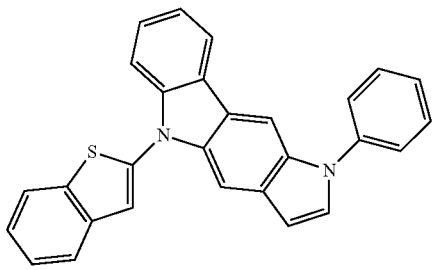
214
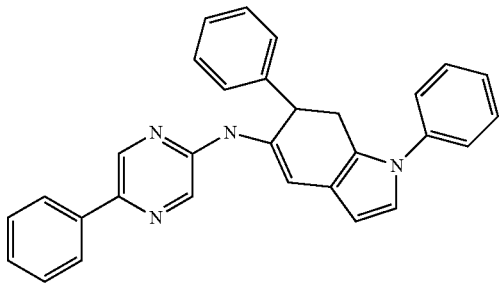
215
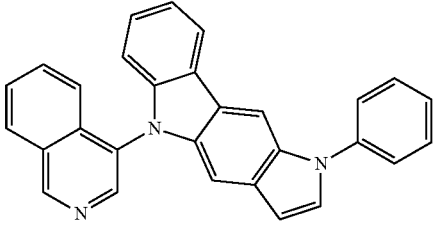
216
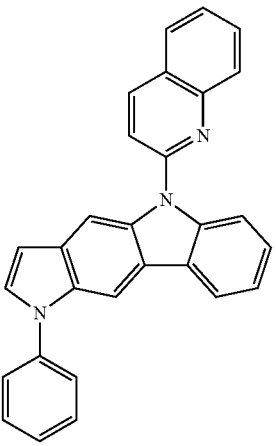

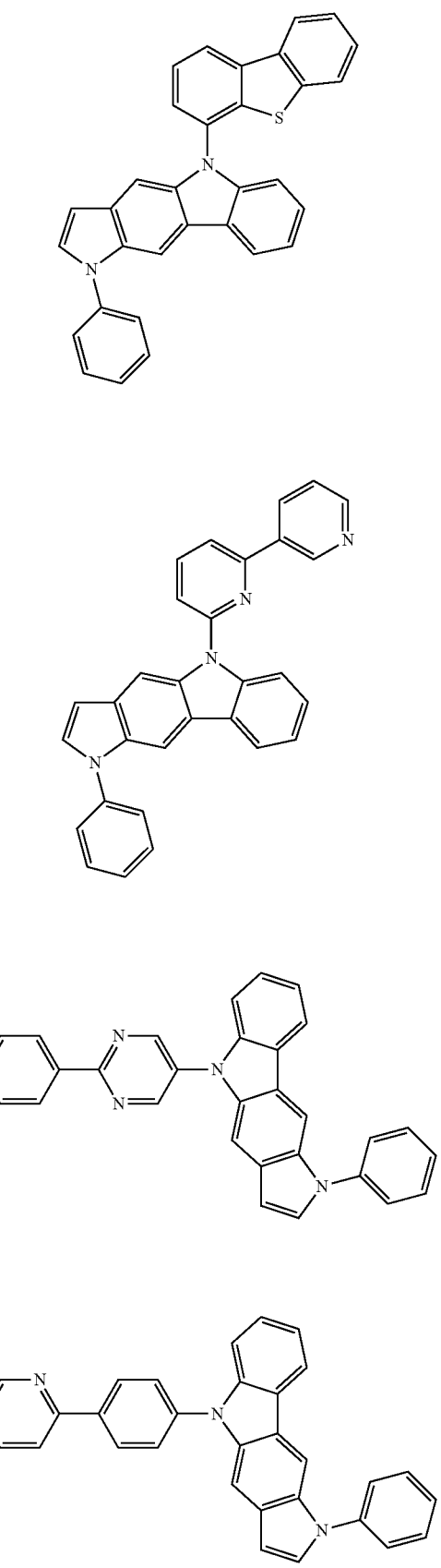

224
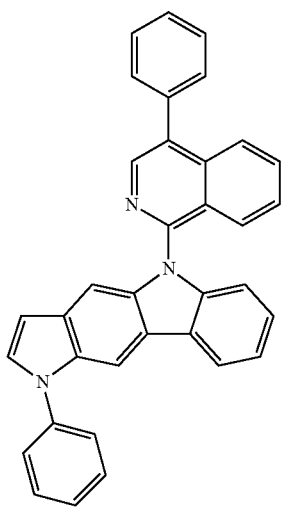
225
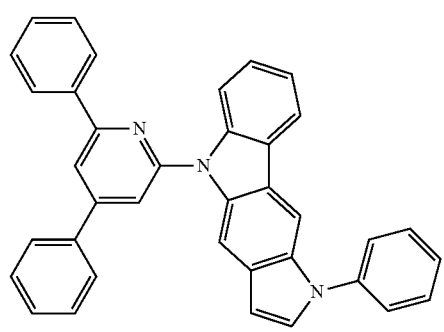
226
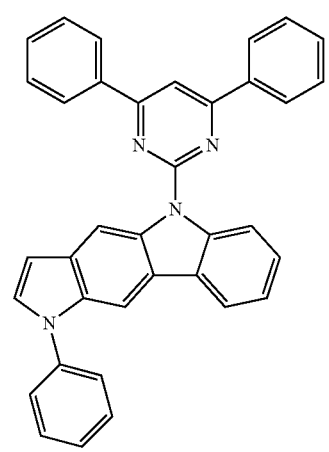
227
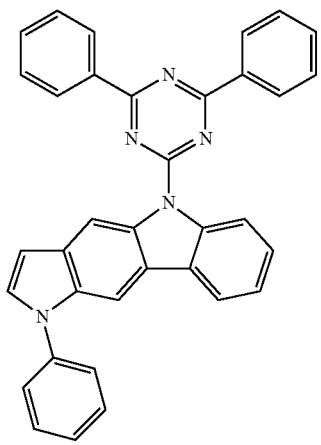
228
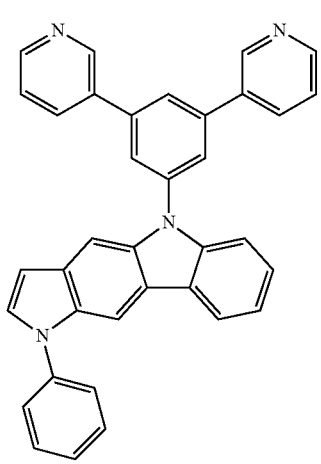
229
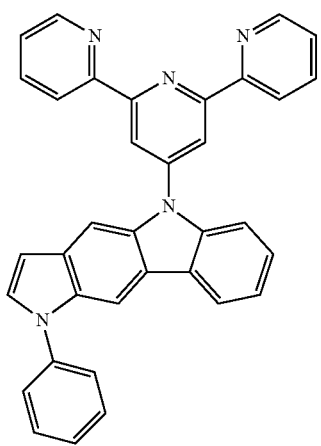

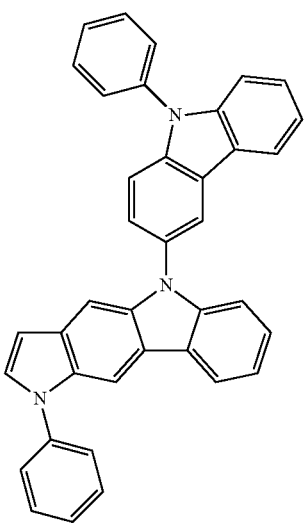
230
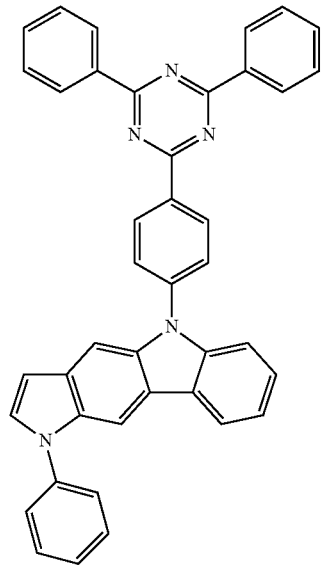
233
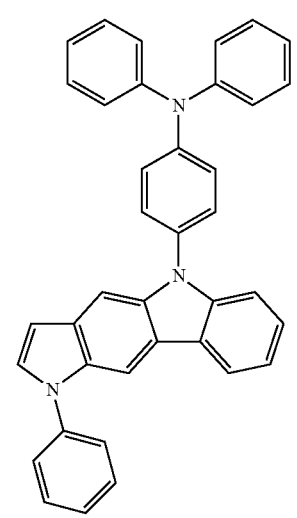
231
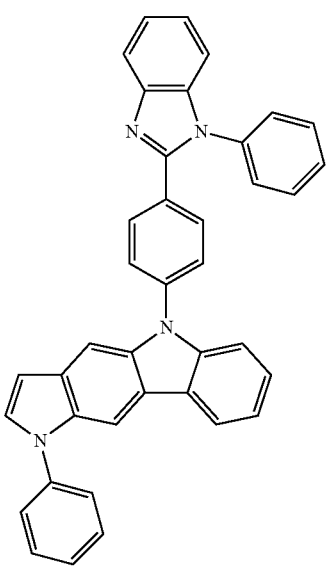
234
232

101
-continued
235
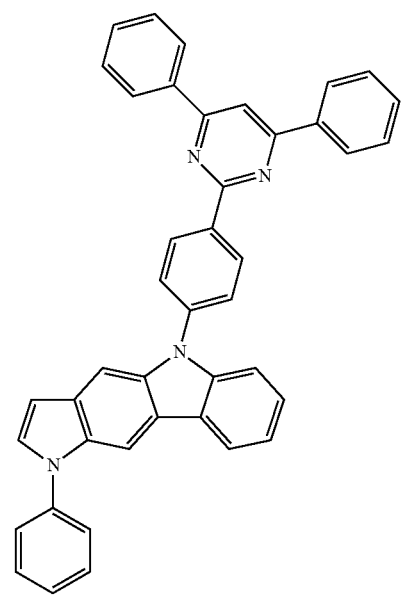
236
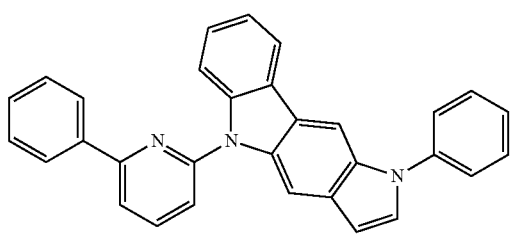
237
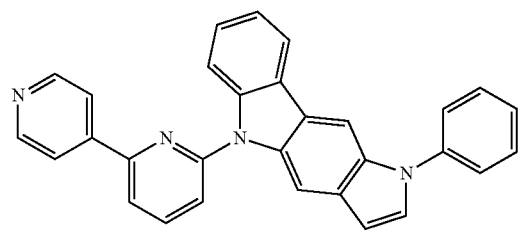
238
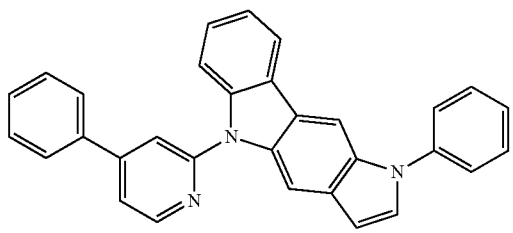
239
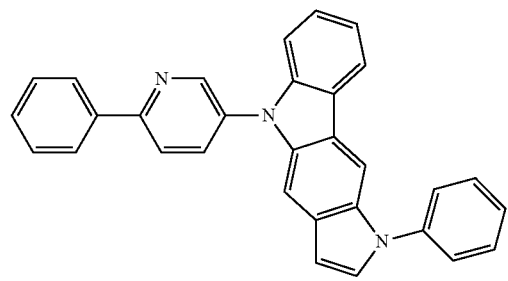
102
-continued
240
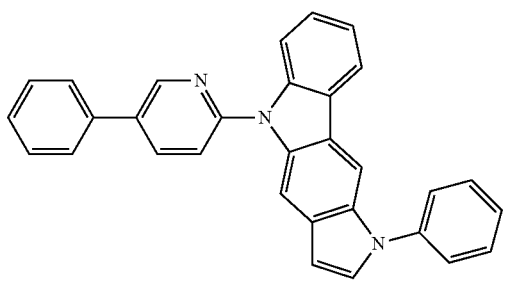
241
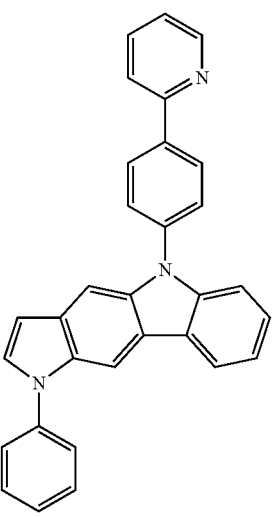
242
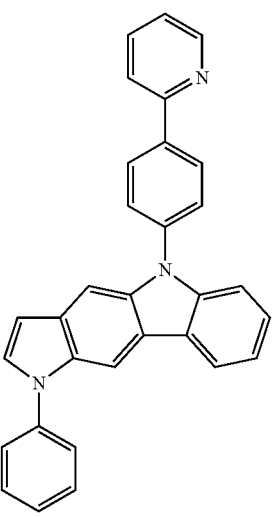

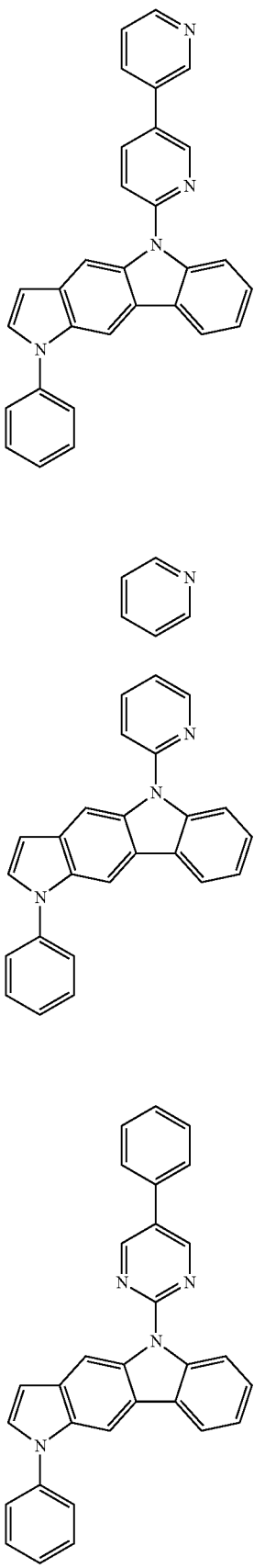
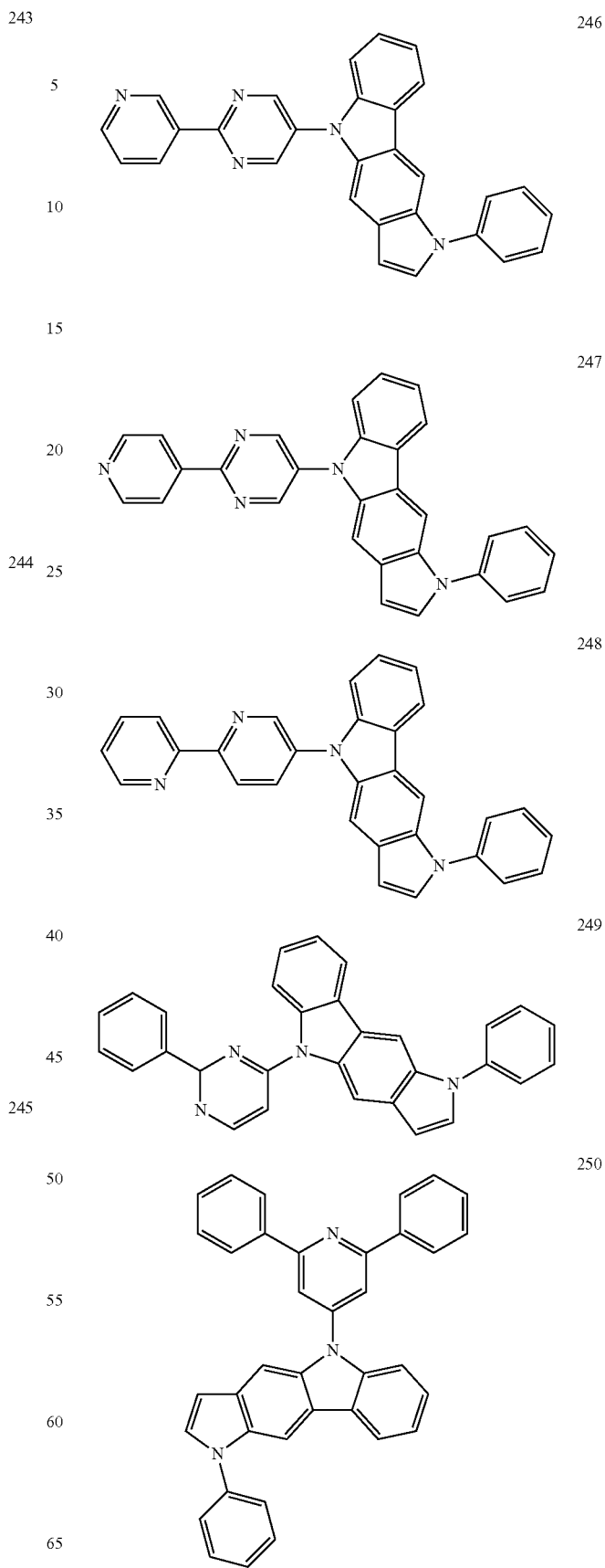

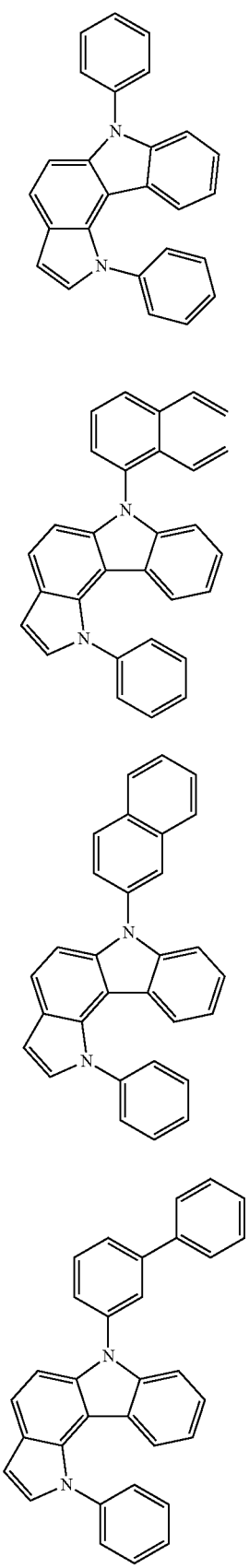
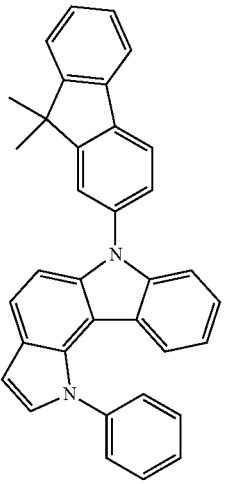
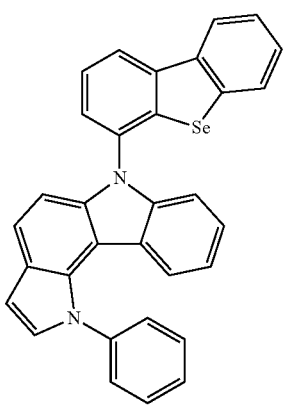
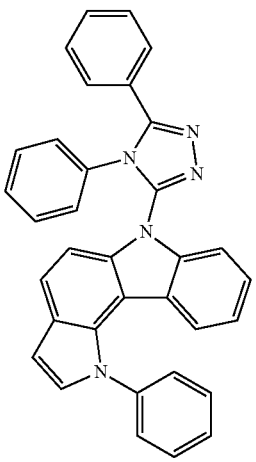

258
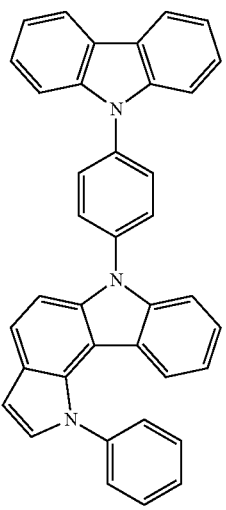
259
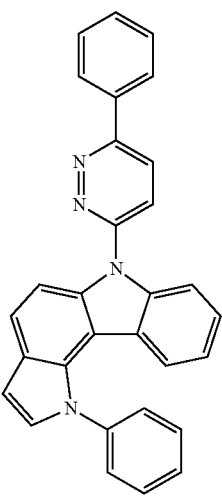
260
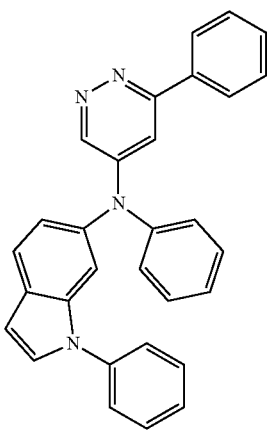
261
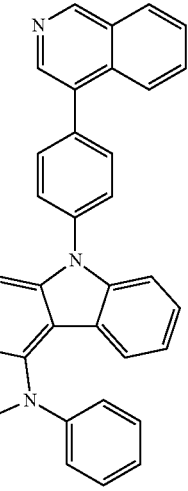
262
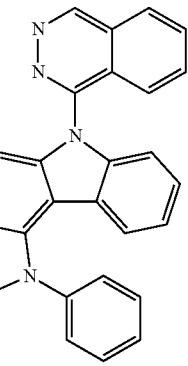
263
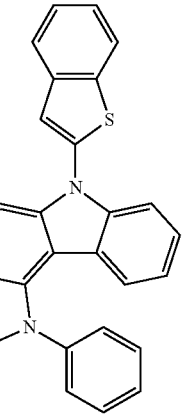
264
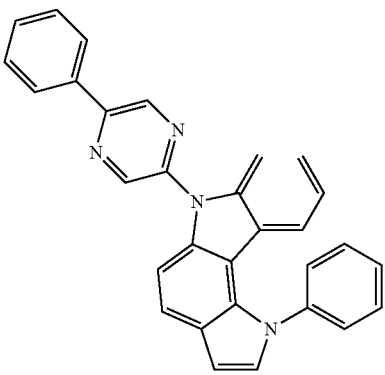

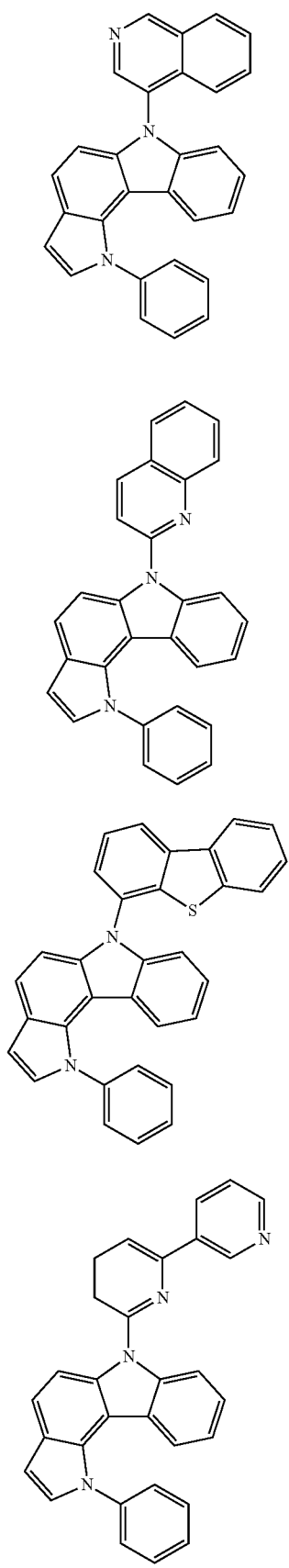
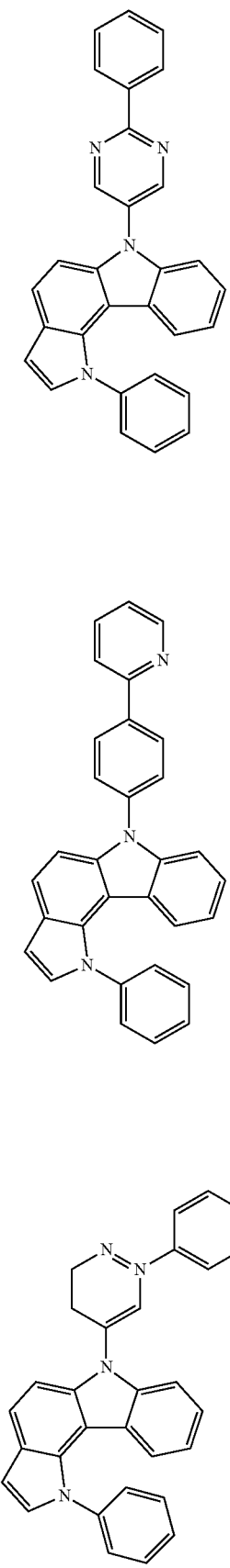

272
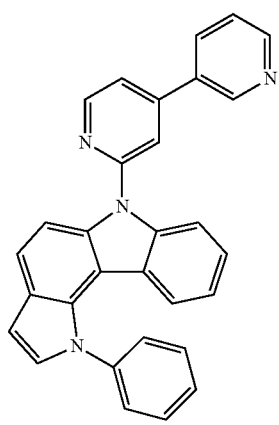
273
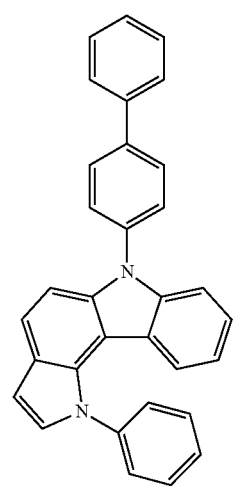
274
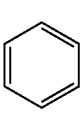
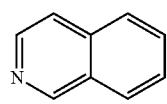
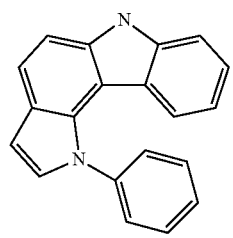
275
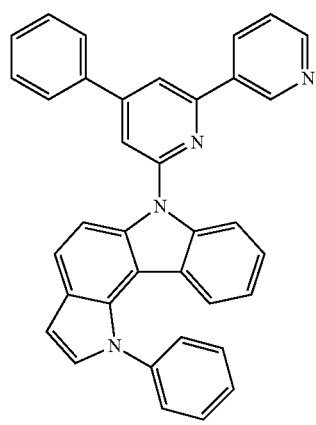
276
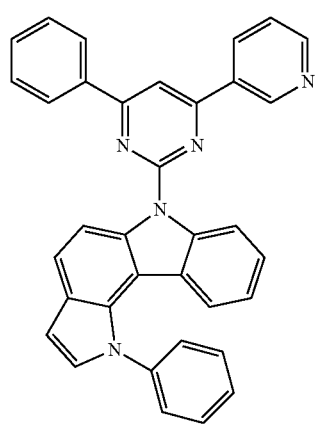
277
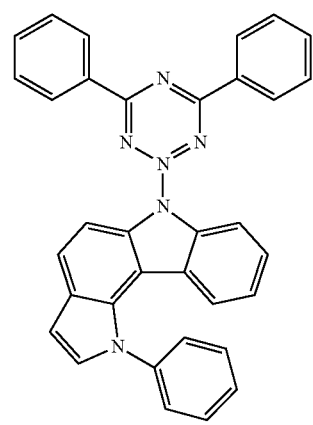

278
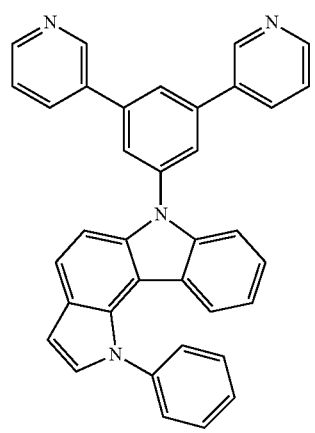
279
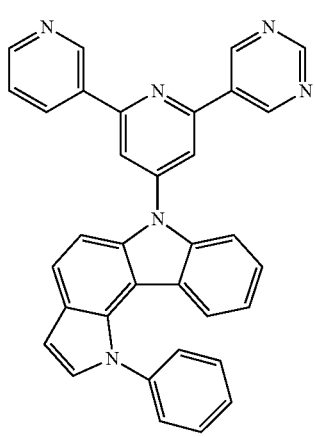
280
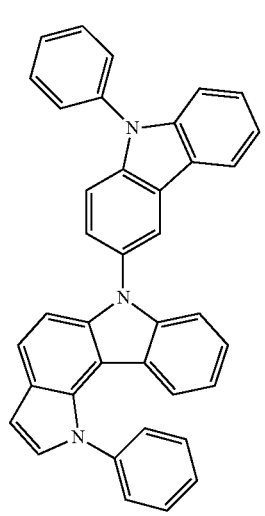
281
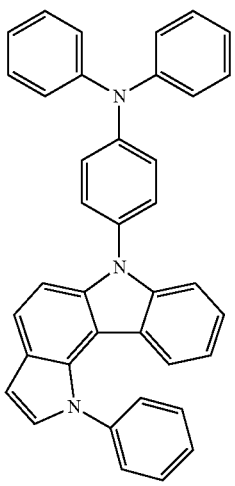
282
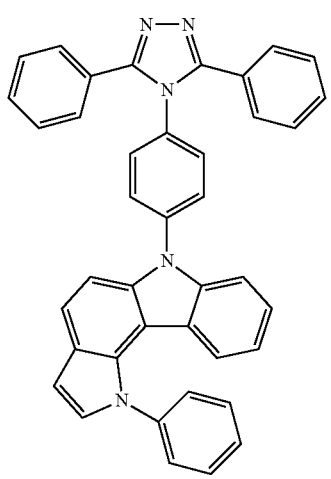
283
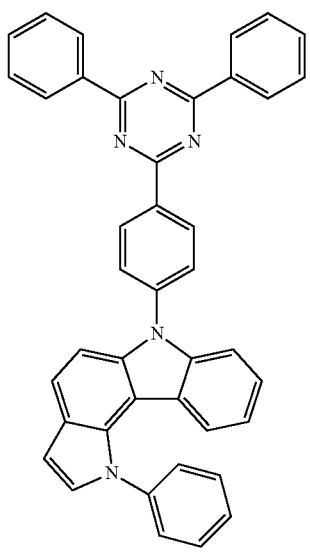

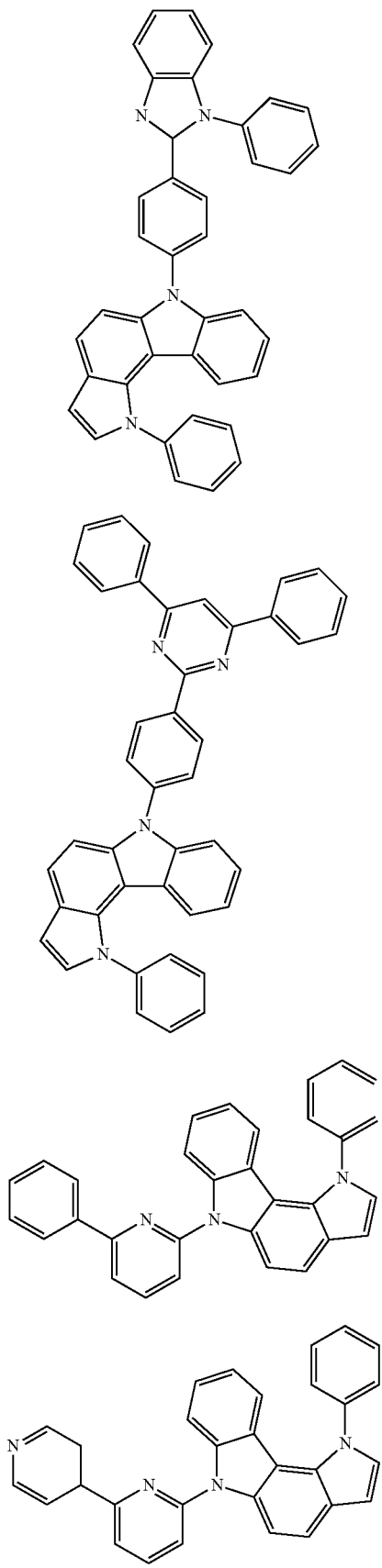
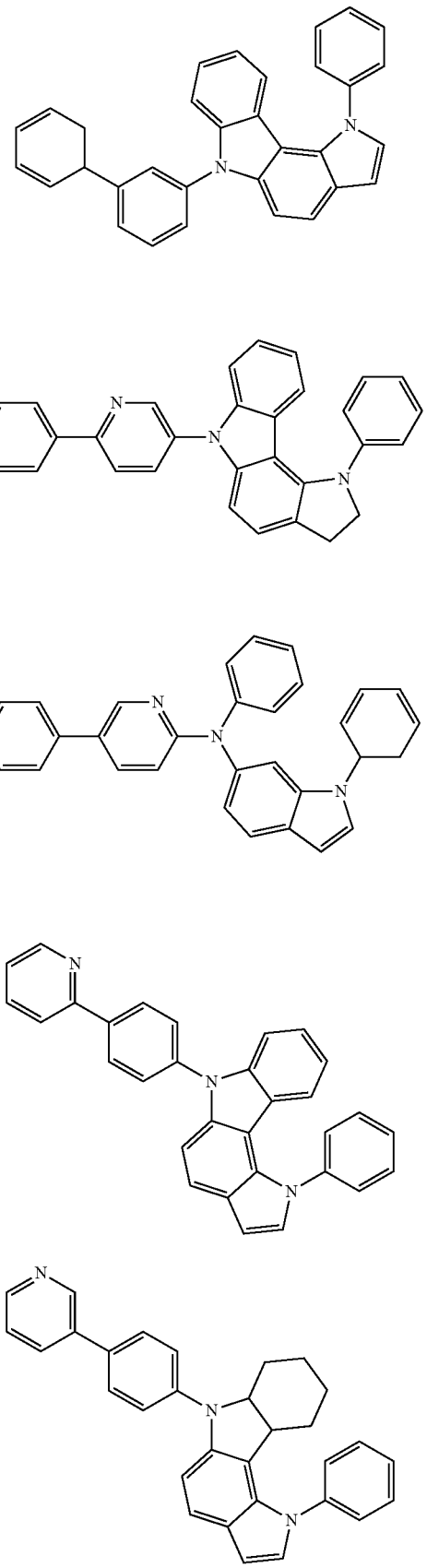

293
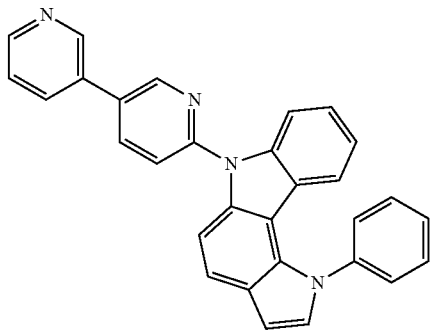
294
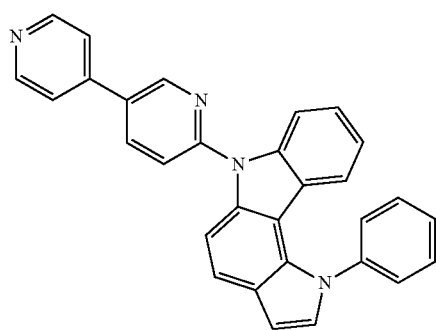
295
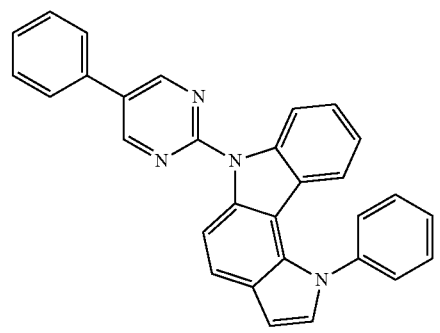
296
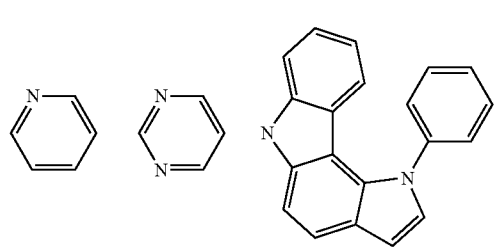
297
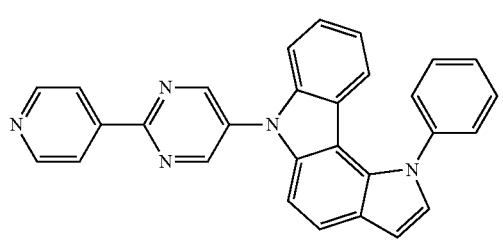
298
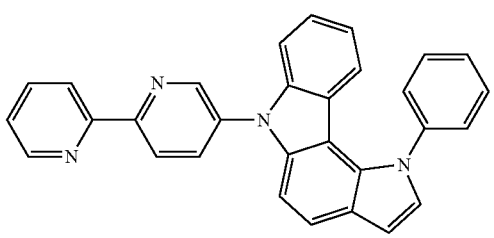
299
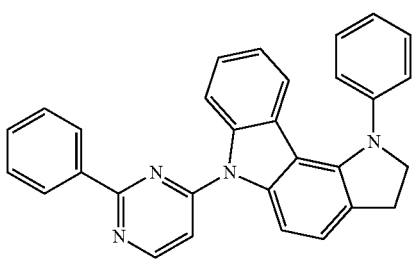
300
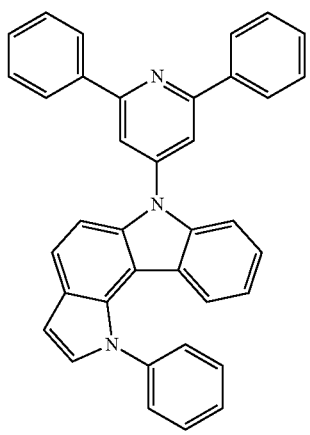
301
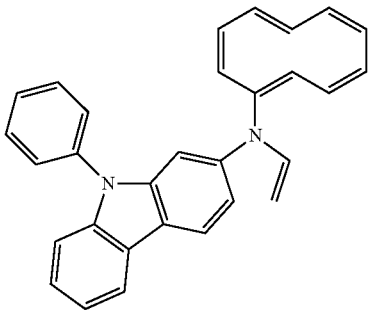
302
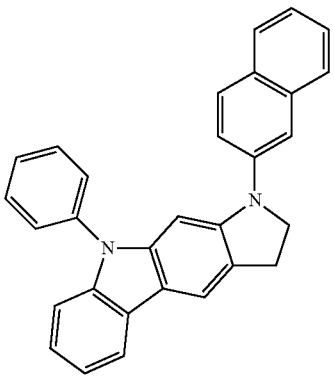

303
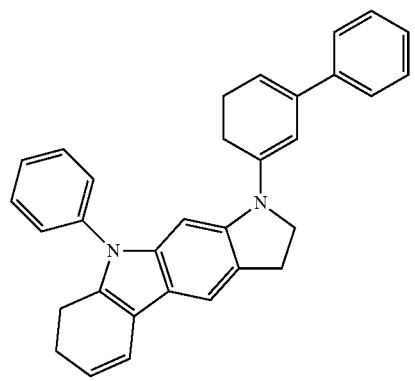
304
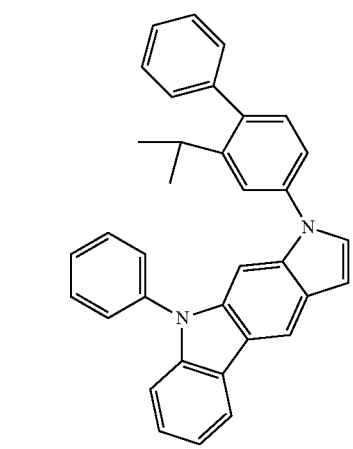
305
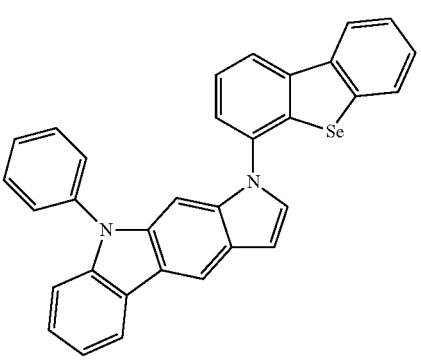
306
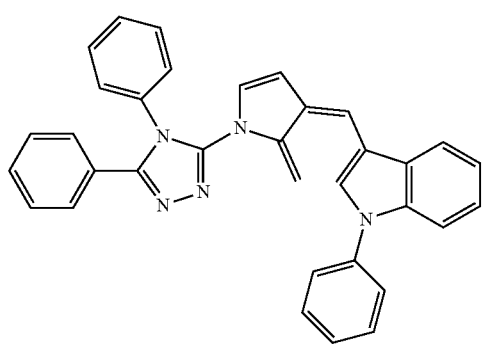
307
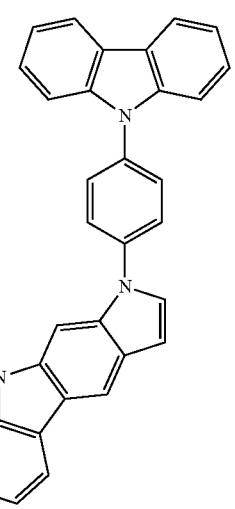
308
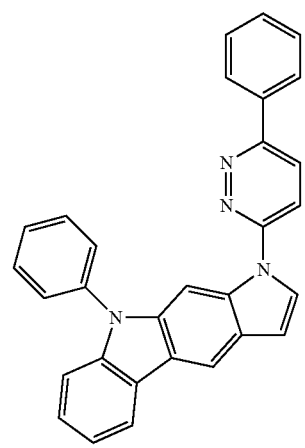
309
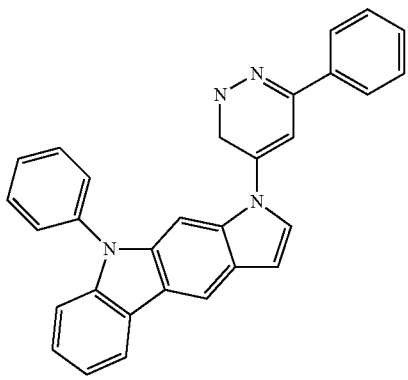

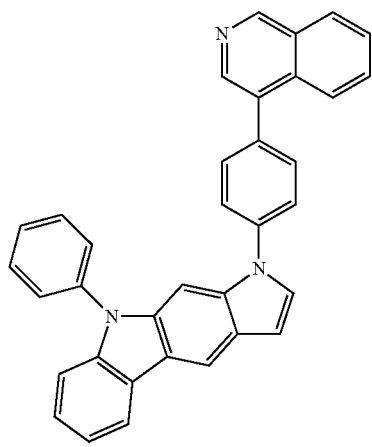
310
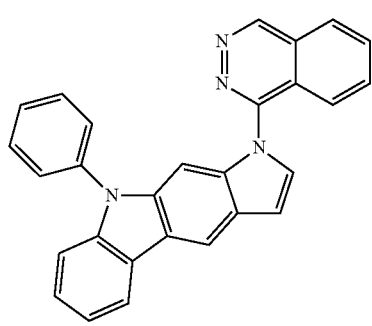
311
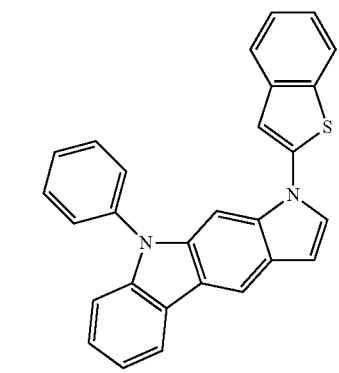
312
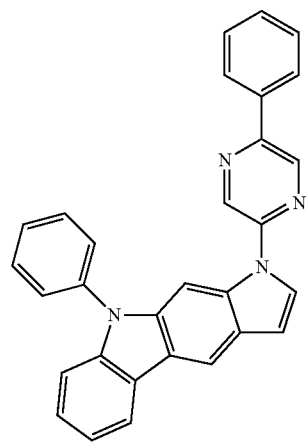
313
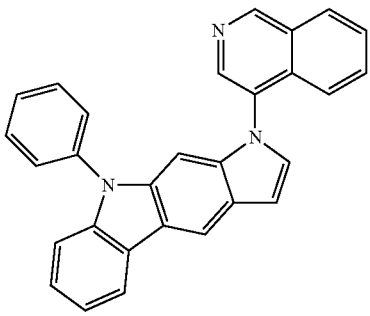
314
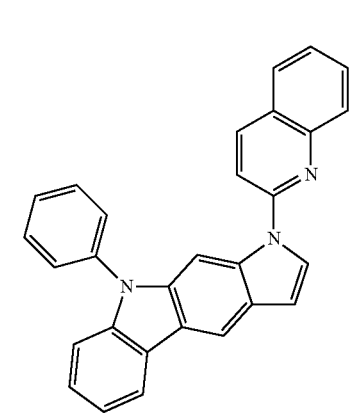
315
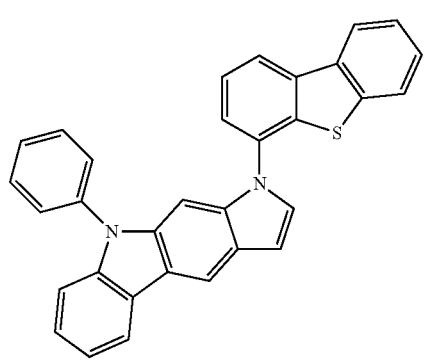
316
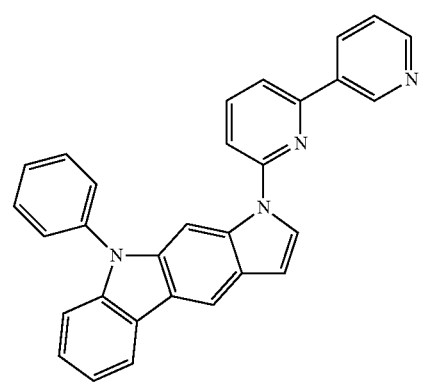
317

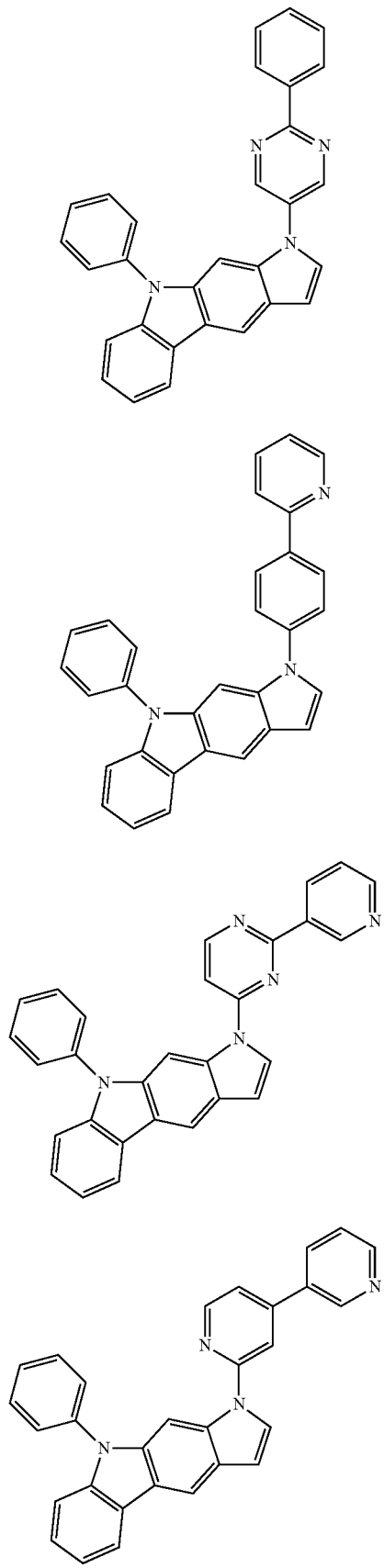
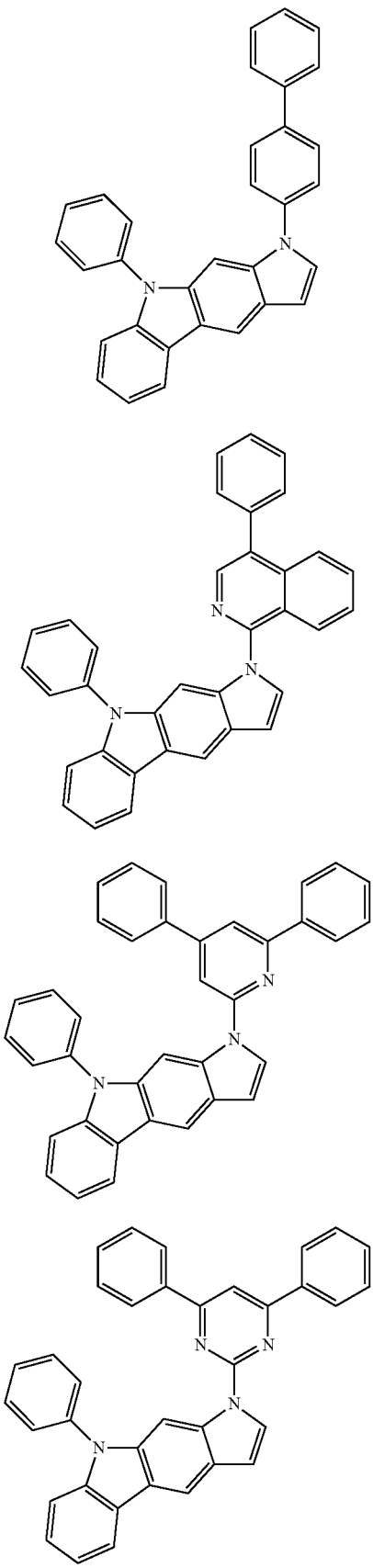

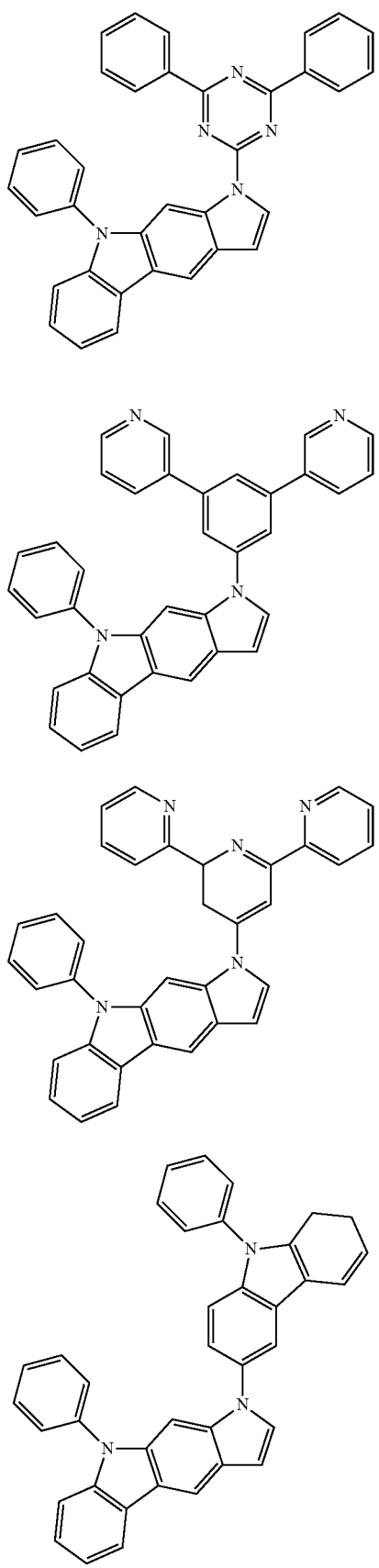
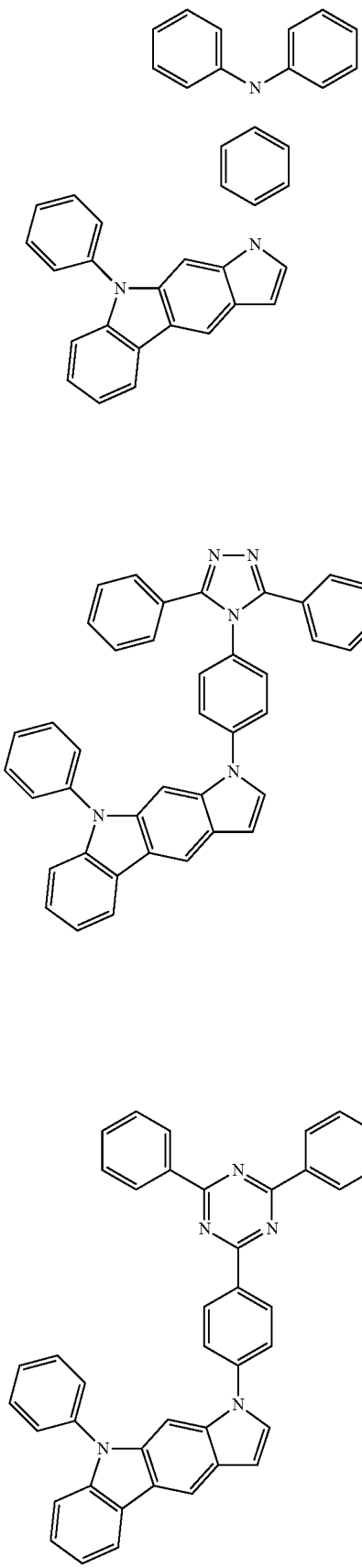

| 333 | 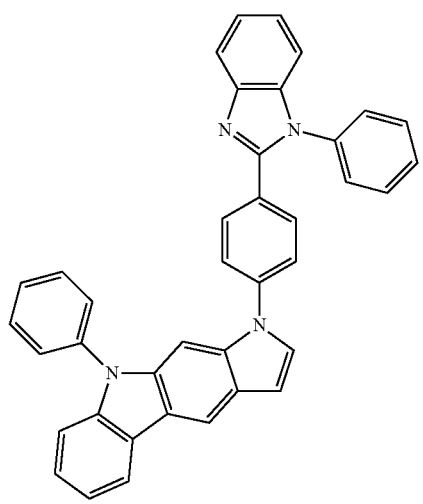 | 336 | 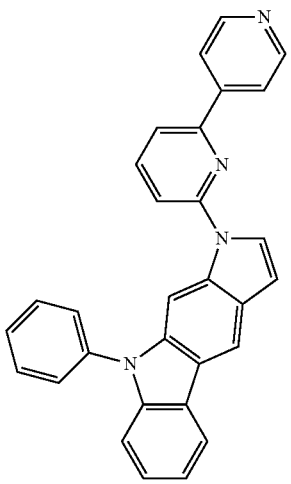 |
| 334 | 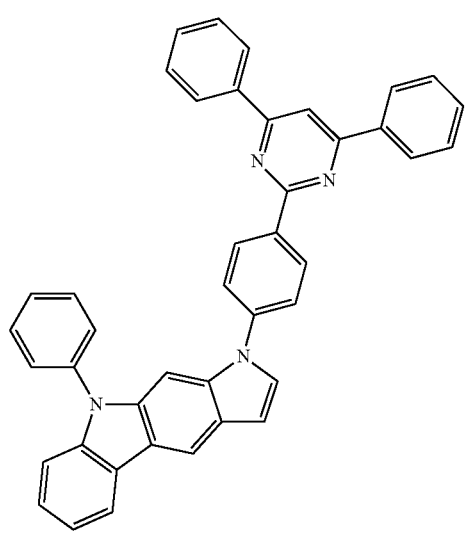 | 337 | 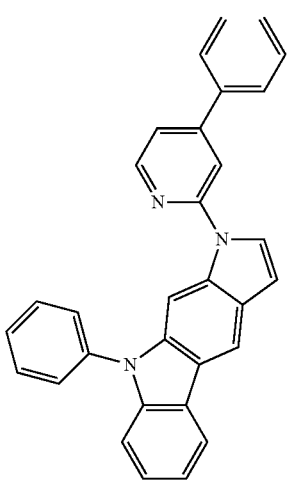 |
| 335 | 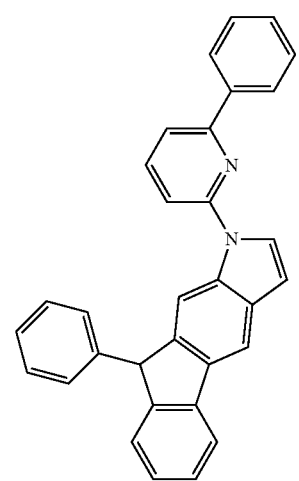 | 338 | 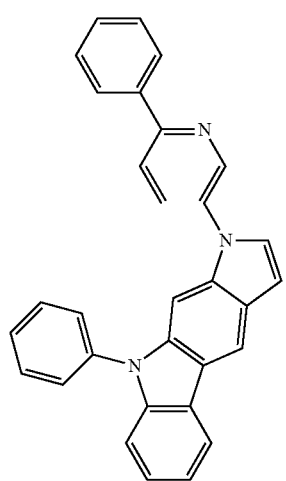 |

339
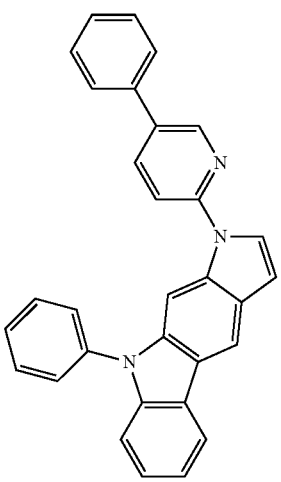
340
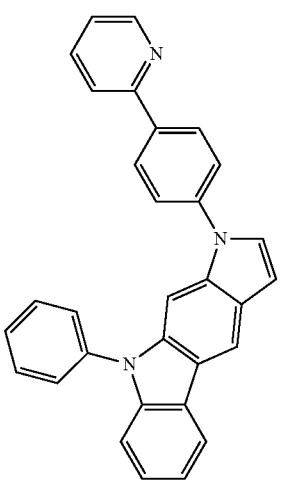
341
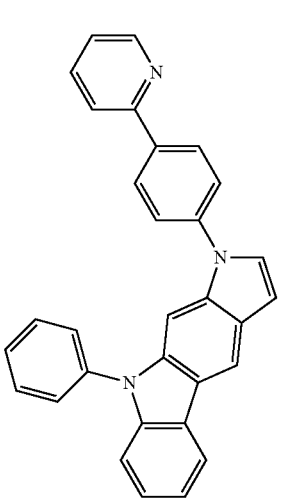
342
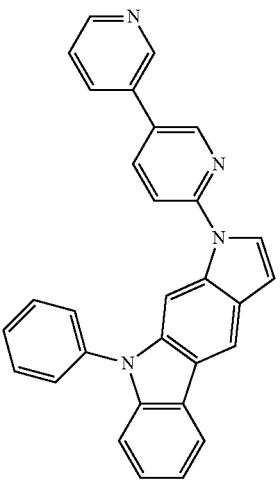
343
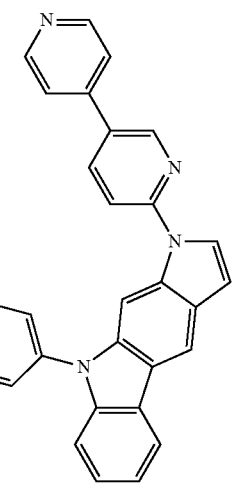
344
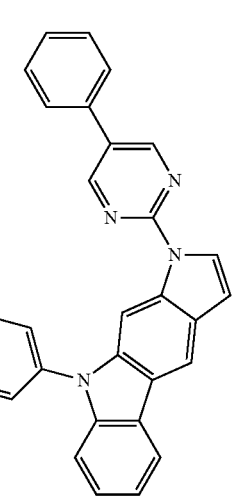

345
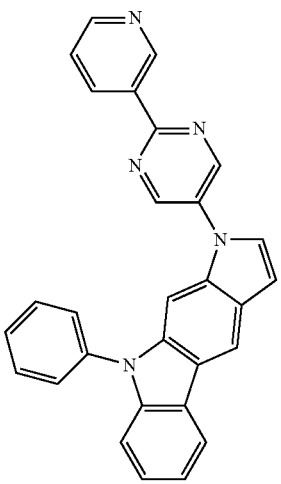
346
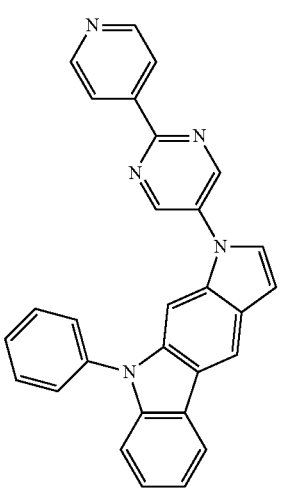
347
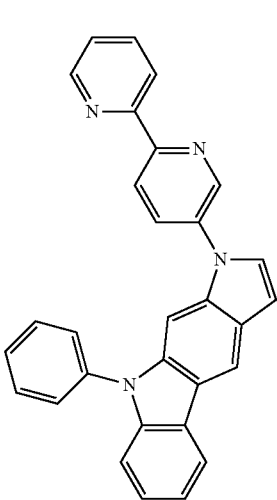
348
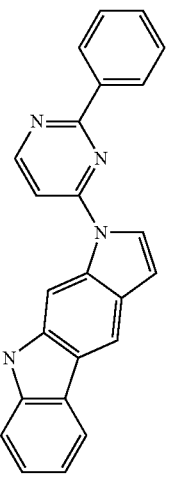
349
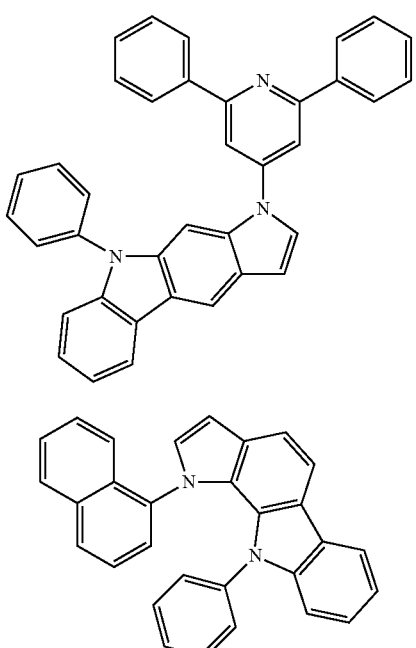
350
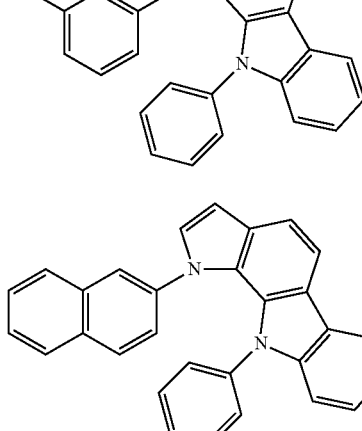
351
352
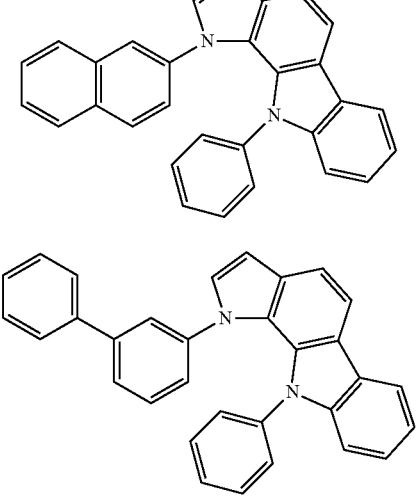

353
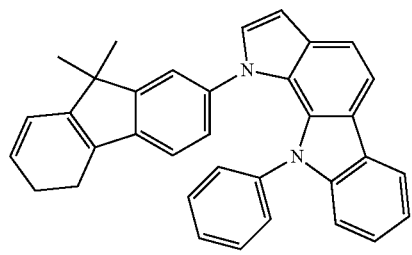
354
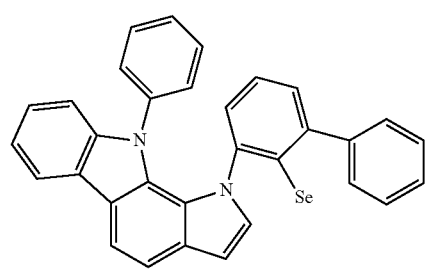
355
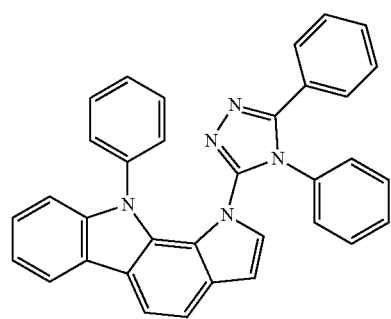
356
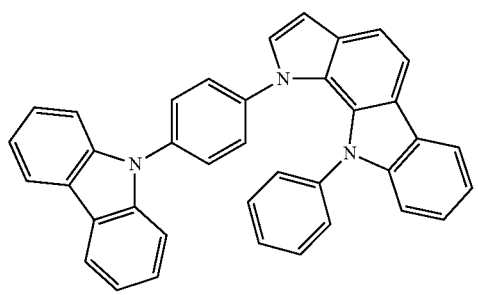
357
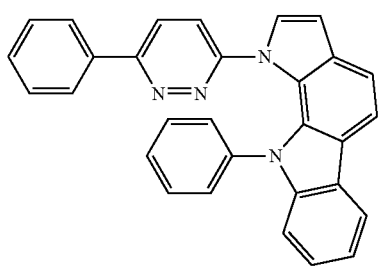
358
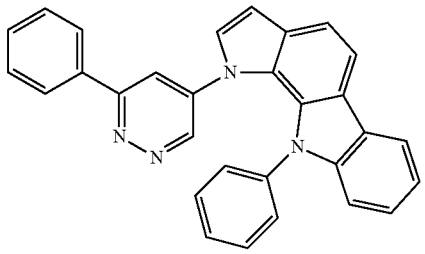
359
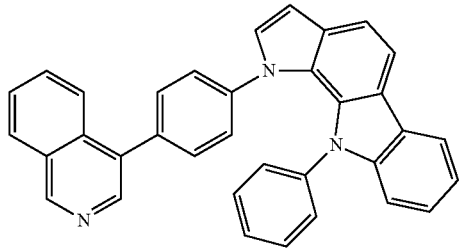
360
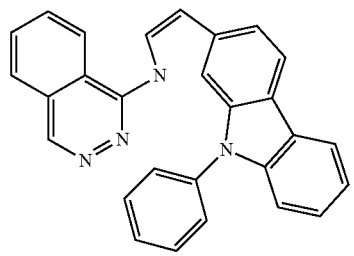
361
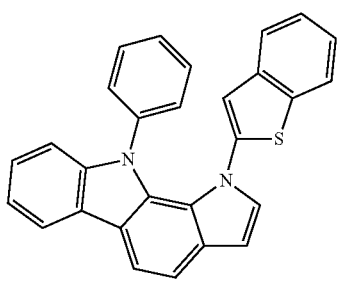
362
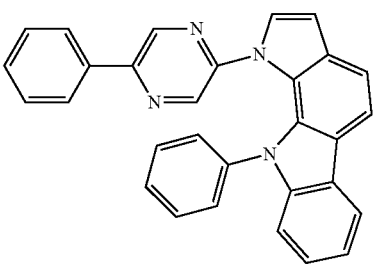
363
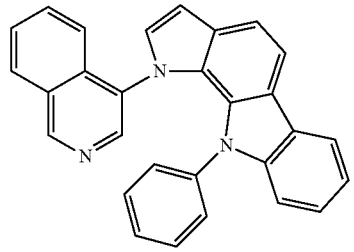

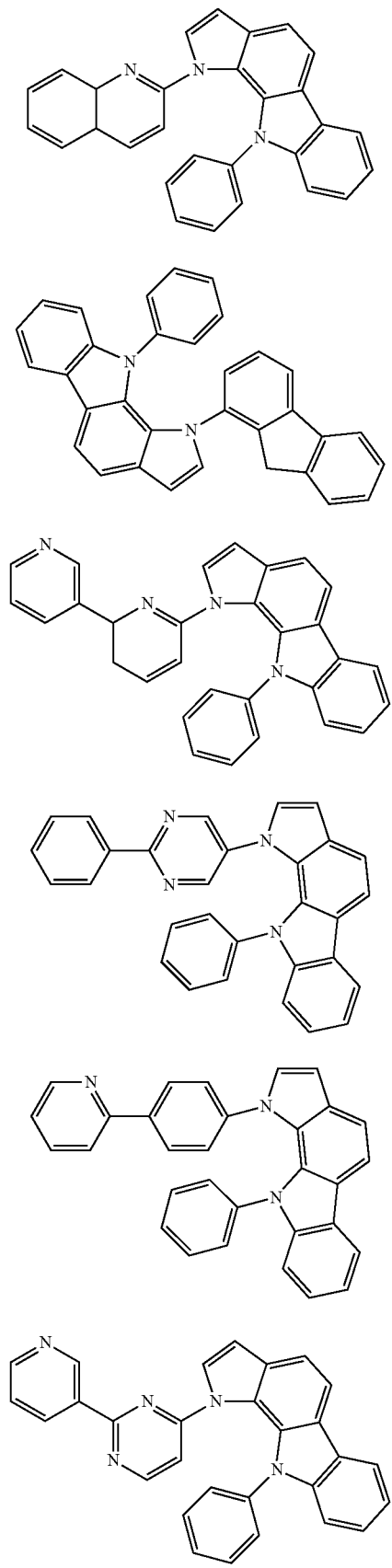
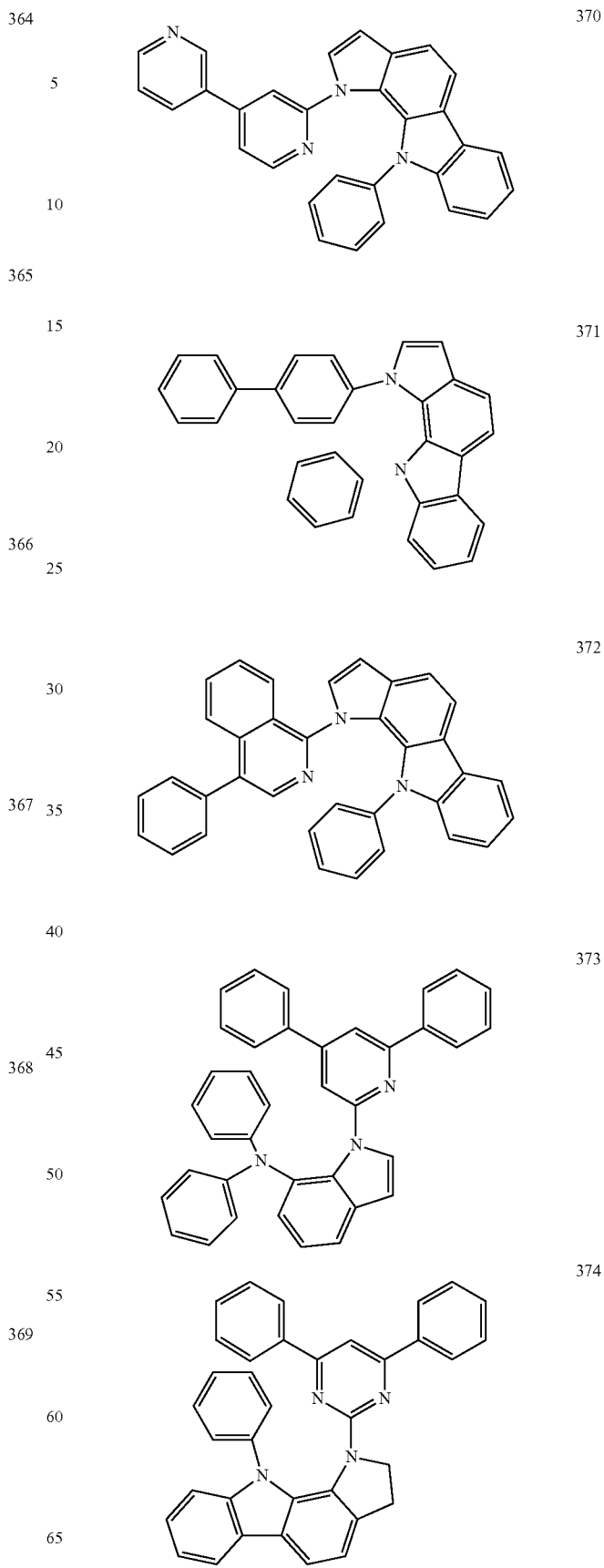

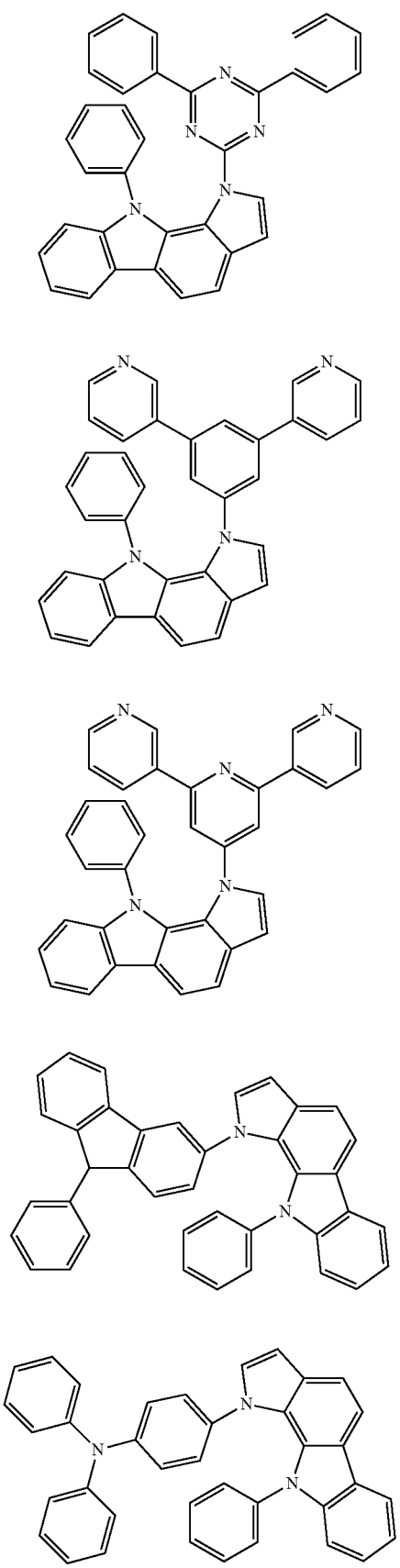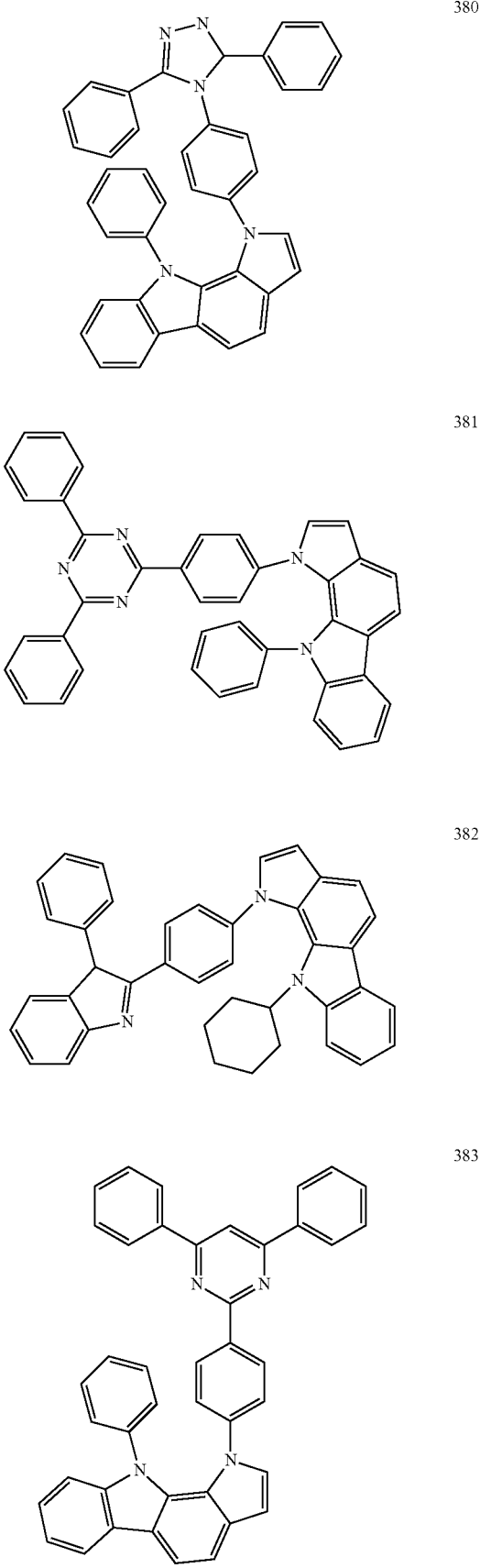

384
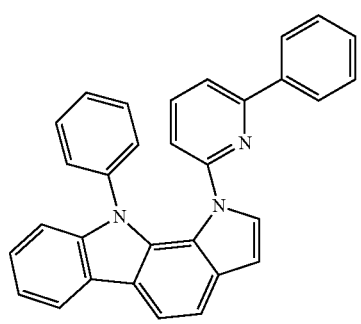
385
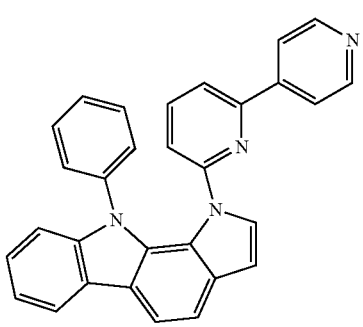
386
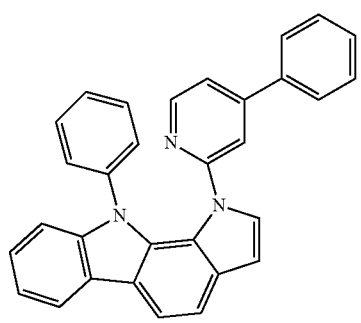
387
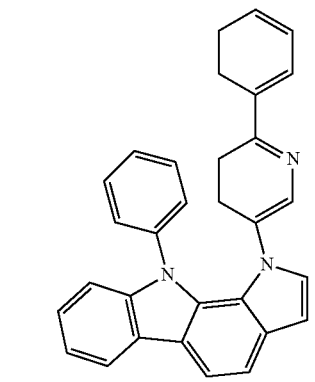
388
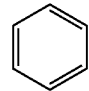
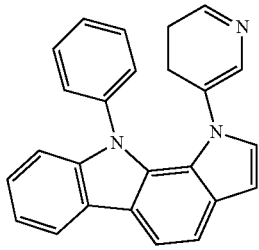
389
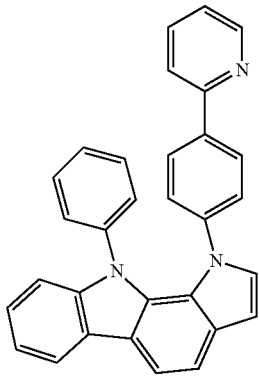
390
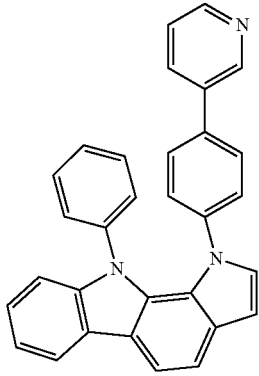
391
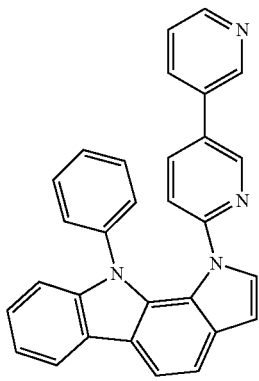

141
-continued
392
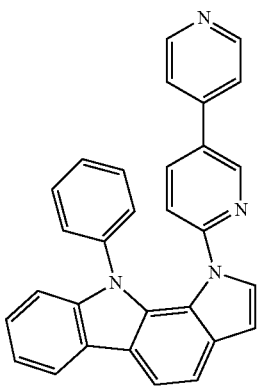
393
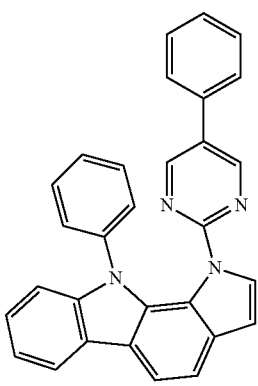
394

395

142
-continued
396
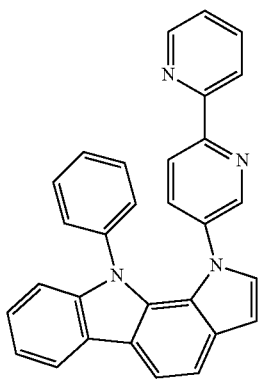
397
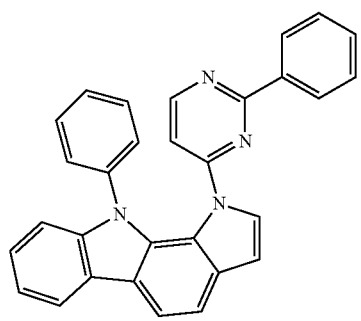
398
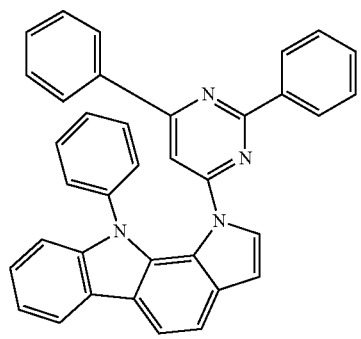
399
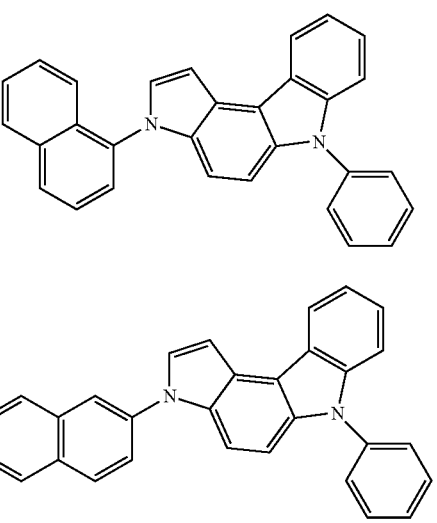
400
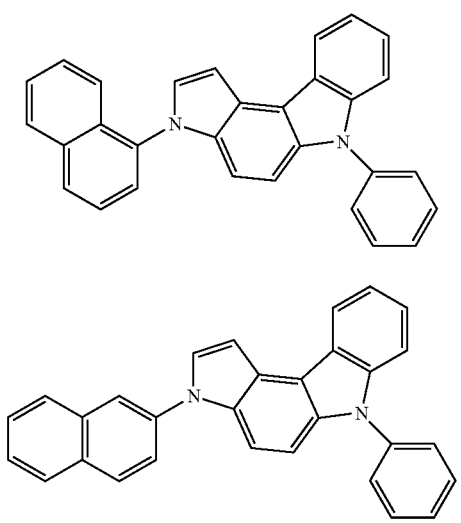

143
-continued
401
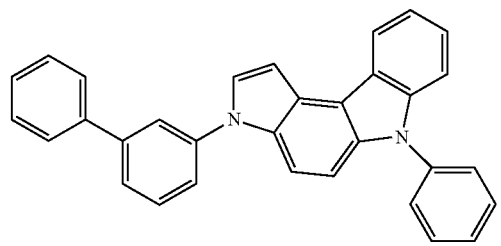
402
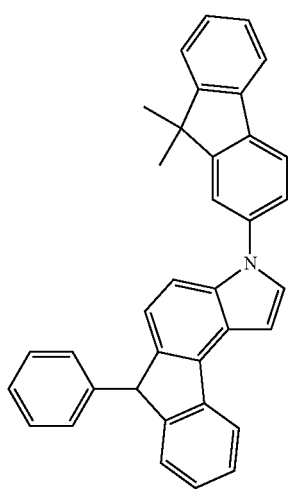
403
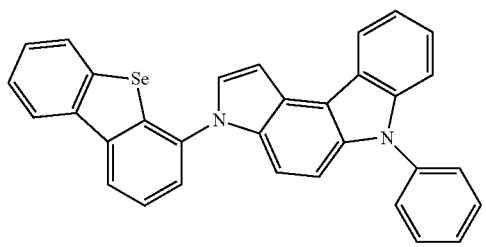
404
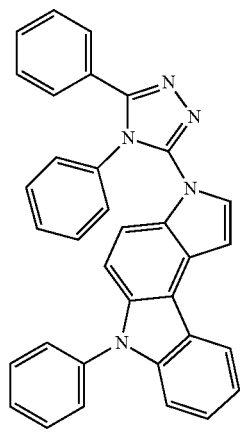
144
-continued
405
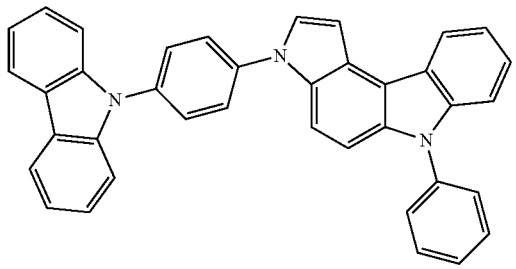
406
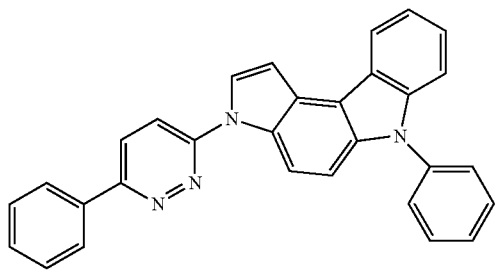
407
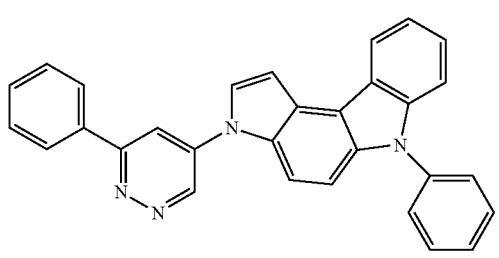
408
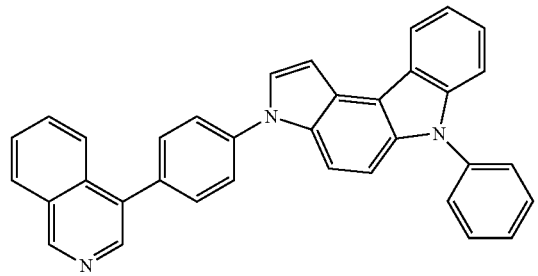
409
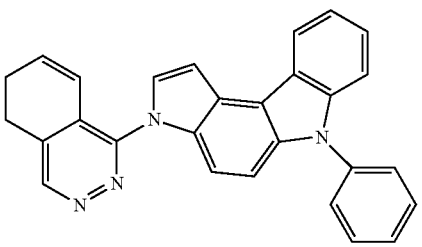
410
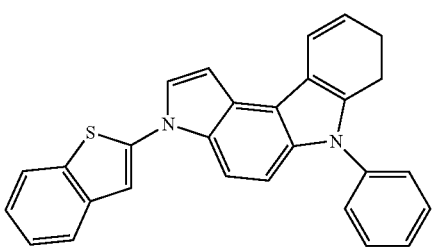

-continued
411
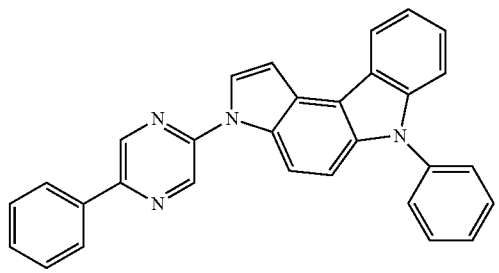
412
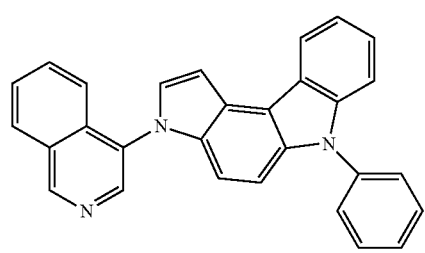
413
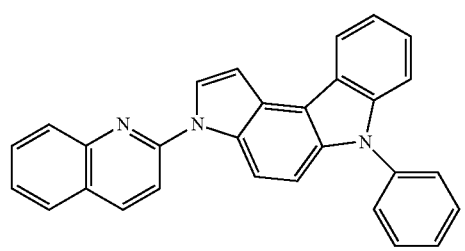
414
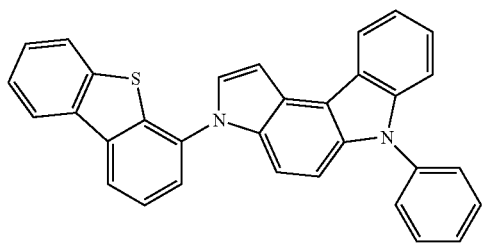
415
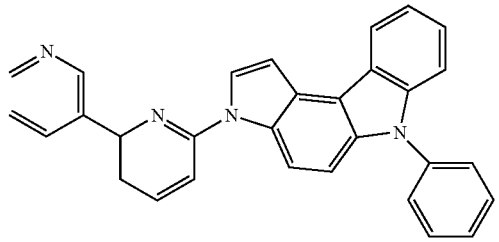
416
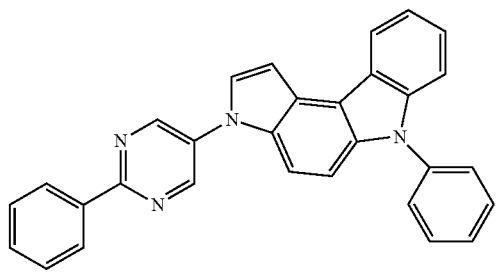
-continued
417
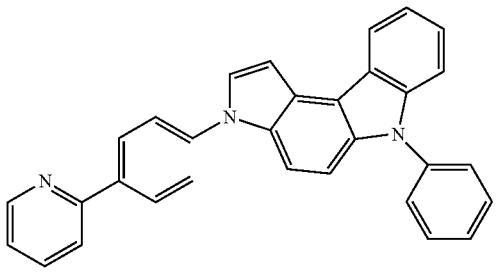
418
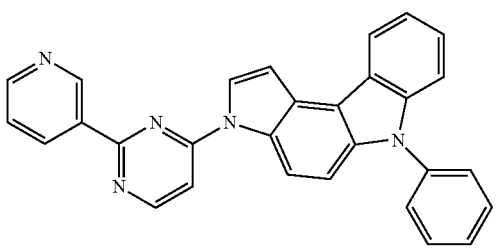
419
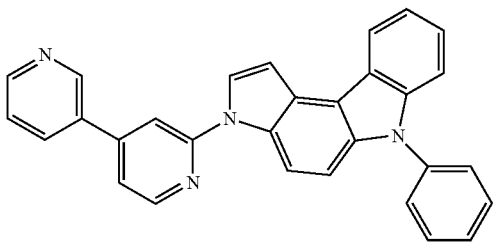
420
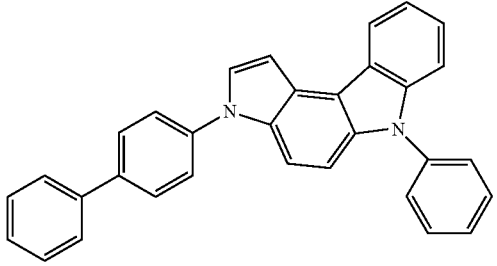
421
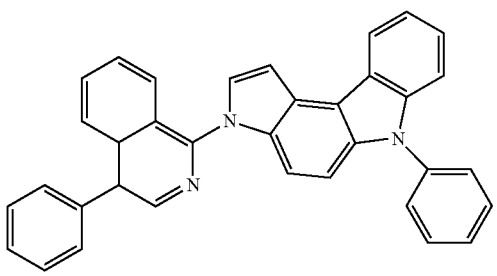

-continued
422
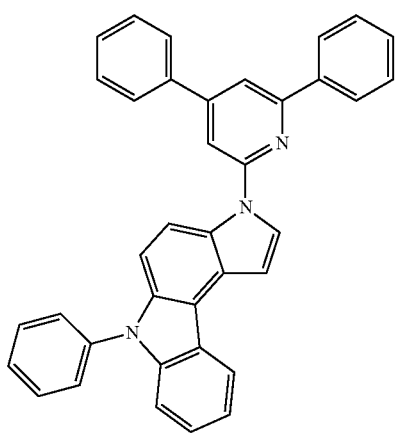
423
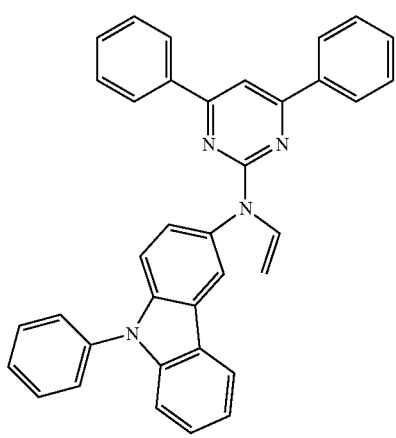
424
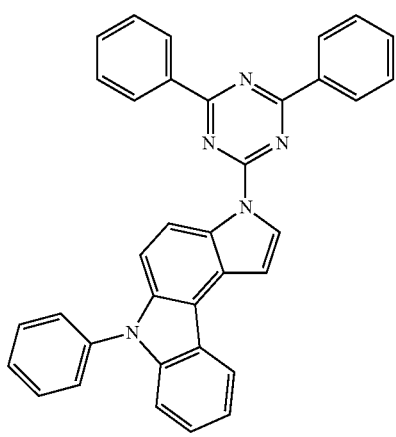
-continued
425
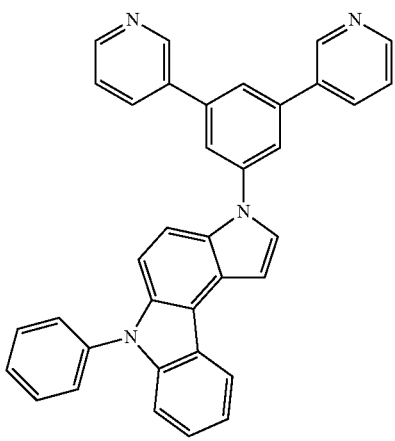
426
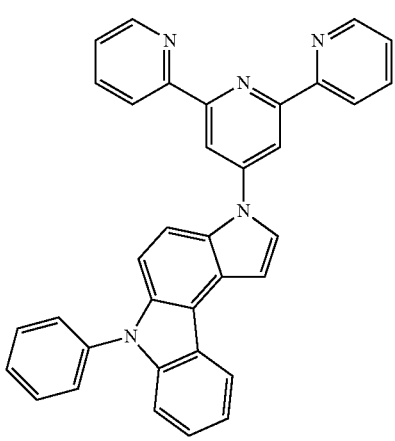
427
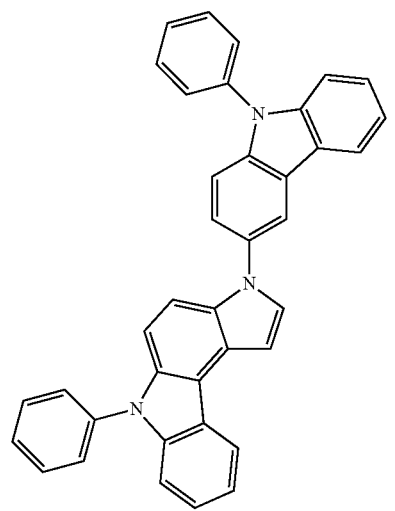

428
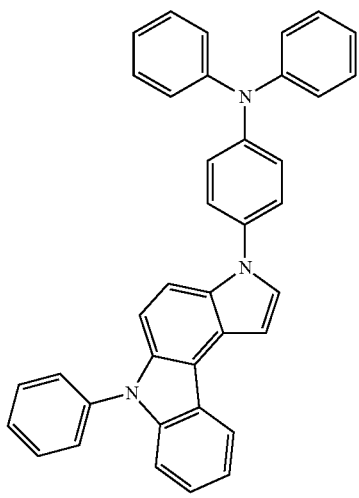
429
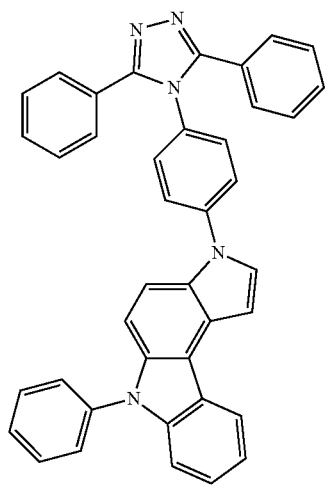
430
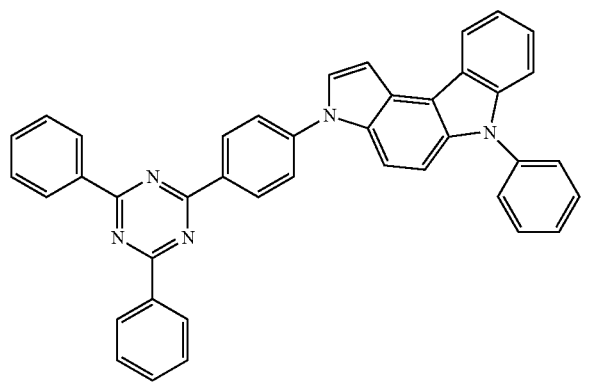
431
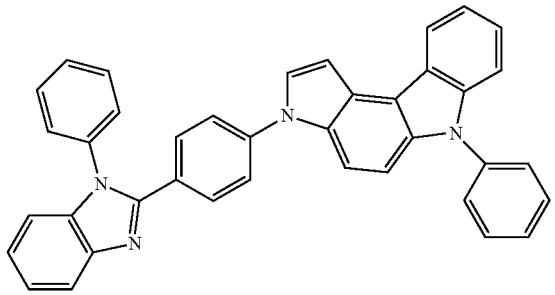
432
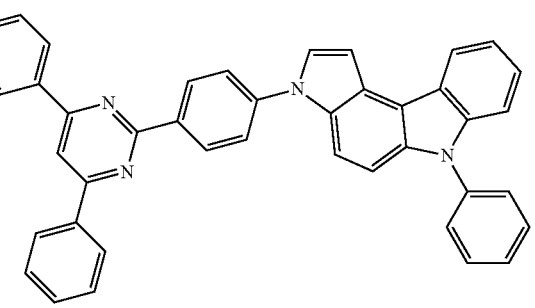
433
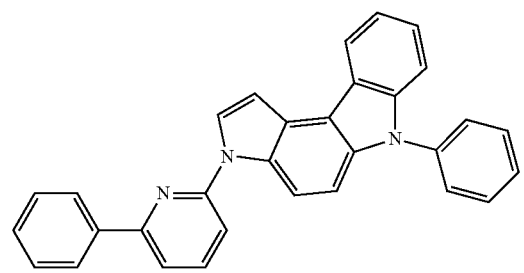
434
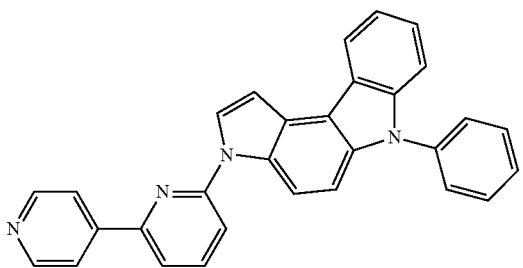
435
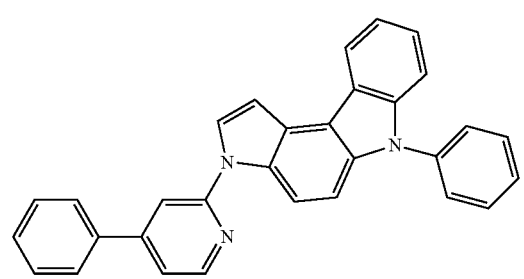

436 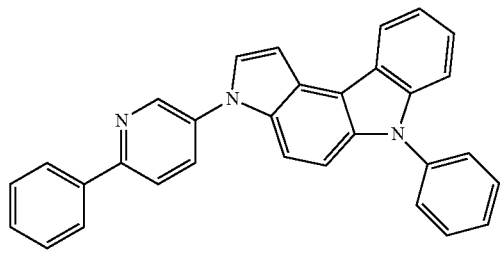
437 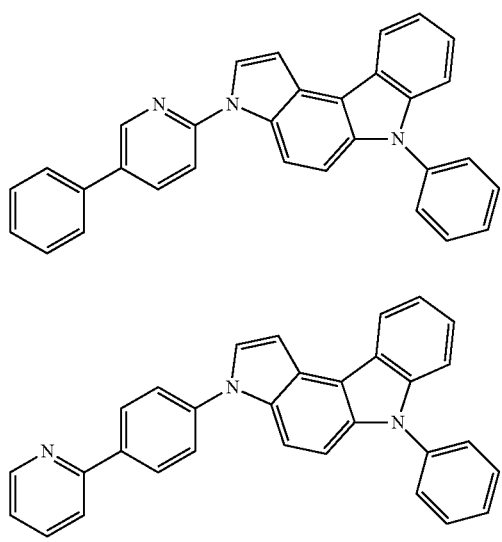
438
439
440
441 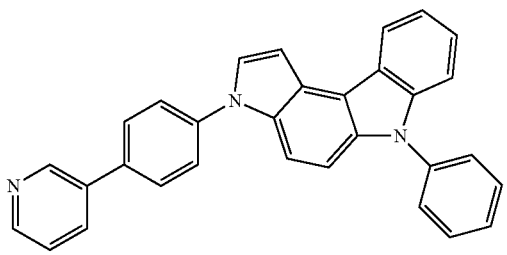
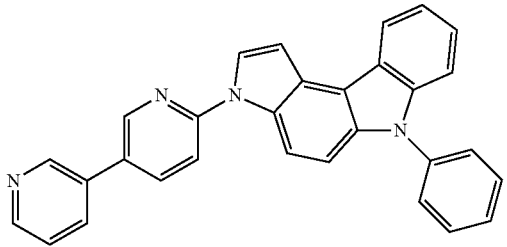
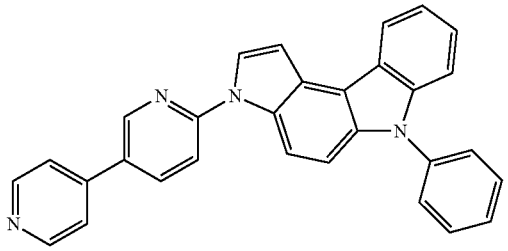
442 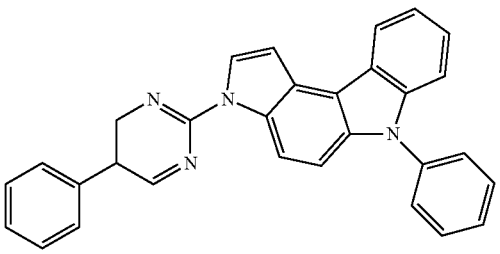
443 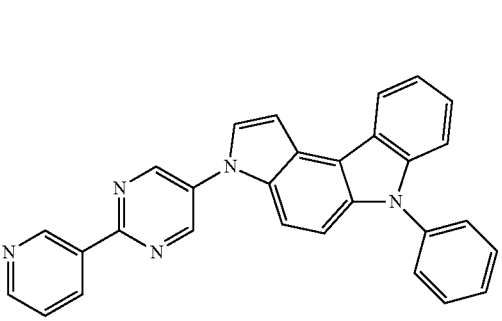
444
445 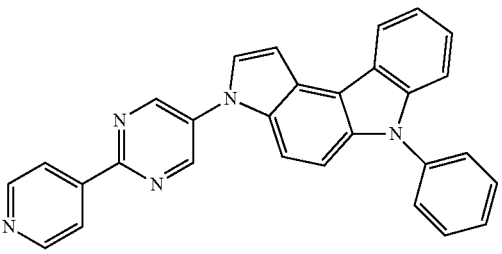
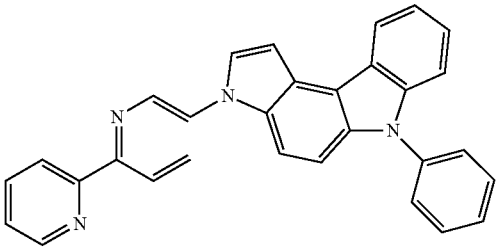
446 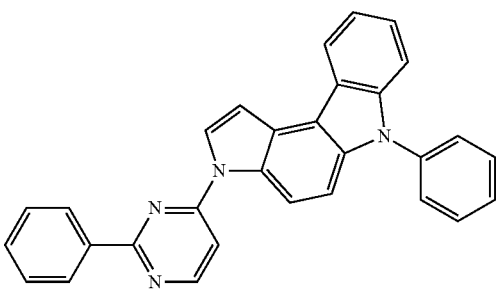

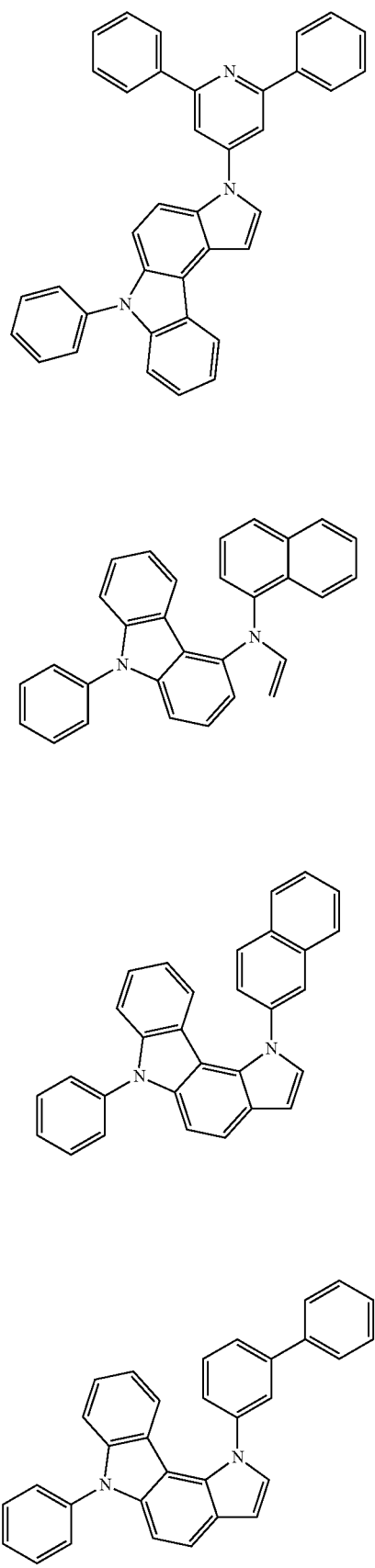
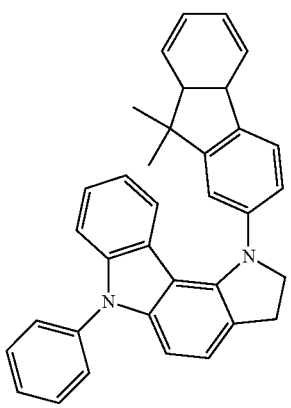
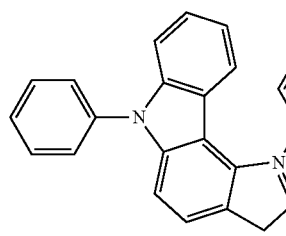
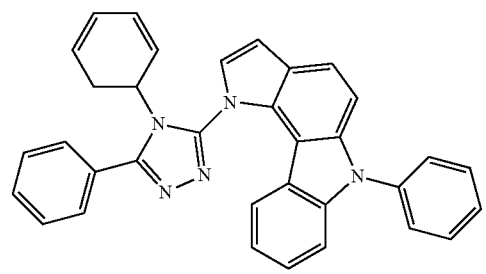
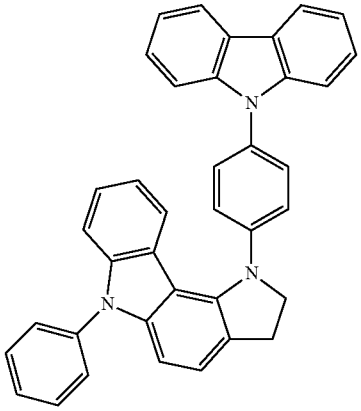
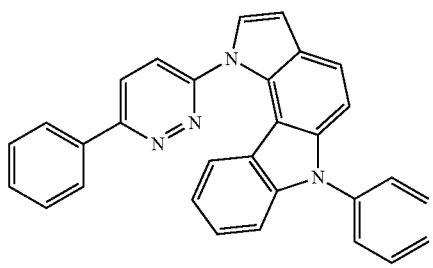

456 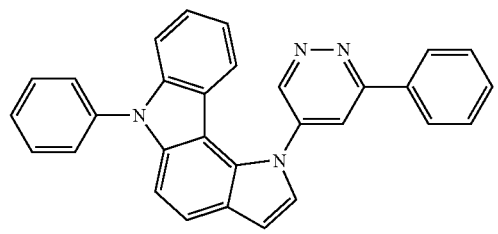
457 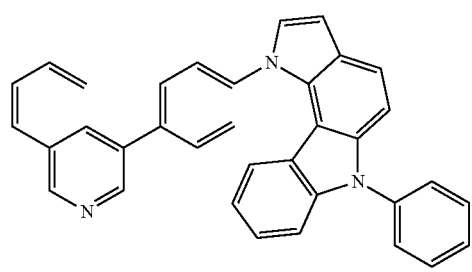
458 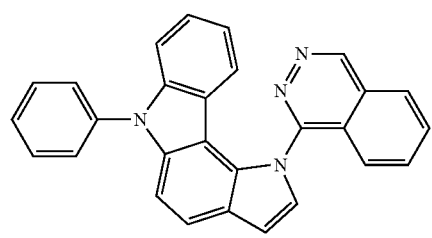
459 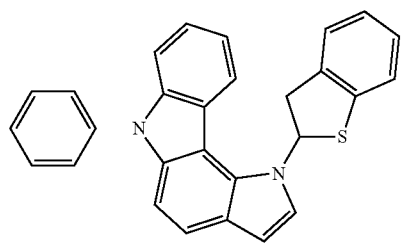
460 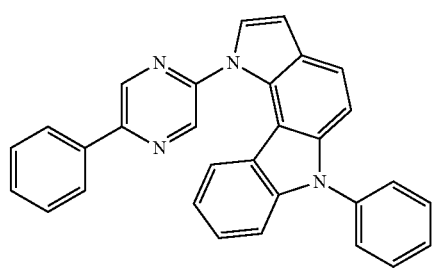
461 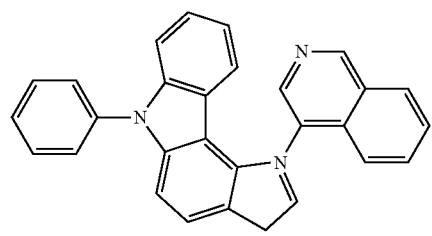
462 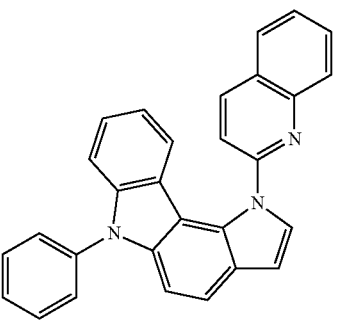
463 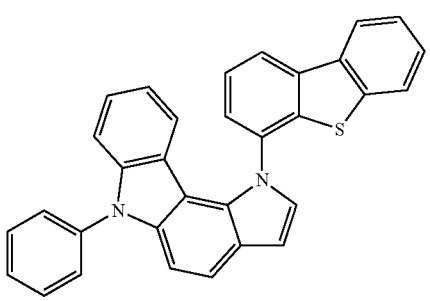
464 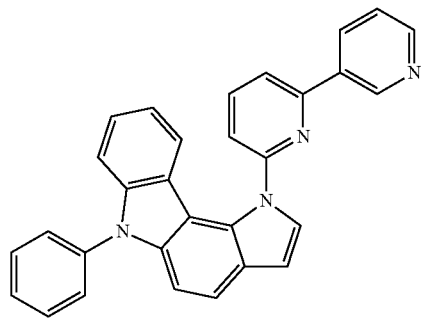
465 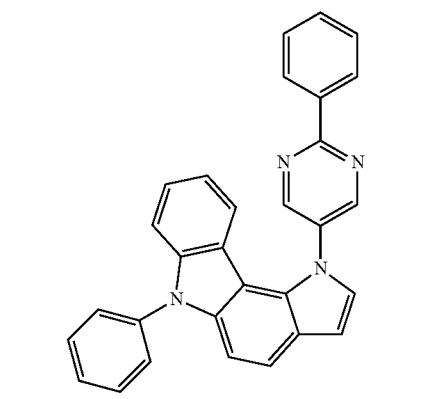

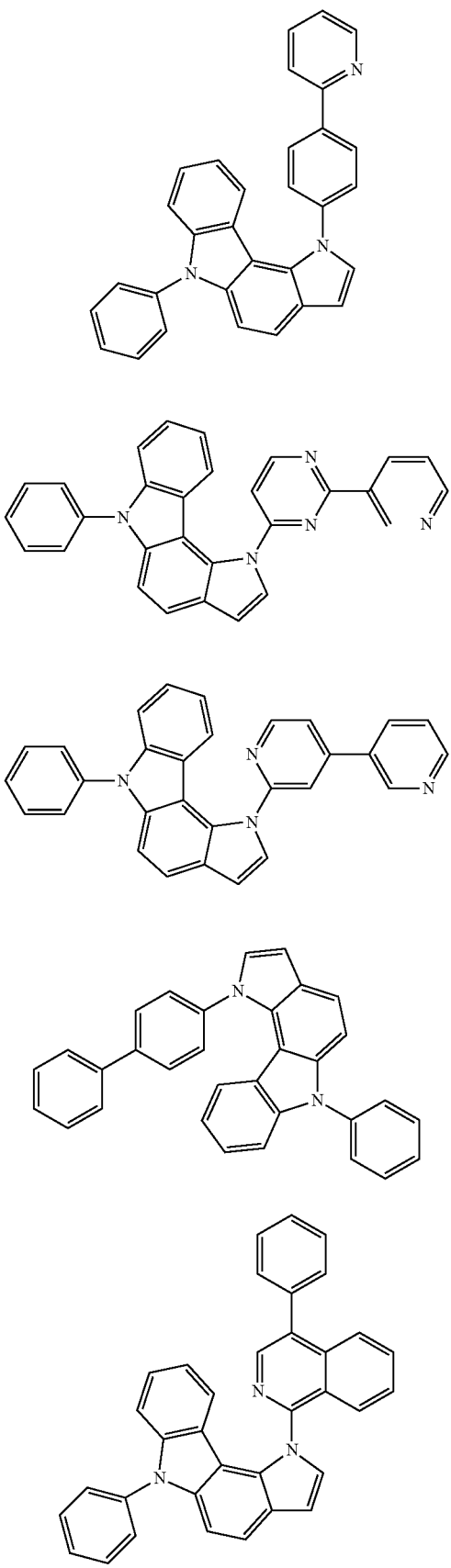
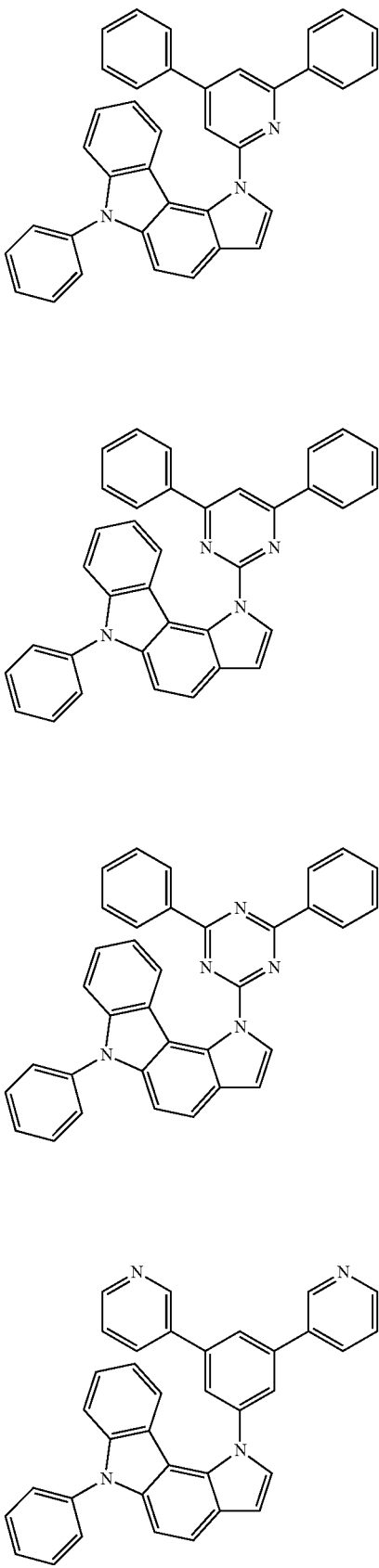

475 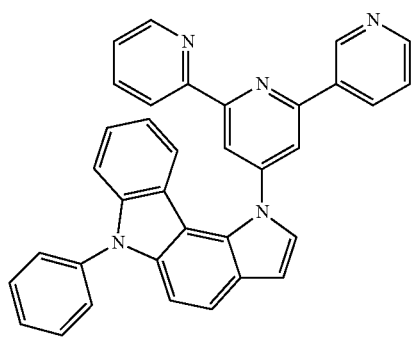
476 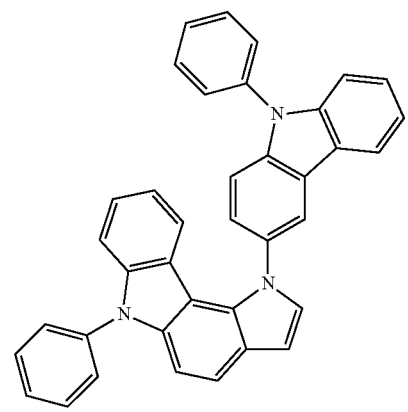
477 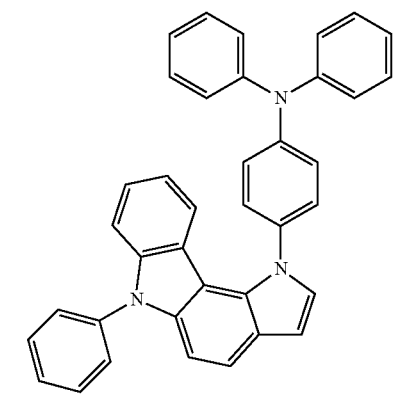
478 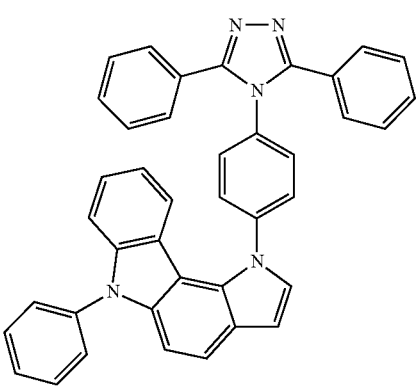
479 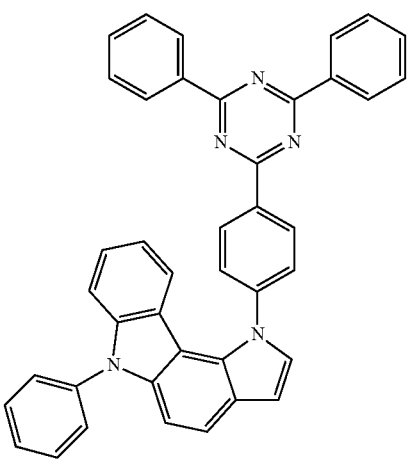
480 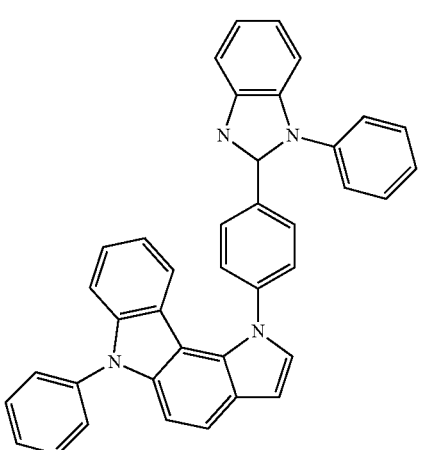
481 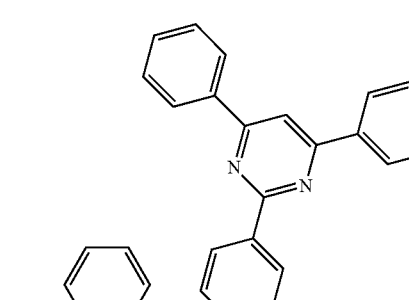
482 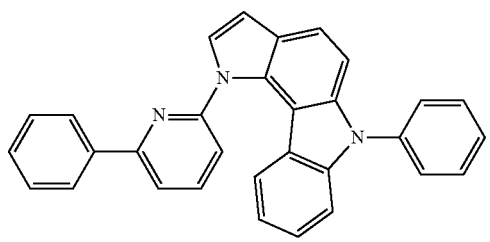

483
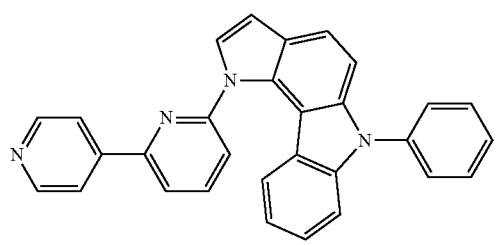
484
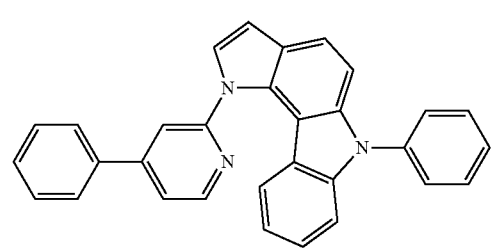
485
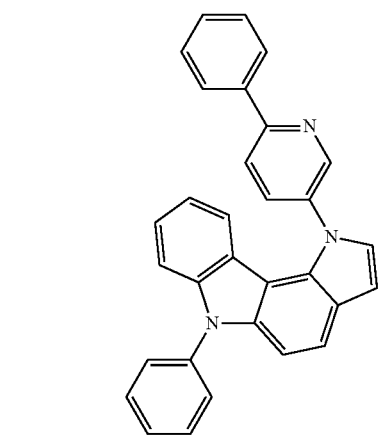
486
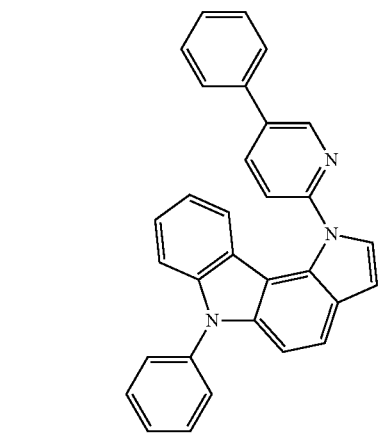
487
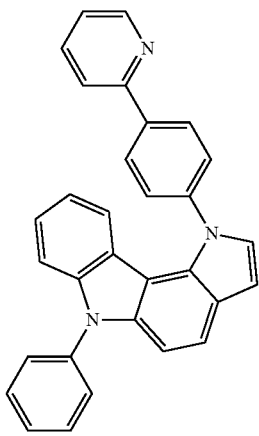
488
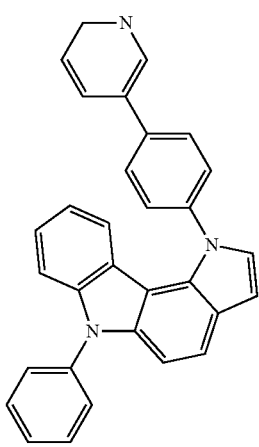
489

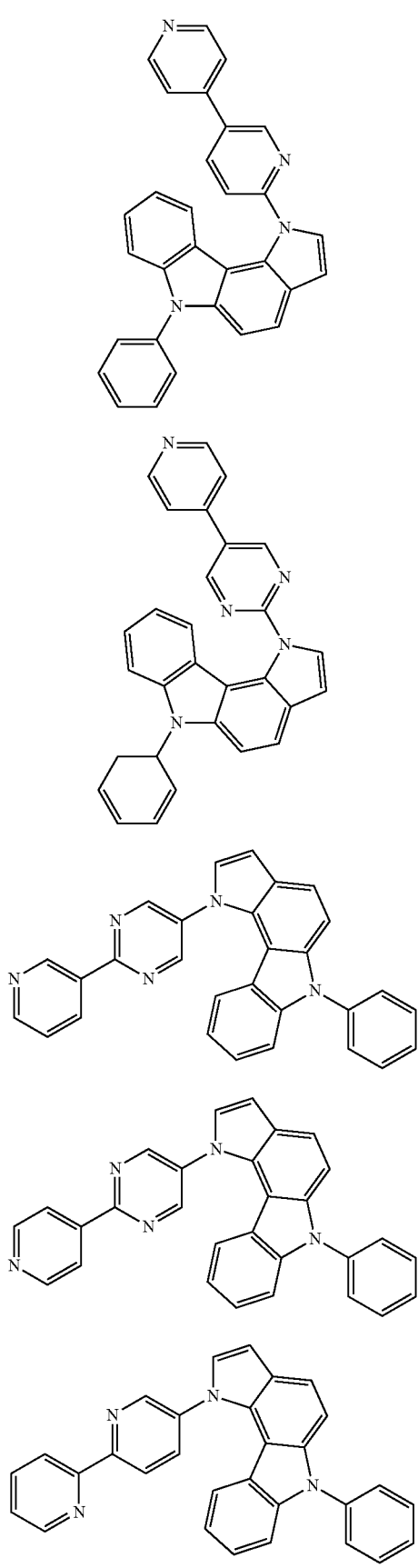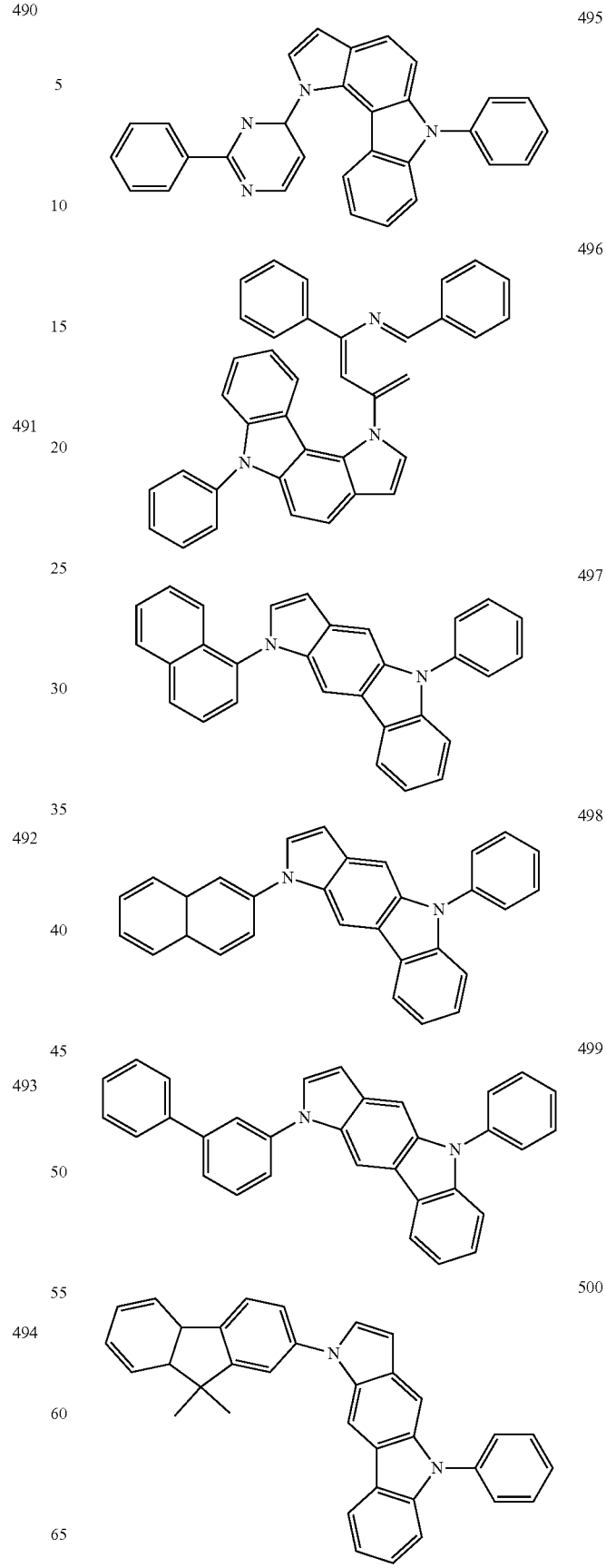

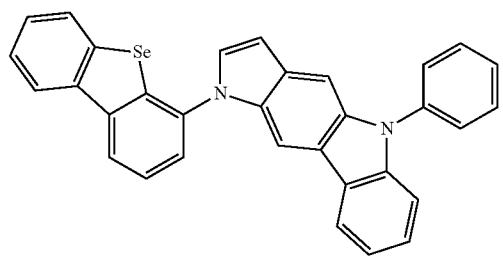
501
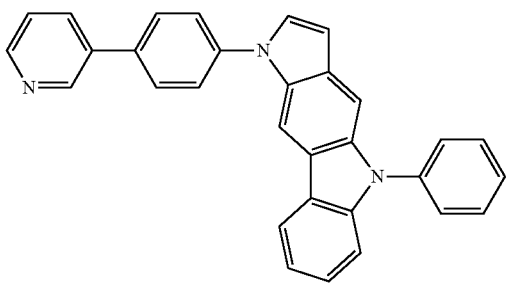
506
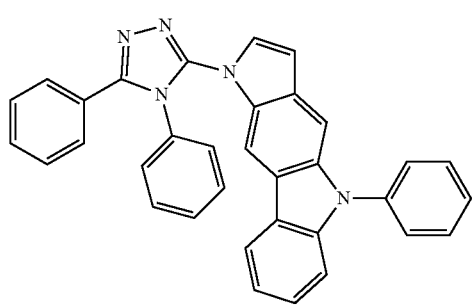
502
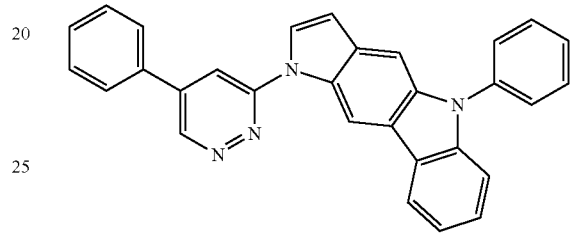
507
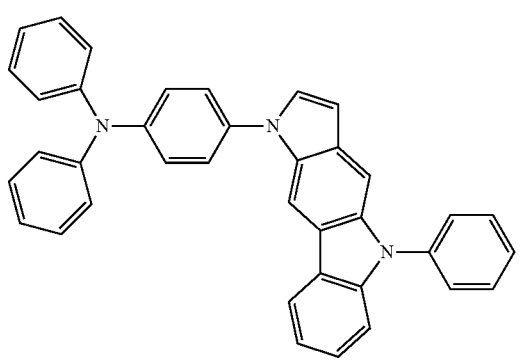
503
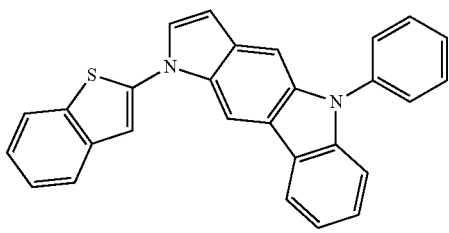
508
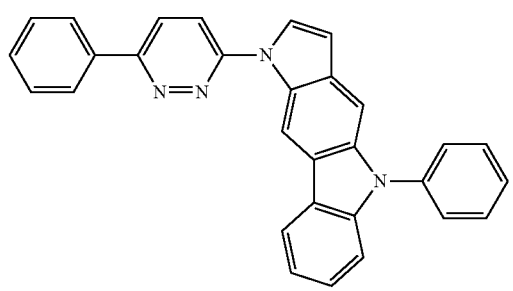
504
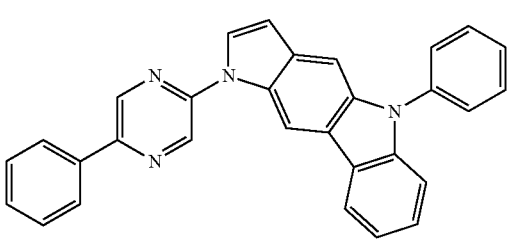
509
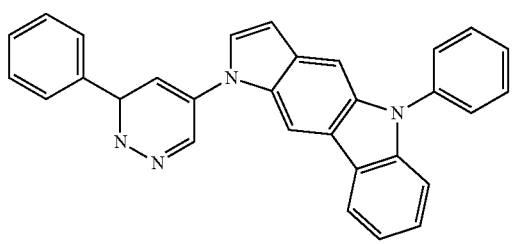
505
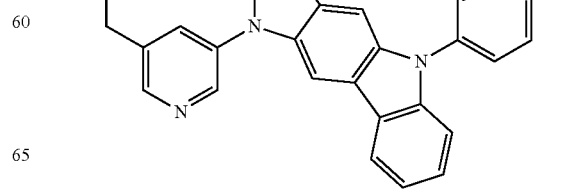
510

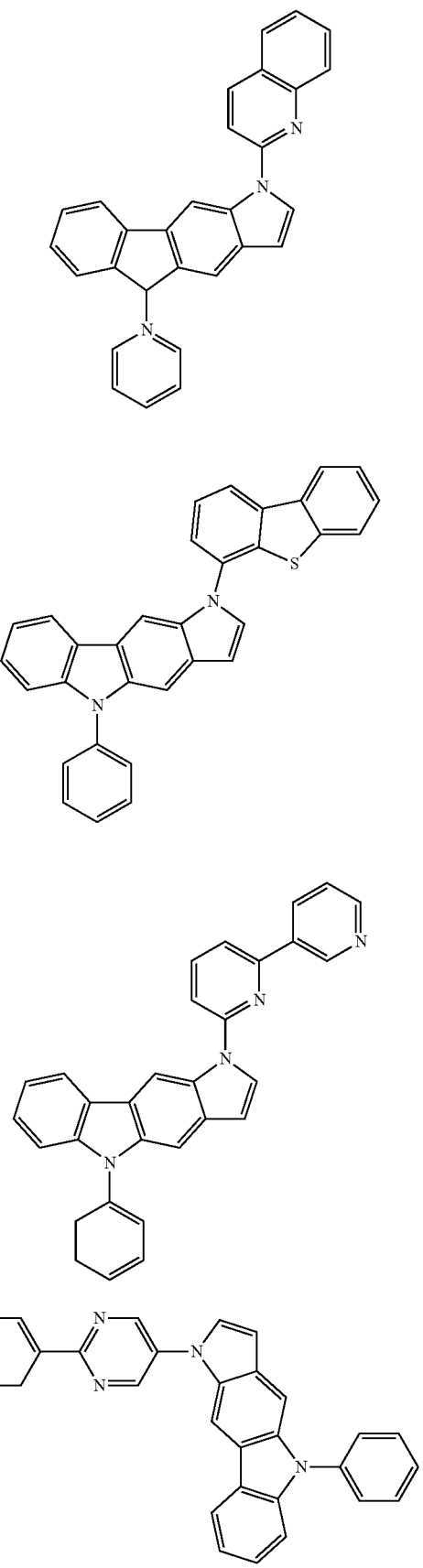
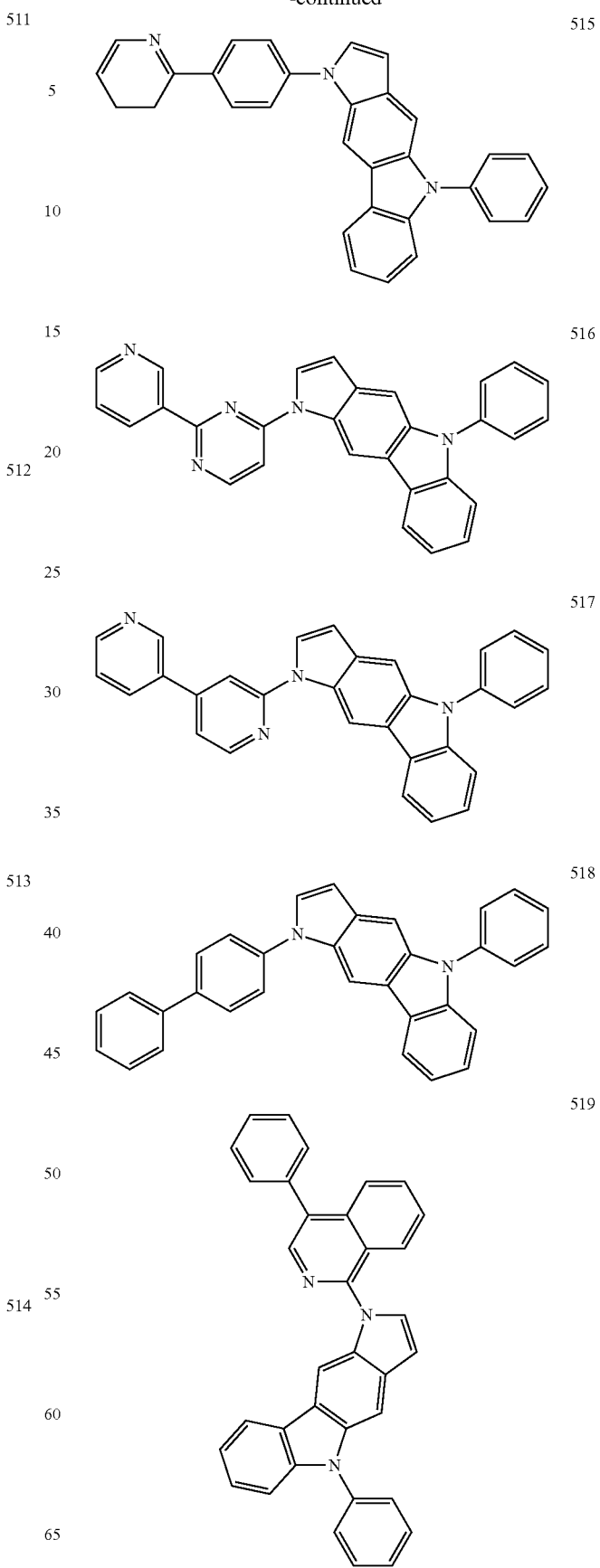

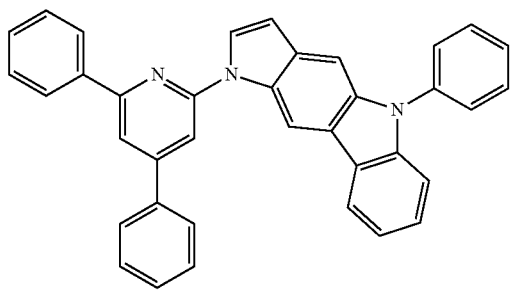
520
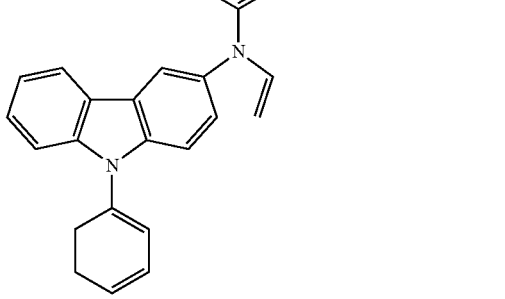
521
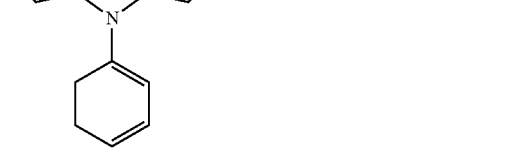
522
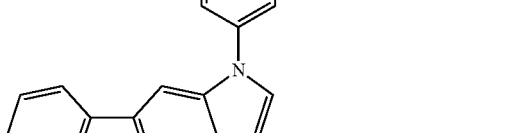
523
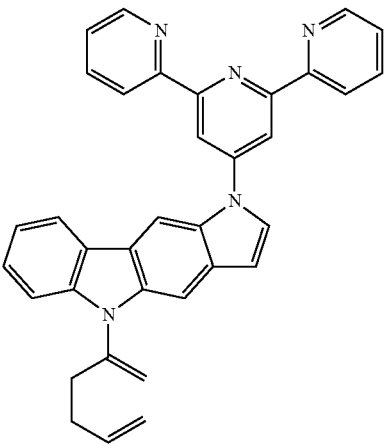
524
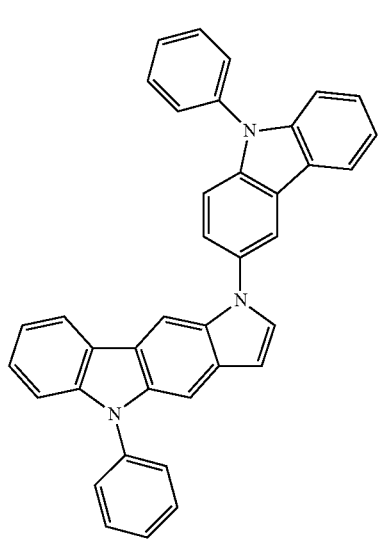
525
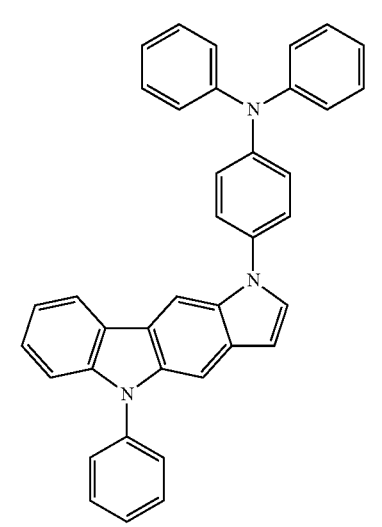
526

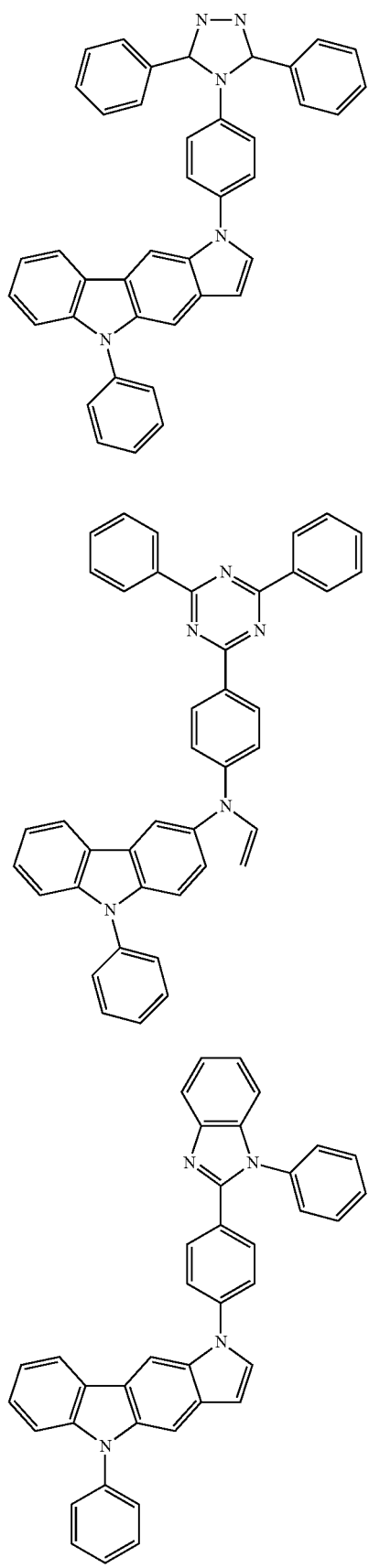
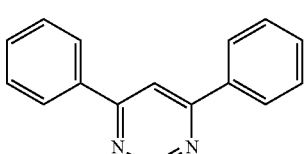
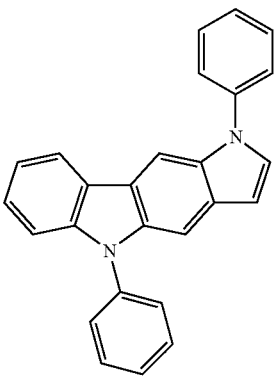
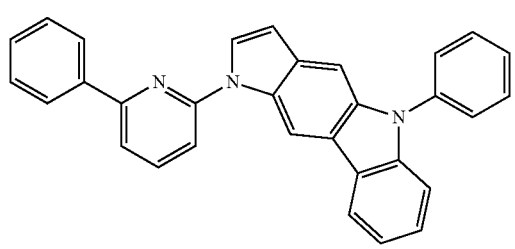
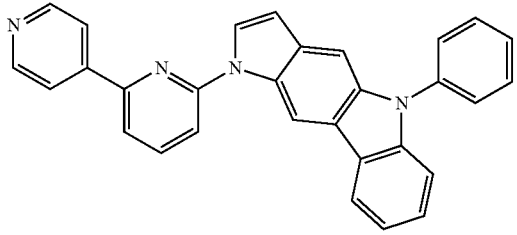
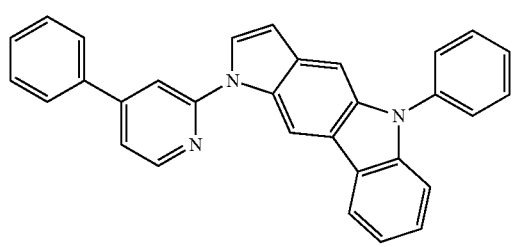
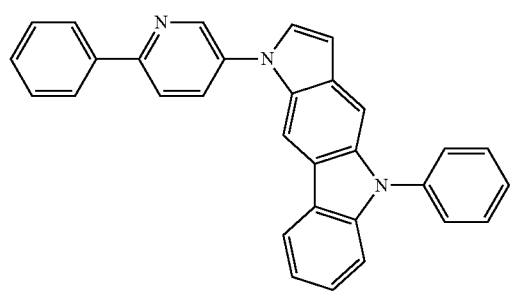

535
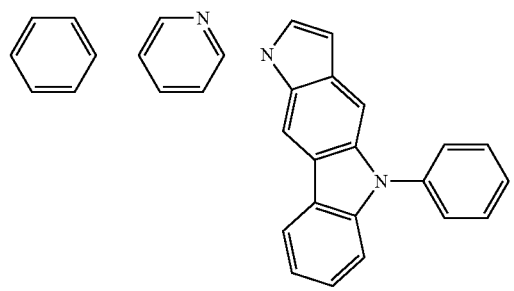
536
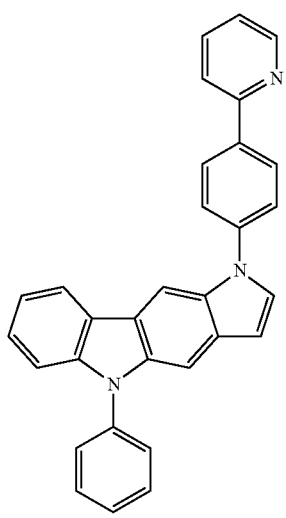
537
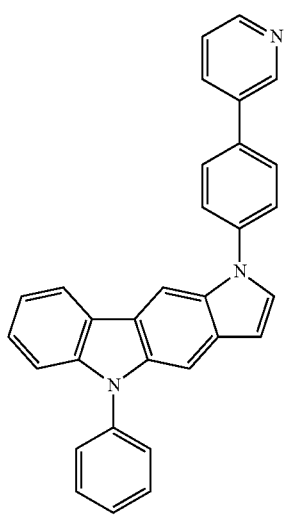
538
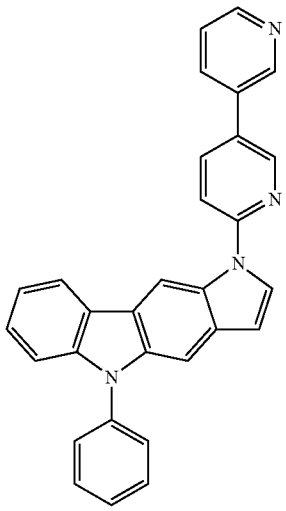
539
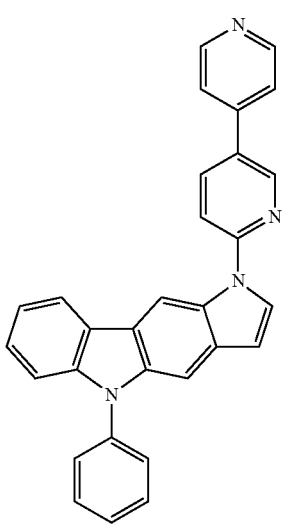
540
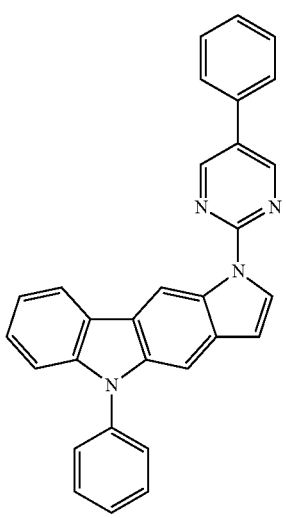

541 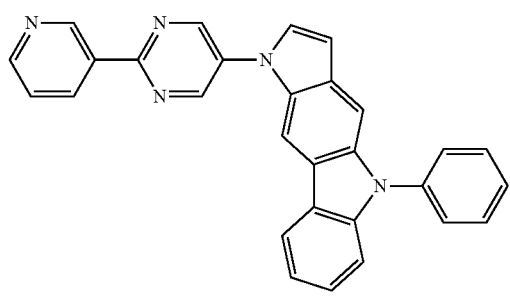
542 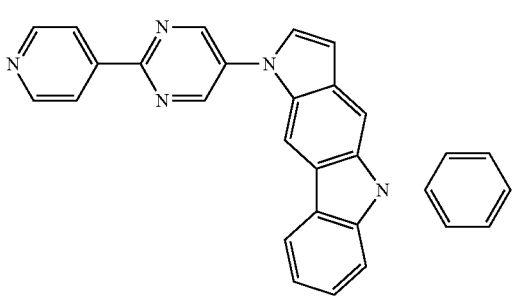
543 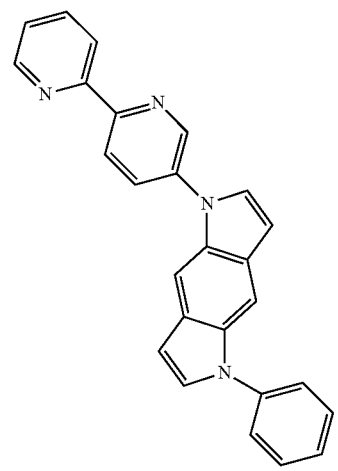
544 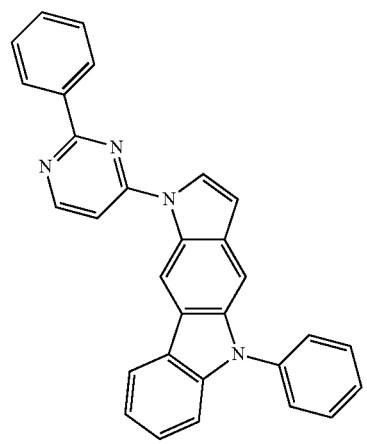
545 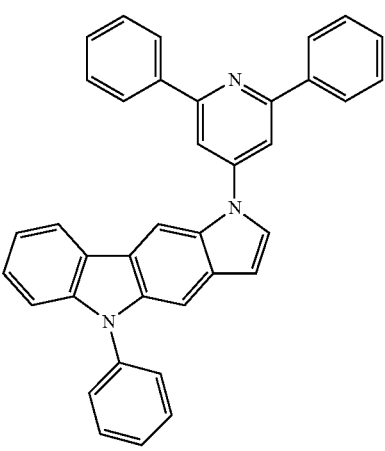
546 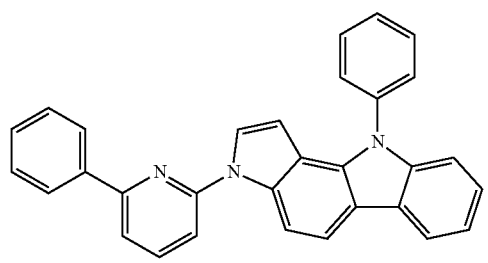
547 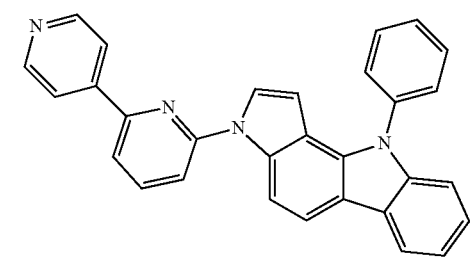
548 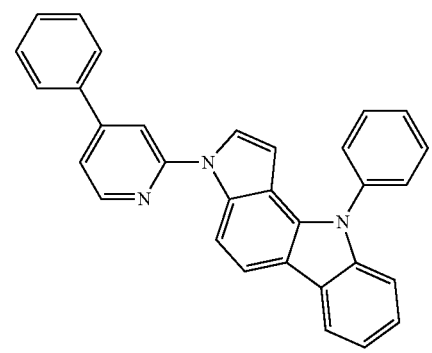

| 549 | 553 |
|---|---|
| 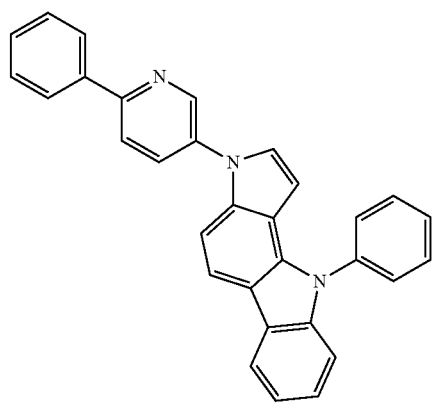 | 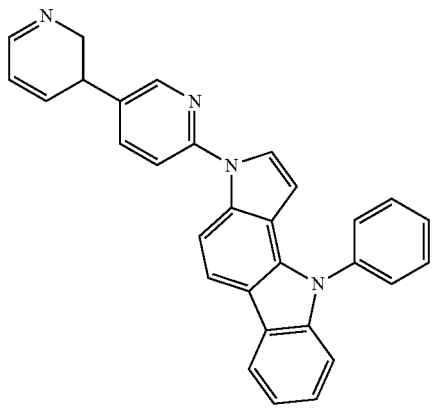 |
| 550 | 554 |
| 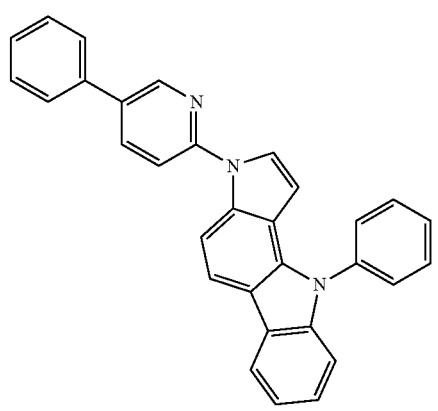 | 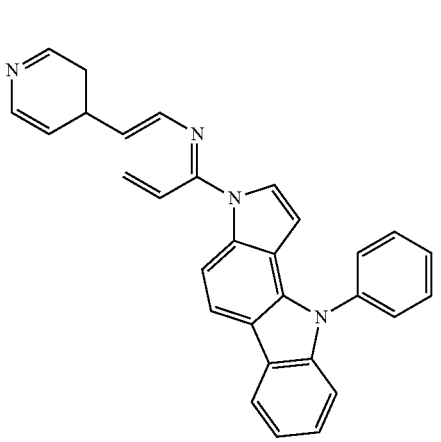 |
| 551 | 555 |
| 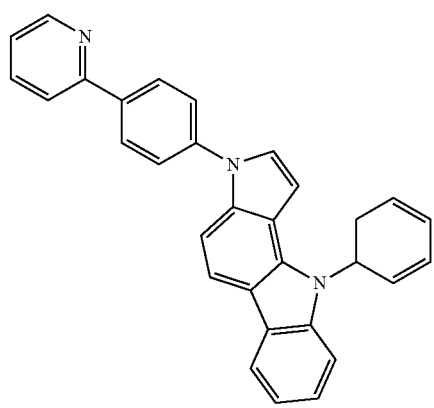 | 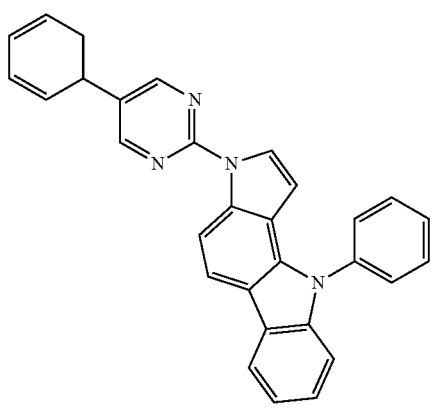 |
| 552 | 556 |
| 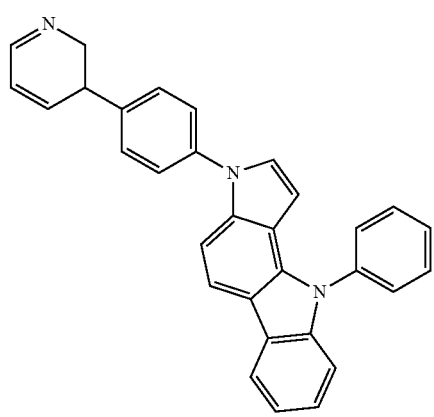 | 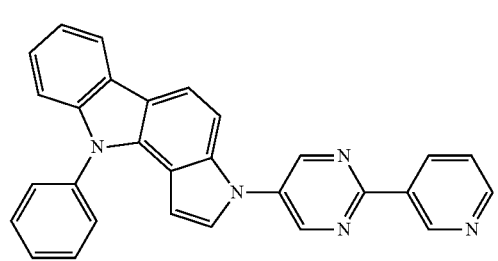 |

179
-continued
557
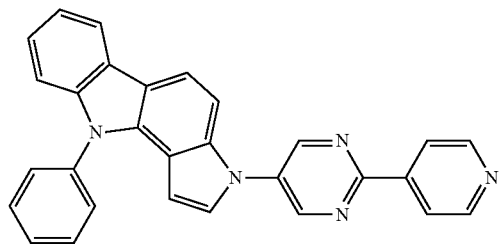
558
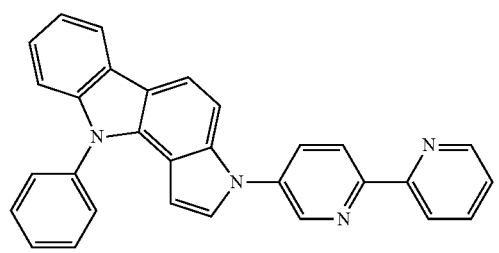
559
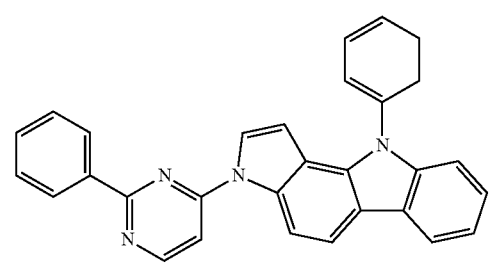
600
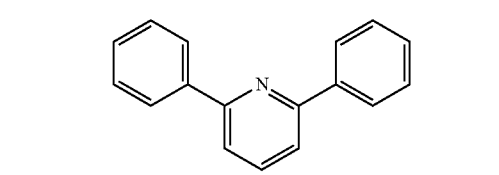
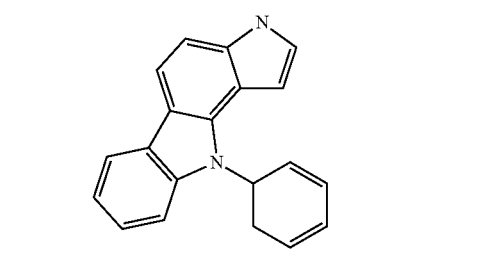
601
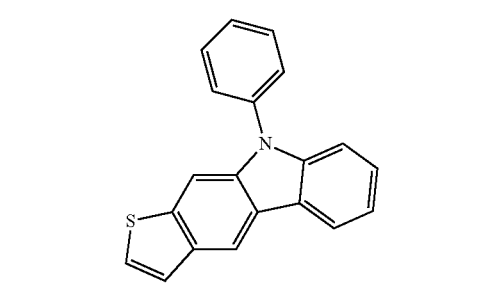
180
-continued
602
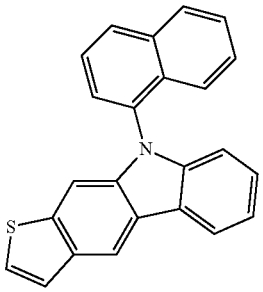
603
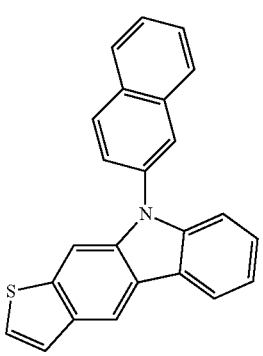
604
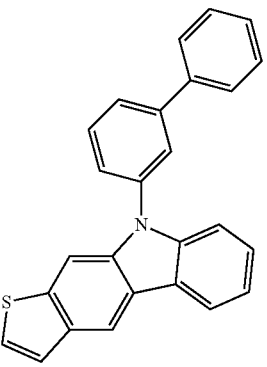
605
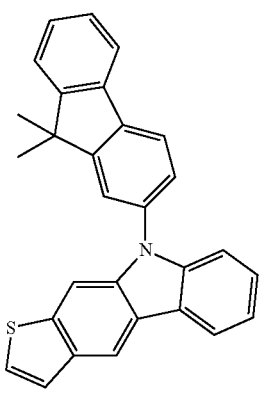

606
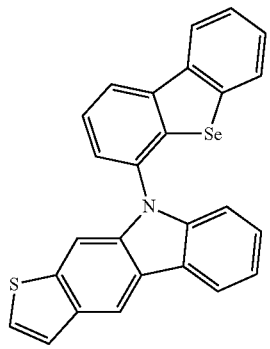
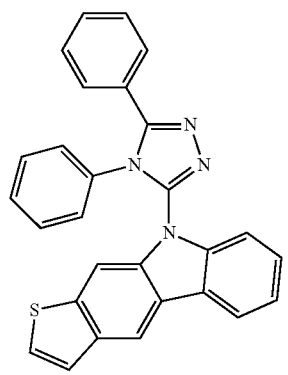
607
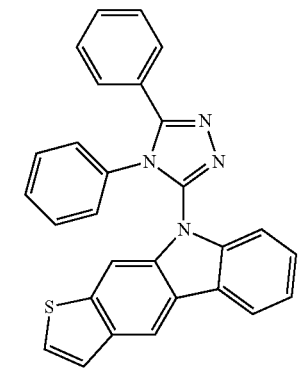
608
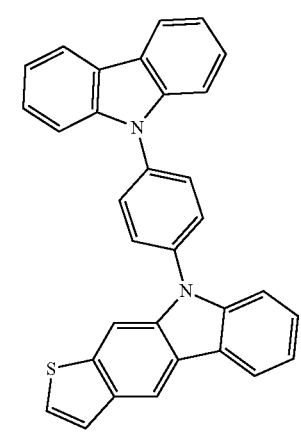
609
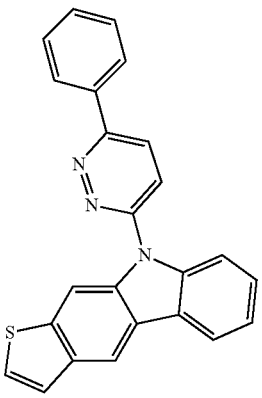
610
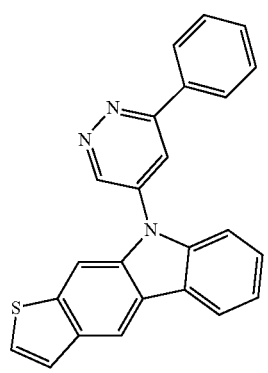
611
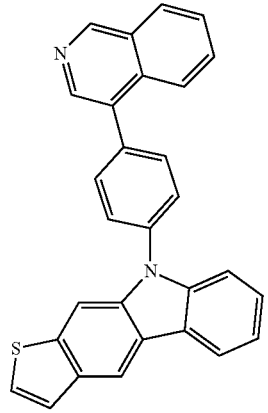
612

613
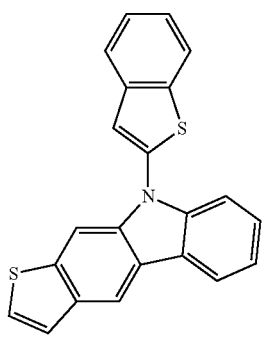
614
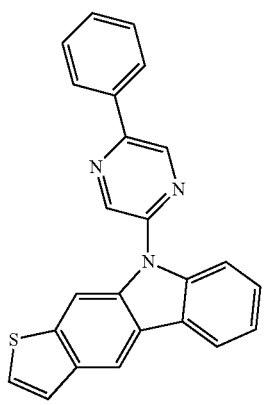
615
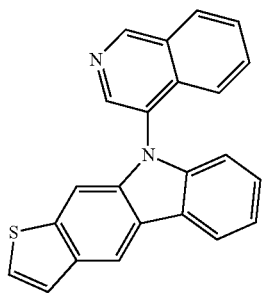
616
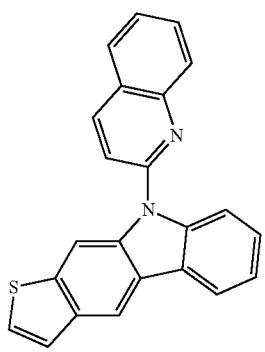
617
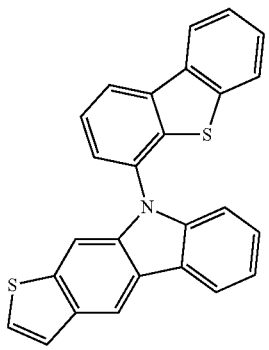
618
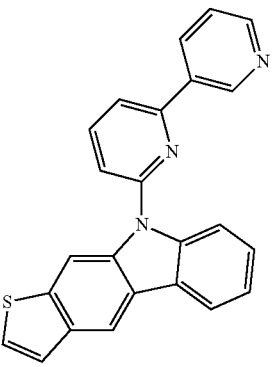
619
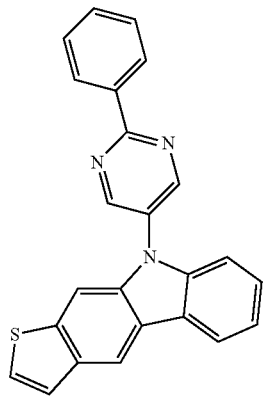
620
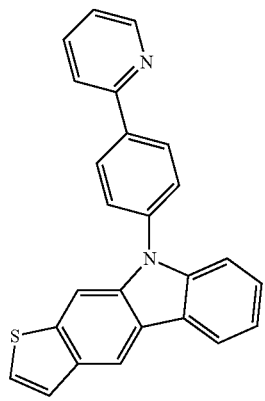

621 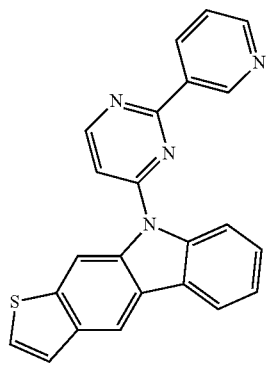
622 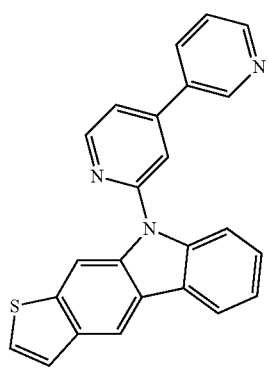
623 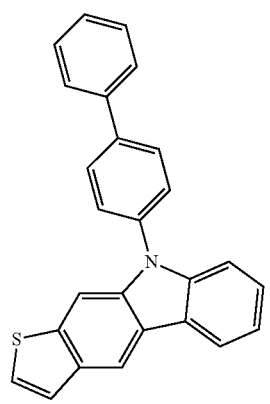
624 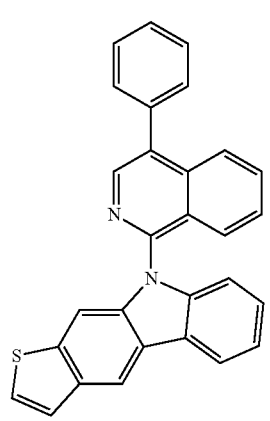
625 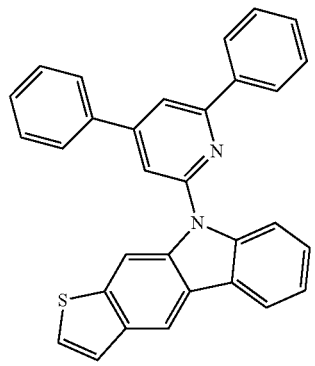
626 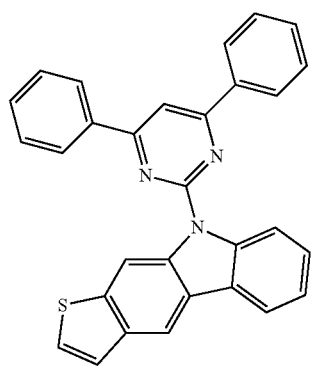
627 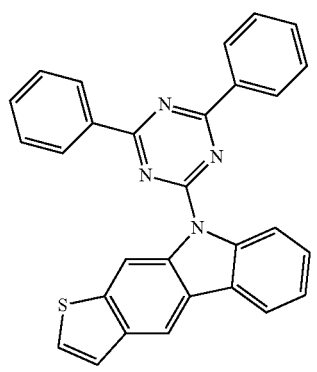
628 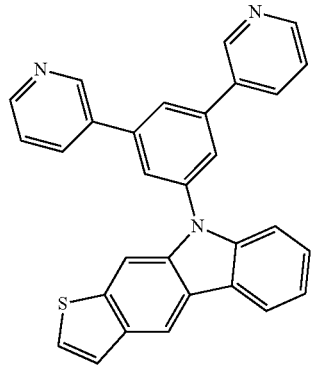

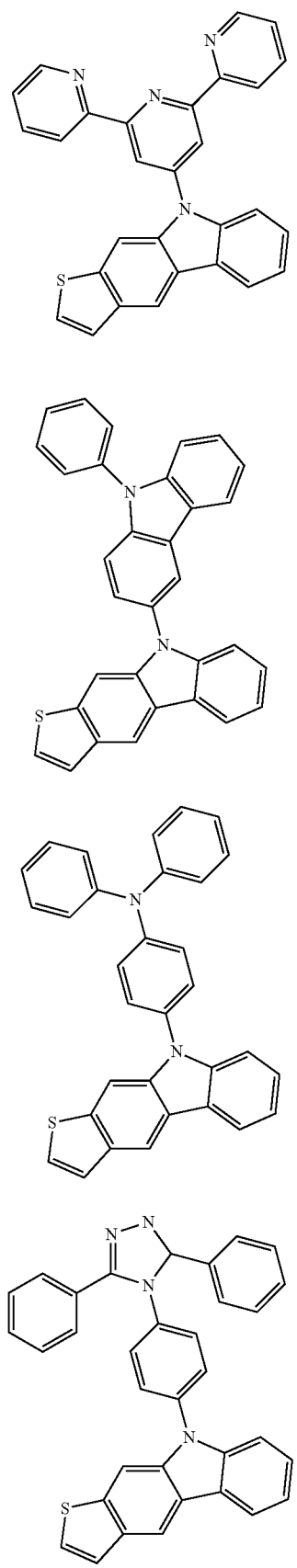
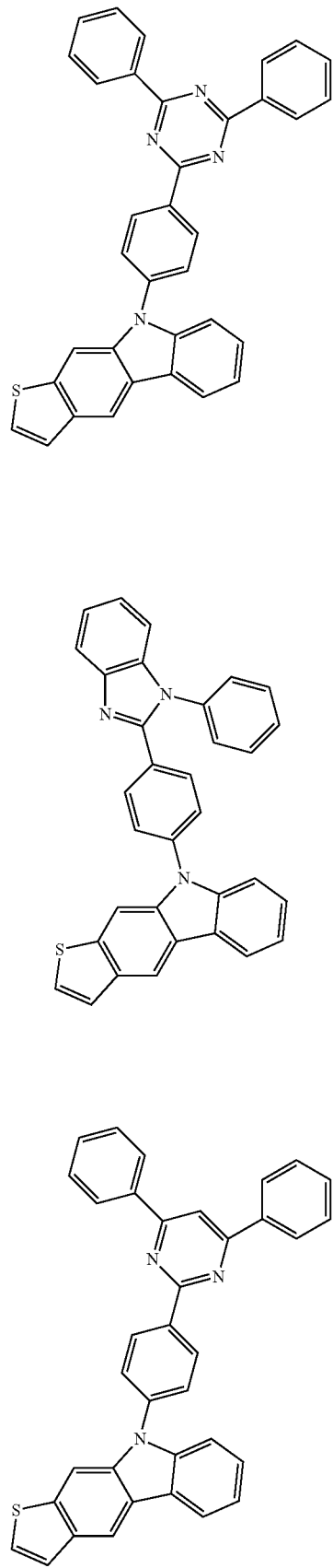

189
-continued
636
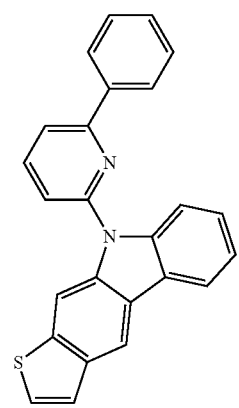
637
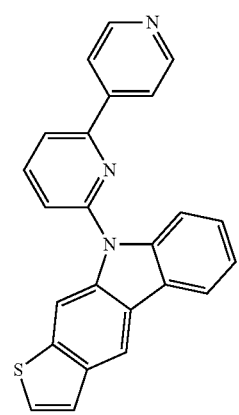
638
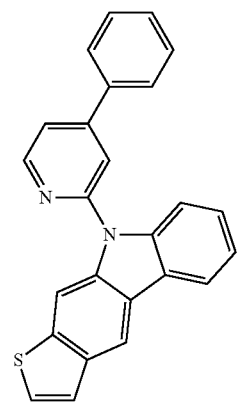
639
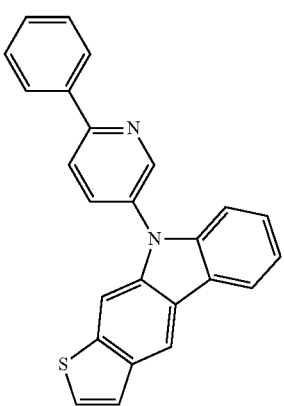
190
-continued
640
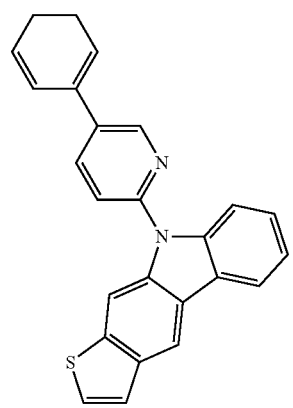
641
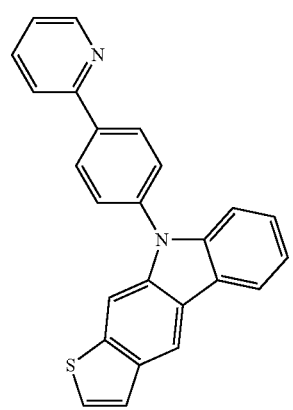
642
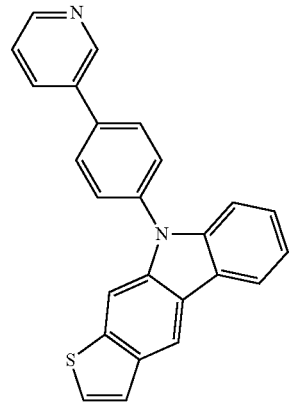
643
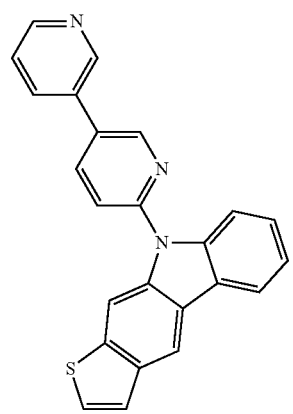

191
-continued
644
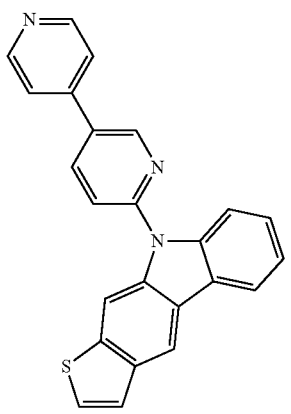
645
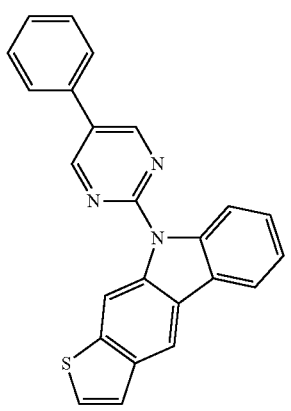
646

647
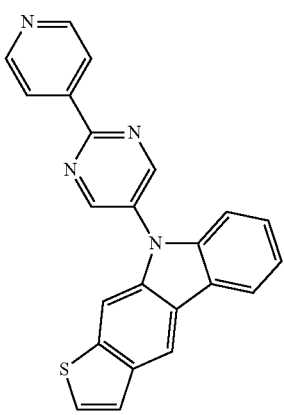
192
-continued
648
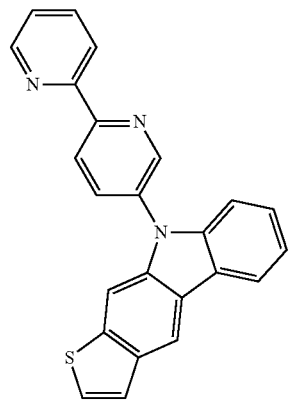
649
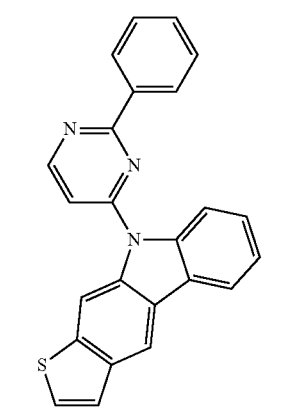
650
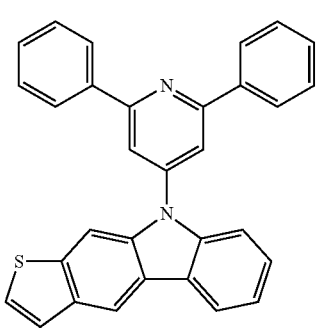
651
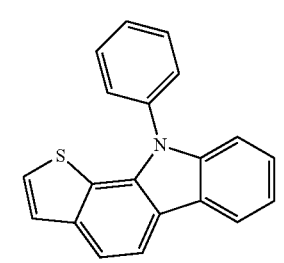

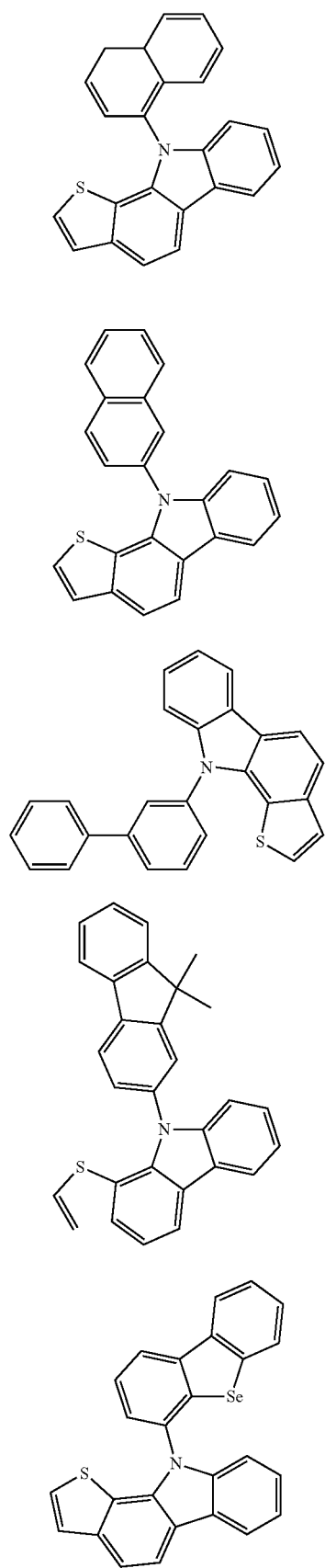
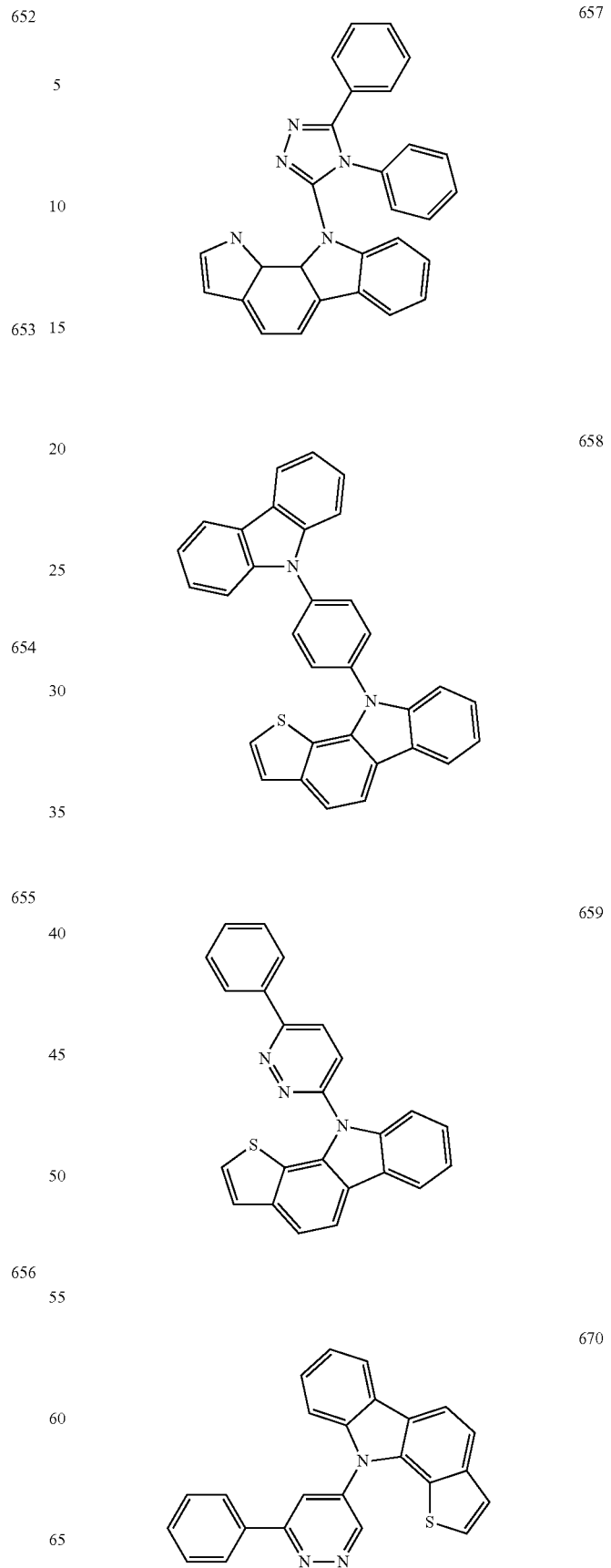

| 671 | 676 |
|---|---|
| 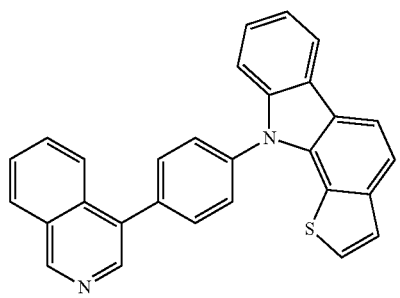 | 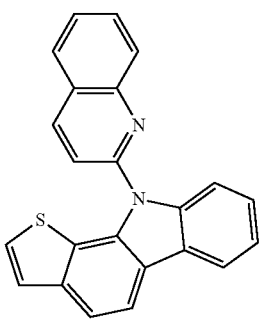 |
| 672 | 677 |
| 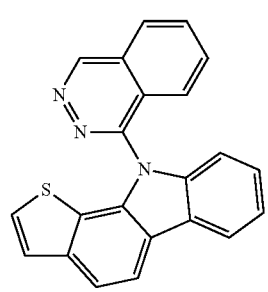 | 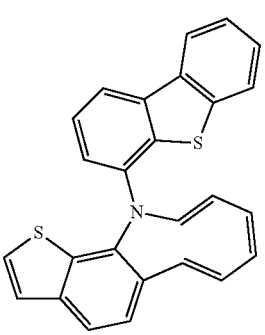 |
| 673 | 678 |
| 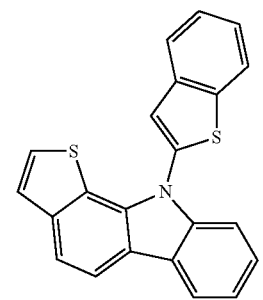 | 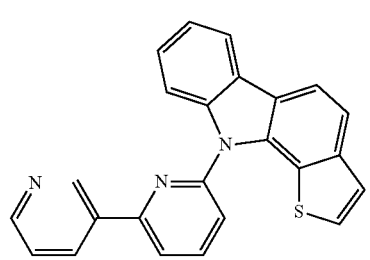 |
| 674 | 679 |
| 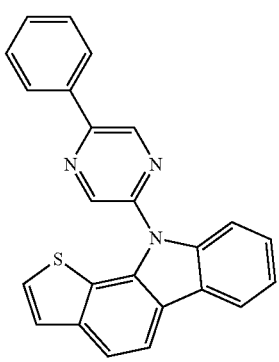 | 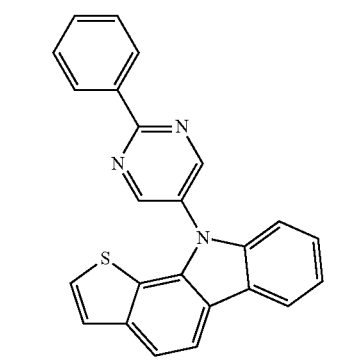 |
| 675 | 680 |
| 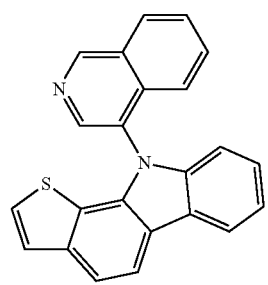 | 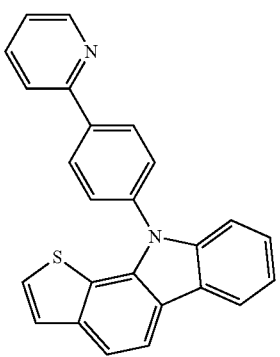 |

681
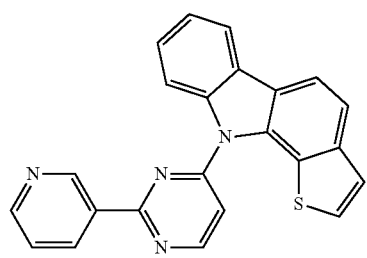
682
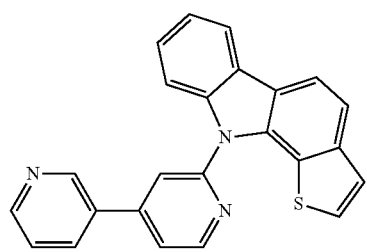
683
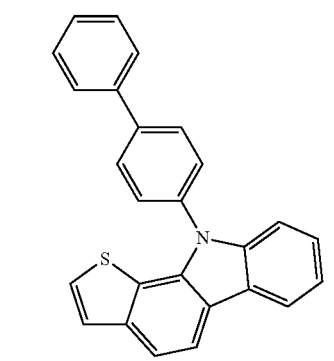
683
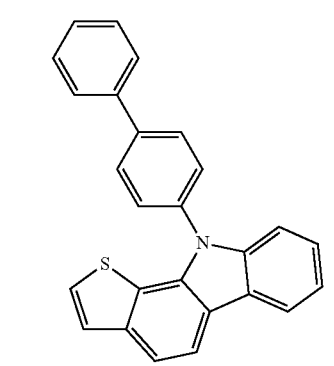
684
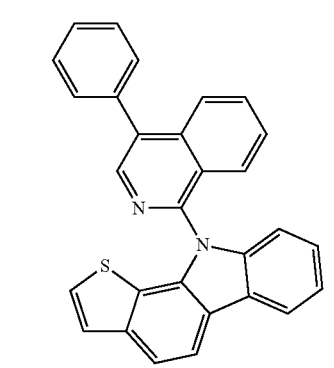
685
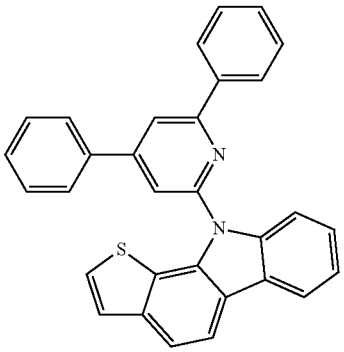
686
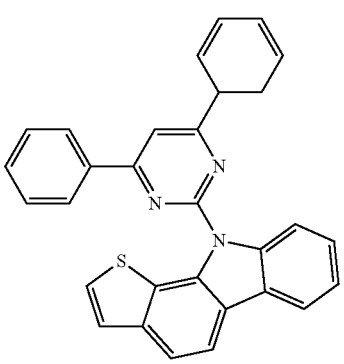
687
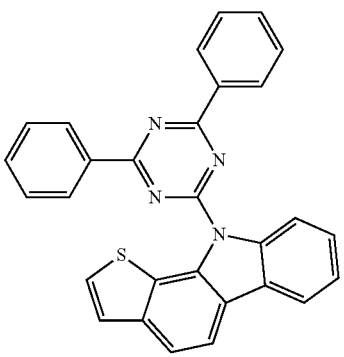
688
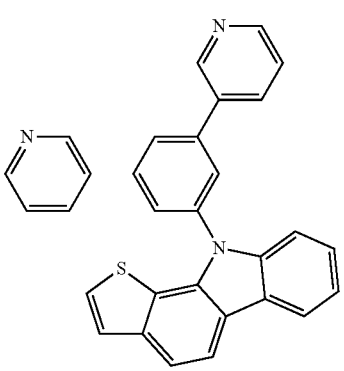

689
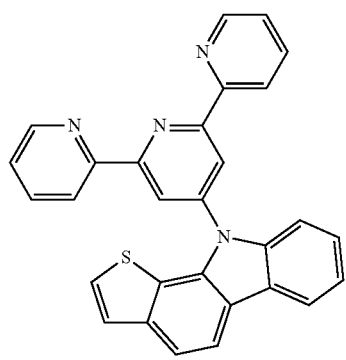
690
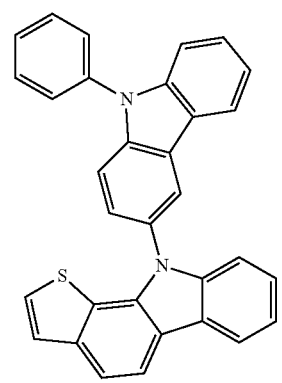
691
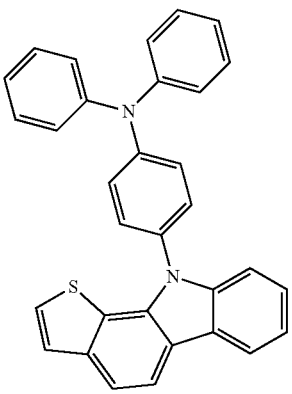
692
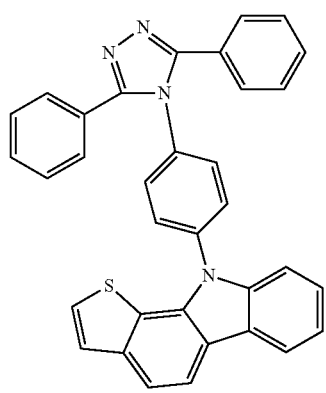
693
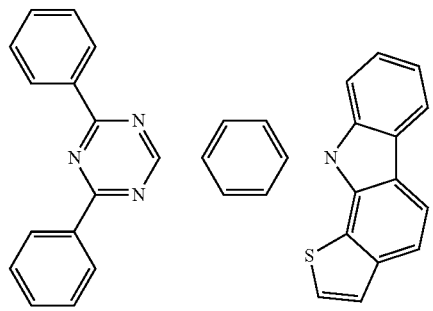
694
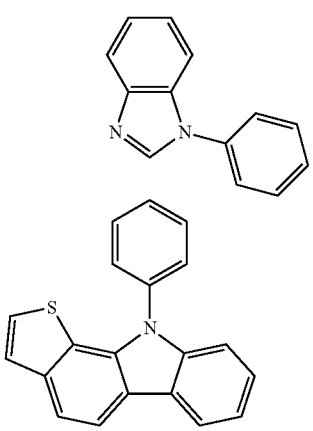
695
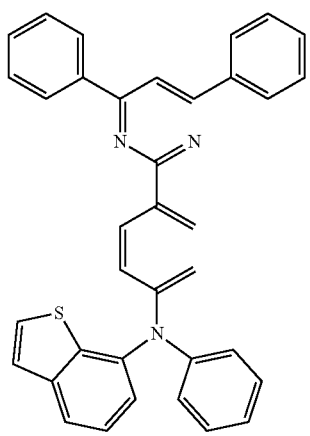
696
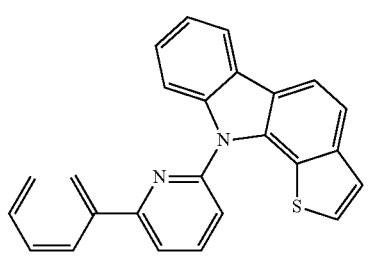

697 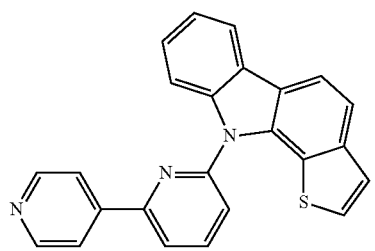
698 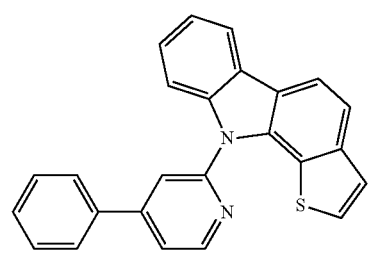
699 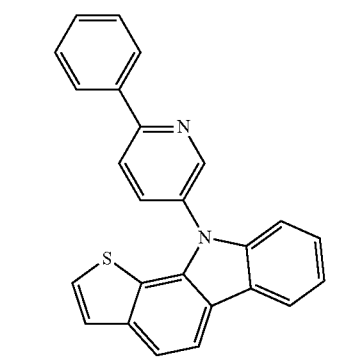
700 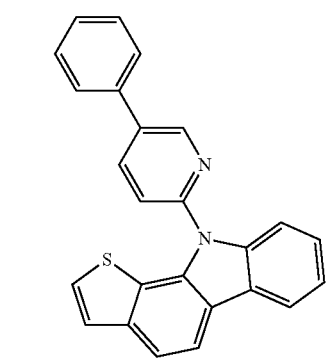
701 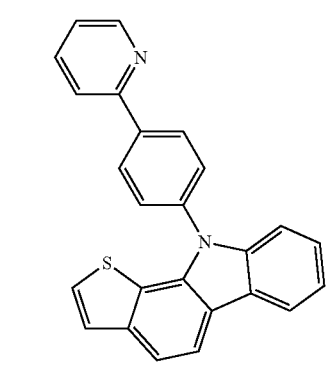
702 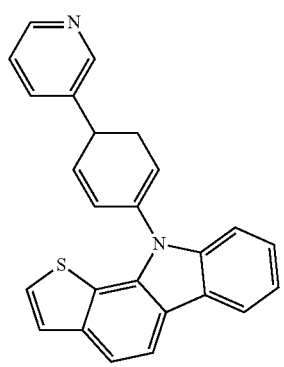
703 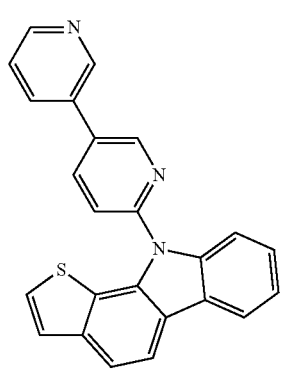
704 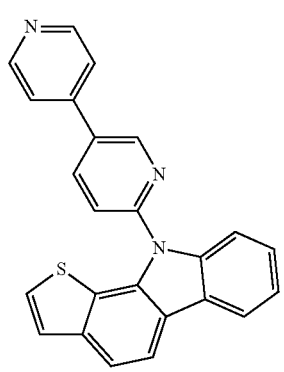
705 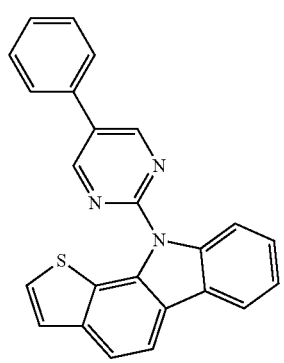

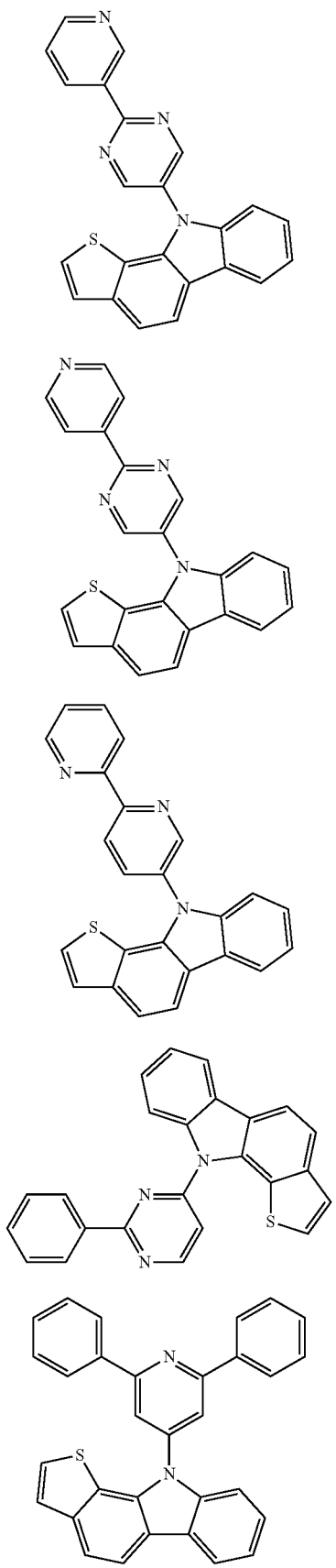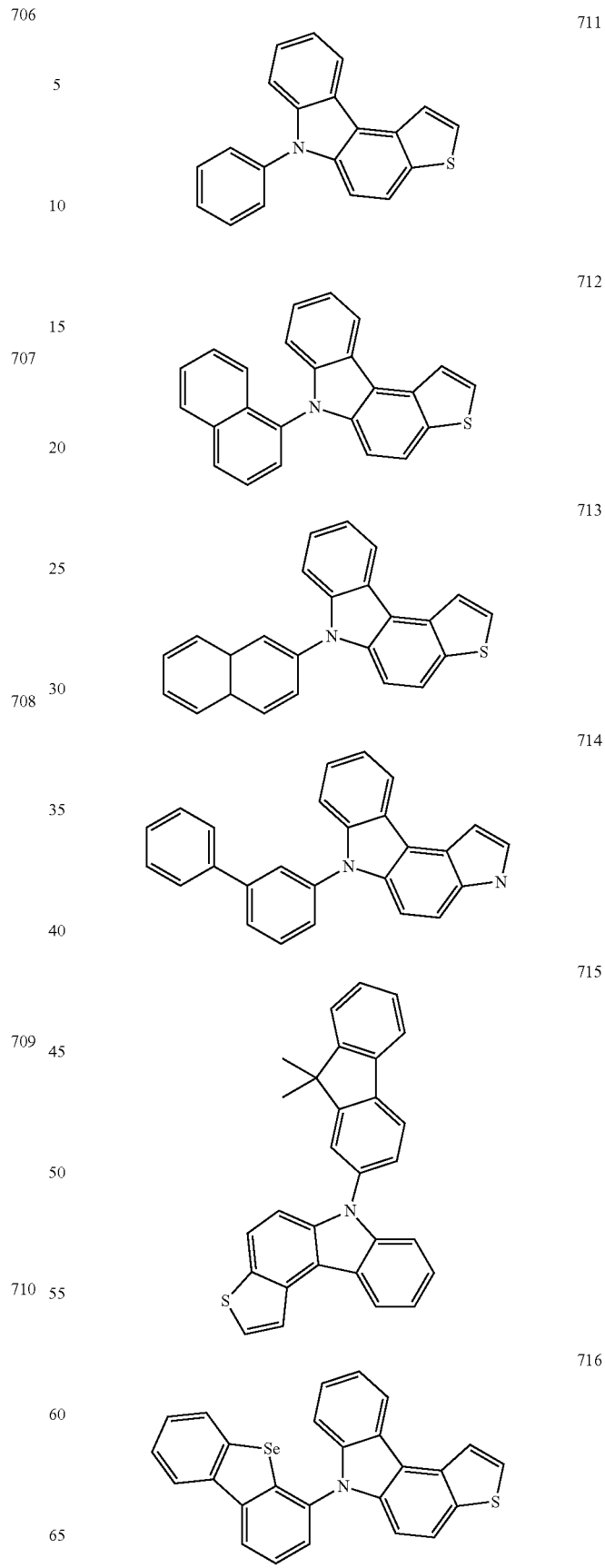

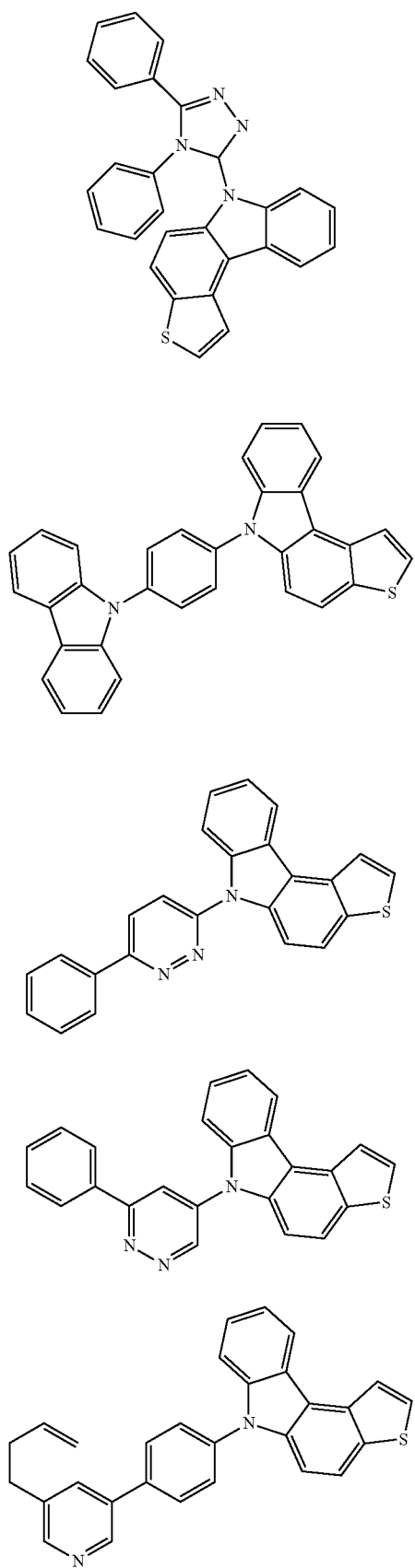
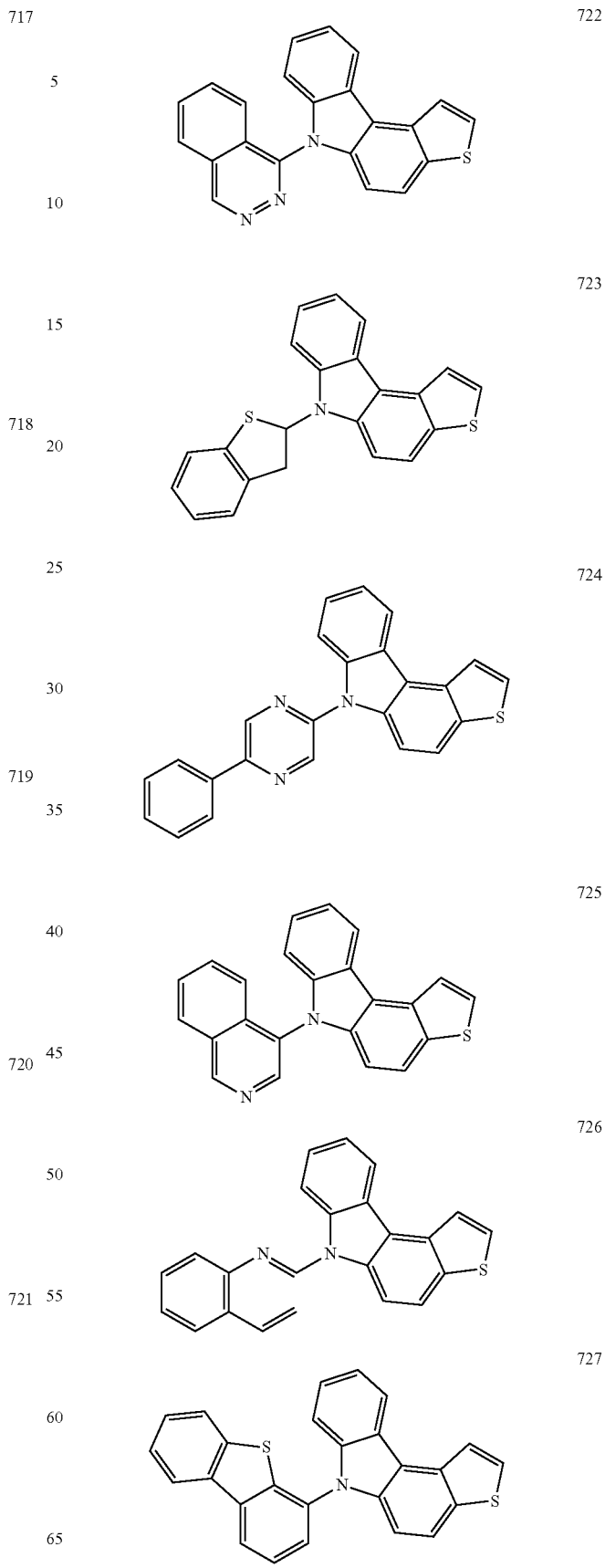

| 207 -continued | 208 -continued |
|---|---|
| 728 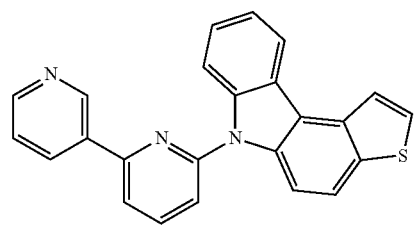 | 734 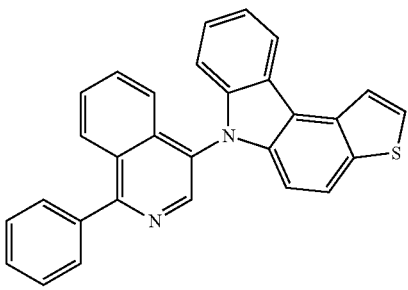 |
| 729 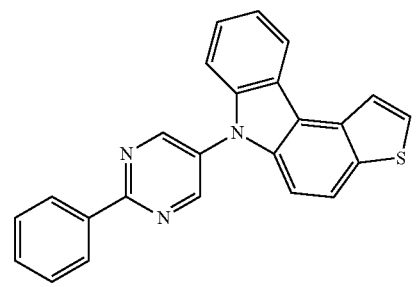 | 735 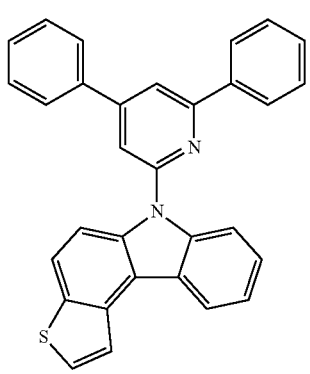 |
| 730 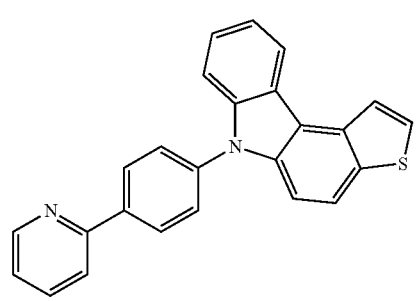 | |
| 731 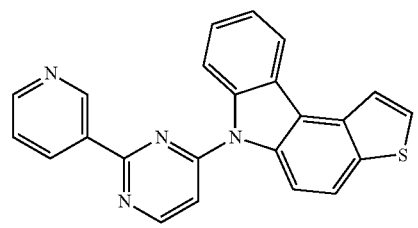 | 736 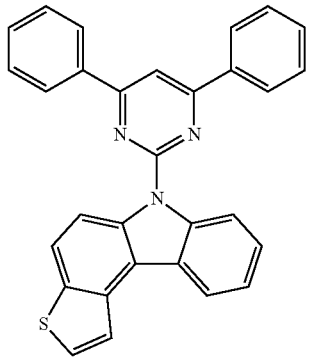 |
| 732 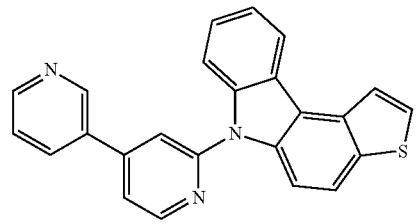 | |
| 733 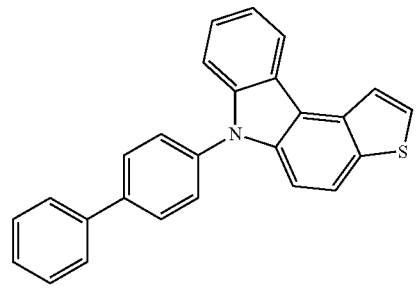 | 737 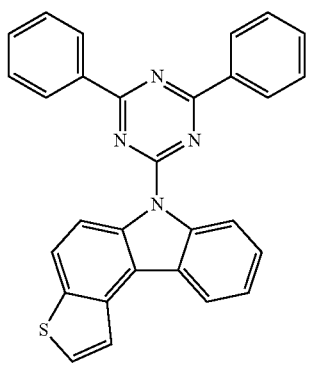 |

| 738 | 742 |
|---|---|
| 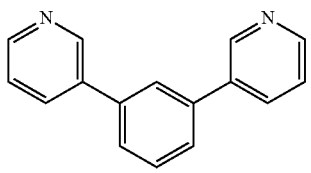 | 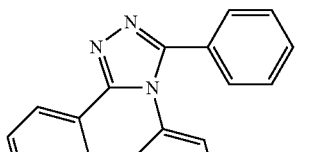 |
| 739 | |
| 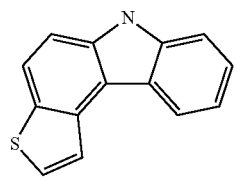 | 743 |
| | 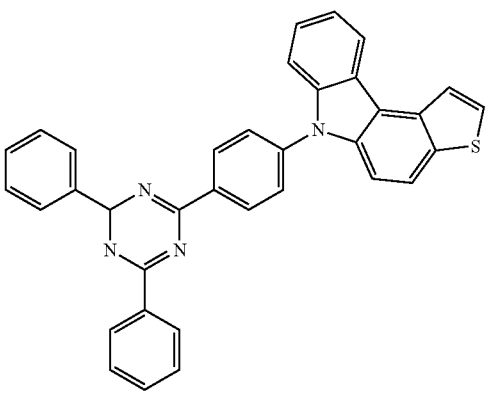 |
| 740 | |
| 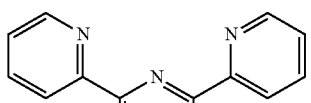 | 744 |
| | 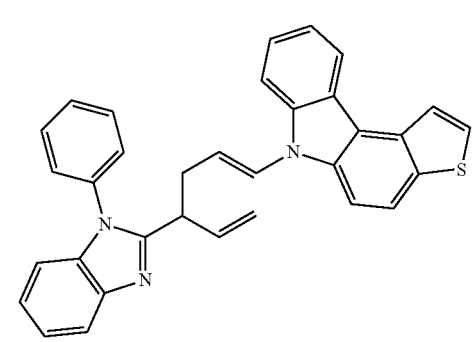 |
| 741 | 745 |
| 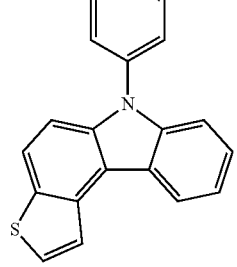... | 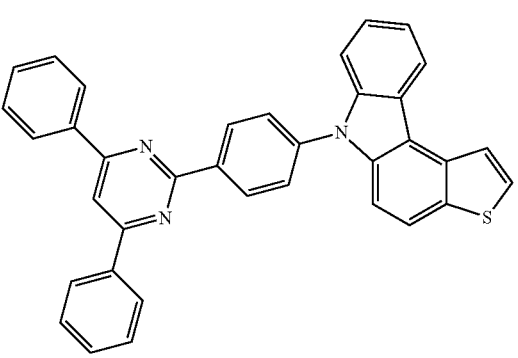 |
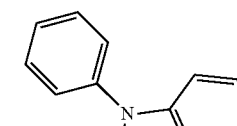
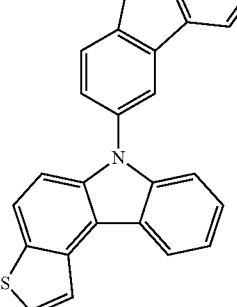
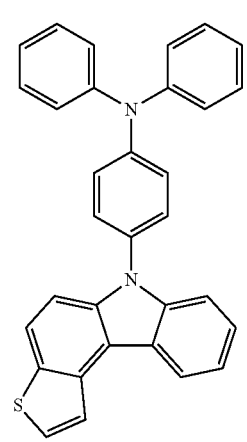

746 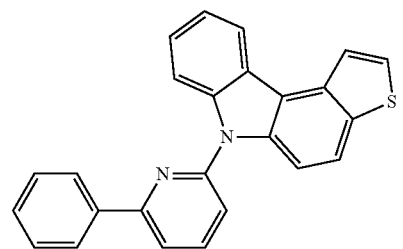
747 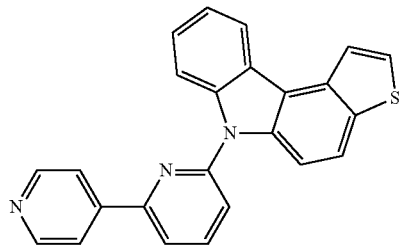
748 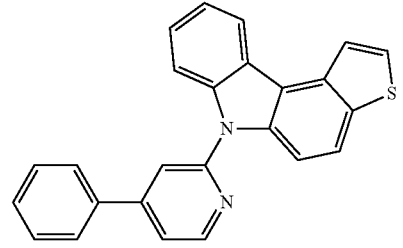
749 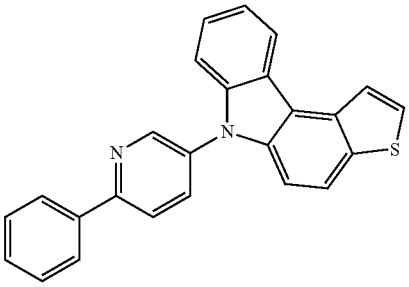
750 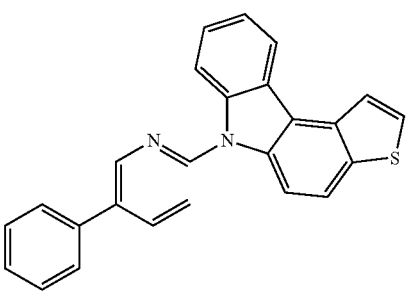
751 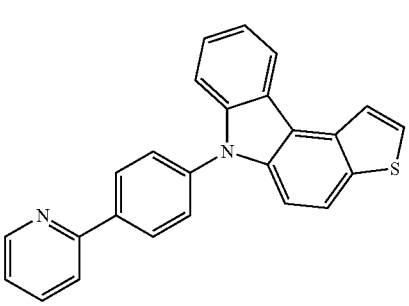
752 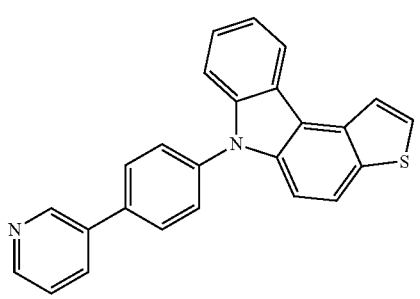
753 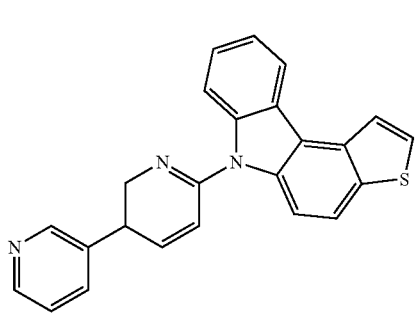
754 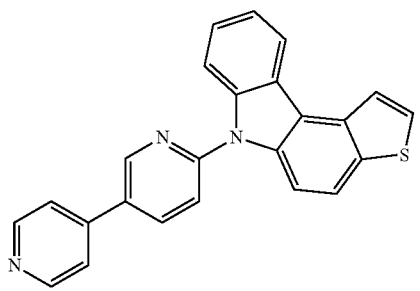
755 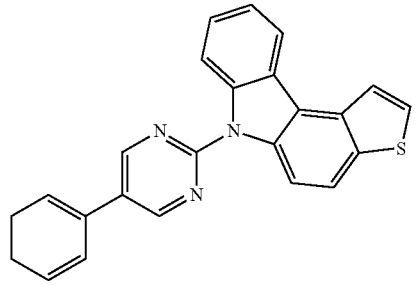
756 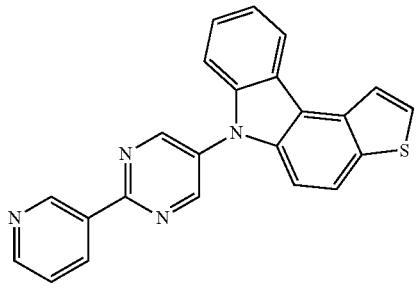

213
-continued
757
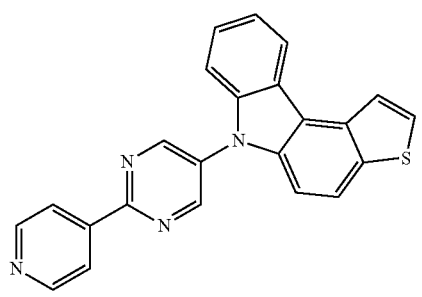
758
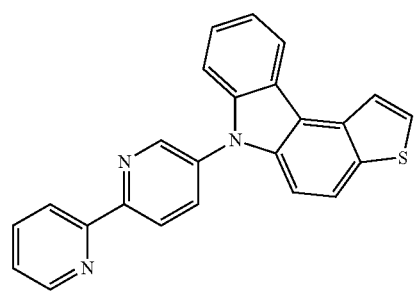
759
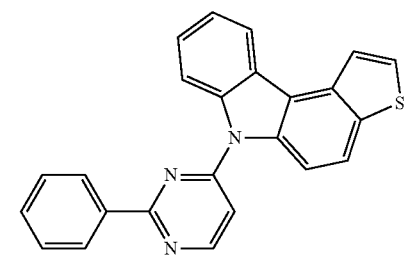
760
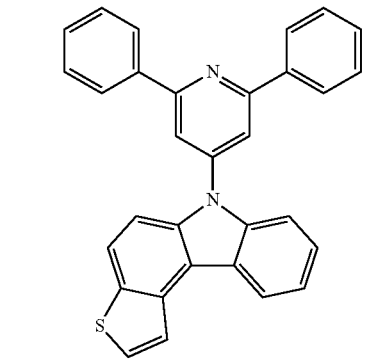
761
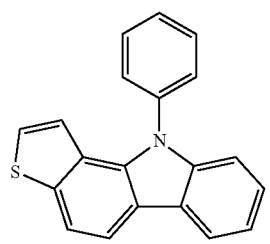
214
-continued
762
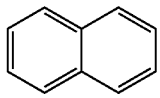
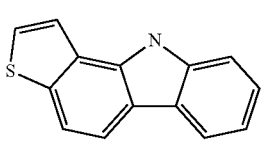
763
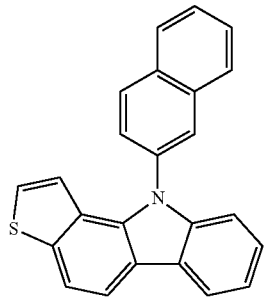
764
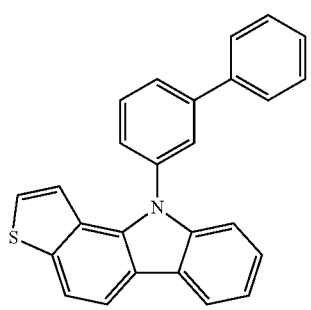
765
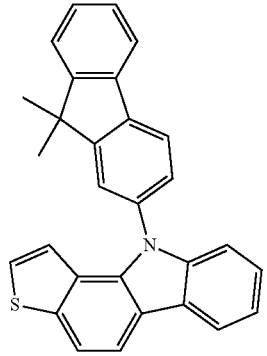
766
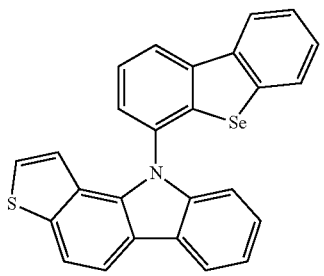

767
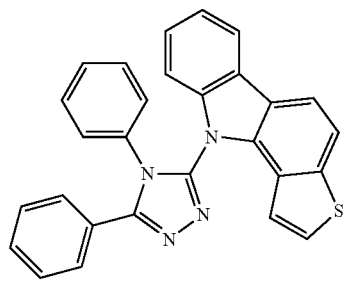
768
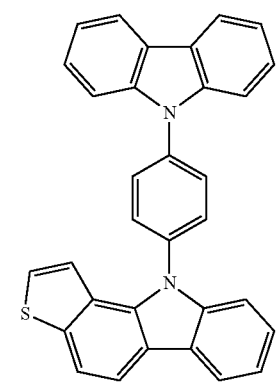
769
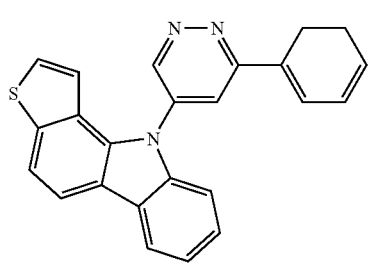
771
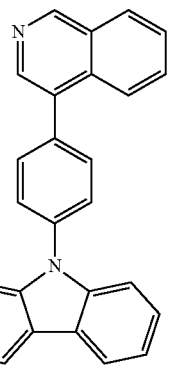
772
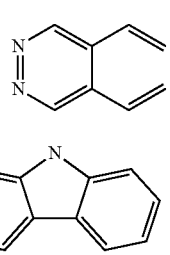
773
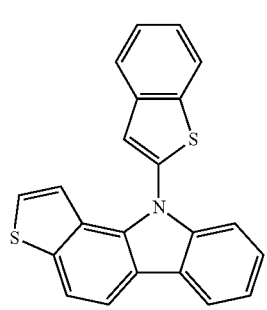
774
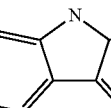
775
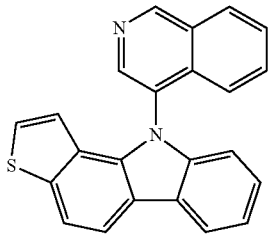

217
-continued
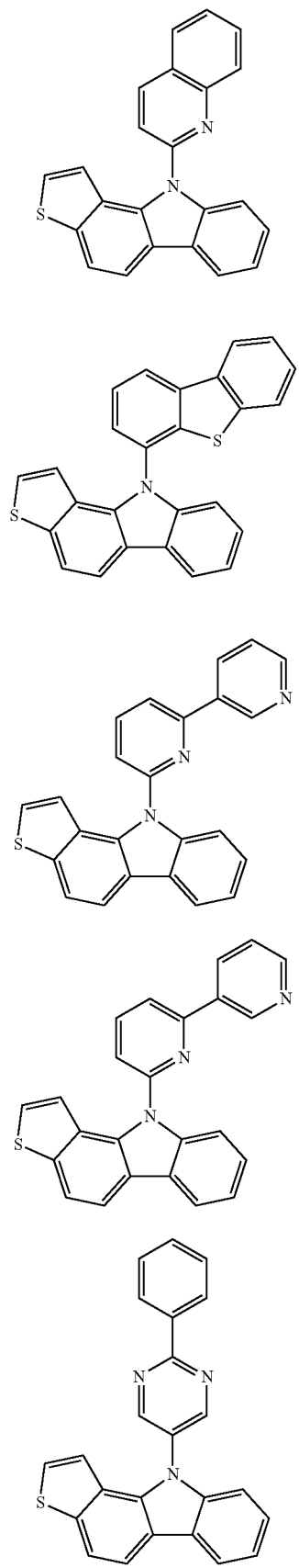
218
-continued
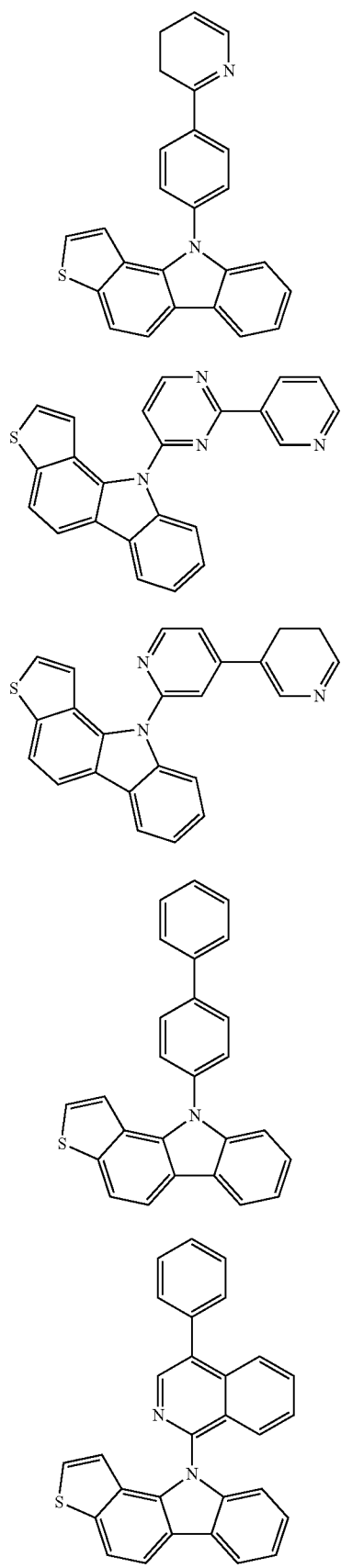

785
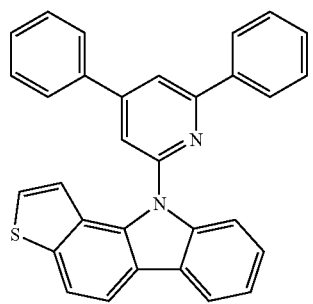
786
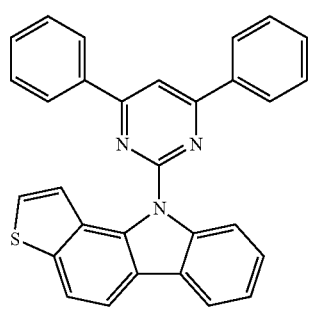
787
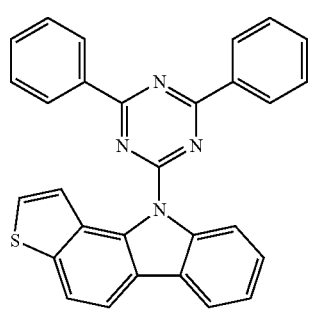
788
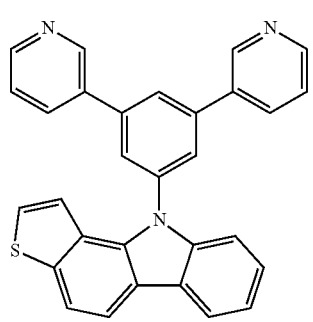
789
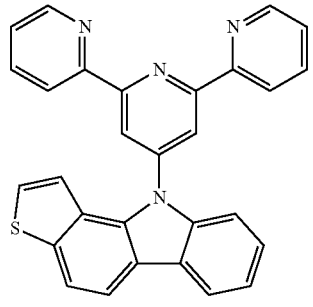
790
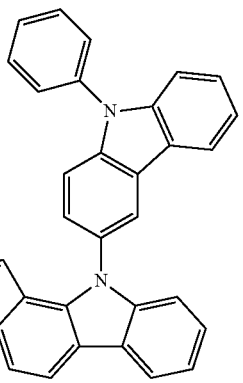
791
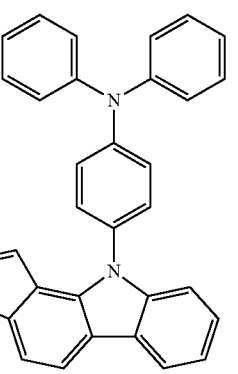
792
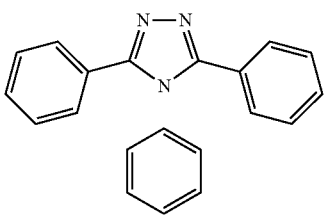
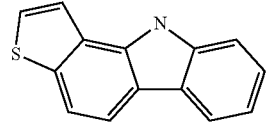
793
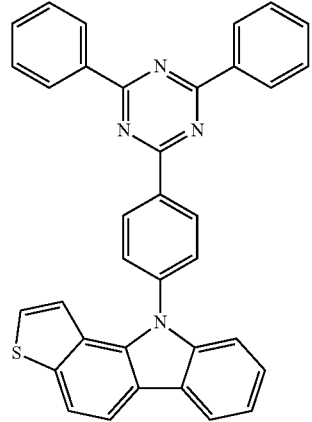

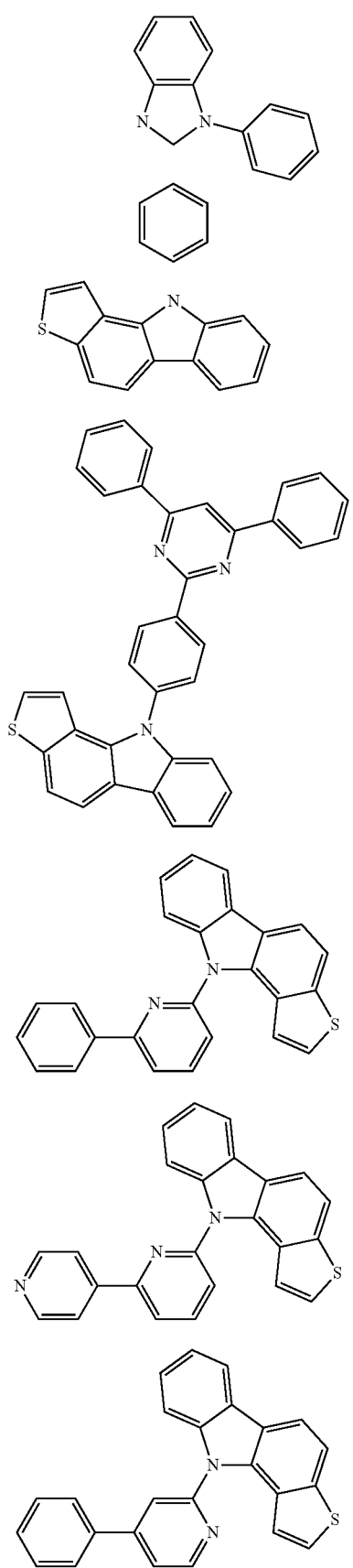

803 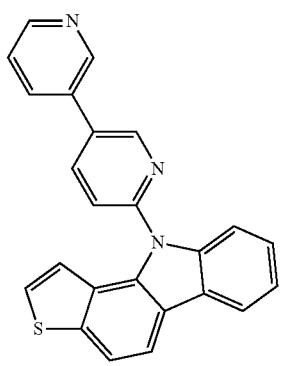
804 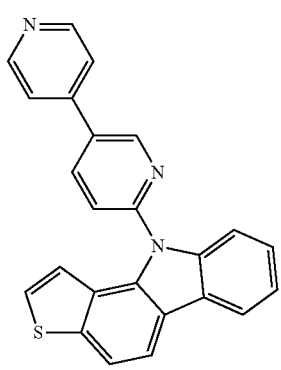
805 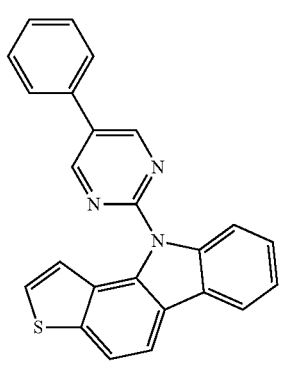
806 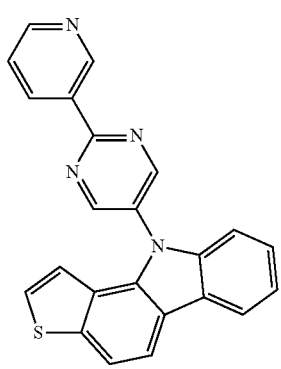
807 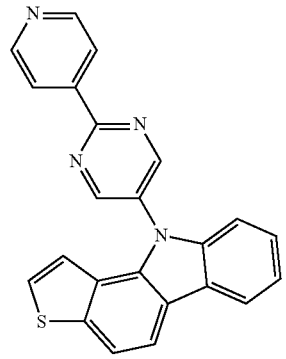
808 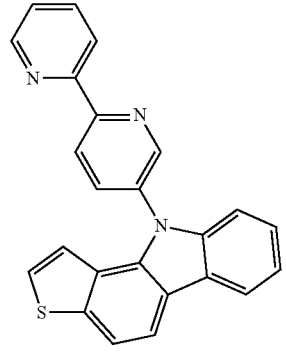
809 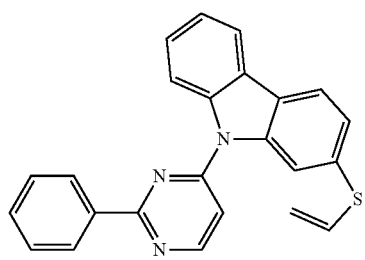
810 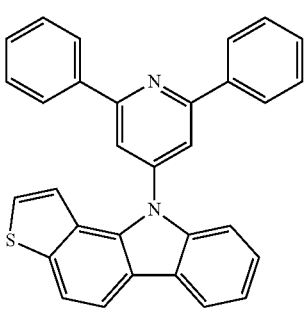
811 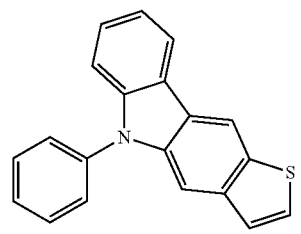

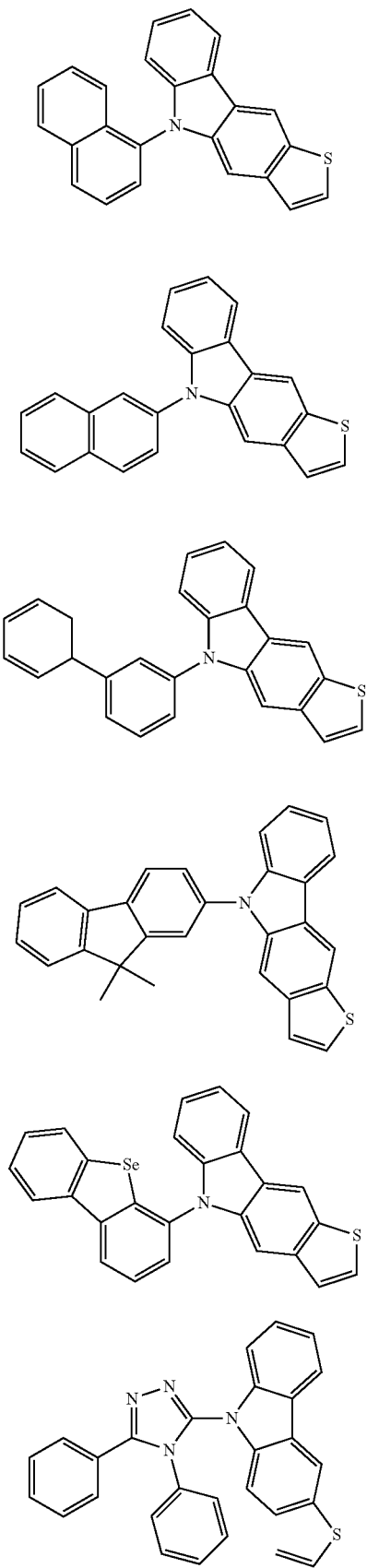

227
-continued
824
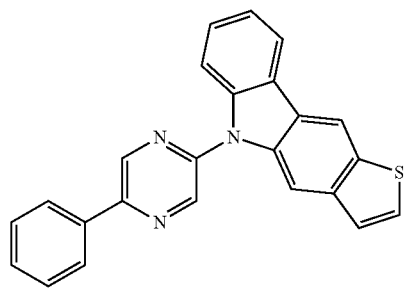
825
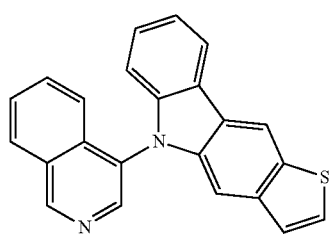
826
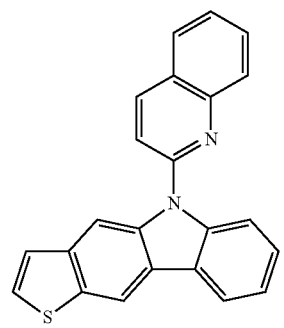
827
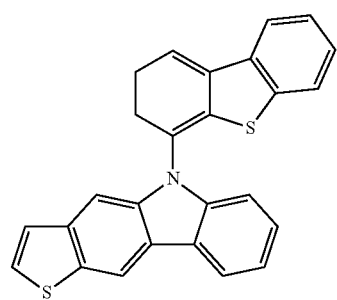
828
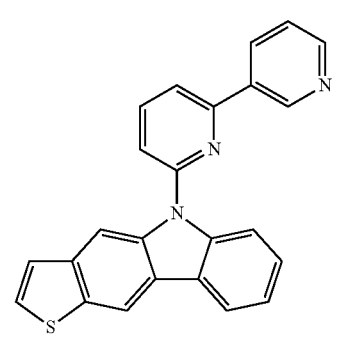
228
-continued
829
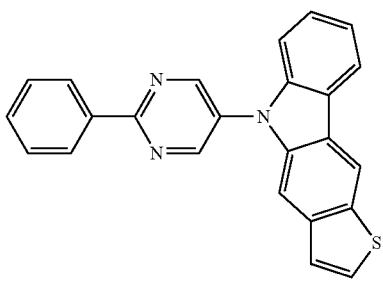
830
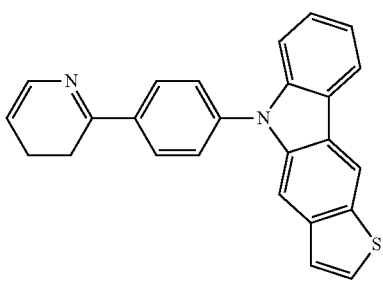
831
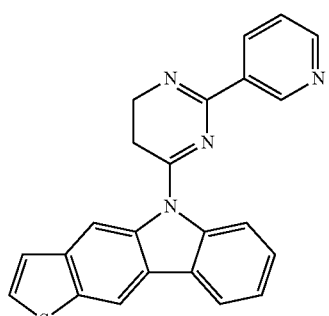
832
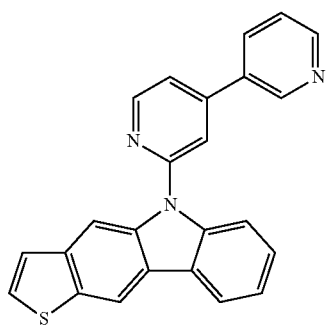
833
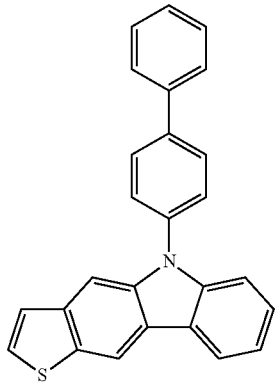

| 229 -continued | | 230 -continued | |
|---|---|---|---|
| 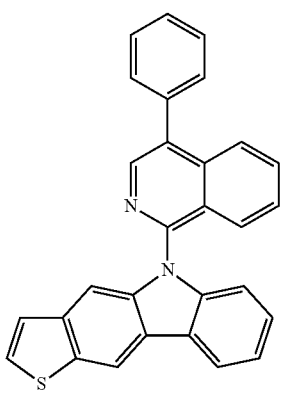 | 834 | 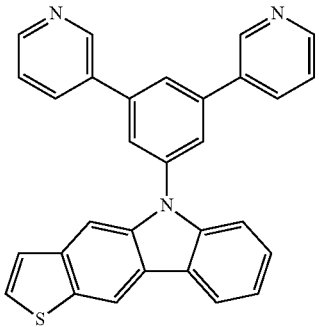 | 838 |
| 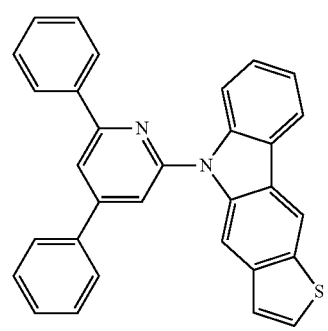 | 835 | 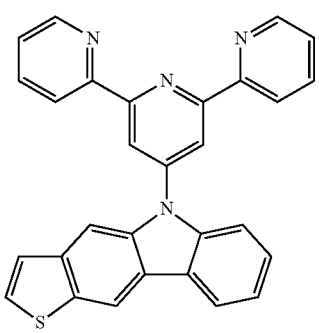 | 839 |
| 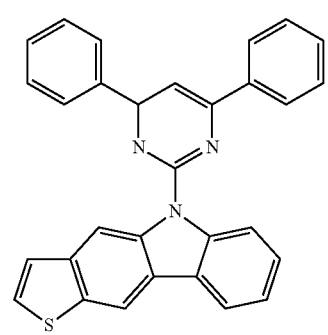 | 836 | 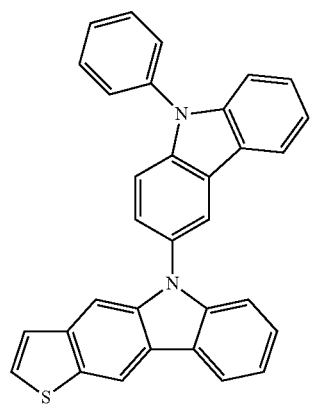 | 840 |
| 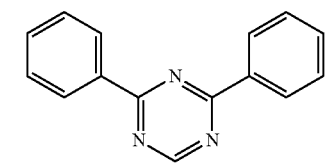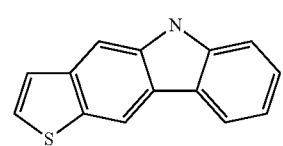 | 837 | 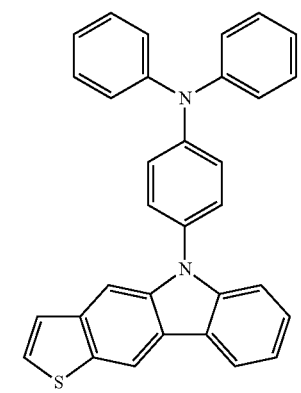 | 841 |

842
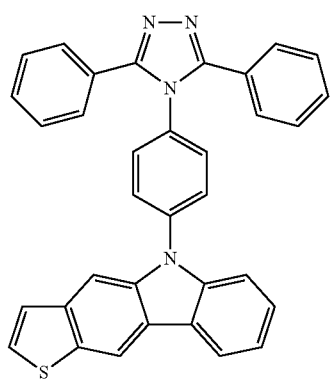
843
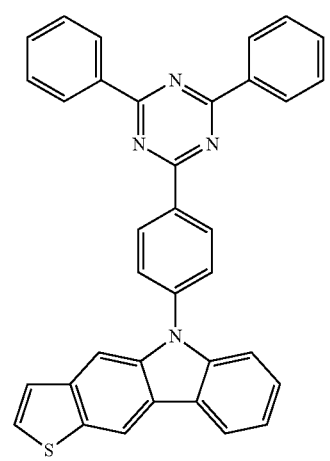
844
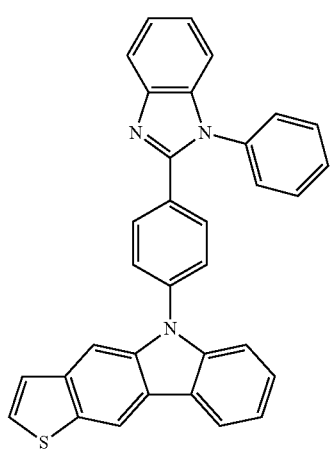
845
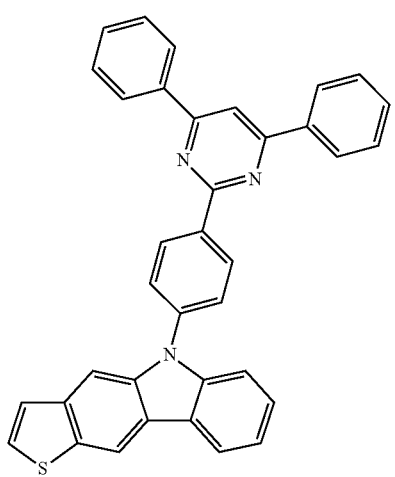
846
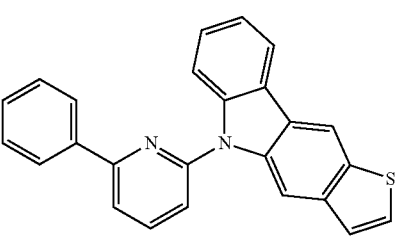
847
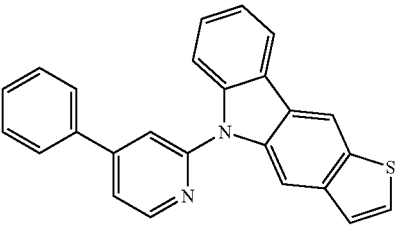
848
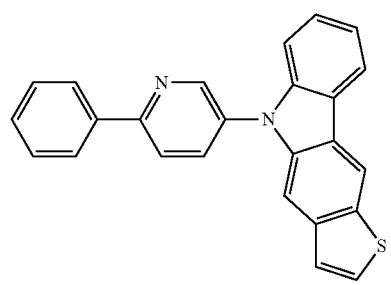
849

233
-continued
850
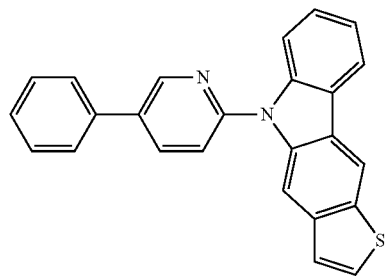
851
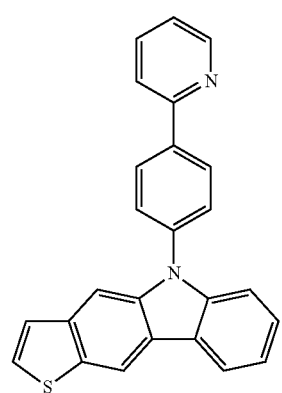
852
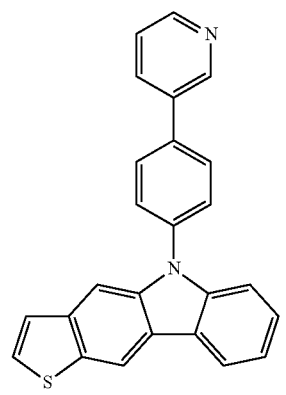
853
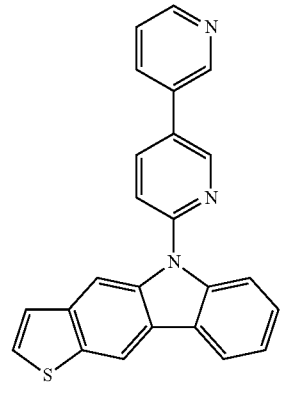
234
-continued
854
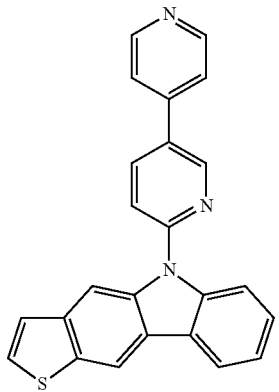
855
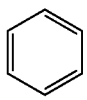
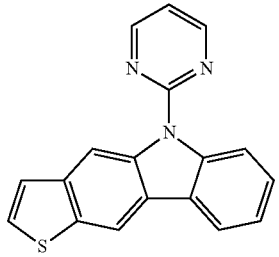
856
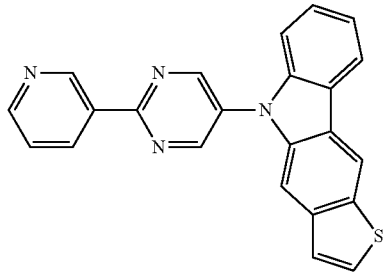
857
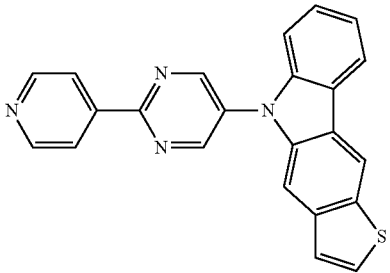
858
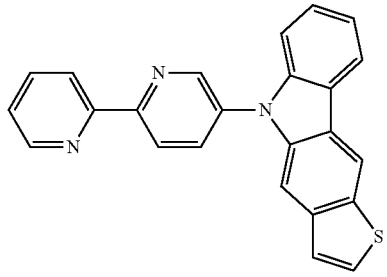

235
-continued
859
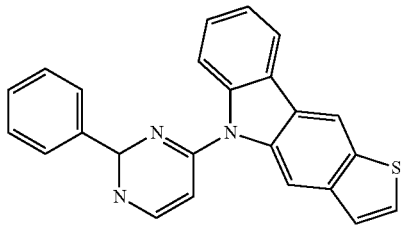
860
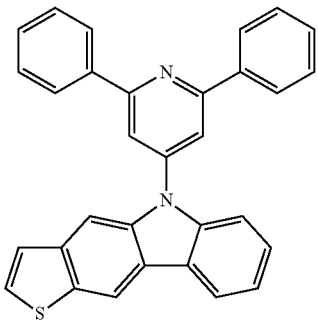
861
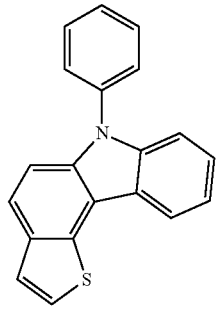
862
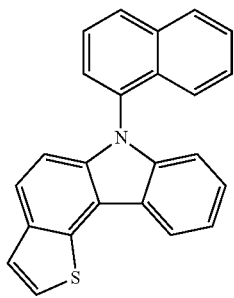
863
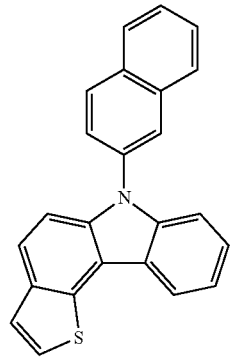
236
-continued
864
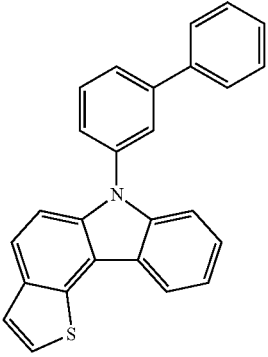
865
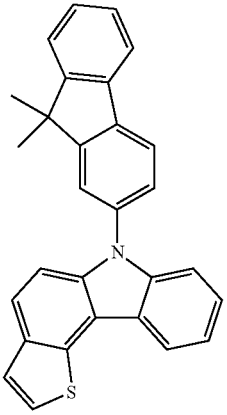
866
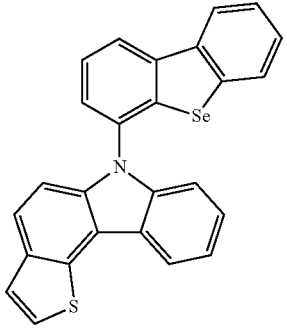
867
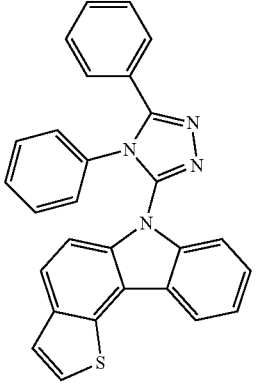

868 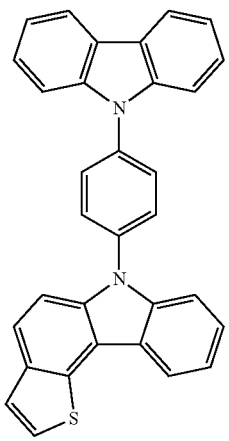
869 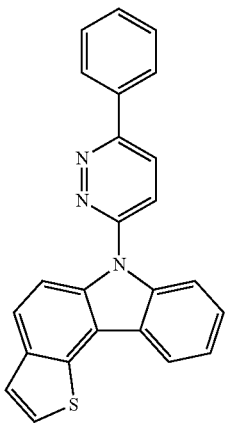
870 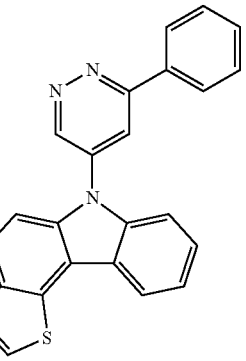
871 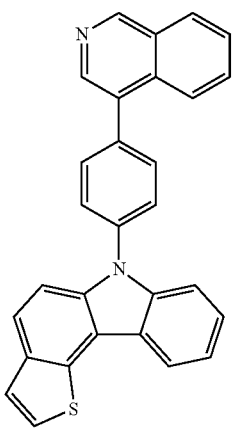
872 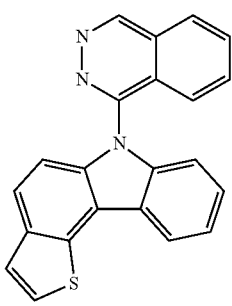
873 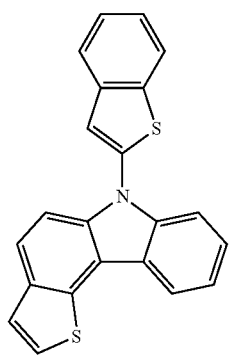
874 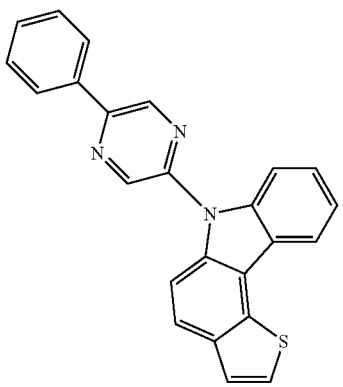
875 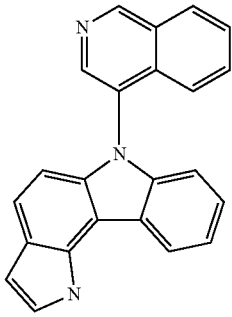

US 10,038,146 B2
239
-continued
876
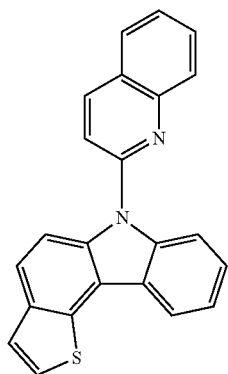
877
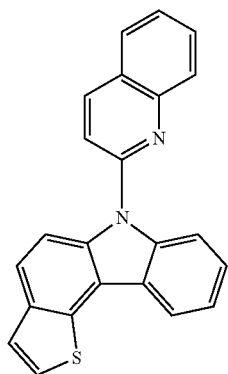
878
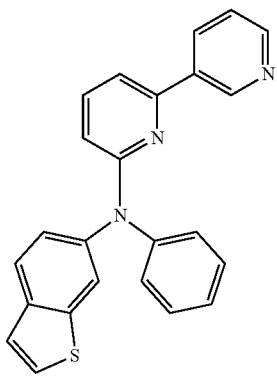
879
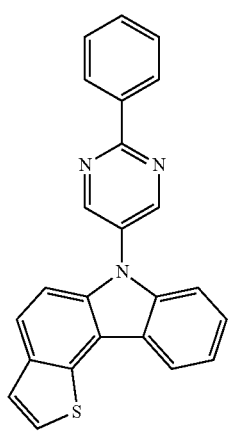
240
-continued
880
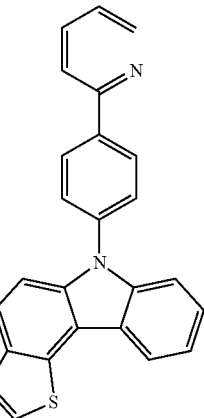
881
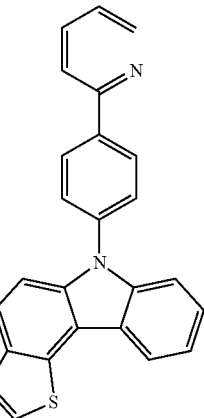
882
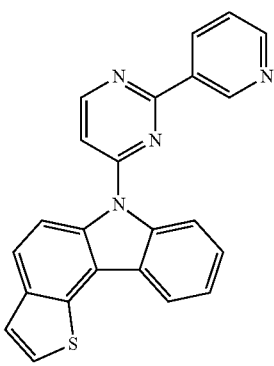
883
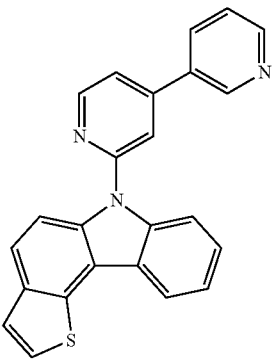

884
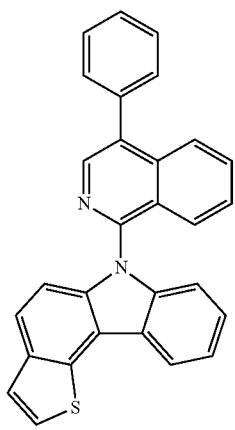
885
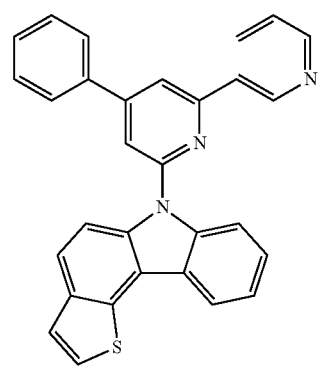
886
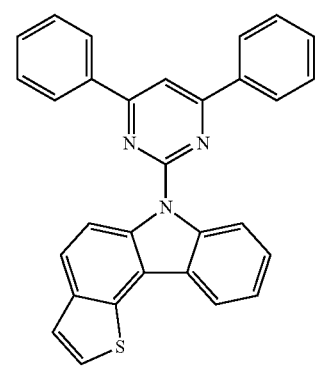
887
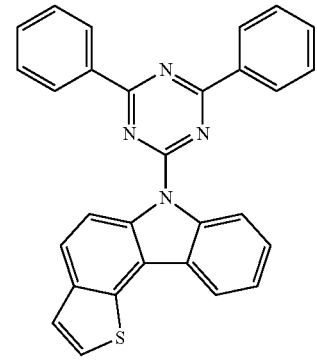
888
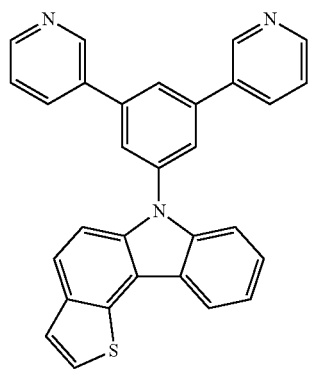
889
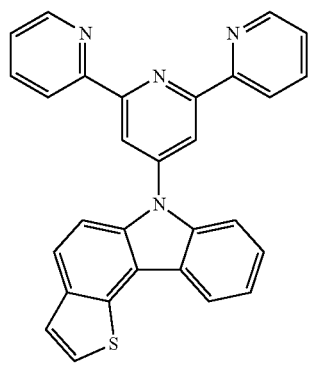
888
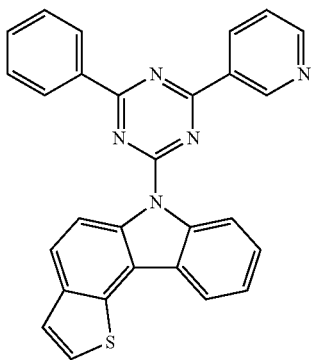
890
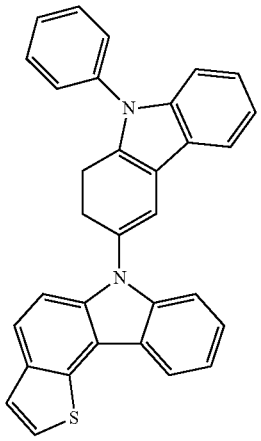

243
-continued
891
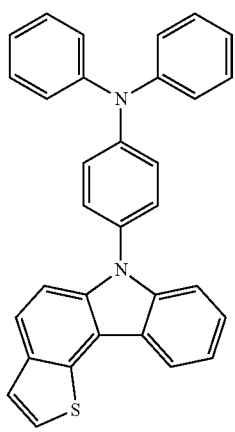
892
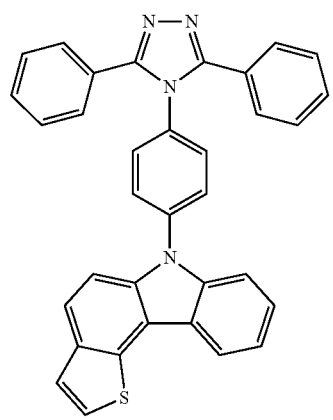
893
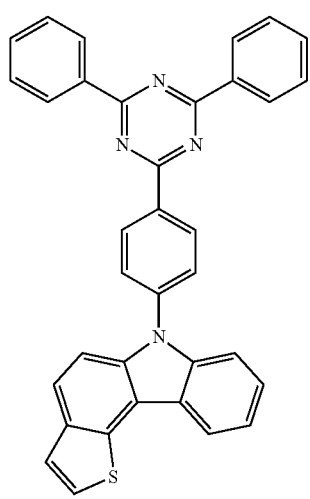
244
-continued
894
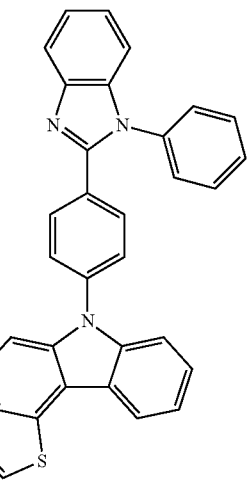
895
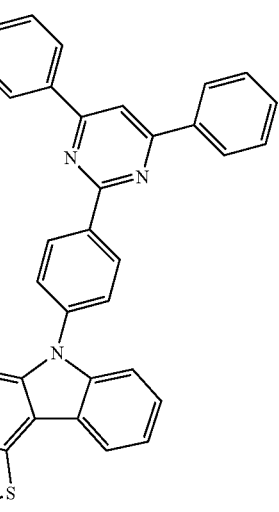
896
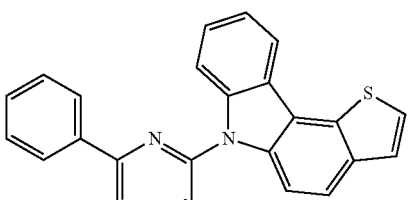
897
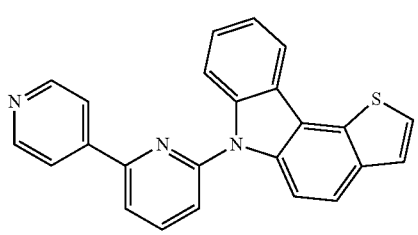

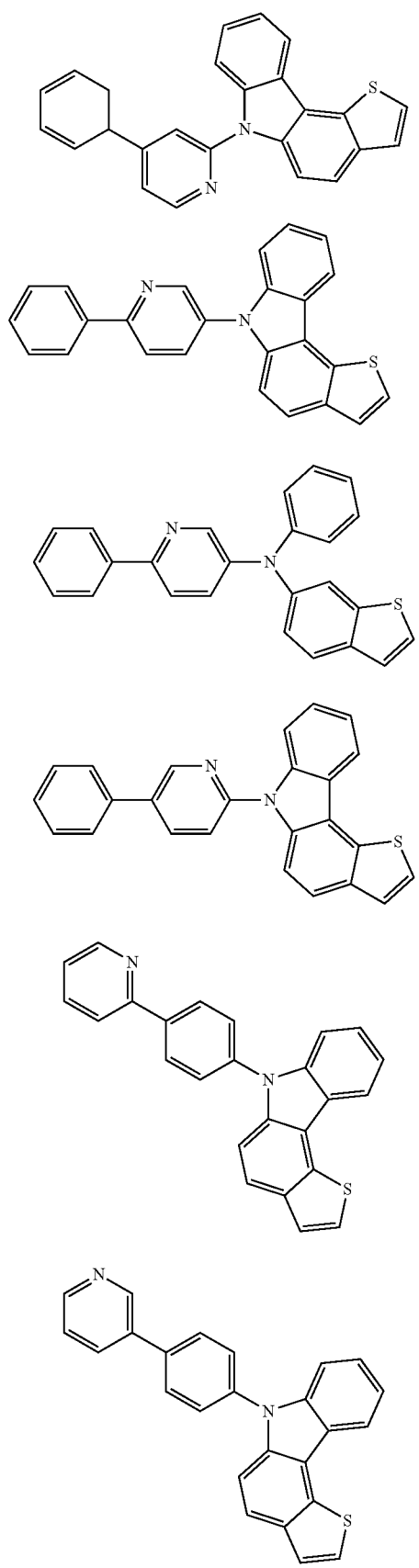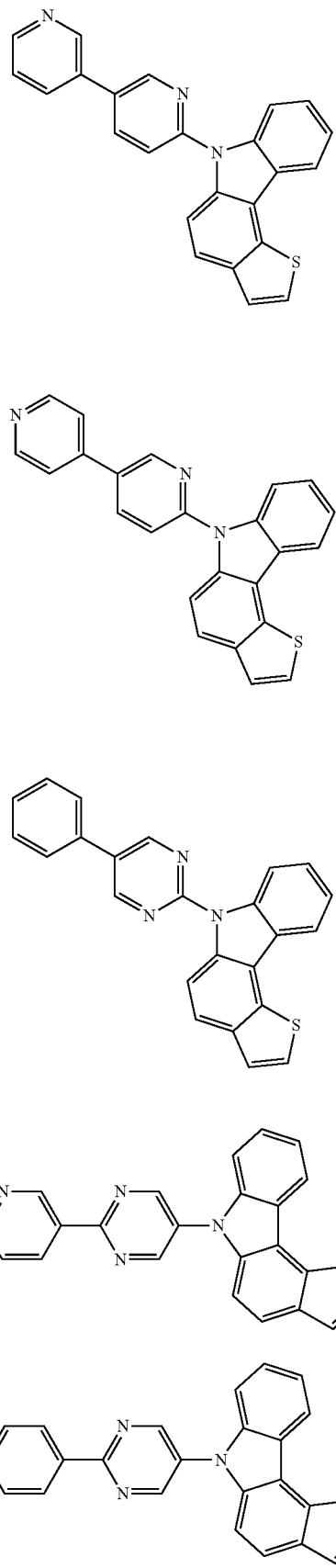

247
-continued
908
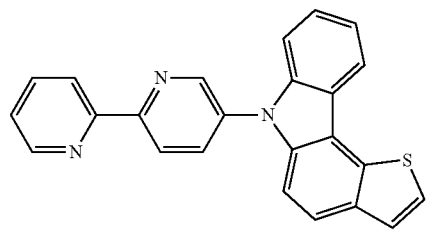
909
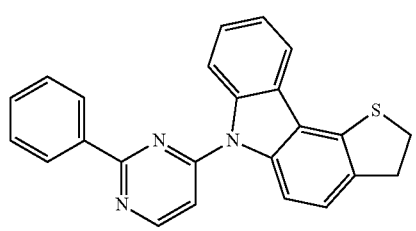
910
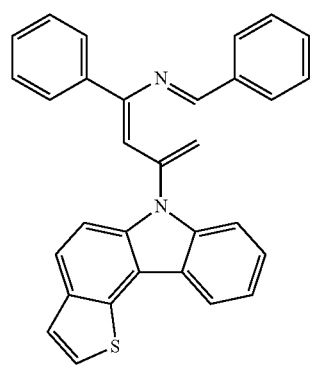
911
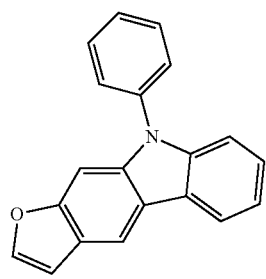
912
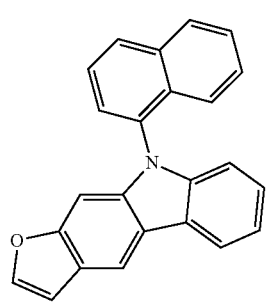
248
-continued
913
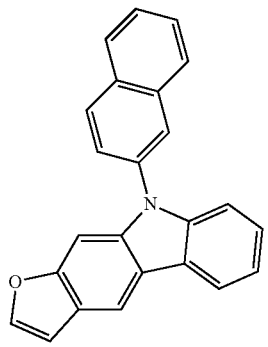
914
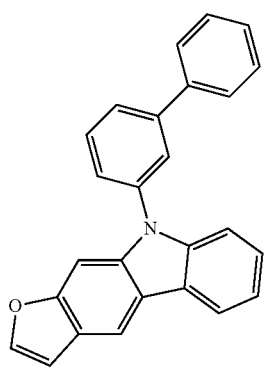
915
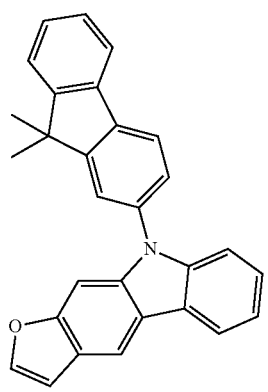
916
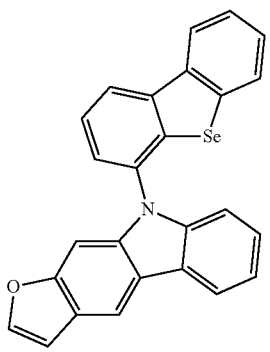

917
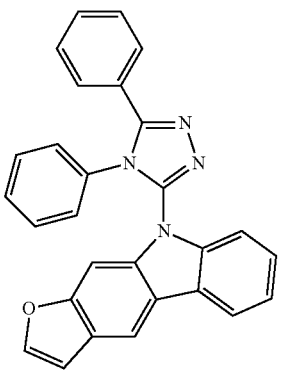
918
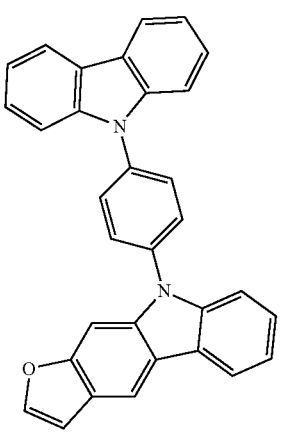
919
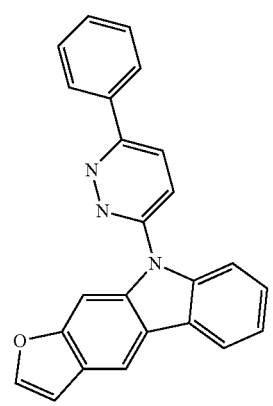
920
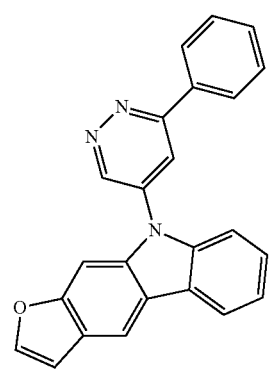
921
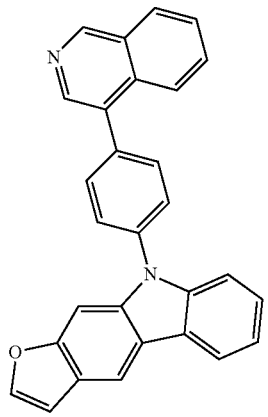
922
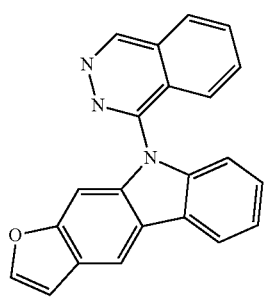
923
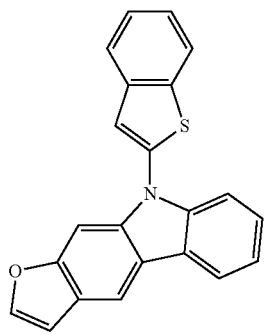
924
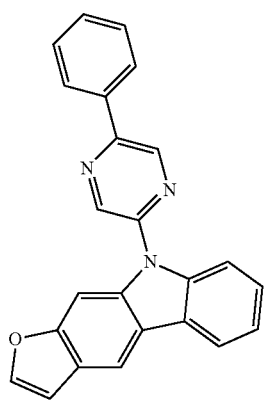

924
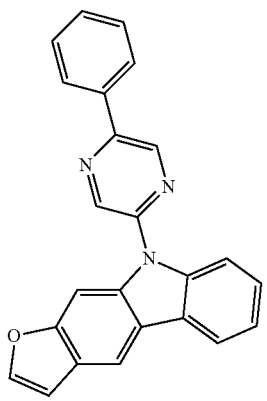
925
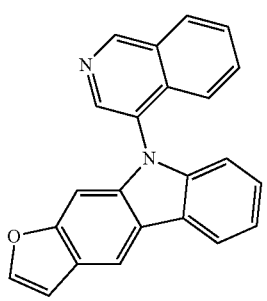
926
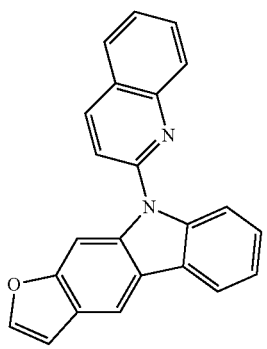
927
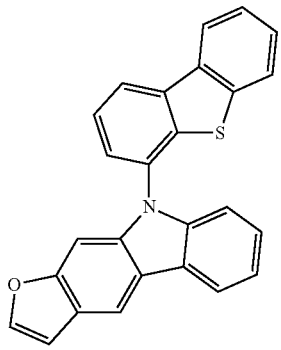
928
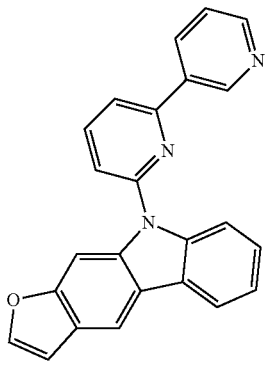
929
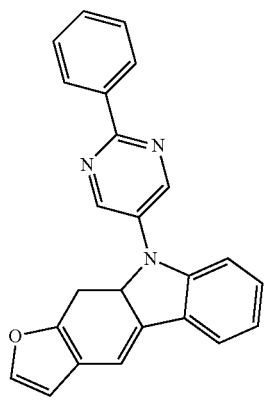
930
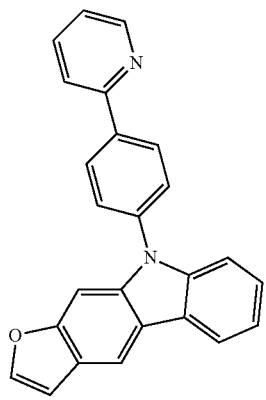
931
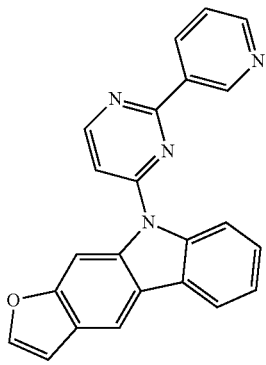

| 932 | 936 |
|---|---|
| 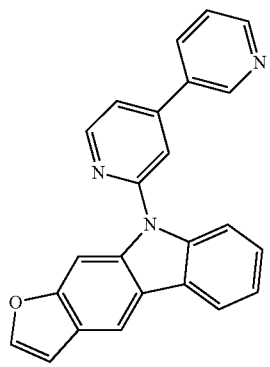 | 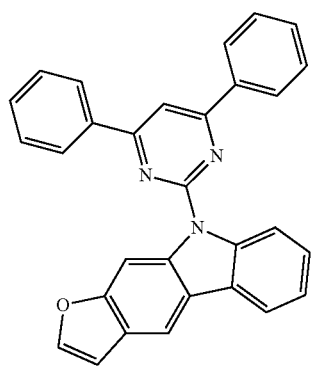 |
| 933 | 937 |
|---|---|
| 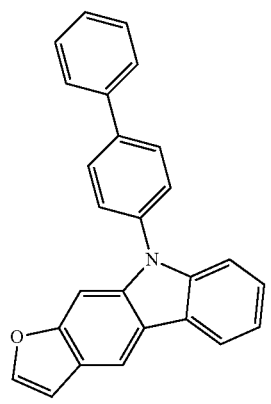 | 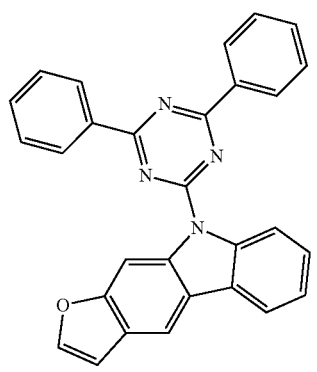 |
| 934 | 938 |
|---|---|
| 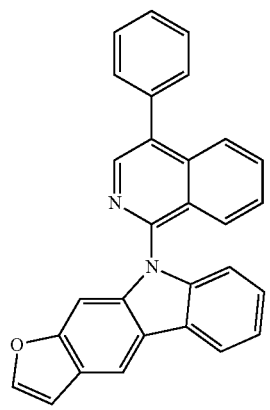 | 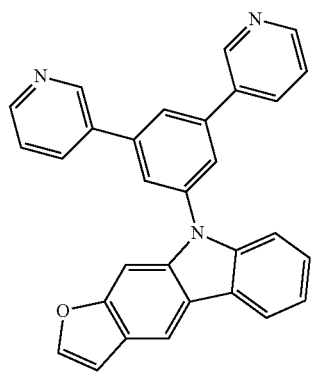 |
| 935 | 939 |
|---|---|
| 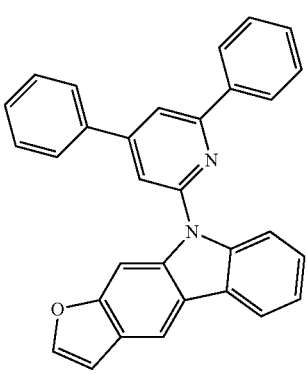 | 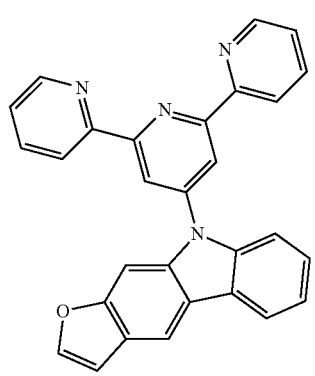 |

255
-continued
940
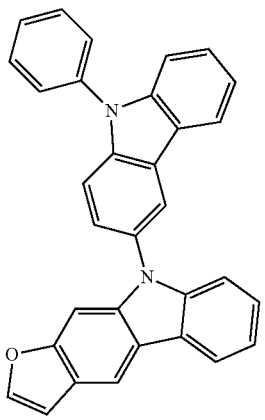
941
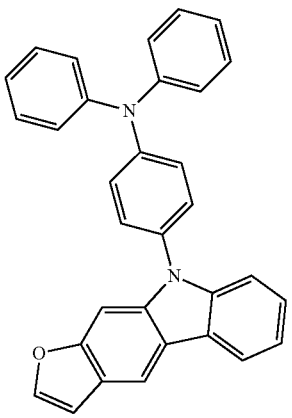
942
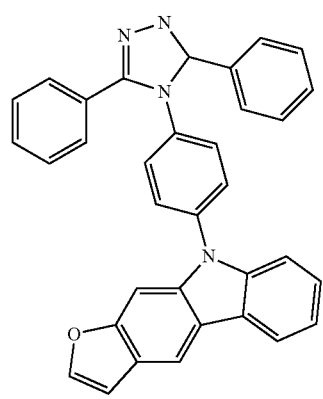
256
-continued
943
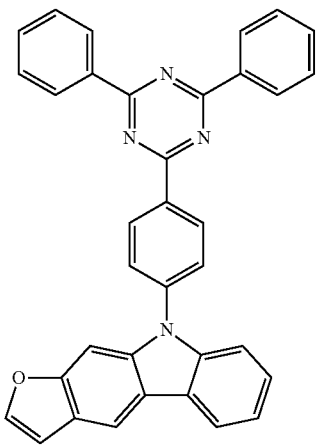
944
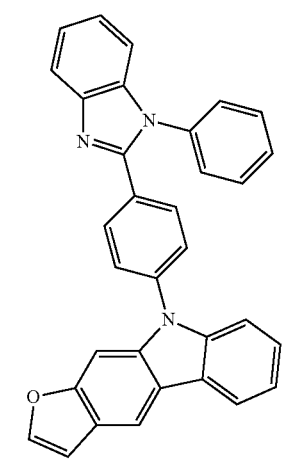
945
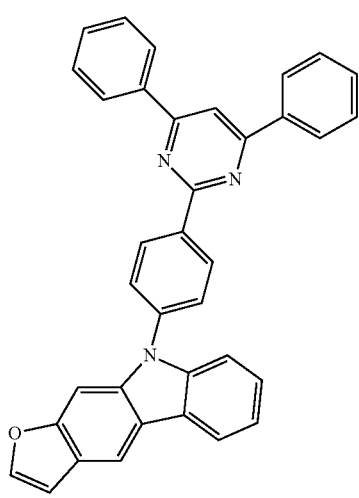

| 257 -continued | | 258 -continued | |
|---|---|---|---|
| 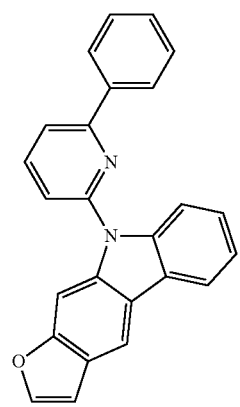 | 946 | 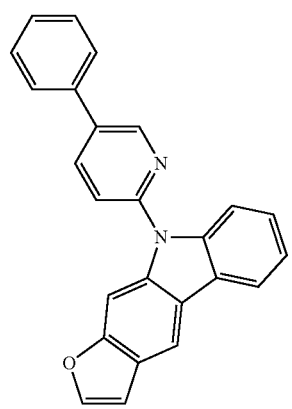 | 950 |
| 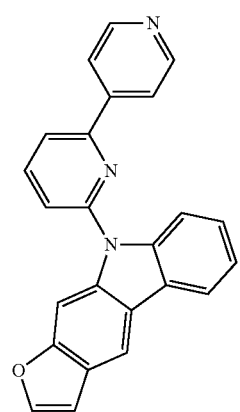 | 947 | 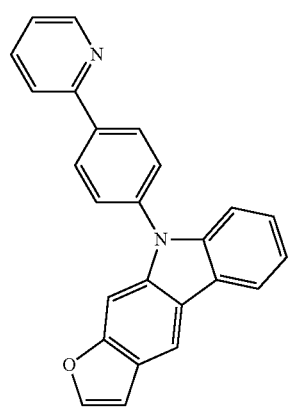 | 951 |
| 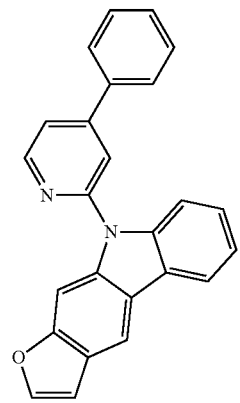 | 948 | 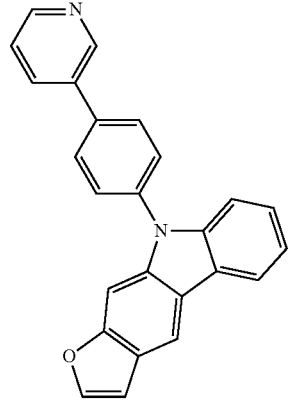 | 952 |
| 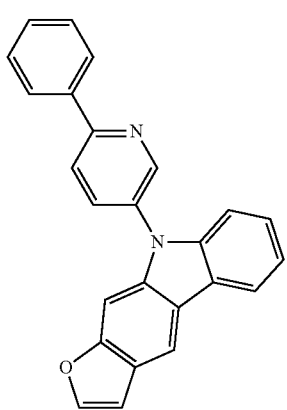 | 949 | 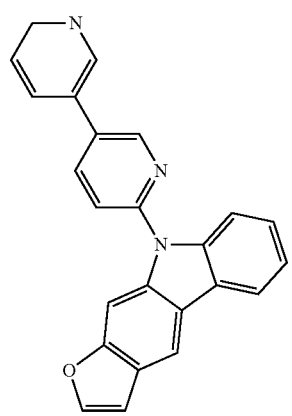 | 953 |

954

955
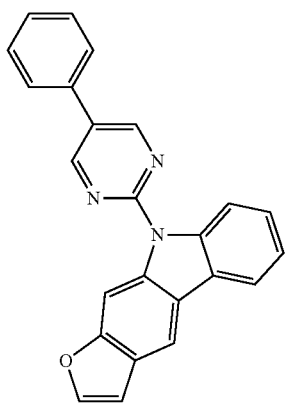
956
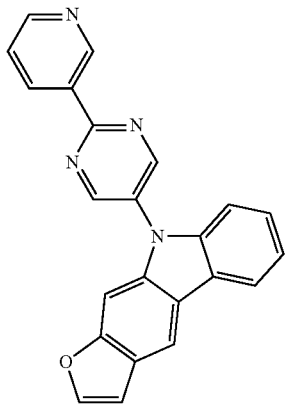
957
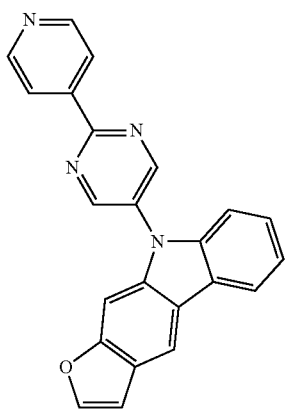
958
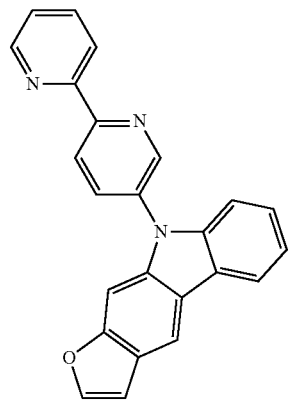
959
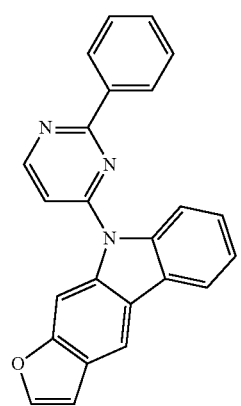
960
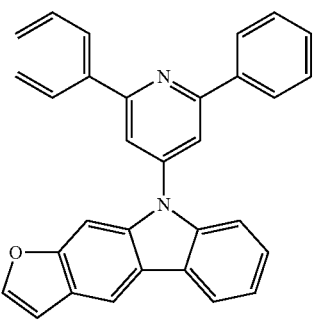
961
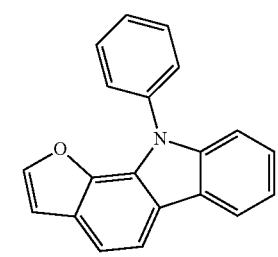

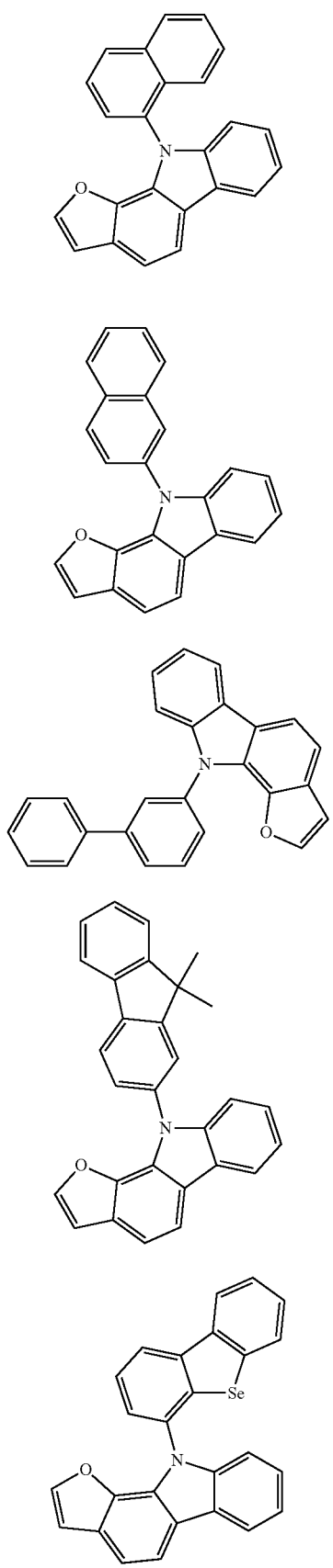

971
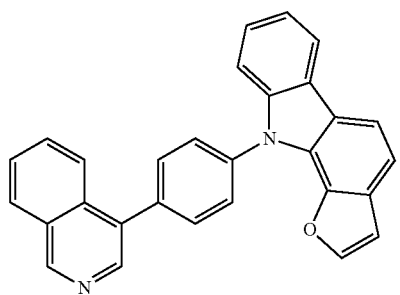
972
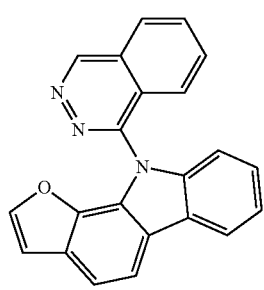
973
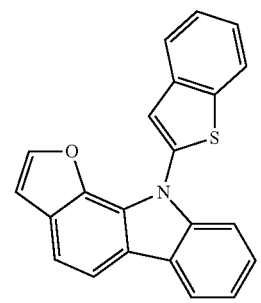
974
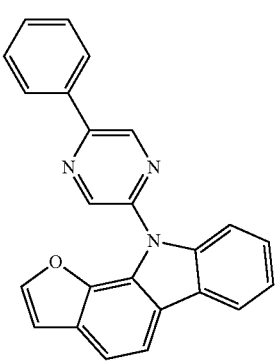
975
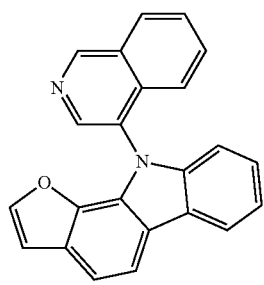
976
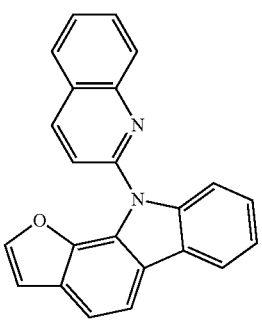
977
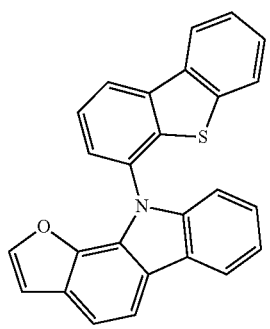
978
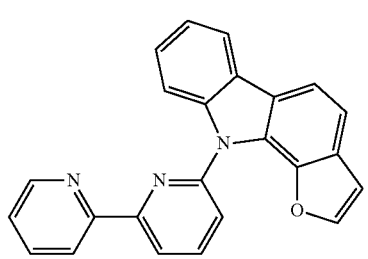
979
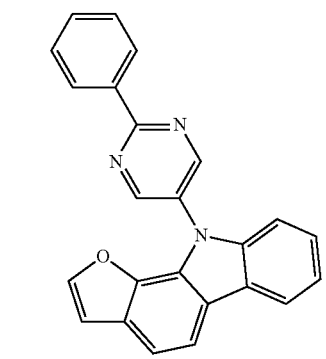
980
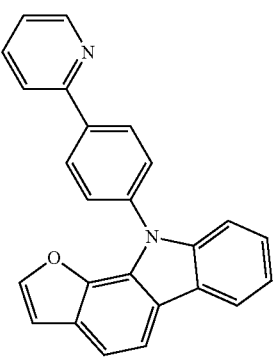

| 981 | 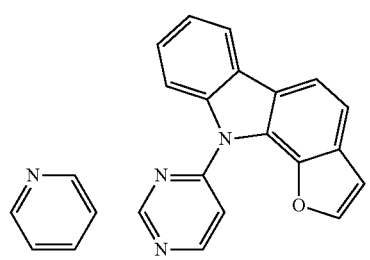 | 986 | 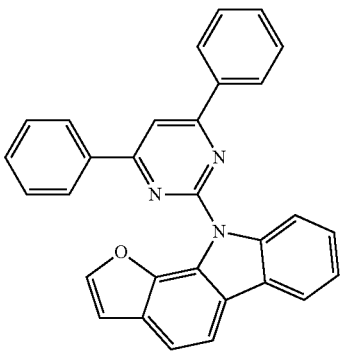 |
| 982 | 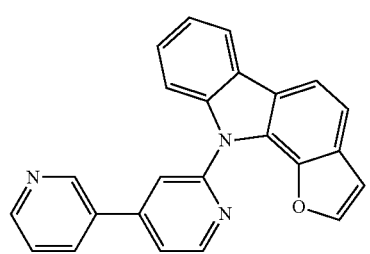 | 987 | 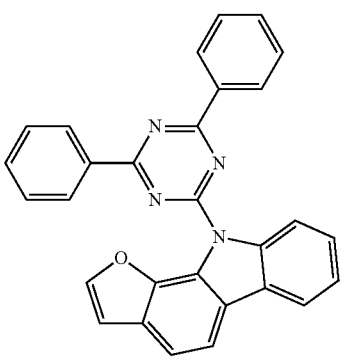 |
| 983 | 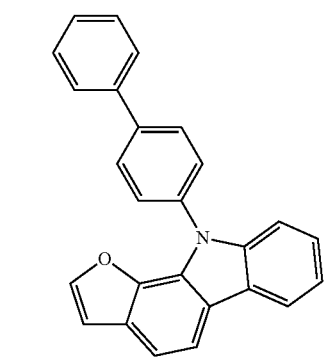 | 988 | 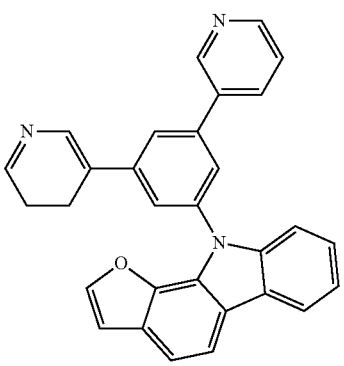 |
| 984 | 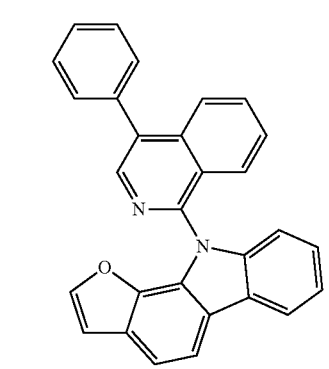 | 989 | 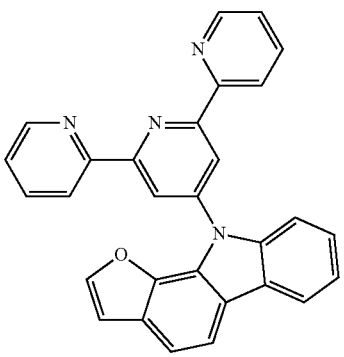 |
| 985 | 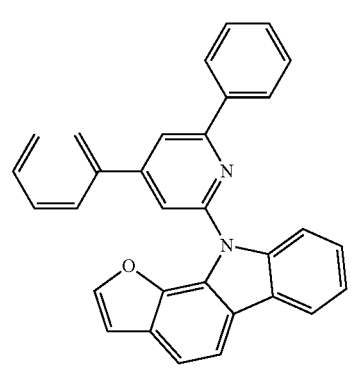 | | |

267
-continued
990
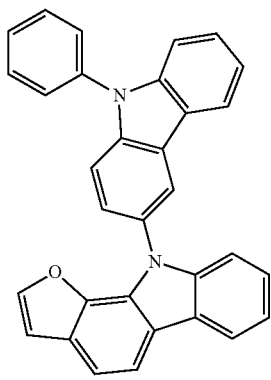
991
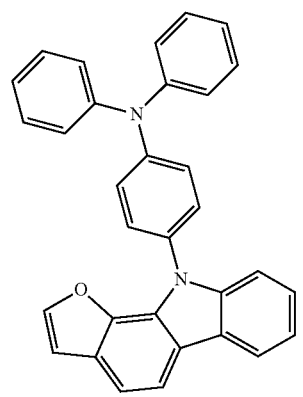
992
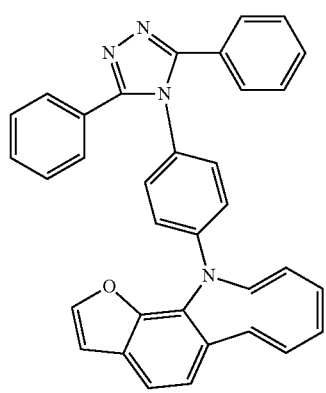
993
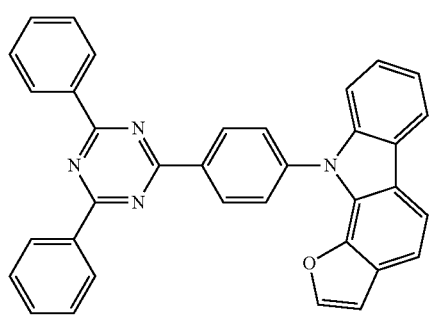
268
-continued
994
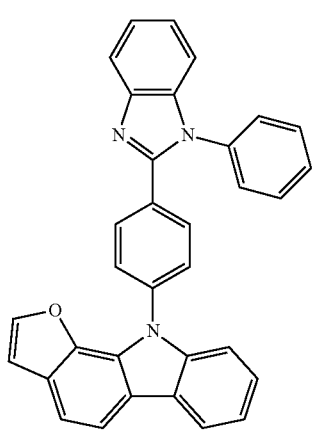
995
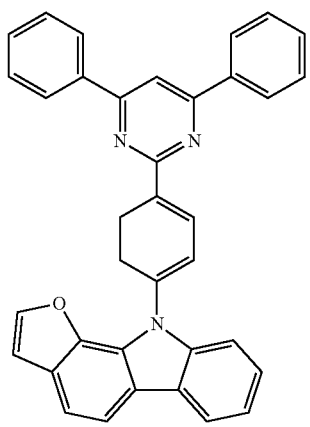
996
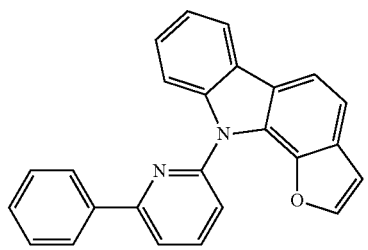
997
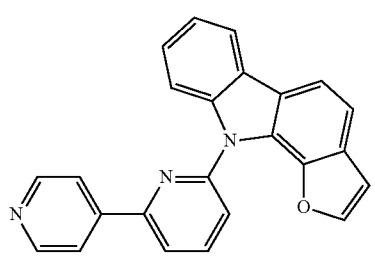
998
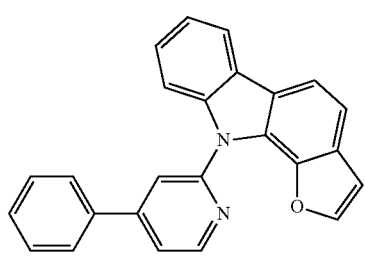

-continued
999
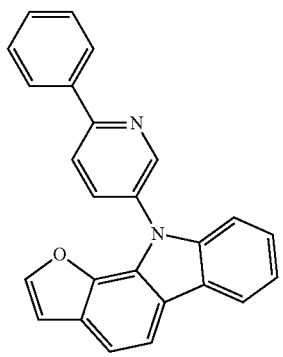
1000
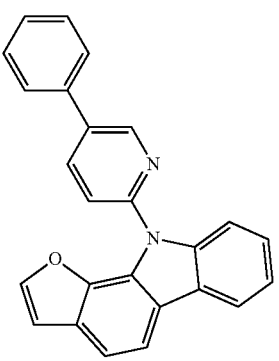
1001
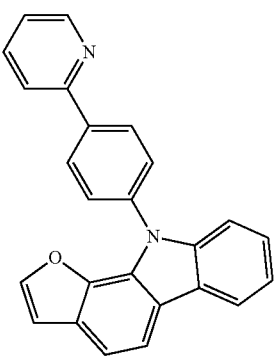
1002
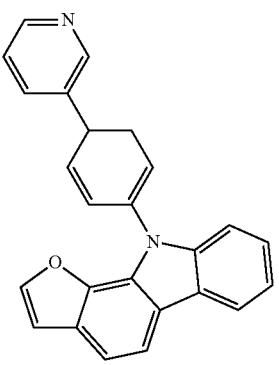
-continued
1003
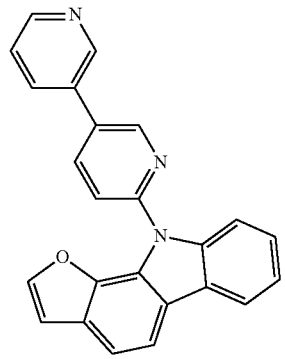
1004
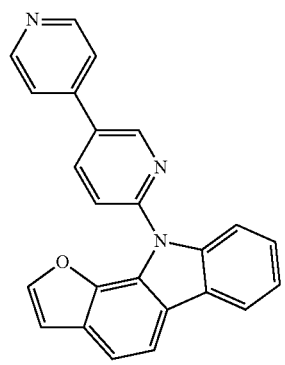
1005
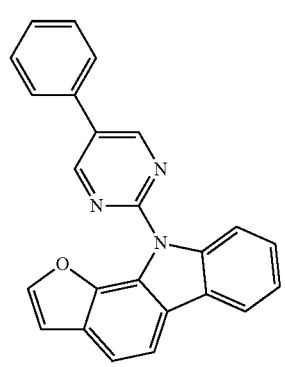
1006
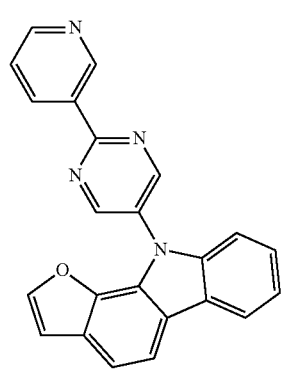

1007 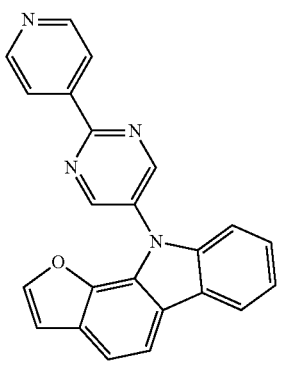
1008 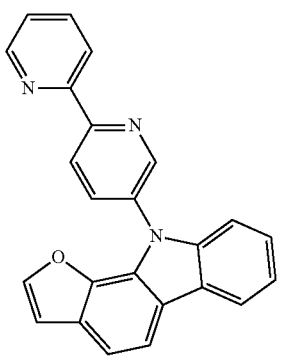
1009 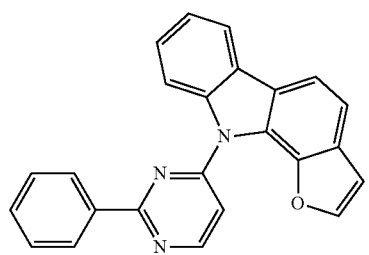
1010 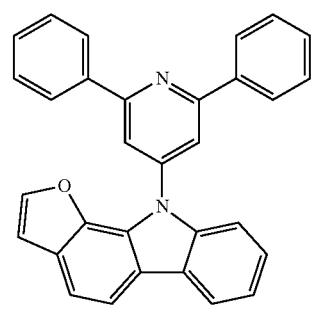
1011 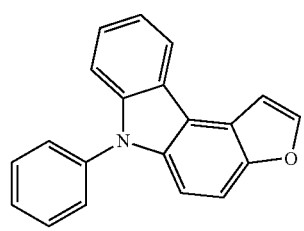
1012 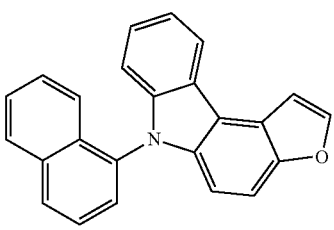
1013 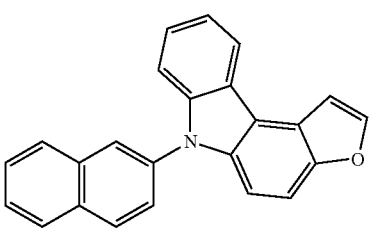
1014 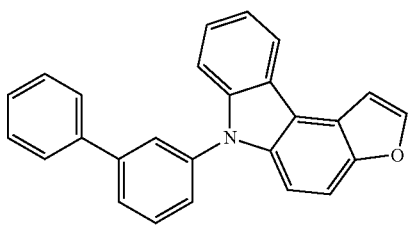
1015 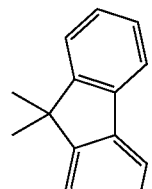 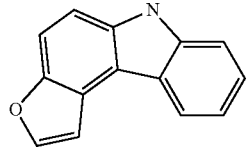
1015 (cont.) 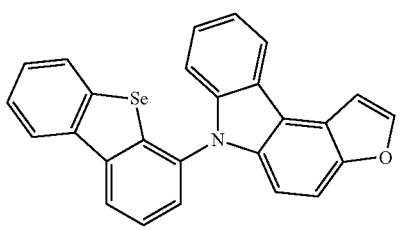
1016 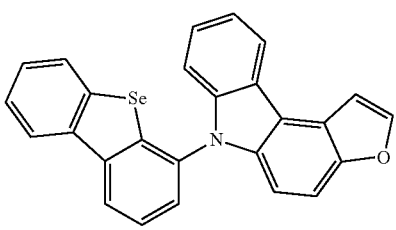

273
-continued
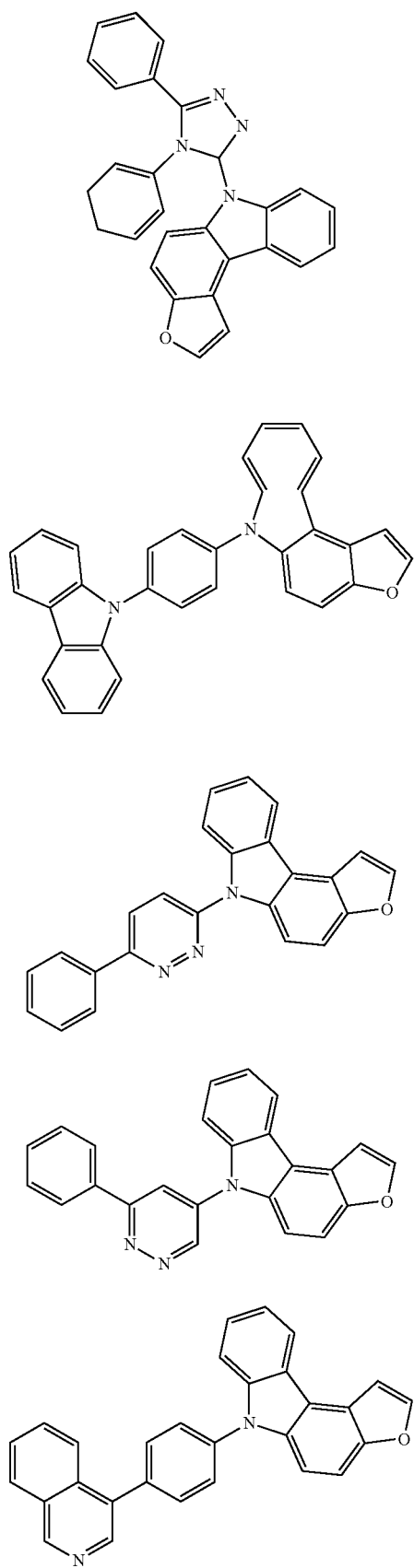
274
-continued
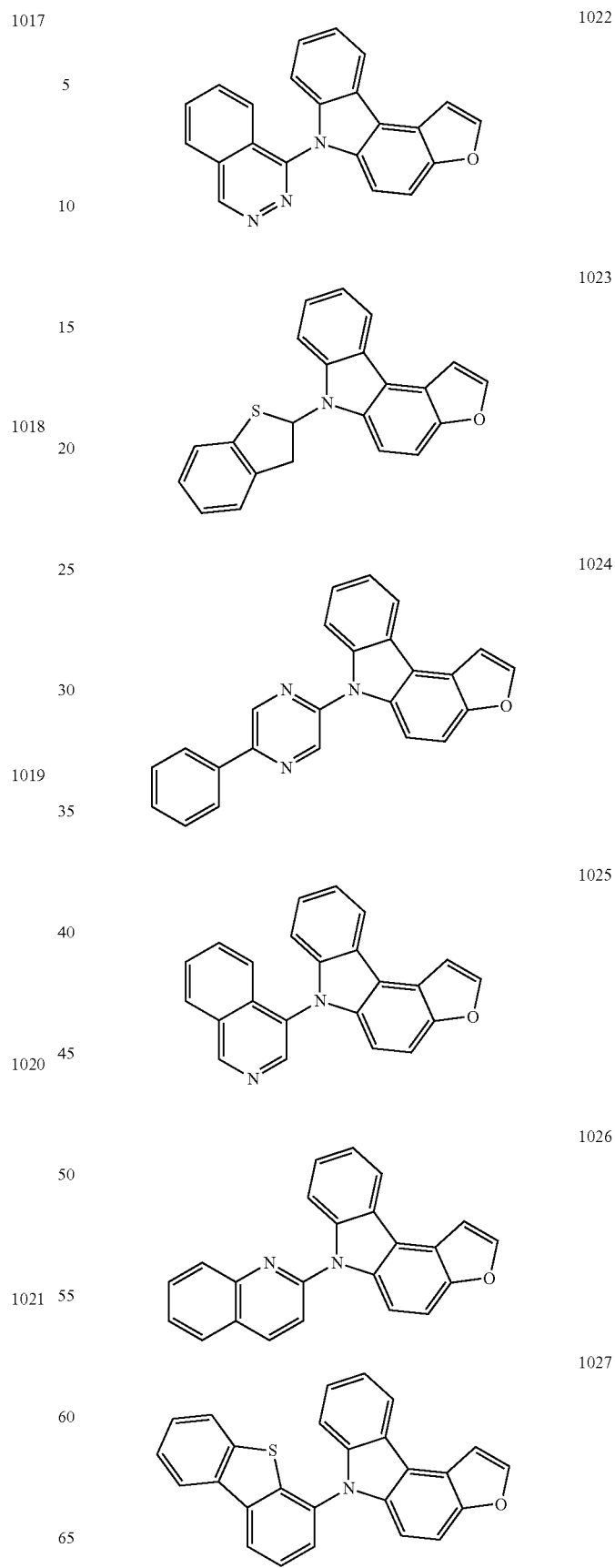

1028
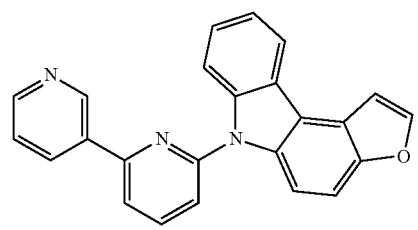
1029
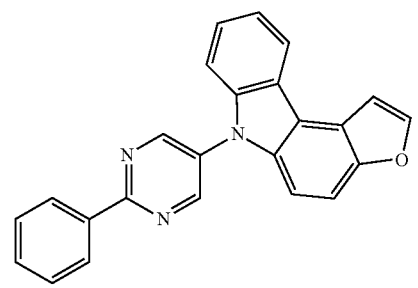
1030
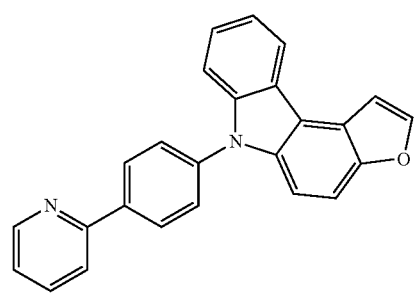
1031
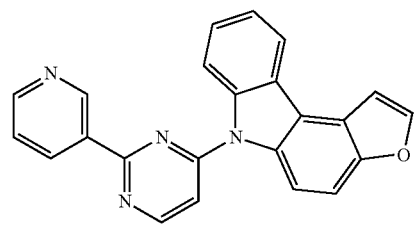
1032
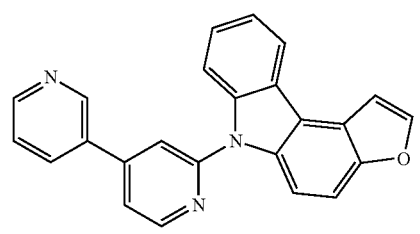
1033
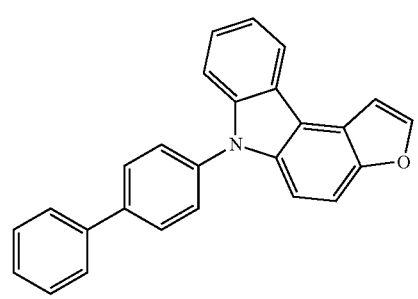
1034
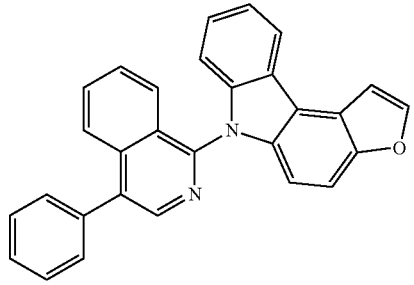
1035
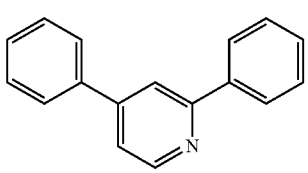
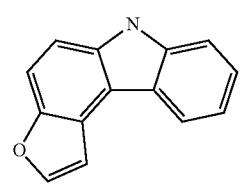
1036
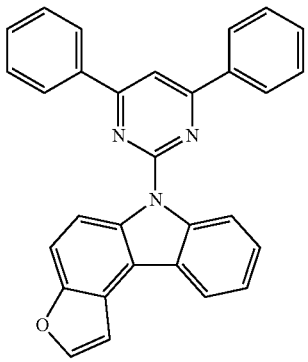
1037
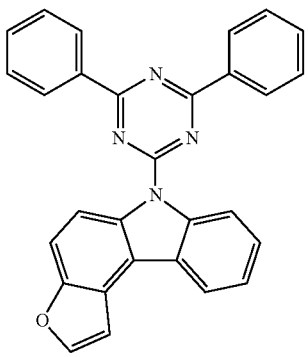

1038 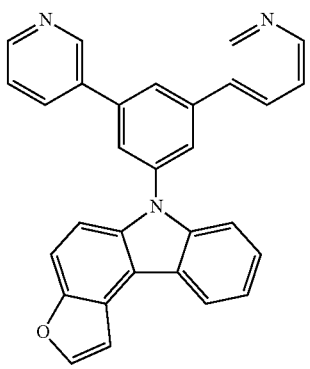
1039 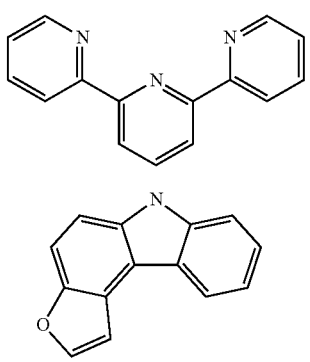
1040 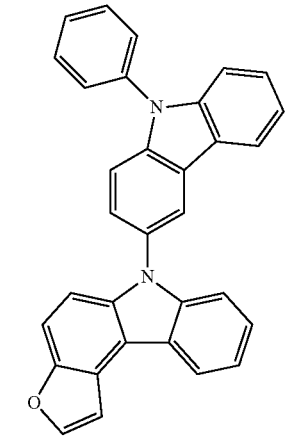
1041 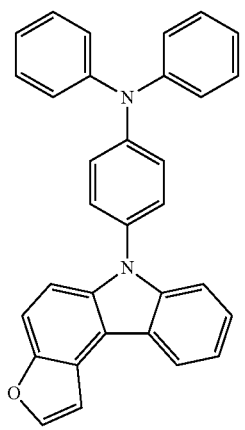
1042 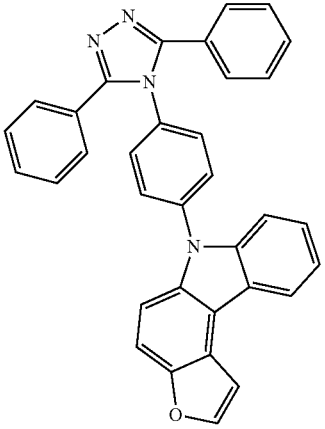
1043 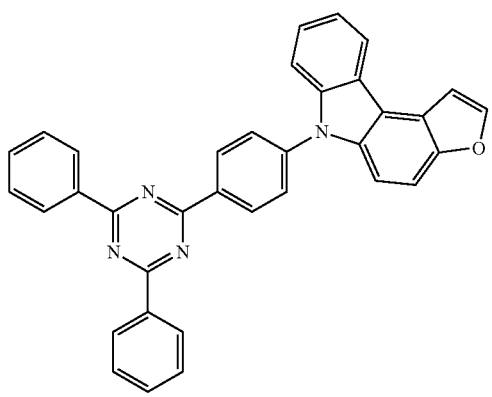
1044 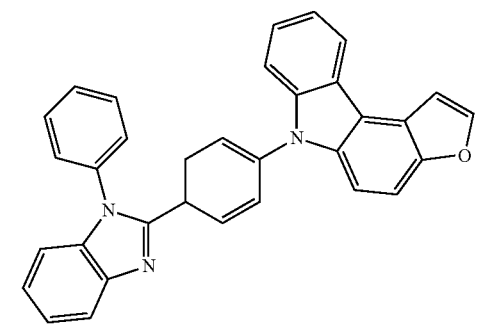
1045 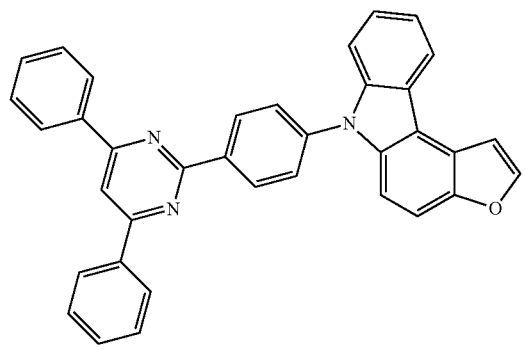

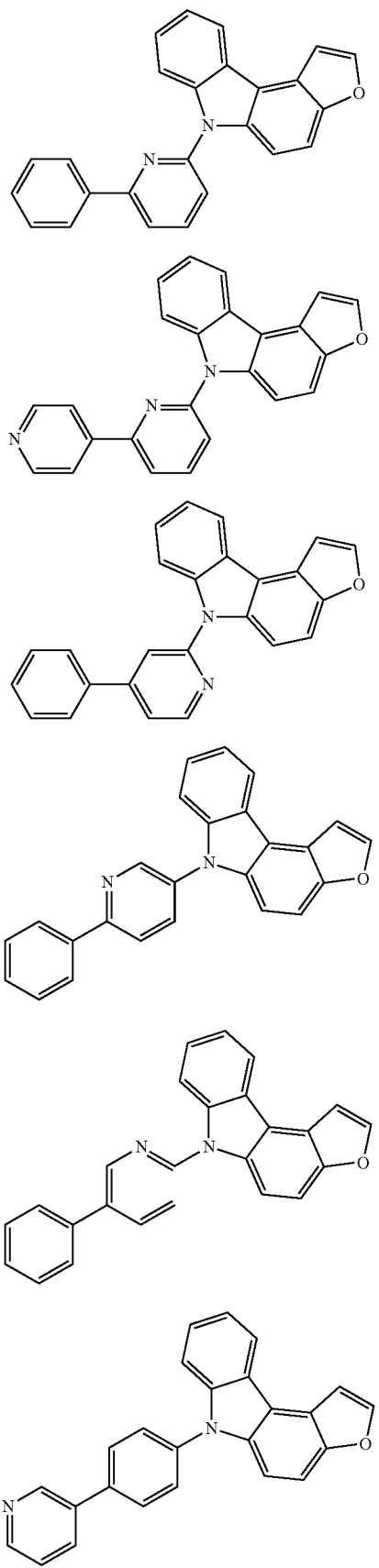
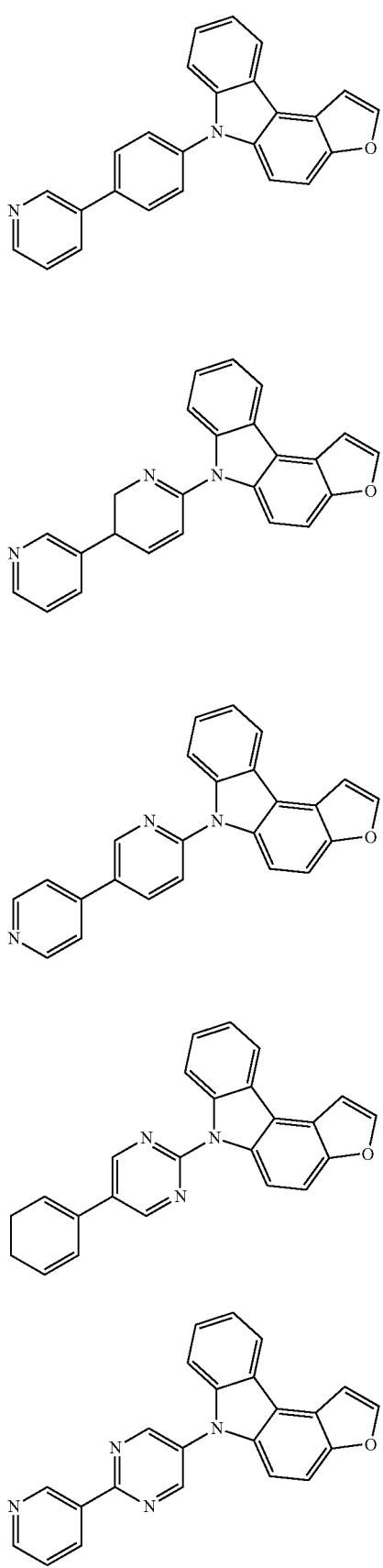

1057 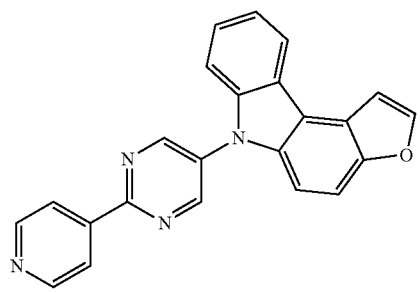
1058 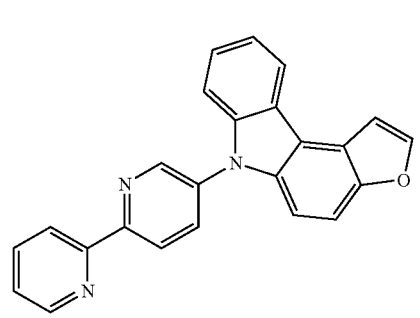
1059 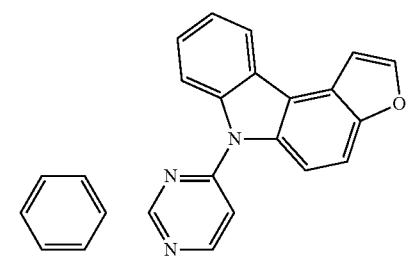
1060 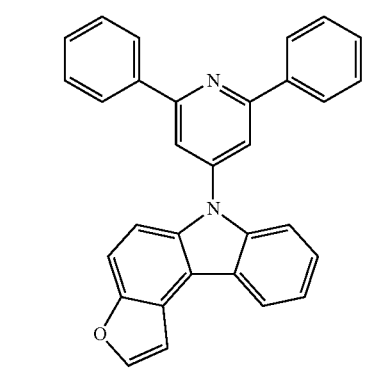
1061 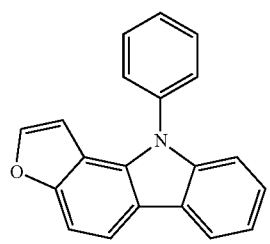
1062 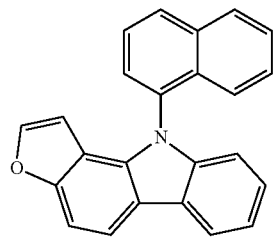
1063 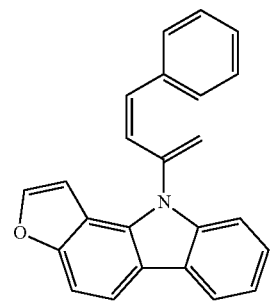
1064 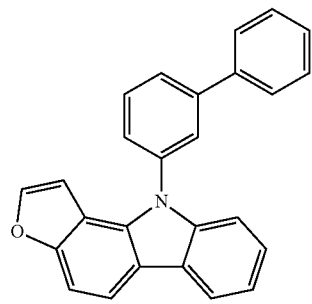
1065 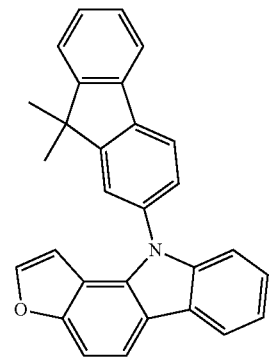
1066 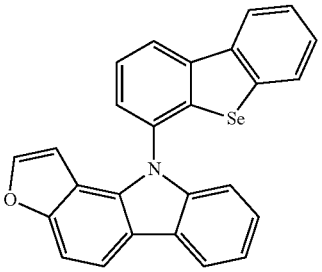

| 1067 | 1072 |
|---|---|
| 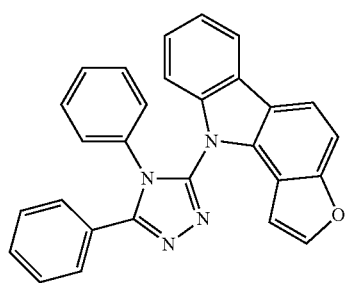 | 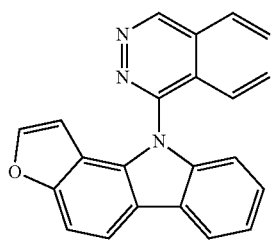 |
| 1068 | 1073 |
| 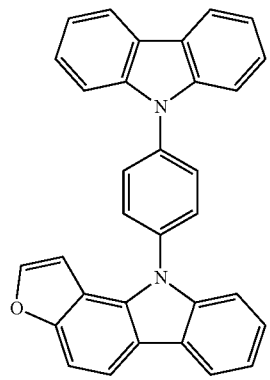 | 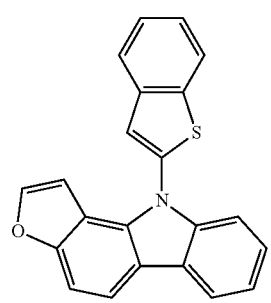 |
| 1069 | 1074 |
| 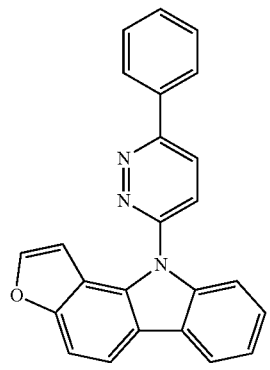 | 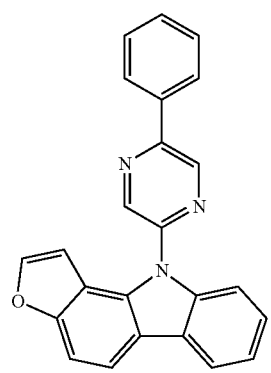 |
| 1070 | 1075 |
| 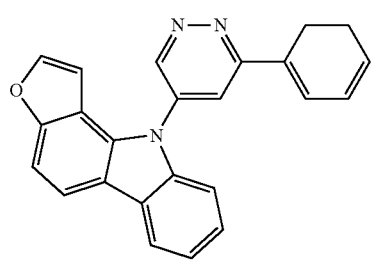 | 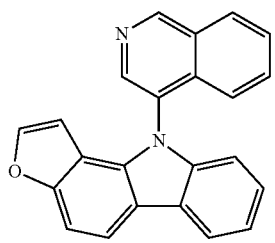 |
| 1071 | 1076 |
| 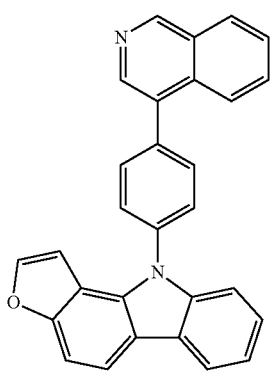 | 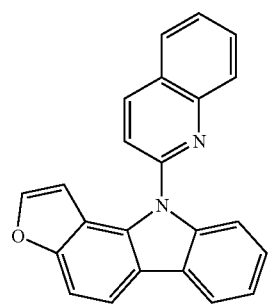 |

1077 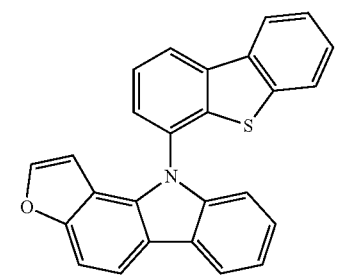
1078 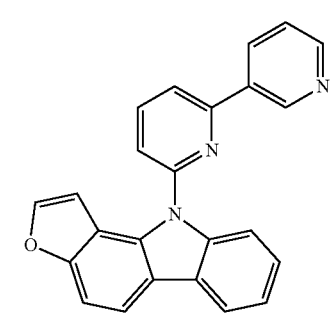
1079 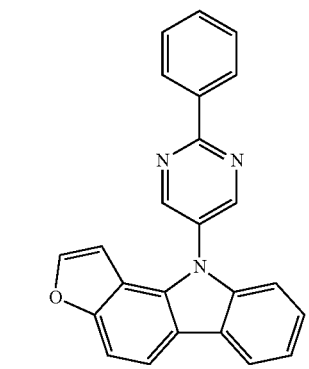
1080 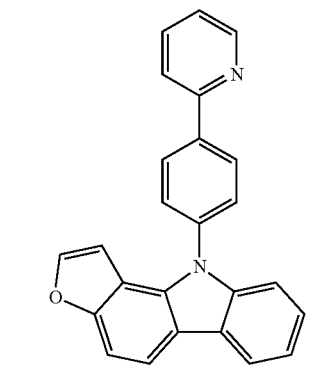
1081 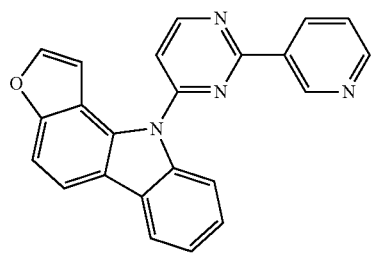
1082 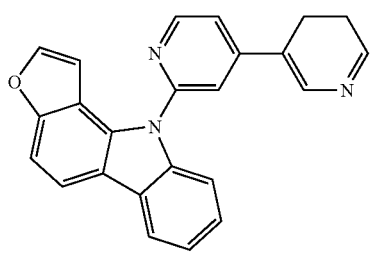
1083 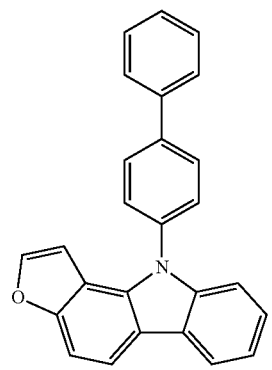
1084 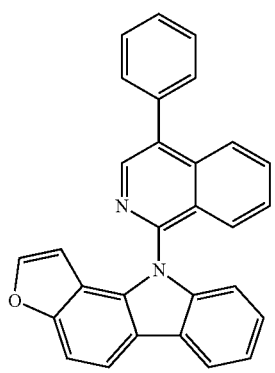
1085 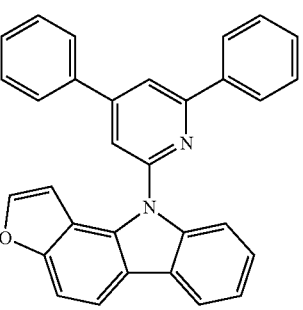
1086 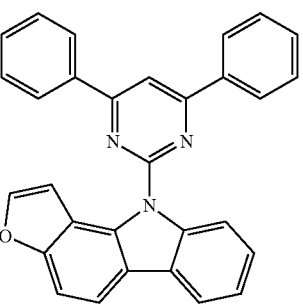

-continued
1087
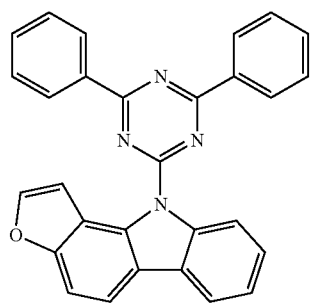
1088
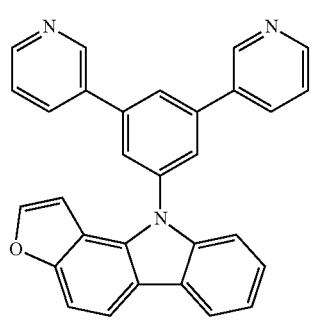
1089
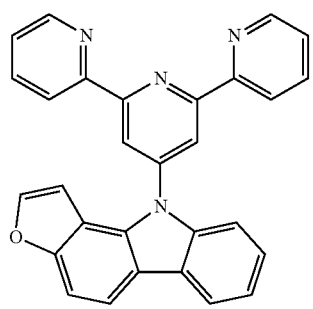
1090
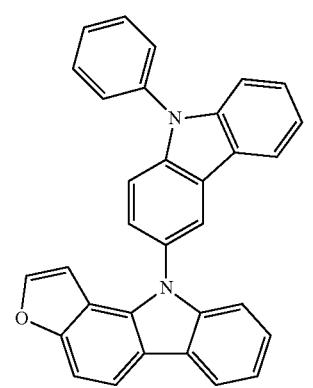
-continued
1091
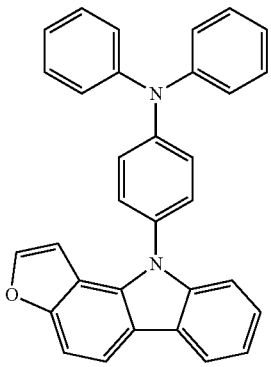
1092
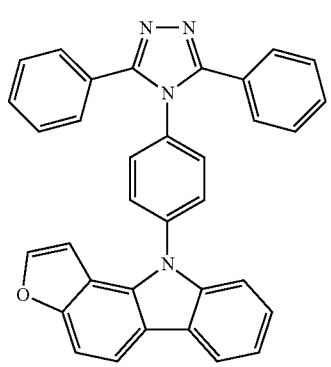
1093
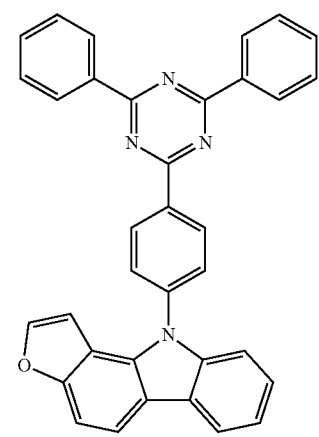
1094
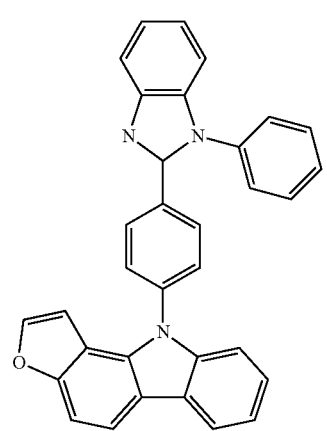

1095 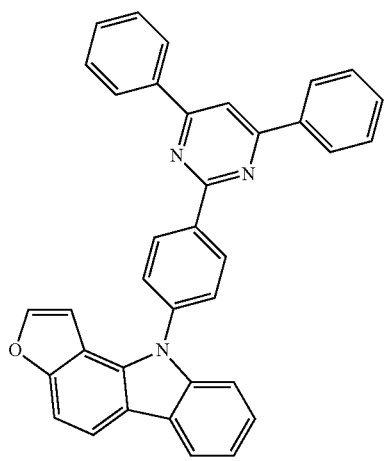
1096 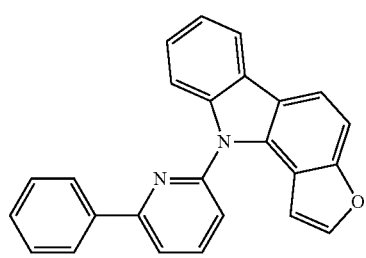
1097 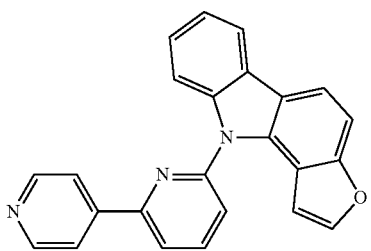
1098 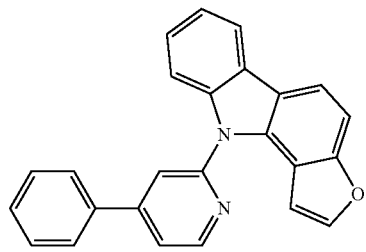
1099 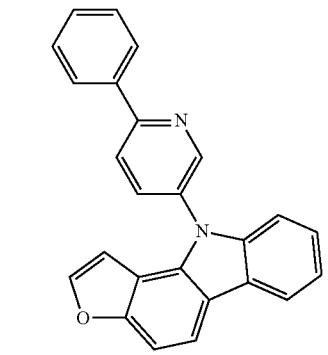
1100 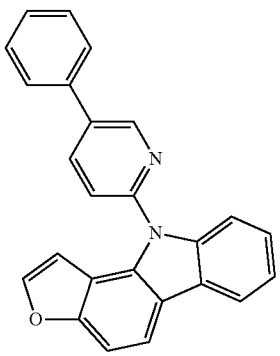
1101 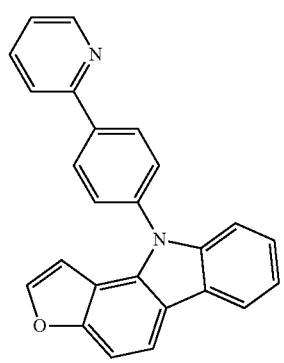
1102 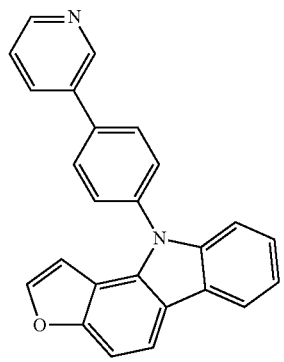
1103 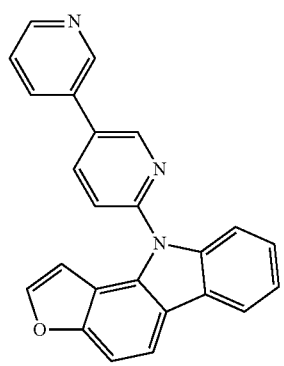

1104
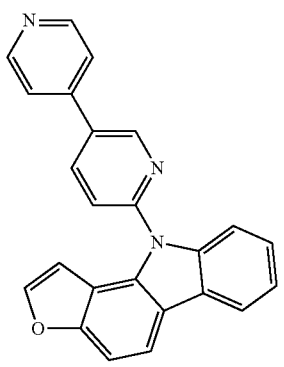
1105
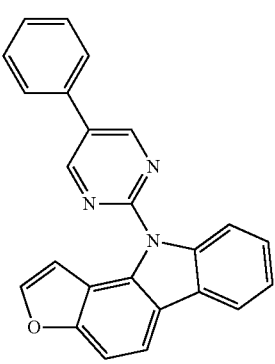
1106
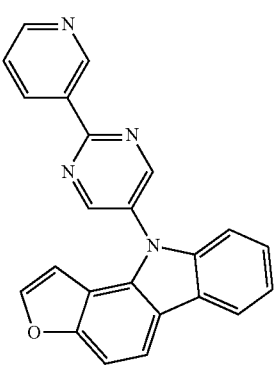
1107
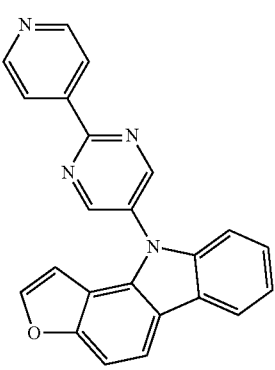
1108
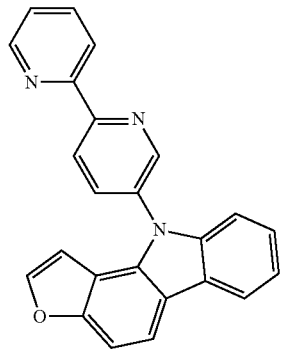
1109
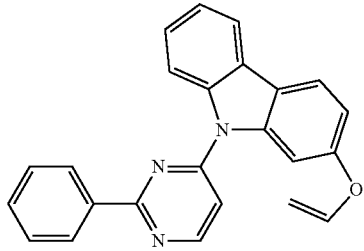
1110
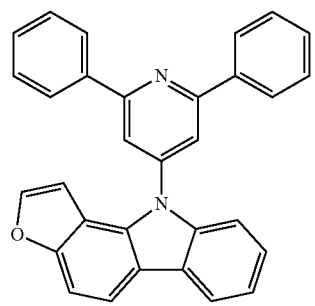
1111
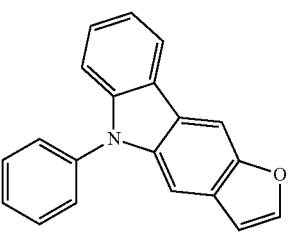
1112
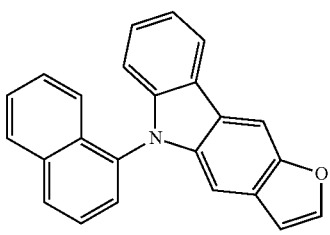
1113
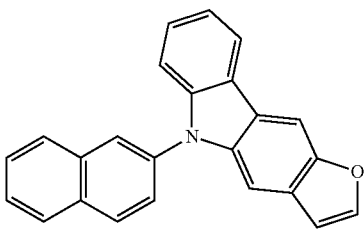

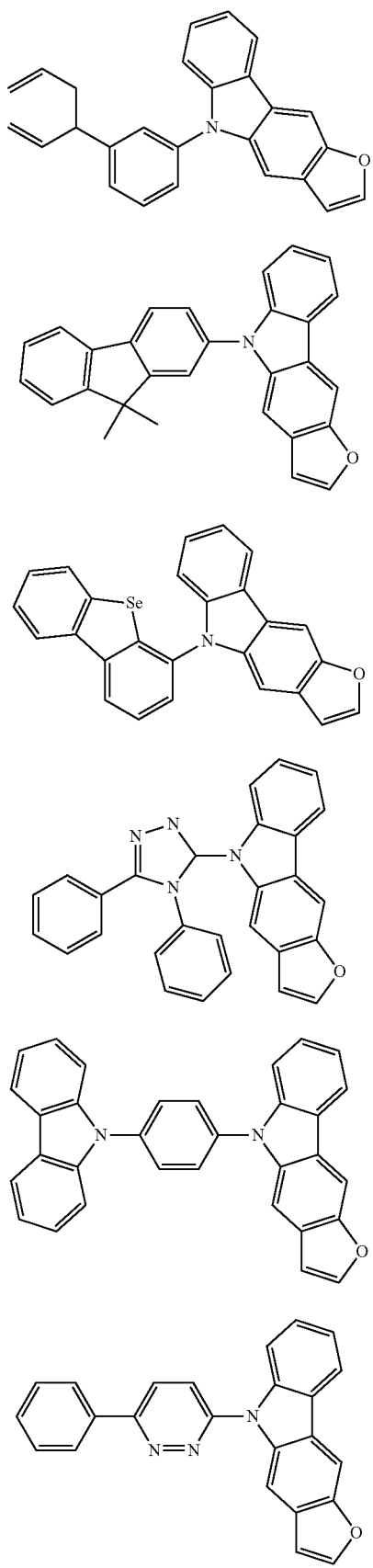
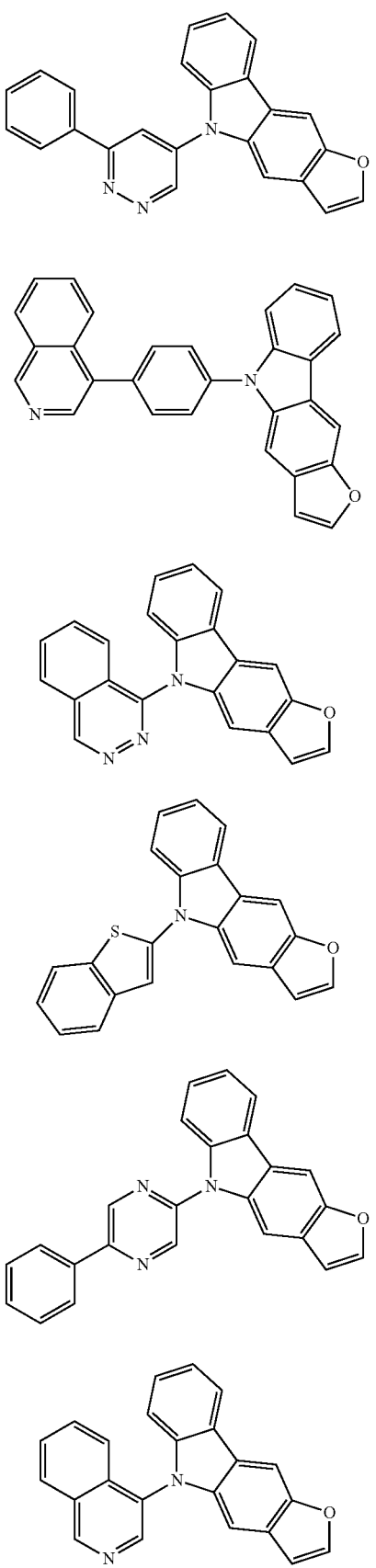

295
-continued
1126
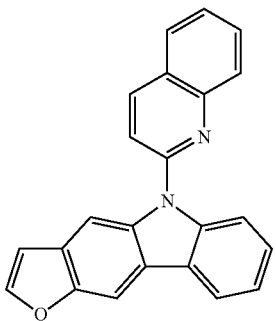
1127
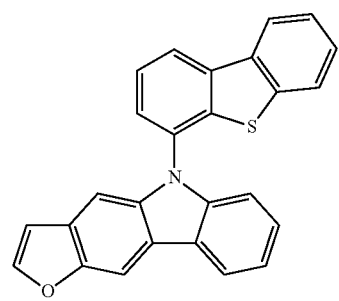
1128
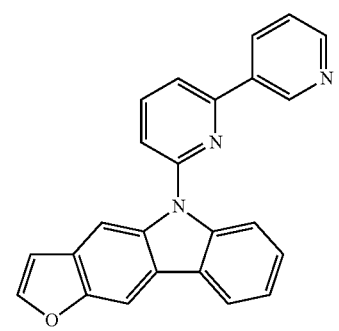
1129
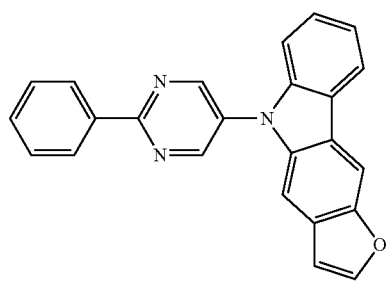
1130
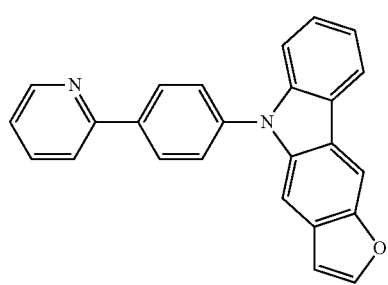
296
-continued
1131
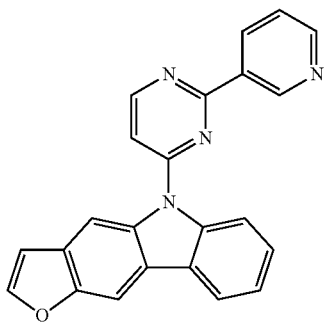
1132
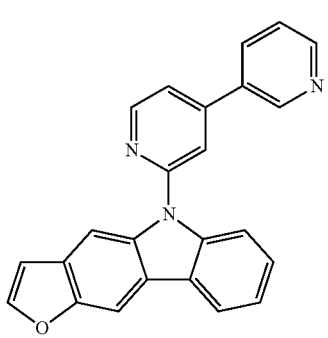
1133
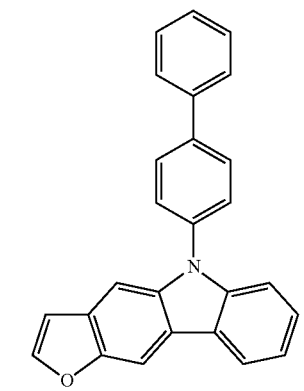
1134
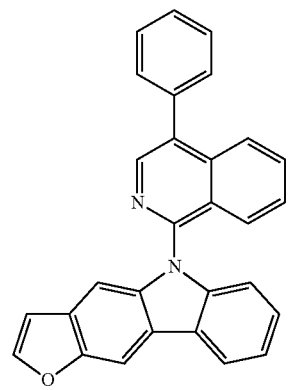

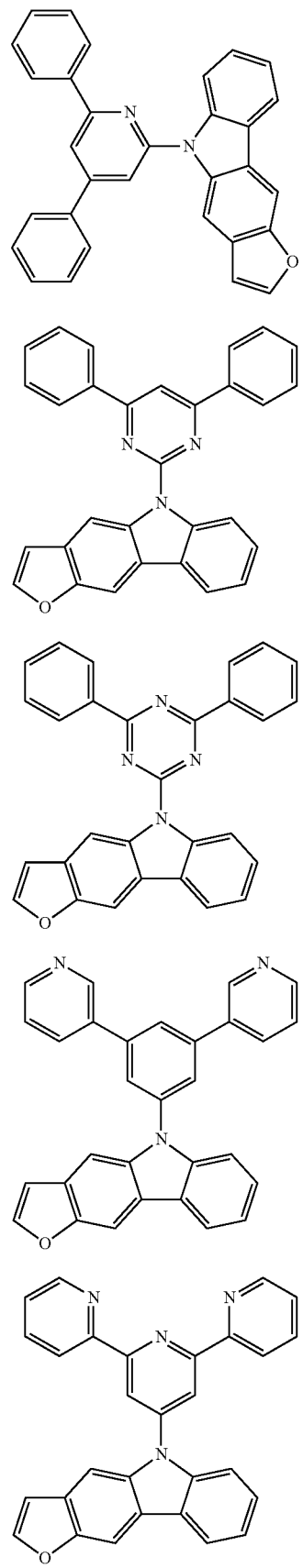
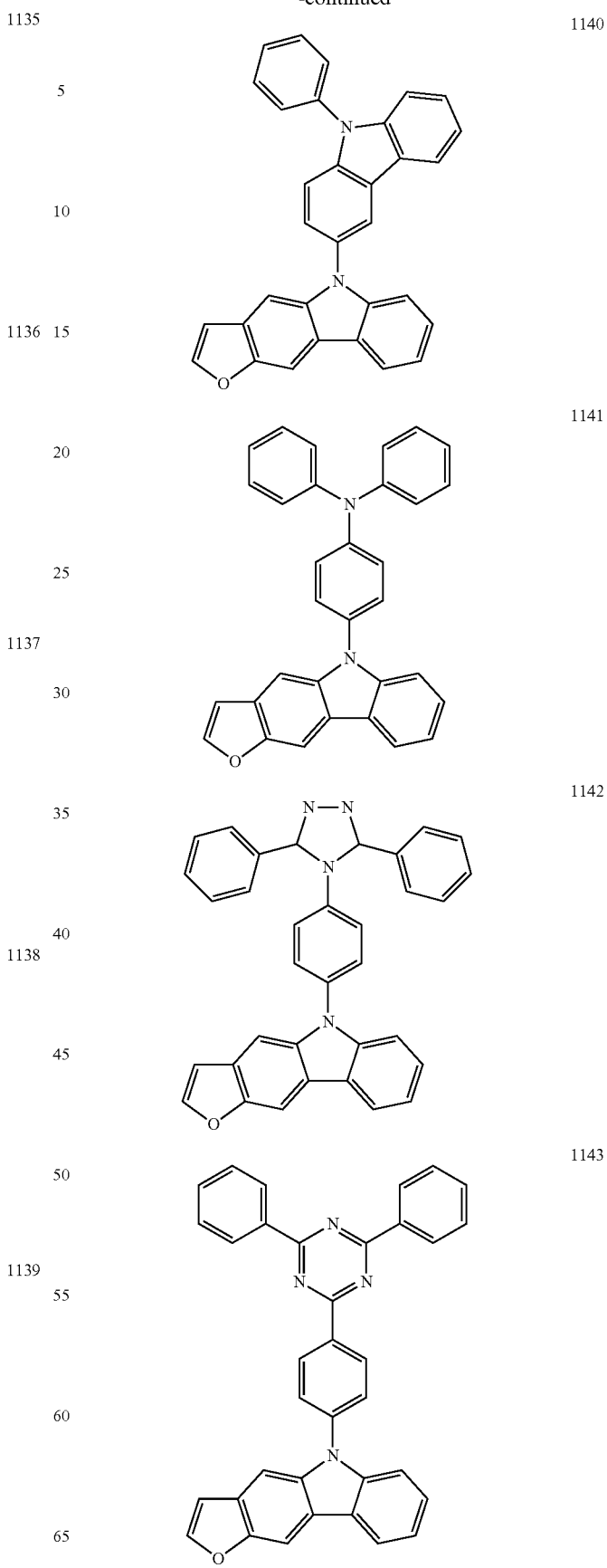

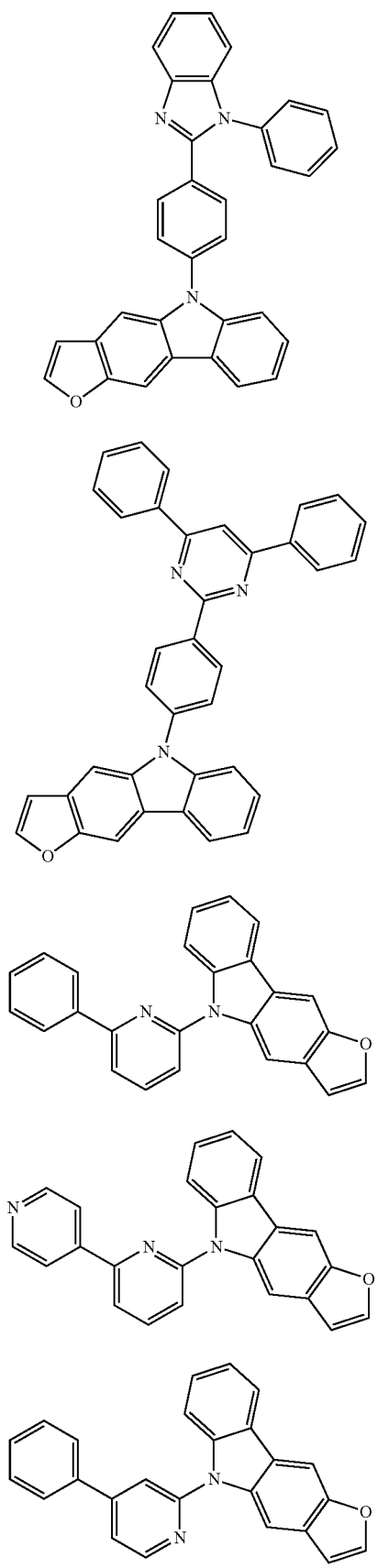

301
-continued
1153
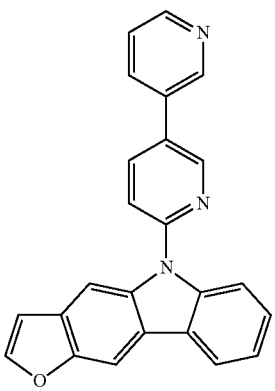
1154
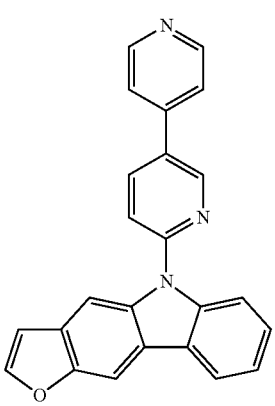
1155
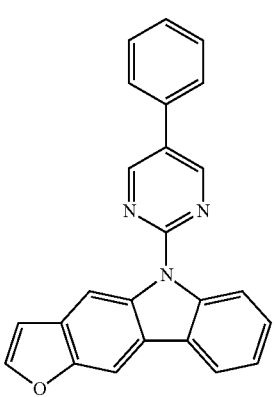
1156
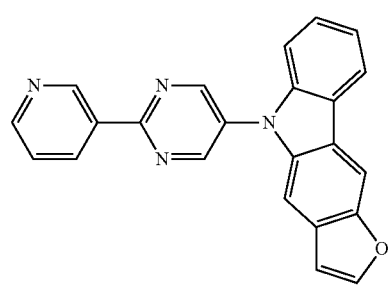
302
-continued
1157
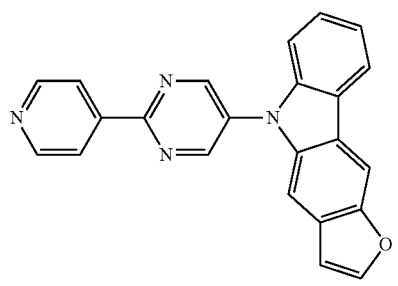
1158
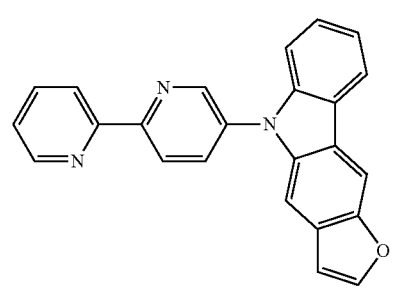
1159
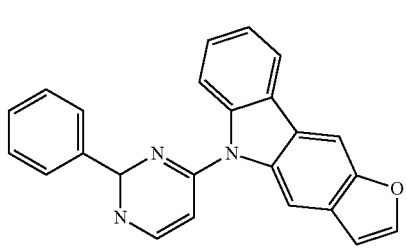
1160
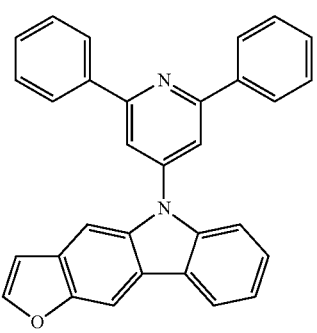
1161
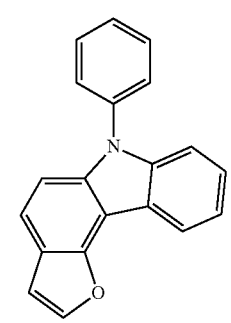

303
-continued
| | |
|---|---|
| 1162 | 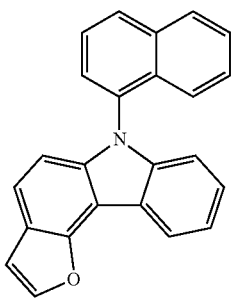 |
| 1163 | 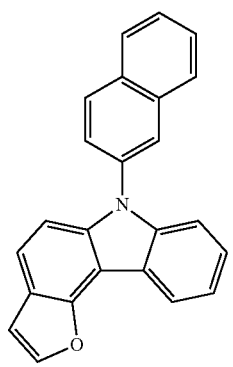 |
| 1164 | 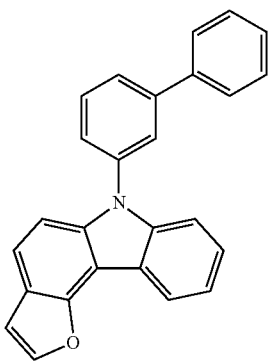 |
| 1165 | 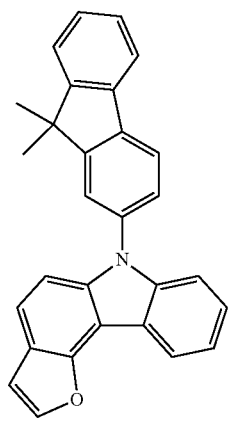 |
304
-continued
| | |
|---|---|
| 1166 | 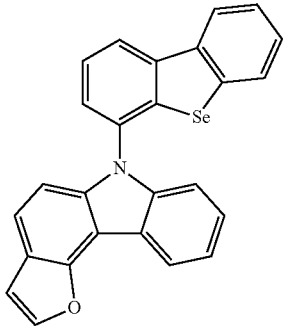 |
| 1167 | 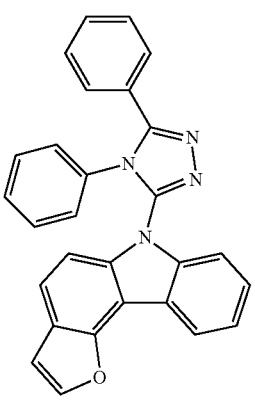 |
| 1168 | 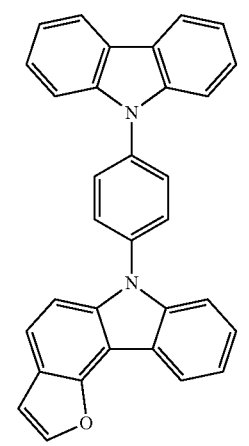 |
| 1169 | 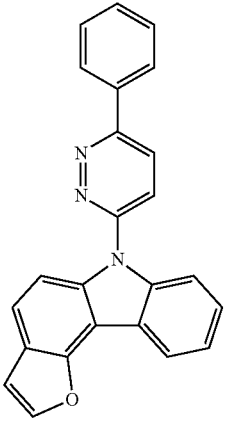 |

1170 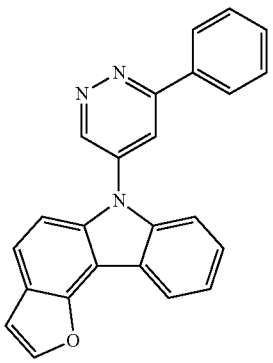
1171 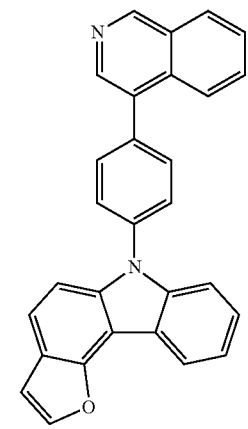
1172 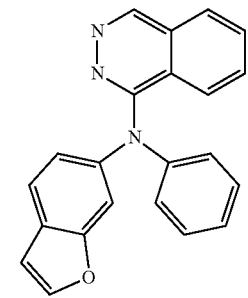
1173 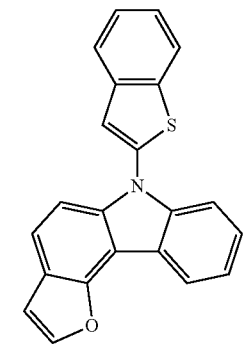
1174 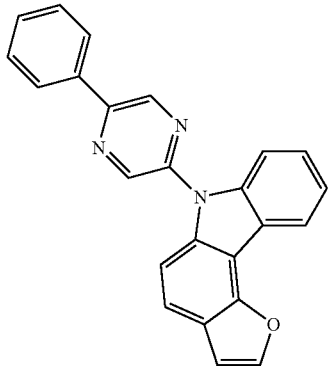
1174 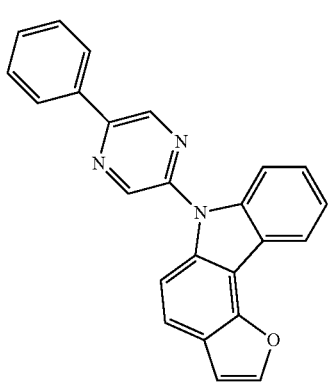
1175 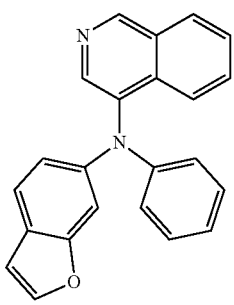
1176 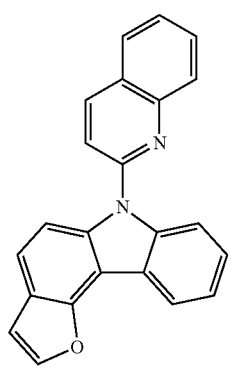

307
-continued
1177
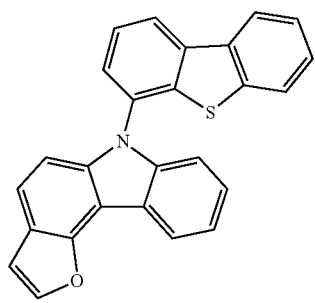
1178
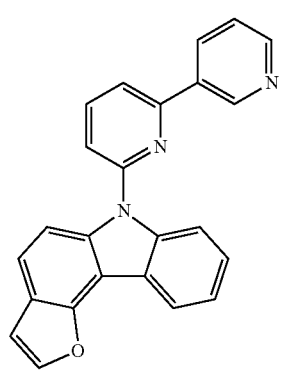
1179
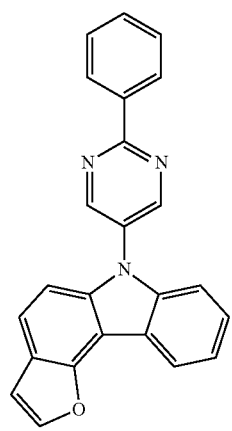
1180
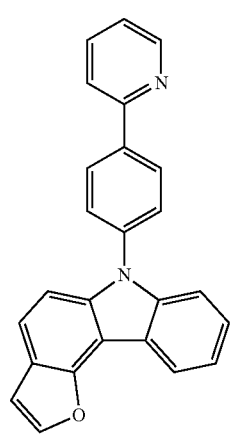
308
-continued
1181
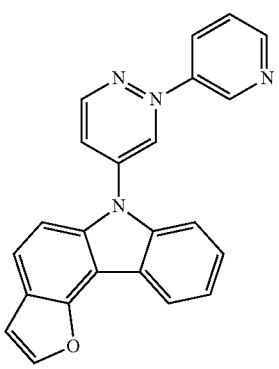
1182
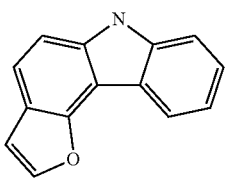
1183
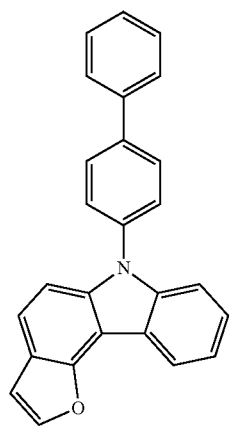
1184
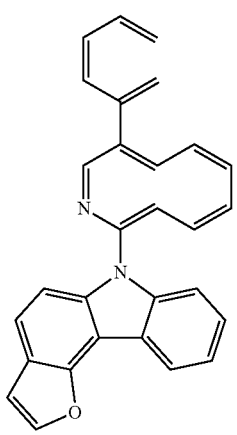

US 10,038,146 B2
309
-continued
1185
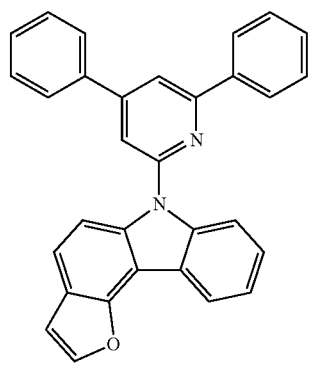
1186
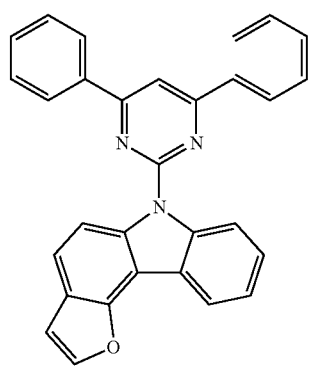
1187
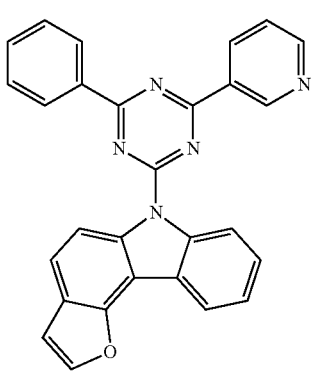
1188
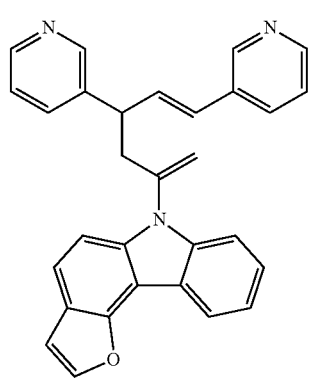
310
-continued
1189
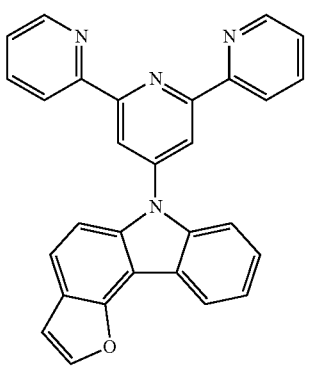
1190
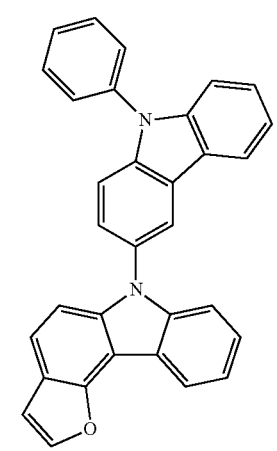
1191
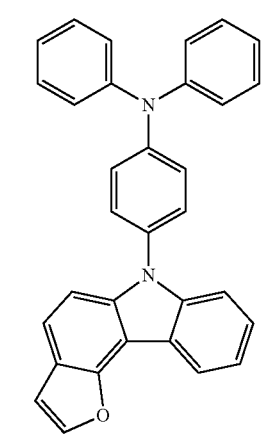
1192
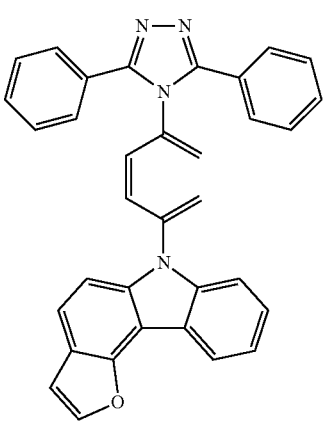

311
-continued
1193
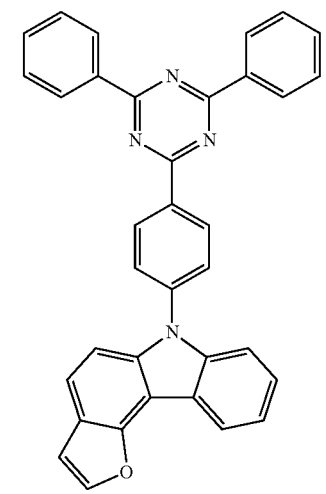
1194
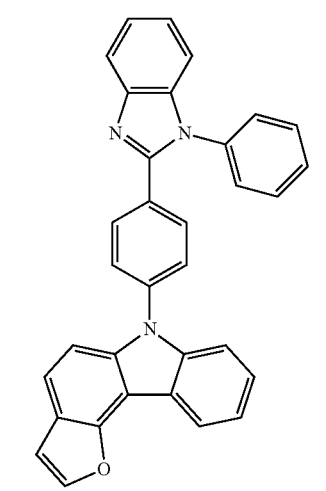
1195
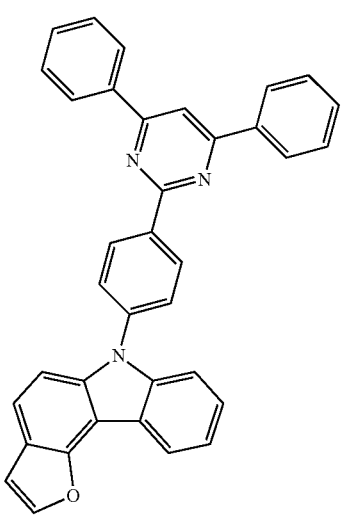
312
-continued
1196
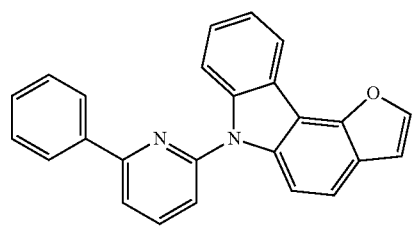
1197
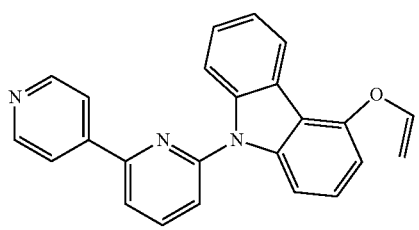
1198
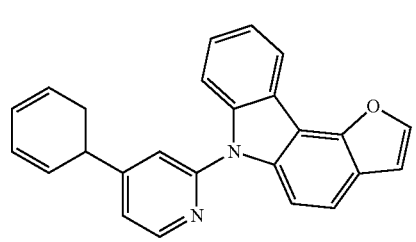
1199
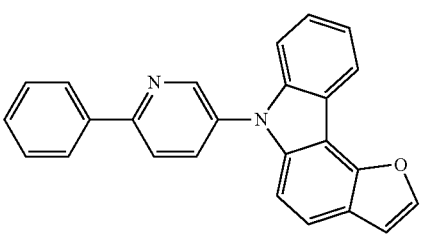
1200
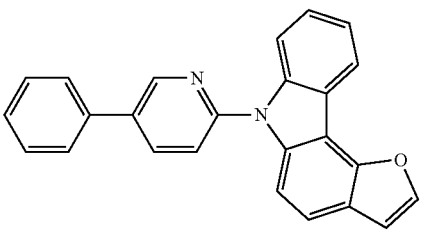
1201
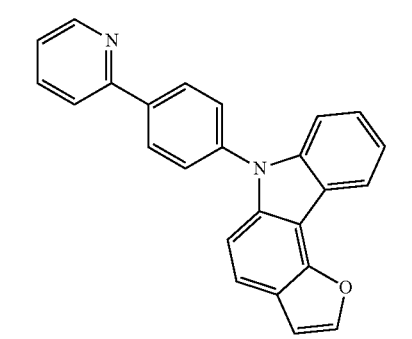

313
-continued
1202
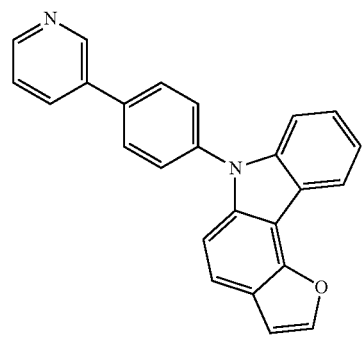
1203
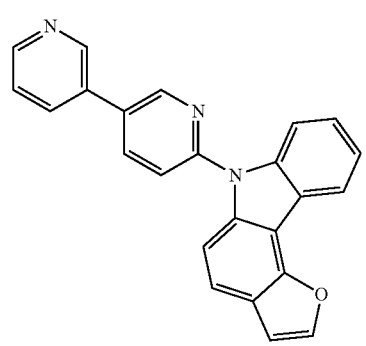
1204
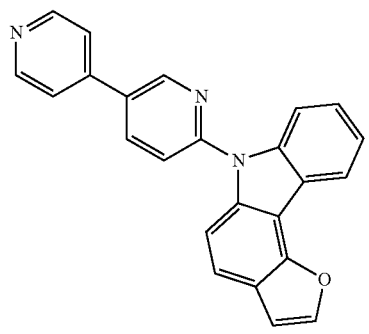
1205
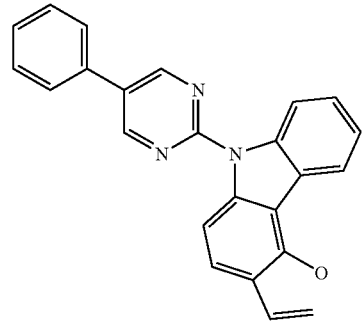
1206
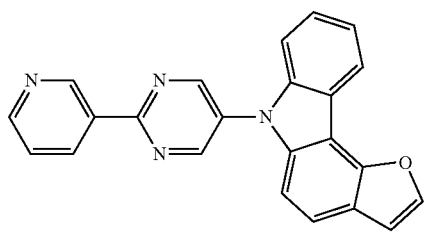
314
-continued
1207
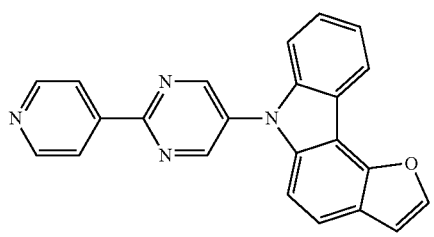
1208
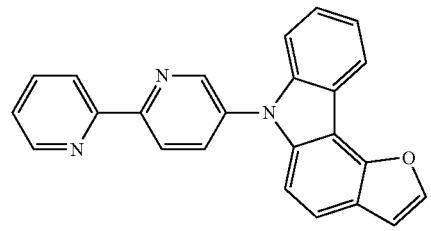
1209
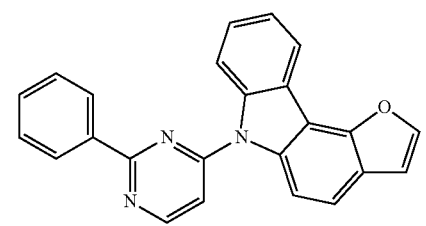
1210
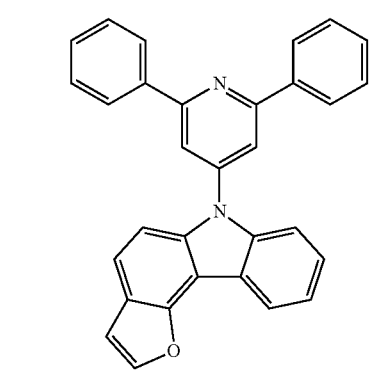
1211
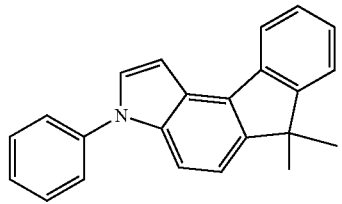
1212
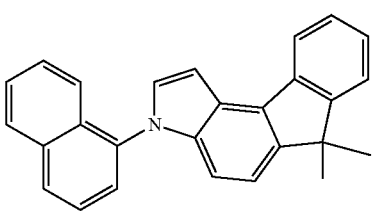

315
-continued
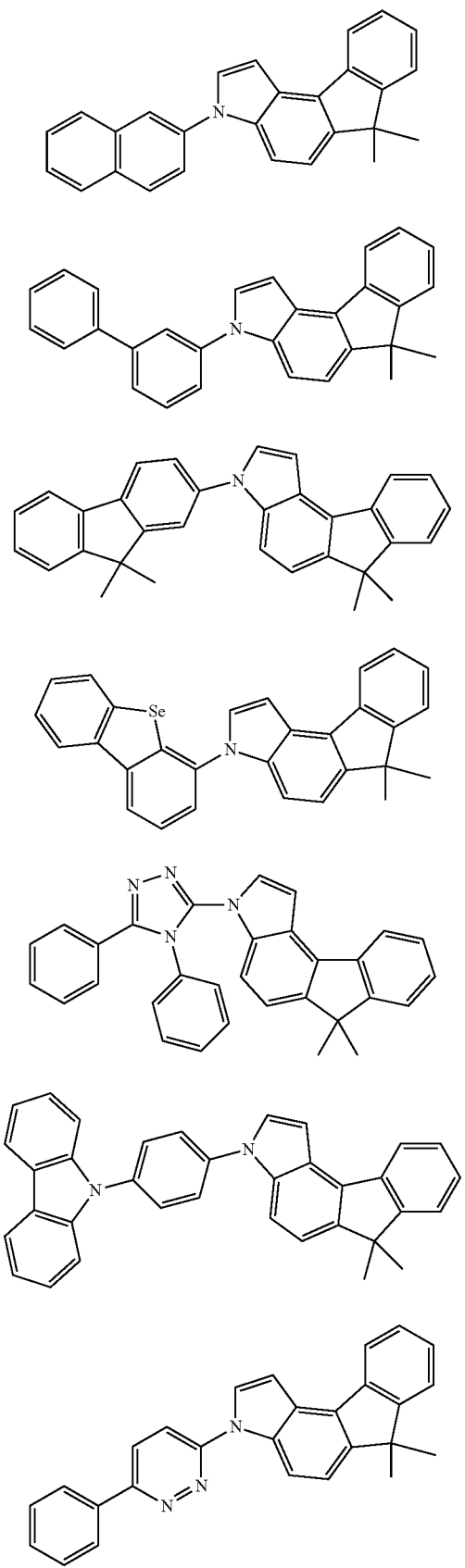
316
-continued
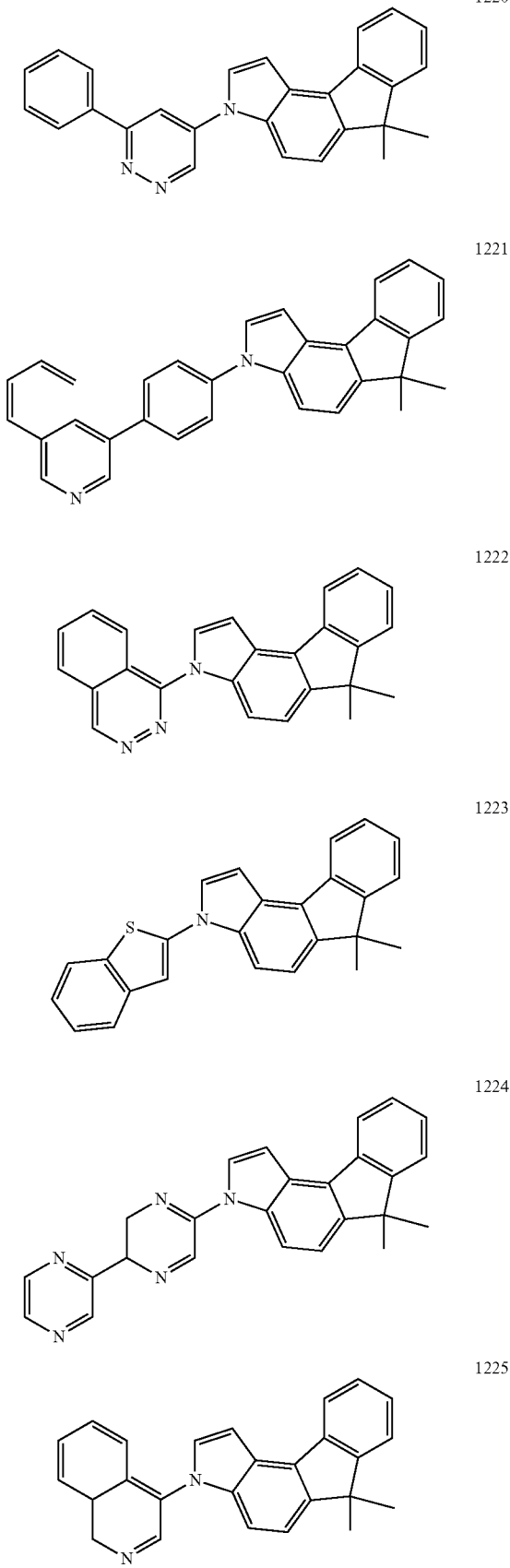

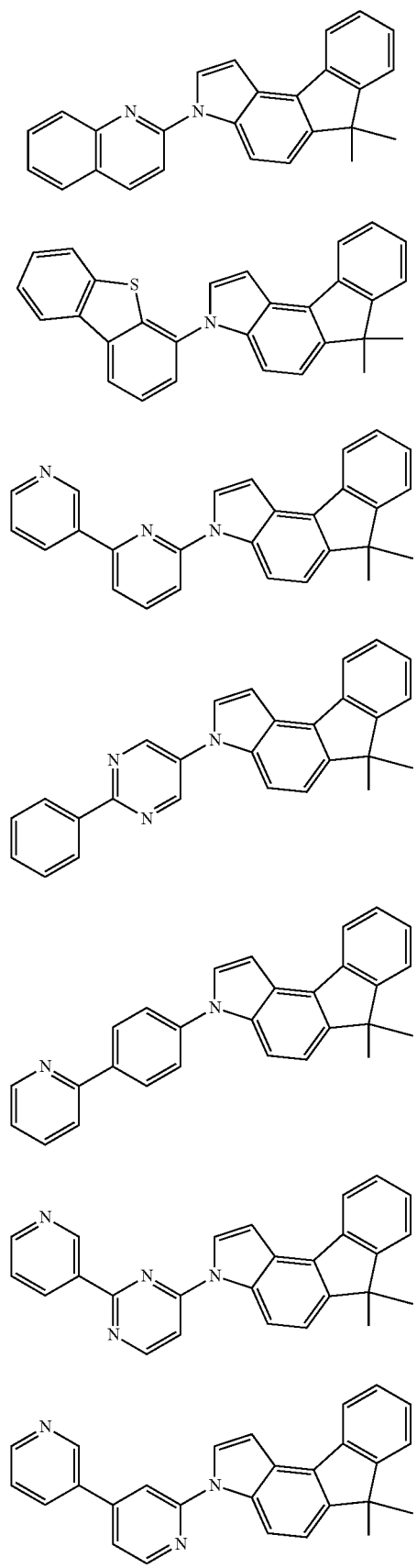
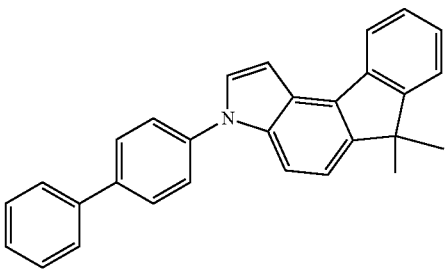

| 319 -continued | 320 -continued |
|---|---|
| 1237 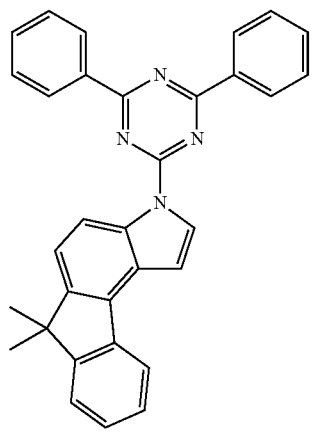 | 1240 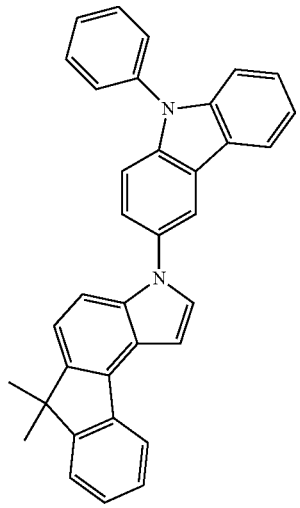 |
| 1238 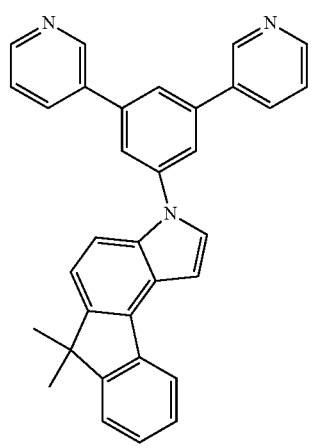 | 1241 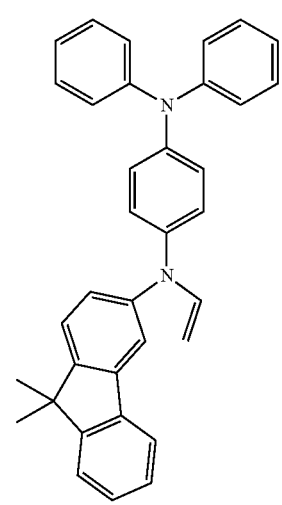 |
| 1239 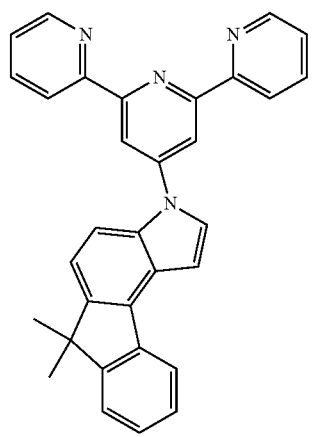 | 1242 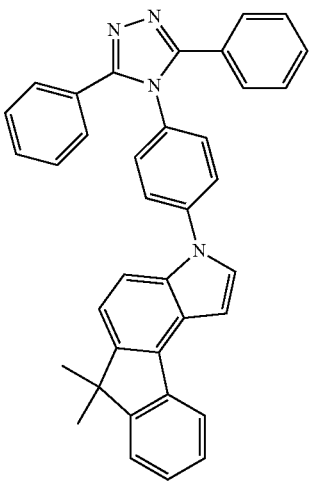 |

1243
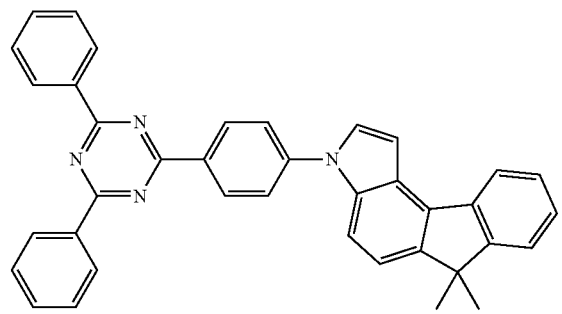
1244
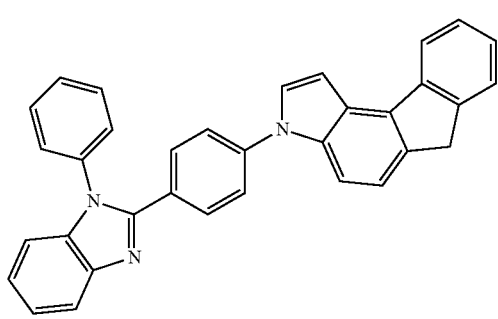
1245
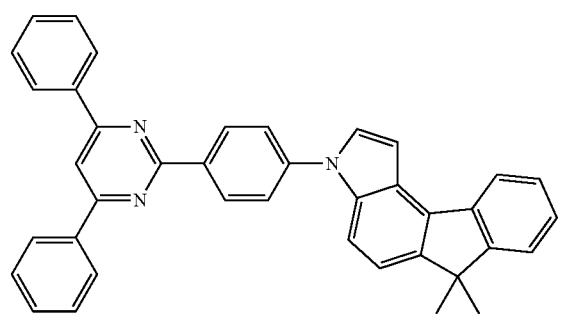
1246
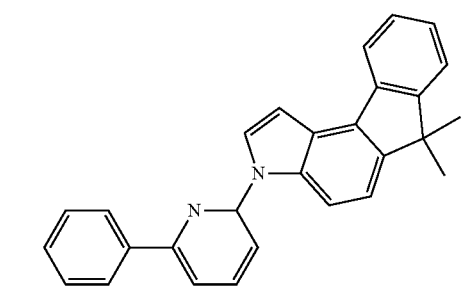
1247
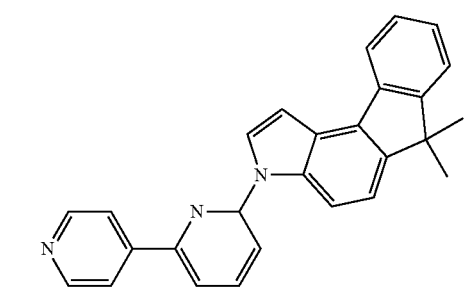
1248
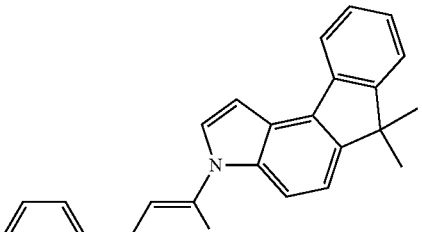
1249
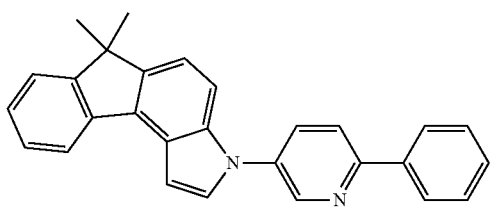
1250
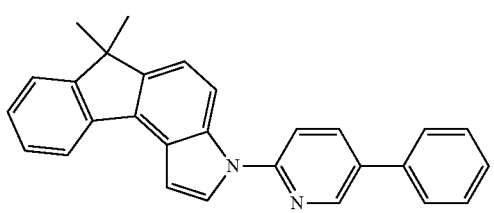
1251
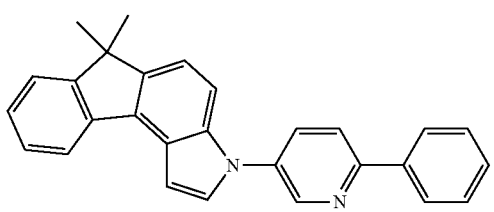
1252
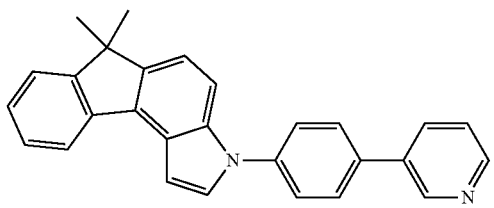
1253
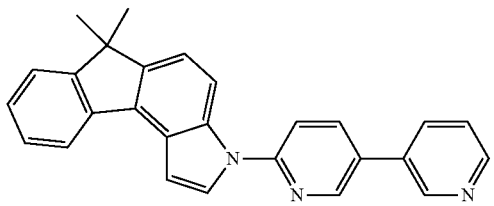
1254
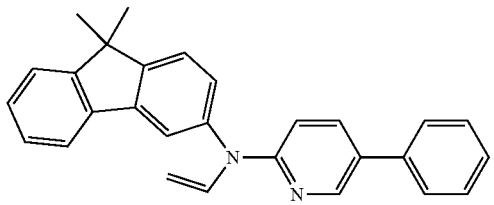

323
-continued
1255
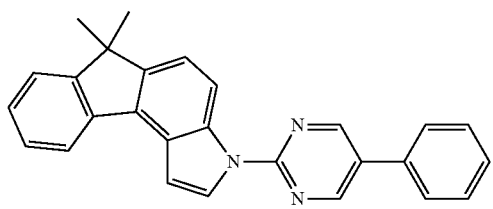
1256
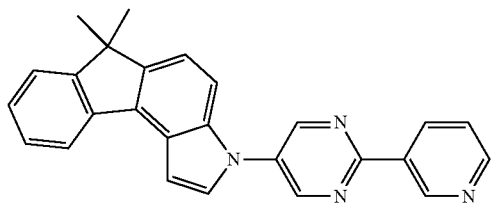
1257
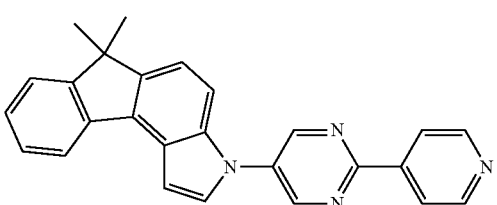
1258
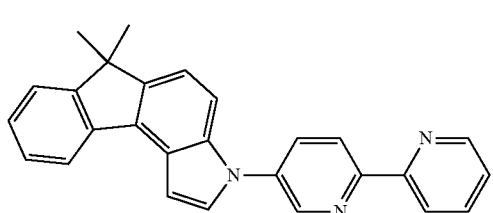
1259
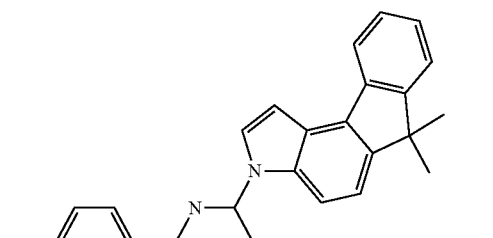
1260
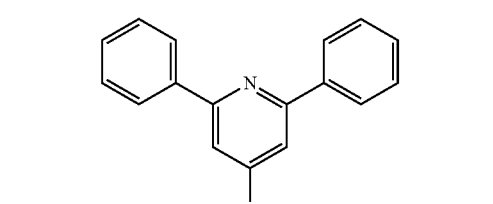
324
-continued
1261
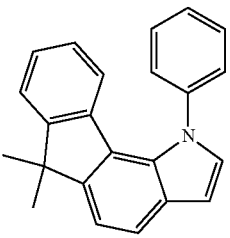
1262
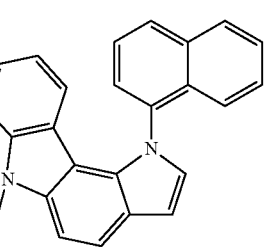
1263
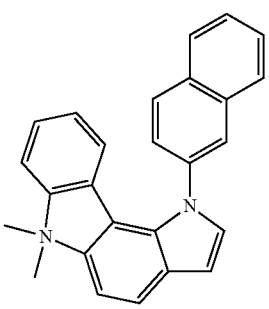
1264
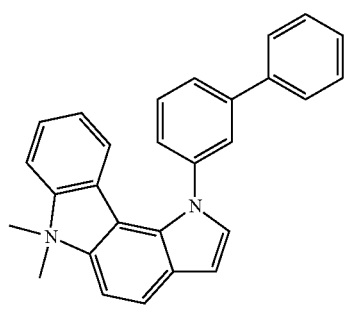
1265
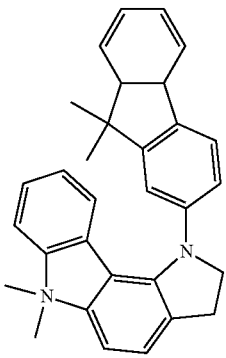

1266 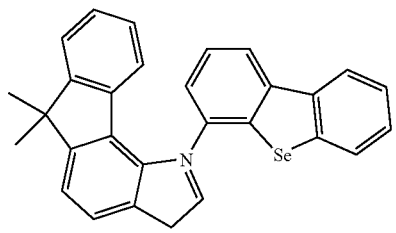
1267 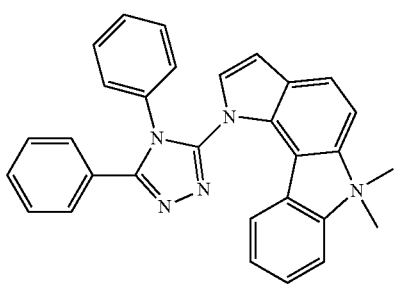
1268 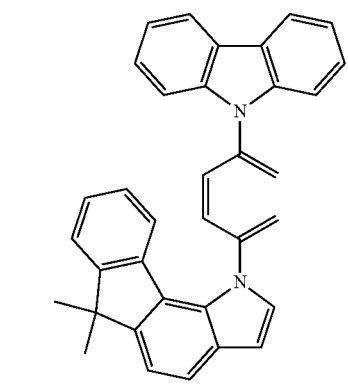
1269 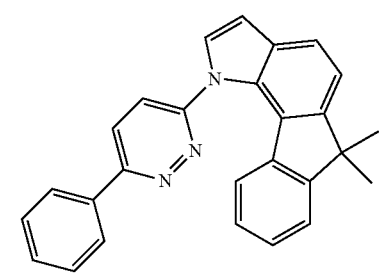
1270 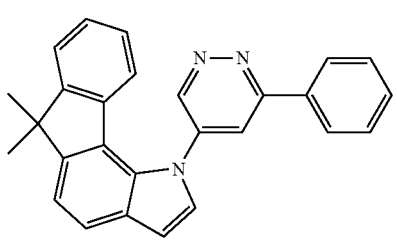
1271 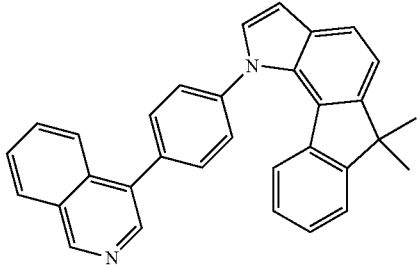
1272 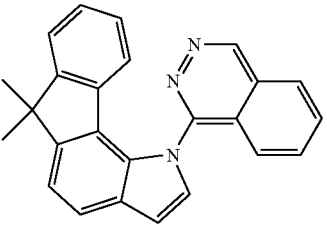
1273 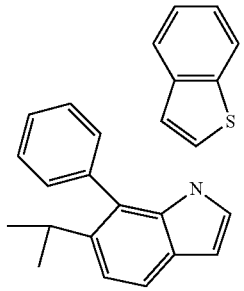
1274 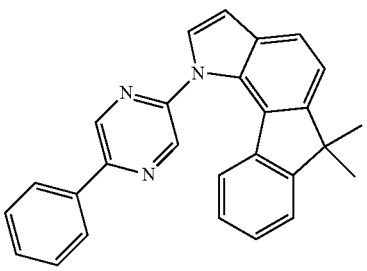
1275 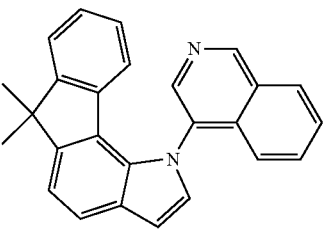
1276 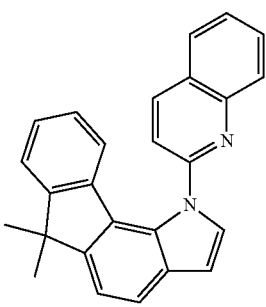

1277
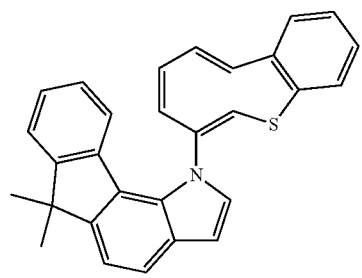
1278
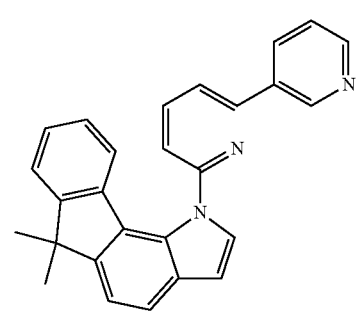
1279
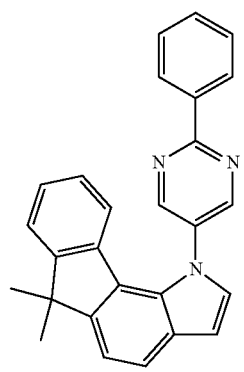
1280
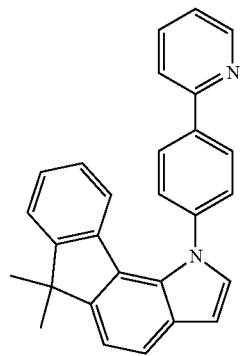
1281
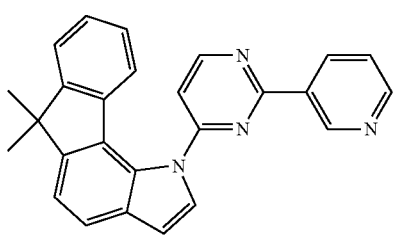
1282
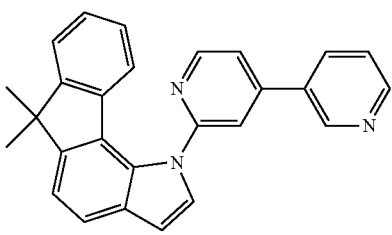
1283
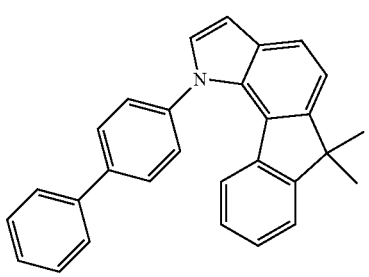
1284
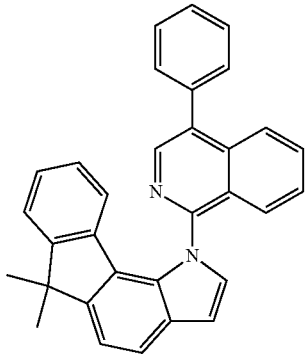
1285
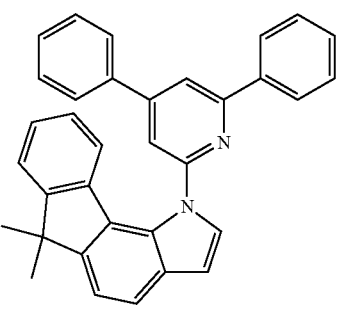
1286
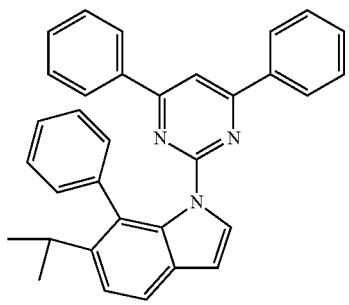

-continued
1287
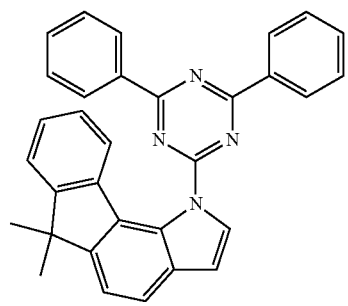
1288
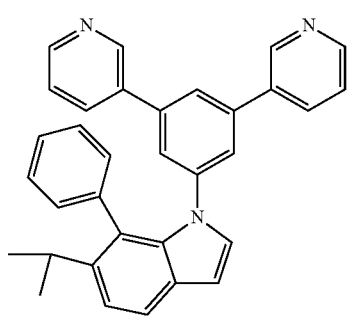
1289
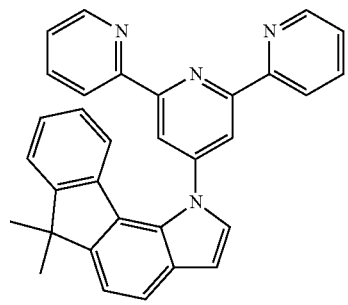
1290
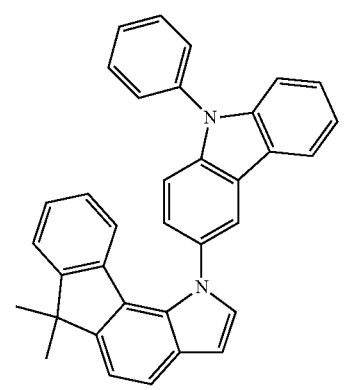
-continued
1291
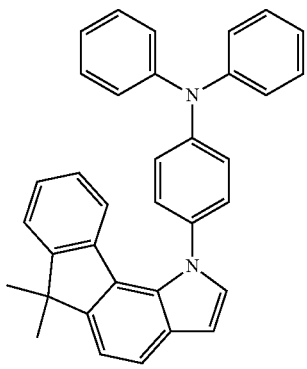
1292
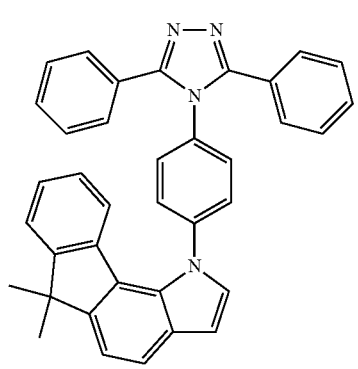
1293
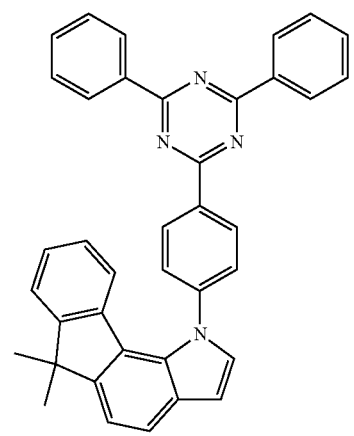
1294
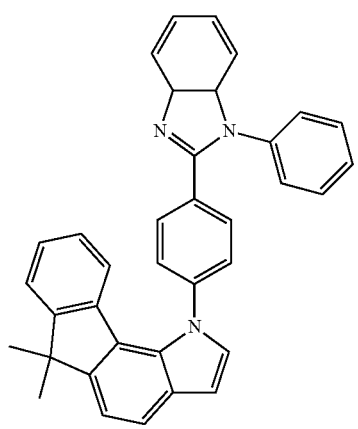

1295 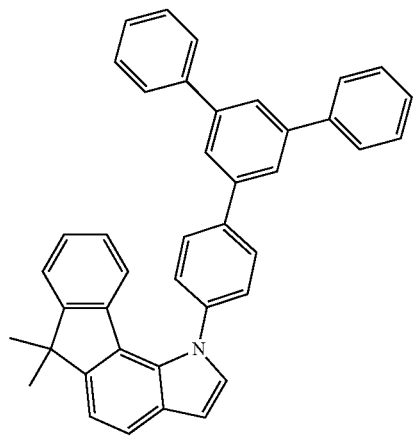
1296 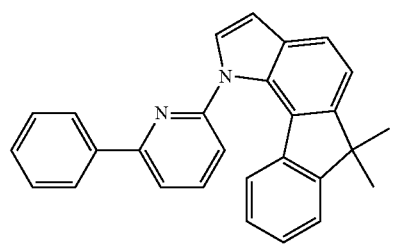
1297 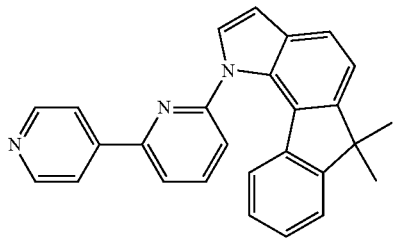
1298 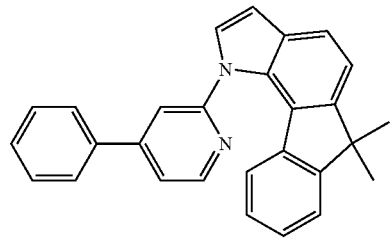
1299 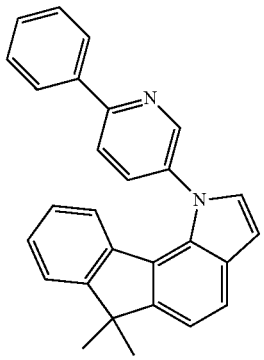
1300 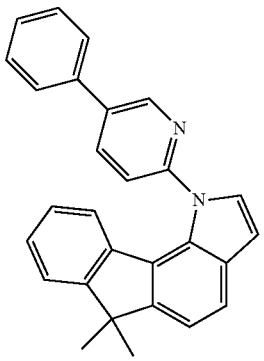
1301 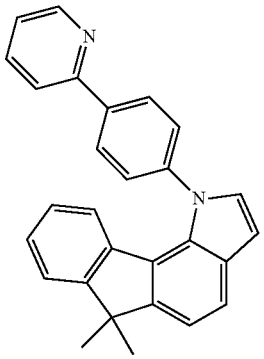
1302 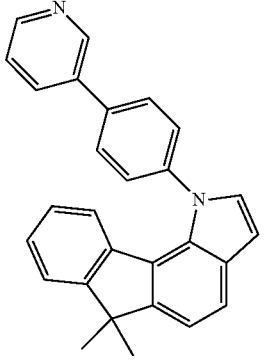
1303 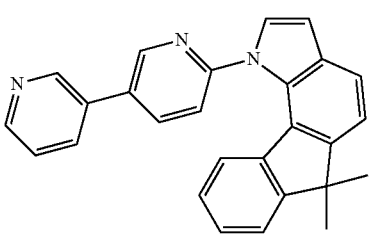

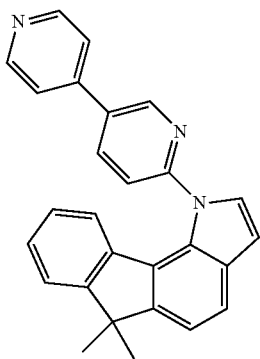
1304
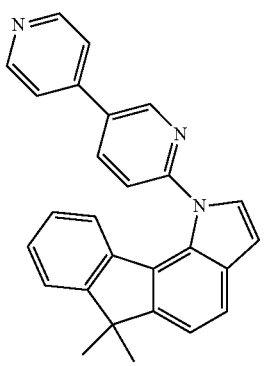
1305
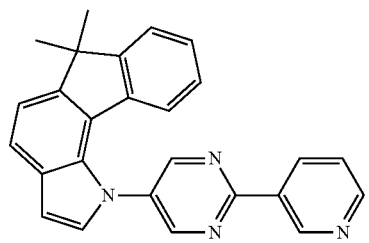
1306
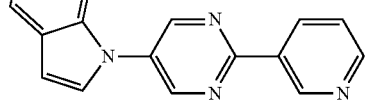
1307
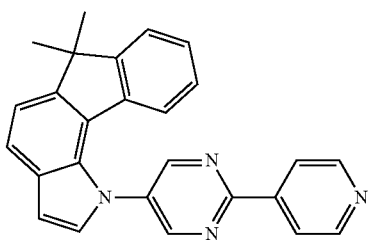
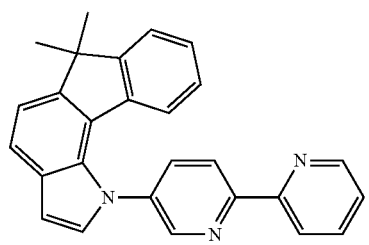
1308
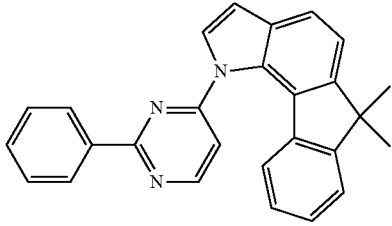
1309
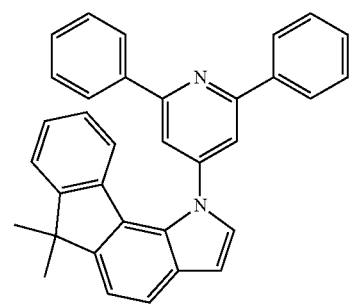
1310
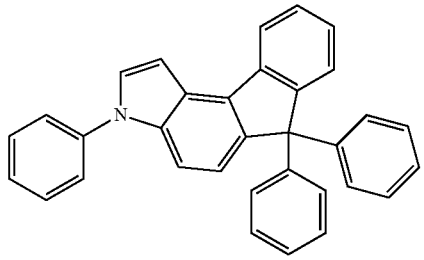
1311
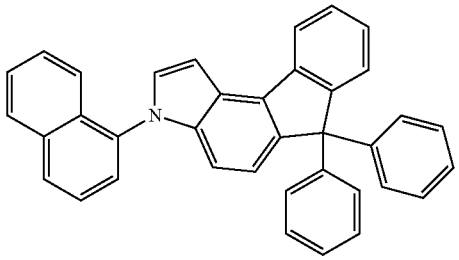
1312
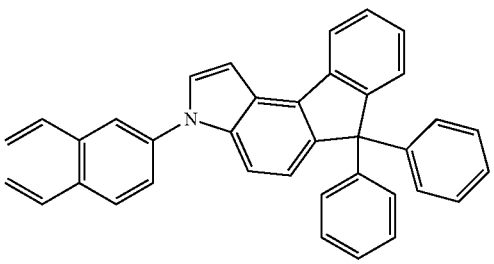
1313

335
-continued
1314
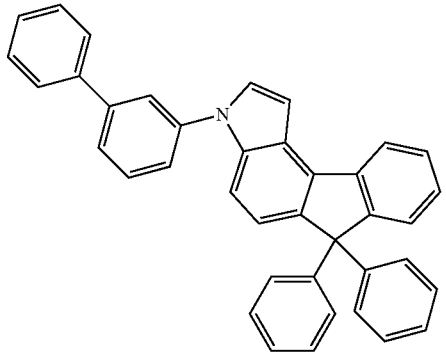
1315
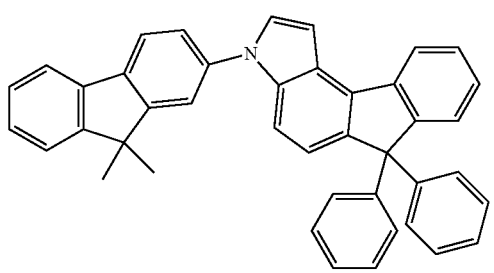
1316
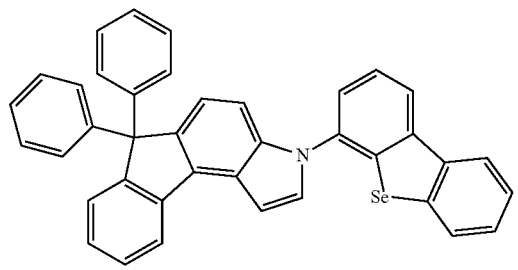
1317
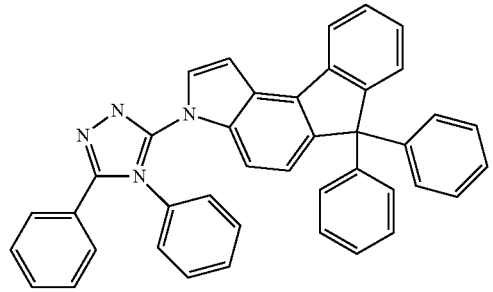
1318
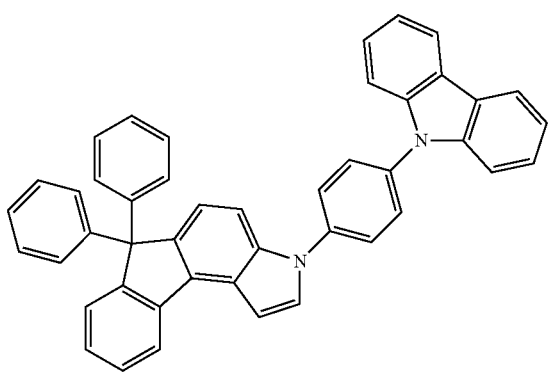
336
-continued
1319
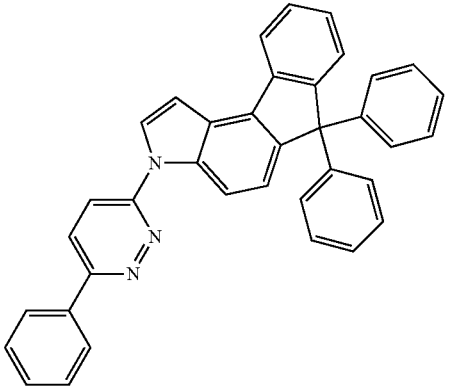
1320
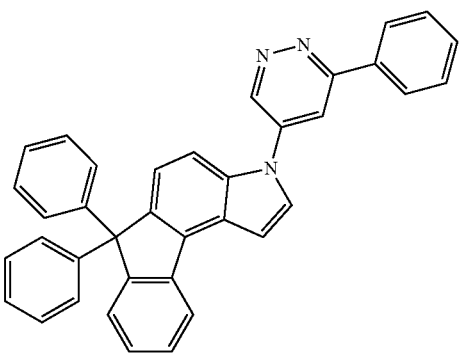
1321
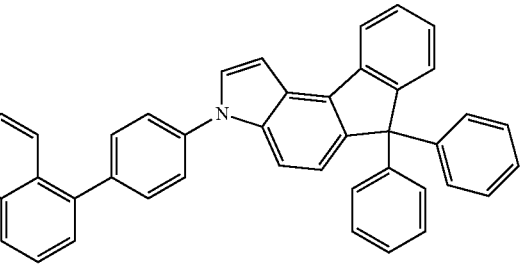
1322
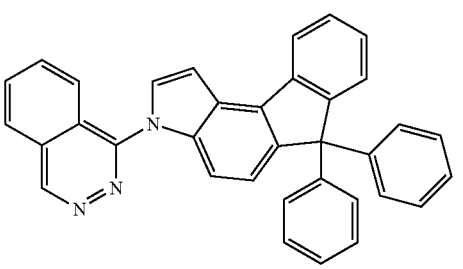
1323
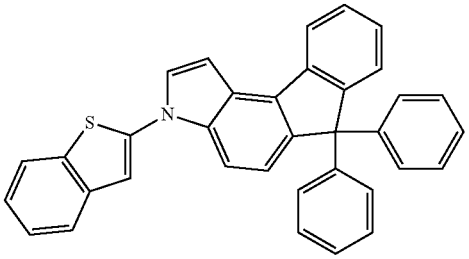

1324
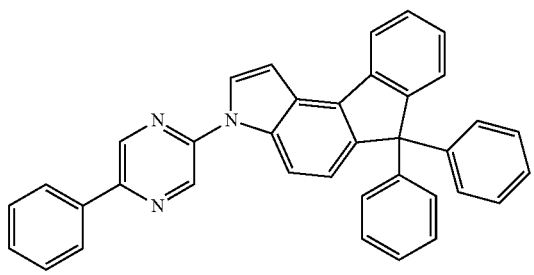
1325
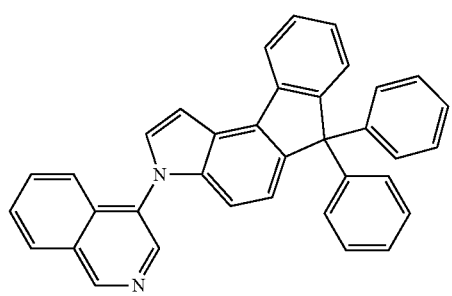
1326
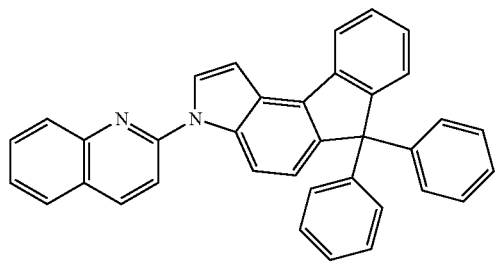
1327
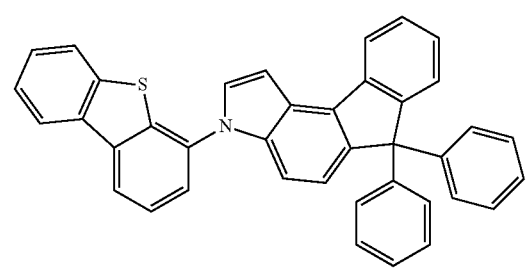
1328
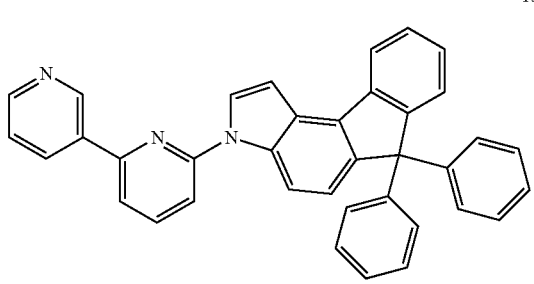
1329
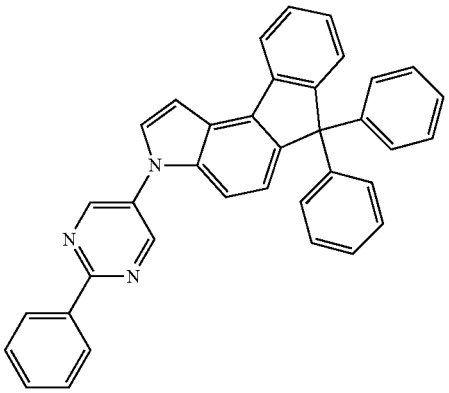
1330
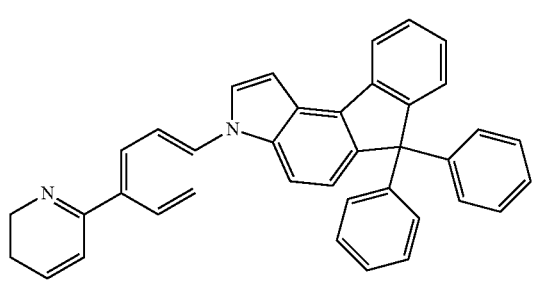
1331
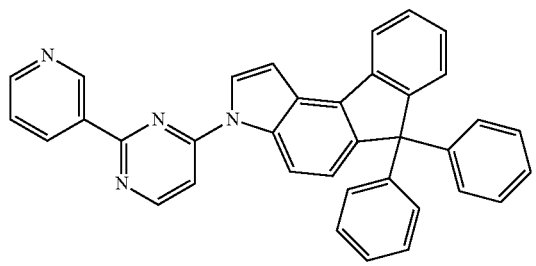
1332
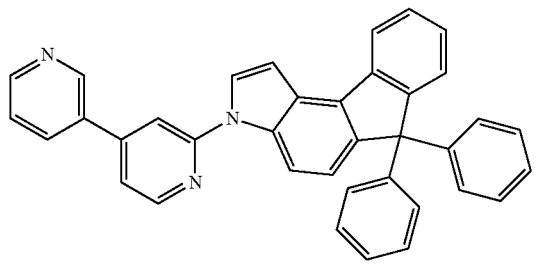
1333
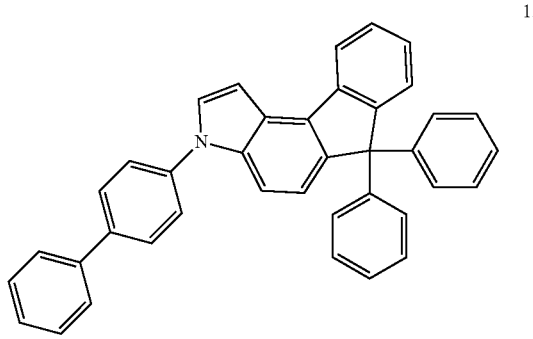

339
-continued
1334
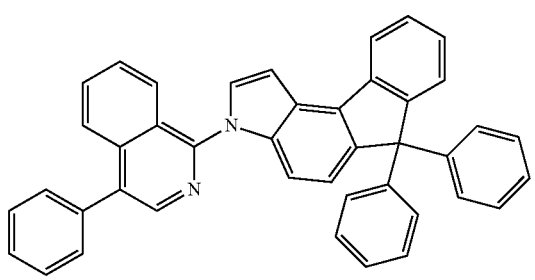
1335
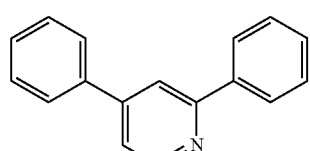
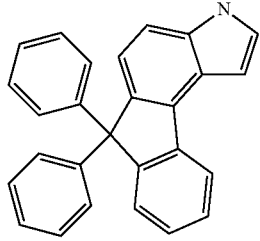
1336
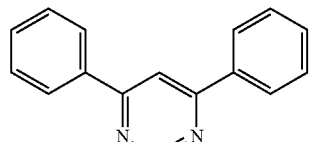
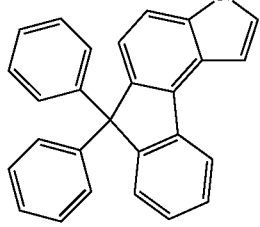
1337
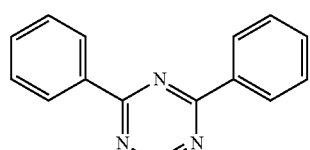
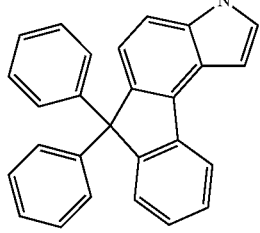
340
-continued
1338
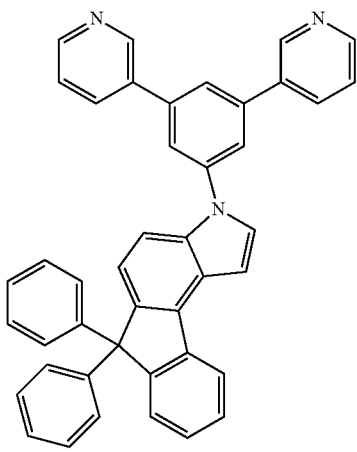
1339
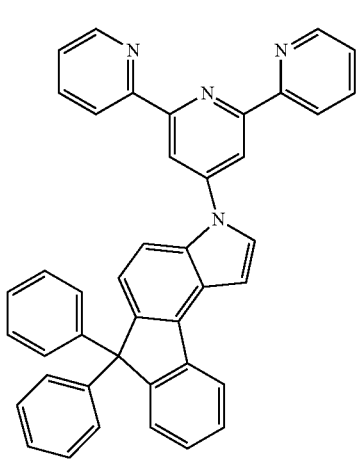
1340
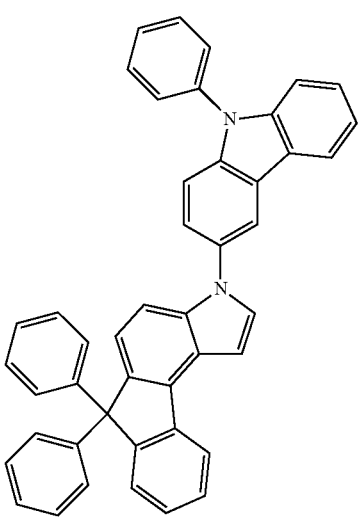

1341 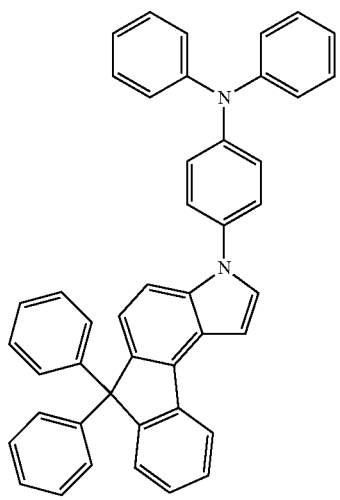
1344 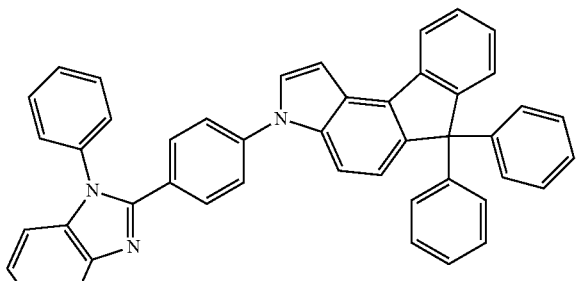
1345 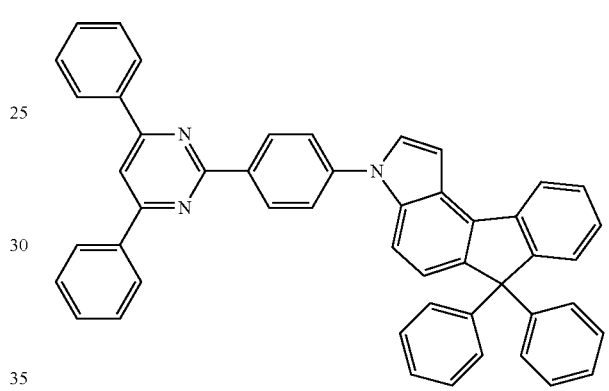
1342 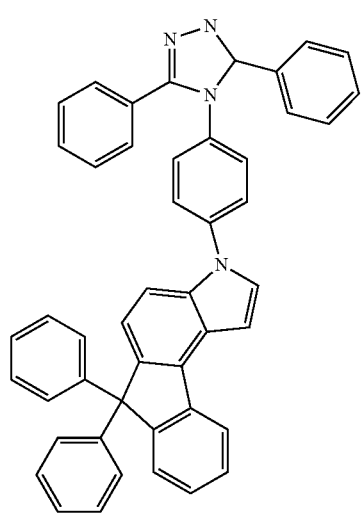
1346 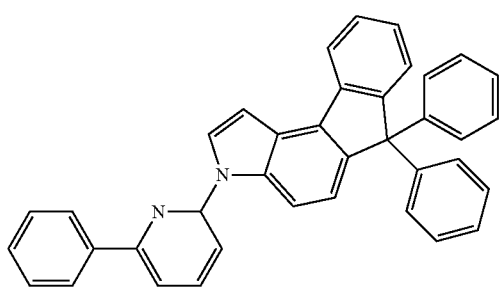
1343 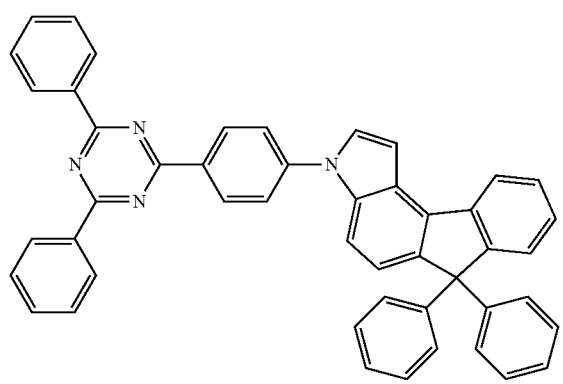
1347 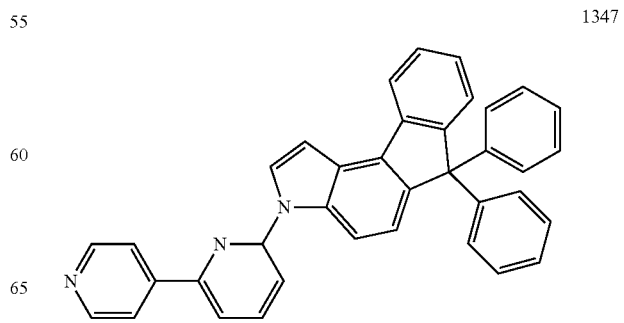

1348
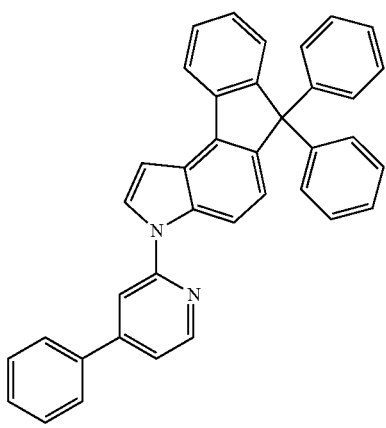
1349
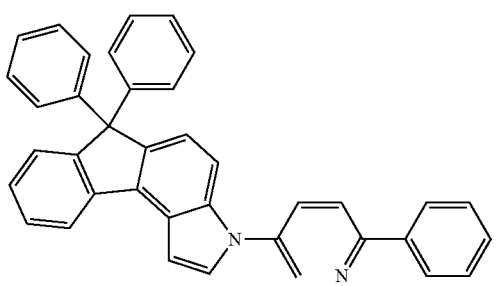
1350
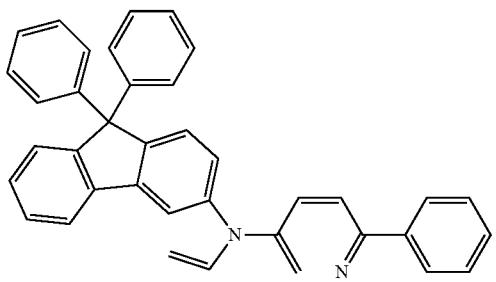
1351
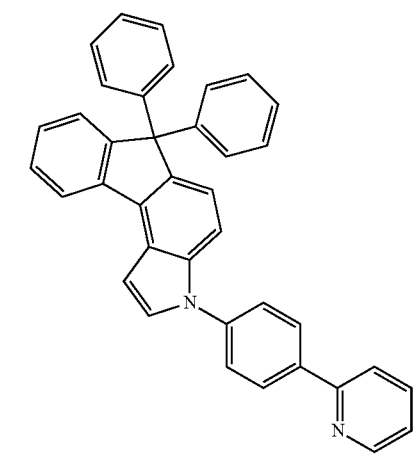
1352
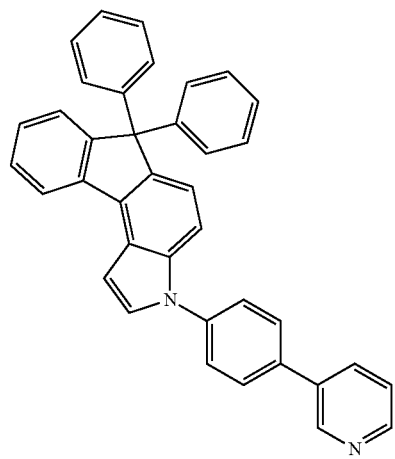
1353
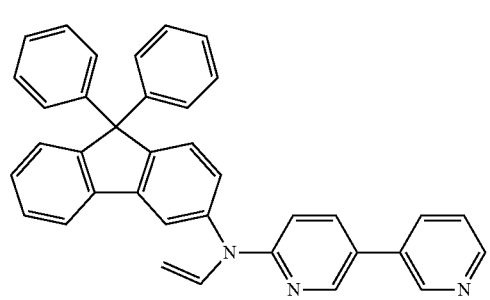
1354
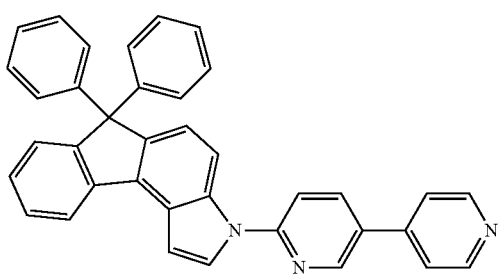
1355
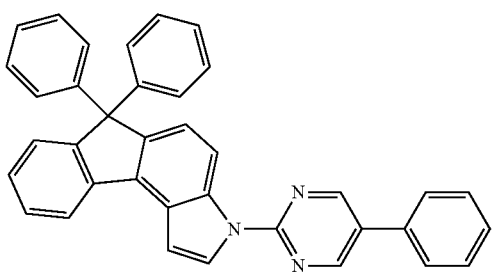

1356
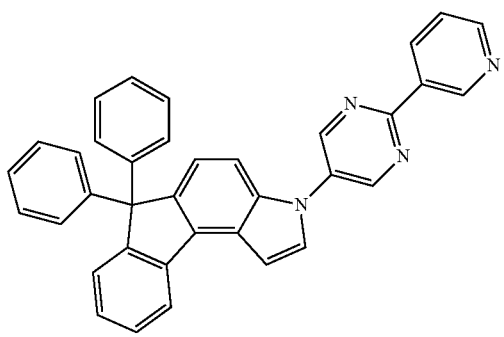
1357
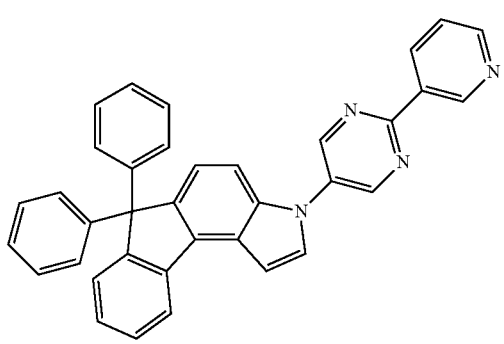
1358
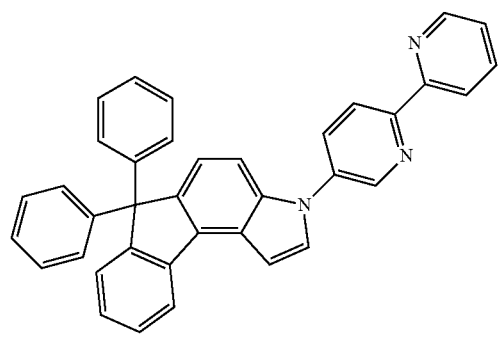
1359
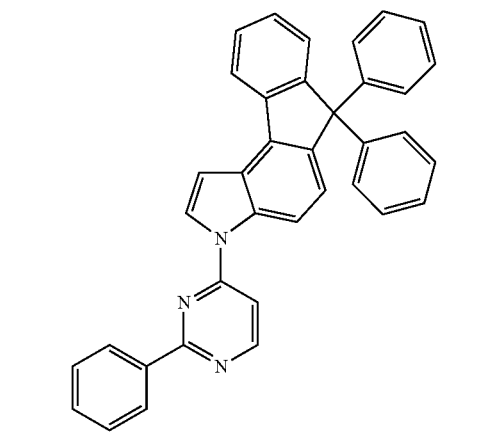
1360
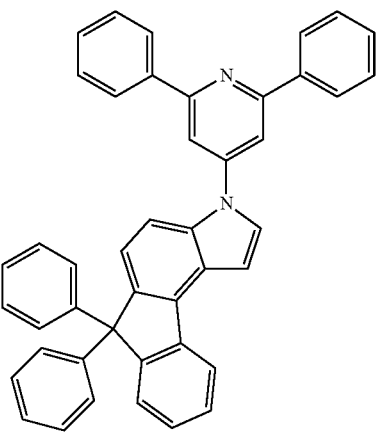
1361
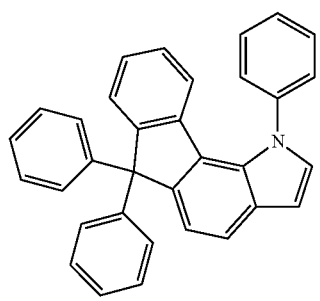
1362
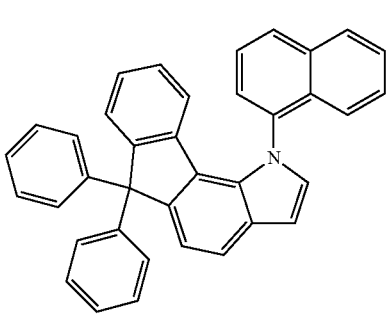
1363
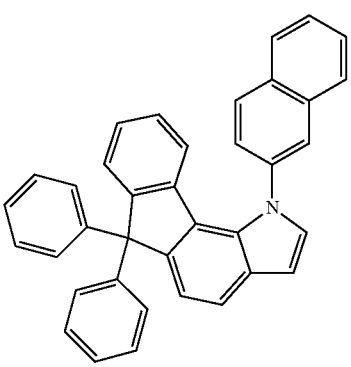

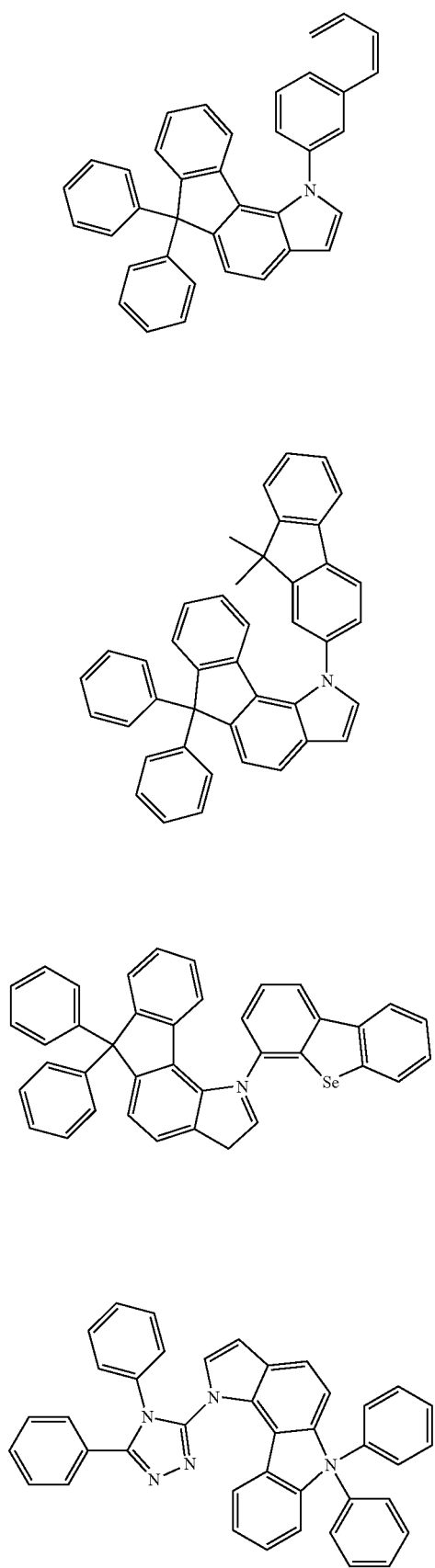
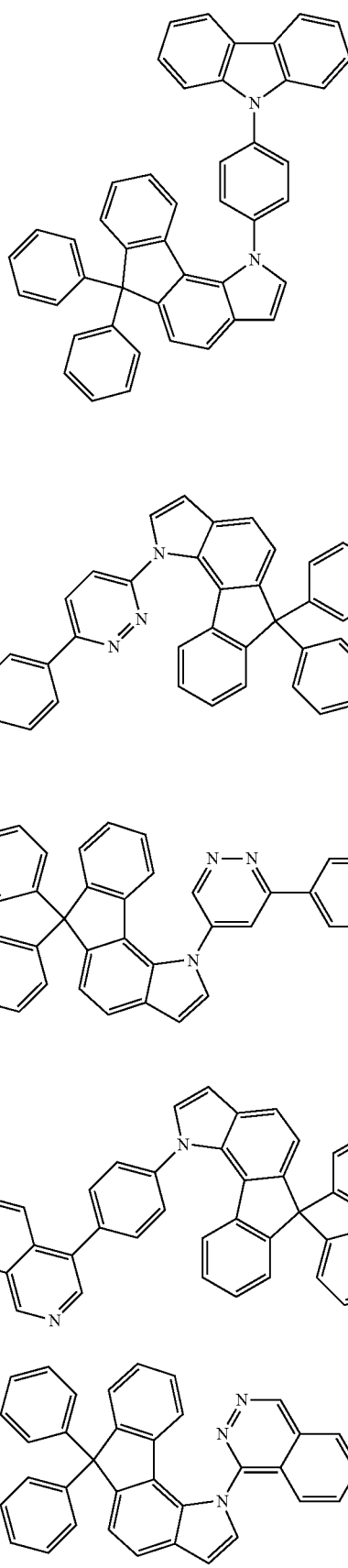

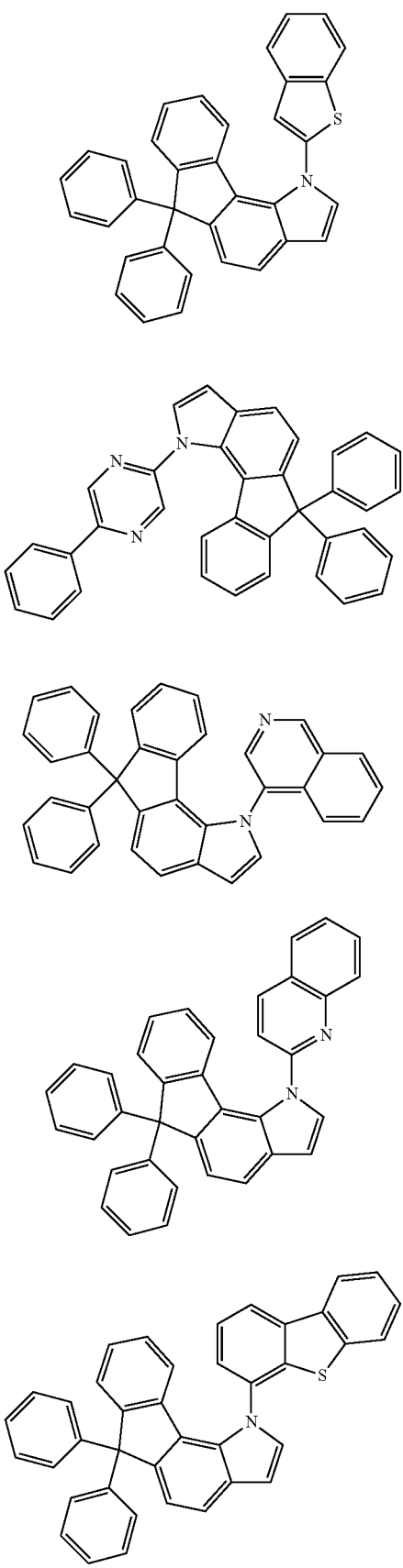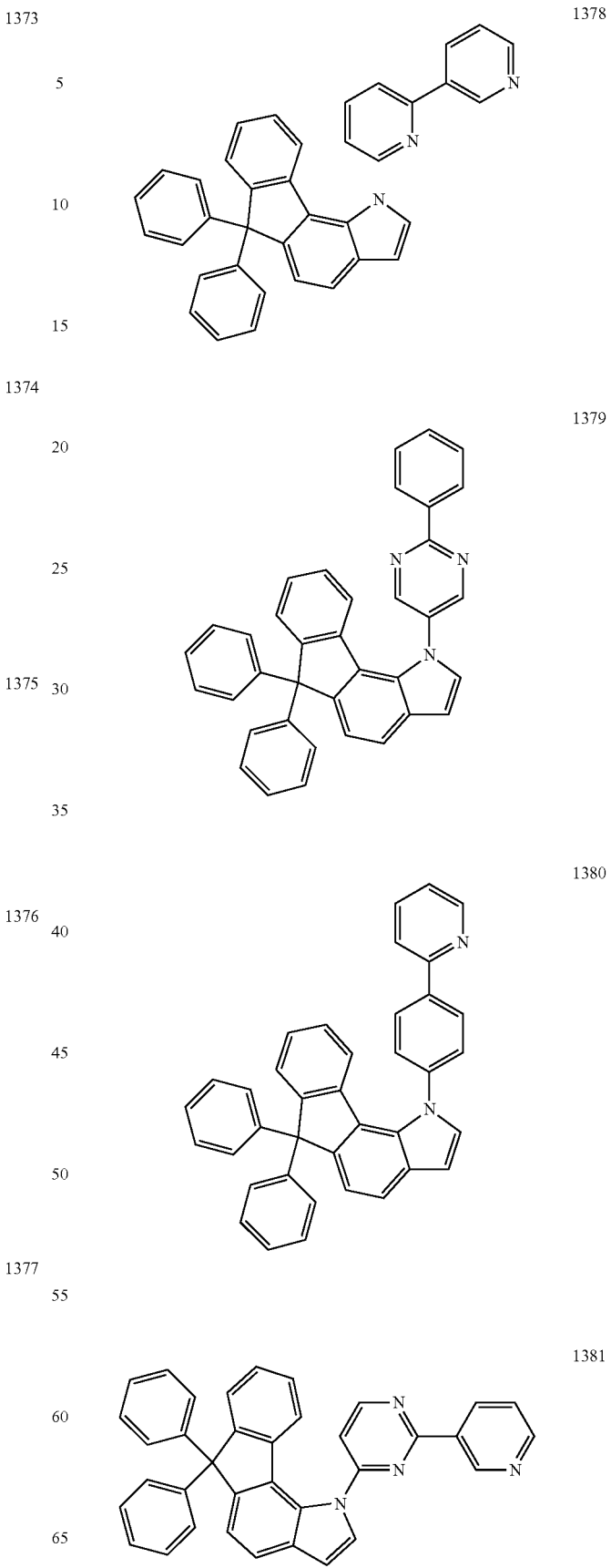

US 10,038,146 B2
351
-continued
1382
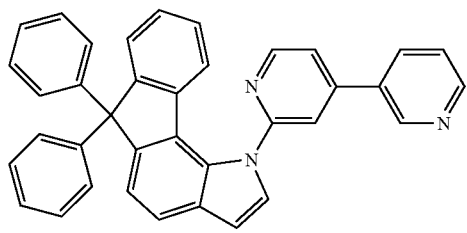
1383
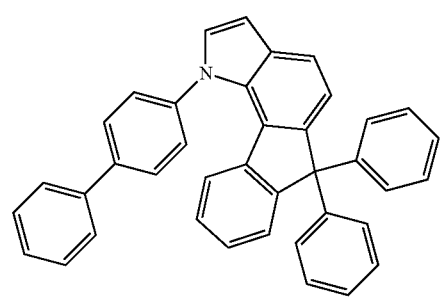
1384
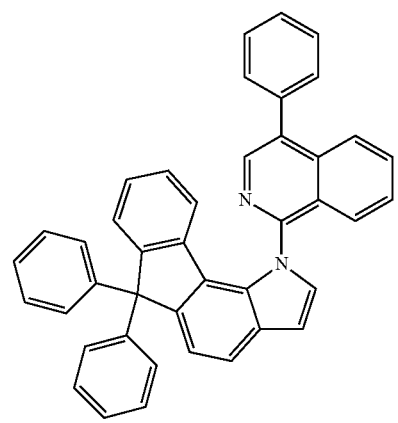
1385
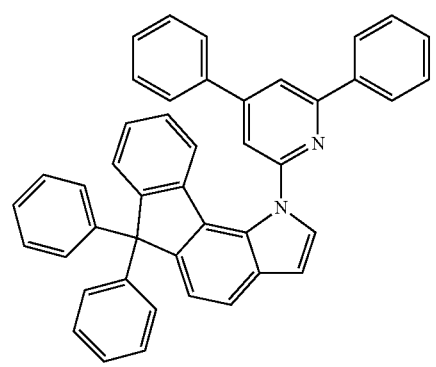
352
-continued
1386
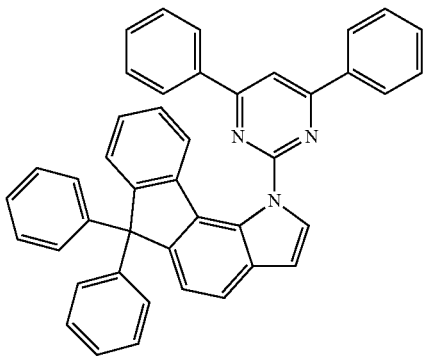
1387
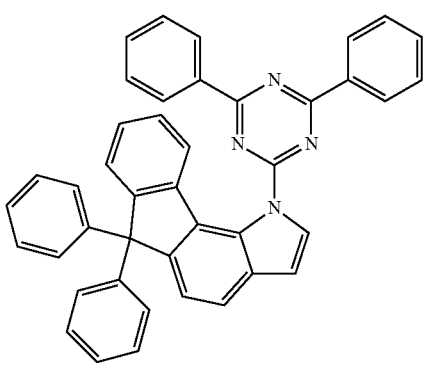
1388
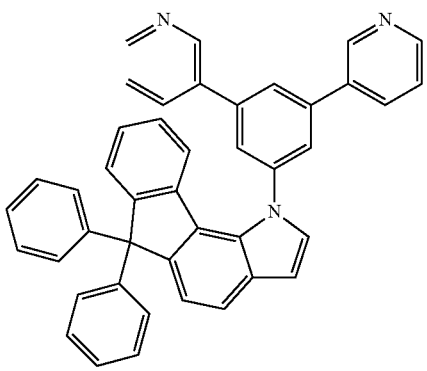
1389
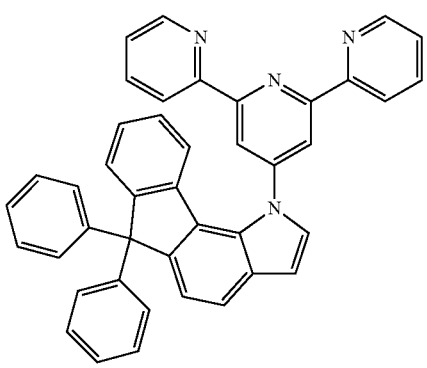

-continued
1390
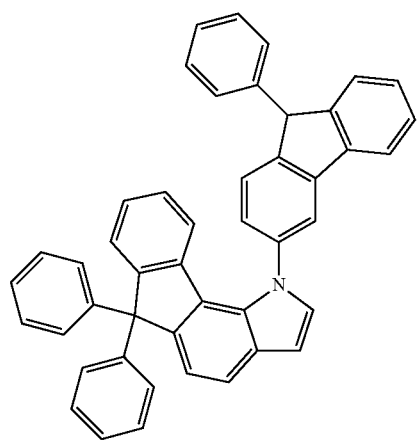
1391
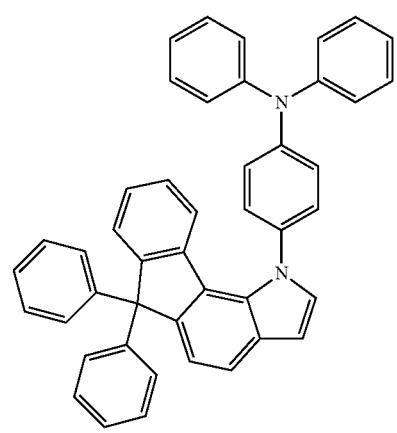
1392
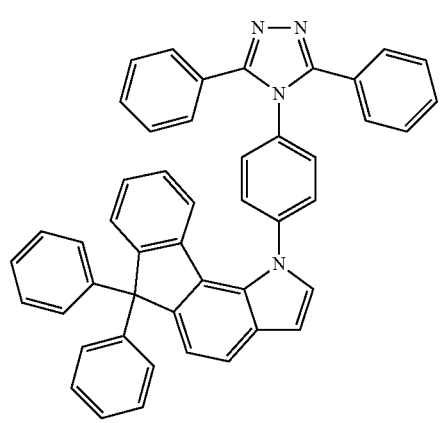
-continued
1393
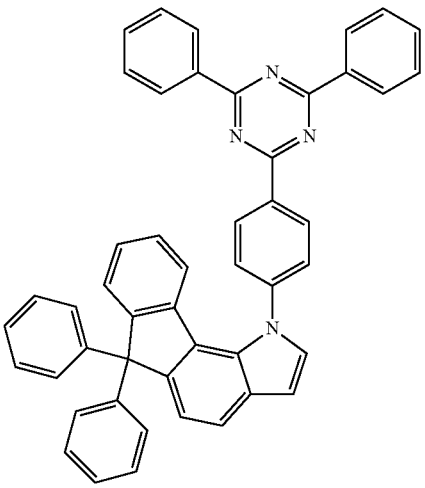
1394
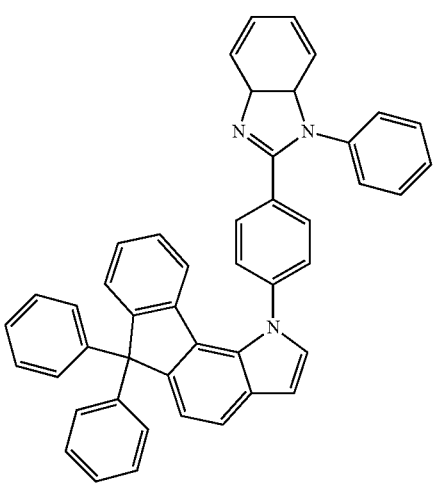
1395
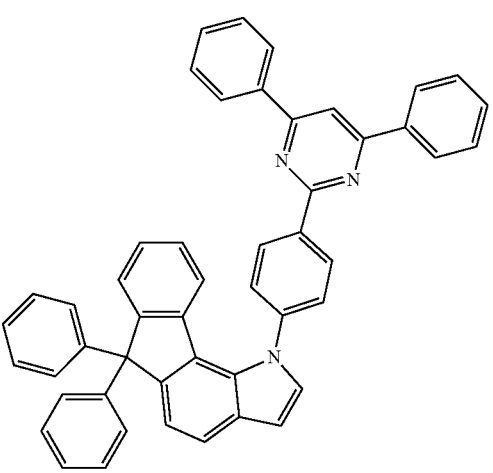

1396
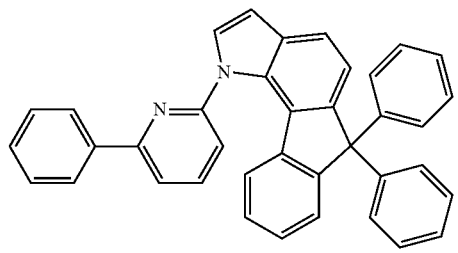
1397
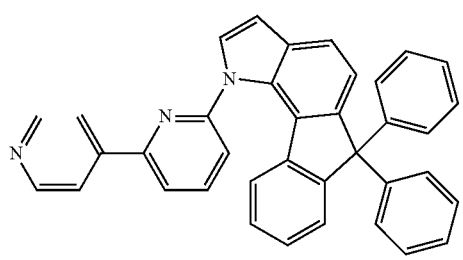
1398
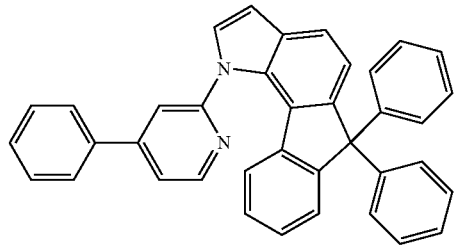
1399
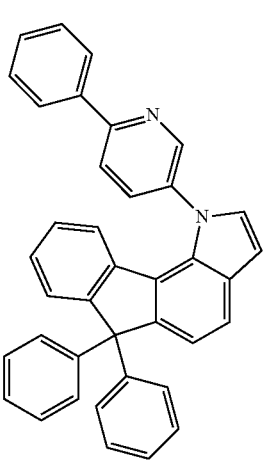
1400
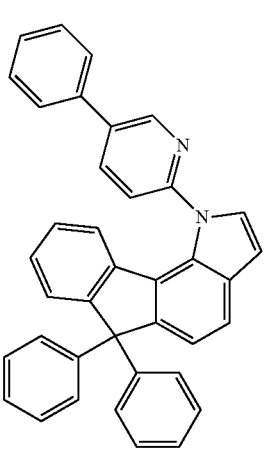
1401
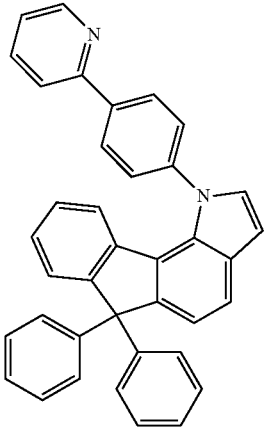
1402
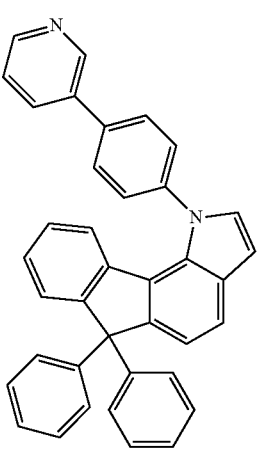
1403
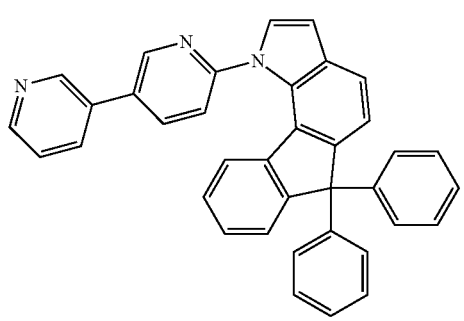
1404
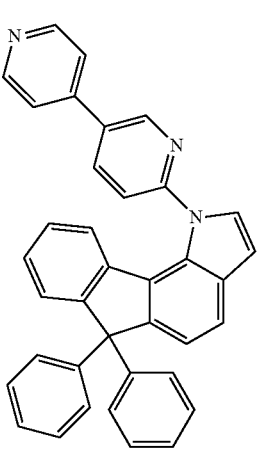

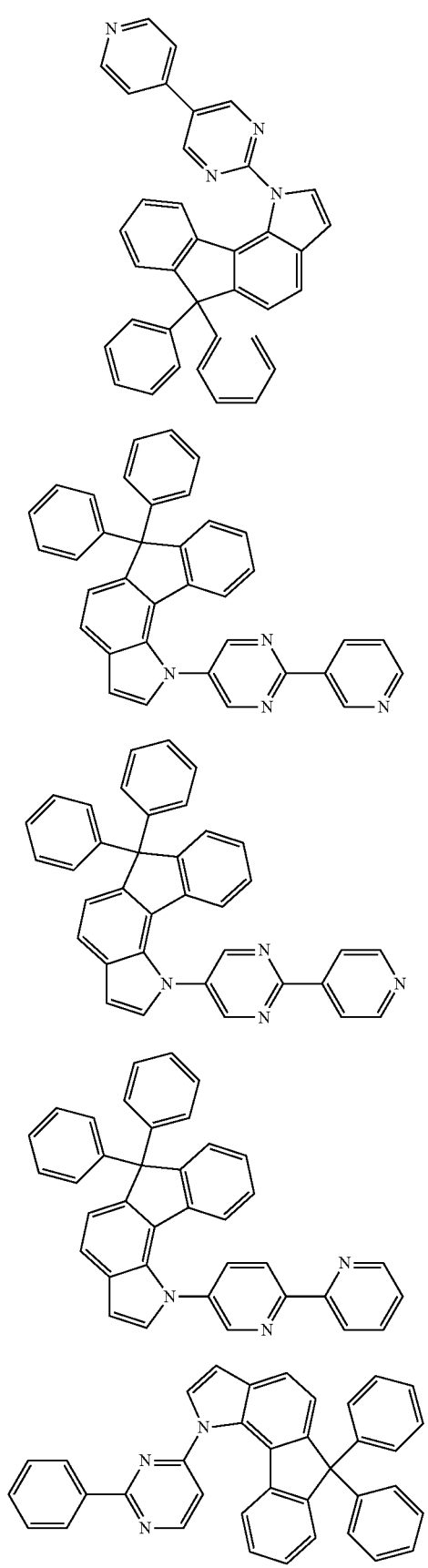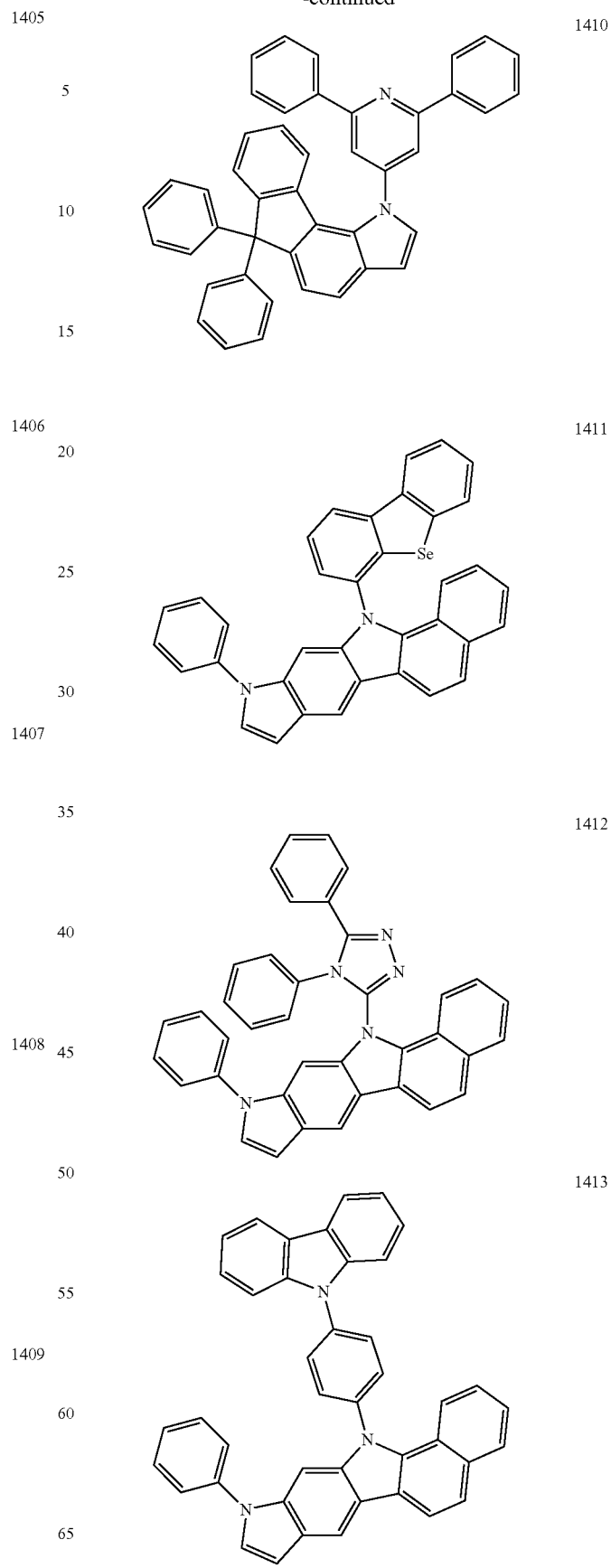

1414
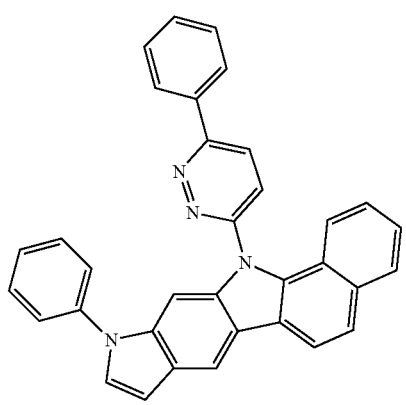
1415
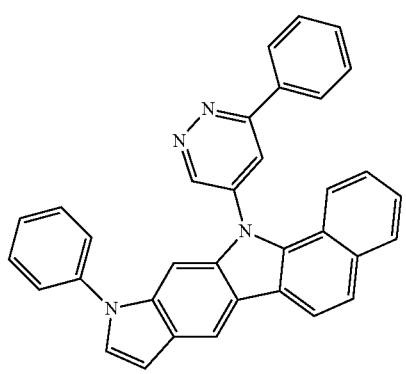
1416
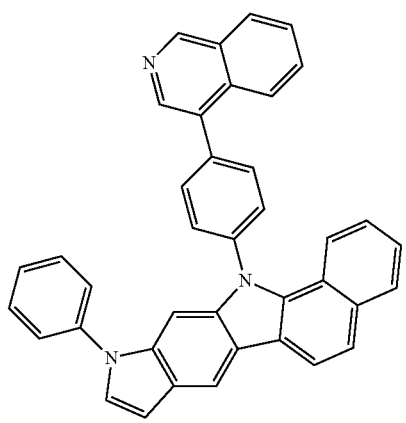
1417
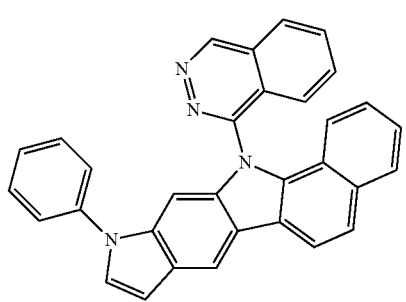
1418
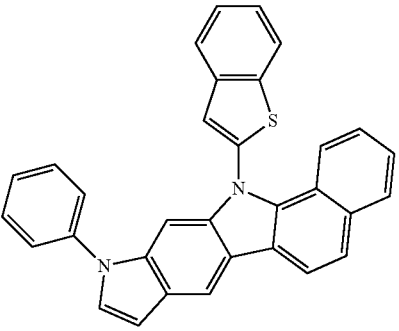
1419
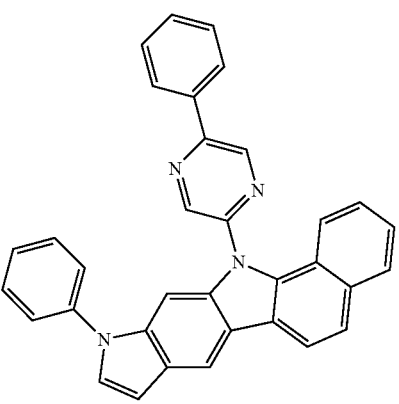
1420
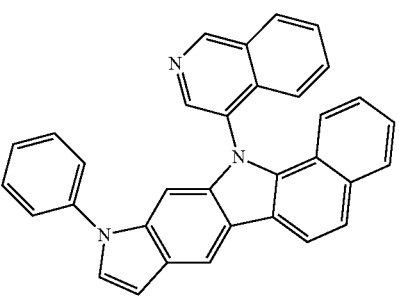
1421
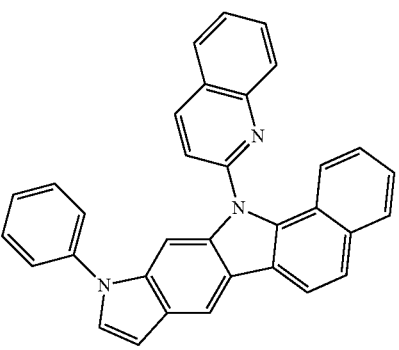

361
-continued
1422
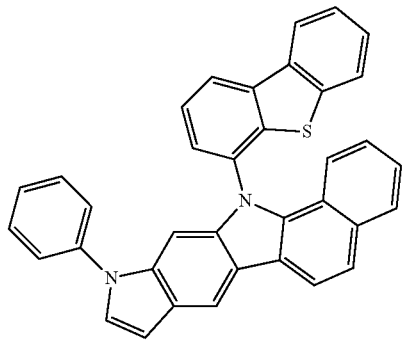
1423
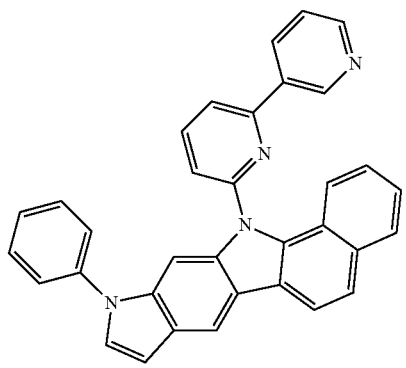
1424
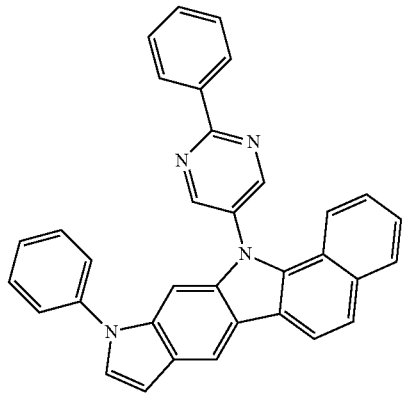
1425
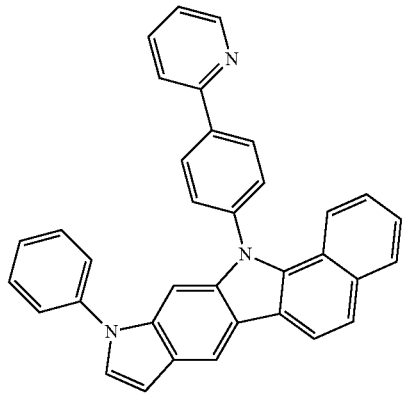
362
-continued
1426
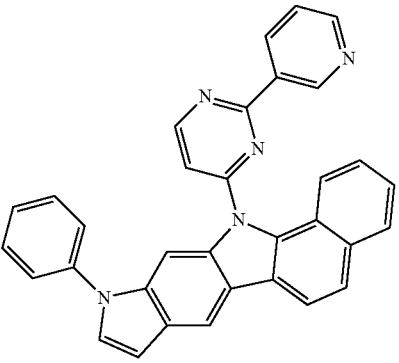
1427
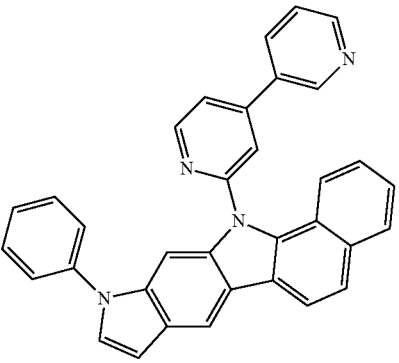
1428
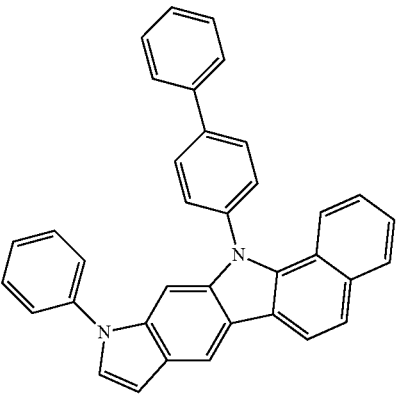
1429
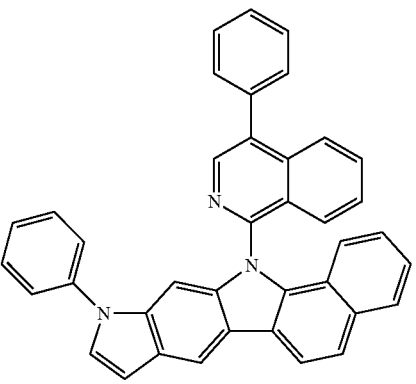

US 10,038,146 B2
363
-continued
1430
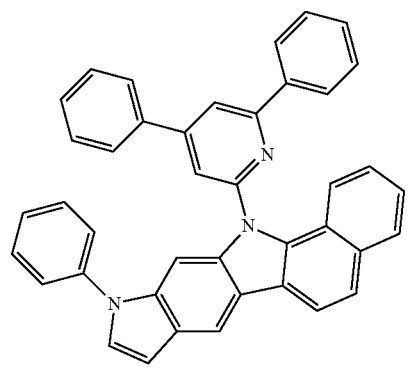
1431
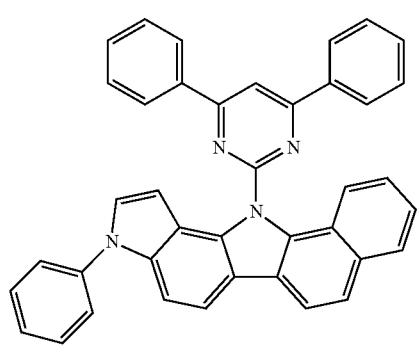
1432
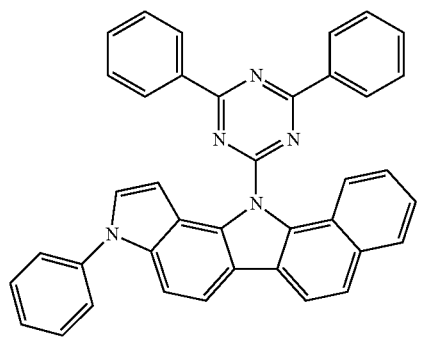
1433
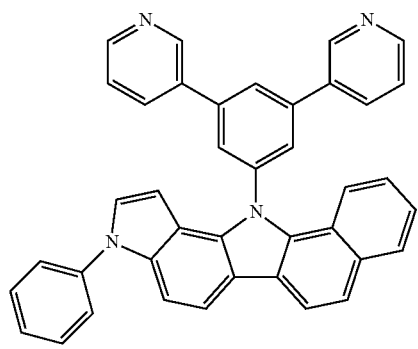
364
-continued
1434
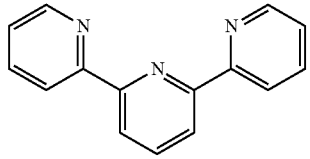
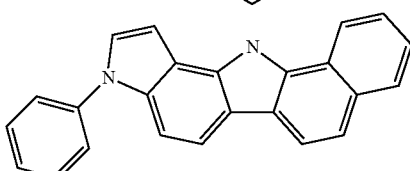
1435
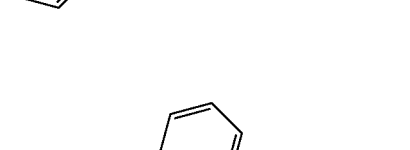
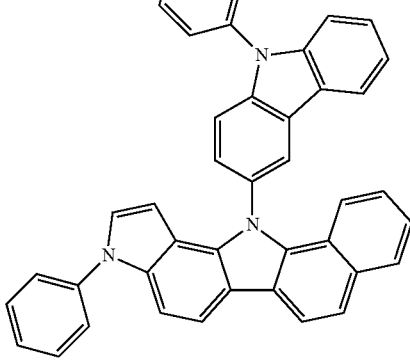
1436
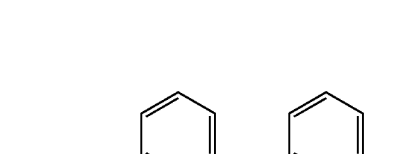
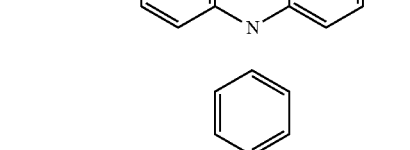
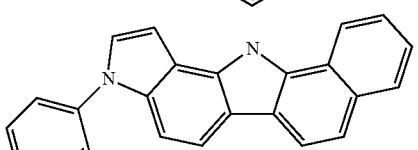
1437
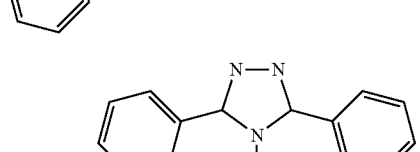
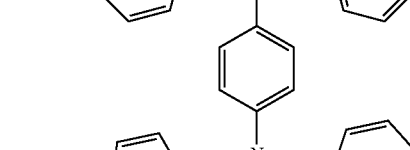
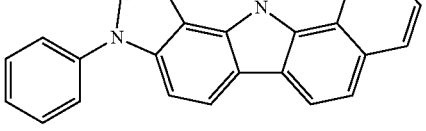

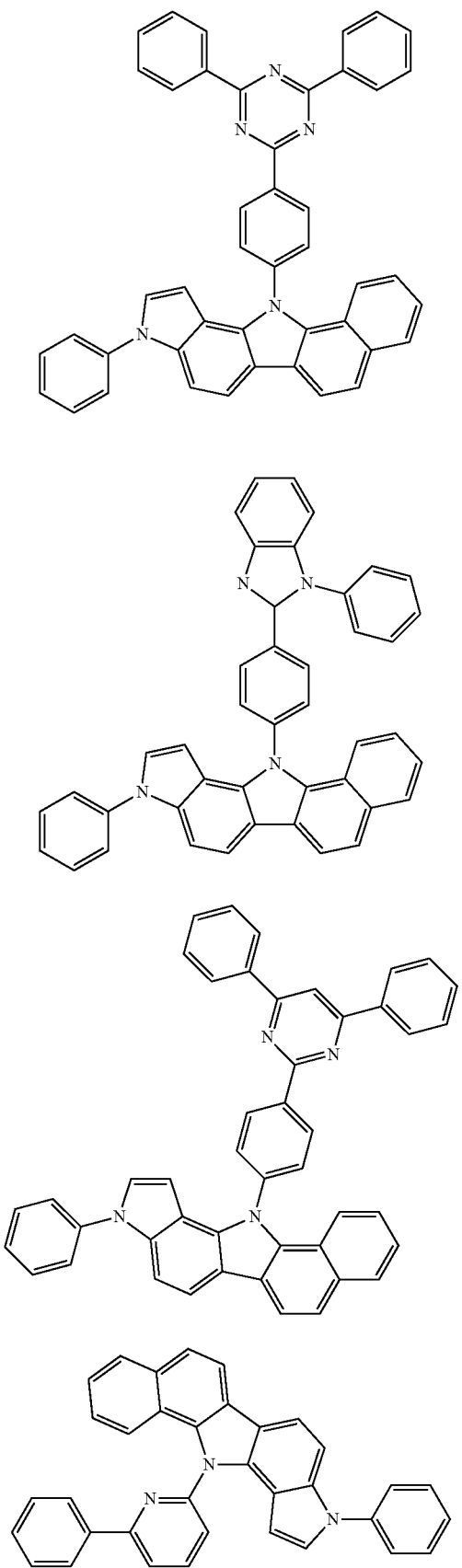

1446 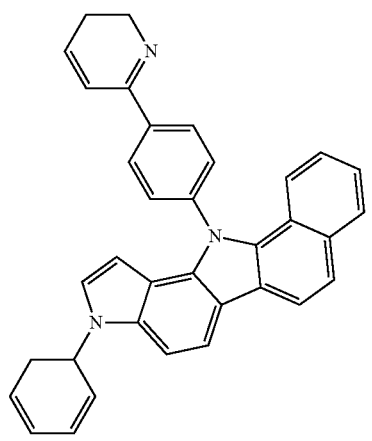
1447 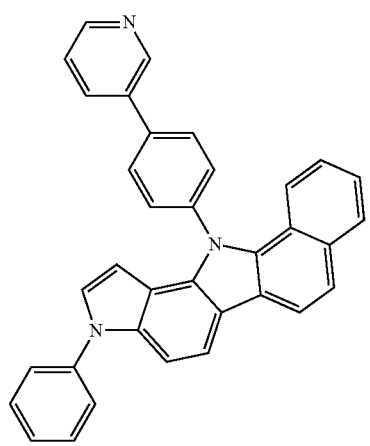
1448
1449 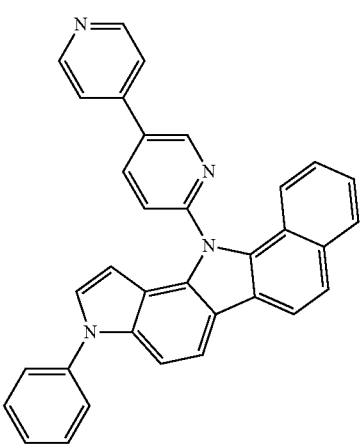
1450 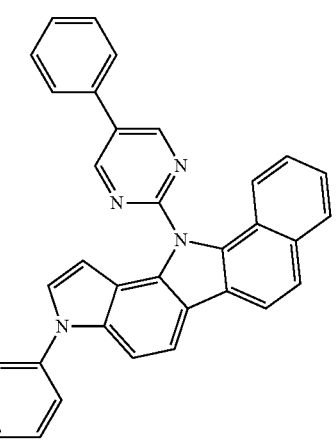
1451 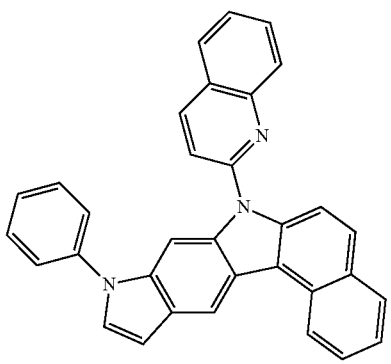
1452 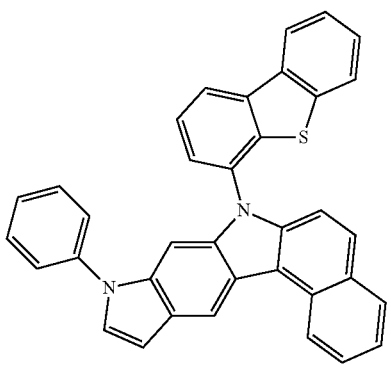

369
-continued
1453
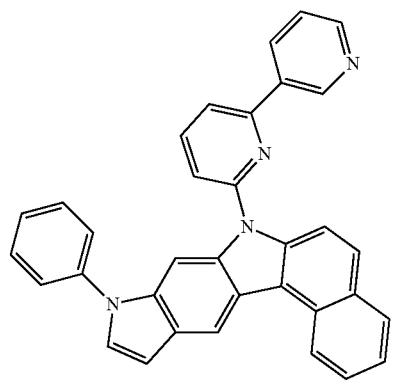
1454
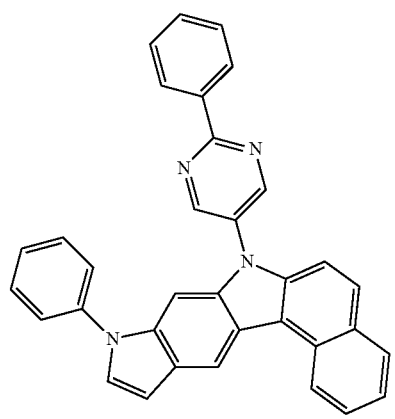
1455
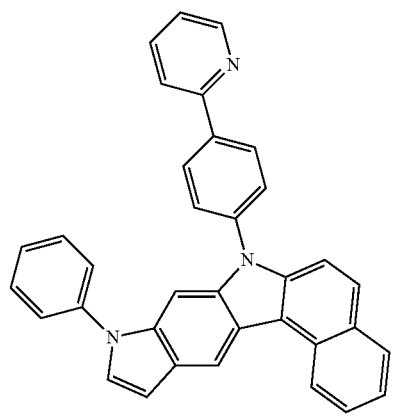
1456
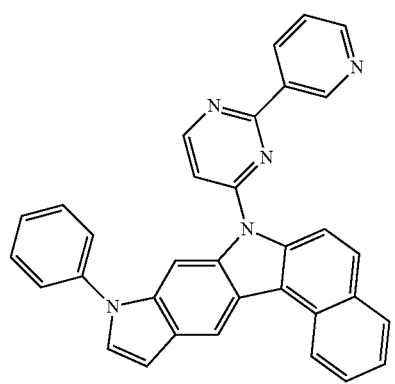
370
-continued
1457
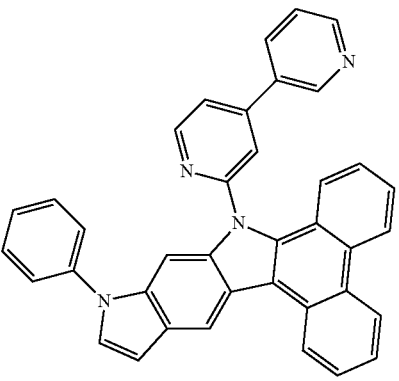
1458
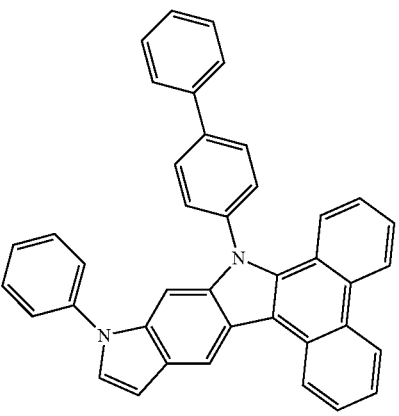
1459
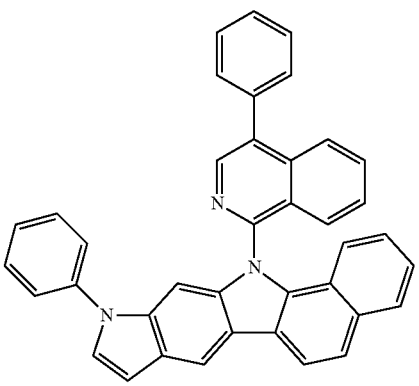
1460
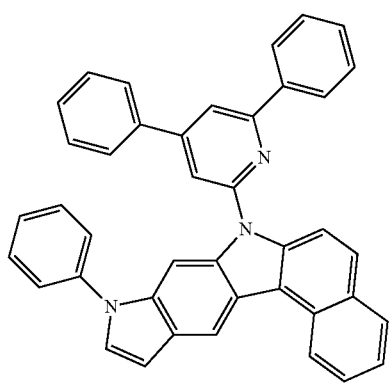

371
-continued
1461
1462
1463
1464
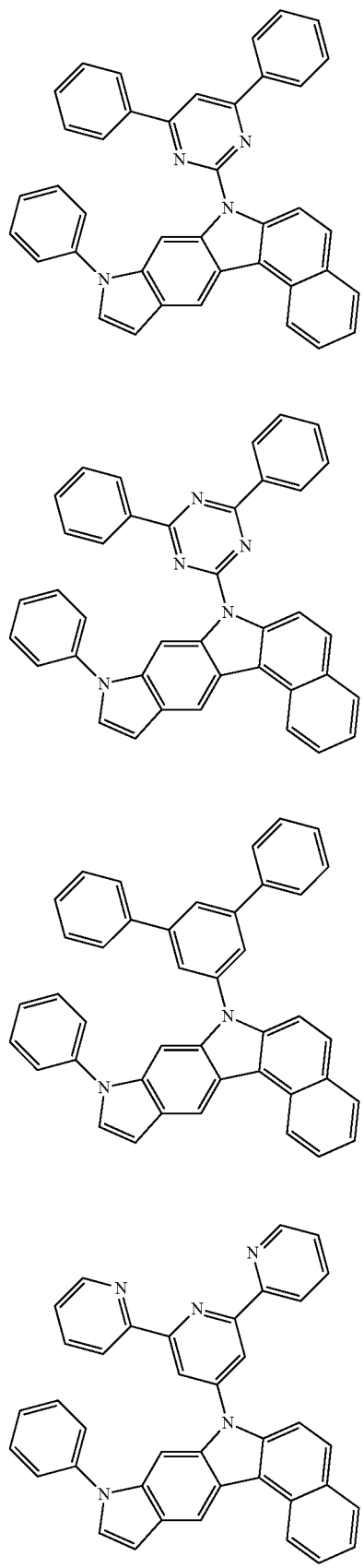
372
-continued
1465
1466
1467
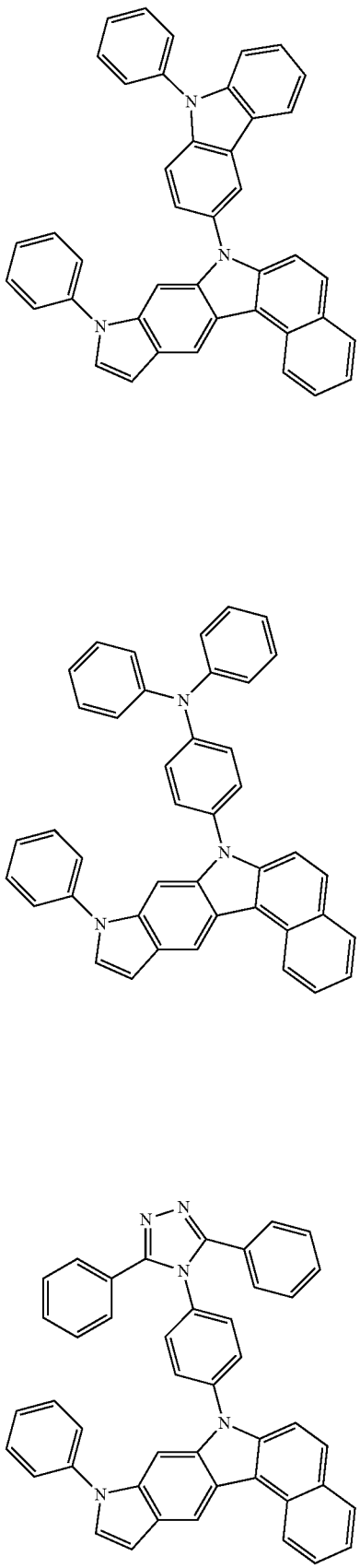

1468
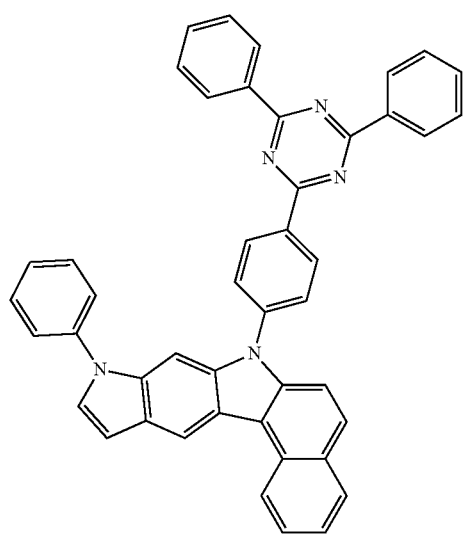
1469
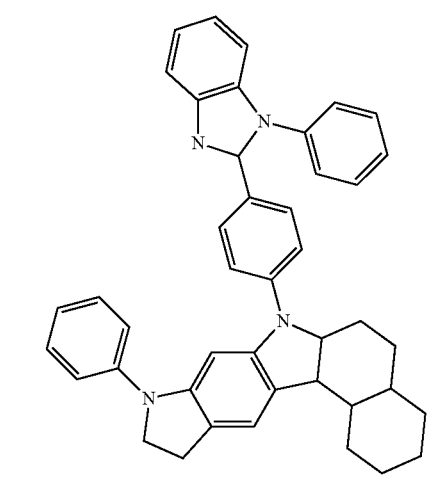
1470
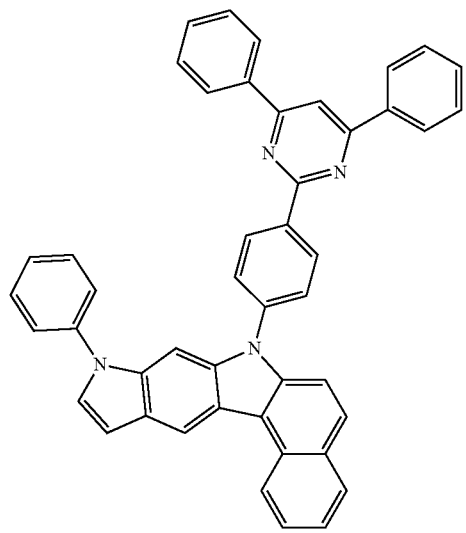
1471
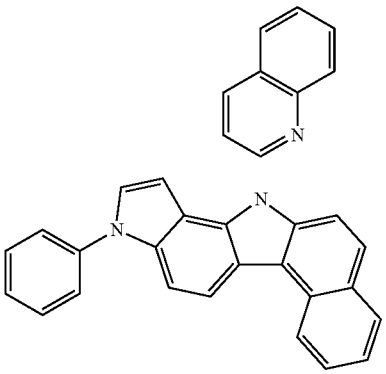
1472
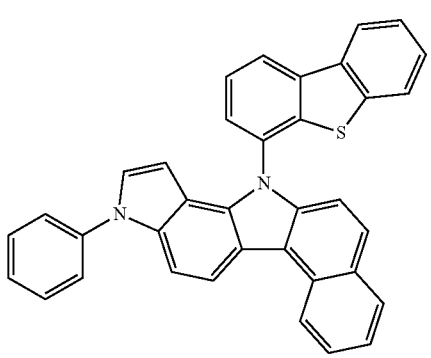
1473
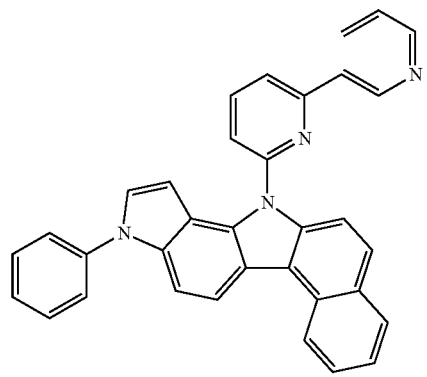
1474
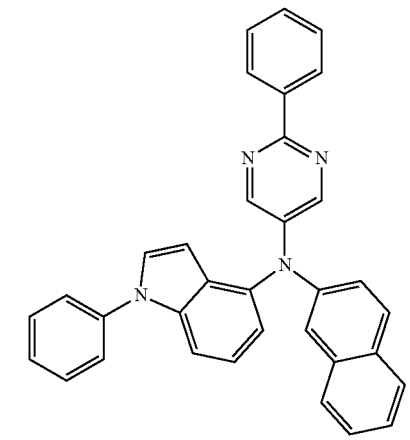

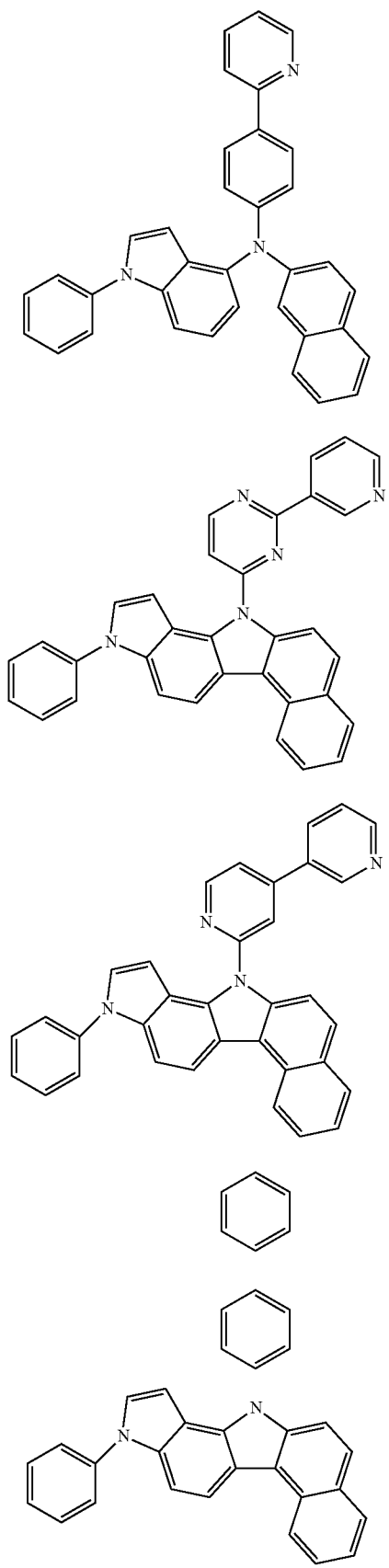
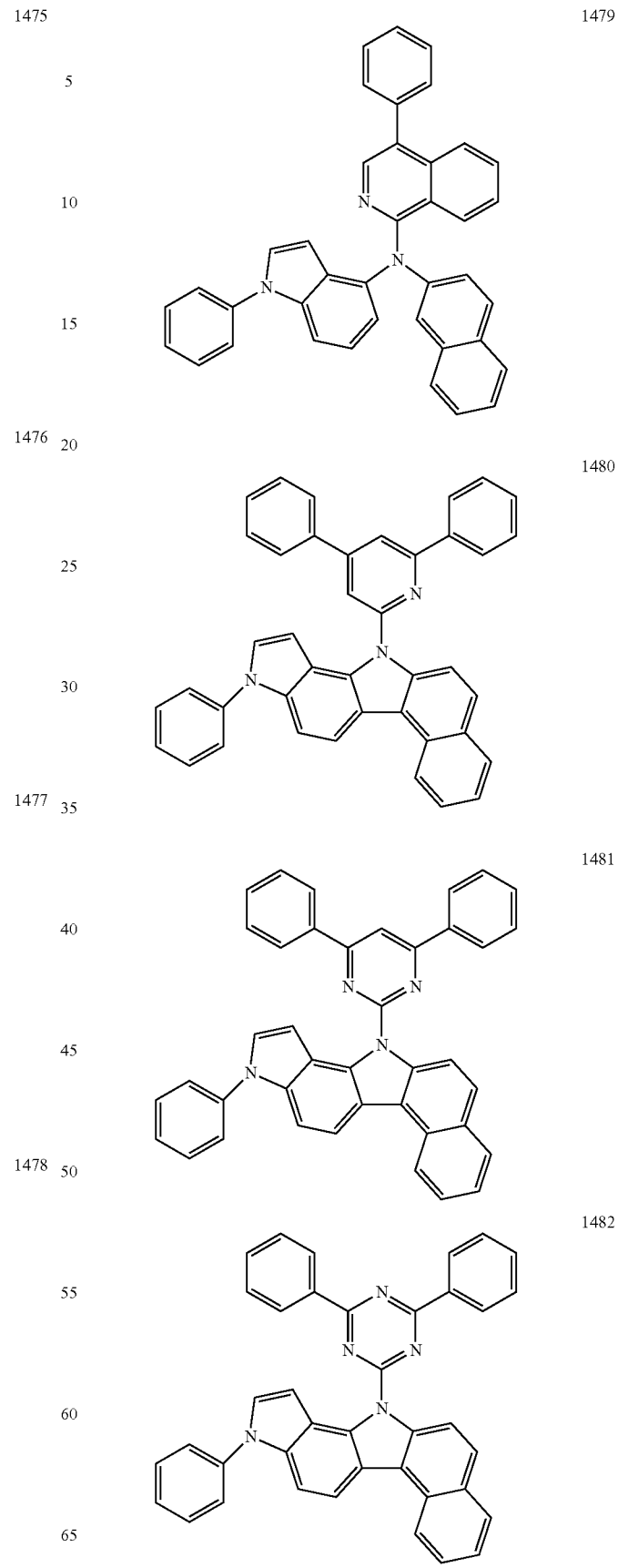

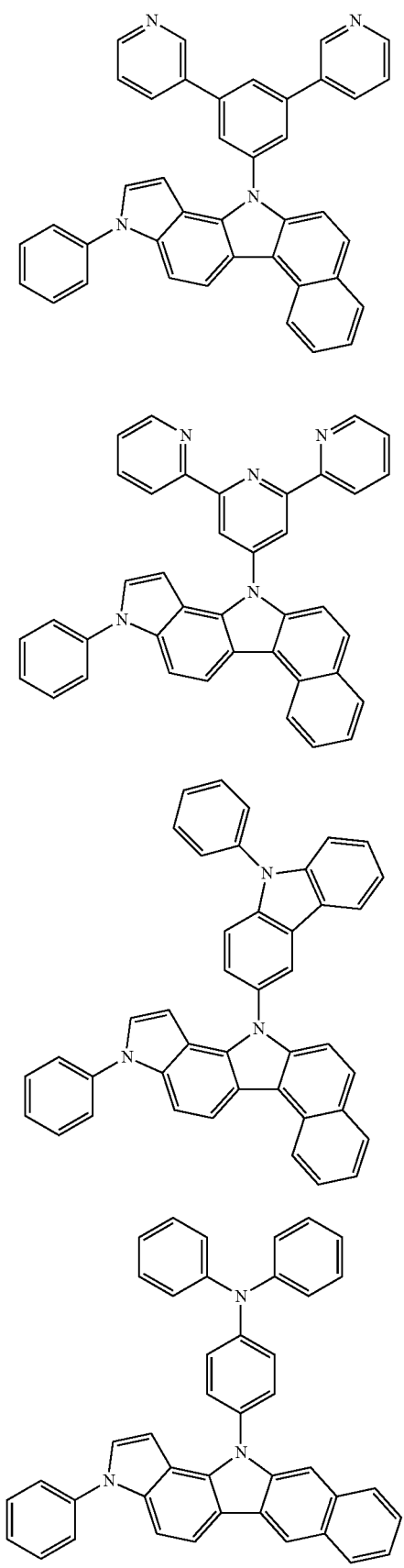

1490
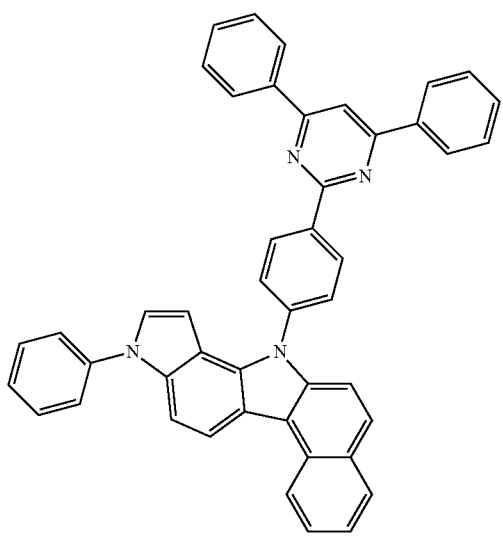
1491
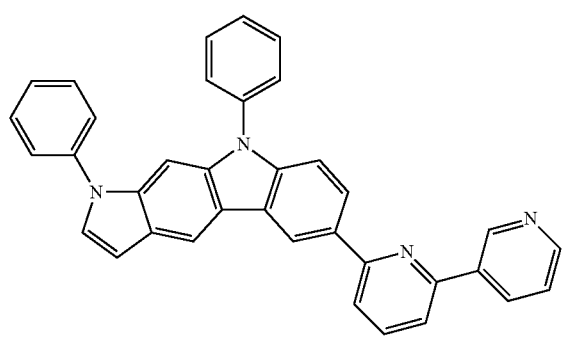
1492
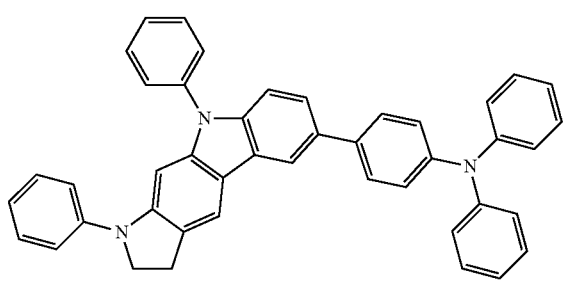
1493
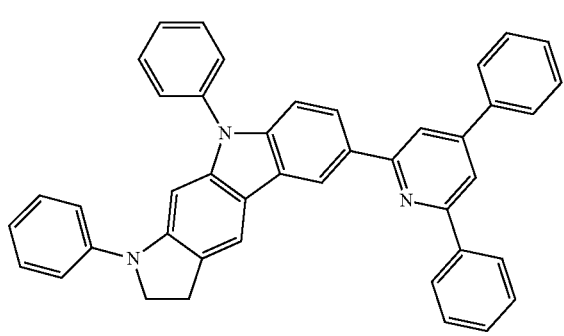
1494
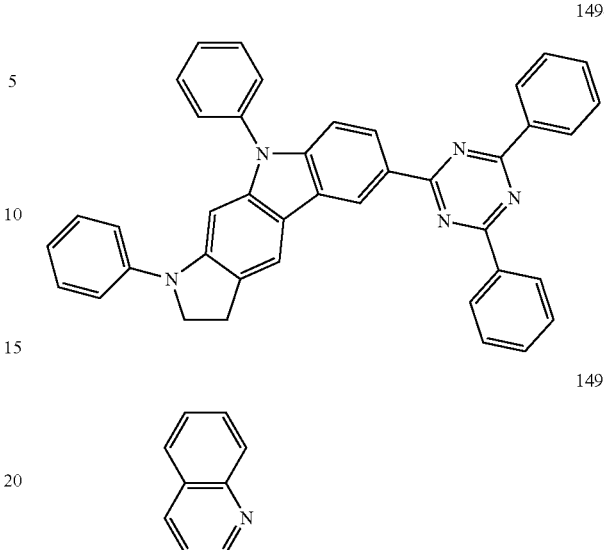
1495
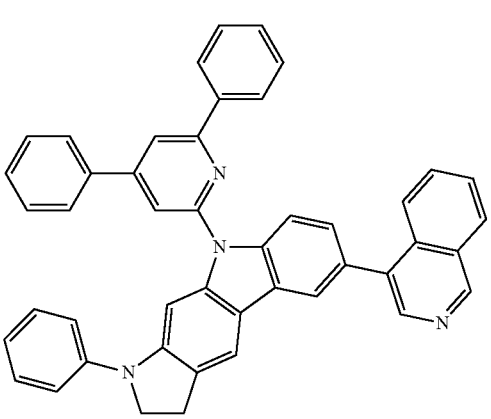
1496
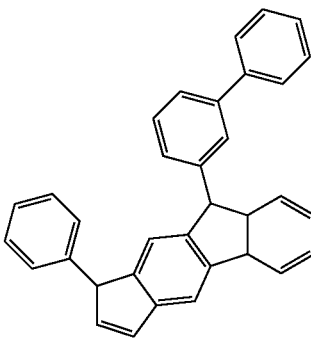
1497
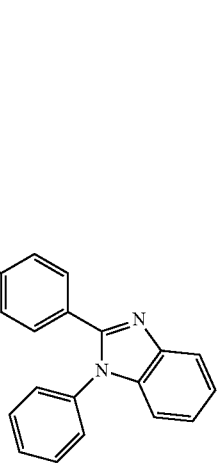

1498
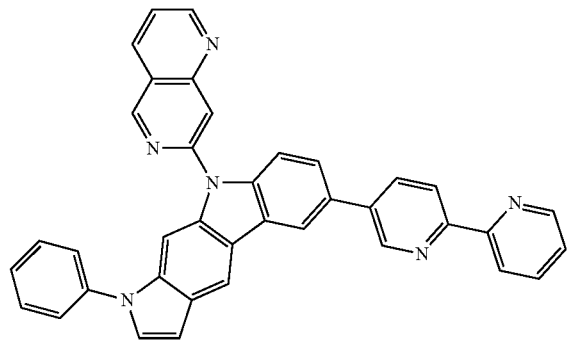
1499
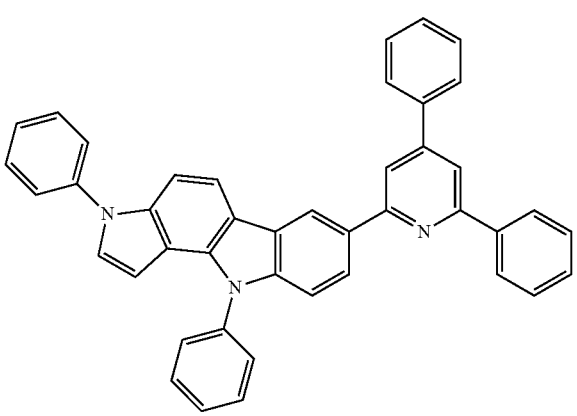
1500
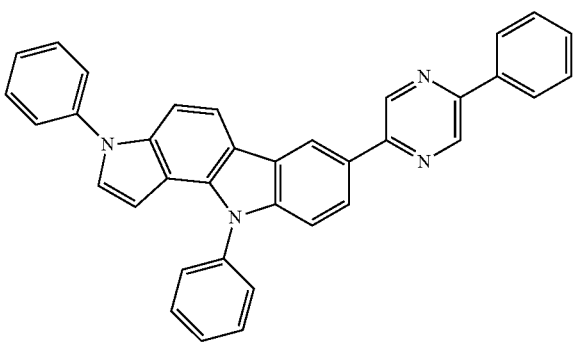
1501
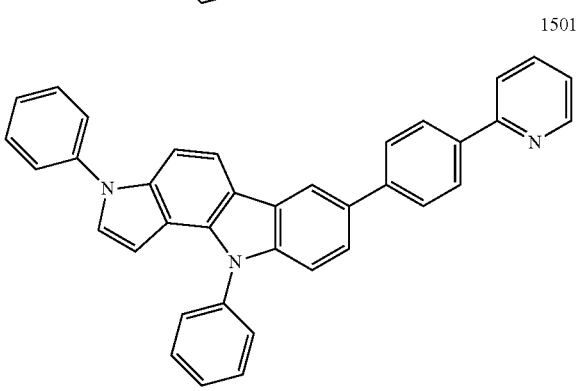
1502
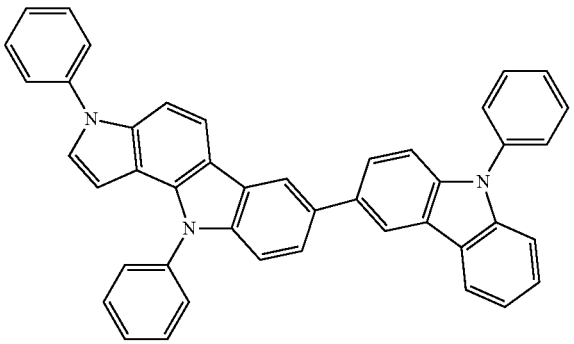
1503
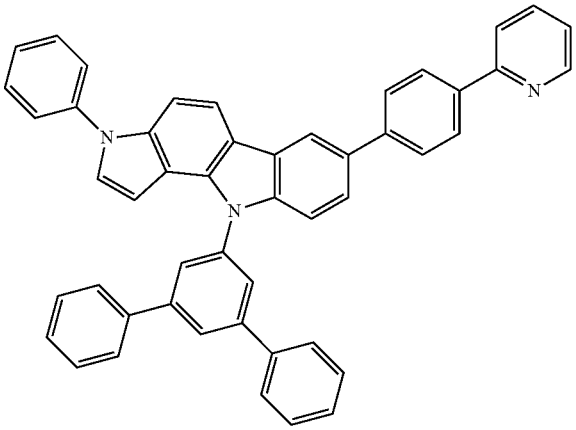
1504
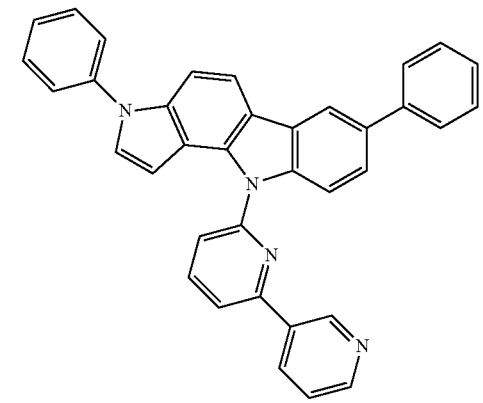

383
-continued
1505
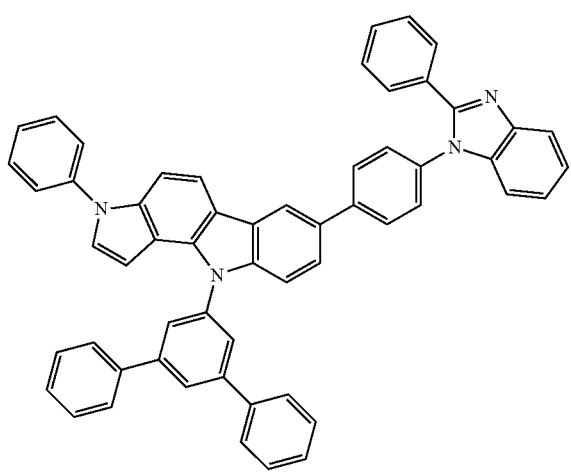
1506
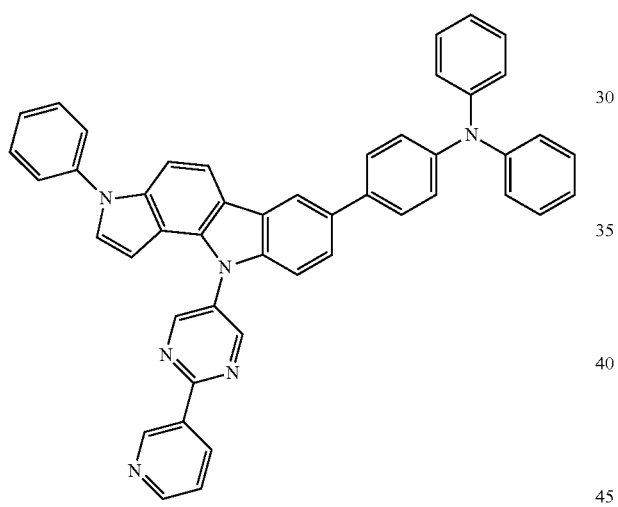
1507
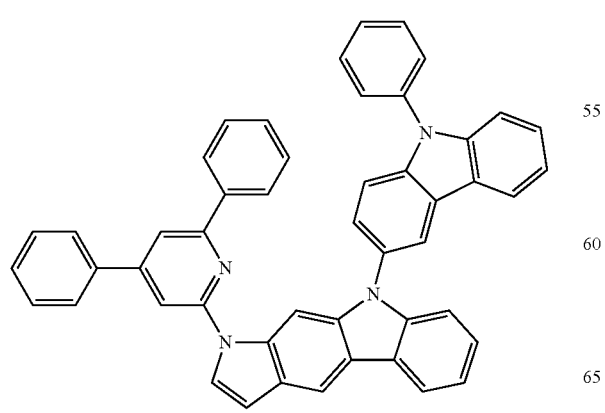
384
-continued
1508
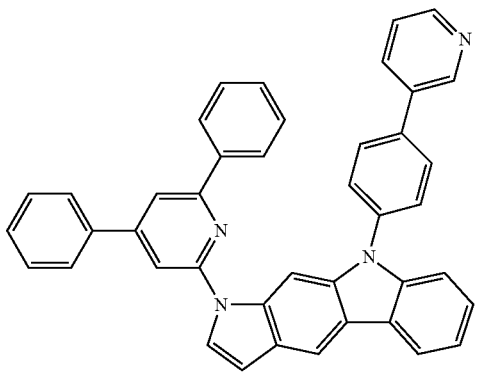
1509
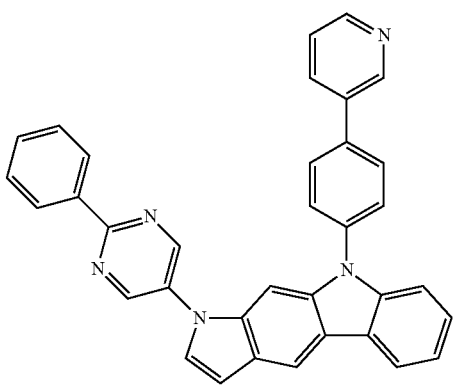
1510
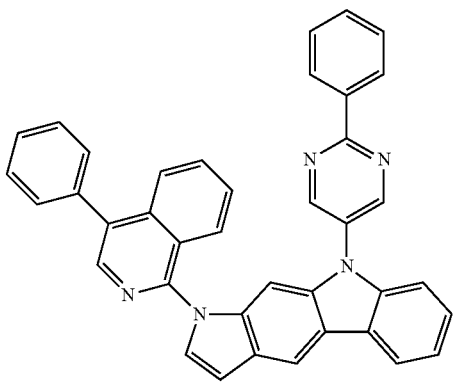

385
-continued
1511
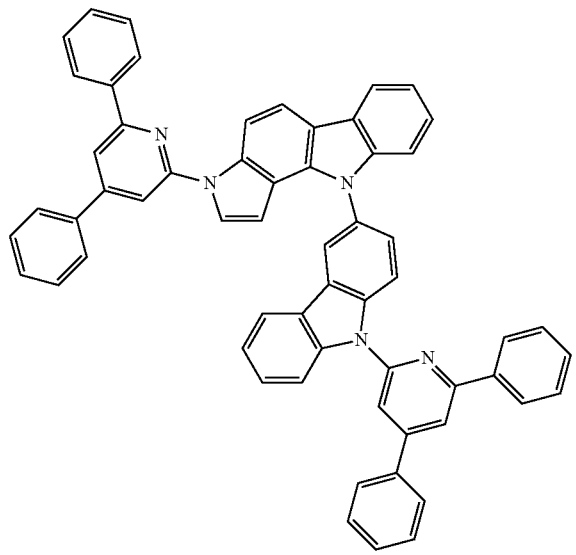
1512
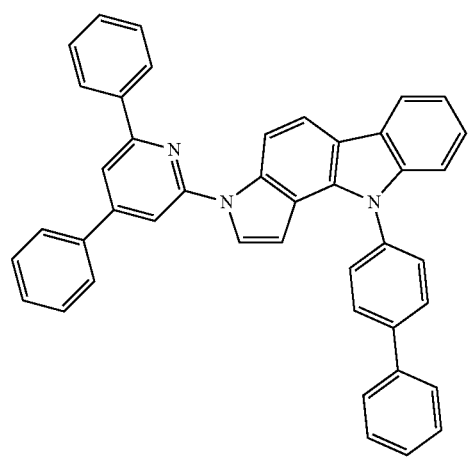
1513
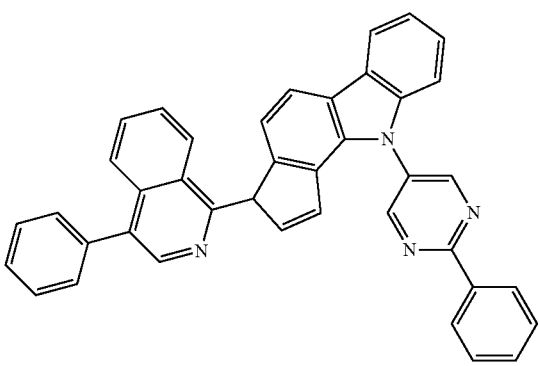
386
-continued
1514
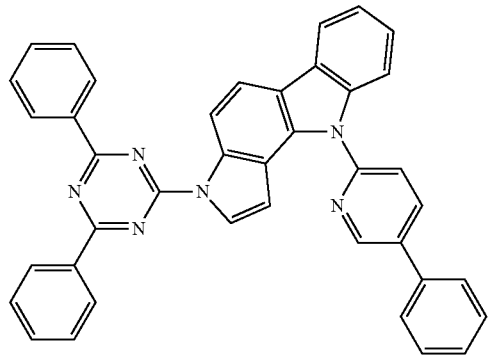
1515
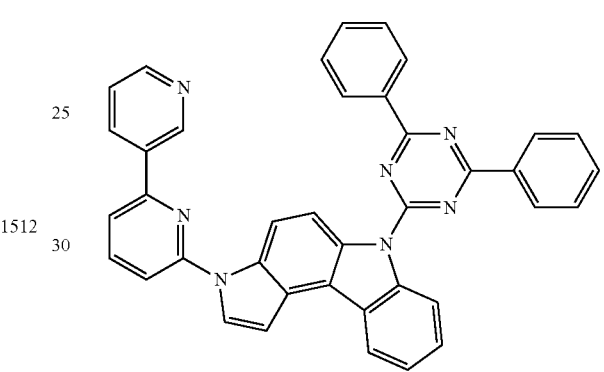
1516
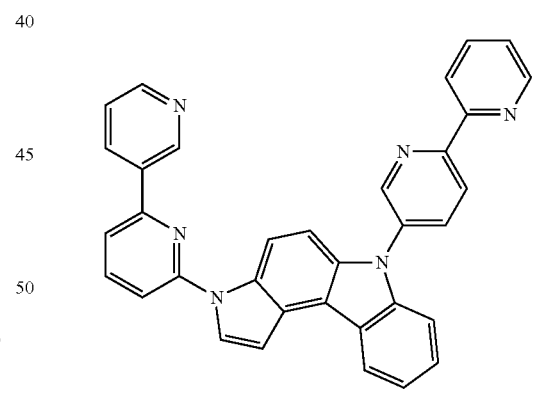
1517
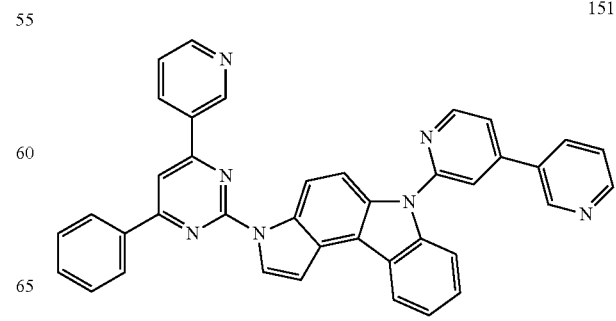

387
-continued
1518
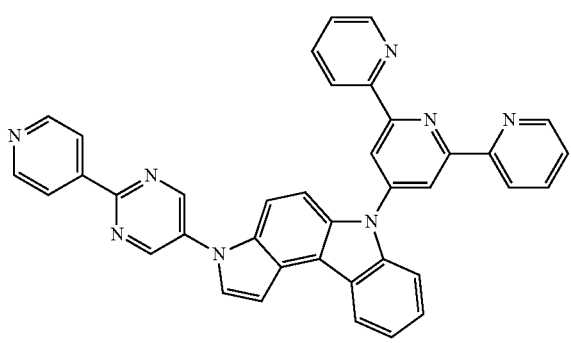
1519
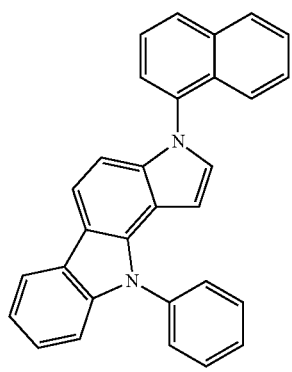
1520
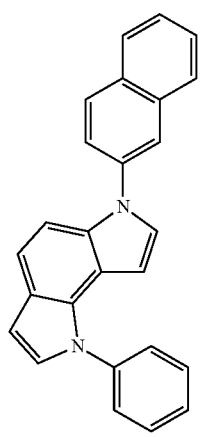
1521
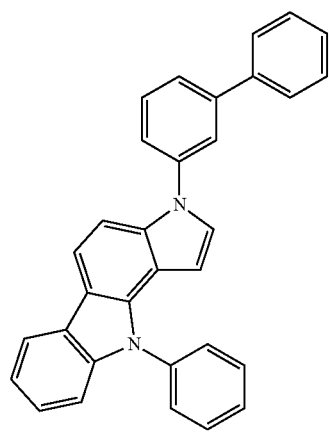
388
-continued
1522
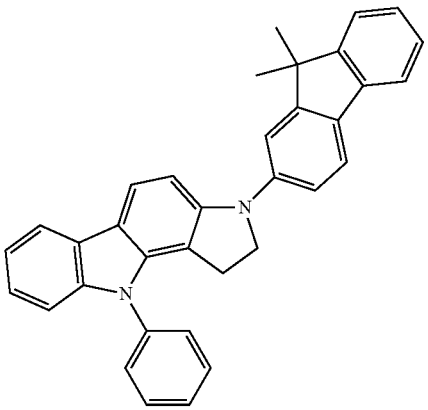
1523
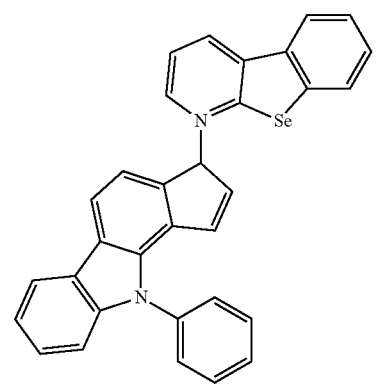
1524
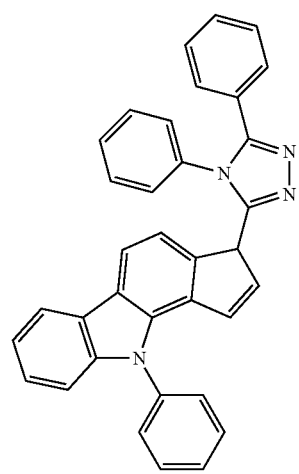

1525
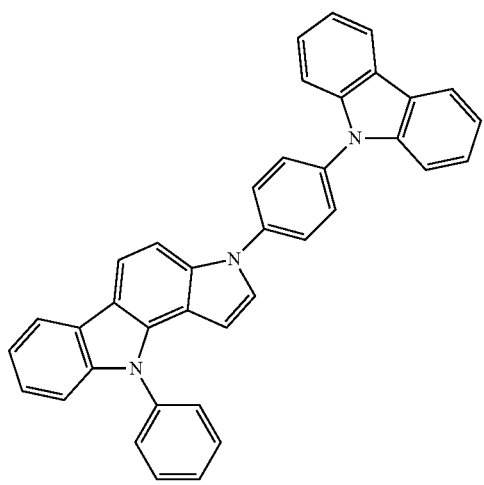
1526
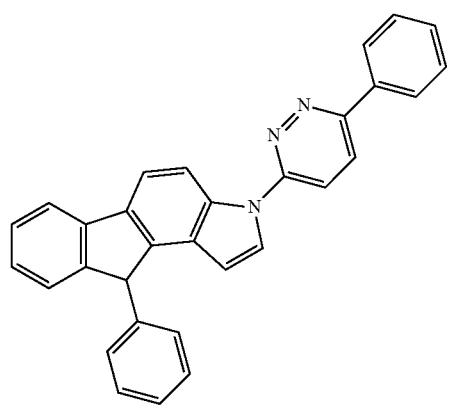
1527
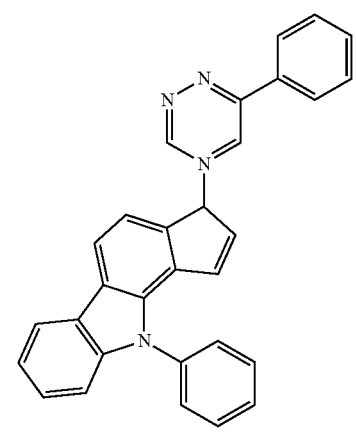
1528
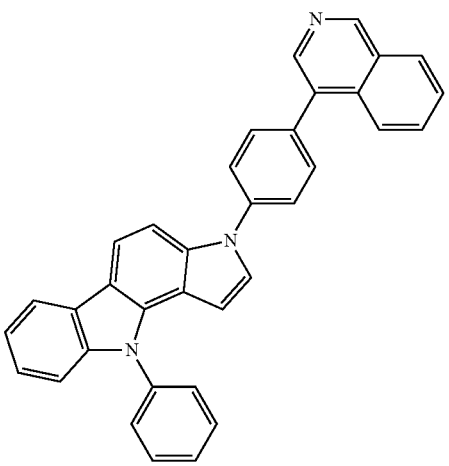
1529
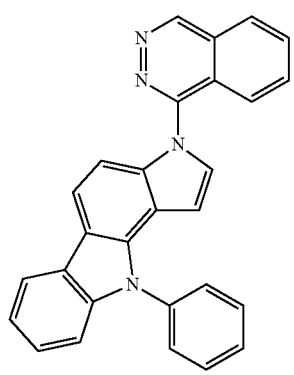
1530
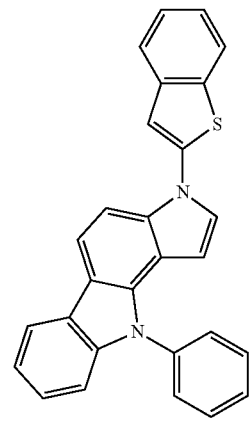
1531
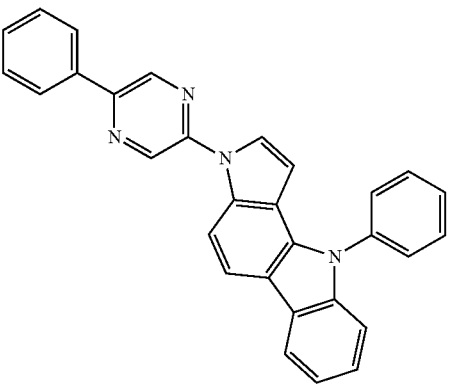

-continued
1532
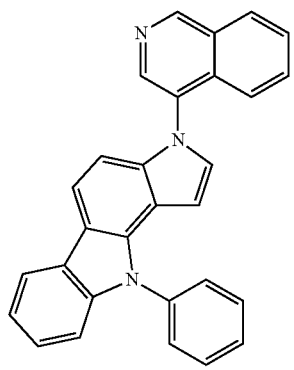
1533
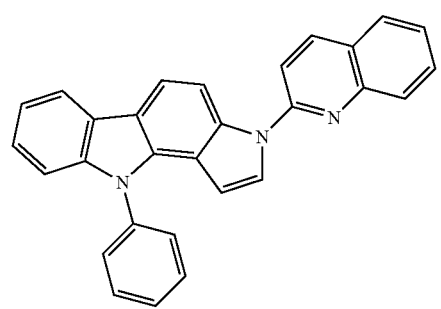
1534
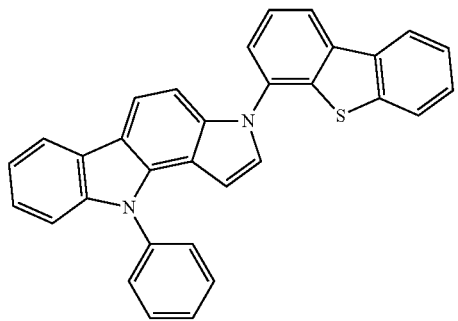
1535
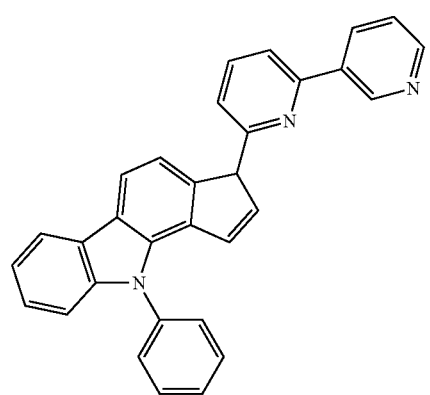
-continued
1536
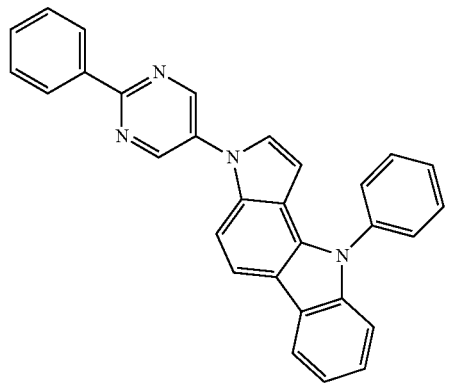
1537
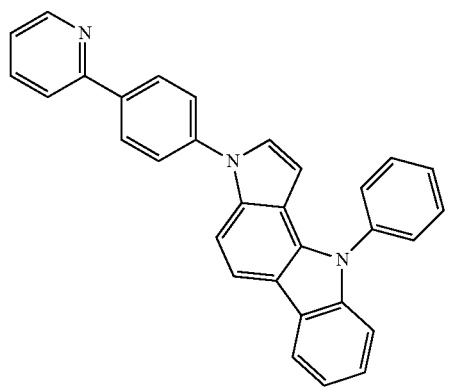
1539
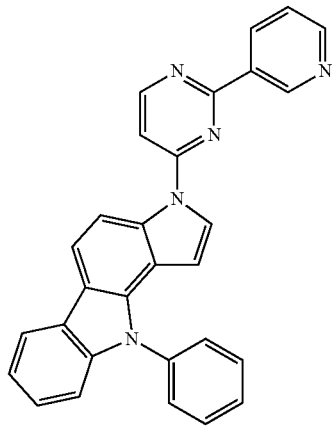
1540
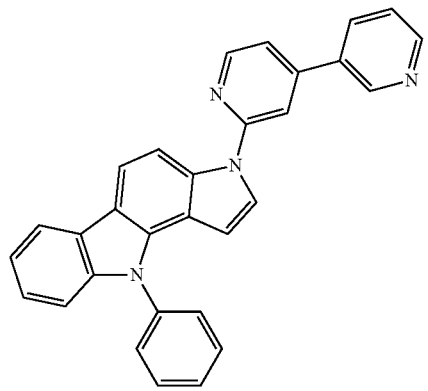

393
-continued
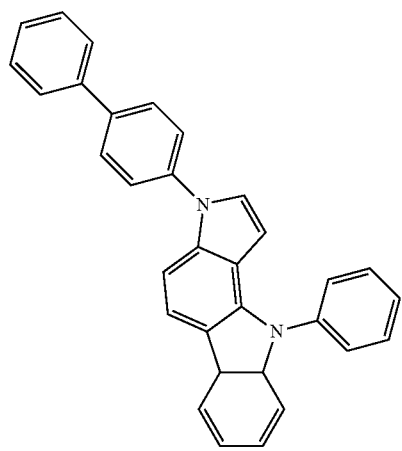
1541
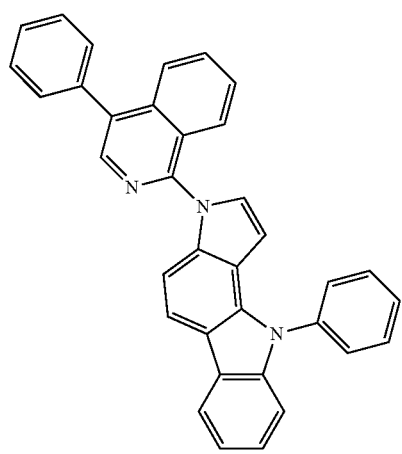
1542
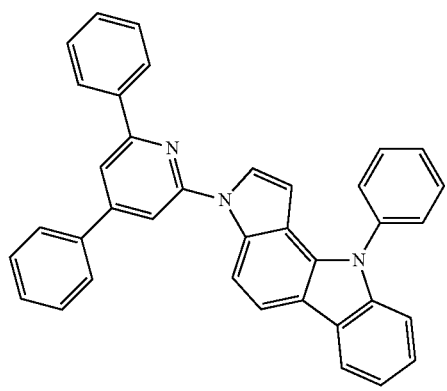
1543
394
-continued
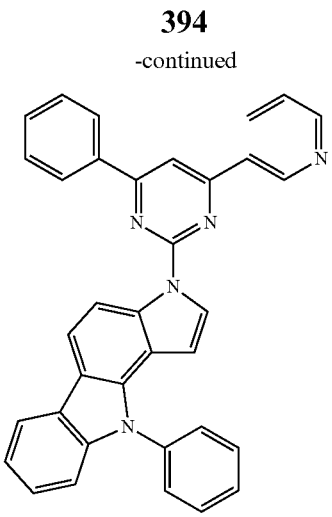
1544
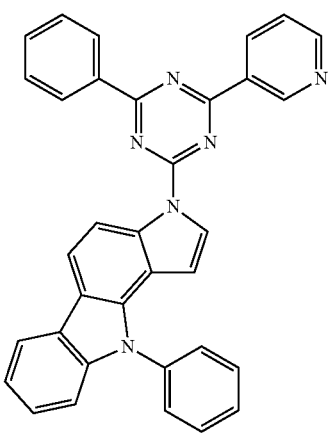
1545
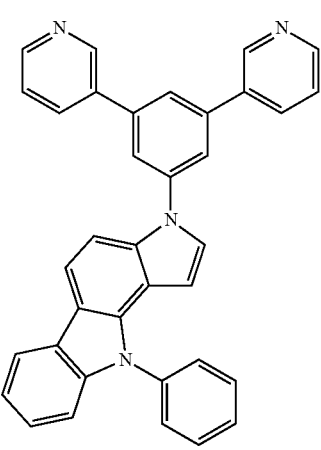
1546

395
-continued
1547
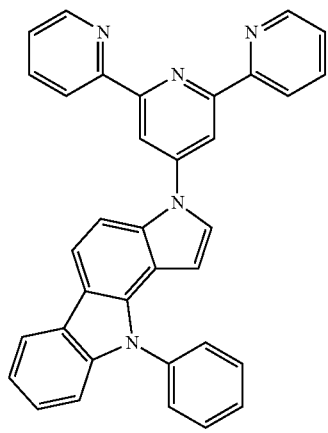
1548
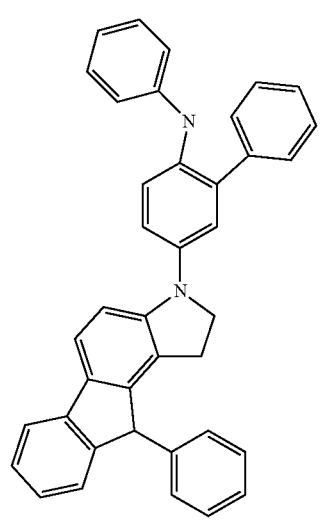
1549
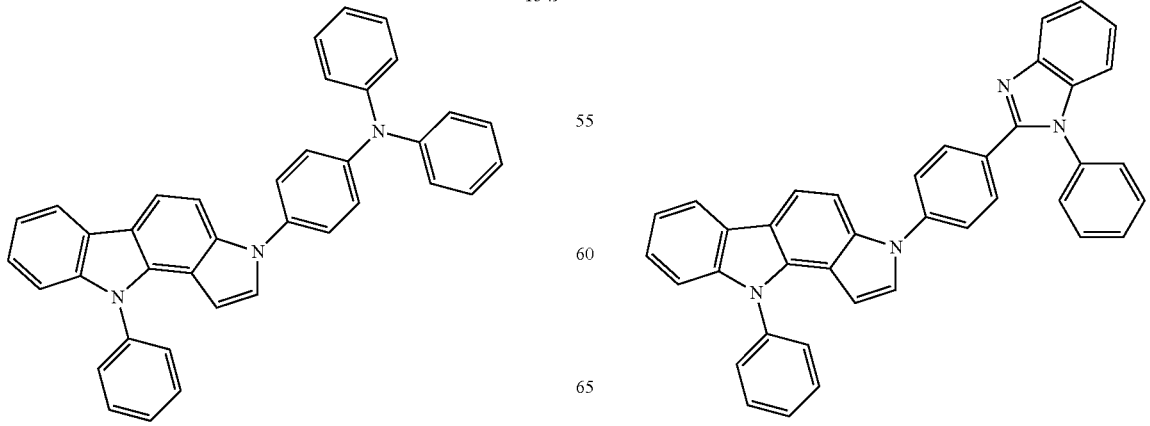
396
-continued
1550
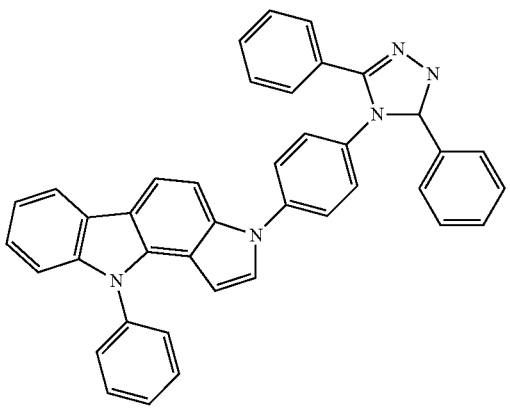
1551
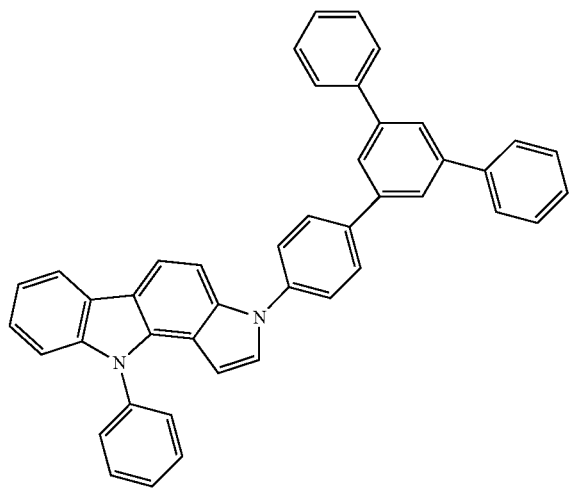
1552

397
-continued
1553
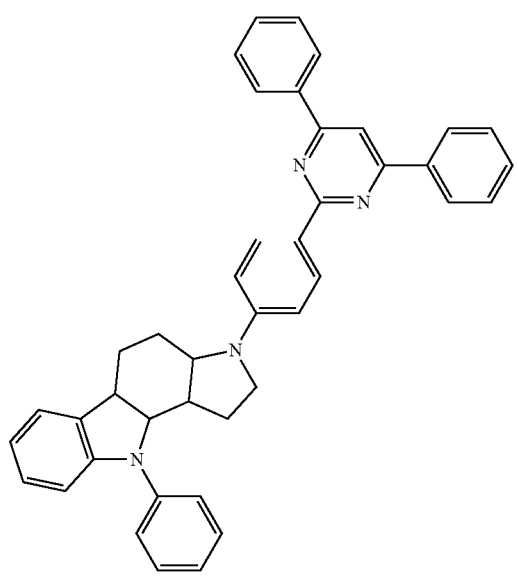
1554
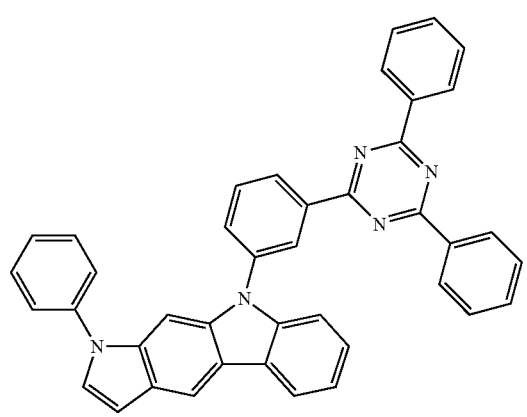
1555
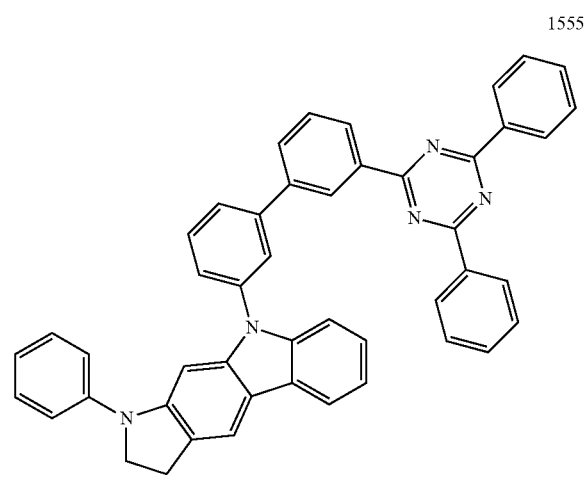
398
-continued
1556
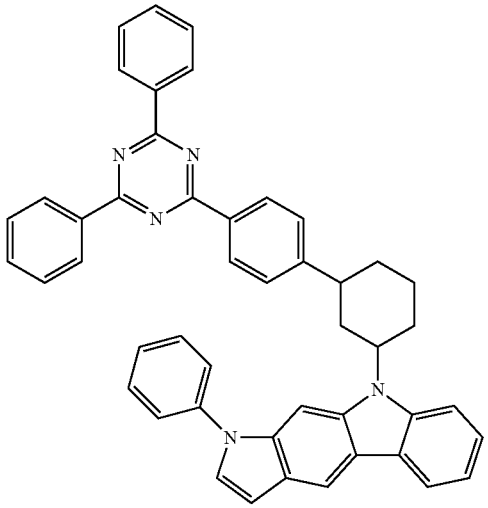
1557
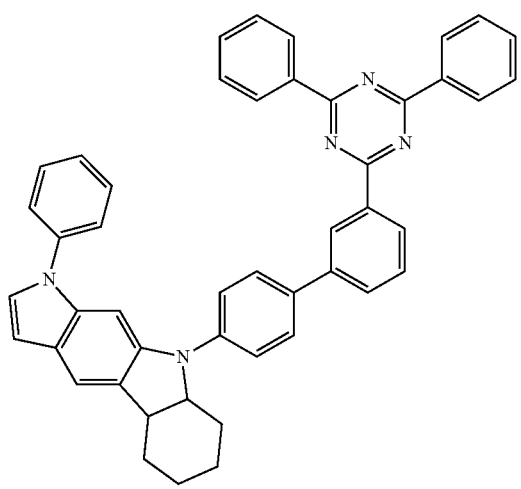
1558
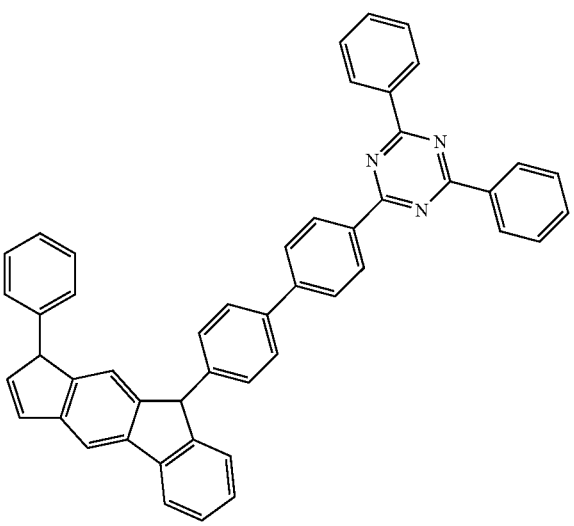

399
-continued
1559
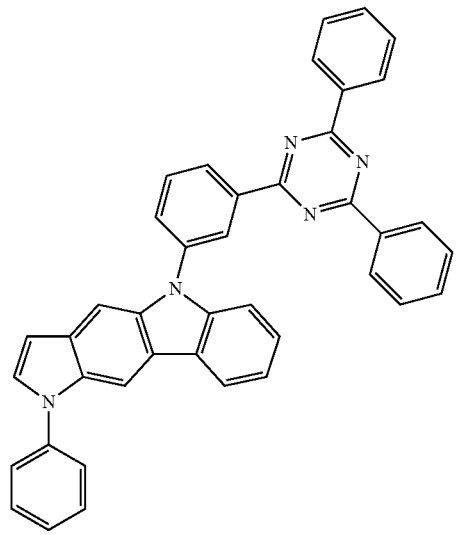
1560
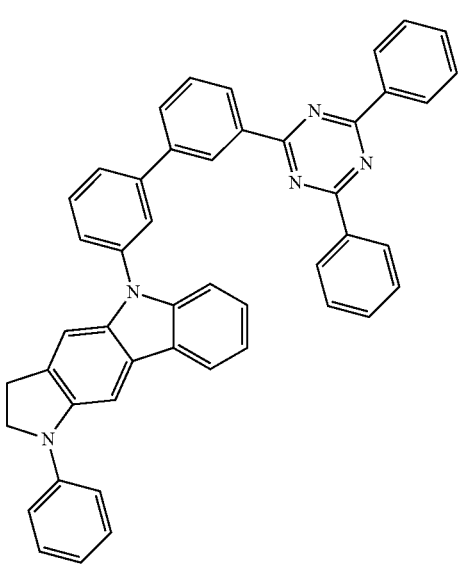
1561
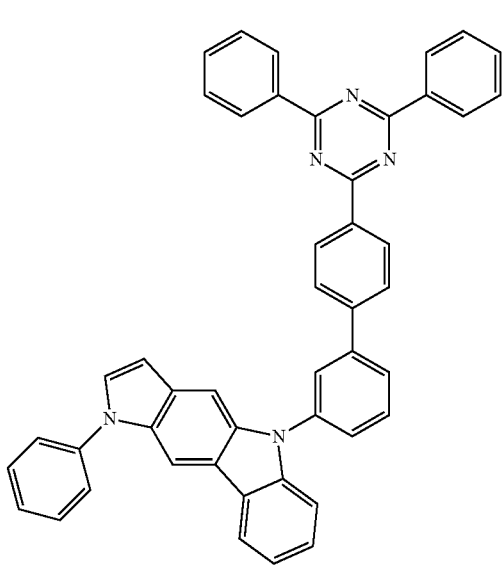
400
-continued
1562
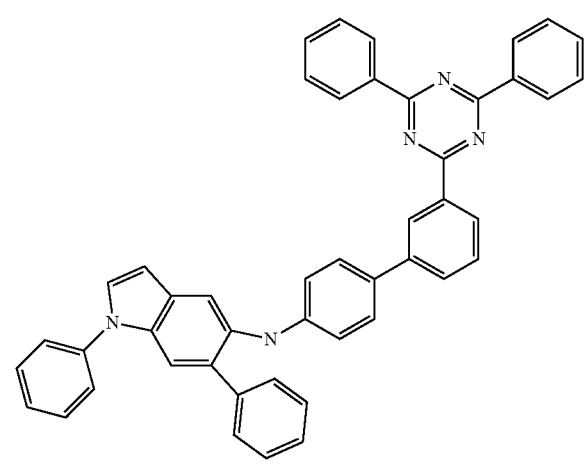
1563
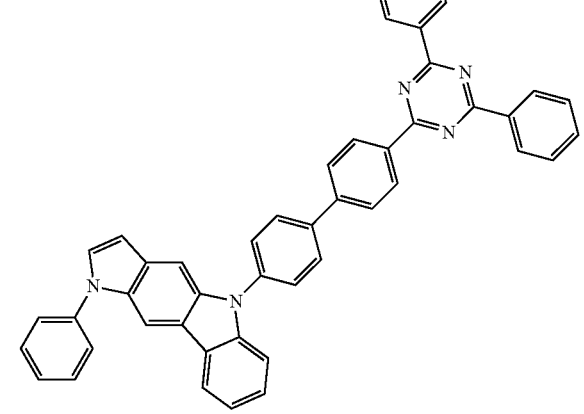
1564
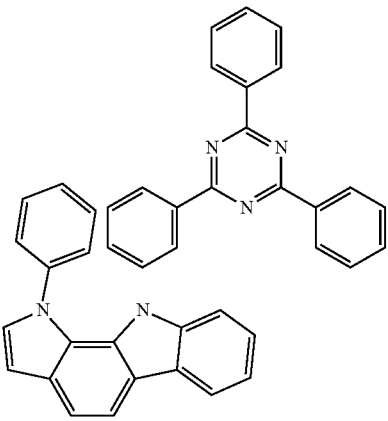

1565 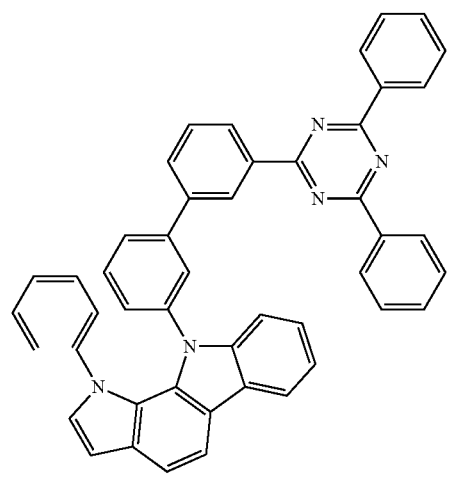
1568 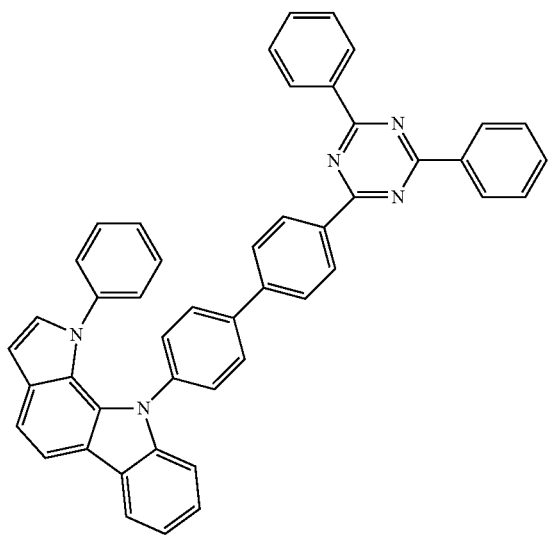
1566 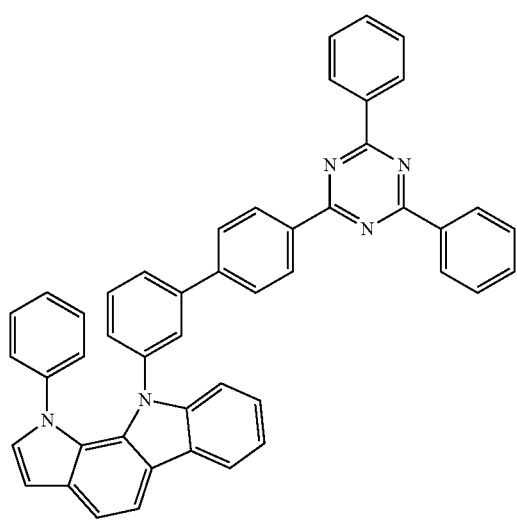
1569 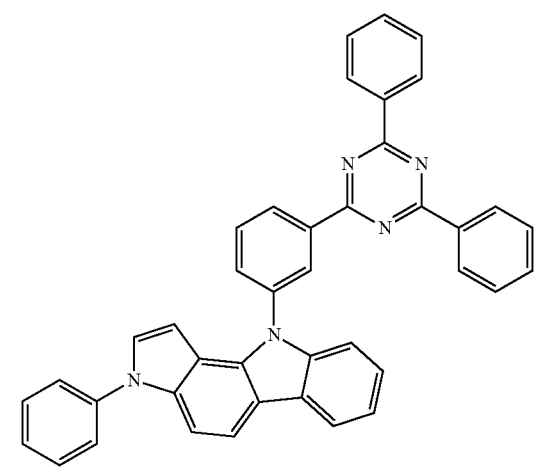
1567 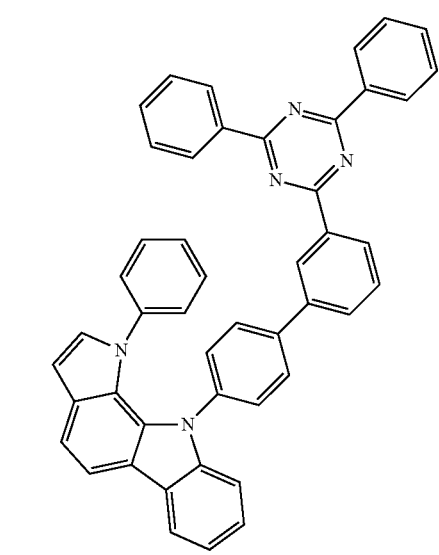
1570 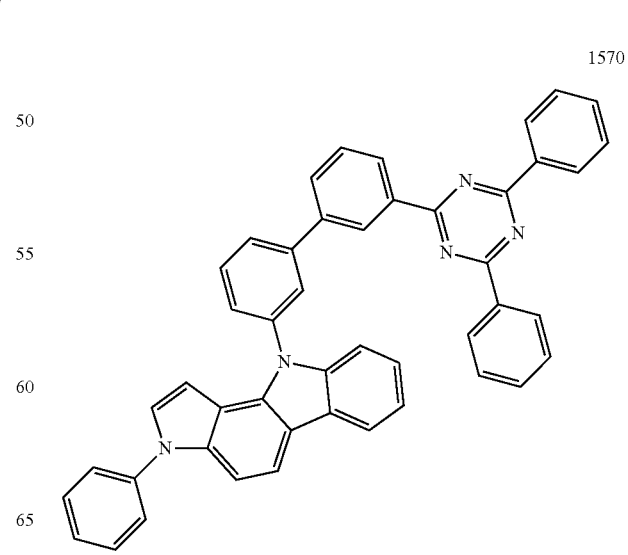

1571
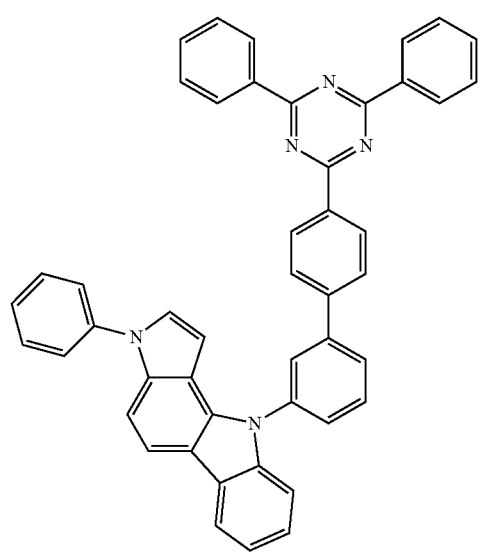
1572
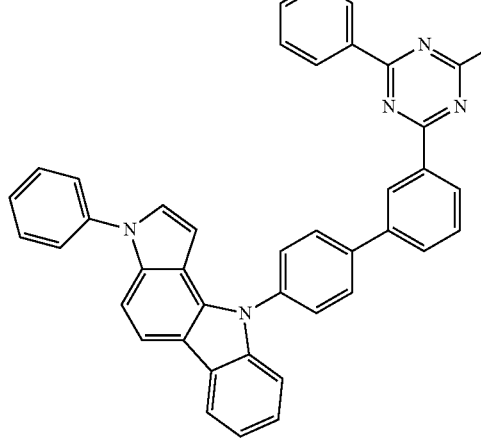
1573
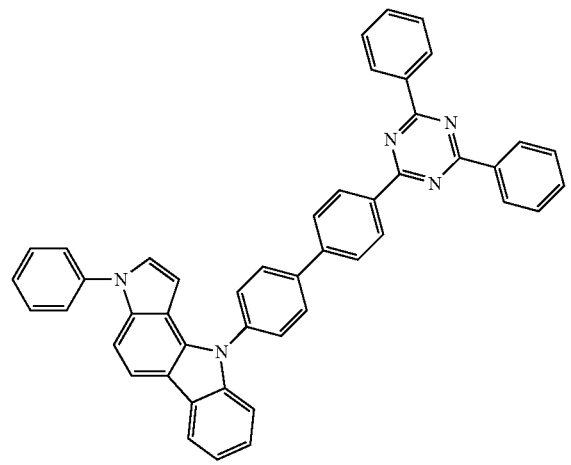
1574
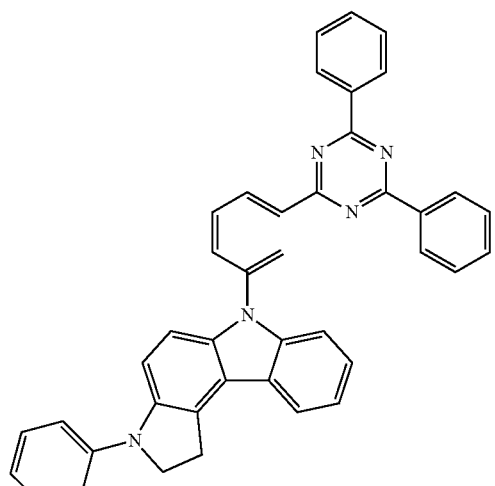
1575
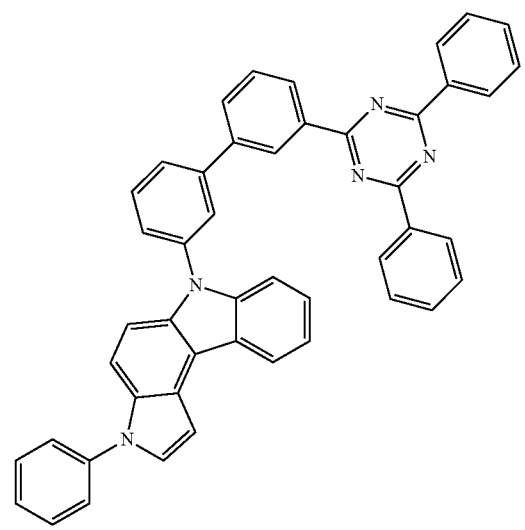
1576
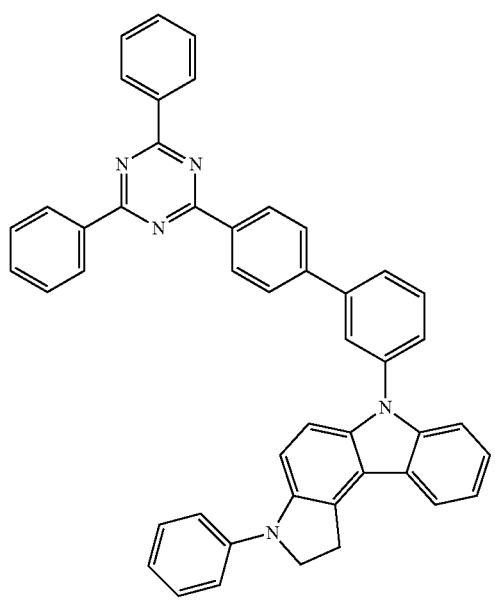

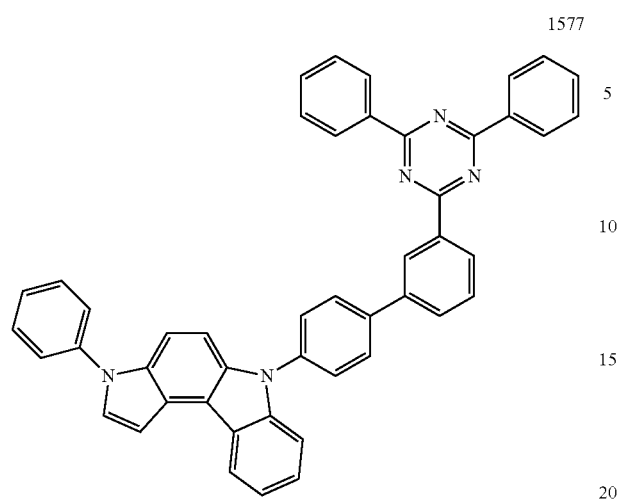
1577
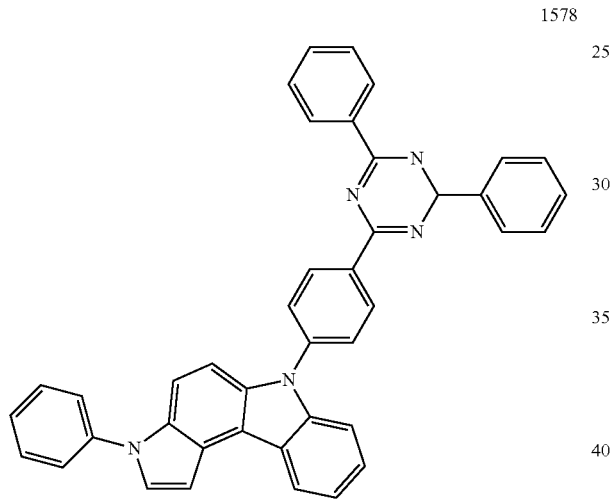
1578
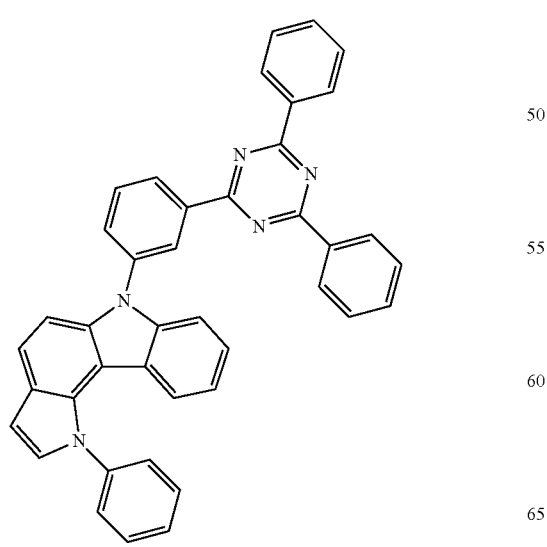
1579
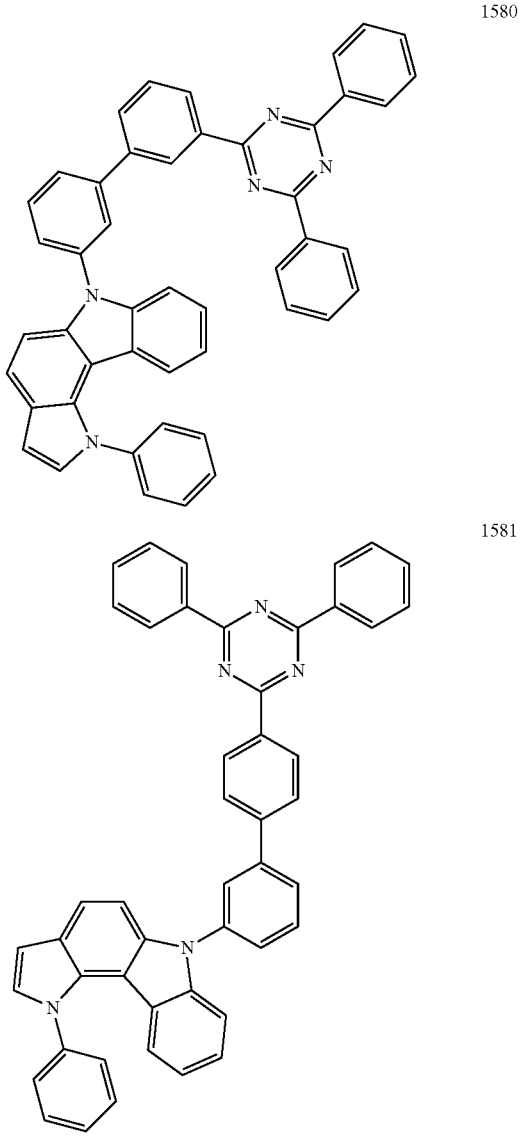

1583

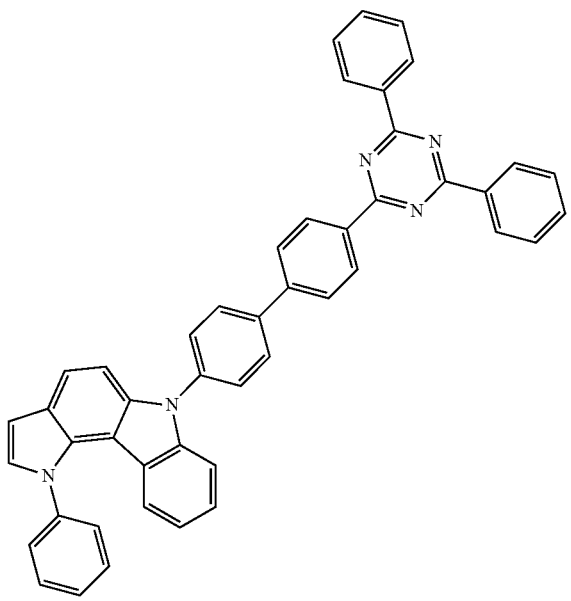

The compound of Formula 1 according to the present invention may be synthesized by a general synthesis method. The detailed synthesis process of the compound of Formula 1 according to the present invention will be specifically described in Examples to be described below.

The present invention also provides an organic EL device including: (i) an anode; (ii) a cathode; and (iii) an organic layer having one or more layers interposed between the anode and the cathode, in which at least one in the organic layer having one or more layers includes one or more of the compounds represented by Formula 1.

A non-limiting example of the organic EL device structure according to the present invention may be a structure in which a substrate, an anode, a hole injection layer, a hole transporting layer, a light-emitting layer, an electron transporting layer, and a cathode are sequentially laminated. In this case, one or more of the hole injection layer, the hole transporting layer, the electron injection layer, the electron transporting layer, and the light-emitting layer may include one or more of the compound represented by Formula 1. Further, the compound represented by Formula 1 according to the present invention may be used as a phosphorescent host of the light-emitting layer. An electron injection layer may be positioned on the electron transporting layer.

In addition, the organic EL device according to the present invention may have not only the aforementioned structure in which an anode, an organic layer having one or more layers and a cathode are sequentially laminated, but also a structure in which an insulation layer or an adhesive layer may be inserted at the interface of the electrode and the organic layer.

In the organic EL device according to the present invention, the organic layer including the compound represented by Formula 1 may be formed by a vacuum deposition method or a solution coating method. Examples of the solution coating method include spin coating, dip coating, doctor blading, inkjet printing or heat transferring method and the like, but are not limited thereto.

The organic EL device according to the present invention may be manufactured by forming organic layers and electrodes using the materials and methods known in the art, except that one or more layers of the organic layers are formed so as to include the compound represented by Formula 1 according to the present invention.

For example, as the substrate, a silicon wafer, quartz or a glass plate, a metal plate, a plastic film, a plastic film or sheet or the like may be used.

Examples of an anode material include: a metal such as vanadium, chromium, copper, zinc and gold, or an alloy thereof; a metal oxide such as zinc oxide, indium oxide, indium tin oxide (ITO) and indium zinc oxide (IZO); a combination of a metal and an oxide, such as ZnO:Al or $SnO_2$:Sb; a conductive polymer such as polythiophene, poly(3-methylthiophene), poly[3,4-(ethylene-1,2-dioxy)thiophene] (PEDT), polypyrrole and polyaniline; or carbon black and the like, but are not limited thereto.

Examples of a cathode material include a metal such as magnesium, calcium, sodium, potassium, titanium, indium, yttrium, lithium, gadolinium, aluminum, silver, tin or lead or an alloy thereof; a multilayer structured material such as LiF/Al or $LiO_2$/Al, and the like, but are not limited thereto.

Furthermore, the hole injection layer, the hole transporting layer, the electron injection layer, and the electron transporting layer are not particularly limited, and a typical material known in the art may be used.

Hereinafter, the present invention will be described in detail through the Examples. However, the following Examples are only provided to illustrate the present invention, and the present invention is not limited by the following Examples.

[Preparation Example 1] Synthesis of IC-1a and IC-1b

<Step 1> Synthesis of 5-(4,4,5,5-tetramethyl-1,3,2-dioxaborolan-2-yl)-1H-indole

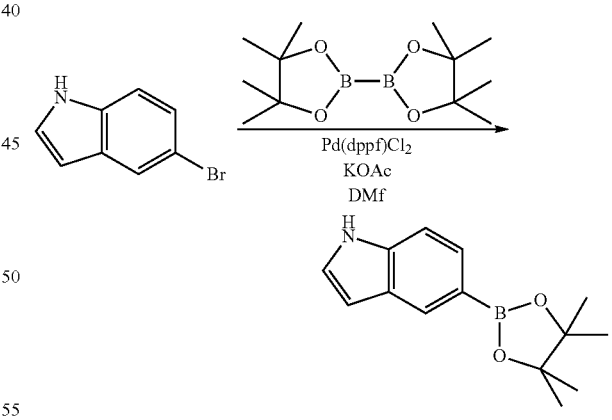

5-bromo-1H-indole (25 g, 0.128 mol), 4,4,4',4',5,5,5',5'-octamethyl-2,2'-bi(1,3,2-dioxaborolane) (48.58 g, 0.191 mol), Pd(dppf)Cl₂ (5.2 g, 5 mol), KOAc (37.55 g, 0.383 mol) and DMF (500 ml) were mixed under nitrogen flow, and the mixture was stirred at 130° C. for 12 hours.

After the reaction was completed, extraction was performed with ethyl acetate, moisture was removed with MgSO₄, and purification was performed by column chromatography (Hexane:EA=10:1 (v/v)), thereby obtaining 5-(4,4,5,5-tetramethyl-1,3,2-dioxaborolan-2-yl)-1H-indole (12.43 g, yield 40%).

¹H-NMR: δ 24 (s, 12H), 6.45 (d, 1H), 7.27 (d, 1H), 7.42 (d, 1H), 7.52 (d, 1H), 7.95 (s, 1H), 8.21 (s, 1H)

<Step 2> Synthesis of 5-(2-nitrophenyl)-1H-indole

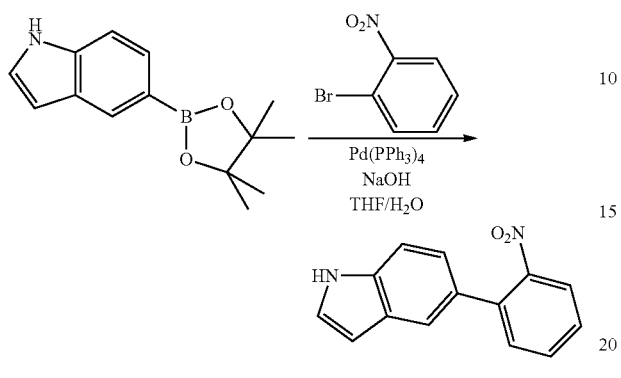

1-bromo-2-nitrobenzene (8 g, 39.6 mmol), 5-(4,4,5,5-tetramethyl-1,3,2-dioxaborolan-2-yl)-1H-indole (11.55 g, 47.5 mmol) obtained in <Step 1>, NaOH (4.75 g, 118.8 mmol) and THF/H₂O (200 ml/100 ml) were mixed under nitrogen flow, then Pd(PPh₃)₄ (2.29 g, 5 mol) was added to the mixture at 40° C., and the resulting mixture was stirred at 80° C. for 12 hours.

After the reaction was completed, the mixture was extracted with methylene chloride, MgSO₄ was added thereto, and extraction was performed. After the solvent was removed from the organic layer obtained, the residue was purified by column chromatography (Hexane:EA=3:1 (v/v)), thereby obtaining 5-(2-nitrophenyl)-1H-indole (6.5 g, yield 69%).

¹H-NMR: δ 6.47 (d, 1H), 7.25 (d, 1H), 7.44 (d, 1H), 7.53 (d, 1H), 7.65 (t, 1H), 7.86 (t, 1H), 7.95 (s, 1H), 8.00 (d, 1H), 8.09 (t, 1H), 8.20 (s, 1H)

<Step 3> Synthesis of 5-(2-nitrophenyl)-1-phenyl-1H-indole

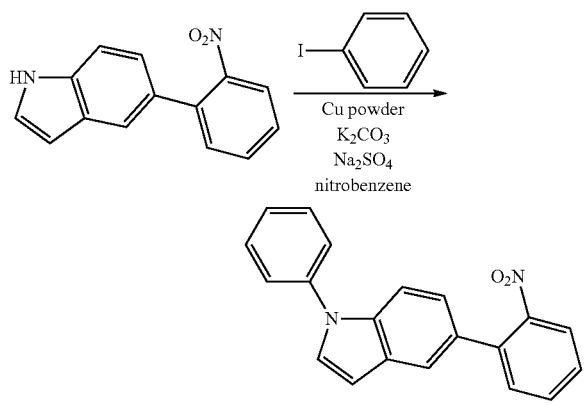

5-(2-nitrophenyl)-1H-indole (6.5 g, 27.28 mmol) obtained in <Step 2>, Iodobenzene (8.35 g, 40.93 mmol), Cu powder (0.17 g, 2.73 mmol), K₂CO₃ (3.77 g, 27.28 mmol), Na₂SO₄ (3.88 g, 27.28 mmol), and nitrobenzene (100 ml) were mixed under nitrogen flow, and the mixture was stirred at 190° C. for 12 hours.

After the reaction was completed, nitrobenzene was removed, the organic layer was separated with methylene chloride, and water was removed by using MgSO₄. After the solvent was removed from the organic layer in which water was removed, the residue was purified by column chromatography (Hexane:MC=3:1 (v/v)), thereby obtaining 5-(2-nitrophenyl)-1-phenyl-H-indole (6.7 g, yield 78%).

¹H-NMR: δ 6.48 (d, 1H), 7.26 (d, 1H), 7.45 (m, 3H), 7.55 (m, 4H), 7.63 (t, 1H), 7.84 (t, 1H), 7.93 (s, 1H), 8.01 (d, 1H), 8.11 (t, 1H)

<Step 4> Synthesis of IC-1a and IC-1b

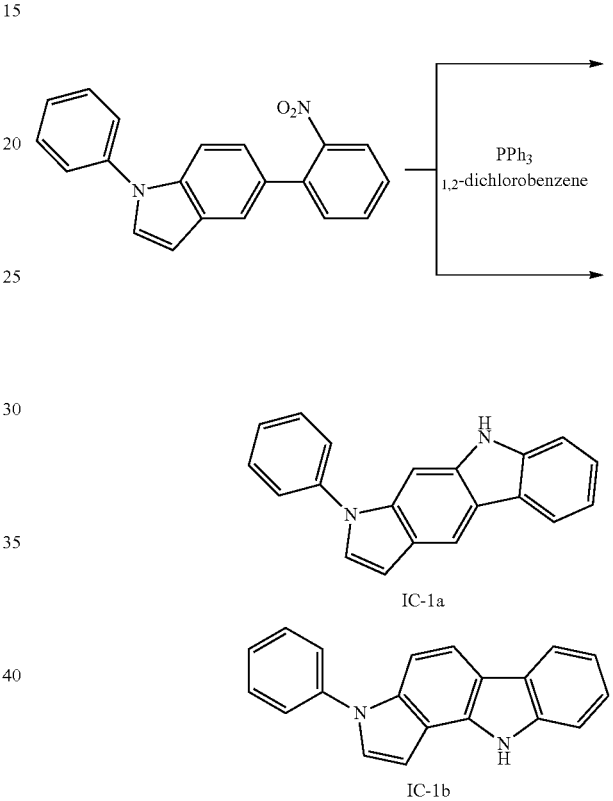

5-(2-nitrophenyl)-1-phenyl-1H-indole (6 g, 19.09 mmol) obtained in <Step 3>, triphenylphosphine(PPh₃) (12.52 g, 47.72 mmol) and 1,2-dichlorobenzene (50 ml) were mixed under nitrogen flow, and the mixture was stirred for 12 hours.

After the reaction was completed, 1,2-dichlorobenzene was removed, and extraction was performed with dichloromethane. For the organic layer obtained, water was removed with MgSO₄, and purification was performed by column chromatography (Hexane:MC=3:1 (v/v)), thereby obtaining IC-1a (2.32 g, yield 43%) and IC-1b (2.21 g, yield 41%).

¹H-NMR for IC-1a: δ 6.51 (d, 1H), 7.28 (d, 1H), 7.46 (m, 3H), 7.51 (s, 1H), 7.56 (m, 3H), 7.64 (t, 1H), 7.85 (m, 2H), 8.08 (t, 1H), 8.24 (s, 1H)

¹H-NMR for IC-1b: δ 6.53 (d, 1H), 7.27 (d, 1H), 7.45 (m, 3H), 7.50 (d, 1H), 7.55 (m, 3H), 7.67 (t, 1H), 7.89 (m, 2H), 8.12 (t, 1H), 8.25 (s, 1H)

[Preparation Example 2] Synthesis of IC-2

<Step 1> Synthesis of 4-(4,4,5,5-tetramethyl-1,3,2-dioxaborolan-2-yl)-1H-indole

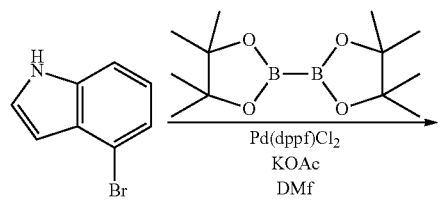

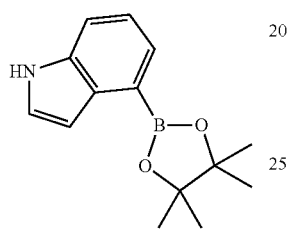

4-(4,4,5,5-tetramethyl-1,3,2-dioxaborolan-2-yl)-1H-indole was obtained by performing the same procedure as in <Step 1> of Preparation Example 1, except that 4-bromo-1H-indole was used instead of 5-bromo-1H-indole.

$^1$H NMR: δ 1.26 (s, 12H), 6.43 (d, 1H), 7.26 (t, 1H), 7.48 (d, 1H), 7.74 (d, 1H), 7.85 (d, 1H), 8.23 (s, 1H)

<Step 2> Synthesis of 4-(2-nitrophenyl)-1H-indole

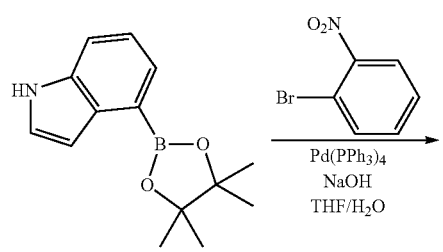

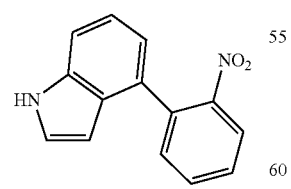

4-(2-nitrophenyl)-1H-indole was obtained by performing the same procedure as in <Step 2> of Preparation Example 1, except that 4-(4,4,5,5-tetramethyl-1,3,2-dioxaborolan-2-yl)-1H-indole obtained in <Step 1> was used instead of 5-(4,4,5,5-tetramethyl-1,3,2-dioxaborolan-2-yl)-1H-indole.

$^1$H NMR: δ 6.45 (d, 1H), 7.27 (t, 1H), 7.50 (d, 1H), 7.66 (t, 1H), 7.75 (d, 1H), 7.89 (m, 2H), 7.99 (d, 1H), 8.04 (d, 1H), 8.24 (s, 1H)

<Step 3> Synthesis of 4-(2-nitrophenyl)-1-phenyl-1H-indole

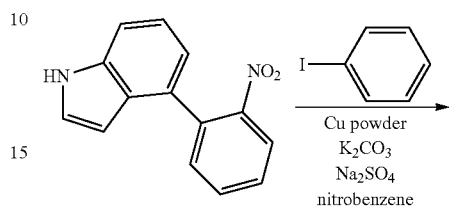

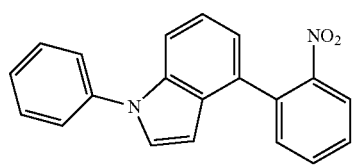

4-(2-nitrophenyl)-1-phenyl-1H-indole was obtained by performing the same procedure as in <Step 3> of Preparation Example 1, except that 4-(2-nitrophenyl)-1H-indole obtained in <Step 2> was used instead of 5-(2-nitrophenyl)-1H-indole.

$^1$H NMR: δ 6.47 (d, 1H), 7.28 (t, 1H), 7.47 (m, 2H), 7.52 (m, 2H), 7.60 (m, 2H), 7.67 (t, 1H), 7.75 (d, 1H), 7.89 (m, 2H), 8.00 (d, 1H), 8.06 (d, 1H)

<Step 4> Synthesis of IC-2

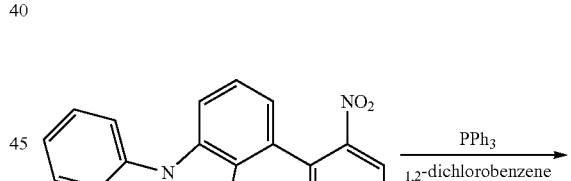

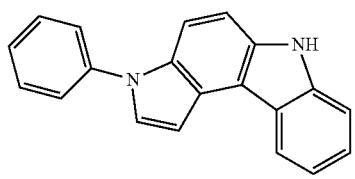

IC-2 was obtained by performing the same procedure as in <Step 4> of Preparation Example 1, except that 4-(2-nitrophenyl)-1-phenyl-1H-indole obtained in <Step 3> was used instead of 5-(2-nitrophenyl)-1-phenyl-1H-indole.

$^1$H NMR: δ 6.49 (d, 1H), 7.29 (t, 1H), 7.46 (m, 2H), 7.54 (m, 2H), 7.61 (d, 1H), 7.69 (t, 1H), 7.74 (d, 1H), 7.88 (m, 2H), 8.01 (d, 1H), 8.04 (d, 1H), 8.23 (s, 1H)

[Preparation Example 3] Synthesis of IC-3

<Step 1> Synthesis of 7-(4,4,5,5-tetramethyl-1,3,2-dioxaborolan-2-yl)-1H-indole

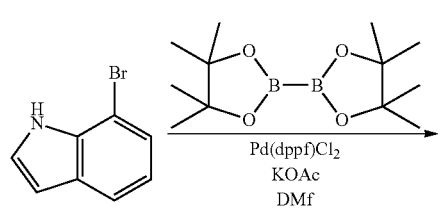

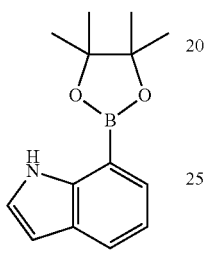

7-(4,4,5,5-tetramethyl-1,3,2-dioxaborolan-2-yl)-1H-indole was obtained by performing the same procedure as in <Step 1> of Preparation Example 1, except that 7-bromo-1H-indole was used instead of 5-bromo-1H-indole.

$^1$H NMR: δ 1.25 (s, 12H), 6.43 (d, 1H), 7.25 (d, 1H), 7.45 (t, 1H), 7.56 (d, 1H), 7.71 (d, 1H), 8.22 (s, 1H)

<Step 2> Synthesis of 7-(2-nitrophenyl)-1H-indole

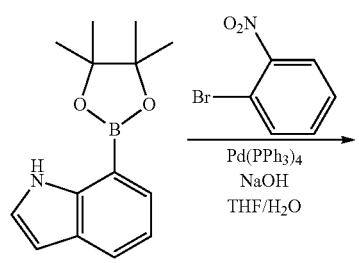

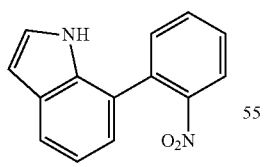

7-(2-nitrophenyl)-1H-indole was obtained by performing the same procedure as in <Step 2> of Preparation Example 1, except that 7-(4,4,5,5-tetramethyl-1,3,2-dioxaborolan-2-yl)-1H-indole obtained in <Step 1> was used instead of 5-(4,4,5,5-tetramethyl-1,3,2-dioxaborolan-2-yl)-1H-indole.

$^1$H NMR: δ 6.42 (d, 1H), 7.24 (d, 1H), 7.43 (t, 1H), 7.55 (d, 1H), 7.70 (m, 2H), 7.88 (t, 1H), 8.01 (d, 1H), 8.11 (d, 1H), 8.23 (s, 1H)

<Step 3> Synthesis of 7-(2-nitrophenyl)-1-phenyl-1H-indole

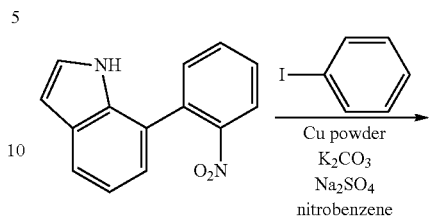

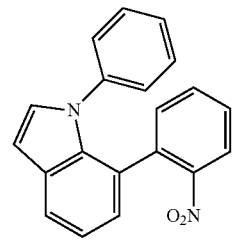

7-(2-nitrophenyl)-1-phenyl-1H-indole was obtained by performing the same procedure as in <Step 3> of Preparation Example 1, except that 7-(2-nitrophenyl)-1H-indole obtained in <Step 2> was used instead of 5-(2-nitrophenyl)-1H-indole.

$^1$H NMR: δ 6.43 (d, 1H), 7.26 (d, 1H), 7.44 (m, 3H), 7.56 (m, 4H), 7.71 (m, 2H), 7.89 (t, 1H), 8.02 (d, 1H), 8.10 (d, 1H)

<Step 4> Synthesis of IC-3

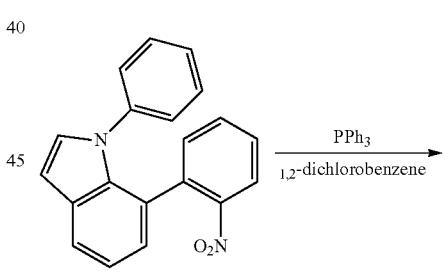

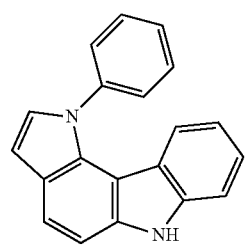

IC-3 was obtained by performing the same procedure as in <Step 4> of Preparation Example 1, except that 7-(2-nitrophenyl)-1-phenyl-1H-indole obtained in <Step 3> was used instead of 5-(2-nitrophenyl)-1-phenyl-1H-indole.

$^1$H NMR: δ 6.45 (d, 1H), 7.24 (d, 1H), 7.45 (m, 3H), 7.57 (m, 3H), 7.63 (d, 1H), 7.70 (d, 1H), 7.88 (t, 1H), 8.00 (d, 1H), 8.09 (d, 1H), 8.22 (s, 1H)

[Preparation Example 4] Synthesis of IC-4a and IC-4-b

\<Step 1\> Synthesis of 5-(1-nitronaphthalen-2-yl)-1H-indole

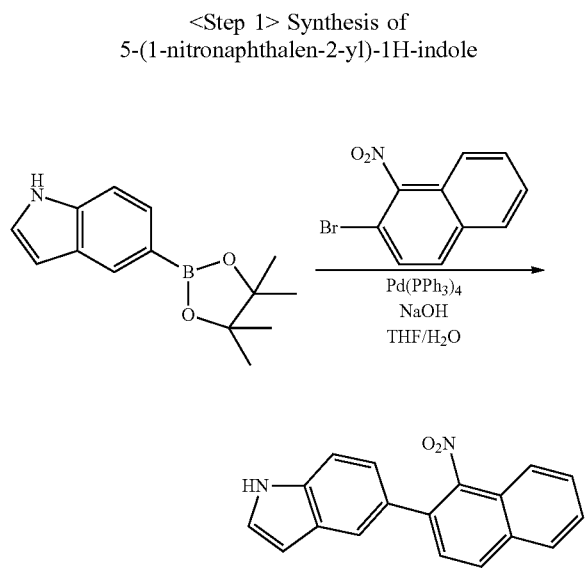

5-(1-nitronaphthalen-2-yl)-1H-indole was obtained by performing the same procedure as in \<Step 2\> of Preparation Example 1, except that 2-bromo-1-nitronaphthalene was used instead of 1-bromo-2-nitrobenzene.

$^1$H NMR: δ 6.44 (d, 1H), 7.26 (d, 1H), 7.43 (d, 1H), 7.53 (d, 1H), 7.64 (m, 3H), 7.80 (m, 3H), 7.94 (s, 1H), 8.23 (s, 1H)

\<Step 2\> Synthesis of 5-(1-nitronaphthalen-2-yl)-1-phenyl-1H-indole

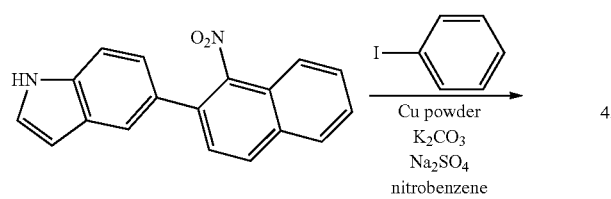

5-(1-nitronaphthalen-2-yl)-1-phenyl-1H-indole was obtained by performing the same procedure as in \<Step 3\> of Preparation Example 1, except that 5-(1-nitronaphthalen-2-yl)-1H-indole obtained in \<Step 1\> was used instead of 5-(2-nitrophenyl)-1H-indole.

$^1$H NMR: δ 6.44 (d, 1H), 7.26 (d, 1H), 7.43 (m, 3H), 7.53 (m, 4H), 7.64 (m, 3H), 7.80 (m, 3H), 7.94 (s, 1H)

\<Step 3\> Synthesis of IC-4a and IC-4-b

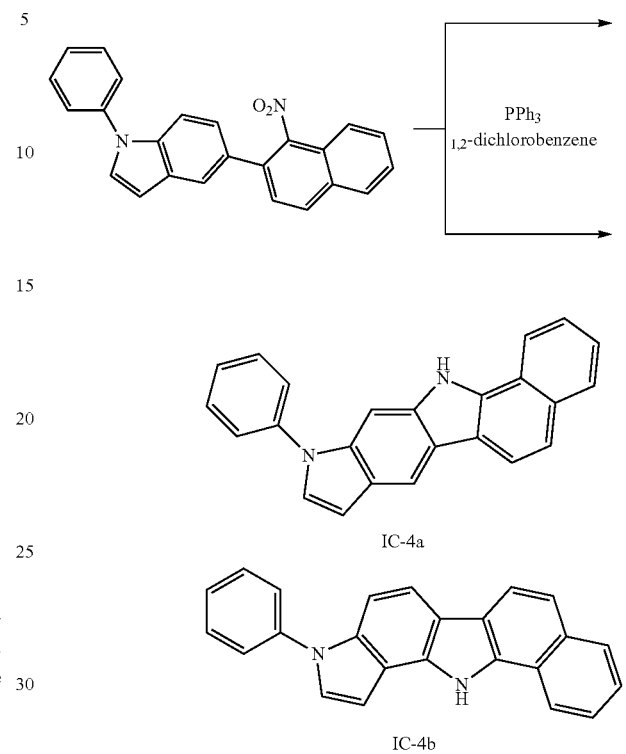

IC-4a and IC-4-b were obtained by performing the same procedure as in \<Step 4\> of Preparation Example 1, except that 5-(1-nitronaphthalen-2-yl)-1-phenyl-1H-indole obtained in \<Step 2\> was used instead of 5-(2-nitrophenyl)-1-phenyl-1H-indole.

$^1$H-NMR for IC-4-a: δ 6.44 (d, 1H), 7.26 (m, 2H), 7.43 (s, 1H), 7.53 (m, 4H), 7.64 (m, 3H), 7.71 (s, 1H), 7.80 (m, 3H), 8.20 (s, 1H)

$^1$H-NMR for IC-4-b: δ 6.43 (d, 1H), 7.27 (m, 2H), 7.42 (d, 1H), 7.55 (m, 4H), 7.65 (d, 1H), 7.72 (m, 3H), 7.82 (m, 3H), 8.20 (s, 1H)

[Preparation Example 5] Synthesis of IC-5a and IC-5b

\<Step 1\> Synthesis of 5-(2-nitronaphthalen-1-yl)-1H-indole

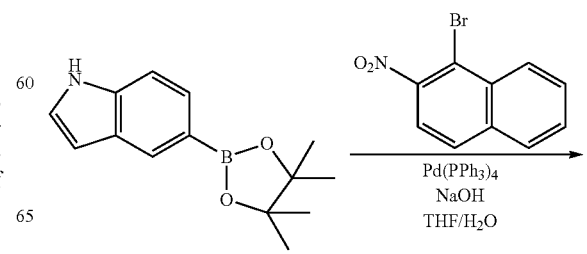

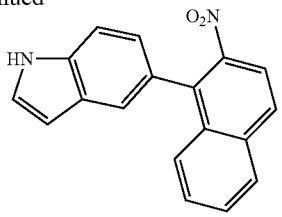

5-(2-nitronaphthalen-1-yl)-1H-indole was obtained by performing the same procedure as in <Step 2> of Preparation Example 1, except that 1-bromo-2-nitronaphthalene was used instead of 1-bromo-2-nitrobenzene.

$^1$H NMR: δ 6.43 (d, 1H), 7.25 (d, 1H), 7.44 (d, 1H), 7.55 (d, 1H), 7.67 (m, 2H), 7.81 (d, 1H), 7.96 (m, 2H), 8.00 (d, 1H), 8.05 (d, 1H), 8.23 (s, 1H)

<Step 2> Synthesis of 5-(2-nitronaphthalen-1-yl)-1-phenyl-1H-indole

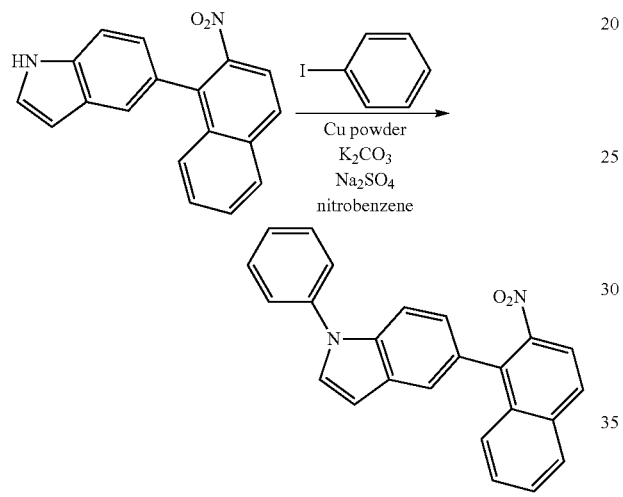

5-(2-nitronaphthalen-1-yl)-1-phenyl-1H-indole was obtained by performing the same procedure as in <Step 3> of Preparation Example 1, except that 5-(2-nitronaphthalen-1-yl)-1H-indole obtained in <Step 1> was used instead of 5-(2-nitrophenyl)-1H-indole.

$^1$H NMR: δ 6.45 (d, 1H), 7.26 (d, 1H), 7.45 (m, 2H), 7.54 (m, 2H), 7.66 (m, 3H), 7.80 (d, 1H), 7.96 (m, 2H), 8.01 (m, 2H), 8.06 (m, 2H)<

<Step 3> Synthesis of IC-5a and IC-5b

IC-5a and IC-56 were obtained by performing the same procedure as in <Step 4> of Preparation Example 1, except that 5-(2-nitronaphthalen-2-yl)-1-phenyl-1H-indole obtained in <Step 2> was used instead of 5-(2-nitrophenyl)-1-phenyl-1H-indole.

$^1$H-NMR for IC-5a: δ 6.45 (d, 1H), 7.26 (d, 1H), 7.45 (s, 1H), 7.54 (s, 1H), 7.66 (m, 2H), 7.80 (m, 3H), 7.96 (m, 2H), 8.01 (m, 2H), 8.06 (m, 2H), 8.21 (s, 1H)

$^1$H-NMR for IC-5b: δ 6.43 (d, 1H), 7.25 (d, 1H), 7.46 (d, 1H), 7.57 (d, 1H), 7.65 (m, 2H), 7.81 (m, 3H), 7.95 (m, 2H), 8.00 (m, 2H), 8.05 (m, 2H), 8.21 (s, 1H)

[Preparation Example 6] Synthesis of IC-6a and IC-6b

<Step 1> Synthesis of 5-(5-bromo-2-nitrophenyl)-1H-indole

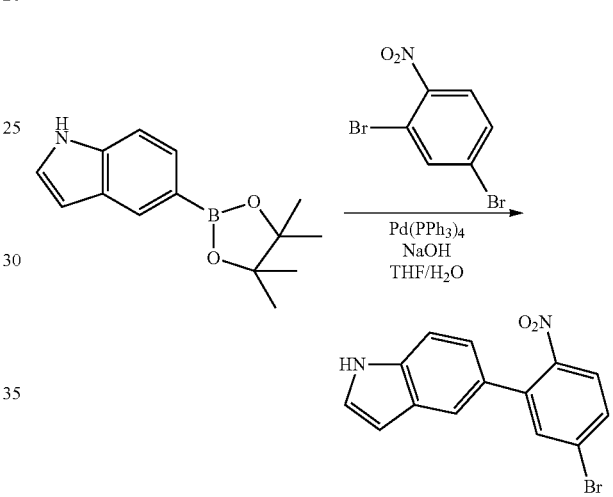

5-(5-bromo-2-nitrophenyl)-1H-indole was obtained by performing the same procedure as in <Step 2> of Preparation Example 1, except that 2,4-dibromo-1-nitrobenzene was used instead of 1-bromo-2-nitrobenzene.

$^1$H NMR: δ 6.45 (d, 1H), 7.26 (d, 1H), 7.45 (d, 1H), 7.55 (d, 1H), 7.64 (d, 1H), 7.85 (d, 1H), 7.96 (s, 1H), 8.13 (s, 1H), 8.21 (s, 1H)

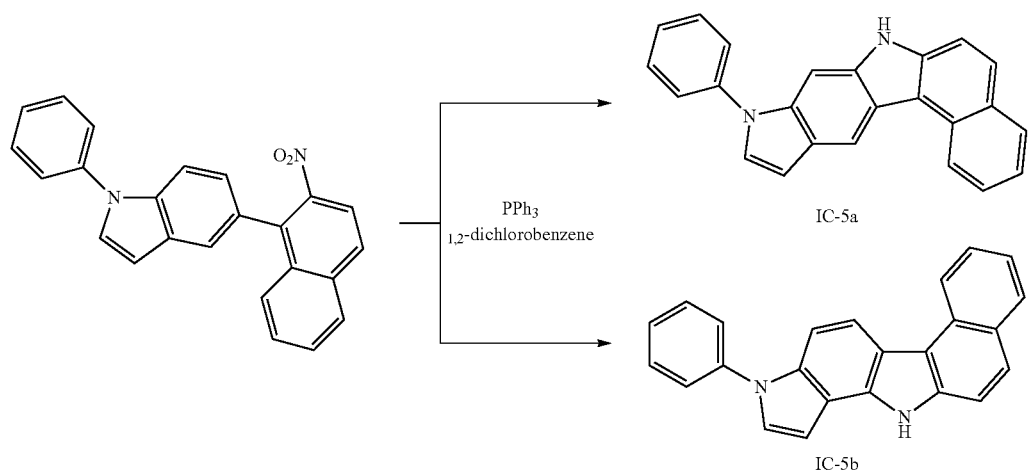

\<Step 2\> Synthesis of
5-(5-bromo-2-nitrophenyl)-1-phenyl-1H-indole

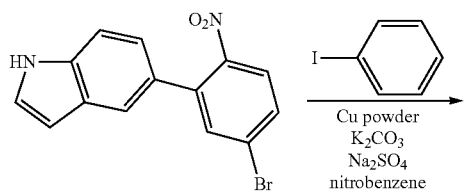

5-(5-bromo-2-nitrophenyl)-1-phenyl-1H-indole was obtained by performing the same procedure as in \<Step 3\> of Preparation Example 1, except that 5-(5-bromo-2-nitrophenyl)-1H-indole obtained in \<Step 1\> was used instead of 5-(2-nitrophenyl)-1H-indole.

¹H NMR: δ 6.44 (d, 1H), 7.25 (d, 1H), 7.46 (m, 3H), 7.56 (m, 4H), 7.65 (d, 1H), 7.86 (d, 1H), 7.95 (s, 1H), 8.11 (s, 1H)

\<Step 3\> Synthesis of IC-6a and IC-6b

IC-6a and IC-6b were obtained by performing the same procedure as in \<Step 4\> of Preparation Example 1, except that 5-(5-bromo-2-nitrophenyl)-1-phenyl-1H-indole obtained in \<Step 2\> was used instead of 5-(2-nitrophenyl)-1-phenyl-1H-indole.

¹H-NMR for IC-6a: δ 6.44 (d, 1H), 7.25 (d, 1H), 7.39 (m, 2H), 7.46 (s, 1H), 7.50 (s, 1H), 7.58 (m, 3H), 7.65 (d, 1H), 7.86 (d, 1H), 8.11 (s, 1H), 8.22 (s, 1H)

¹H-NMR for IC-6b: δ 6.45 (d, 1H), 7.26 (d, 1H), 7.38 (m, 2H), 7.45 (d, 1H), 7.51 (d, 1H), 7.57 (m, 3H), 7.64 (d, 1H), 7.85 (d, 1H), 8.10 (s, 1H), 8.23 (s, 1H)

[Preparation Example 7] Synthesis of IC-7

\<Step 1\> Synthesis of 1-(4,6-diphenylpyridin-2-yl)-4-(2-nitrophenyl)-1H-indole

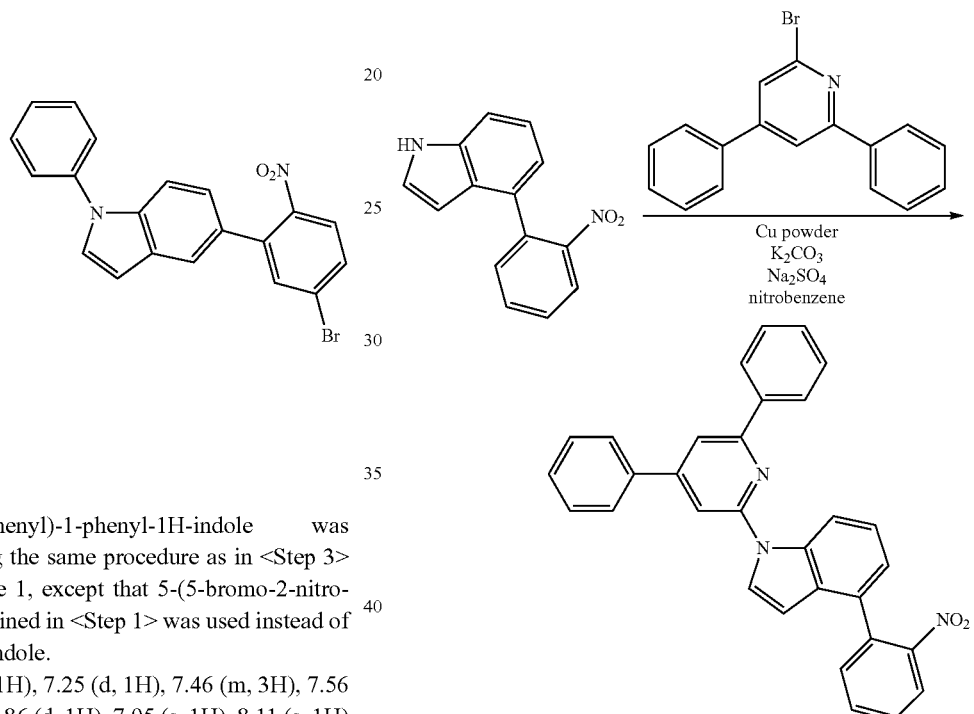

1-(4,6-diphenylpyridin-2-yl)-4-(2-nitrophenyl)-1H-indole was obtained by performing the same procedure as in

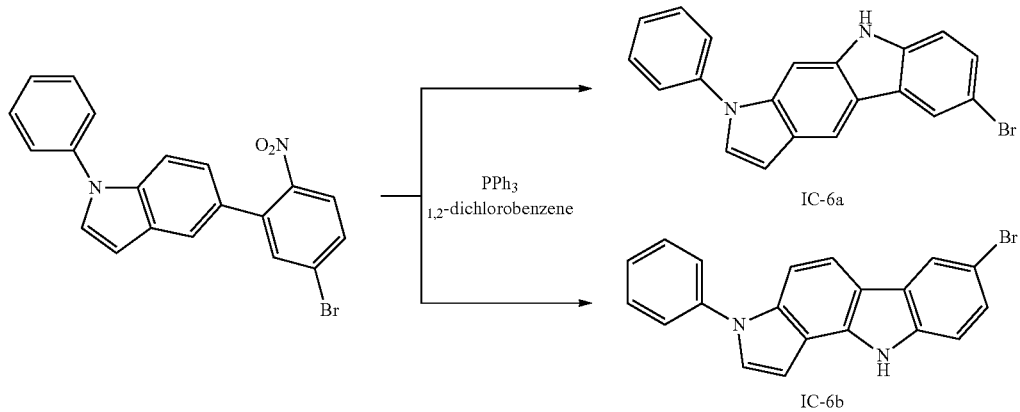 [SMILES: O=[N+]([O-])c1ccc(Br)cc1-c1ccc2c(ccn2-c2ccccc2)c1 ; Brc1ccc2[nH]c3c(ccc4c3ccn4-c3ccccc3)c2c1 ; Brc1ccc2[nH]c3cc4c(ccn4-c4ccccc4)cc3c2c1]

<Step 3> of Preparation Example 1, except that 4-(2-nitrophenyl)-1H-indole was used instead of 5-(2-nitrophenyl)-1H-indole and 2-bromo-4,6-diphenylpyridine was used instead of iodobenzene.

GC-Mass (theoretical value: 467.16 g/mol, measured value: 467 g/mol).

<Step 2> Synthesis of IC-7

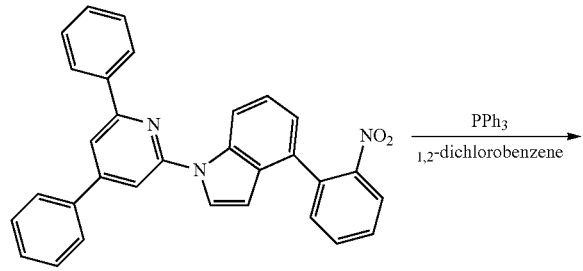

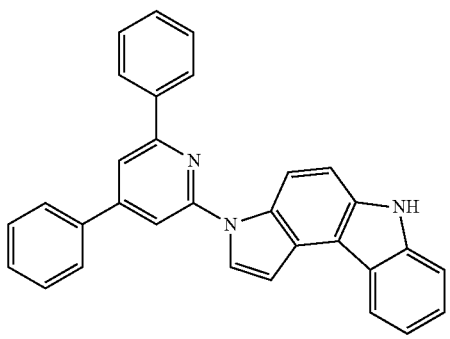

IC-7 was obtained by performing the same procedure as in <Step 4> of Preparation Example 1, except that 1-(4,6-diphenylpyridin-2-yl)-4-(2-nitrophenyl)-1H-indole obtained in <Step 1> was used instead of 5-(2-nitrophenyl)-1-phenyl-1H-indole.

GC-Mass (theoretical value: 435.17 g/mol, measured value: 435 g/mol)

[Preparation Example 8] Synthesis of IC-8

<Step 1> Synthesis of 1-(4,6-diphenylpyridin-2-yl)-7-(2-nitrophenyl)-1H-indole

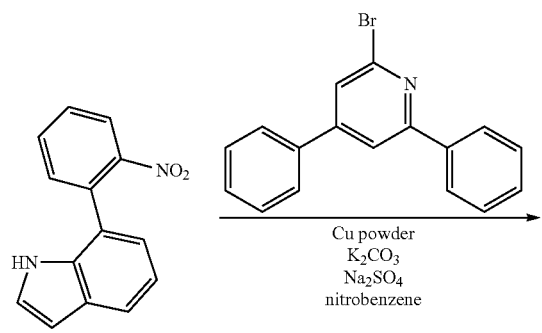

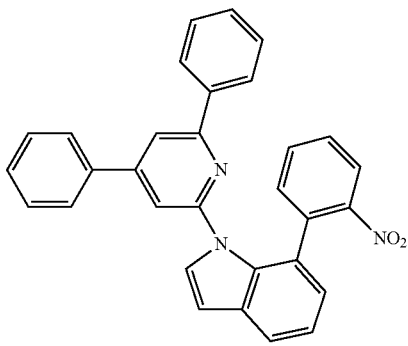

1-(4,6-diphenylpyridin-2-yl)-7-(2-nitrophenyl)-1H-indole was obtained by performing the same procedure as in <Step 3> of Preparation Example 1, except that 7-(2-nitrophenyl)-1H-indole was used instead of 5-(2-nitrophenyl)-1H-indole and 2-bromo-4,6-diphenylpyridine was used instead of iodobenzene.

GC-Mass (theoretical value: 467.16 g/mol, measured value: 467 g/mol)

<Step 2> Synthesis of IC-8

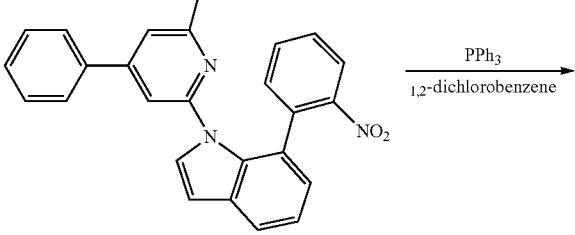

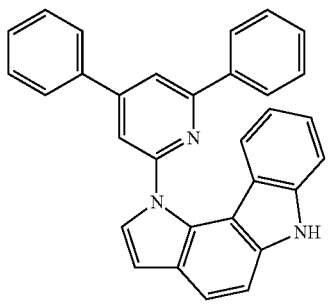

IC-8 was obtained by performing the same procedure as in <Step 4> of Preparation Example 1, except that 1-(4,6-diphenylpyridin-2-yl)-7-(2-nitrophenyl)-1H-indole obtained in <Step 1> was used instead of 5-(2-nitrophenyl)-1-phenyl-1H-indole.

GC-Mass (theoretical value: 435.17 g/mol, measured value: 435 g/mol)

[Preparation Example 9] Synthesis of IC-9

<Step 1> Synthesis of 1-(2,3'-bipyridin-6-yl)-4-(2-nitrophenyl)-1H-indole

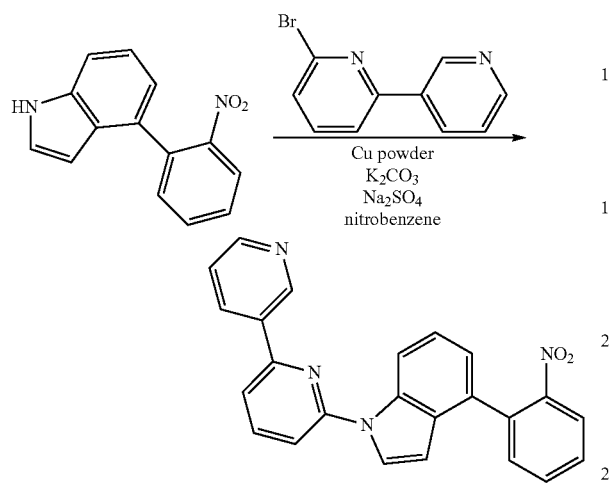

1-(2,3'-bipyridin-6-yl)-4-(2-nitrophenyl)-1H-indole was obtained by performing the same procedure as in <Step 3> of Preparation Example 2, except that 6-bromo-2,3'-bipyridine was used instead of iodobenzene.

GC-Mass (theoretical value: 392.13 g/mol, measured value: 392 g/mol)<

<Step 2> Synthesis of IC-9

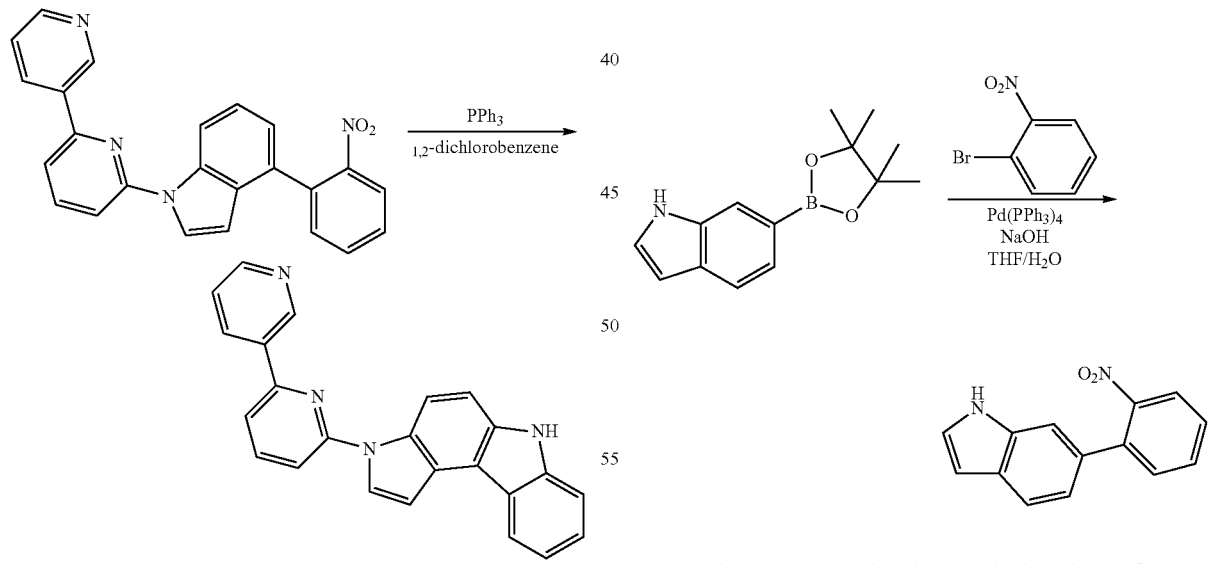

IC-9 was obtained by performing the same procedure as in <Step 4> of Preparation Example 1, except that 1-(2,3'-bipyridin-6-yl)-4-(2-nitrophenyl)-1H-indole obtained in <Step 1> was used instead of 5-(2-nitrophenyl)-1-phenyl-1H-indole.

GC-Mass (theoretical value: 360.14 g/mol, measured value: 360 g/mol)

[Preparation Example 10] Synthesis of IC-10a and IC-10b

<Step 1> Synthesis of 6-(4,4,5,5-tetramethyl-1,3,2-dioxaborolan-2-yl)-1H-indole

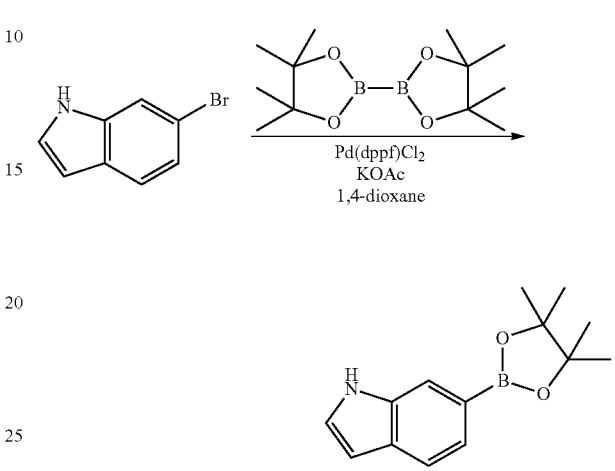

6-(4,4,5,5-tetramethyl-1,3,2-dioxaborolan-2-yl)-1H-indole was obtained by performing the same procedure as in <Step 1> of Preparation Example 1, except that 6-bromo-1H-indole was used instead of 5-bromo-1H-indole.

$^1$H-NMR: δ 1.25 (s, 12H), 6.52 (d, 1H), 7.16 (d, 1H), 7.21 (d, 1H), 7.49 (d, 1H), 7.53 (s, 1H), 8.15 (s, 1H)

<Step 2> Synthesis of 6-(2-nitrophenyl)-1H-indole 6-(2-nitrophenyl)-1H-indole was obtained by performing the same procedure as in <Step 2> of Preparation Example 1, except that 6-(4,4,5,5-tetramethyl-1,3,2-dioxaborolan-2-yl)-1H-indole was used instead of 5-(4,4,5,5-tetramethyl-1,3,2-dioxaborolan-2-yl)-1H-indole.

$^1$H-NMR: δ 6.57 (d, 1H), 7.07 (d, 1H), 7.24 (d, 1H), 7.35 (s, 1H), 7.43 (t, 1H), 7.50 (d, 1H), 7.58 (t, 1H), 7.66 (d, 1H), 7.78 (d, 1H), 8.19 (s, 1H)

\<Step 3\> Synthesis of 6-(2-nitrophenyl)-1-phenyl-1H-indole

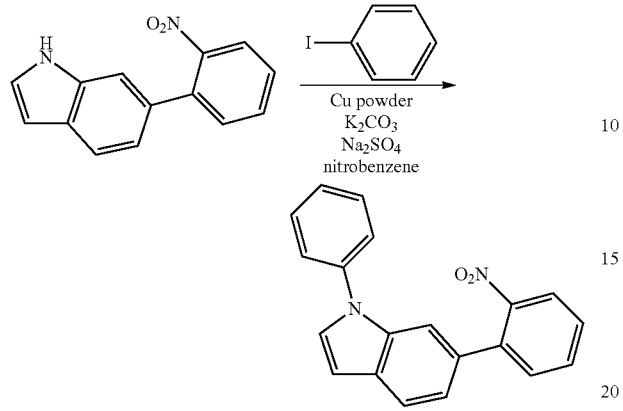

6-(2-nitrophenyl)-1-phenyl-1H-indole was obtained by performing the same procedure as in \<Step 3\> of Preparation Example 1, except that 6-(2-nitrophenyl)-1H-indole was used instead of 5-(2-nitrophenyl)-1H-indole.

$^1$H-NMR: δ 6.81 (d, 1H), 7.12 (t, 1H), 7.22 (t, 1H), 7.35 (s, 1H), 7.43 (d, 1H), 7.51 (m, 3H), 7.56 (m, 2H), 7.62 (m, 2H), 7.85 (d, 1H), 8.02 (d, 1H)

\<Step 4\> Synthesis of IC-10a and IC-10b

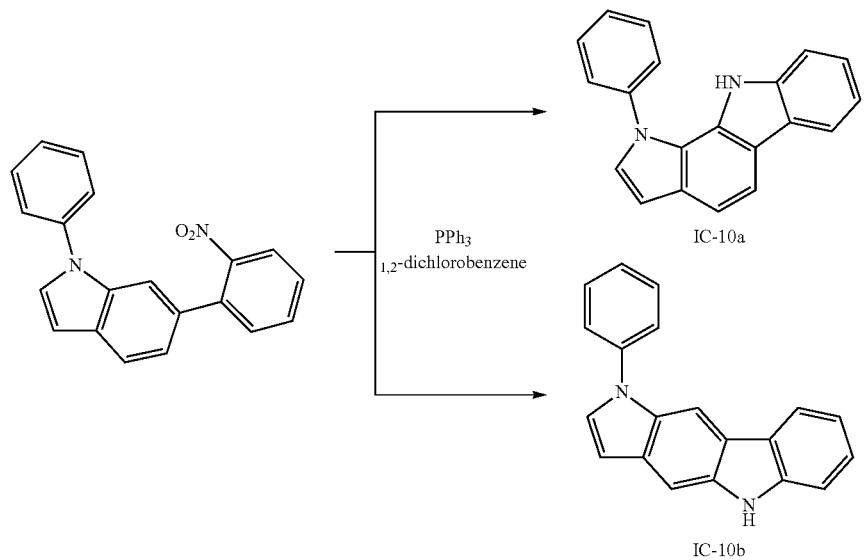 [SMILES: O=[N+]([O-])c1ccccc1-c1ccc2ccn(-c3ccccc3)c2c1 ; c1ccc(-n2ccc3ccc4c5ccccc5[nH]c4c32)cc1 ; c1ccc(-n2ccc3cc4[nH]c5ccccc5c4cc32)cc1]

IC-10a and IC-10b were obtained by performing the same procedure as in \<Step 4\> of Preparation Example 1, except that 6-(2-nitrophenyl)-1-phenyl-1H-indole was used instead of 5-(2-nitrophenyl)-1-phenyl-1H-indole.

$^1$H-NMR: δ 6.80 (d, 1H), 7.11 (t, 1H), 7.23 (t, 1H), 7.42 (d, 1H), 7.50 (m, 3H), 7.57 (m, 2H), 7.63 (m, 2H), 7.86 (d, 1H), 8.03 (d, 1H), 9.81 (s, 1H)

[Preparation Example 11] Synthesis of IC-11

\<Step 1\> Synthesis of 6-(5-bromo-2-nitrophenyl)-1H-indole

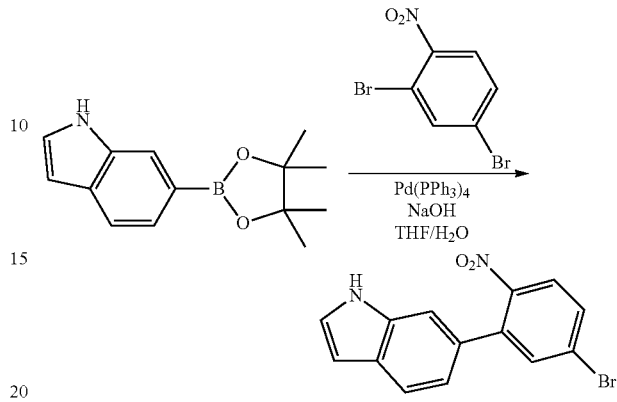

6-(5-bromo-2-nitrophenyl)-1H-indole was obtained by performing the same procedure as in \<Step 2\> of Preparation Example 1, except that 2,4-dibromo-1-nitrobenzene and 6-(4,4,5,5-tetramethyl-1,3,2-dioxaborolan-2-yl)-1H-indole were used instead of 1-bromo-2-nitrobenzene and 5-(4,4,5,5-tetramethyl-1,3,2-dioxaborolan-2-yl)-1H-indole.

$^1$H NMR: δ 6.51 (d, 1H), 7.31 (d, 1H), 7.50 (d, 1H), 7.60 (d, 1H), 7.69 (d, 1H), 7.90 (d, 1H), 8.01 (s, 1H), 8.14 (s, 1H), 8.25 (s, 1H)

\<Step 2\> Synthesis of 6-(5-bromo-2-nitrophenyl)-1-phenyl-1H-indole

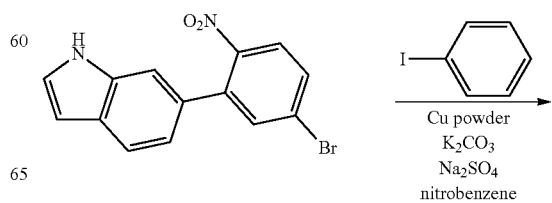

-continued

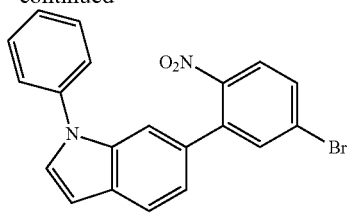

6-(5-bromo-2-nitrophenyl)-1-phenyl-1H-indole was obtained by performing the same procedure as in <Step 3> of Preparation Example 1, except that 6-(5-bromo-2-nitrophenyl)-1H-indole obtained in <Step 1> was used instead of 5-(2-nitrophenyl)-1H-indole.

$^1$H NMR: δ 6.49 (d, 1H), 7.30 (d, 1H), 7.51 (m, 3H), 7.61 (m, 4H), 7.70 (d, 1H), 7.91 (d, 1H), 8.00 (s, 1H), 8.16 (s, 1H),

<Step 3> Synthesis of IC-11

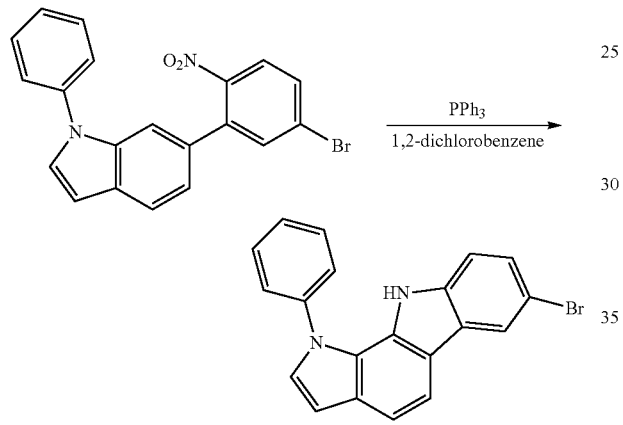

IC-11 was obtained by performing the same procedure as in <Step 4> of Preparation Example 1, except that 6-(5-bromo-2-nitrophenyl)-1-phenyl-1H-indole obtained in <Step 2> was used instead of 5-(2-nitrophenyl)-1-phenyl-1H-indole.

$^1$H-NMR: δ 6.47 (d, 1H), 7.28 (d, 1H), 7.40 (m, 2H), 7.47 (d, 1H), 7.53 (d, 1H), 7.59 (m, 3H), 7.66 (d, 1H), 7.87 (d, 1H), 8.12 (s, 1H), 8.25 (s, 1H)

[Preparation Example 12] Synthesis of IC-12

<Step 1> Synthesis of 5-(2-nitrophenyl)-1-o-tolyl-1H-indole

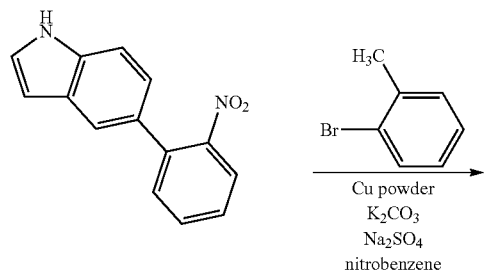

-continued

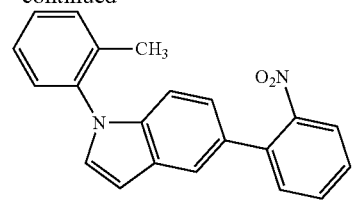

5-(2-nitrophenyl)-1-o-tolyl-1H-indole was obtained by performing the same procedure as in <Step 3> of Preparation Example 1, except that 1-bromo-2-methylbenzene was used instead of iodobenzene.

$^1$H-NMR: δ 1.92 (s, 3H), 6.47 (d, 1H), 7.25 (d, 1H), 7.46 (m, 3H), 7.56 (m, 3H), 7.64 (t, 1H), 7.85 (t, 1H), 7.94 (s, 1H), 8.00 (d, 1H), 8.12 (t, 1H)

<Step 2> Synthesis of IC-12

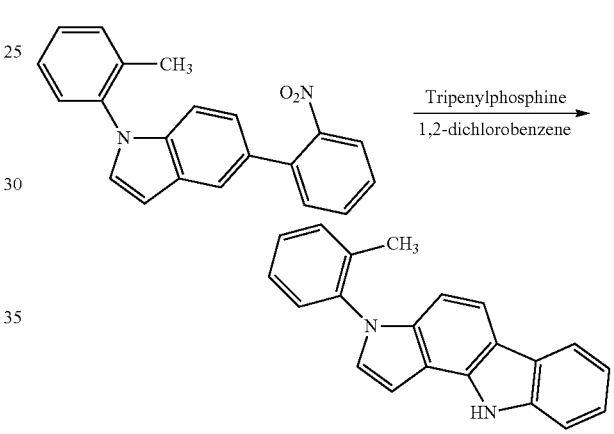

IC-12 was obtained by performing the same procedure as in <Step 4> of Preparation Example 1, except that 5-(2-nitrophenyl)-1-o-tolyl-1H-indole obtained in <Step 1> was used instead of 5-(2-nitrophenyl)-1-phenyl-1H-indole.

$^1$H-NMR: δ 1.93 (s, 3H), 6.98 (d, 1H), 7.11 (t, 1H), 7.28 (t, 1H), 7.31 (d, 1H), 7.42 (t, 1H), 7.51 (d, 1H), 7.61 (m, 4H), 7.86 (d, 1H), 8.01 (d, 1H), 10.58 (s, 1H)

[Preparation Example 13] Synthesis of IC-13

<Step 1> Synthesis of 1-(biphenyl-4-yl)-5-(2-nitrophenyl)-1H-indole

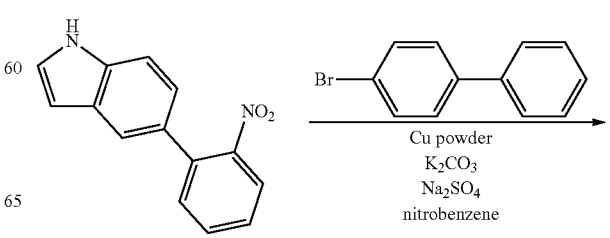

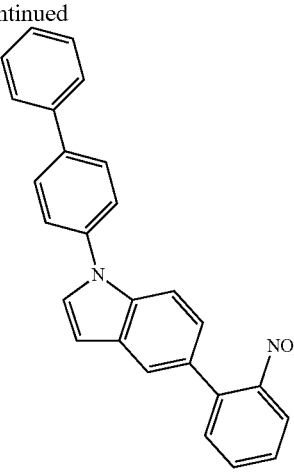

1-(biphenyl-4-yl)-5-(2-nitrophenyl)-1H-indole was obtained by performing the same procedure as in <Step 3> of Preparation Example 1, except that 4-bromobiphenyl was used instead of iodobenzene.

$^1$H-NMR: δ 6.73 (d, 1H), 7.18 (d, 1H), 7.39 (m, 2H), 7.47 (m, 3H), 7.54 (d, 1H), 7.59 (m, 3H), 7.64 (m, 4H), 7.75 (d, 2H), 7.82 (d, 1H)

<Step 2> Synthesis of IC-13

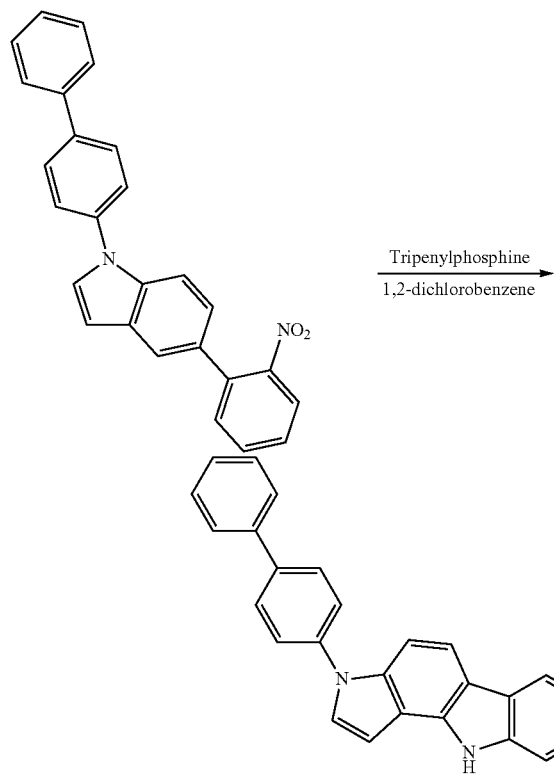

IC-13 was obtained by performing the same procedure as in <Step 4> of Preparation Example 1, except that 1-(biphenyl-4-yl)-5-(2-nitrophenyl)-1H-indole obtained in <Step 1> was used instead of 5-(2-nitrophenyl)-1-phenyl-1H-indole.

$^1$H-NMR: δ 6.75 (d, 1H), 7.20 (d, 1H), 7.42 (m, 2H), 7.51 (m, 3H), 7.56 (d, 1H), 7.62 (m, 3H), 7.68 (m, 3H), 7.76 (d, 2H), 7.85 (d, 1H), 10.45 (s, 1H)

[Preparation Example 14] Synthesis of IC-14

<Step 2> Synthesis of IC-14-1

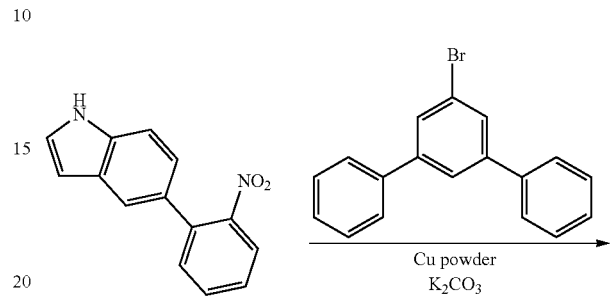

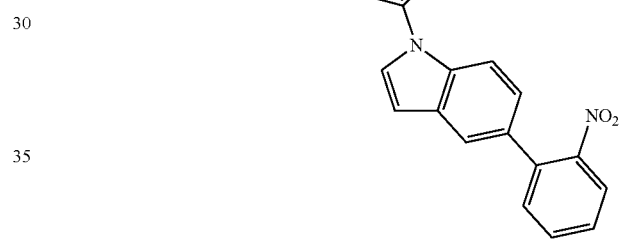

IC-14-1 was obtained by performing the same procedure as in <Step 3> of Preparation Example 1, except that 1-bromo-3,5-diphenyl benzene was used instead of iodobenzene.

$^1$H-NMR: δ 6.98 (d, 1H), 7.11 (t, 1H), 7.24 (t, 1H), 7.38 (t, 2H), 7.46 (m, 6H), 7.58 (d, 1H), 7.81 (d, 4H), 7.87 (m, 4H), 7.93 (d, 1H), 7.99 (d, 1H)

<Step 2> Synthesis of IC-14

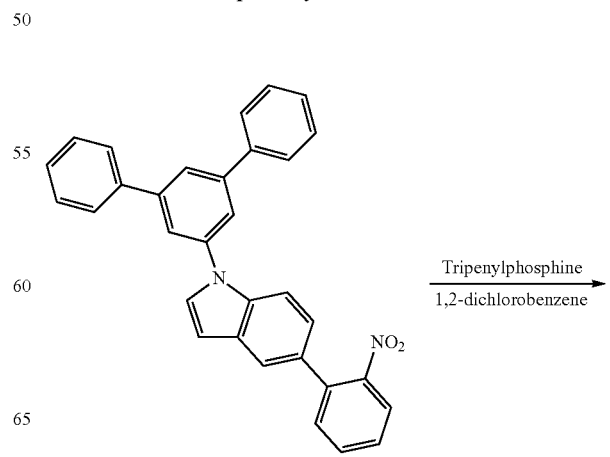

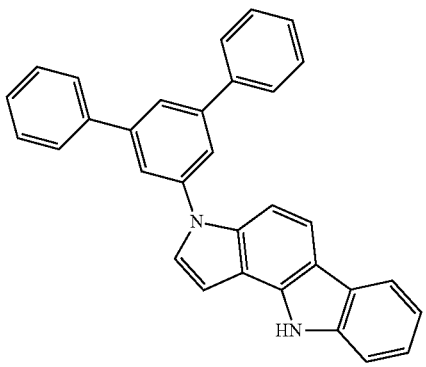

IC-14 was obtained by performing the same procedure as in <Step 4> of Preparation Example 1, except that IC-11-1 obtained in <Step 1> was used instead of 5-(2-nitrophenyl)-1-phenyl-1H-indole.

$^1$H-NMR: δ 6.97 (d, 1H), 7.10 (t, 1H), 7.23 (t, 1H), 7.37 (t, 2H), 7.45 (m, 6H), 7.58 (d, 1H), 7.80 (d, 4H), 7.86 (m, 3H), 7.92 (d, 1H), 7.98 (d, 1H), 10.60 (s, 1H)

[Preparation Example 15] Synthesis of IC-15

<Step 1> Synthesis of 5-(2-nitrophenyl)-1-(2-(trifluoromethyl)phenyl)-1H-indole

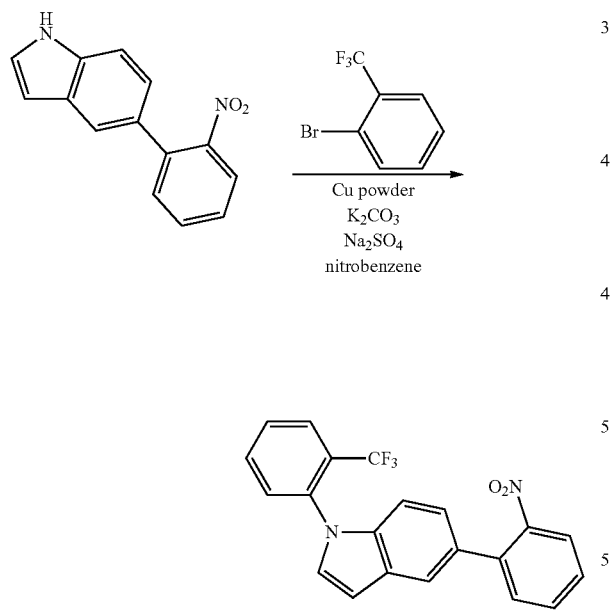

5-(2-nitrophenyl)-1-(2-(trifluoromethyl)phenyl)-1H-indole was obtained by performing the same procedure as in <Step 3> of Preparation Example 1, except that 1-bromo-2-(trifluoromethyl)benzene was used instead of iodobenzene.

$^1$H-NMR: δ 6.48 (d, 1H), 7.26 (d, 1H), 7.47 (m, 3H), 7.57 (m, 3H), 7.63 (t, 1H), 7.84 (t, 1H), 7.95 (s, 1H), 8.01 (d, 1H), 8.13 (t, 1H)

<Step 2> Synthesis of IC-15

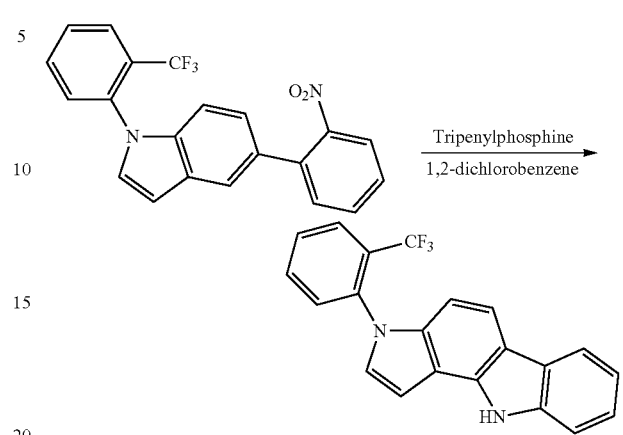

IC-15 was obtained by performing the same procedure as in <Step 4> of Preparation Example 1, except that 5-(2-nitrophenyl)-1-(2-(trifluoromethyl)phenyl)-1H-indole obtained in <Step 1> was used instead of 5-(2-nitrophenyl)-1-phenyl-1H-indole.

$^1$H-NMR: δ 6.97 (d, 1H), 7.12 (t, 1H), 7.29 (t, 1H), 7.32 (d, 1H), 7.41 (t, 1H), 7.52 (d, 1H), 7.60 (m, 4H), 7.85 (d, 1H), 8.01 (d, 1H), 10.57 (s, 1H)

[Preparation Example 16] Synthesis of IC-16

<Step 1> Synthesis of 1-(biphenyl-3-yl)-5-(2-nitrophenyl)-1H-indole

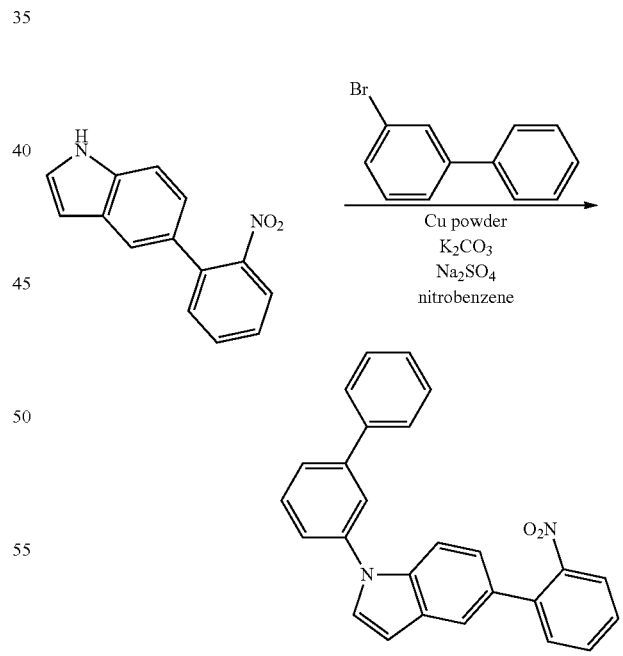

1-(biphenyl-3-yl)-5-(2-nitrophenyl)-1H-indole was obtained by performing the same procedure as in <Step 3> of Preparation Example 1, except that 3-bromobiphenyl was used instead of iodobenzene.

$^1$H-NMR: δ 6.75 (d, 1H), 7.19 (d, 1H), 7.38 (m, 2H), 7.48 (m, 3H), 7.52 (d, 1H), 7.58 (m, 3H), 7.65 (m, 4H), 7.76 (m, 2H), 7.85 (d, 1H)

<Step 2> Synthesis of IC-16

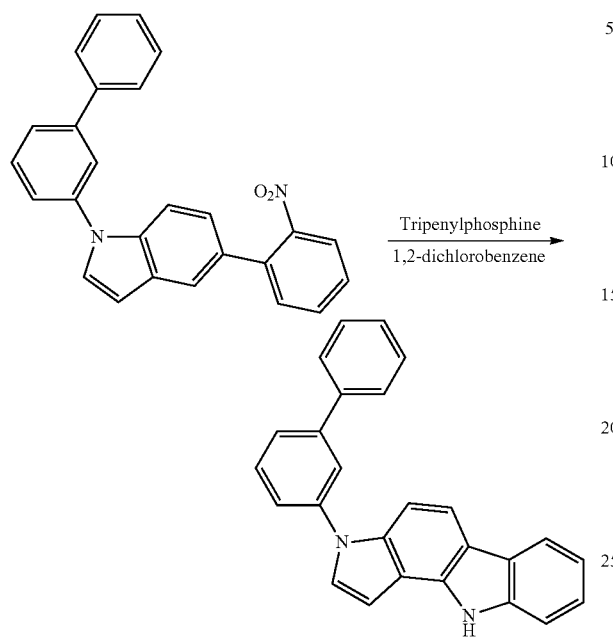

IC-16 was obtained by performing the same procedure as in <Step 4> of Preparation Example 1, except that 1-(biphenyl-3-yl)-5-(2-nitrophenyl)-1H-indole obtained in <Step 1> was used instead of 5-(2-nitrophenyl)-1-phenyl-1H-indole.

$^1$H-NMR: δ 6.74 (d, 1H), 7.21 (d, 1H), 7.41 (m, 2H), 7.52 (m, 3H), 7.56 (d, 1H), 7.61 (m, 3H), 7.69 (m, 3H), 7.77 (m, 2H), 7.86 (d, 1H), 10.44 (s, 1H)

[Preparation Example 17] Synthesis of IC-17

<Step 1> Synthesis of 1-(biphenyl-3-yl)-6-(2-nitrophenyl)-1H-indole

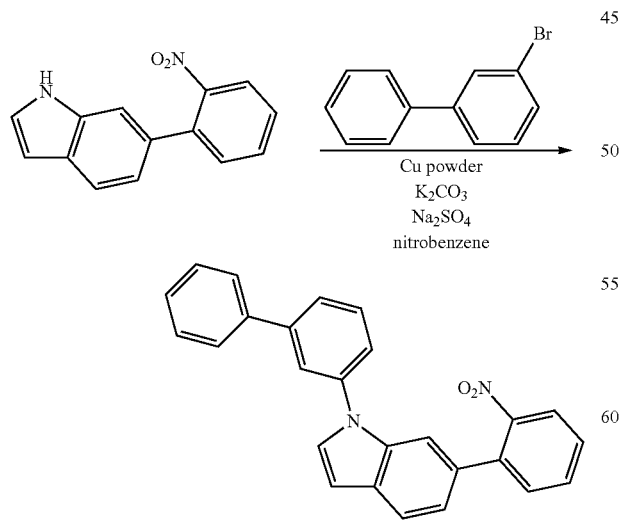

1-(biphenyl-3-yl)-6-(2-nitrophenyl)-1H-indole was obtained by performing the same procedure as in <Step 3> of Preparation Example 1, except that 6-(2-nitrophenyl)-1H-indole and 3-bromobiphenyl were used instead of instead of 5-(2-nitrophenyl)-1H-indole and Iodobenzene.

$^1$H-NMR: δ 6.76 (d, 1H), 7.18 (d, 1H), 7.37 (m, 2H), 7.47 (m, 3H), 7.51 (d, 1H), 7.57 (m, 3H), 7.64 (m, 4H), 7.75 (m, 2H), 7.86 (d, 1H)

<Step 2> Synthesis of IC-17

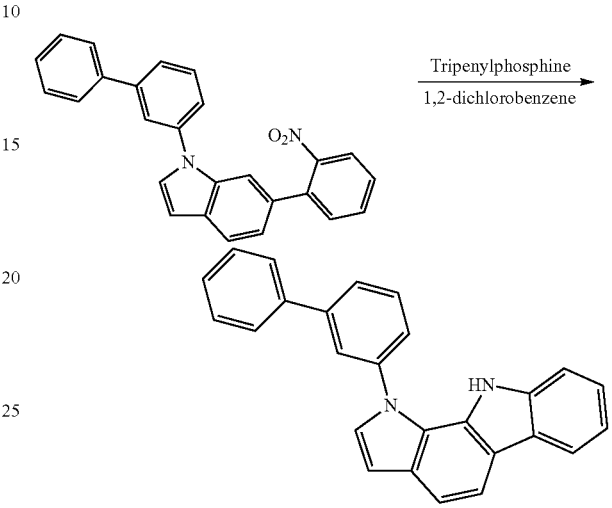

IC-17 was obtained by performing the same procedure as in <Step 4> of Preparation Example 1, except that 1-(biphenyl-3-yl)-6-(2-nitrophenyl)-1H-indole obtained in <Step 1> was used instead of 5-(2-nitrophenyl)-1-phenyl-1H-indole.

$^1$H-NMR: δ 6.75 (d, 1H), 7.20 (d, 1H), 7.40 (m, 2H), 7.51 (m, 3H), 7.57 (d, 1H), 7.62 (m, 3H), 7.70 (m, 3H), 7.76 (m, 2H), 7.85 (d, 1H), 10.43 (s, 1H)

[Preparation Example 18] Synthesis of IC-18

<Step 1> Synthesis of 1-(biphenyl-4-yl)-6-(2-nitrophenyl)-1H-indole

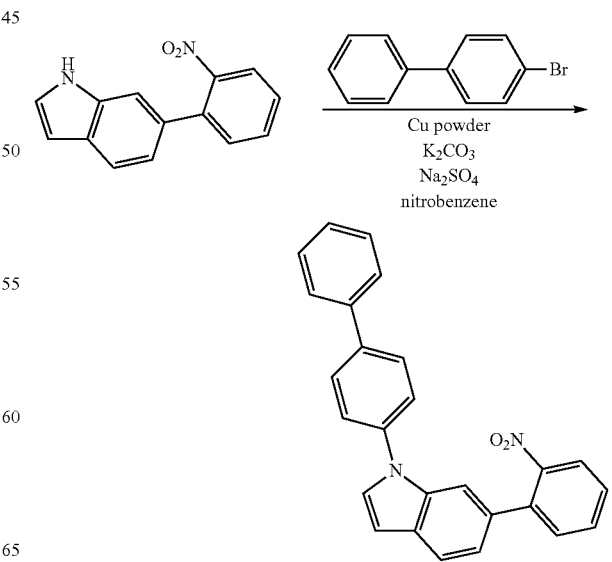

1-(biphenyl-4-yl)-6-(2-nitrophenyl)-1H-indole was obtained by performing the same procedure as in <Step 3> of Preparation Example 1, except that 6-(2-nitrophenyl)-1H-indole and 4-bromobiphenyl were used instead of 5-(2-nitrophenyl)-1H-indole and iodobenzene.

¹H-NMR: δ 6.74 (d, 1H), 7.19 (d, 1H), 7.40 (m, 2H), 7.46 (m, 3H), 7.55 (d, 1H), 7.58 (m, 3H), 7.63 (m, 4H), 7.75 (d, 2H), 7.83 (d, 1H)

<Step 2> Synthesis of IC-18

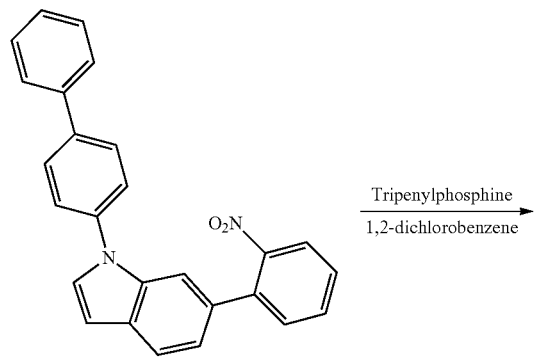

IC-18 was obtained by performing the same procedure as in <Step 4> of Preparation Example 1, except that 1-(biphenyl-4-yl)-6-(2-nitrophenyl)-1H-indole obtained in <Step 1> was used instead of 5-(2-nitrophenyl)-1-phenyl-1H-indole.

¹H-NMR: δ 6.74 (d, 1H), 7.19 (d, 1H), 7.43 (m, 2H), 7.52 (m, 3H), 7.57 (d, 1H), 7.63 (m, 3H), 7.69 (m, 3H), 7.75 (d, 2H), 7.86 (d, 1H), 10.46 (s, 1H)

[Preparation Example 19] Synthesis of IC-19

<Step 1> Synthesis of IC-19-1

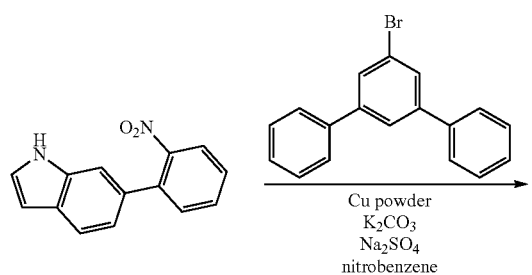

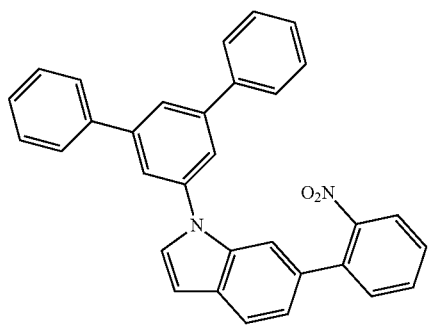

IC-19-1 was obtained by performing the same procedure as in <Step 3> of Preparation Example 1, except that 6-(2-nitrophenyl)-1H-indole and 1-bromo-3,5-diphenyl benzene were used instead of 5-(2-nitrophenyl)-1-phenyl-1H-indole and iodobenzene.

¹H-NMR: δ 6.98 (d, 1H), 7.11 (t, 1H), 7.24 (t, 1H), 7.38 (m, 2H), 7.45 (m, 6H), 7.57 (d, 1H), 7.80 (d, 4H), 7.86 (m, 4H), 7.92 (d, 1H), 7.98 (d, 1H)

<Step 2> Synthesis of IC-19

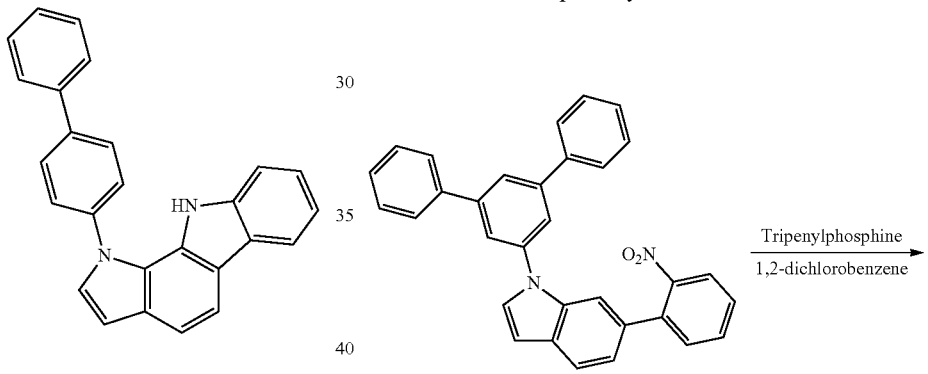

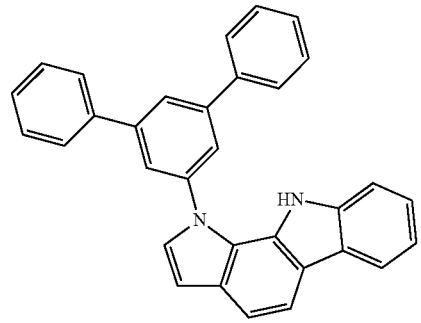

IC-19 was obtained by performing the same procedure as in <Step 4> of Preparation Example 1, except that IC-19-1 obtained in <Step 1> was used instead of 5-(2-nitrophenyl)-1-phenyl-1H-indole.

¹H-NMR: δ 6.97 (d, 1H), 7.10 (t, 1H), 7.23 (t, 1H), 7.37 (t, 2H), 7.45 (m, 6H), 7.58 (d, 1H), 7.80 (d, 4H), 7.86 (m, 3H), 7.92 (d, 1H), 7.98 (d, 1H), 10.59 (s, 1H)

[Preparation Example 20] Synthesis of IC-20

<Step 1> Synthesis of 6-(2-nitrophenyl)-1-(3-(trifluoromethyl)phenyl)-1H-indole

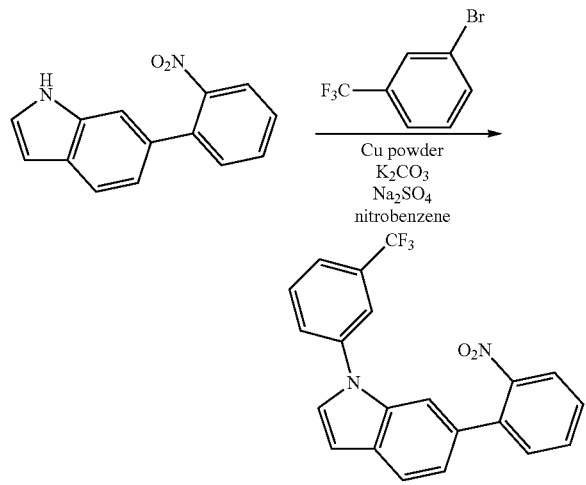

6-(2-nitrophenyl)-1-(3-(trifluoromethyl)phenyl)-1H-indole was obtained by performing the same procedure as in <Step 3> of Preparation Example 1, except that 6-(2-nitrophenyl)-1H-indole and 1-bromo-3-(trifluoromethyl)benzene were used instead of 5-(2-nitrophenyl)-1-phenyl-1H-indole and iodobenzene.

$^1$H-NMR: δ 6.80 (d, 1H), 7.11 (t, 1H), 7.21 (t, 1H), 7.36 (s, 1H), 7.42 (s, 1H), 7.50 (m, 2H), 7.55 (m, 2H), 7.63 (m, 2H), 7.86 (d, 1H), 8.01 (d, 1H)

<Step 2> Synthesis of IC-20

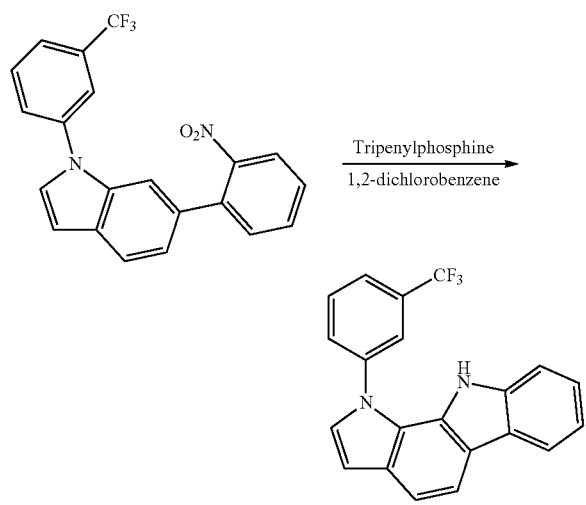

IC-20 was obtained by performing the same procedure as in <Step 4> of Preparation Example 1, except that 6-(2-nitrophenyl)-1-(3-(trifluoromethyl)phenyl)-1H-indole obtained in <Step 1> was used instead of 5-(2-nitrophenyl)-1-phenyl-1H-indole.

$^1$H-NMR: δ 6.81 (d, 1H), 7.12 (t, 1H), 7.24 (t, 1H), 7.43 (d, 1H), 7.51 (m, 2H), 7.58 (m, 2H), 7.64 (m, 2H), 7.85 (d, 1H), 8.02 (d, 1H), 9.82 (s, 1H)

[Preparation Example 21] Synthesis of IC-21

Step 1> Synthesis of 3-(5-(2-nitrophenyl)-1H-indol-1-yl)-9-phenyl-9H-carbazole

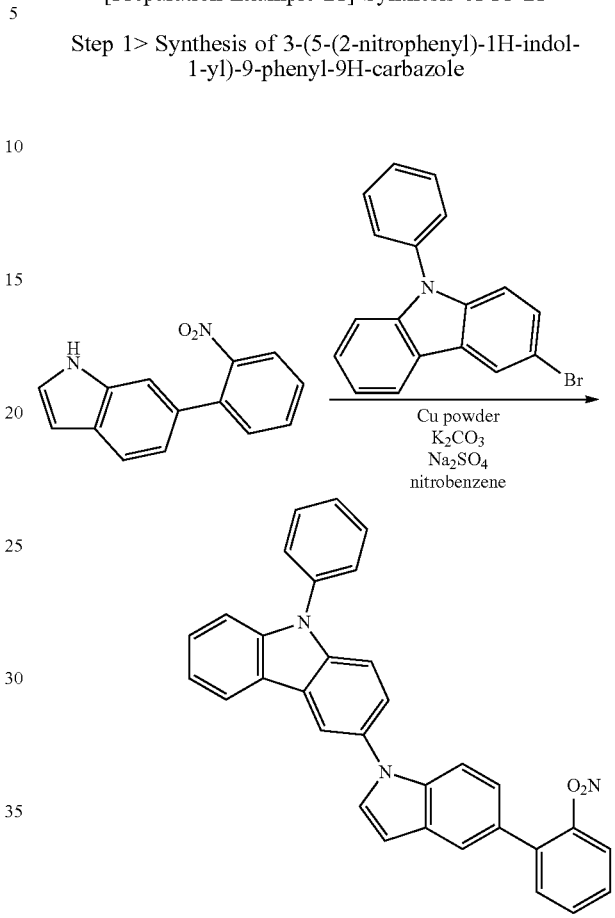

3-(5-(2-nitrophenyl)-1H-indol-1-yl)-9-phenyl-9H-carbazole was obtained by performing the same procedure as in <Step 3> of Preparation Example 1, except that 6-(2-nitrophenyl)-1H-indole and 3-bromo-9-phenyl-9H-carbazole were used instead of 5-(2-nitrophenyl)-1-phenyl-1H-indole and iodobenzene.

GC-Mass (theoretical value: 479.16 g/mol, measured value: 479 g/mol)<

<Step 2> Synthesis of IC-21

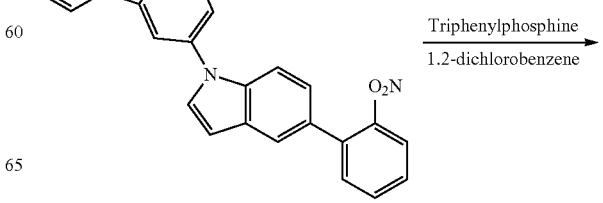

-continued

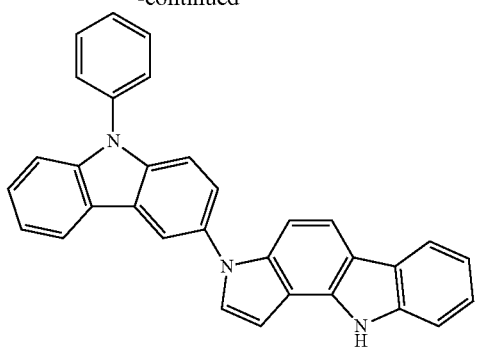

IC-21 was obtained by performing the same procedure as in <Step 4> of Preparation Example 1, except that 3-(5-(2-nitrophenyl)-1H-indol-1-yl)-9-phenyl-9H-carbazole obtained in <Step 1> was used instead of 5-(2-nitrophenyl)-1-phenyl-1H-indole.

GC-Mass (theoretical value: 447.17 g/mol, measured value: 447 g/mol)

[Preparation Example 22] Synthesis of IC-22

<Step 1> Synthesis of 9-(4,6-diphenyl-1,3,5-triazin-2-yl)-3-(5-(2-nitrophenyl)-1H-indol-1-yl)-9H-carbazole

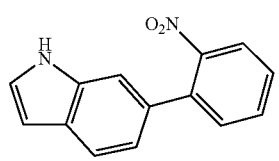
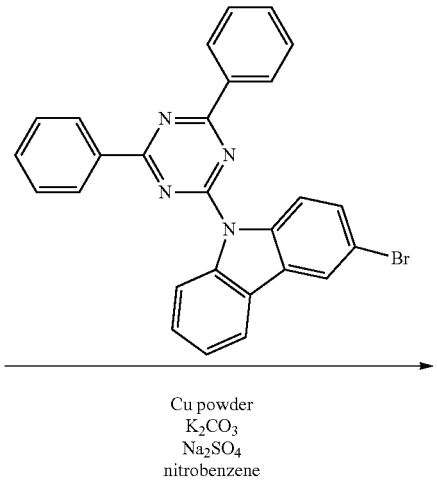

Cu powder
K₂CO₃
Na₂SO₄
nitrobenzene

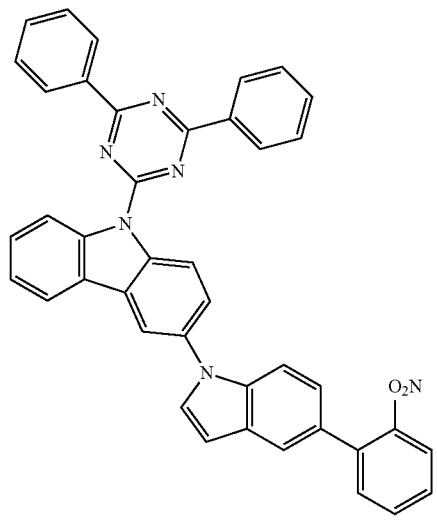

9-(4,6-diphenyl-1,3,5-triazin-2-yl)-3-(5-(2-nitrophenyl)-1H-indol-1-yl)-9H-carbazole was obtained by performing the same procedure as in <Step 3> of Preparation Example 1, except that 6-(2-nitrophenyl)-1H-indole and 3-bromo-9-(4,6-diphenyl-1,3,5-triazin-2-yl)-9H-carbazole were used instead of 5-(2-nitrophenyl)-1H-indole and iodobenzene.

GC-Mass (theoretical value: 634.21 g/mol, measured value: 634 g/mol)<

<Step 2> Synthesis of IC-22

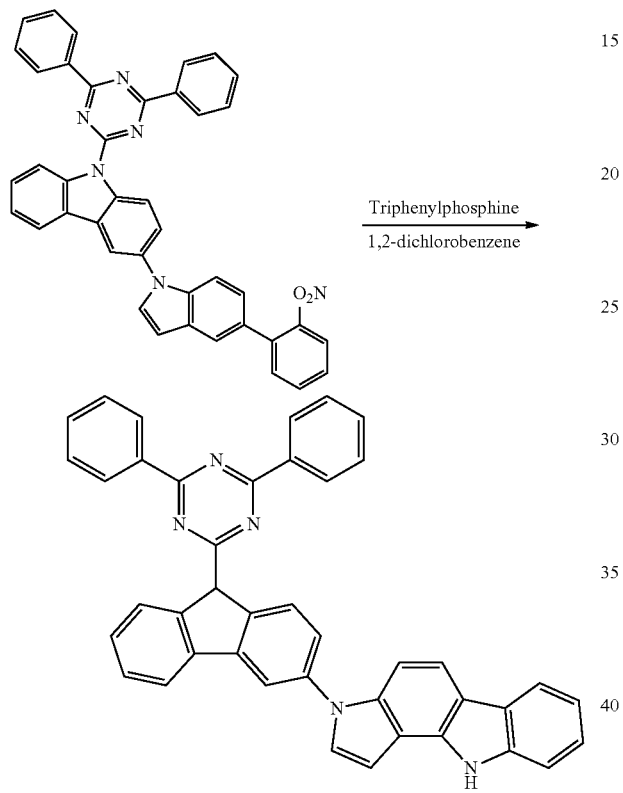

IC-22 was obtained by performing the same procedure as in <Step 4> of Preparation Example 1, except that 9-(4,6-diphenyl-1,3,5-triazin-2-yl)-3-(5-(2-nitrophenyl)-1H-indol-1-yl)-9H-carbazole obtained in <Step 1> was used instead of 5-(2-nitrophenyl)-1-phenyl-1H-indole.

GC-Mass (theoretical value: 602.22 g/mol, measured value: 602 g/mol)

[Preparation Example 23] Synthesis of IC-23

<Step 1> Synthesis of 5-bromo-2-phenyl-1H-indole

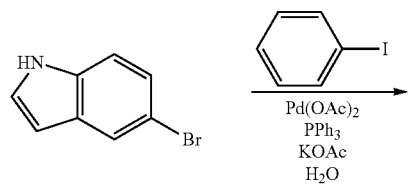

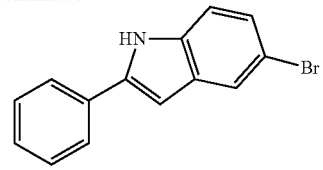

5-bromo-1H-indole (25 g, 0.13 mol), iodobenzene (31.22 g, 0.15 mol), Pd(OAc)$_2$ (1.43 g, 5 mol %), triphenylphosphine (1.67 g, 5 mol %), KOAc (37.55 g, 0.38 mol), and H$_2$O (300 ml) were mixed under nitrogen flow, and the mixture was stirred at 110° C. for 24 hours.

After the reaction was completed, extraction was performed with ethyl acetate, moisture was removed with MgSO$_4$, and purification was performed by column chromatography (Hexane:EA=10:1 (v/v)), thereby obtaining 5-bromo-2-phenyl-1H-indole (16.66 g, yield 48%).

$^1$H-NMR: δ 6.89 (dd, 1H), 7.20 (dd, 1H), 7.34 (m, 1H), 7.36 (d, 1H), 7.47 (t, 2H), 7.71 (d, 1H), 7.86 (dd, 2H), 11.74 (s, 1H)

<Step 2> Synthesis of 5-(2-nitrophenyl)-2-phenyl-1H-indole

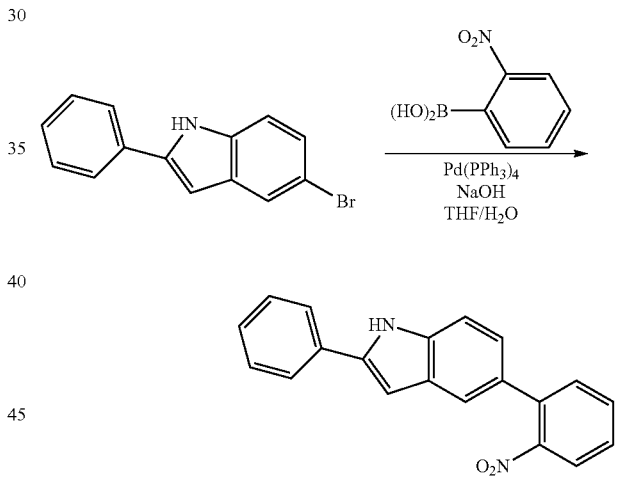

2-nitrophenylboronic acid (11.04 g, 66.14 mmol), 5-bromo-2-phenyl-1H-indole (15 g, 55.12 mmol) obtained in <Step 1>, NaOH (6.61 g, 165.36 mmol) and THF/H$_2$O (200 ml/100 ml) were mixed under nitrogen flow, then Pd(PPh$_3$)$_4$ (3.18 g, 5 mol) was added to the mixture at 40° C., and the resulting mixture was stirred at 80° C. for 12 hours.

After the reaction was completed, extraction was performed with methylene chloride, MgSO$_4$ was added thereto, and the mixture was filtered. After the solvent was removed from the organic layer obtained, the residue was purified by column chromatography (Hexane:EA=5:1 (v/v)), thereby obtaining 5-(2-nitrophenyl)-2-phenyl-1H-indole (10.74 g, yield 62%).

$^1$H-NMR: δ 6.88 (dd, 1H), 7.21 (d, 1H), 7.32 (m, 1H), 7.34 (d, 1H), 7.46 (m, 3H), 7.64 (m, 2H), 7.77 (d, 2H), 8.02 (d, 2H), 11.73 (s, 1H)

\<Step 3\> Synthesis of 5-(2-nitrophenyl)-1,2-diphenyl-1H-indole

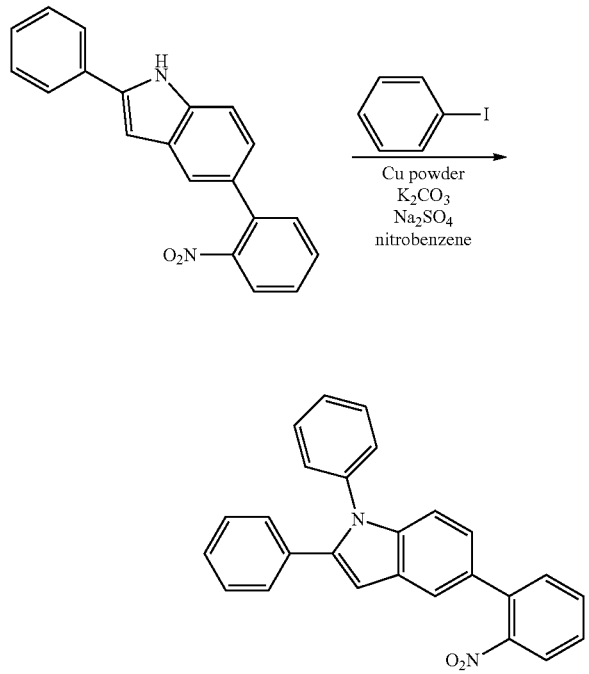

5-(2-nitrophenyl)-1,2-diphenyl-1H-indole was obtained by performing the same procedure as in \<Step 3\> of Preparation Example 1, except that 5-(2-nitrophenyl)-2-phenyl-1H-indole obtained in \<Step 2\> was used instead of 5-(2-nitrophenyl)-1H-indole.

GC-Mass (theoretical value: 390.14 g/mol, measured value: 390 g/mol)<

\<Step 3\> Synthesis of IC-23

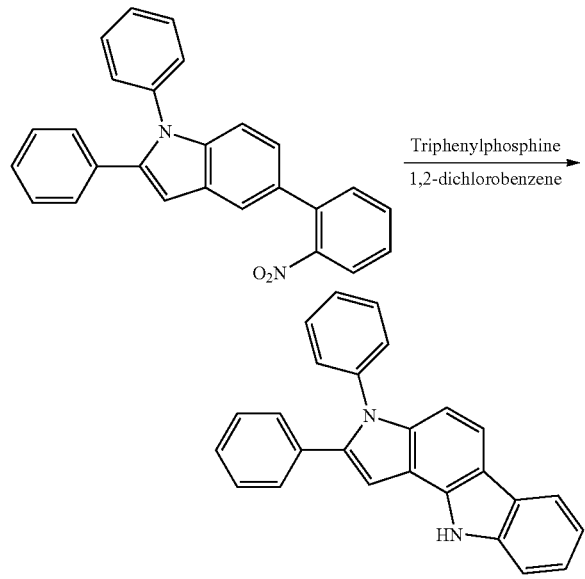

IC-23 was obtained by performing the same procedure as in \<Step 4\> of Preparation Example 1, except that 5-(2-nitrophenyl)-1,2-diphenyl-1H-indole obtained in \<Step 3\> was used instead of 5-(2-nitrophenyl)-1-phenyl-1H-indole.

GC-Mass (theoretical value: 358.15 g/mol, measured value: 358 g/mol)

[Preparation Example 24] Synthesis of IC-24

\<Step 1\> Synthesis of 6-chloro-2-phenyl-1H-indole

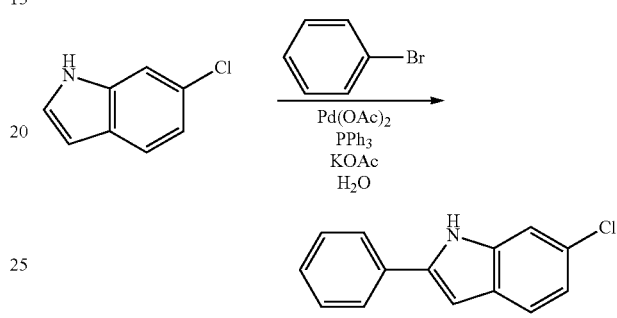

6-chloro-2-phenyl-1H-indole was obtained by performing the same procedure as in \<Step 1\> of Preparation Example 23, except that 6-chloro-1H-indole and bromobenzene were used instead of 5-bromo-1H-indole and iodobenzene.

$^1$H-NMR: δ 6.92 (d, 1H), 7.02 (dd, 1H), 7.33 (t, 1H), 7.41 (s, 1H), 7.47 (t, 2H), 7.54 (d, 1H), 7.85 (d, 2H), 11.68 (s, 1H)

\<Step 2\> Synthesis of 6-(2-nitrophenyl)-2-phenyl-1H-indole

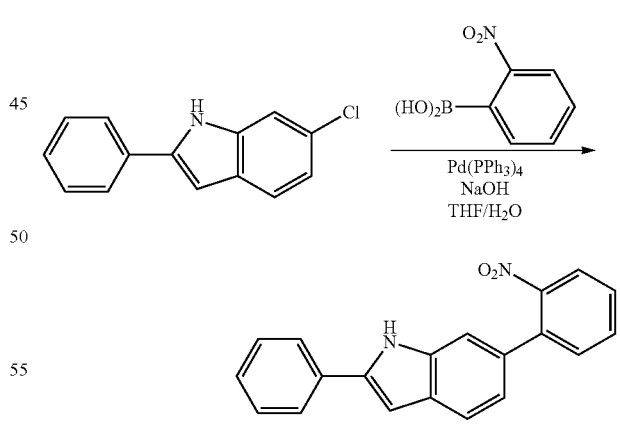

6-(2-nitrophenyl)-2-phenyl-1H-indole was obtained by performing the same procedure as in \<Step 2\> of Preparation Example 23, except that 6-chloro-2-phenyl-1H-indole obtained in \<Step 1\> was used instead of 5-bromo-2-phenyl-1H-indole.

$^1$H-NMR: δ 6.91 (d, 1H), 7.03 (d, 1H), 7.31 (t, 1H), 7.42 (s, 1H), 7.48 (m, 3H), 7.53 (d, 1H), 7.76 (m, 3H), 8.01 (d, 2H), 11.66 (s, 1H)

<Step 3> Synthesis of 6-(2-nitrophenyl)-1,2-diphenyl-1H-indole

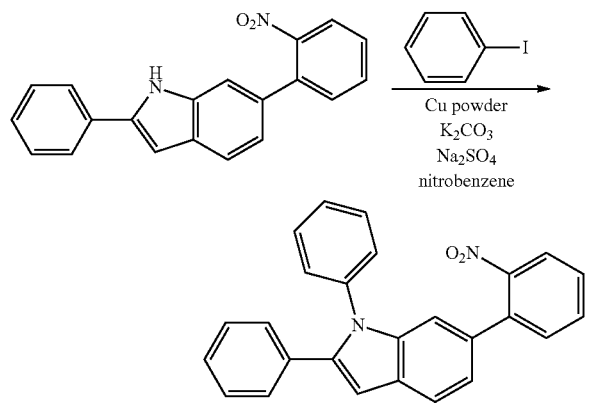

6-(2-nitrophenyl)-1,2-diphenyl-1H-indole was obtained by performing the same procedure as in <Step 3> of Preparation Example 1, except that 6-(2-nitrophenyl)-2-phenyl-1H-indole obtained in <Step 2> was used instead of 5-(2-nitrophenyl)-1H-indole.

GC-Mass (theoretical value: 390.14 g/mol, measured value: 390 g/mol)

<Step 4> Synthesis of IC-24

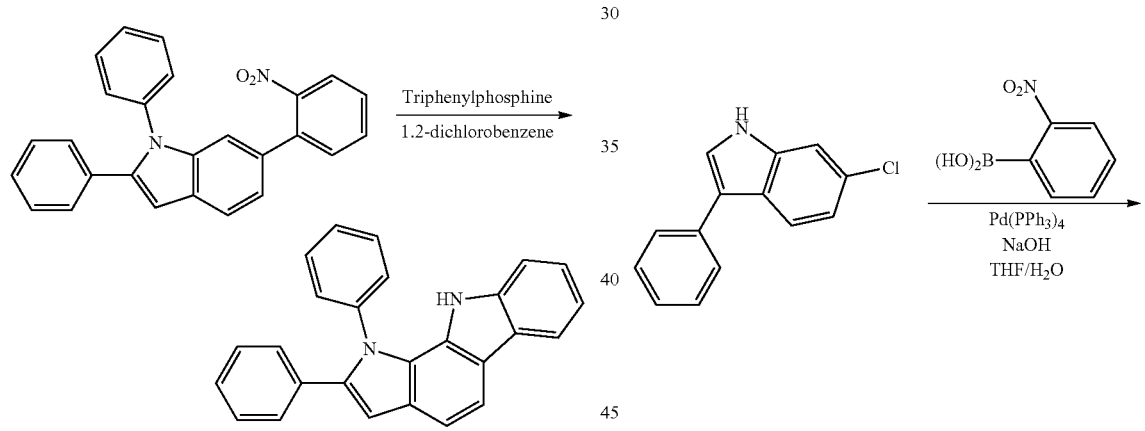

IC-24 was obtained by performing the same procedure as in <Step 4> of Preparation Example 1, except that 6-(2-nitrophenyl)-1,2-diphenyl-1H-indole obtained in <Step 2> was used instead of 5-(2-nitrophenyl)-1-phenyl-1H-indole.

GC-Mass (theoretical value: 358.15 g/mol, measured value: 358 g/mol)

[Preparation Example 25] Synthesis of IC-25

<Step 1> Synthesis of 6-chloro-3-phenyl-1H-indole

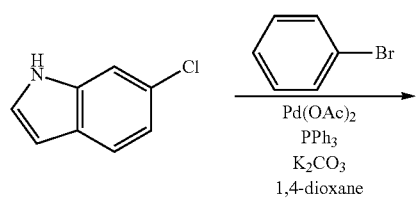

6-chloro-1H-indole (25 g, 0.17 mol), bromobenzene (31.19 g, 0.20 mol), Pd(OAc)$_2$ (1.86 g, 5 mol %), triphenylphosphine (2.17 g, 5 mol %), K$_2$CO$_3$ (68.64 g, 0.50 mol), and 1,4-dioxane (300 ml) were mixed under nitrogen flow, and the mixture was stirred at 130° C. for 18 hours.

After the reaction was completed, extraction was performed with ethyl acetate, moisture was removed with MgSO$_4$, and purification was performed by column chromatography (Hexane:EA=10:1 (v/v)), thereby obtaining 6-chloro-3-phenyl-1H-indole (24.5 g, yield 65%).

$^1$H-NMR: δ 7.10 (dd, 1H), 7.25 (m, 1H), 7.43 (t, 2H), 7.49 (d, 1H), 7.67 (dd, 2H), 7.73 (d, 1H), 7.85 (d, 1H), 11.49 (s, 1H)

<Step 2> Synthesis of 6-(2-nitrophenyl)-3-phenyl-1H-indole

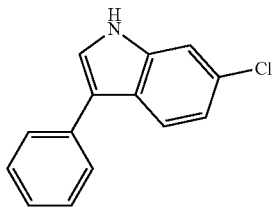

6-(2-nitrophenyl)-3-phenyl-1H-indole was obtained by performing the same procedure as in <Step 2> of Preparation Example 23, except that 6-chloro-3-phenyl-1H-indole obtained in <Step 1> was used instead of 5-bromo-2-phenyl-1H-indole.

$^1$H-NMR: δ 7.11 (d, 1H), 7.26 (m, 1H), 7.44 (t, 2H), 7.48 (m, 2H), 7.55 (m, 3H), 7.61 (d, 1H), 7.73 (d, 1H), 8.00 (d, 2H), 11.48 (s, 1H)

\<Step 3\> Synthesis of 6-(2-nitrophenyl)-1,3-diphenyl-1H-indole

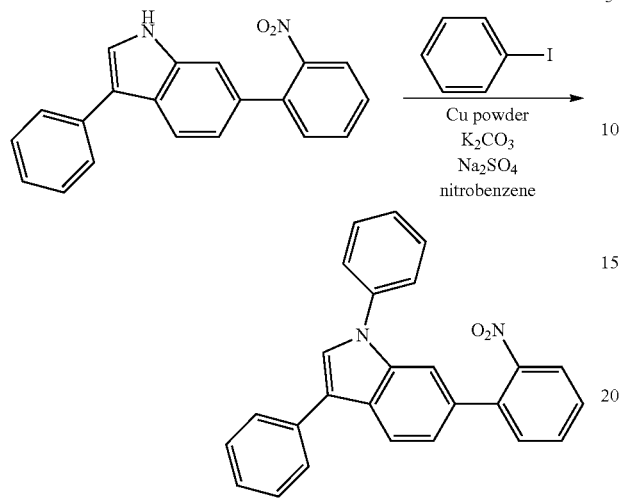

6-(2-nitrophenyl)-1,3-diphenyl-1H-indole was obtained by performing the same procedure as in \<Step 3\> of Preparation Example 1, except that 6-(2-nitrophenyl)-3-phenyl-1H-indole obtained in \<Step 2\> was used instead of 5-(2-nitrophenyl)-1H-indole.

GC-Mass (theoretical value: 390.14 g/mol, measured value: 390 g/mol)<

\<Step 4\> Synthesis of IC-25

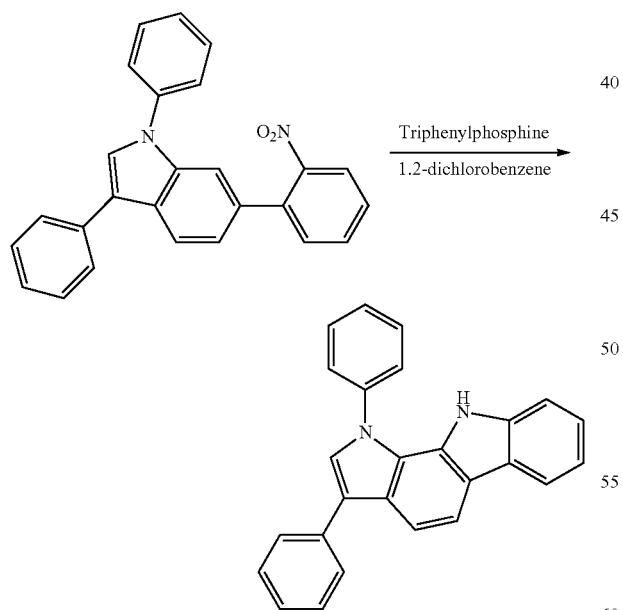

IC-25 was obtained by performing the same procedure as in \<Step 4\> of Preparation Example 1, except that 6-(2-nitrophenyl)-1,3-diphenyl-1H-indole obtained in \<Step 3\> was used instead of 5-(2-nitrophenyl)-1-phenyl-1H-indole.

GC-Mass (theoretical value: 358.15 g/mol, measured value: 358 g/mol)

[Preparation Example 26] Synthesis of IC-26

\<Step 1\> Synthesis of 5-bromo-2,3-diphenyl-1H-indole

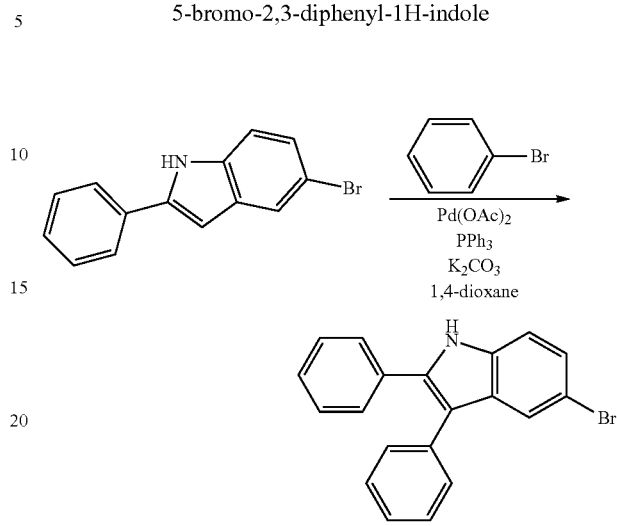

5-bromo-2,3-diphenyl-1H-indole was obtained by performing the same procedure as in \<Step 1\> of Preparation Example 25, except that 5-bromo-2-phenyl-1H-indole was used instead of 6-chloro-1H-indole.

$^1$H-NMR: δ 7.23 (d, 1H), 7.31 (t, 2H), 7.43 (m, 6H), 7.67 (d, 1H), 7.71 (d, 1H), 7.84 (d, 2H), 11.34 (s, 1H)

\<Step 2\> Synthesis of 5-(2-nitrophenyl)-2,3-diphenyl-1H-indole

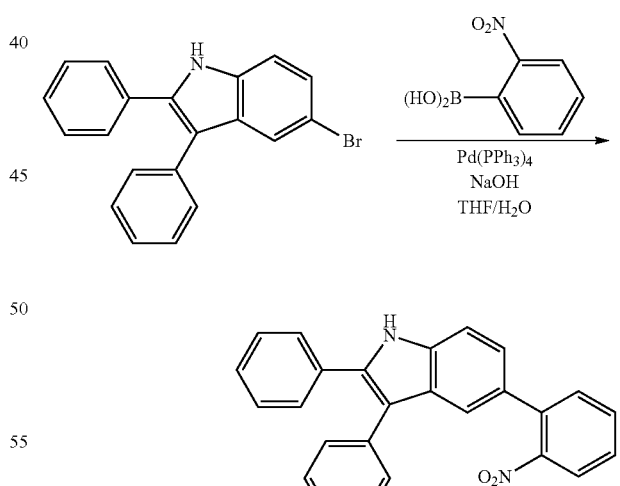

5-(2-nitrophenyl)-2,3-diphenyl-1H-indole was obtained by performing the same procedure as in \<Step 2\> of Preparation Example 23, except that 5-bromo-2,3-diphenyl-1H-indole obtained in \<Step 1\> was used instead of 5-bromo-2-phenyl-1H-indole.

GC-Mass (theoretical value: 390.14 g/mol, measured value: 390 g/mol)<

<Step 3> Synthesis of
5-(2-nitrophenyl)-2,3-diphenyl-1H-indole

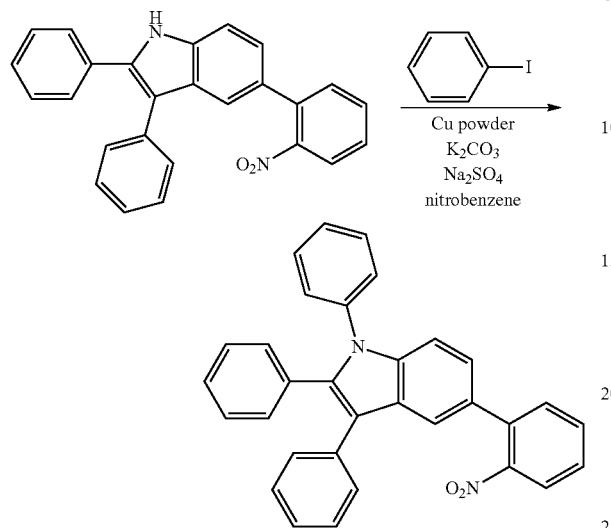

5-(2-nitrophenyl)-1,2,3-triphenyl-1H-indole was obtained by performing the same procedure as in <Step 3> of Preparation Example 1, except that 5-(2-nitrophenyl)-2,3-diphenyl-1H-indole obtained in <Step 2> was used instead of 5-(2-nitrophenyl)-1H-indole.

GC-Mass (theoretical value: 466.17 g/mol, measured value: 466 g/mol)<

<Step 4> Synthesis of IC-26

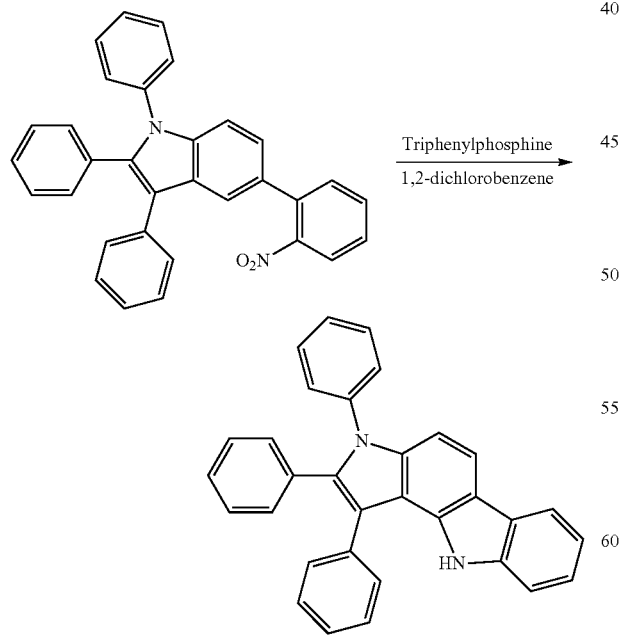

IC-23 was obtained by performing the same procedure as in <Step 4> of Preparation Example 1, except that 5-(2-nitrophenyl)-1,2,3-triphenyl-1H-indole obtained in <Step 3> was used instead of 5-(2-nitrophenyl)-1-phenyl-1H-indole.

GC-Mass (theoretical value: 434.18 g/mol, measured value: 434 g/mol)

[Preparation Example 27] Synthesis of IC-27

<Step 1> Synthesis of
6-chloro-2,3-diphenyl-1H-indole

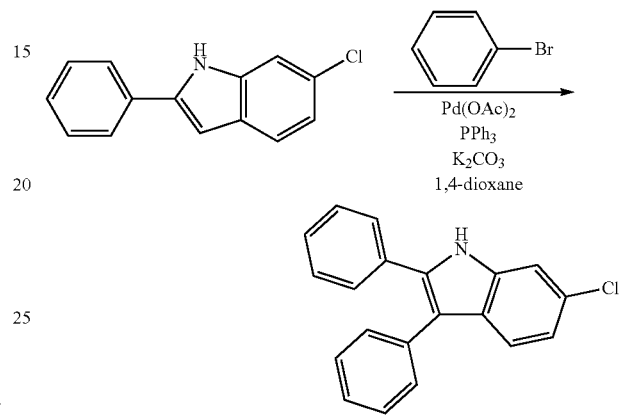

6-chloro-2,3-diphenyl-1H-indole was obtained by performing the same procedure as in <Step 1> of Preparation Example 25, except that 6-chloro-2-phenyl-1H-indole was used instead of 6-chloro-1H-indole.

$^1$H-NMR: δ 7.18 (d, 1H), 7.29 (t, 2H), 7.50 (m, 6H), 7.62 (d, 1H), 7.75 (d, 1H), 7.89 (d, 2H), 11.35 (s, 1H)

<Step 2> Synthesis of
6-(2-nitrophenyl)-2,3-diphenyl-1H-indole

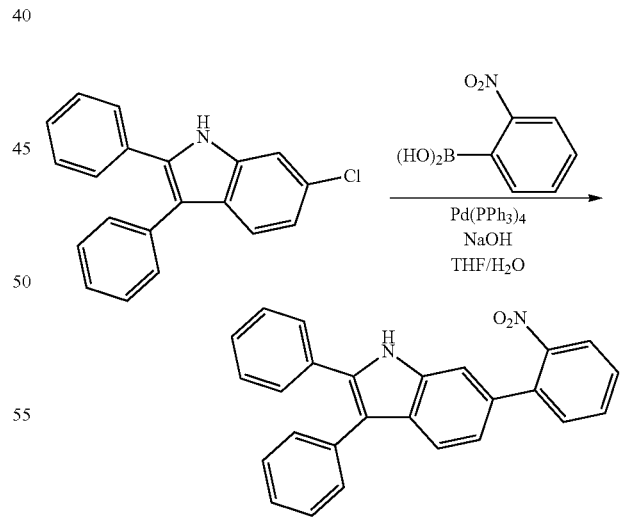

6-(2-nitrophenyl)-2,3-diphenyl-1H-indole was obtained by performing the same procedure as in <Step 2> of Preparation Example 23, except that 6-chloro-2,3-diphenyl-1H-indole obtained in <Step 1> was used instead of 5-bromo-2-phenyl-1H-indole.

GC-Mass (theoretical value: 390.14 g/mol, measured value: 390 g/mol)<

<Step 3> Synthesis of
6-(2-nitrophenyl)-1,2,3-triphenyl-1H-indole

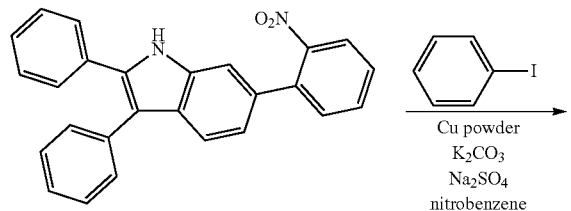

6-(2-nitrophenyl)-1,2,3-triphenyl-1H-indole was obtained by performing the same procedure as in <Step 3> of Preparation Example 1, except that 6-(2-nitrophenyl)-2,3-diphenyl-1H-indole obtained in <Step 2> was used instead of 5-(2-nitrophenyl)-1H-indole.

GC-Mass (theoretical value: 466.17 g/mol, measured value: 466 g/mol)<

<Step 4> Synthesis of IC-27

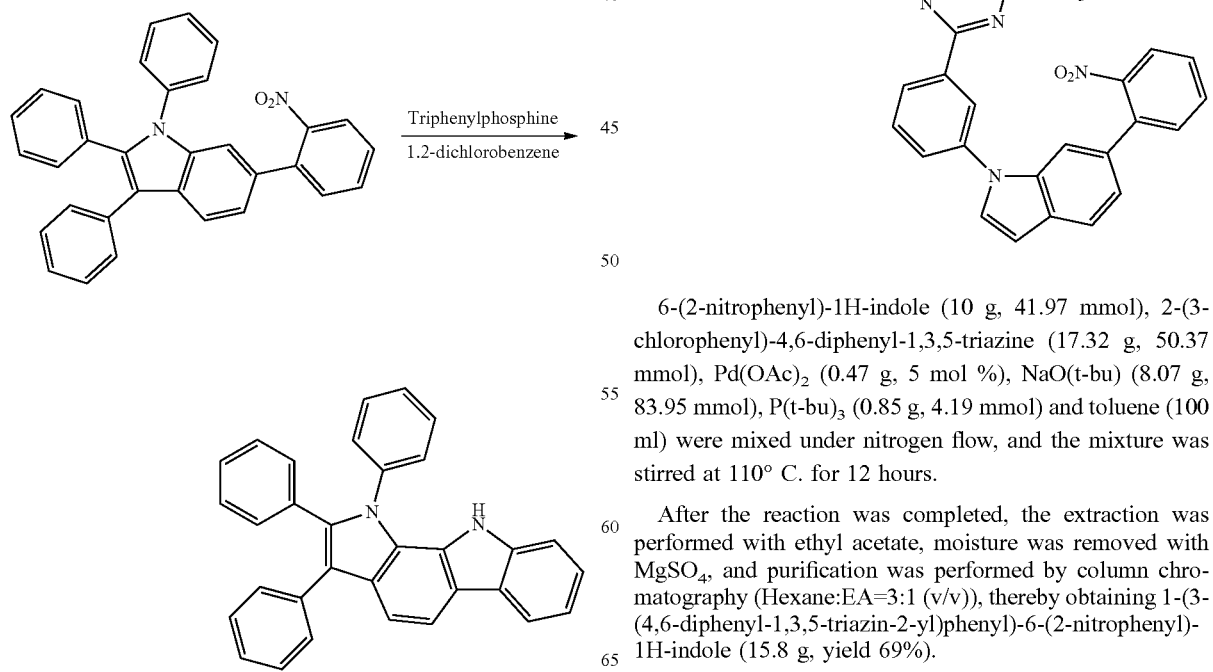

IC-27 was obtained by performing the same procedure as in <Step 4> of Preparation Example 1, except that 6-(2-nitrophenyl)-1,2,3-triphenyl-1H-indole obtained in <Step 3> was used instead of 5-(2-nitrophenyl)-1-phenyl-1H-indole.

GC-Mass (theoretical value: 434.18 g/mol, measured value: 434 g/mol)

[Preparation Example 28] Synthesis of IC-28

<Step 1> Synthesis of 1-(3-(4,6-diphenyl-1,3,5-triazin-2-yl)phenyl)-6-(2-nitrophenyl)-1H-indole

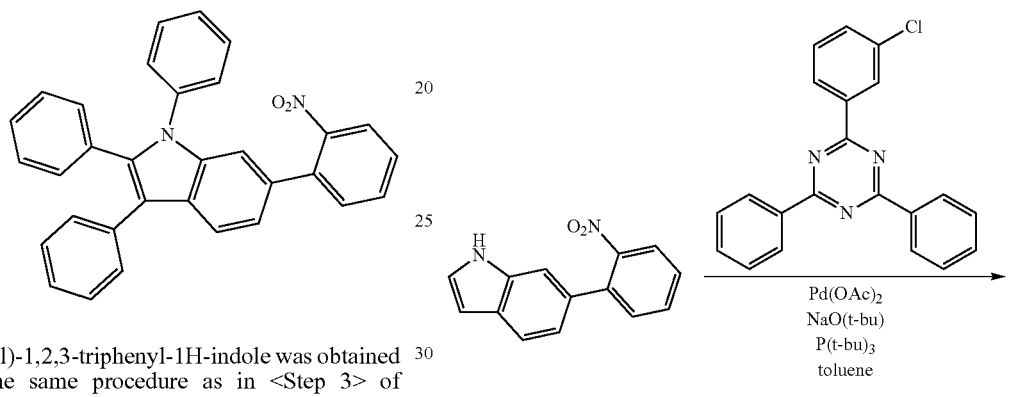

6-(2-nitrophenyl)-1H-indole (10 g, 41.97 mmol), 2-(3-chlorophenyl)-4,6-diphenyl-1,3,5-triazine (17.32 g, 50.37 mmol), Pd(OAc)$_2$ (0.47 g, 5 mol %), NaO(t-bu) (8.07 g, 83.95 mmol), P(t-bu)$_3$ (0.85 g, 4.19 mmol) and toluene (100 ml) were mixed under nitrogen flow, and the mixture was stirred at 110° C. for 12 hours.

After the reaction was completed, the extraction was performed with ethyl acetate, moisture was removed with MgSO$_4$, and purification was performed by column chromatography (Hexane:EA=3:1 (v/v)), thereby obtaining 1-(3-(4,6-diphenyl-1,3,5-triazin-2-yl)phenyl)-6-(2-nitrophenyl)-1H-indole (15.8 g, yield 69%).

GC-Mass (theoretical value: 545.19 g/mol, measured value: 545 g/mol)<

<Step 2> Synthesis of IC-28

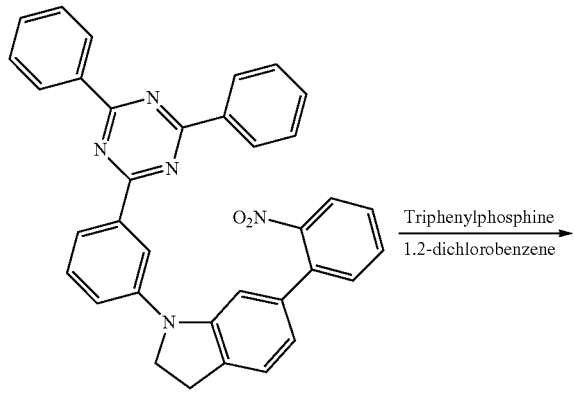

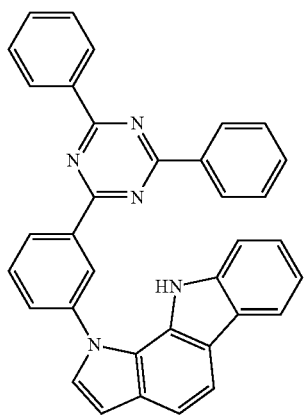

IC-28 was obtained by performing the same procedure as in <Step 4> of Preparation Example 1, except that 1-(3-(4,6-diphenyl-1,3,5-triazin-2-yl)phenyl)-6-(2-nitrophenyl)-1H-indole obtained in <Step 1> was used instead of 5-(2-nitrophenyl)-1-phenyl-1H-indole.

GC-Mass (theoretical value: 513.20 g/mol, measured value: 513 g/mol)

[Preparation Example 29] Synthesis of IC-29

<Step 1> Synthesis of 1-(3-(4,6-diphenylpyrimidin-2-yl)phenyl)-6-(2-nitrophenyl)-1H-indole

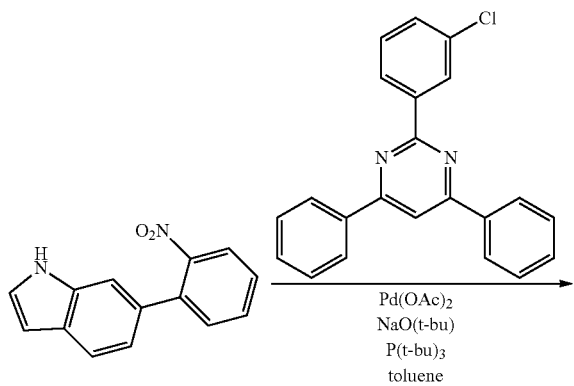

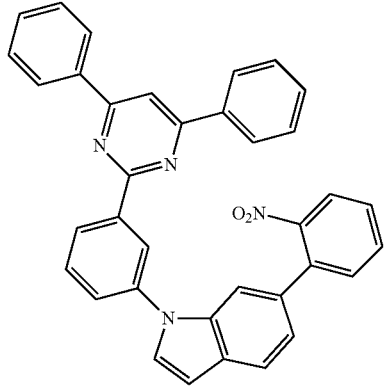

1-(3-(4,6-diphenylpyrimidin-2-yl)phenyl)-6-(2-nitrophenyl)-1H-indole was obtained by performing the same procedure as in <Step 1> of Preparation Example 28, except that 2-(3-chloro phenyl)-4,6-diphenylpyrimidine was used instead of 2-(3-chlorophenyl)-4,6-diphenyl-1,3,5-triazine.

GC-Mass (theoretical value: 544.19 g/mol, measured value: 544 g/mol)<

<Step 2> Synthesis of IC-29

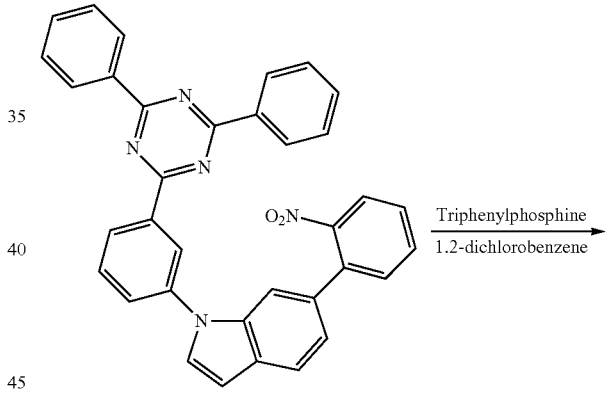

IC-29 was obtained by performing the same procedure as in <Step 4> of Preparation Example 1, except that 1-(3-(4,6-diphenylpyrimidin-2-yl)phenyl)-6-(2-nitrophenyl)-1H-indole obtained in <Step 1> was used instead of 5-(2-nitrophenyl)-1-phenyl-1H-indole.

GC-Mass (theoretical value: 512.20 g/mol, measured value: 512 g/mol)

[Preparation Example 30] Synthesis of IC-30

<Step 1> Synthesis of 1-(3-(4,6-diphenyl-1,3,5-triazin-2-yl)phenyl)-5-(2-nitrophenyl)-1H-indole

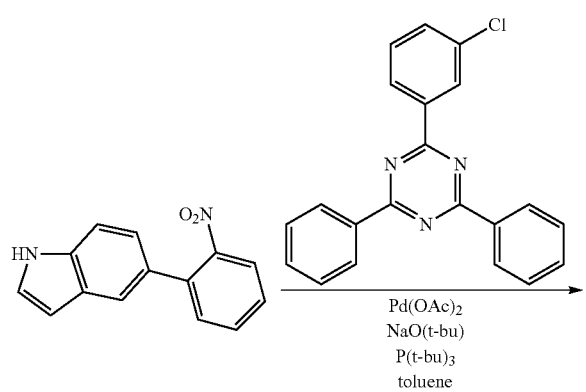

11-(3-(4,6-diphenyl-1,3,5-triazin-2-yl)phenyl)-5-(2-nitrophenyl)-1H-indole was obtained by performing the same procedure as in <Step 1> of Preparation Example 28, except that 5-(2-nitrophenyl)-1H-indole was used instead of 6-(2-nitrophenyl)-1H-indole.

GC-Mass (theoretical value: 545.19 g/mol, measured value: 545 g/mol)<

<Step 2> Synthesis of IC-30

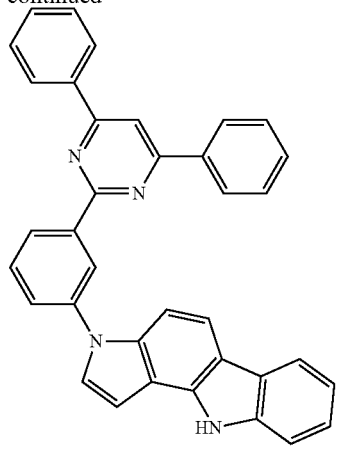

IC-30 was obtained by performing the same procedure as in <Step 4> of Preparation Example 1, except that 11-(3-(4,6-diphenyl-1,3,5-triazin-2-yl)phenyl)-5-(2-nitrophenyl)-1H-indole obtained in <Step 1> was used instead of 5-(2-nitrophenyl)-1-phenyl-1H-indole.

GC-Mass (theoretical value: 513.20 g/mol, measured value: 513 g/mol)

[Preparation Example 31] Synthesis of IC-31

<Step 1> Synthesis of 1-(3-[4,6-d]phenylpyrimidin-2-yl)phenyl)-5-(2-nitrophenyl)-1H-indole

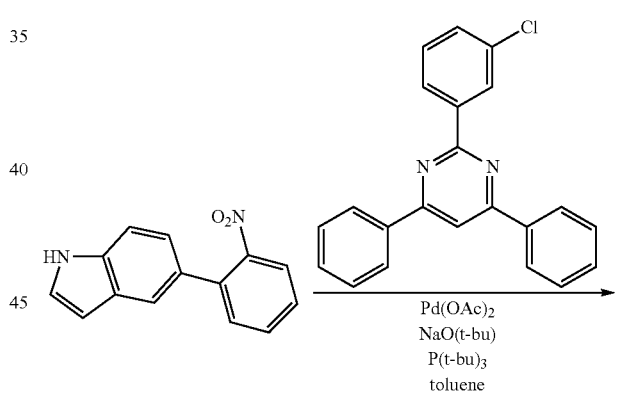

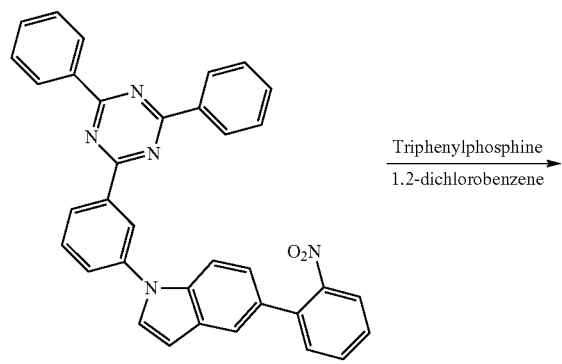

1-(3-(4,6-diphenylpyrimidin-2-yl)phenyl)-5-(2-nitrophenyl)-1H-indole was obtained by performing the same procedure as in <Step 1> of Preparation Example 28, except that 5-(2-nitrophenyl)-1H-indole and 2-(3-chloro phenyl)-4,6-diphenylpyrimidine were used instead of 6-(2-nitrophenyl)-1H-indole and 2-(3-chlorophenyl)-4,6-diphenyl-1,3,5-triazine.

GC-Mass (theoretical value: 544.19 g/mol, measured value: 544 g/mol)

<Step 2> Synthesis of IC-31

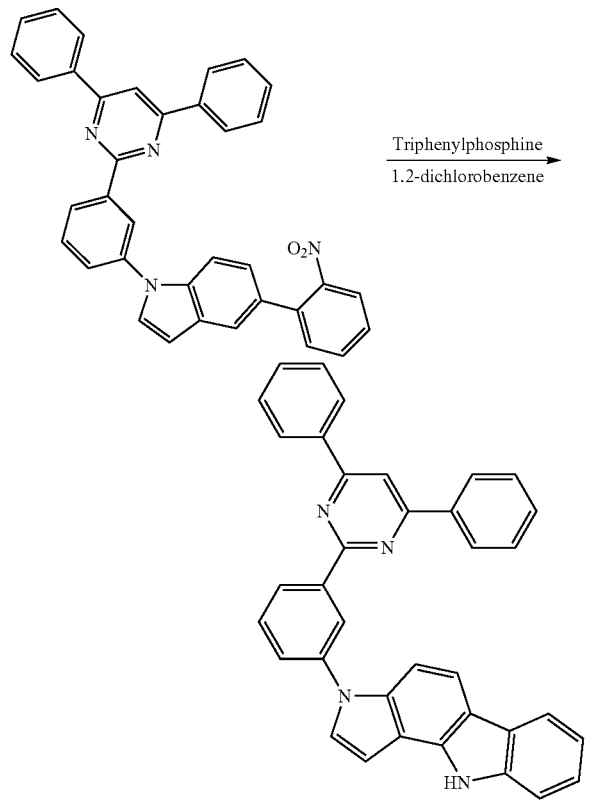

IC-31 was obtained by performing the same procedure as in <Step 4> of Preparation Example 1, except that 1-(3-(4,6-diphenylpyrimidin-2-yl)phenyl)-5-(2-nitrophenyl)-1H-indole obtained in <Step 1> was used instead of 5-(2-nitrophenyl)-1-phenyl-1H-indole.

GC-Mass (theoretical value: 512.20 g/mol, measured value: 512 g/mol)

[Synthesis Example 1] Synthesis of Inv-1

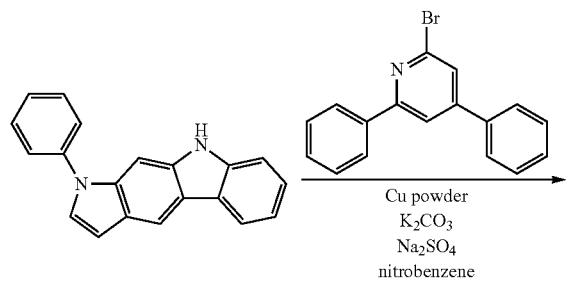

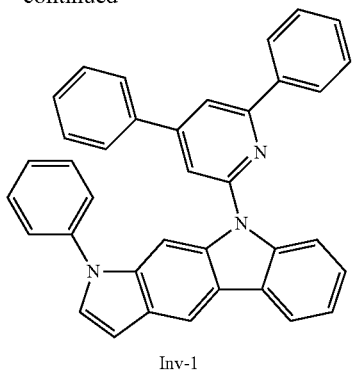

Inv-1

IC-1a (5 g, 17.71 mmol) as a compound prepared in Preparation Example 1, 2-bromo-4,6-diphenylpyridine (8.24 g, 26.56 mmol), Cu powder (0.11 g, 1.77 mmol), $K_2CO_3$ (2.44 g, 17.71 mmol), $Na_2SO_4$ (2.52 g, 17.71 mmol), and nitrobenzene (100 ml) were mixed under nitrogen flow, and the mixture was stirred at 190° C. for 12 hours.

After the reaction was completed, nitrobenzene was removed, the organic layer was separated with methylene chloride, and water was removed by using $MgSO_4$. After the solvent was removed from the organic layer, the residue was purified by column chromatography (Hexane:EA=1:1 (v/v)), thereby obtaining a target compound Inv-1 (6.25 g, yield 69%).

GC-Mass (theoretical value: 511.20 g/mol, measured value: 511 g/mol)

[Synthesis Example 2] Synthesis of Inv-2

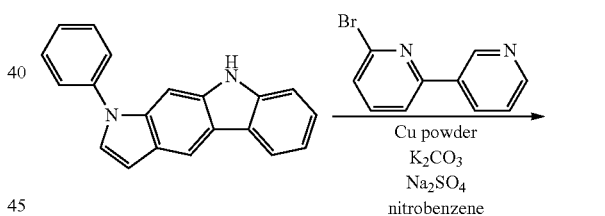

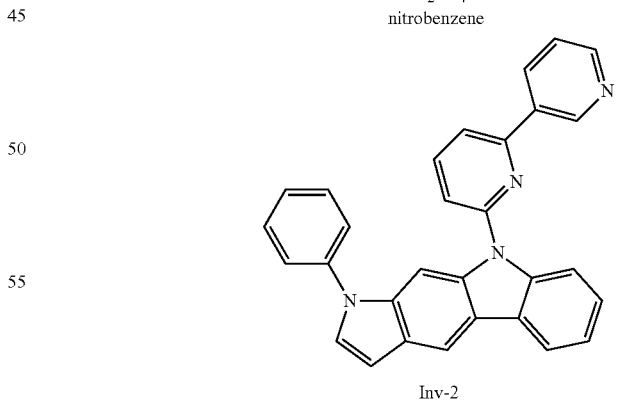

Inv-2

A target compound Inv-2 (5.02 g, yield 65%) was obtained by performing the same procedure as in Synthesis Example 1, except that 6-bromo-2,3'-bipyridine was used instead of 2-bromo-4,6-diphenylpyridine.

GC-Mass (theoretical value: 436.17 g/mol, measured value: 436 g/mol)

[Synthesis Example 3] Synthesis of Inv-3

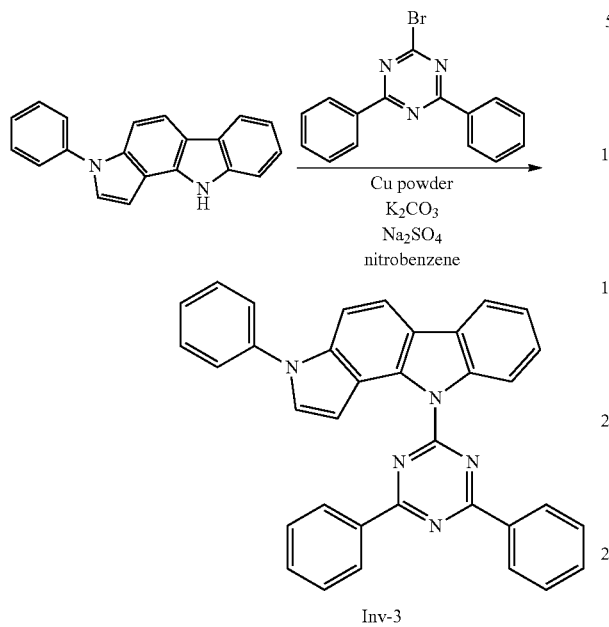

Inv-3

A target compound Inv-3 (3.91 g, yield 43%) was obtained by performing the same procedure as in Synthesis Example 1, except that IC-1b as another compound prepared in Preparation Example 1 was used instead of IC-1a, and 2-bromo-4,6-diphenyl-1,3,5-triazine was used instead of 2-bromo-4,6-diphenylpyridine.

GC-Mass (theoretical value: 513.20 g/mol, measured value: 513 g/mol)

[Synthesis Example 4] Synthesis of Inv-4

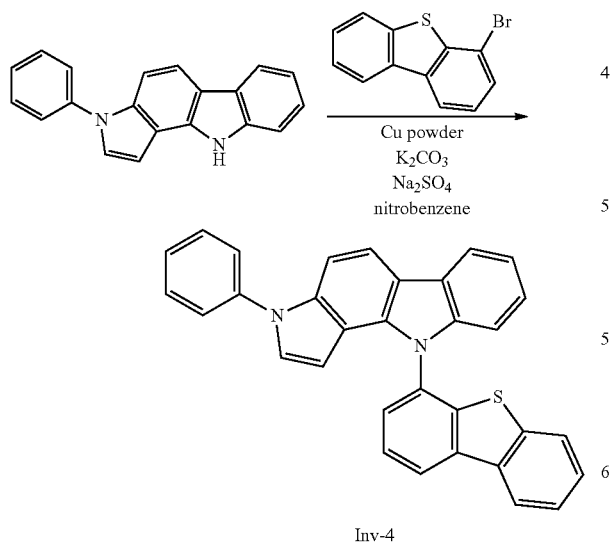

Inv-4

A target compound Inv-4 (5.02 g, yield 61%) was obtained by performing the same procedure as in Synthesis Example 1, except that IC-1b as another compound prepared in Preparation Example 1 was used instead of IC-1a, and 4-bromodibenzo[b,d]thiophene was used instead of 2-bromo-4,6-diphenylpyridine.

GC-Mass (theoretical value: 464.13 g/mol, measured value: 464 g/mol)

[Synthesis Example 5] Synthesis of Inv-5

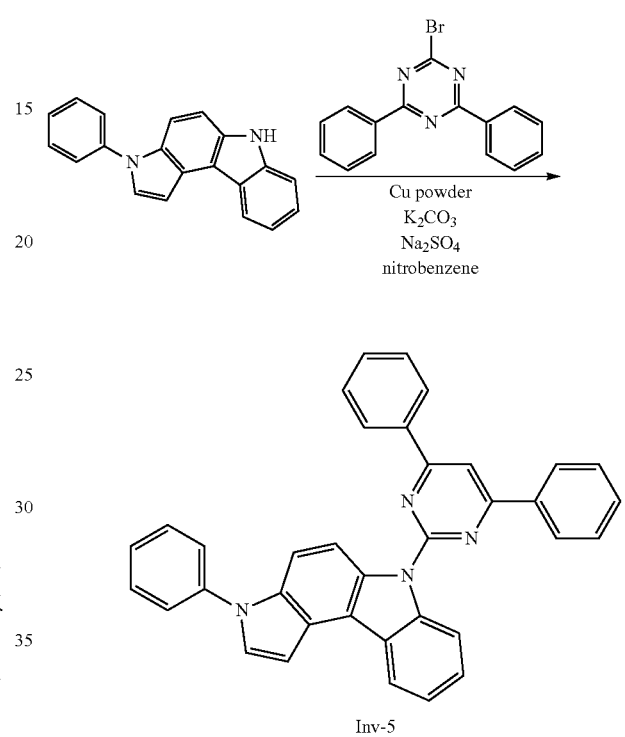

Inv-5

A target compound Inv-5 (5.36 g, yield 59%) was obtained by performing the same procedure as in Synthesis Example 1, except that 3-phenyl-3,6-dihydropyrrolo[2,3-c]carbazole prepared in Preparation Example 2 was used instead of IC-1a, and 2-bromo-4,6-diphenylpyrimidine was used instead of 2-bromo-4,6-diphenylpyridine.

GC-Mass (theoretical value: 512.20 g/mol, measured value: 512 g/mol)

[Synthesis Example 6] Synthesis of Inv-6

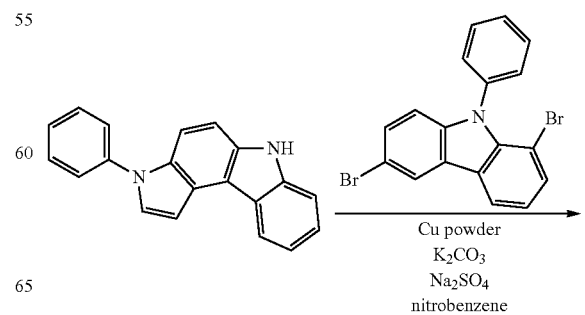

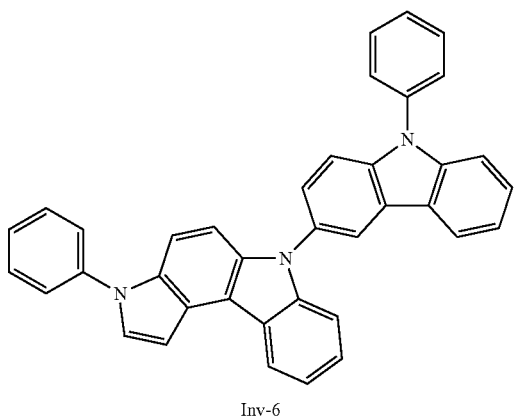

Inv-6

A target compound Inv-6 (6.58 g, yield 71%) was obtained by performing the same procedure as in Synthesis Example 1, except that 3-phenyl-3,6-dihydropyrrolo[2,3-c]carbazole prepared in Preparation Example 2 was used instead of IC-1a, and 3-bromo-9-phenyl-9H-carbazole was used instead of 2-bromo-4,6-diphenylpyridine.

GC-Mass (theoretical value: 523.20 g/mol, measured value: 523 g/mol)

[Synthesis Example 7] Synthesis of Inv-7

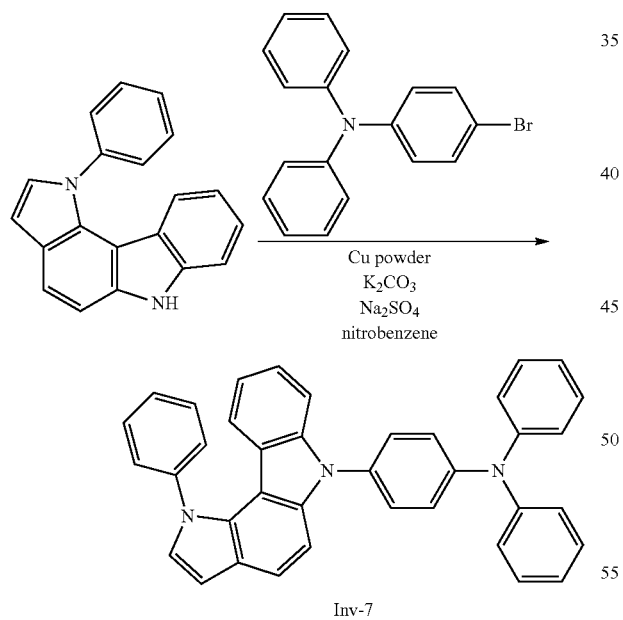

Inv-7

A target compound Inv-7 (6.8 g, yield 73%) was obtained by performing the same procedure as in Synthesis Example 1, except that 1-phenyl-1,6-dihydropyrrolo[3.2-c]carbazole prepared in Preparation Example 3 was used instead of IC-1a, and 4-bromo-N,N-diphenylaniline was used instead of 2-bromo-4,6-diphenylpyridine.

GC-Mass (theoretical value: 525.22 g/mol, measured value: 525 g/mol)

[Synthesis Example 8] Synthesis of Inv-8

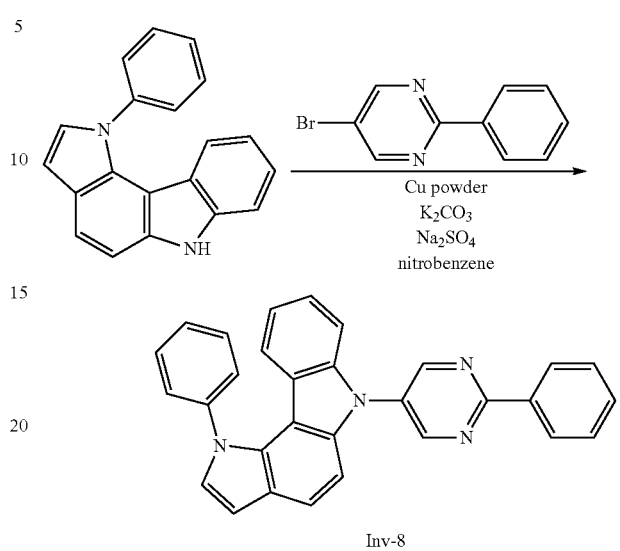

Inv-8

A target compound Inv-8 (3.48 g, yield 45%) was obtained by performing the same procedure as in Synthesis Example 1, except that 1-phenyl-1,6-dihydropyrrolo[3.2-c]carbazole prepared in Preparation Example 3 was used instead of IC-1a, and 5-bromo-2-phenylpyrimidine was used instead of 2-bromo-4,6-diphenylpyridine.

GC-Mass (theoretical value: 436.17 g/mol, measured value: 436 g/mol)

[Synthesis Example 9] Synthesis of Inv-9

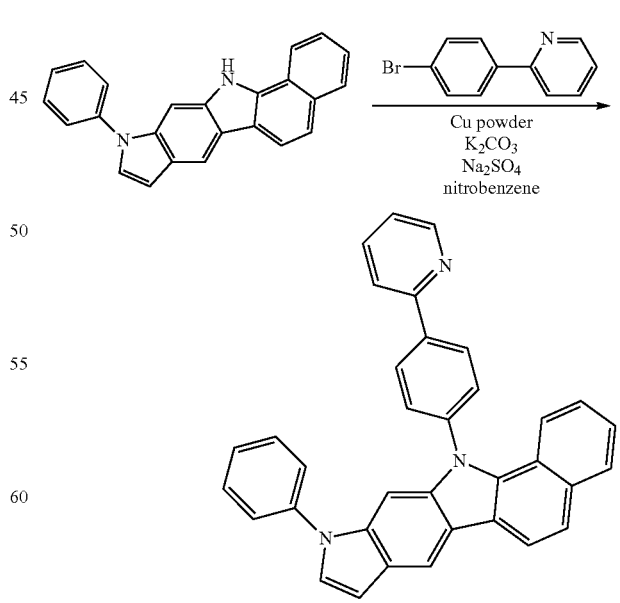

Inv-9

A target compound Inv-9 (4.97 g, yield 68%) was obtained by performing the same procedure as in Synthesis Example 1, except that IC-4-a as a compound prepared in Preparation Example 4 was used instead of IC-1a, and 2-(4-bromophenyl)pyridine was used instead of 2-bromo-4,6-diphenylpyridine.

GC-Mass (theoretical value: 485.19 g/mol, measured value: 485 g/mol)

[Synthesis Example 10] Synthesis of Inv-10

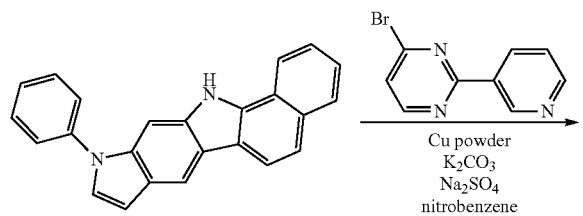

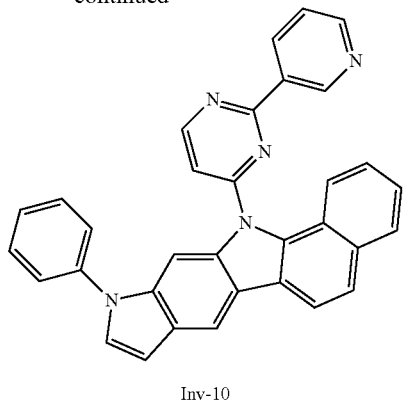

Inv-10

A target compound Inv-10 (3.08 g, yield 42%) was obtained by performing the same procedure as in Synthesis Example 1, except that IC-4-a as a compound prepared in Preparation Example 4 was used instead of IC-1a, and 4-bromo-2-(pyridin-3-yl)pyrimidine was used instead of 2-bromo-4,6-diphenylpyridine.

GC-Mass (theoretical value: 487.18 g/mol, measured value: 487 g/mol)

[Synthetic Example 11] Synthesis of Inv-11

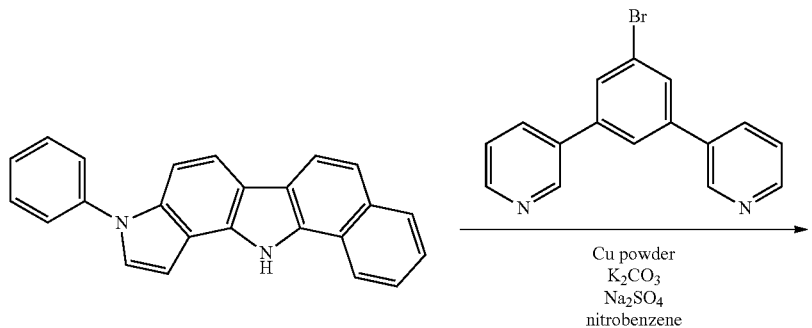

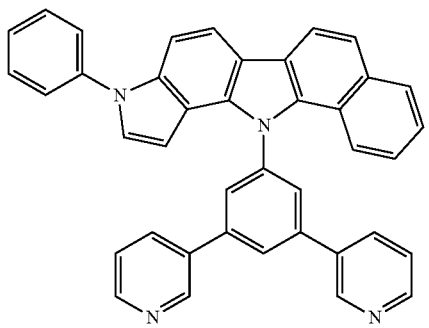

Inv-11

A target compound Inv-11 (5.08 g, yield 60%) was obtained by performing the same procedure as in Synthesis Example 1, except that IC-4-b as another compound prepared in Preparation Example 4 was used instead of IC-1a, and 3,3'-(5-bromo-1,3-phenylene)dipyridine was used instead of 2-bromo-4,6-diphenylpyridine.

GC-Mass (theoretical value: 562.22 g/mol, measured value: 562 g/mol)

[Synthesis Example 12] Synthesis of Inv-12

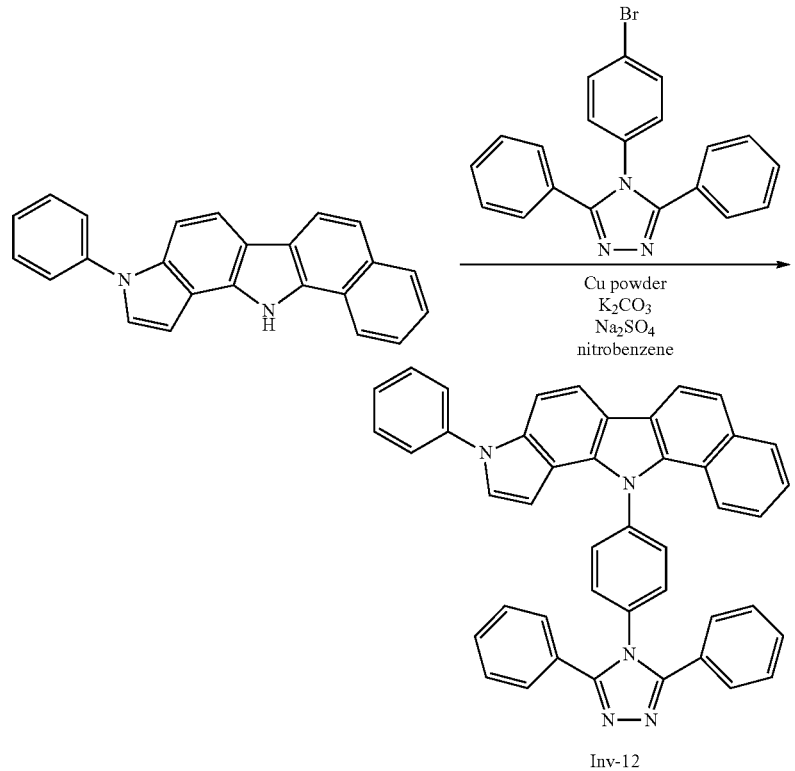

A target compound Inv-12 (4.91 g, yield 52%) was obtained by performing the same procedure as in Synthesis Example 1, except that IC-4-b as another compound prepared in Preparation Example 4 was used instead of IC-1a, and 4-(4-bromophenyl)-3,5-diphenyl-4H-1,2,4-triazole was used instead of 2-bromo-4,6-diphenylpyridine.

GC-Mass (theoretical value: 627.24 g/mol, measured value: 627 g/mol)

[Synthesis Example 13] Synthesis of Inv-13

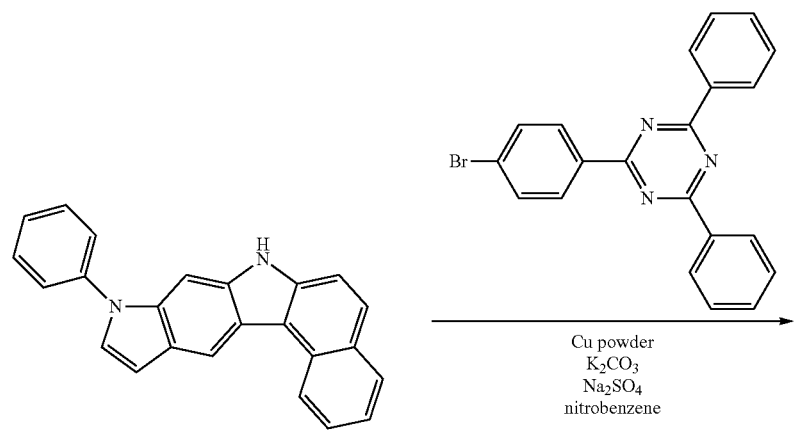

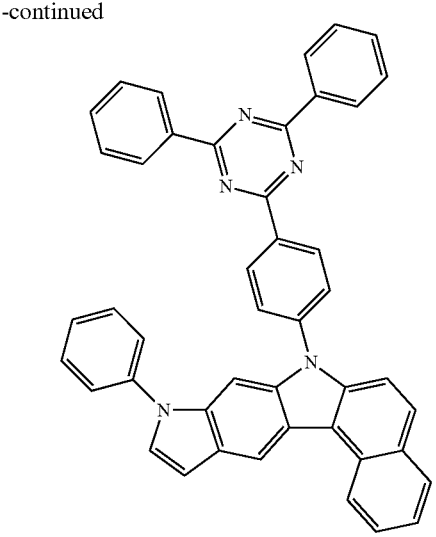

Inv-13

A target compound Inv-13 (6.06 g, yield 63%) was obtained by performing the same procedure as in Synthesis Example 1, except that IC-5a as a compound prepared in Preparation Example 5 was used instead of IC-1a, and 2-(4-bromophenyl)-4,6-diphenyl-1,3,5-triazine was used instead of 2-bromo-4,6-diphenylpyridine.

GC-Mass (theoretical value: 639.24 g/mol, measured value: 639 g/mol)

[Synthesis Example 14] Synthesis of Inv-14

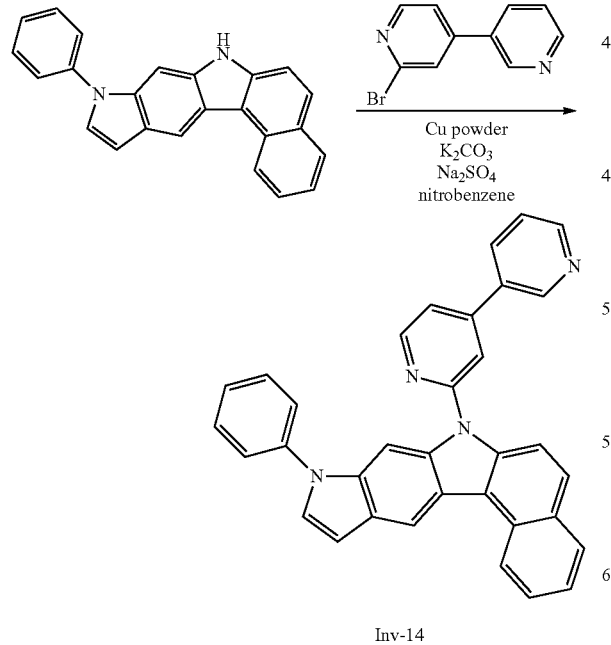

Inv-14

A target compound Inv-14 (5.05 g, yield 69%) was obtained by performing the same procedure as in Synthesis Example 1, except that IC-5a as a compound prepared in Preparation Example 5 was used instead of IC-1a, and 2'-bromo-3,4'-bipyridine was used instead of 2-bromo-4,6-diphenylpyridine.

GC-Mass (theoretical value: 486.18 g/mol, measured value: 486 g/mol)

[Synthesis Example 15] Synthesis of Inv-15

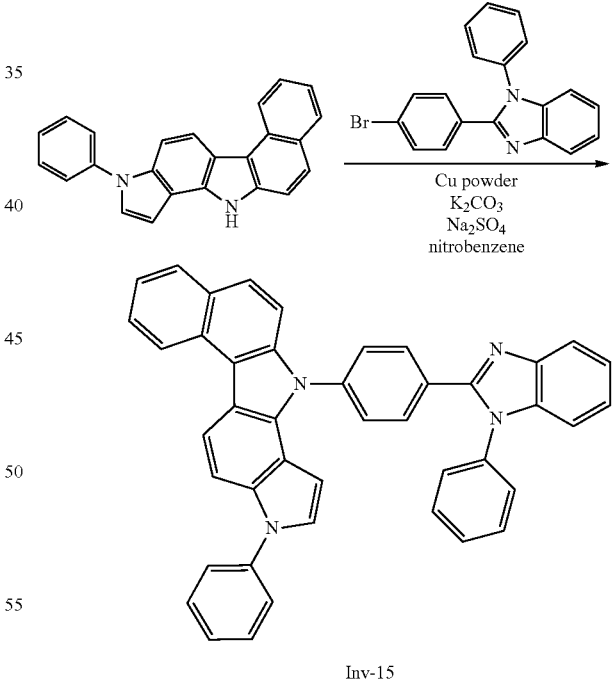

Inv-15

A target compound Inv-15 (4.34 g, yield 48%) was obtained by performing the same procedure as in Synthesis Example 1, except that IC-5b as another compound prepared in Preparation Example 5 was used instead of IC-1a, and 2-(4-bromophenyl)-1-phenyl-1H-benzo[d]imidazole was used instead of 2-bromo-4,6-diphenylpyridine.

GC-Mass (theoretical value: 600.23 g/mol, measured value: 600 g/mol)

[Synthesis Example 16] Synthesis of Inv-16

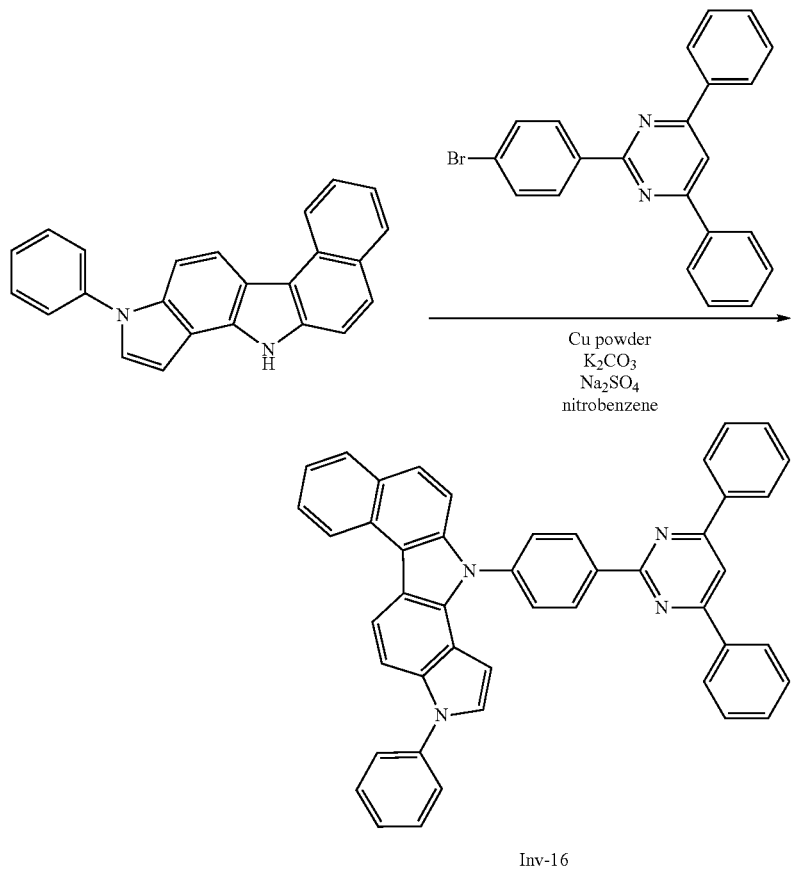

A target compound Inv-16 (4.13 g, yield 43%) was obtained by performing the same procedure as in Synthesis Example 1, except that IC-5b as another compound prepared in Preparation Example 5 was used instead of IC-1a, and 2-(4-bromophenyl)-4,6-diphenylpyrimidine was used instead of 2-bromo-4,6-diphenylpyridine.

GC-Mass (theoretical value: 638.25 g/mol, measured value: 638 g/mol)

[Synthesis Example 17] Synthesis of Inv-17

IC-6a (5 g, 13.84 mmol) as a compound prepared in Preparation Example 6, iodobenzene (4.24 g, 20.76 mmol), Cu powder (0.09 g, 1.38 mmol), $K_2CO_3$ (1.91 g, 13.84 mmol), $Na_2SO_4$ (1.97 g, 13.84 mmol), and nitrobenzene (80 ml) were mixed under nitrogen flow, and the mixture was stirred at 190° C. for 12 hours. After the reaction was completed, nitrobenzene was removed, the organic layer was separated with methylene chloride, and water was removed by using $MgSO_4$. After the solvent was removed from the organic layer, the residue was purified by column chromatography (Hexane:EA=5:1 (v/v)), thereby obtaining an intermediate compound 6-bromo-1,9-diphenyl-1,9-dihydropyrrolo[2,3-b]carbazole (3.45 g, yield 57%).

The intermediate material (3.45 g, 7.89 mmol) obtained, 2,3'-bipyridin-6-ylboronic acid (1.89 g, 9.47 mmol), NaOH (0.95 g, 23.67 mmol), and THF/H₂O (100 ml/50 ml) were mixed under nitrogen flow, then 0.46 g (5 mol %) of Pd(PPh₃)₄ was added to the mixture, and the resulting mixture was stirred at 80° C. for 12 hours. After the reaction was completed, extraction was performed with methylene chloride, MgSO₄ was added thereto, and the mixture was filtered. After the solvent was removed from the organic layer obtained, the residue was purified by column chromatography (Hexane:EA=3:1 (v/v)), thereby obtaining a target compound Inv-17 (3.36 g, yield 83%).

GC-Mass (theoretical value: 512.20 g/mol, measured value: 512 g/mol)

[Synthesis Example 18] Synthesis of Inv-18

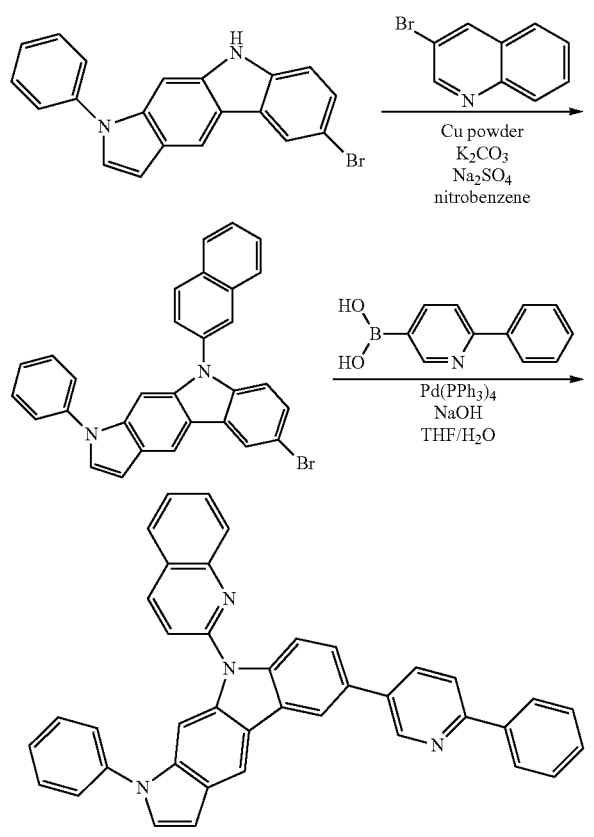

Inv-18

The same procedure as Synthesis Example 17 was performed, but an intermediate compound 6-bromo-1-phenyl-9-(quinolin-2-yl)-1,9-dihydropyrrolo[2,3-b]carbazole was obtained by using 3-bromoquinoline instead of iodobenzene, and a target compound Inv-18 (2.63 g, yield 76%) was obtained by using 6-phenylpyridin-3-ylboronic acid instead of 2,3'-bipyridin-6-ylboronic acid.

GC-Mass (theoretical value: 562.22 g/mol, measured value: 562 g/mol)

[Synthesis Example 19] Synthesis of Inv-19

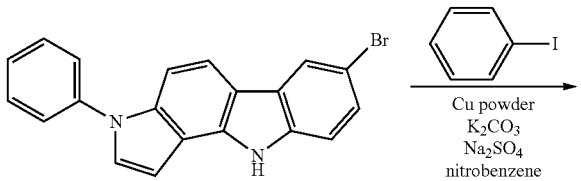

Inv-19

The same procedure as Synthesis Example 17 was performed, but an intermediate compound 7-bromo-3,10-diphenyl-3,10-dihydropyrrolo[3,2-a]carbazole was obtained by using IC-6b as another compound prepared in Preparation Example 6 instead of IC-6a, and a target compound Inv-19 (3.1 g, yield 77%) was obtained by using 4,6-diphenylpyridin-2-ylboronic acid instead of 2,3'-bipyridin-6-ylboronic acid.

GC-Mass (theoretical value: 587.24 g/mol, measured value: 587 g/mol)

[Synthesis Example 20] Synthesis of Inv-20

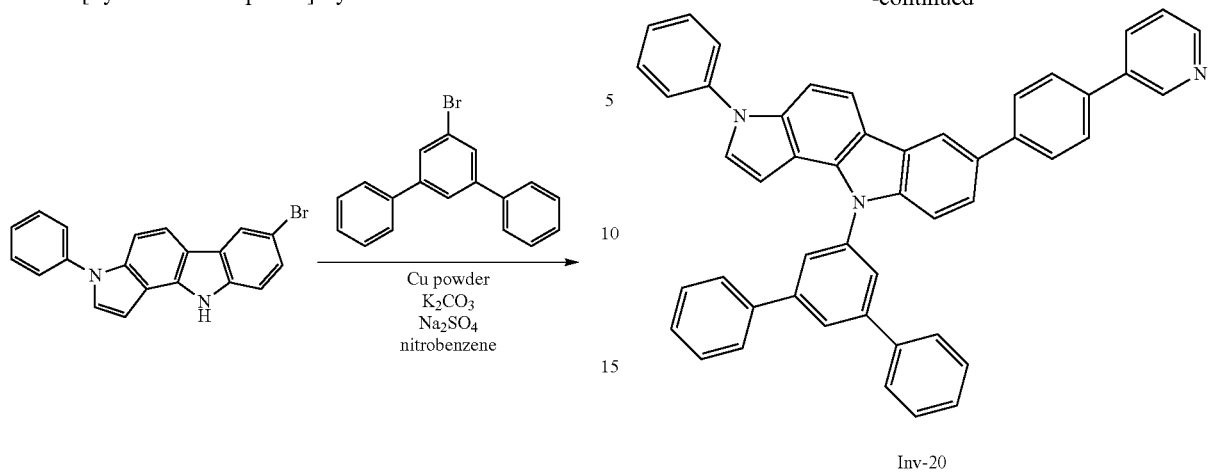

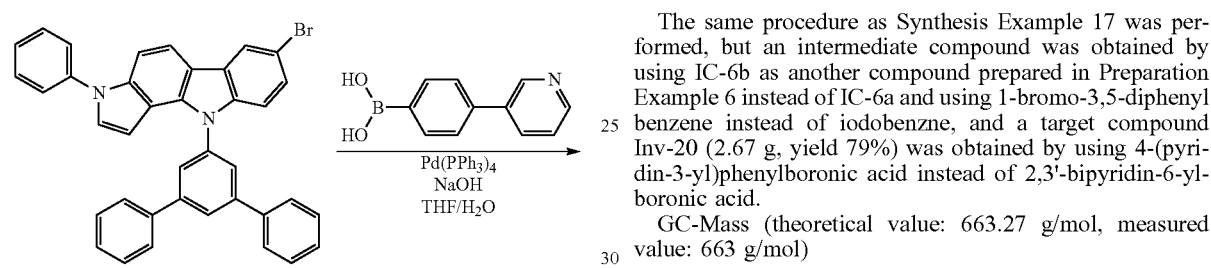

Inv-20

The same procedure as Synthesis Example 17 was performed, but an intermediate compound was obtained by using IC-6b as another compound prepared in Preparation Example 6 instead of IC-6a and using 1-bromo-3,5-diphenyl benzene instead of iodobenzne, and a target compound Inv-20 (2.67 g, yield 79%) was obtained by using 4-(pyridin-3-yl)phenylboronic acid instead of 2,3'-bipyridin-6-yl-boronic acid.

GC-Mass (theoretical value: 663.27 g/mol, measured value: 663 g/mol)

[Synthetic Example 21] Synthesis of Inv-21

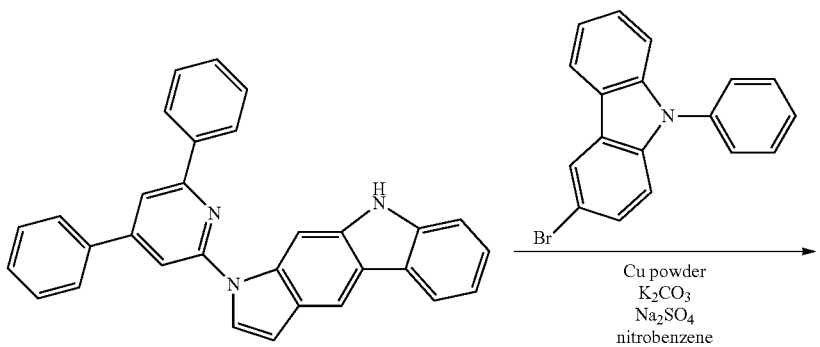

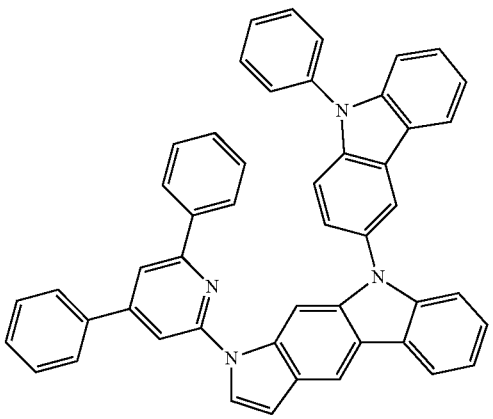

Inv-21

A target compound Inv-21 (2.84 g, yield 61%) was obtained by performing the same procedure as in Synthesis Example 1, except that 1-(4,6-diphenylpyridin-2-yl)-1,9-dihydropyrrolo[2,3-b]carbazole prepared in Preparation Example 8 was used instead of IC-1a, and 3-bromo-9-phenyl-9H-carbazole was used instead of 2-bromo-4,6-diphenylpyridine.

GC-Mass (theoretical value: 676.26 g/mol, measured value: 676 g/mol)

[Synthesis Example 22] Synthesis of Inv-22

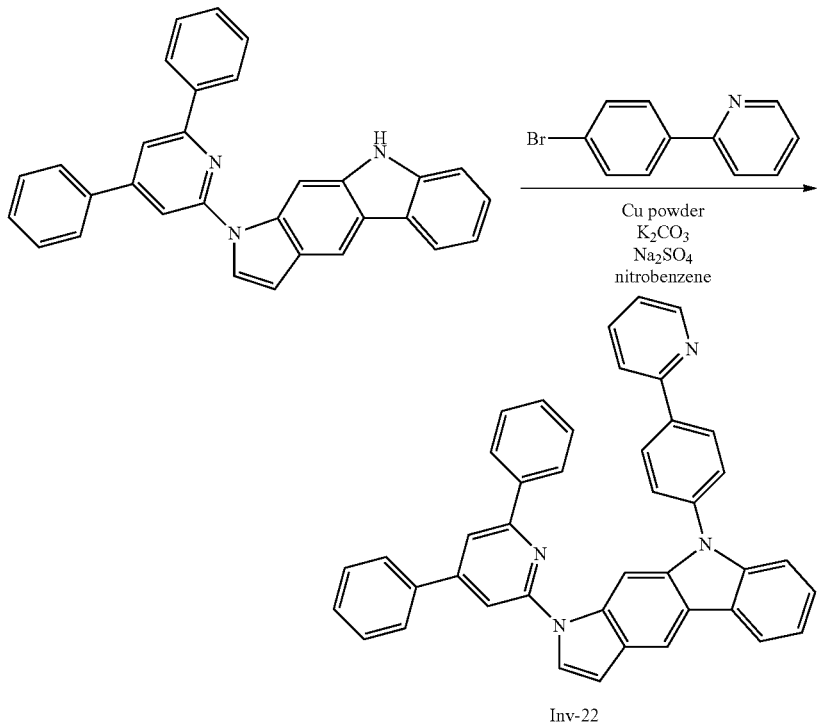

Inv-22

A target compound Inv-22 (2.64 g, yield 65%) was obtained by performing the same procedure as in Synthesis Example 1, except that 1-(4,6-diphenylpyridin-2-yl)-1,9-dihydropyrrolo[2,3-b]carbazole prepared in Preparation Example 8 was used instead of IC-1a, and 2-(4-bromophenyl)pyridine was used instead of 2-bromo-4,6-diphenylpyridine.

GC-Mass (theoretical value: 588.23 g/mol, measured value: 588 g/mol)

[Synthesis Example 23] Synthesis of Inv-23

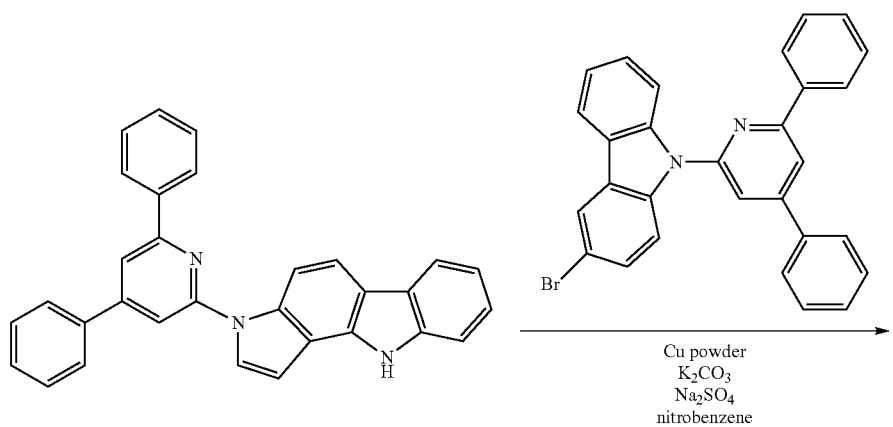

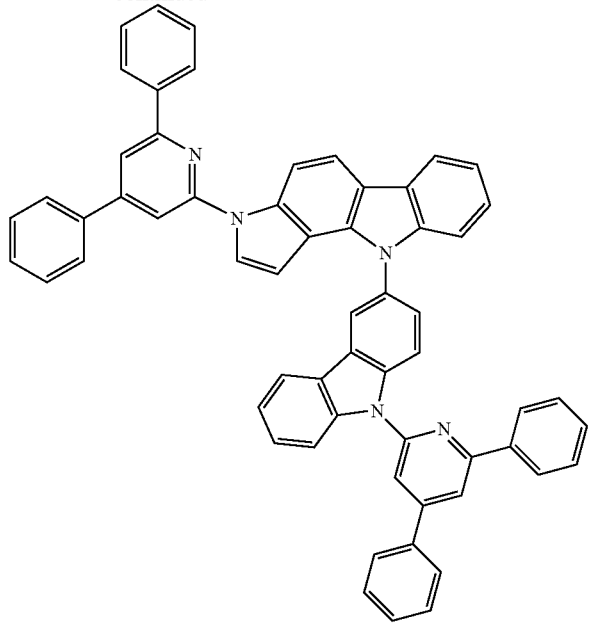

Inv-23

A target compound Inv-23 (2.74 g, yield 48%) was obtained by performing the same procedure as in Synthesis Example 1, except that 3-(4,6-diphenylpyridin-2-yl)-3,10-dihydropyrrolo[3,2-a]carbazole prepared in Preparation Example 7 was used instead of IC-1a, and 3-bromo-9-(4,6-diphenylpyridin-2-yl)-9H-carbazole was used instead of 2-bromo-4,6-diphenylpyridine.

GC-Mass (theoretical value: 829.32 g/mol, measured value: 829 g/mol)

[Synthesis Example 24] Synthesis of Inv-24

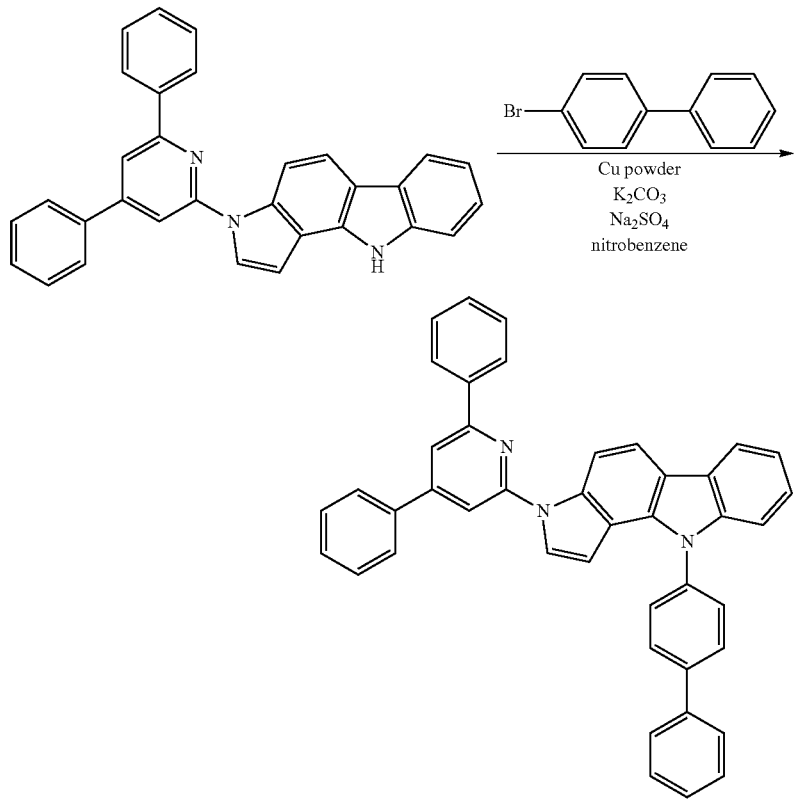

Inv-24

A target compound Inv-24 (2.83 g, yield 70%) was obtained by performing the same procedure as in Synthesis Example 1, except that 3-(4,6-diphenylpyridin-2-yl)-3,10-dihydropyrrolo[3,2-a]carbazole prepared in Preparation Example 7 was used instead of IC-1a, and 4-bromobiphenyl was used instead of 2-bromo-4,6-diphenylpyridine.

GC-Mass (theoretical value: 587.24 g/mol, measured value: 587 g/mol)

[Synthesis Example 25] Synthesis of Inv-25

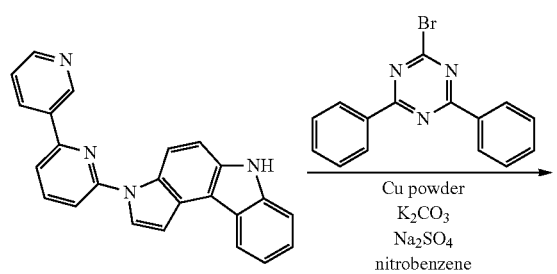

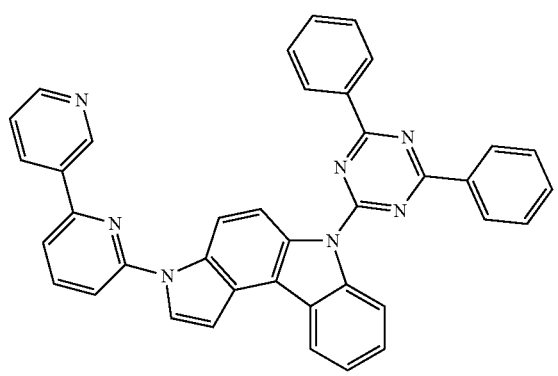

Inv-25

A target compound Inv-25 (2.12 g, yield 43%) was obtained by performing the same procedure as in Synthesis Example 1, except that 3-(2,3'-bipyridin-6-yl)-3,6-dihydropyrrolo[2,3-c]carbazole prepared in Preparation Example 9 was used instead of IC-1a, and 2-bromo-4,6-diphenyl-1,3,5-triazine was used instead of 2-bromo-4,6-diphenylpyridine.

GC-Mass (theoretical value: 591.22 g/mol, measured value: 591 g/mol)

[Synthesis Example 26] Synthesis of Inv-26

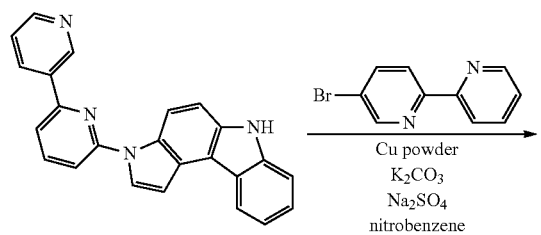

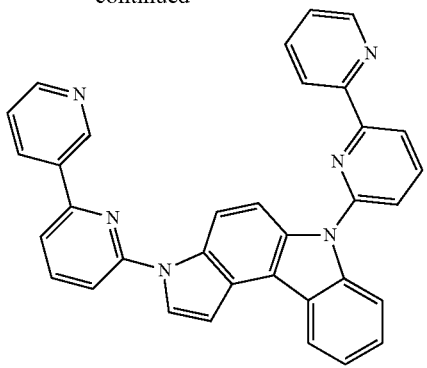

Inv-26

A target compound Inv-26 (2.23 g, yield 52%) was obtained by performing the same procedure as in Synthesis Example 1, except that 3-(2,3'-bipyridin-6-yl)-3,6-dihydropyrrolo[2,3-c]carbazole prepared in Preparation Example 9 was used instead of IC-1a, and 5-bromo-2,2'-bipyridine was used instead of 2-bromo-4,6-diphenylpyridine.

GC-Mass (theoretical value: 514.19 g/mol, measured value: 514 g/mol)

[Synthesis Example 27] Synthesis of Inv-27

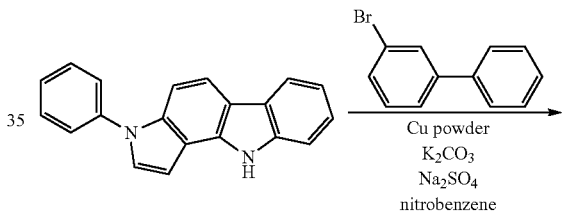

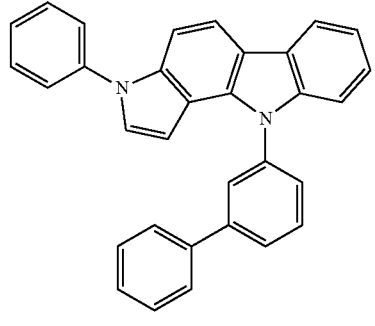

Inv-27

IC-1a (3 g, 10.63 mmol), 3-bromobiphenyl (3.72 g, 15.94 mmol), Cu powder (0.07 g, 1.06 mmol), $K_2CO_3$ (1.47 g, 10.63 mmol), $Na_2SO_4$ (1.51 g, 10.63 mmol), and nitrobenzene (100 ml) were mixed under nitrogen flow, and the mixture was stirred at 200° C. for 24 hours.

After the reaction was completed, nitrobenzene was removed, the organic layer was separated with methylene chloride, and water was removed by using $MgSO_4$. After the solvent was removed from the organic layer in which water was removed, the residue was purified by column chromatography (Hexane:MC=1:1 (v/v)), thereby obtaining a target compound Inv-27 (2.26 g, yield 49%).

GC-Mass (theoretical value: 434.18 g/mol, measured value: 434 g/mol)

[Synthesis Example 28] Synthesis of Inv-28

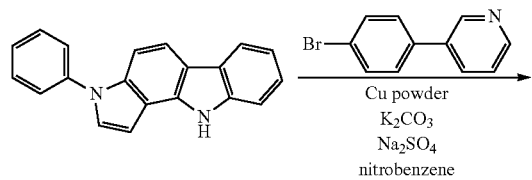

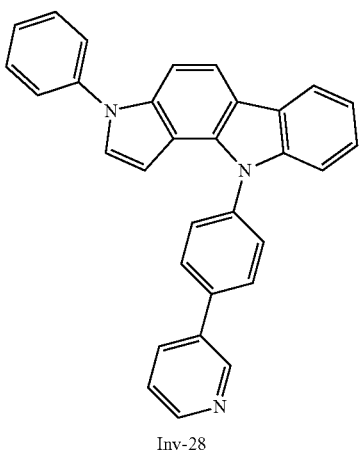

Inv-28

A target compound Inv-28 (2.13 g, 46%) was obtained by performing the same procedure as in Synthesis Example 27, except that 3-(4-bromophenyl)pyridine was used instead of 3-bromobiphenyl.

GC-Mass (theoretical value: 435.17 g/mol, measured value: 435.17 g/mol)

[Synthesis Example 29] Synthesis of Inv-29

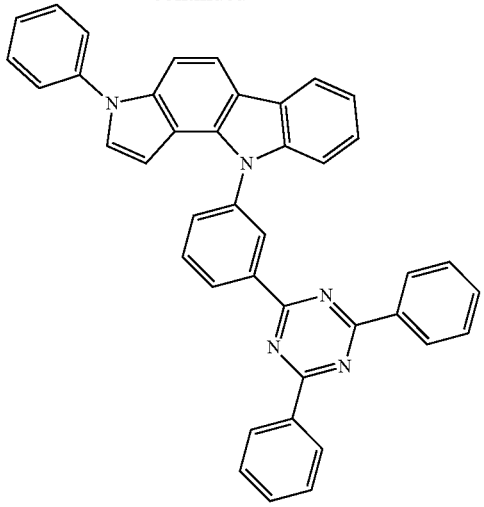

Inv-29

IC-1a (3 g, 10.63 mmol), 2-(3-chlorophenyl)-4,6-diphenyl-1,3,5-triazine (4.38 g, 12.75 mmol), Pd(OAc)$_2$ (0.12 g, 5 mol %), NaO(t-bu) (2.04 g, 21.25 mmol), P(t-bu)$_3$ (0.21 g, 1.06 mmol), and Toluene (100 ml) were mixed under nitrogen flow, and the mixture was stirred at 110° C. for 12 hours.

After the reaction was completed, extraction was performed with ethyl acetate, moisture was removed with MgSO$_4$, and purification was performed by column chromatography (Hexane:EA=2:1 (v/v)), thereby obtaining a target compound Inv-29 (4.89 g, yield 78%).

GC-Mass (theoretical value: 589.23 g/mol, measured value: 589 g/mol)

[Synthesis Example 30] Synthesis of Inv-30

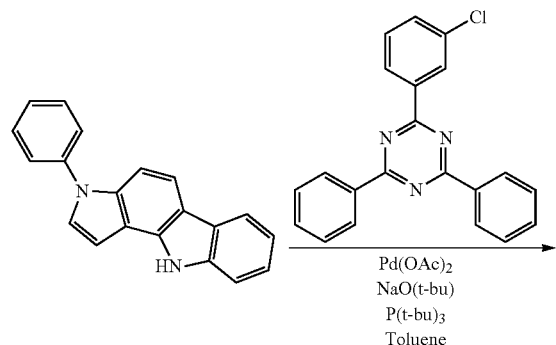

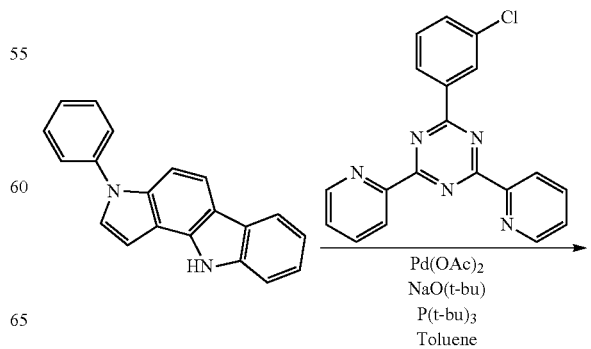

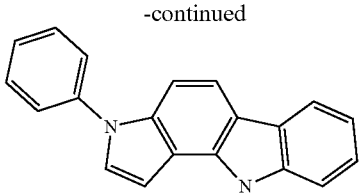

Inv-30

A target compound Inv-30 (4.97 g, 79%) was obtained by performing the same procedure as in Synthesis Example 29, except that 2-(3-chlorophenyl)-4,6-di(pyridin-2-yl)-1,3,5-triazine was used instead of 2-(3-chlorophenyl)-4,6-diphenyl-1,3,5-triazine.

GC-Mass (theoretical value: 591.22 g/mol, measured value: 591 g/mol)

[Synthesis Example 31] Synthesis of Inv-31

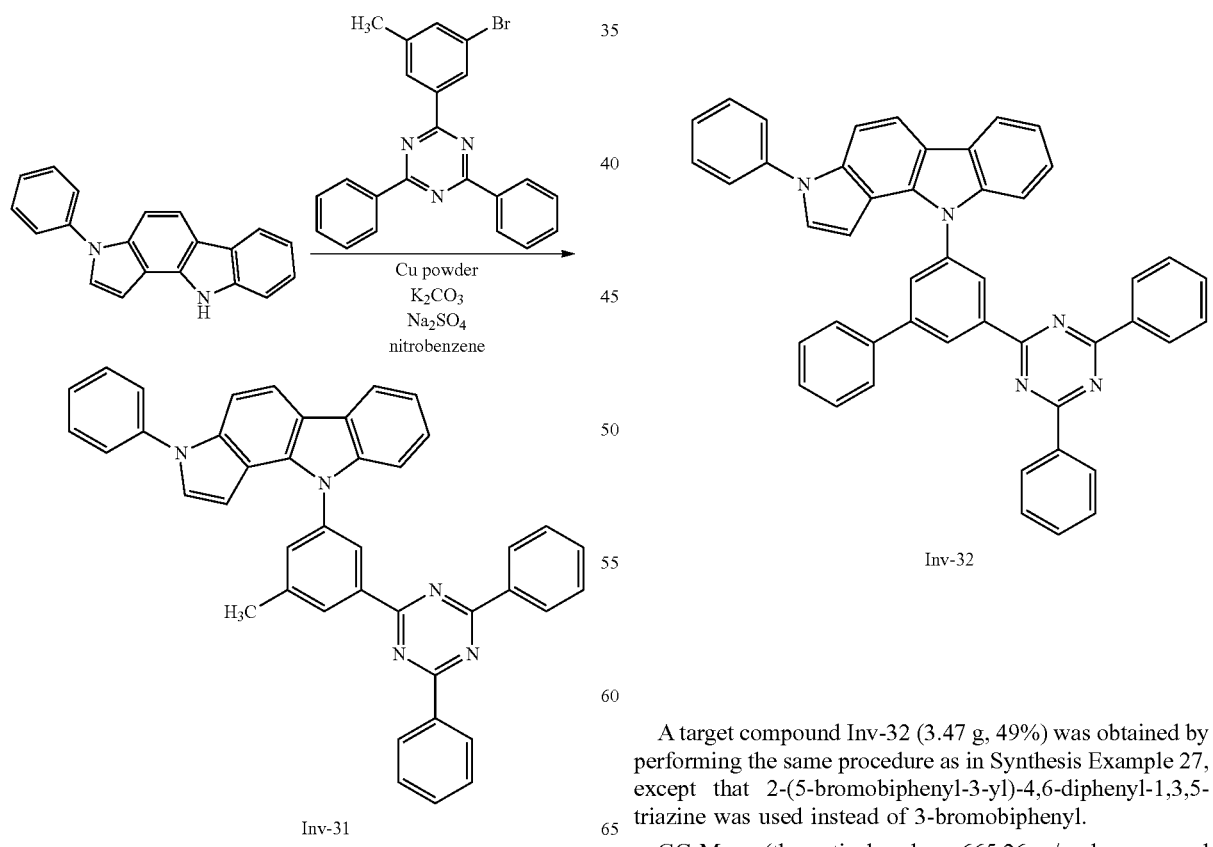

Inv-31

A target compound Inv-31 (3.21 g, 50%) was obtained by performing the same procedure as in Synthesis Example 27, except that 2-(3-bromo-5-methylphenyl)-4,6-diphenyl-1,3,5-triazine was used instead of 3-bromobiphenyl.

GC-Mass (theoretical value: 603.24 g/mol, measured value: 603 g/mol)

[Synthesis Example 32] Synthesis of Inv-32

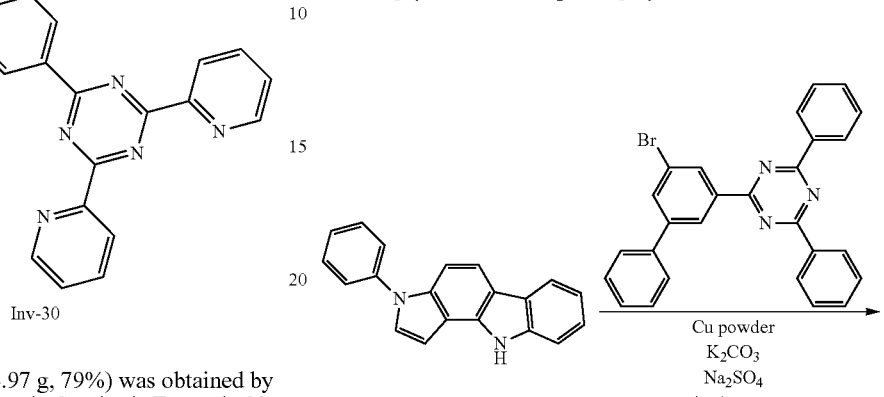

Inv-32

A target compound Inv-32 (3.47 g, 49%) was obtained by performing the same procedure as in Synthesis Example 27, except that 2-(5-bromobiphenyl-3-yl)-4,6-diphenyl-1,3,5-triazine was used instead of 3-bromobiphenyl.

GC-Mass (theoretical value: 665.26 g/mol, measured value: 665 g/mol)

[Synthesis Example 33] Synthesis of Inv-33

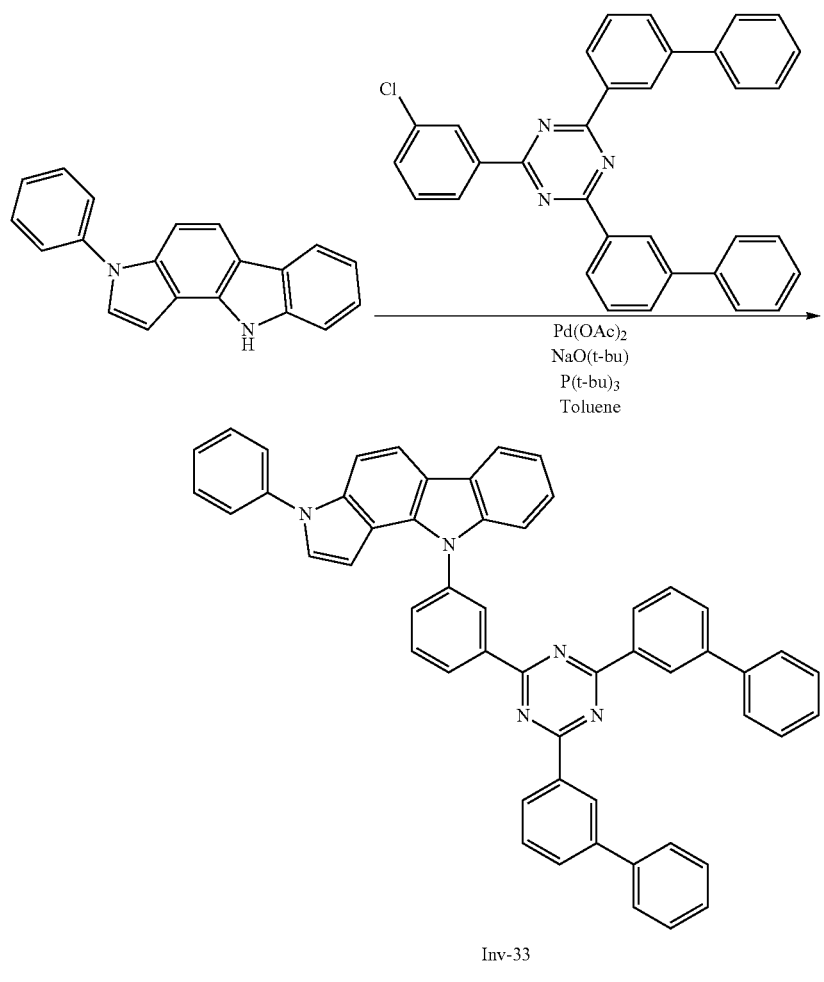

Inv-33

A target compound Inv-33 (5.38 g, 76%) was obtained by performing the same procedure as in Synthesis Example 29, except that 2,4-di(biphenyl-3-yl)-6-(3-chlorophenyl)-1,3,5-triazine was used instead of 2-(3-chlorophenyl)-4,6-diphenyl-1,3,5-triazine.

GC-Mass (theoretical value: 665.26 g/mol, measured value: 665 g/mol)

[Synthesis Example 34] Synthesis of Inv-34

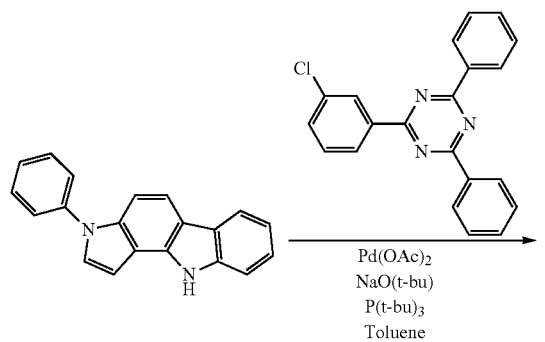

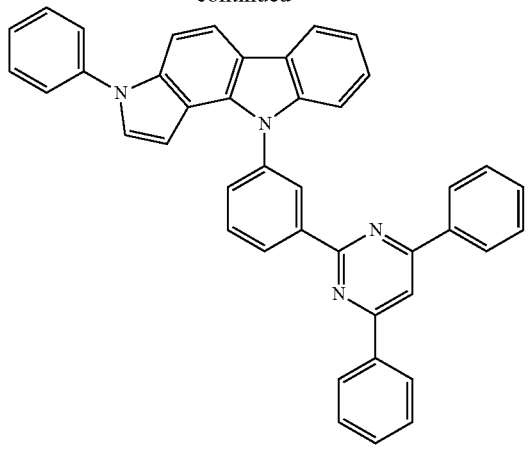

Inv-34

A target compound Inv-34 (4.63 g, 74%) was obtained by performing the same procedure as in Synthesis Example 29, except that 2-(3-chlorophenyl)-4,6-diphenylpyrimidine was used instead of 2-(3-chlorophenyl)-4,6-diphenyl-1,3,5-triazine.

GC-Mass (theoretical value: 588.23 g/mol, measured value: 588 g/mol)

[Synthesis Example 35] Synthesis of Inv-35

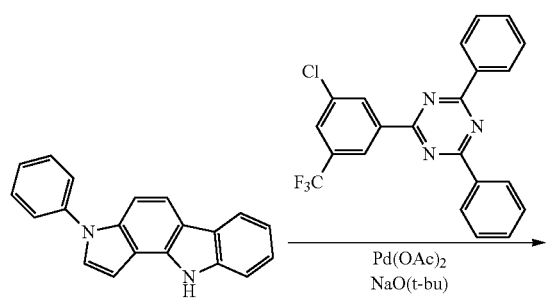

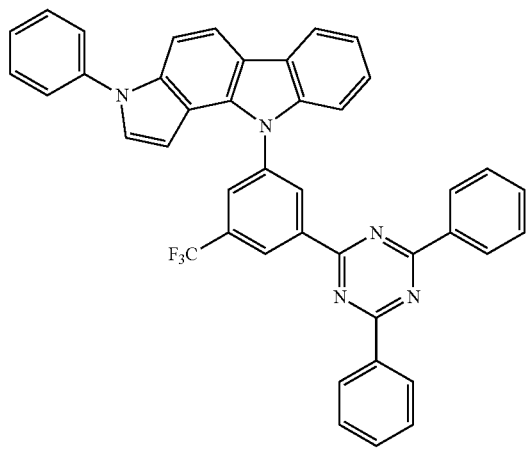

Inv-35

A target compound Inv-35 (4.89 g, 70%) was obtained by performing the same procedure as in Synthesis Example 29, except that 2-(3-chloro-5-(trifluoromethyl)phenyl)-4,6-diphenyl-1,3,5-triazine was used instead of 2-(3-chlorophenyl)-4,6-diphenyl-1,3,5-triazine.

GC-Mass (theoretical value: 657.21 g/mol, measured value: 657 g/mol)

[Synthesis Example 36] Synthesis of Inv-36

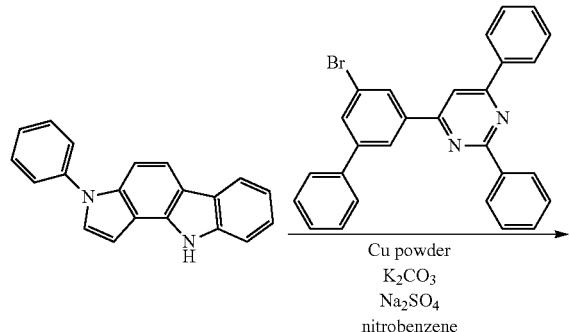

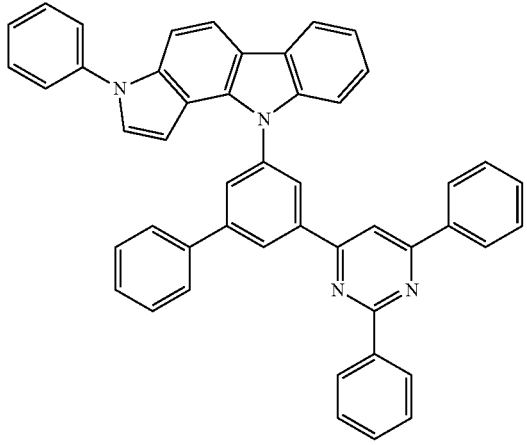

Inv-36

A target compound Inv-36 (3.53 g, 50%) was obtained by performing the same procedure as in Synthesis Example 27, except that 4-(5-bromobiphenyl-3-yl)-2,6-diphenylpyrimidine was used instead of 3-bromobiphenyl.

GC-Mass (theoretical value: 664.26 g/mol, measured value: 664 g/mol)

[Synthesis Example 37] Synthesis of Inv-37

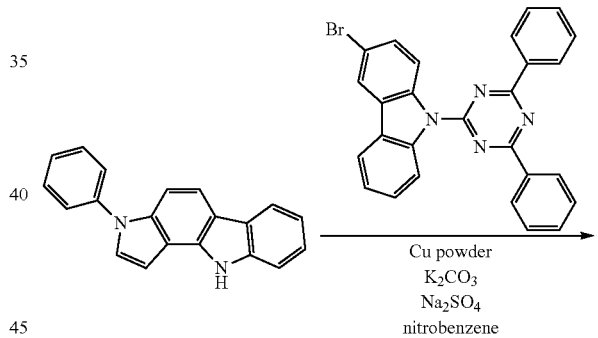

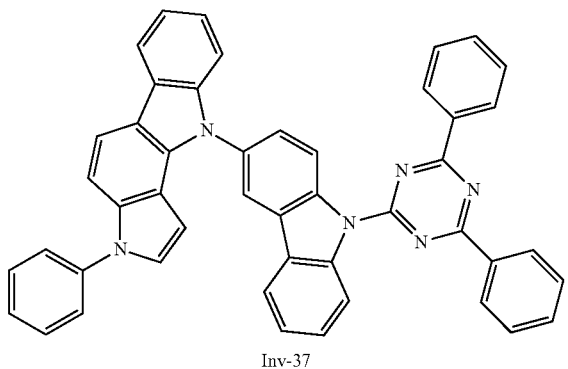

Inv-37

A target compound Inv-37 (3.39 g, 47%) was obtained by performing the same procedure as in Synthesis Example 27, except that 3-bromo-9-(4,6-diphenyl-1,3,5-triazin-2-yl)-9H-carbazole was used instead of 3-bromobiphenyl.

GC-Mass (theoretical value: 678.25 g/mol, measured value: 678 g/mol)

[Synthesis Example 38] Synthesis of Inv-38

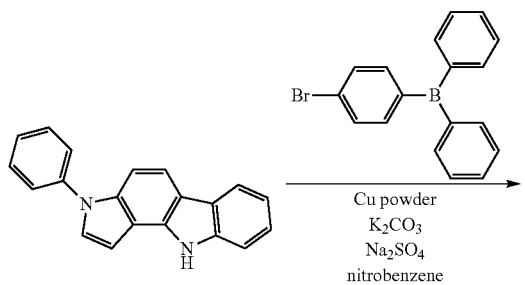

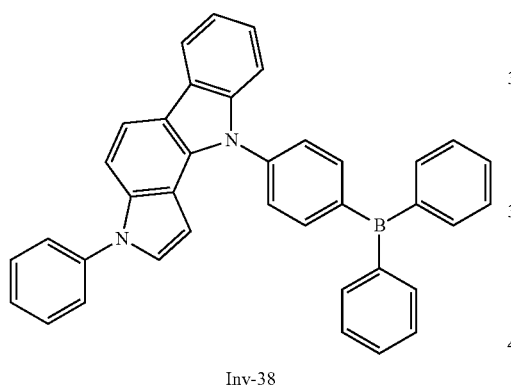

Inv-38

A target compound Inv-38 (2.44 g, 44%) was obtained by performing the same procedure as in Synthesis Example 27, except that (4-bromophenyl)diphenylborane was used instead of 3-bromobiphenyl.

GC-Mass (theoretical value: 522.23 g/mol, measured value: 522 g/mol)

[Synthesis Example 39] Synthesis of Inv-39

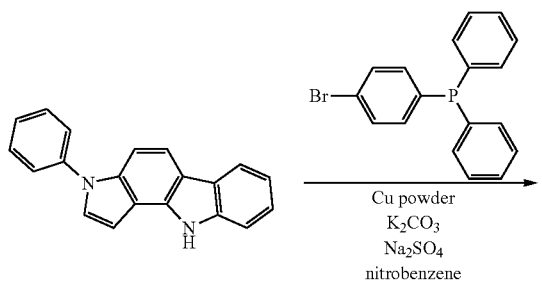

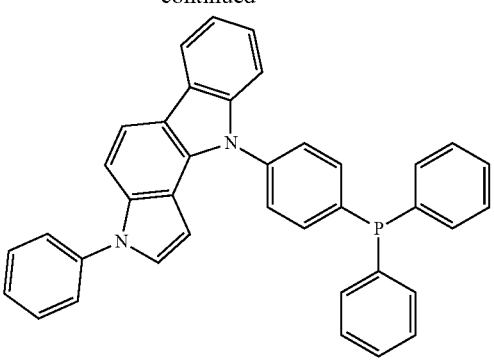

Inv-39

A target compound Inv-39 (2.59 g, 45%) was obtained by performing the same procedure as in Synthesis Example 27, except that (4-bromophenyl)diphenylphosphine was used instead of 3-bromobiphenyl.

GC-Mass (theoretical value: 542.19 g/mol, measured value: 542 g/mol)

[Synthesis Example 40] Synthesis of Inv-40

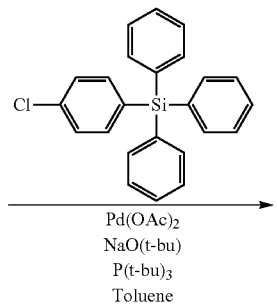

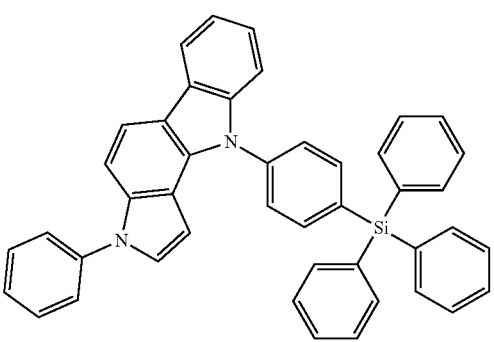

Inv-40

A target compound Inv-40 (4.92 g, 75%) was obtained by performing the same procedure as in Synthesis Example 29, except that 4-chlorophenyl)triphenylsilane was used instead of 2-(3-chlorophenyl)-4,6-diphenyl-1,3,5-triazine.

GC-Mass (theoretical value: 616.23 g/mol, measured value: 616 g/mol)

[Synthesis Example 41] Synthesis of Inv-41

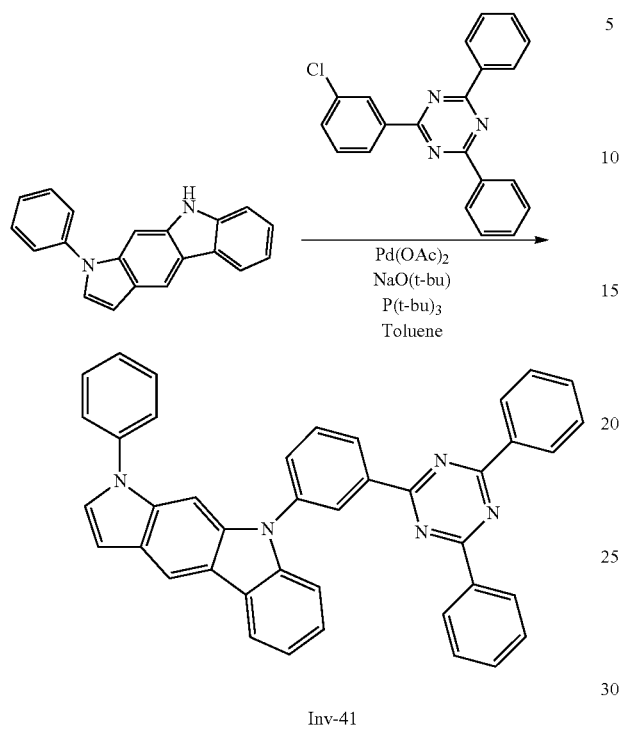

A target compound Inv-41 (4.51 g, 72%) was obtained by performing the same procedure as in Synthesis Example 29, except that IC-1a was used instead of IC-1b.

GC-Mass (theoretical value: 589.23 g/mol, measured value: 589 g/mol)

[Synthesis Example 42] Synthesis of Inv-42

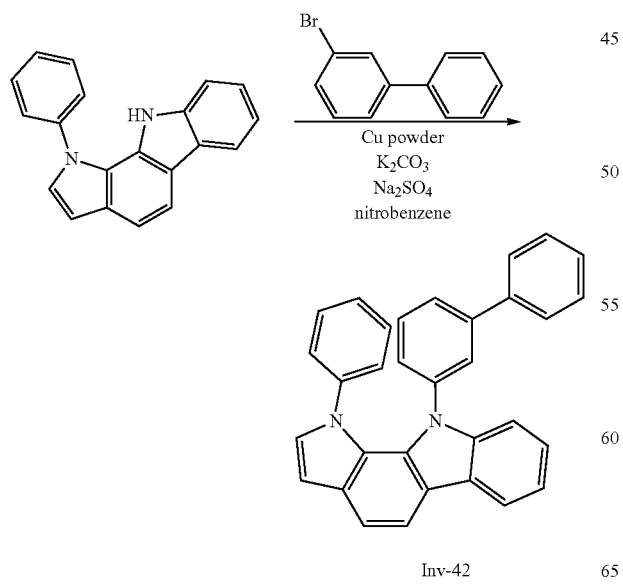

A target compound Inv-42 (2.35 g, 51%) was obtained by performing the same procedure as in Synthesis Example 27, except that IC-10a was used instead of IC-1b.

GC-Mass (theoretical value: 434.18 g/mol, measured value: 434 g/mol)

[Synthesis Example 43] Synthesis of Inv-43

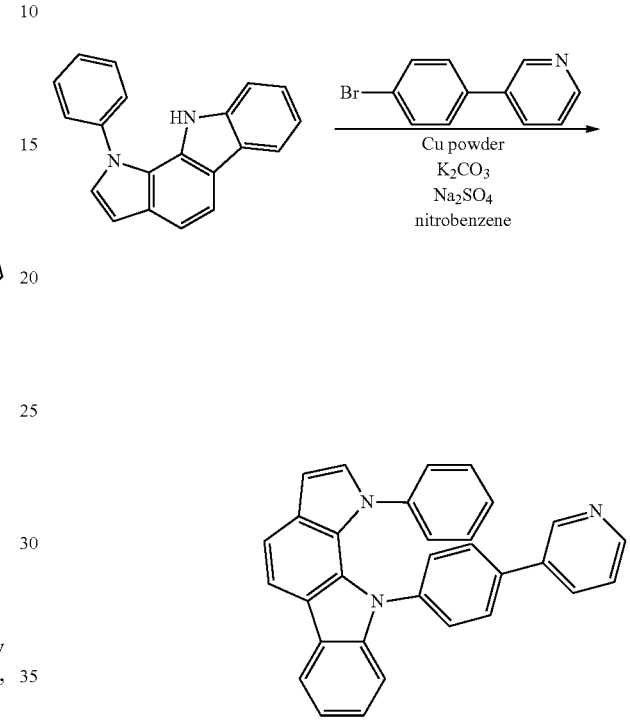

A target compound Inv-43 (2.45, 53%) was obtained by performing the same procedure as in Synthesis Example 27, except that IC-10a and 3-(4-bromophenyl)pyridine were used instead of IC-1b and 3-bromobiphenyl.

GC-Mass (theoretical value: 435.17 g/mol, measured value: 435 g/mol)

[Synthesis Example 44] Synthesis of Inv-44

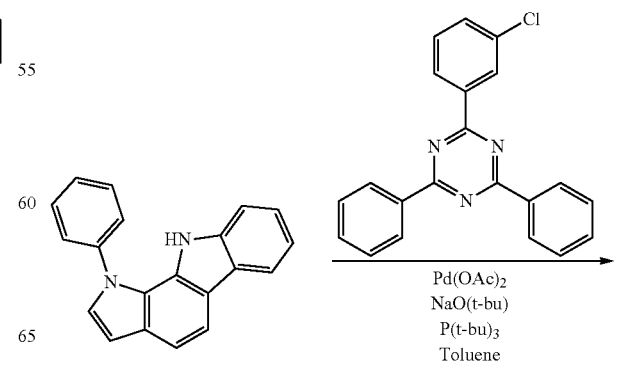

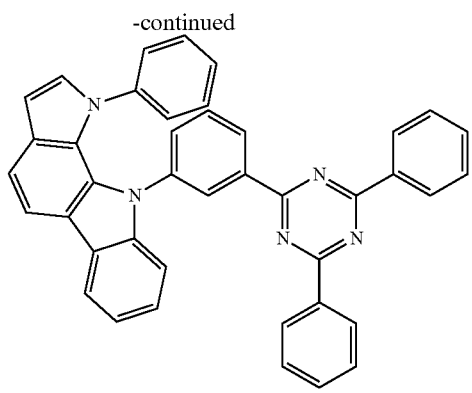

Inv-44

A target compound Inv-44 (4.32 g, 69%) was obtained by performing the same procedure as in Synthesis Example 29, except that IC-10a was used instead of IC-1b.

GC-Mass (theoretical value: 589.23 g/mol, measured value: 589 g/mol)

[Synthesis Example 45] Synthesis of Inv-45

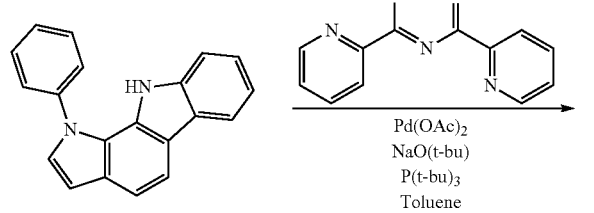

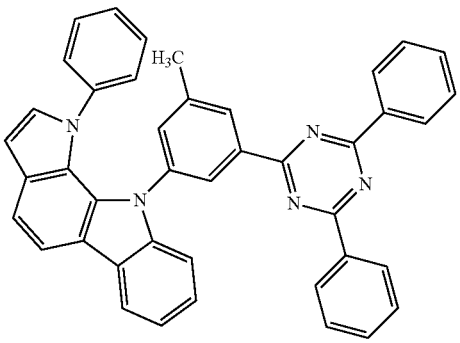

Inv-45

A target compound Inv-45 (4.53 g, 72%) was obtained by performing the same procedure as in Synthesis Example 29, except that IC-10a and 2-(3-chlorophenyl)-4,6-di(pyridin-2-yl)-1,3,5-triazine were used instead of IC-1b and 2-(3-chlorophenyl)-4,6-diphenyl-1,3,5-triazine.

GC-Mass (theoretical value: 591.22 g/mol, measured value: 591 g/mol)

[Synthesis Example 46] Synthesis of Inv-46

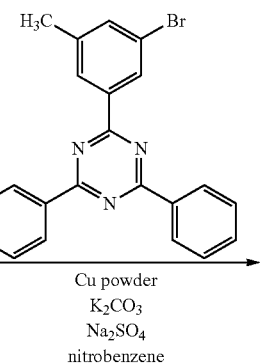

Inv-46

A target compound Inv-46 (2.95 g, 46%) was obtained by performing the same procedure as in Synthesis Example 27, except that IC-10a and 2-(3-bromo-5-methylphenyl)-4,6-diphenyl-1,3,5-triazine were used instead of IC-1b and 3-bromobiphenyl.

GC-Mass (theoretical value: 603.24 g/mol, measured value: 603 g/mol)

[Synthesis Example 47] Synthesis of Inv-47

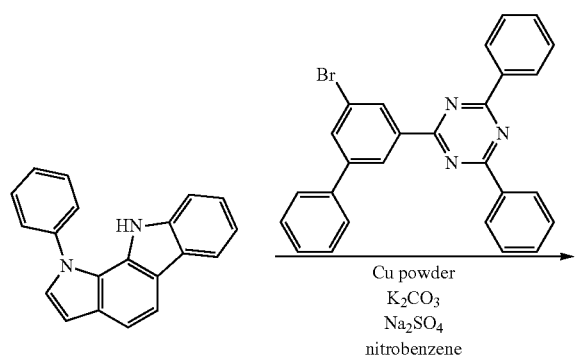

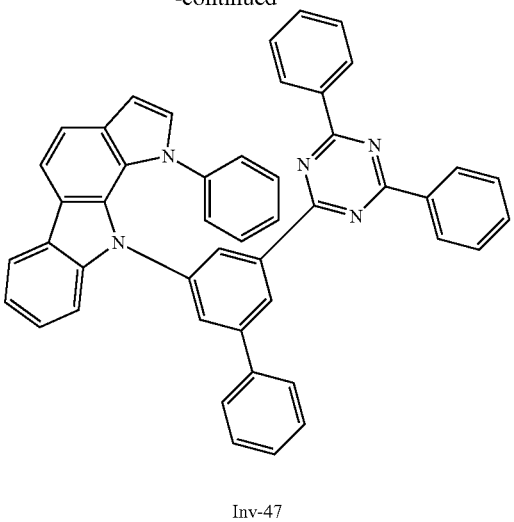

Inv-47

A target compound Inv-47 (3.18, 45%) was obtained by performing the same procedure as in Synthesis Example 27, except that IC-10a and 2-(5-bromobiphenyl-3-yl)-4,6-diphenyl-1,3,5-triazine were used instead of IC-1b and 3-bromobiphenyl.

GC-Mass (theoretical value: 665.26 g/mol, measured value: 665 g/mol)

[Synthesis Example 48] Synthesis of Inv-48

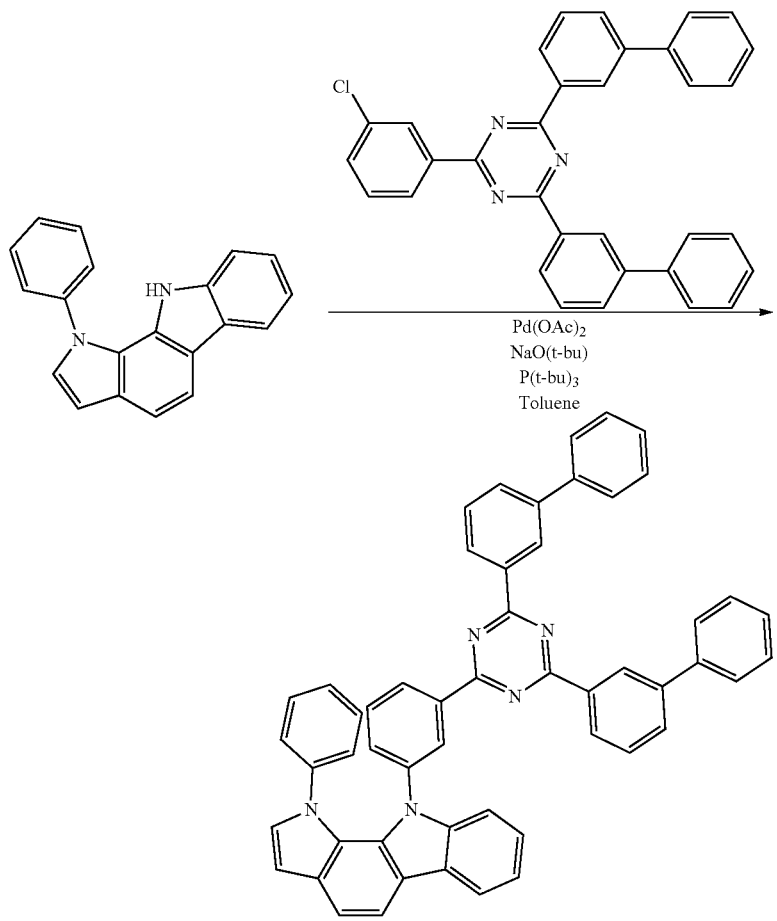

Inv-48

A target compound Inv-48 (6.07 g, 72%) was obtained by performing the same procedure as in Synthesis Example 29, except that IC-10a and 2,4-di(biphenyl-3-yl)-6-(3-chlorophenyl)-1,3,5-triazine were used instead of IC-1b and 2-(3-chlorophenyl)-4,6-diphenyl-1,3,5-triazine.

GC-Mass (theoretical value: 741.29 g/mol, measured value: 741 g/mol)

[Synthesis Example 49] Synthesis of Inv-49

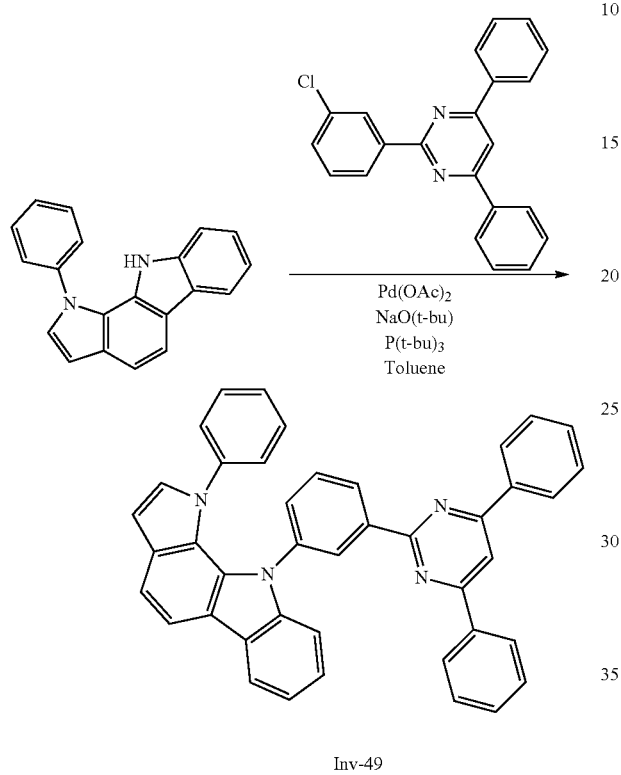

Inv-49

A target compound Inv-49 (4.69 g, 75%) was obtained by performing the same procedure as in Synthesis Example 29, except that IC-10a and 2-(3-chlorophenyl)-4,6-diphenylpyrimidine were used instead of IC-1b and 2-(3-chlorophenyl)-4,6-diphenyl-1,3,5-triazine.

GC-Mass (theoretical value: 588.23 g/mol, measured value: 588 g/mol)

[Synthesis Example 50] Synthesis of Inv-50

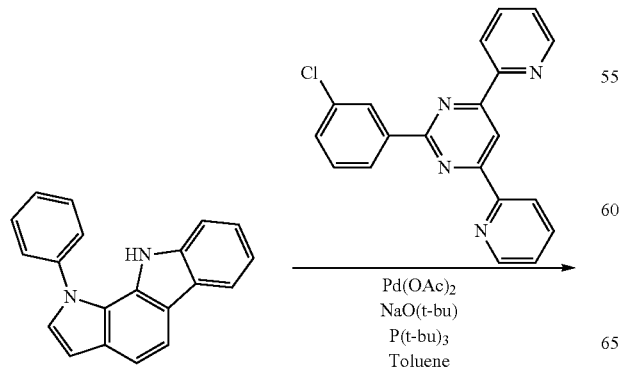

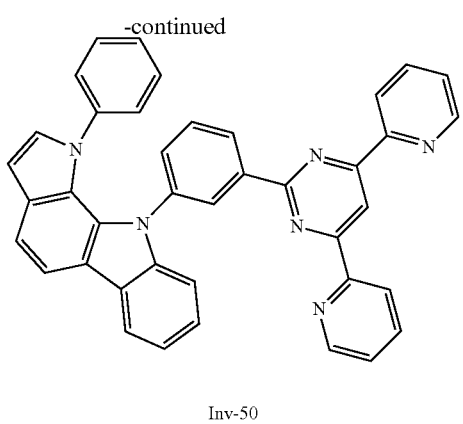

Inv-50

A target compound Inv-50 (4.46 g, 71%) was obtained by performing the same procedure as in Synthesis Example 29, except that IC-10a and 2-(3-chlorophenyl)-4,6-di(pyridin-2-yl)pyrimidine were used instead of IC-1b and 2-(3-chlorophenyl)-4,6-diphenyl-1,3,5-triazine.

GC-Mass (theoretical value: 590.22 g/mol, measured value: 590 g/mol)

[Synthesis Example 51] Synthesis of Inv-51

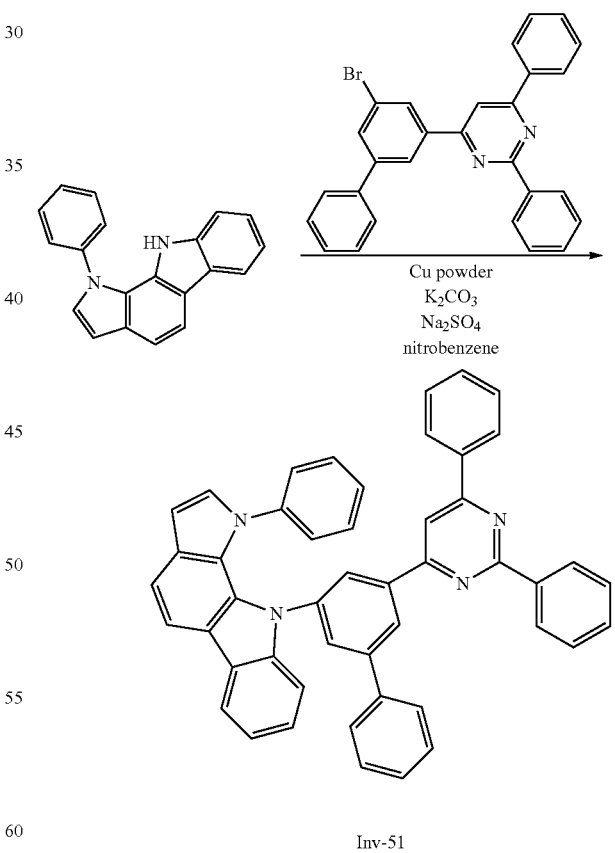

Inv-51

A target compound Inv-51 (3.04 g, 43%) was obtained by performing the same procedure as in Synthesis Example 27, except that IC-10a and 4-(5-bromobiphenyl-3-yl)-2,6-diphenylpyrimidine were used instead of IC-1b and 3-bromobiphenyl.

GC-Mass (theoretical value: 664.26 g/mol, measured value: 664 g/mol)

[Synthesis Example 52] Synthesis of Inv-52

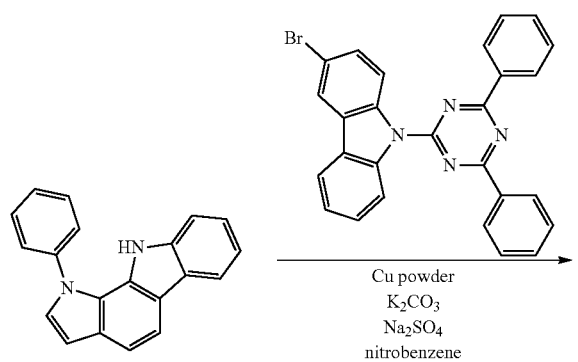

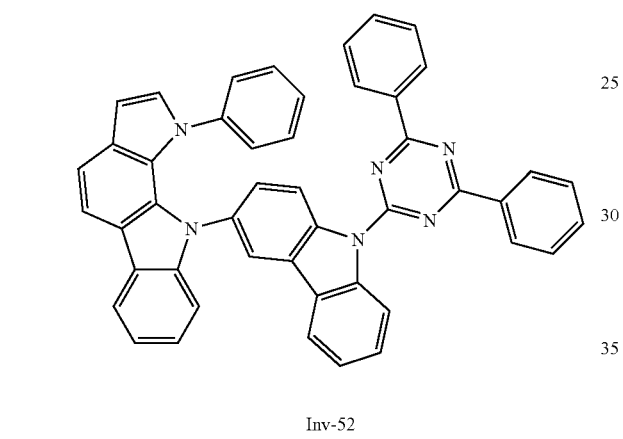

Inv-52

A target compound Inv-52 (2.96 g, 41%) was obtained by performing the same procedure as in Synthesis Example 27, except that IC-10a and 3 3-bromo-9-(4,6-diphenyl-1,3,5-triazin-2-yl)-9H-carbazole were used instead of IC-1b and 3-bromobiphenyl.

GC-Mass (theoretical value: 678.25 g/mol, measured value: 678 g/mol)

[Synthesis Example 53] Synthesis of Inv-53

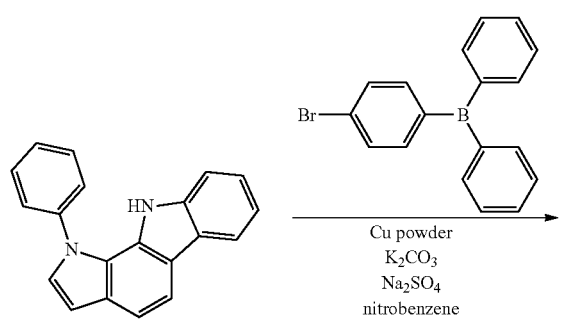

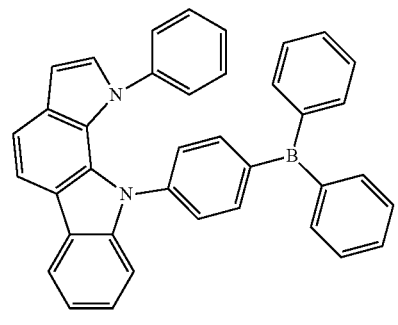

Inv-53

A target compound Inv-53 (2.66 g, 48%) was obtained by performing the same procedure as in Synthesis Example 27, except that IC-10a and (4-bromophenyl)diphenylborane were used instead of IC-1b and 3-bromobiphenyl.

GC-Mass (theoretical value: 522.23 g/mol, measured value: 522 g/mol)

[Synthesis Example 54] Synthesis of Inv-54

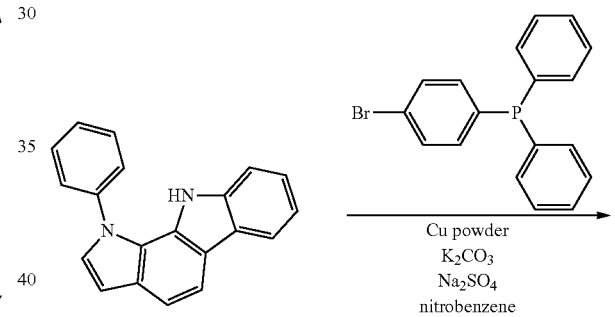

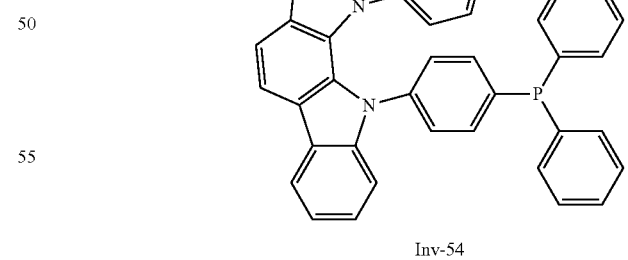

Inv-54

A target compound Inv-54 (2.54 g, 44%) was obtained by performing the same procedure as in Synthesis Example 27, except that IC-10a and (4-bromophenyl)diphenylphosphine were used instead of IC-1b and 3-bromobiphenyl.

GC-Mass (theoretical value: 542.19 g/mol, measured value: 542 g/mol)

[Synthesis Example 55] Synthesis of Inv-55

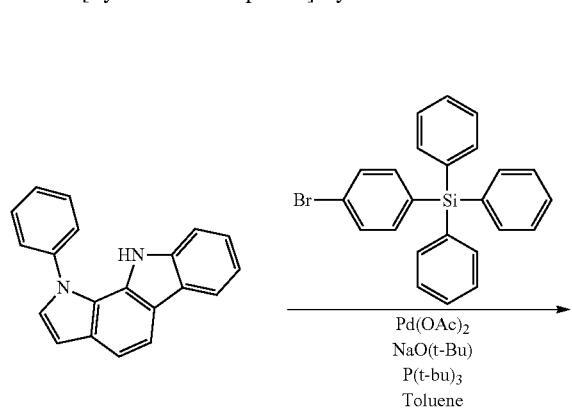

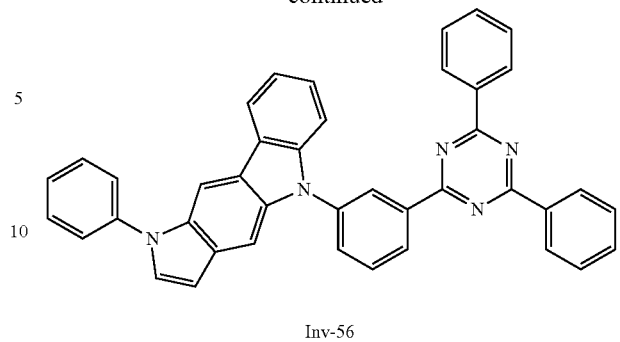

Inv-55

A target compound Inv-55 (4.65 g, 71%) was obtained by performing the same procedure as in Synthesis Example 29, except that IC-10a and (4-chlorophenyl)triphenylsilane were used instead of IC-1b and 2-(3-chlorophenyl)-4,6-diphenyl-1,3,5-triazine.

GC-Mass (theoretical value: 616.23 g/mol, measured value: 616 g/mol)

[Synthesis Example 56] Synthesis of Inv-56

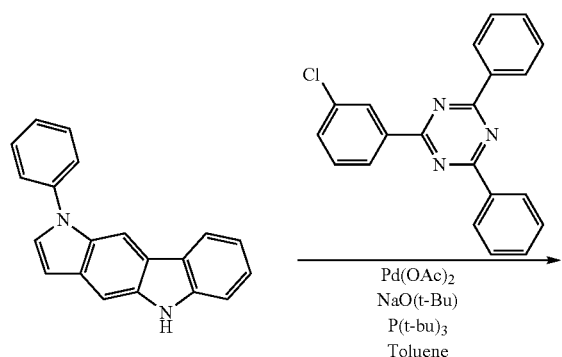

Inv-56

A target compound Inv-56 (4.70 g, 75%) was obtained by performing the same procedure as in Synthesis Example 29, except that IC-10b was used instead of IC-1b. GC-Mass (theoretical value: 589.23 g/mol, measured value: 589 g/mol)

[Synthesis Example 57] Synthesis of Inv-57

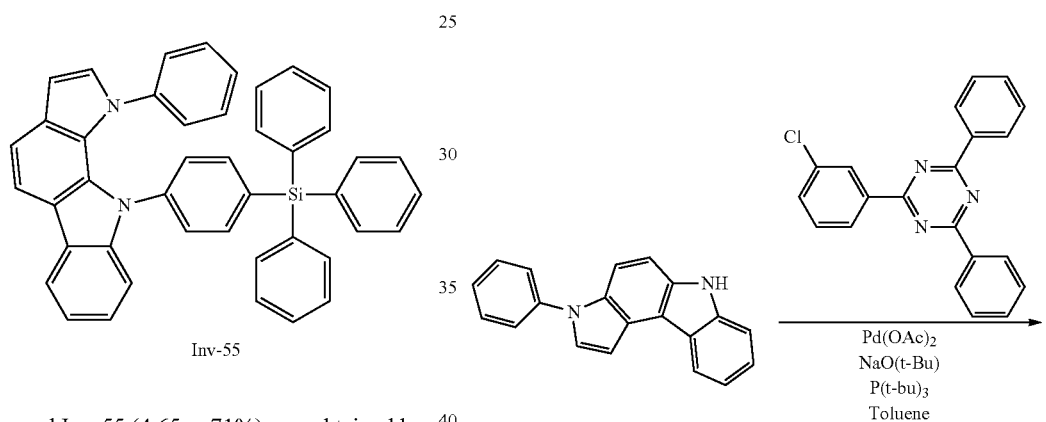

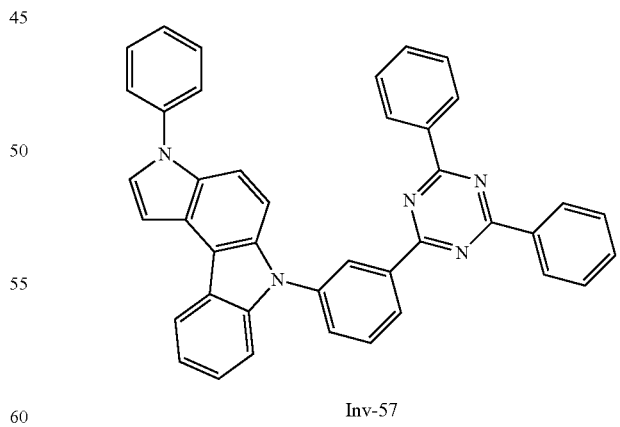

Inv-57

A target compound Inv-57 (4.57 g, 73%) was obtained by performing the same procedure as in Synthesis Example 29, except that IC-2 was used instead of IC-1b.

GC-Mass (theoretical value: 589.23 g/mol, measured value: 589 g/mol)

[Synthesis Example 58] Synthesis of Inv-58

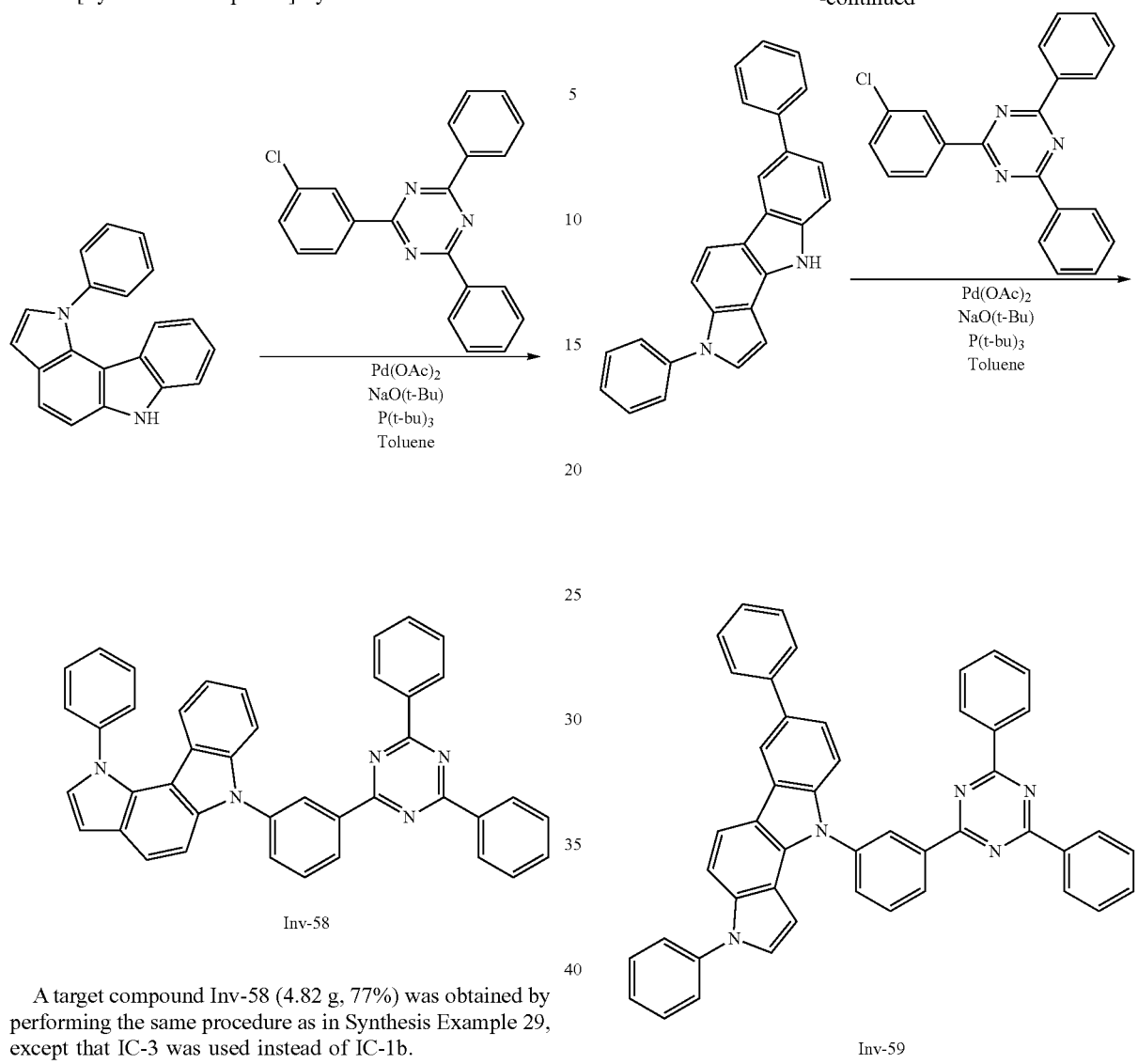

A target compound Inv-58 (4.82 g, 77%) was obtained by performing the same procedure as in Synthesis Example 29, except that IC-3 was used instead of IC-1b.

GC-Mass (theoretical value: 589.23 g/mol, measured value: 589 g/mol)

[Synthesis Example 59] Synthesis of Inv-59

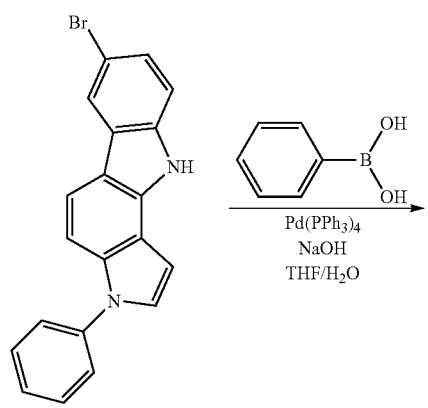

IC-6b (5 g, 13.84 mmol), phenylboronic acid (2.03 g, 16.61 mmol), NaOH (1.66 g, 41.52 mmol), and THF/H$_2$O (100 ml/500 ml) were mixed under nitrogen flow, and the mixture was stirred at 80° C. for 12 hours.

After the reaction was completed, extraction was performed with methylene chloride, MgSO$_4$ was added thereto, and the mixture was filtered. After the solvent was removed from the organic layer obtained, purification was performed by column chromatography (Hexane:EA=3:1 (v/v)) to obtain 3,7-diphenyl-3,10-dihydropyrrolo[3,2-a]carbazole, and a target compound Inv-59 (6.27 g, 68%) was obtained by performing the same procedure as in Synthesis Example 29 using the obtained compound instead of IC-1b.

GC-Mass (theoretical value: 665.26 g/mol, measured value: 665 g/mol)

505
[Synthesis Example 60] Synthesis of Inv-60
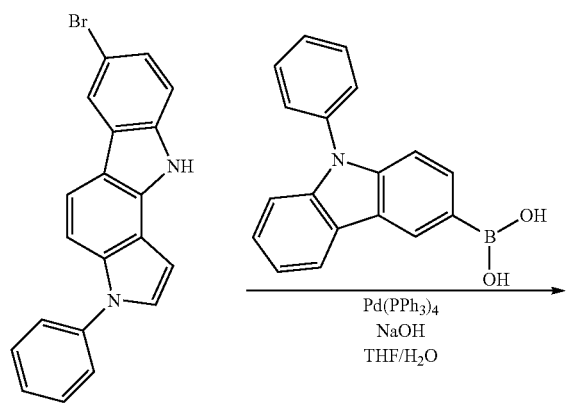
506
A target compound Inv-60 (7.94 g, 69%) was obtained by performing the same procedure as in Synthesis Example 59, except that 9-phenyl-9H-carbazol-3-ylboronic acid was used instead of phenylboronic acid.
GC-Mass (theoretical value: 830.32 g/mol, measured value: 830 g/mol)
[Synthesis Example 61] Synthesis of Inv-61
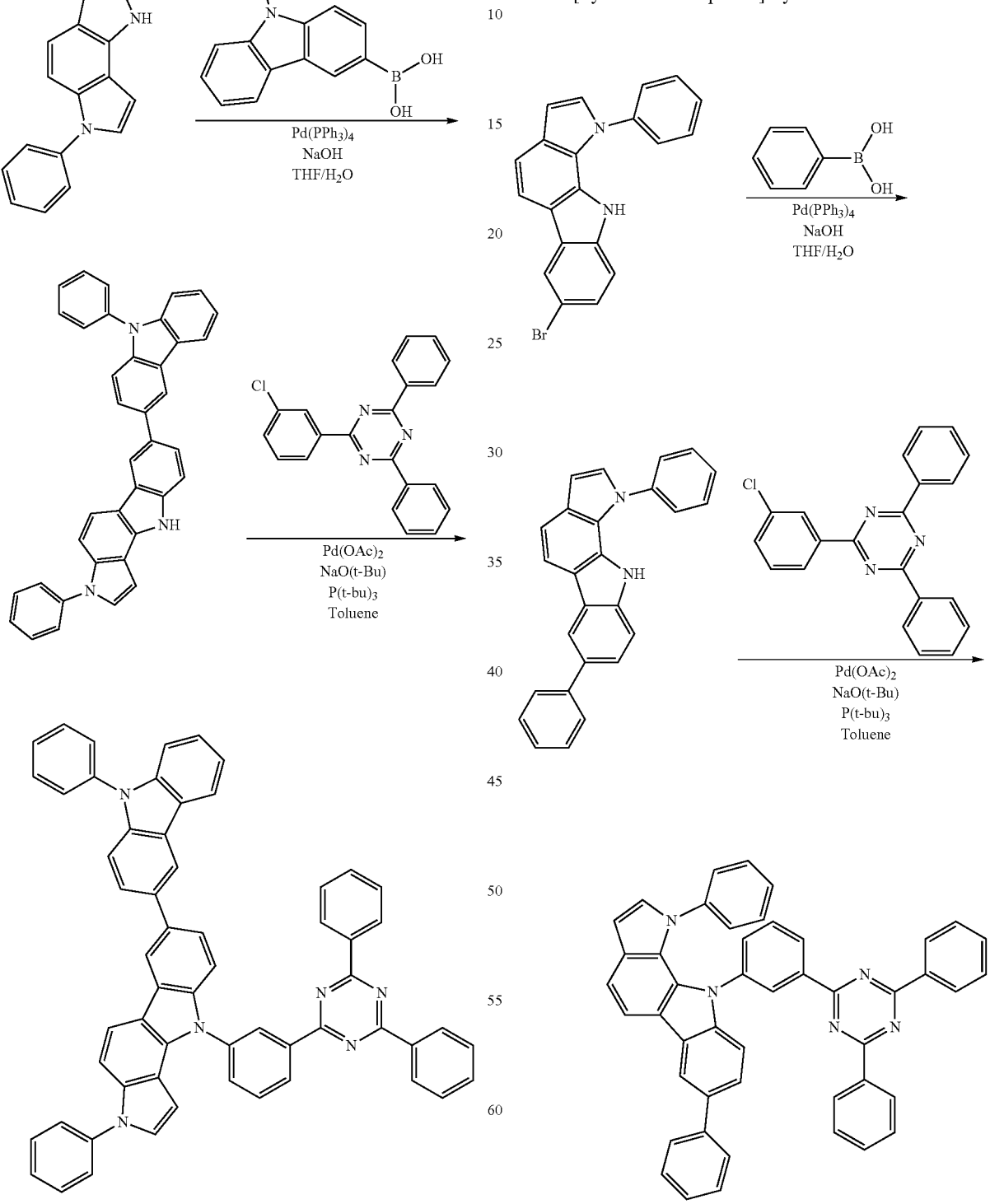

A target compound Inv-61 (6.64 g, 72%) was obtained by performing the same procedure as in Synthesis Example 59, except that IC-11 was used instead of IC-6b.

GC-Mass (theoretical value: 665.26 g/mol, measured value: 665 g/mol)

[Synthesis Example 62] Synthesis of Inv-62

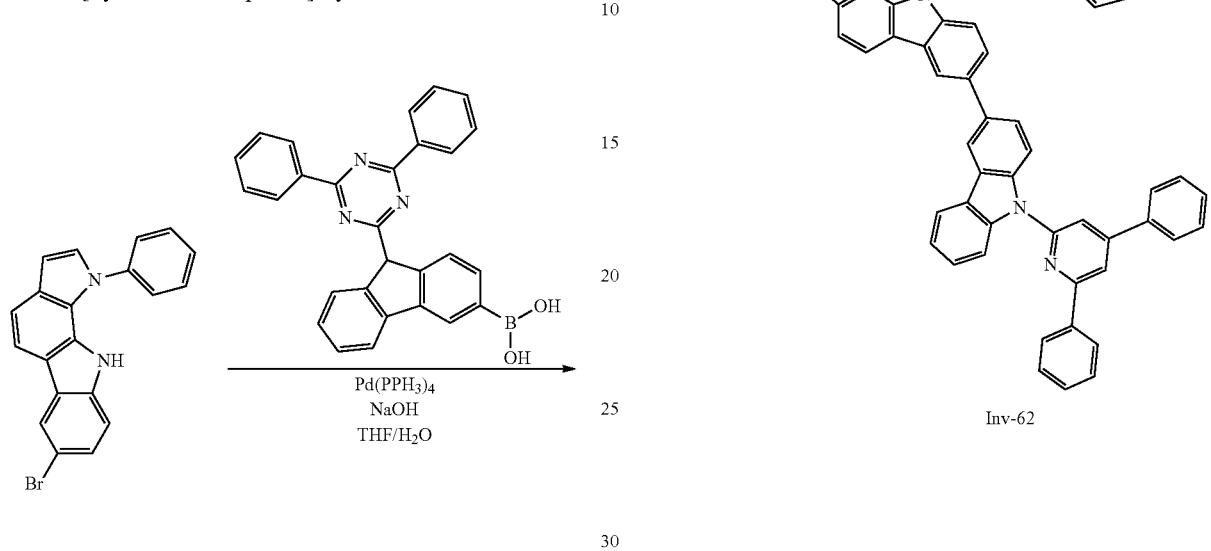

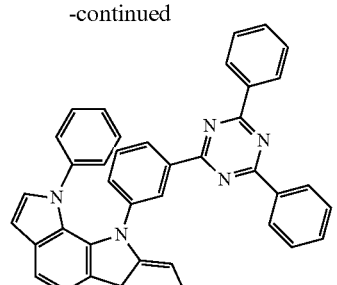

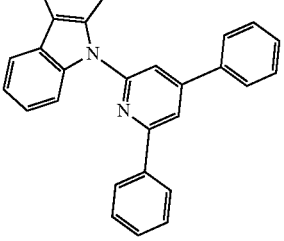

Inv-62

A target compound Inv-62 (10.22 g, 75%) was obtained by performing the same procedure as in Synthesis Example 59, except that IC-11 and 9-(4,6-diphenylpyridin-2-yl)-9H-carbazol-3-ylboronic acid were used instead of IC-6b and phenylboronic acid.

GC-Mass (theoretical value: 983.37 g/mol, measured value: 983 g/mol)

[Synthesis Example 63] Synthesis of Inv-63

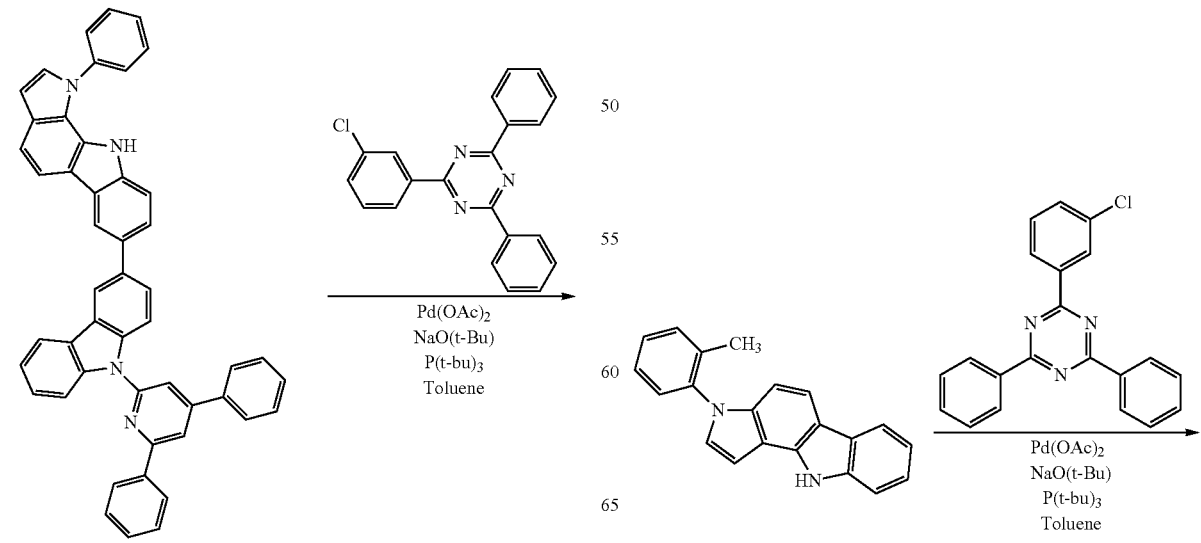

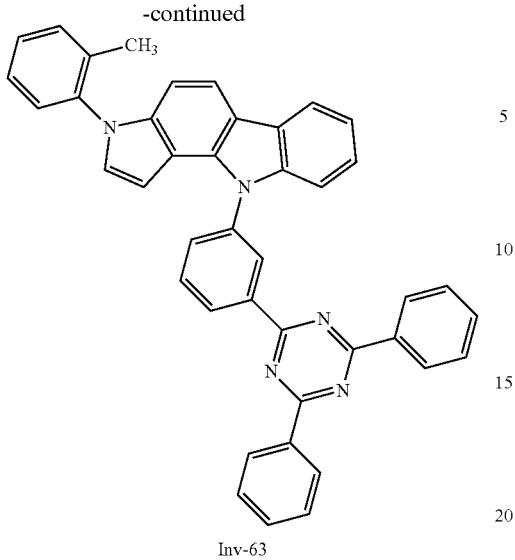

Inv-63

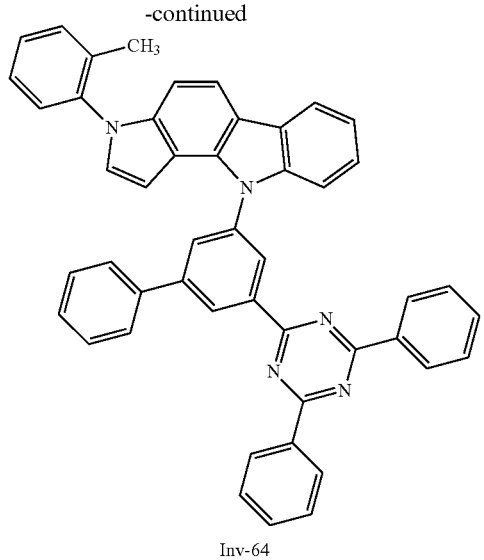

Inv-64

A target compound Inv-63 (4.34 g, 71%) was obtained by performing the same procedure as in Synthesis Example 29, except that IC-12 was used instead of IC-1b.

GC-Mass (theoretical value: 603.24 g/mol, measured value: 603 g/mol)

[Synthesis Example 64] Synthesis of Inv-64

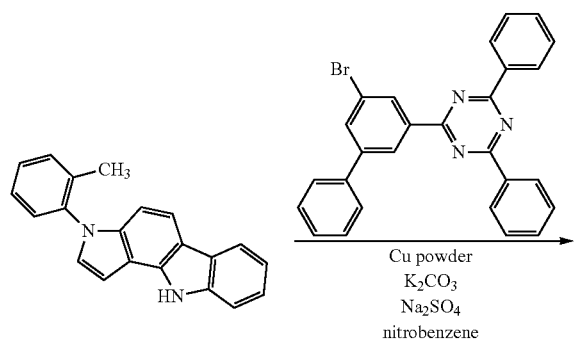

A target compound Inv-64 (3.58 g, 52%) was obtained by performing the same procedure as in Synthesis Example 27, except that IC-12 and 2-(5-bromobiphenyl-3-yl)-4,6-diphenyl-1,3,5-triazine were used instead of IC-1b and 3-bromobiphenyl.

GC-Mass (theoretical value: 679.27 g/mol, measured value: 679 g/mol)

[Synthesis Example 65] Synthesis of Inv-65

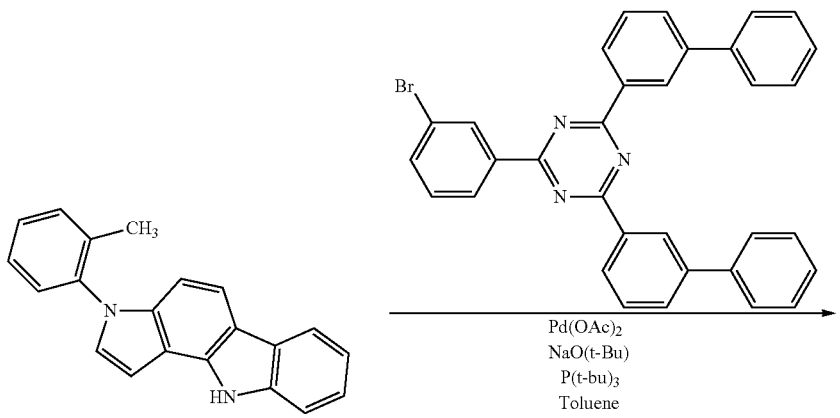

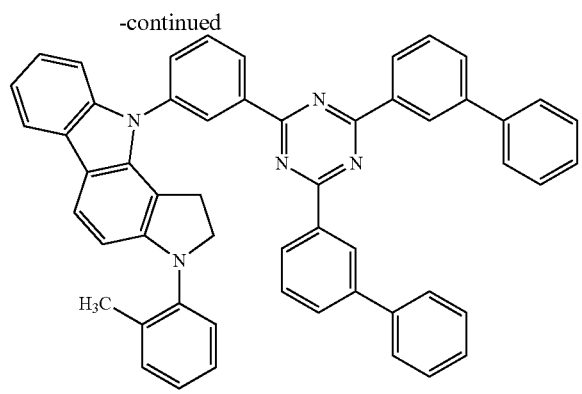

Inv-65

A target compound Inv-65 (5.20 g, 68%) was obtained by performing the same procedure as in Synthesis Example 29, except that IC-12 and 2,4-di(biphenyl-3-yl)-6-(3-chlorophenyl)-1,3,5-triazine were used instead of IC-1b and 2-(3-chlorophenyl)-4,6-diphenyl-1,3,5-triazine.

GC-Mass (theoretical value: 775.30 g/mol, measured value: 775 g/mol)

[Synthesis Example 66] Synthesis of Inv-66

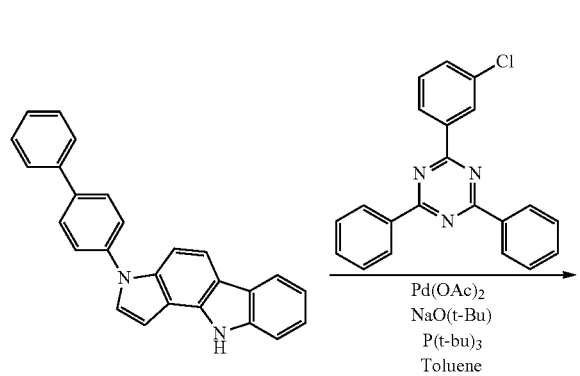

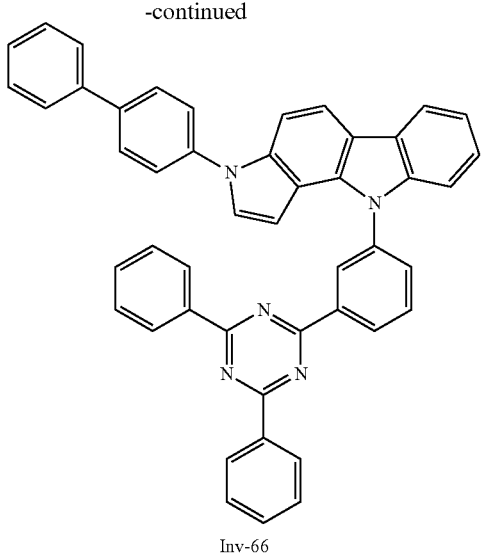

Inv-66

A target compound Inv-66 (3.90 g, 70%) was obtained by performing the same procedure as in Synthesis Example 29, except that IC-13 was used instead of IC-1b.

GC-Mass (theoretical value: 665.26 g/mol, measured value: 665 g/mol)

[Synthesis Example 67] Synthesis of Inv-67

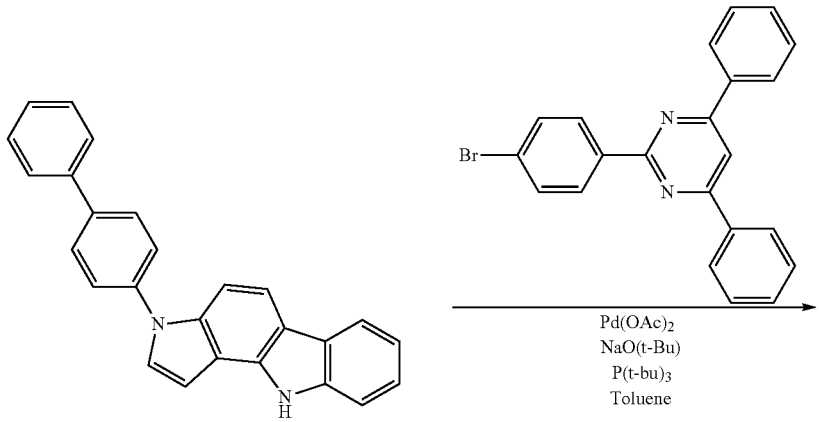

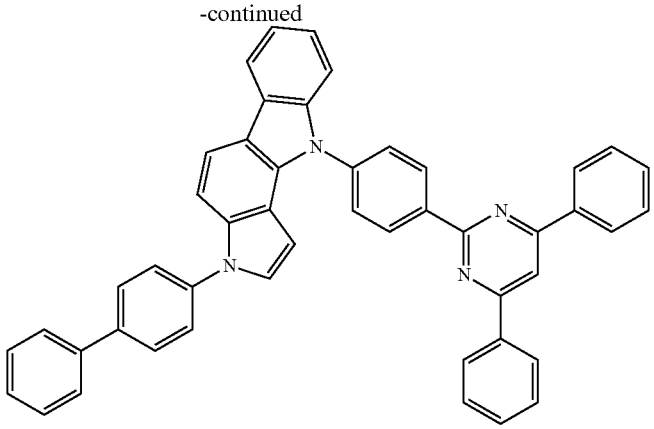
Inv-67
A target compound Inv-67 (2.67 g, 48%) was obtained by performing the same procedure as in Synthesis Example 3, except that IC-13 and 2-(4-bromophenyl)-4,6-diphenylpyrimidine were used instead of IC-1b and 2-bromo-4,6-diphenyl-1,3,5-triazine.
GC-Mass (theoretical value: 664.26 g/mol, measured value: 664 g/mol)
[Synthesis Example 68] Synthesis of Inv-68
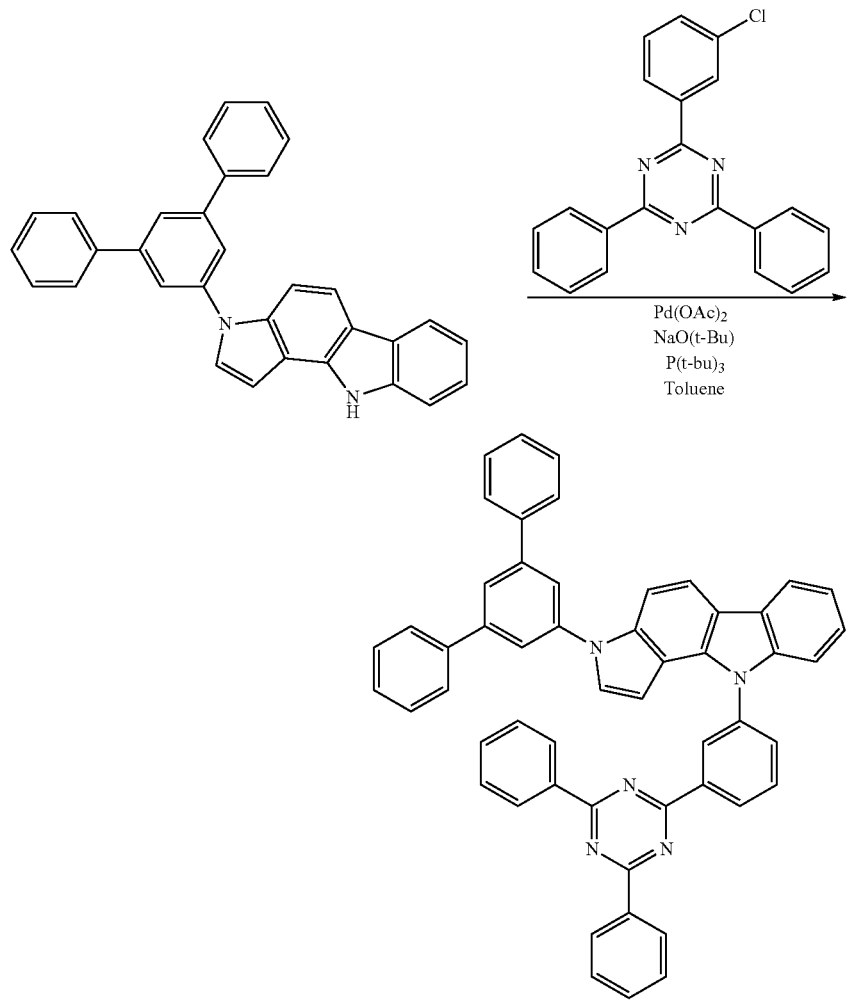
Inv-68

A target compound Inv-68 (3.74 g, 73%) was obtained by performing the same procedure as in Synthesis Example 29, except that IC-14 was used instead of IC-1b.
GC-Mass (theoretical value: 741.29 g/mol, measured value: 741 g/mol)
[Synthesis Example 69] Synthesis of Inv-69
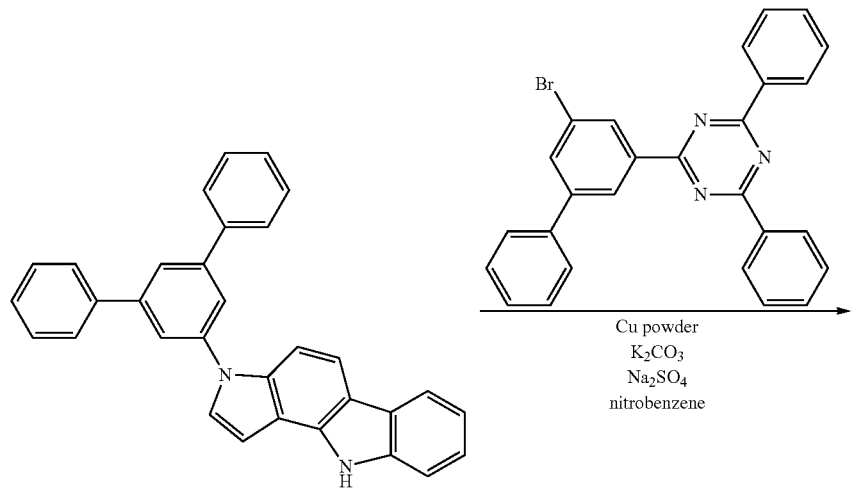
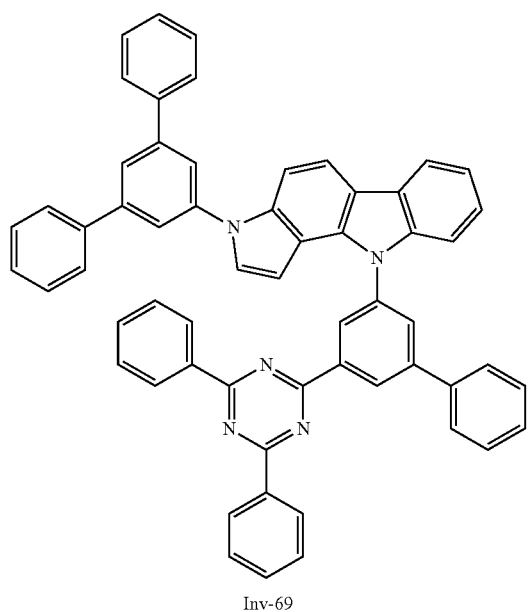
Inv-69

A target compound Inv-69 (2.94 g, 52%) was obtained by performing the same procedure as in Synthesis Example 27, except that IC-14 and 2-(5-bromobiphenyl-3-yl)-4,6-diphenyl-1,3,5-triazine were used instead of IC-1b and 3-bromobiphenyl.
GC-Mass (theoretical value: 817.32 g/mol, measured value: 817 g/mol)
[Synthesis Example 70] Synthesis of Inv-70
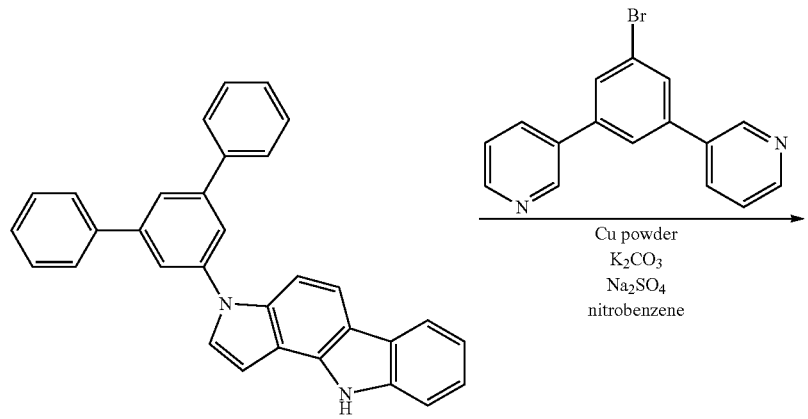
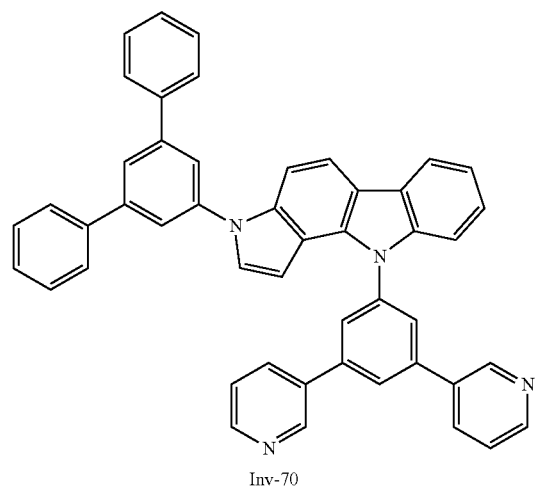
Inv-70

A target compound Inv-70 (2.34 g, 51%) was obtained by performing the same procedure as in Synthesis Example 27, except that IC-14 and 3,3'-(5-bromo-1,3-phenylene)dipyridine were used instead of IC-1b and 3-bromobiphenyl.
GC-Mass (theoretical value: 664.26 g/mol, measured value: 664 g/mol)
[Synthesis Example 71] Synthesis of Inv-71
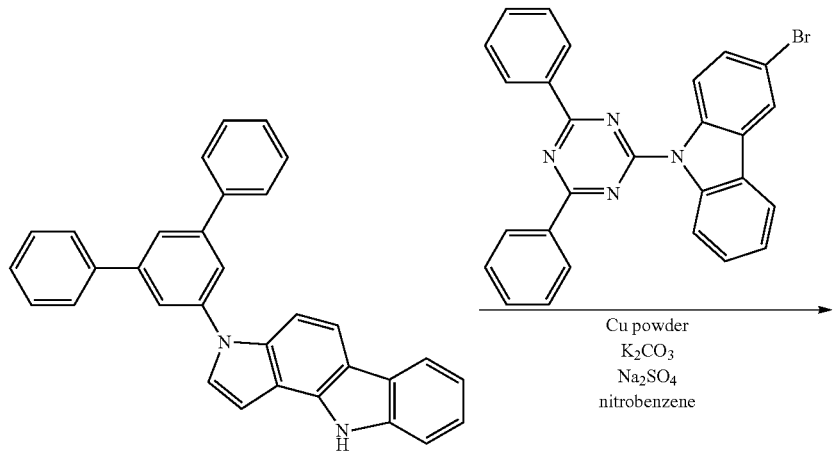
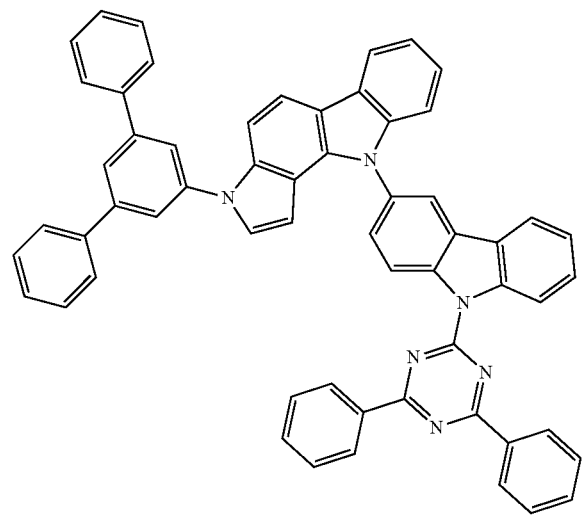
Inv-71

A target compound Inv-71 (2.81 g, 49%) was obtained by performing the same procedure as in Synthesis Example 27, except that IC-14 and 3-bromo-9-(4,6-diphenyl-1,3,5-triazin-2-yl)-9H-carbazole were used instead of IC-1b and 3-bromobiphenyl.

GC-Mass (theoretical value: 830.32 g/mol, measured value: 830 g/mol)

[Synthesis Example 72] Synthesis of Inv-72

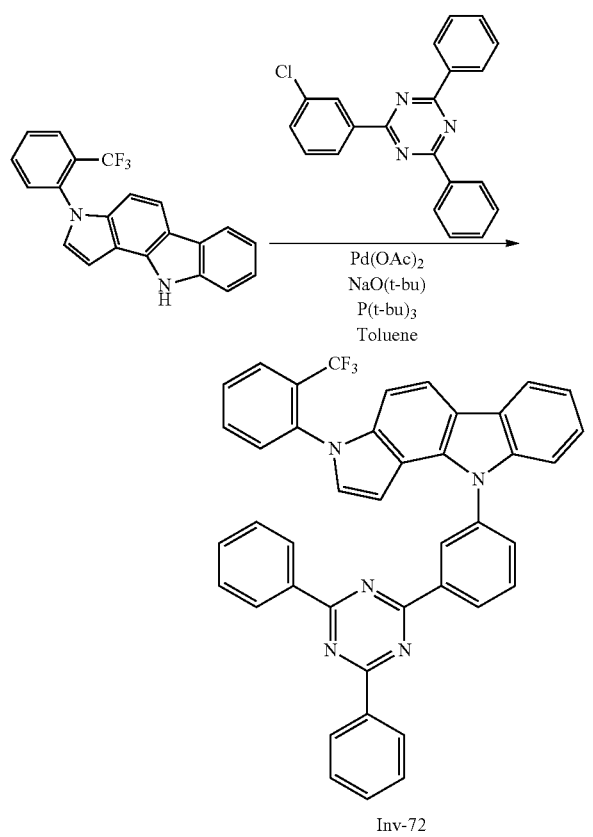

Inv-72

A target compound Inv-72 (4.05 g, 72%) was obtained by performing the same procedure as in Synthesis Example 29, except that IC-15 was used instead of IC-1b.

GC-Mass (theoretical value: 657.21 g/mol, measured value: 657 g/mol)

[Synthesis Example 73] Synthesis of Inv-73

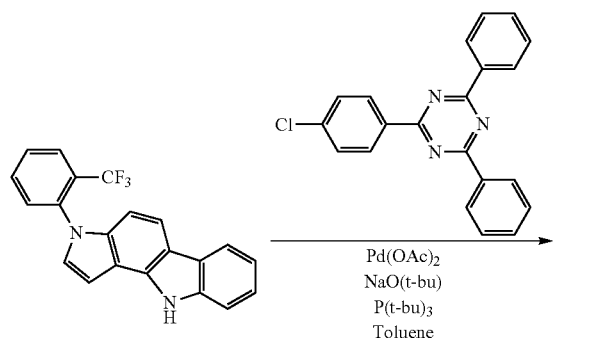

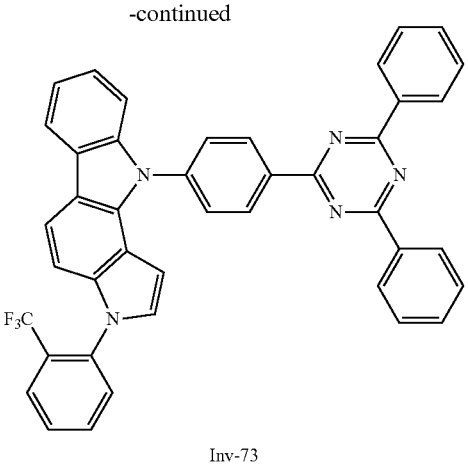

Inv-73

A target compound Inv-73 (3.66 g, 65%) was obtained by performing the same procedure as in Synthesis Example 29, except that IC-15 and 3-bromo-9-(4,6-diphenyl-1,3,5-triazin-2-yl)-9H-carbazole were used instead of IC-1b and 2-(3-chlorophenyl)-4,6-diphenyl-1,3,5-triazine.

GC-Mass (theoretical value: 657.21 g/mol, measured value: 657 g/mol)

[Synthesis Example 74] Synthesis of Inv-74

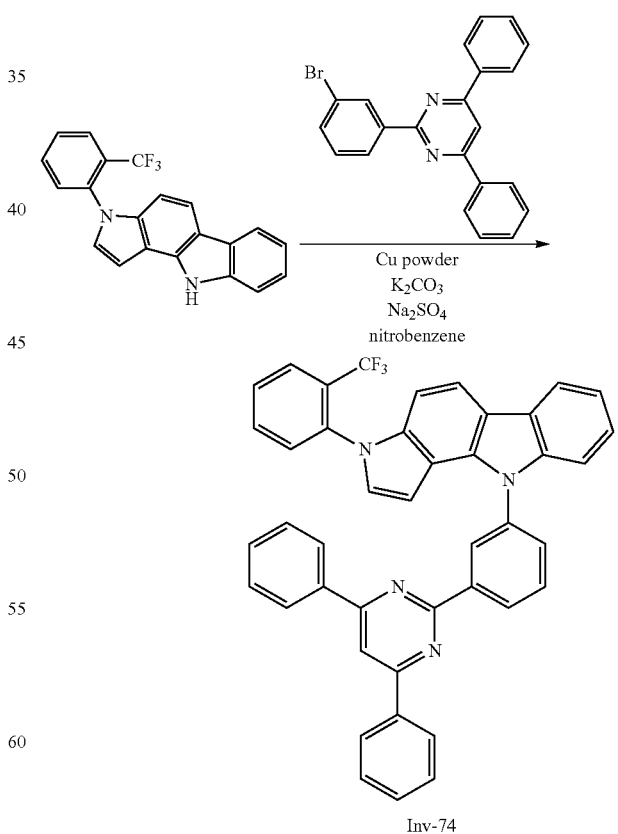

Inv-74

A target compound Inv-74 (2.64 g, 47%) was obtained by performing the same procedure as in Synthesis Example 27, except that IC-15 and 2-(3-bromophenyl)-4,6-diphenylpyrimidine were used instead of IC-1b and 3-bromobiphenyl.

GC-Mass (theoretical value: 656.22 g/mol, measured value: 656 g/mol)

[Synthesis Example 75] Synthesis of Inv-75

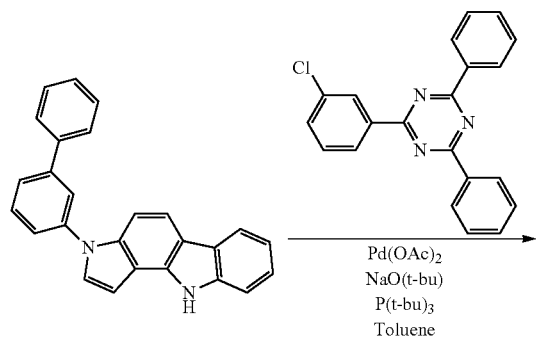

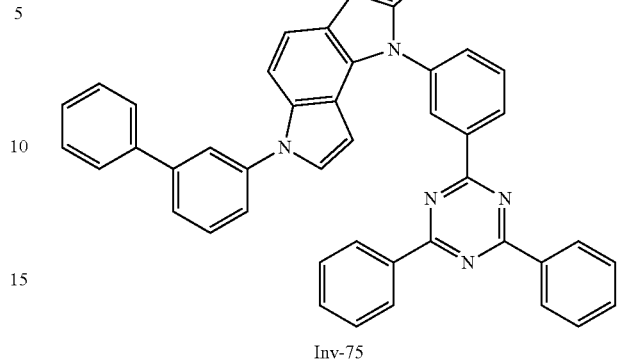

A target compound Inv-75 (3.90 g, 70%) was obtained by performing the same procedure as in Synthesis Example 29, except that IC-16 was used instead of IC-1b.

GC-Mass (theoretical value: 665.26 g/mol, measured value: 665 g/mol)

[Synthesis Example 76] Synthesis of Inv-76

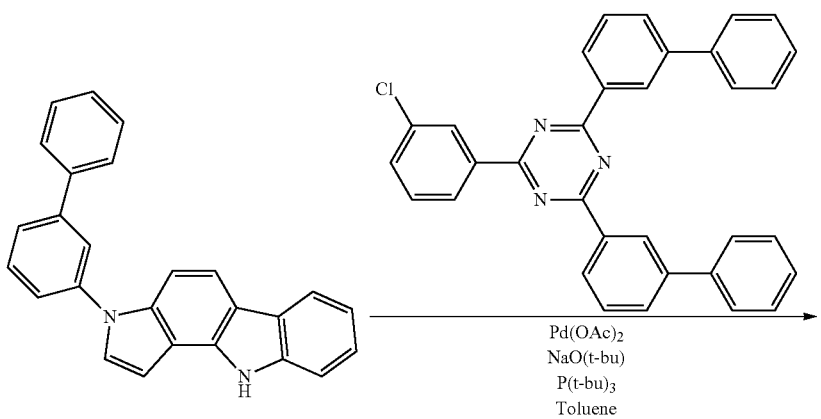

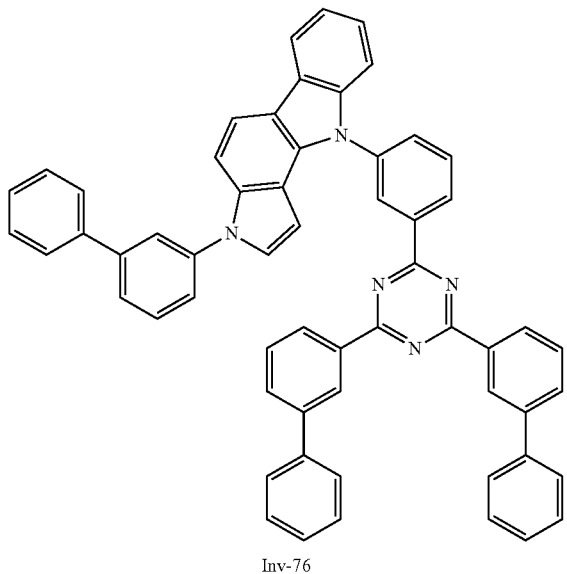

Inv-76

A target compound Inv-76 (5.00 g, 73%) was obtained by performing the same procedure as in Synthesis Example 29, except that IC-16 and 2,4-di(biphenyl-3-yl)-6-(3-chlorophenyl)-1,3,5-triazine were used instead of IC-1b and 2-(3-chlorophenyl)-4,6-diphenyl-1,3,5-triazine.

GC-Mass (theoretical value: 817.32 g/mol, measured value: 817 g/mol)

[Synthesis Example 77] Synthesis of Inv-77

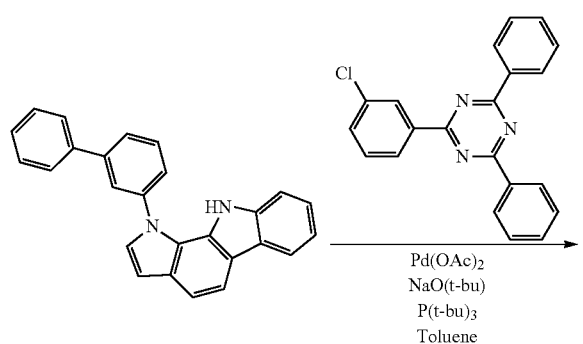

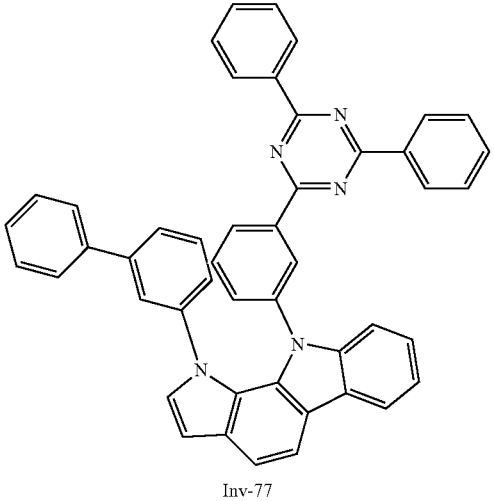

Inv-77

A target compound Inv-77 (3.85 g, 69%) was obtained by performing the same procedure as in Synthesis Example 29, except that IC-17 was used instead of IC-1b.

GC-Mass (theoretical value: 665.26 g/mol, measured value: 665 g/mol)

[Synthesis Example 78] Synthesis of Inv-78

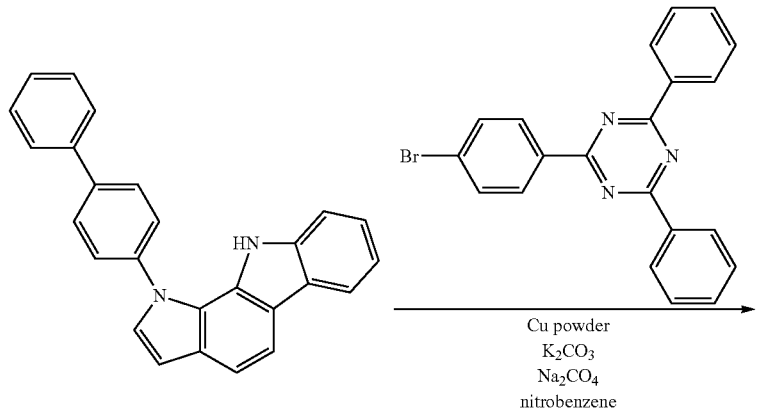

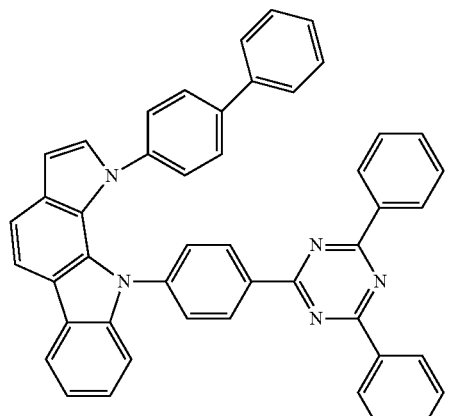

Inv-78

A target compound Inv-78 (2.90 g, 52%) was obtained by performing the same procedure as in Synthesis Example 27, except that IC-18 and 2-(4-bromophenyl)-4,6-diphenyl-1,3,5-triazine were used instead of IC-1b and 3-bromobiphenyl.

GC-Mass (theoretical value: 665.26 g/mol, measured value: 665 g/mol)

[Synthesis Example 79] Synthesis of Inv-79

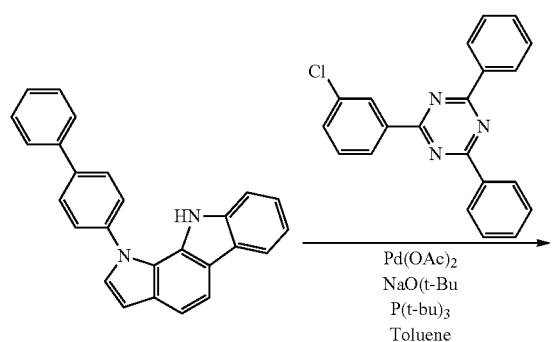

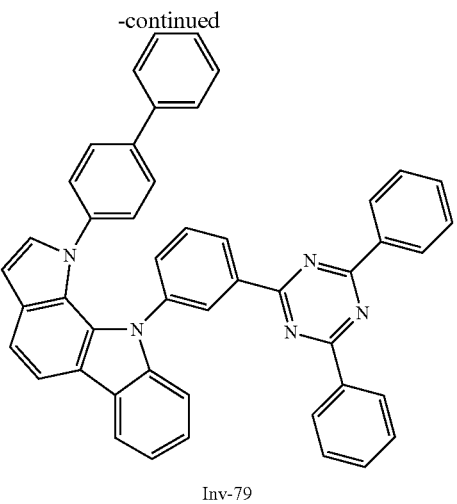

Inv-79

A target compound Inv-79 (3.85 g, 69%) was obtained by performing the same procedure as in Synthesis Example 29, except that IC-18 was used instead of IC-1b.

GC-Mass (theoretical value: 665.26 g/mol, measured value: 665 g/mol)

[Synthesis Example 80] Synthesis of Inv-80

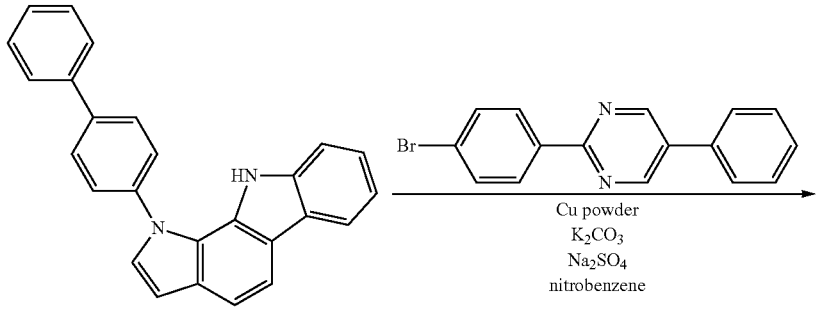

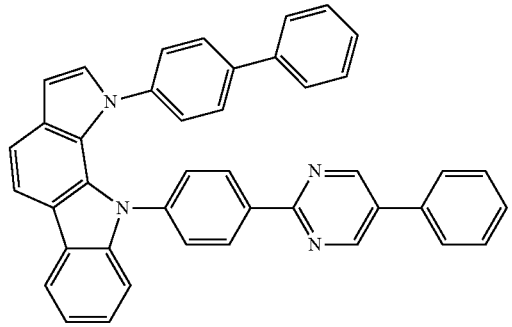

Inv-80

A target compound Inv-80 (2.66 g, 54%) was obtained by performing the same procedure as in Synthesis Example 27, except that IC-18 and 2-(4-bromophenyl)-5-phenylpyrimidine were used instead of IC-1b and 3-bromobiphenyl.

GC-Mass (theoretical value: 588.23 g/mol, measured value: 588 g/mol)

[Synthesis Example 81] Synthesis of Inv-81

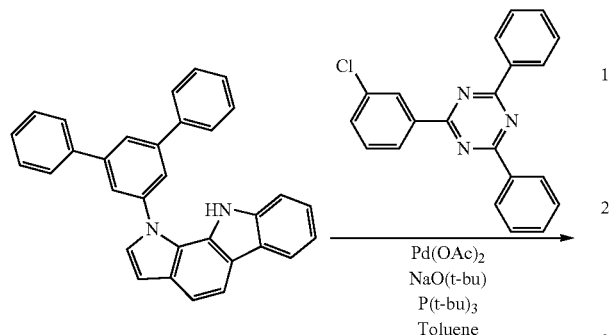

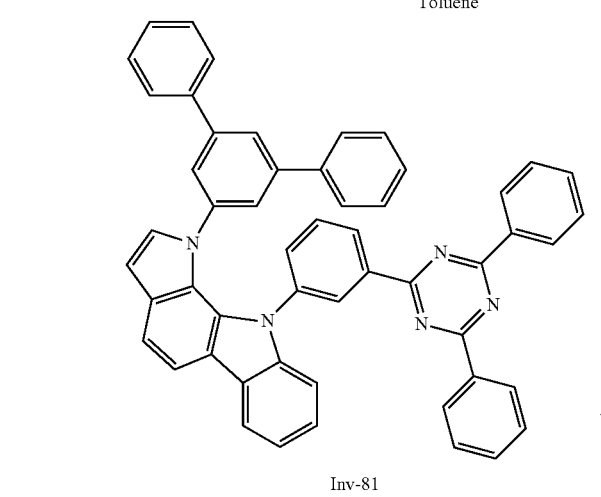

Inv-81

A target compound Inv-81 (3.48 g, 68%) was obtained by performing the same procedure as in Synthesis Example 29, except that IC-19 was used instead of IC-1b.

GC-Mass (theoretical value: 741.29 g/mol, measured value: 741 g/mol)

[Synthesis Example 82] Synthesis of Inv-82

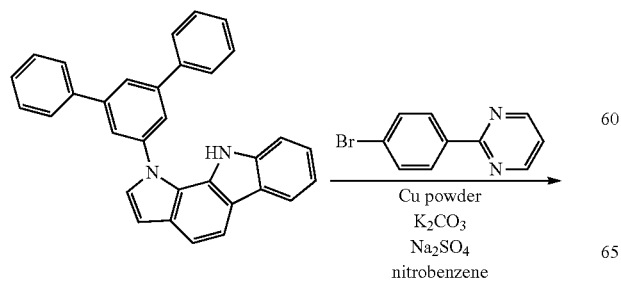

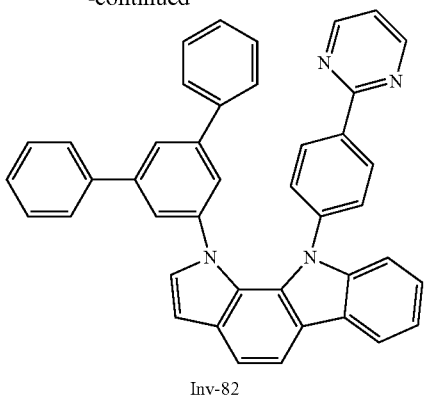

Inv-82

A target compound Inv-82 (1.99 g, 49%) was obtained by performing the same procedure as in Synthesis Example 27, except that IC-19 and 2-(4-bromophenyl)pyrimidine were used instead of IC-1b and 3-bromobiphenyl.

GC-Mass (theoretical value: 588.23 g/mol, measured value: 588 g/mol)

[Synthesis Example 83] Synthesis of Inv-83

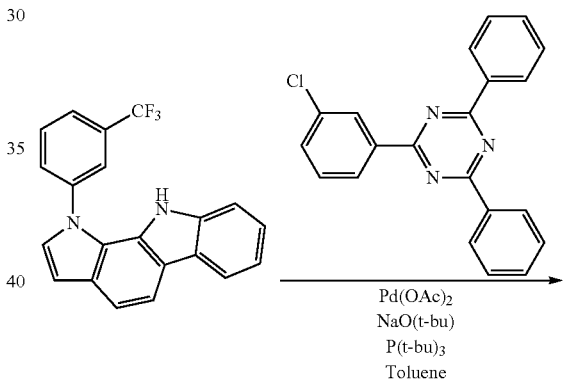

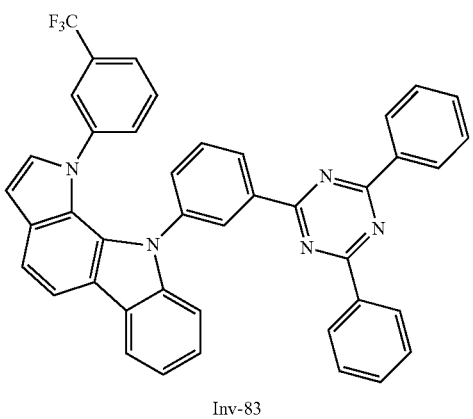

Inv-83

A target compound Inv-83 (4.00 g, 71%) was obtained by performing the same procedure as in Synthesis Example 29, except that IC-20 was used instead of IC-1b.

GC-Mass (theoretical value: 657.21 g/mol, measured value: 657 g/mol)

[Synthesis Example 84] Synthesis of Inv-84

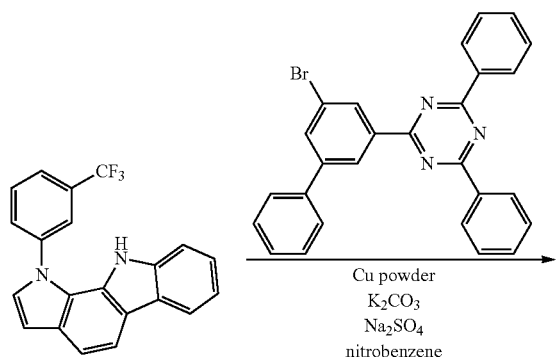

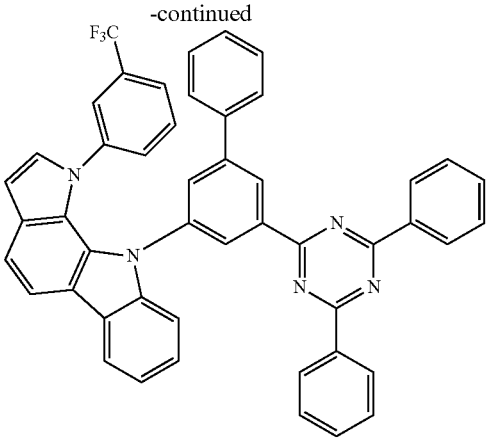

Inv-84

A target compound Inv-84 (2.89 g, 46%) was obtained by performing the same procedure as in Synthesis Example 27, except that IC-20 and 2-(5-bromobiphenyl-3-yl)-4,6-diphenyl-1,3,5-triazine were used instead of IC-1b and 3-bromobiphenyl.

GC-Mass (theoretical value: 733.25 g/mol, measured value: 733 g/mol)

[Synthesis Example 85] Synthesis of Inv-85

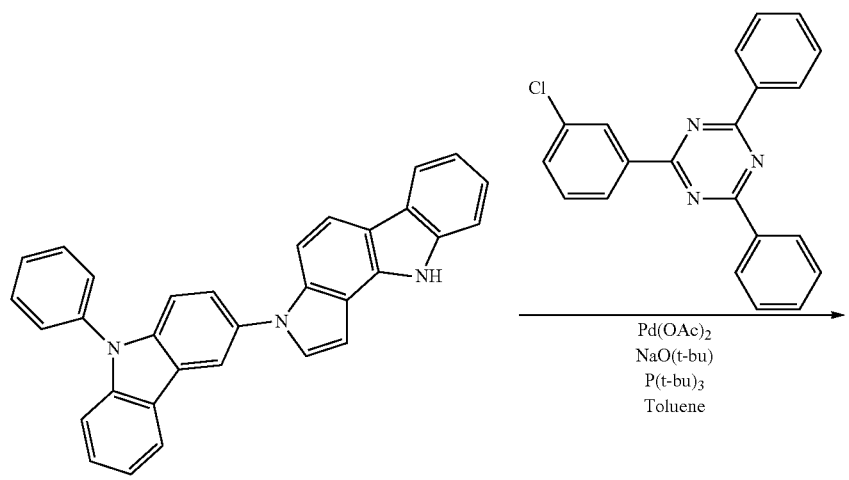

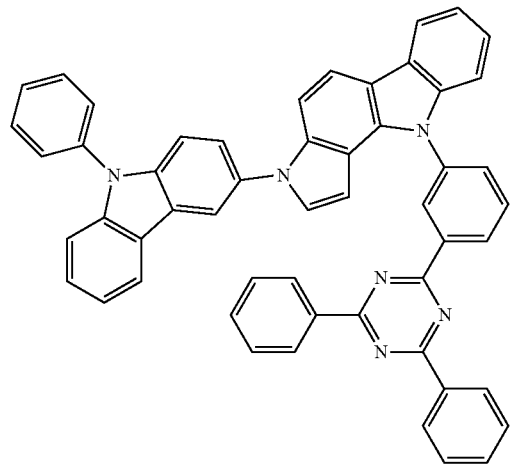

Inv-85

A target compound Inv-85 (3.49 g, 69%) was obtained by performing the same procedure as in Synthesis Example 29, except that IC-21 was used instead of IC-1b.
GC-Mass (theoretical value: 754.28 g/mol, measured value: 754 g/mol)
[Synthesis Example 86] Synthesis of Inv-86
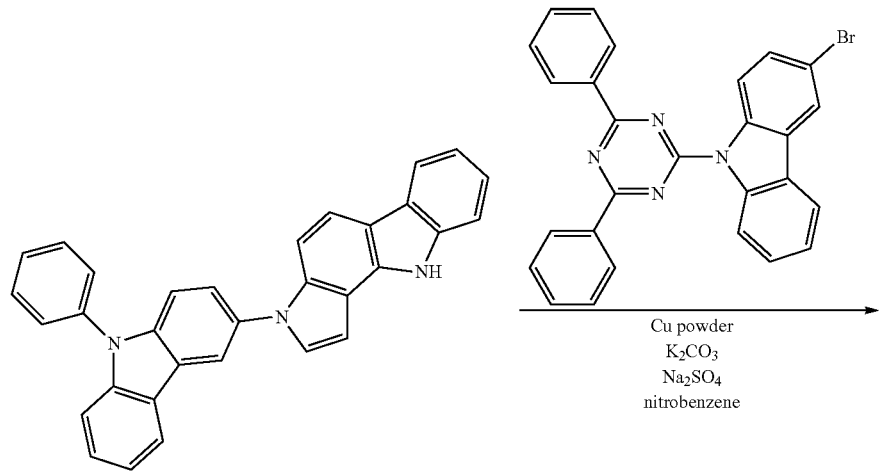
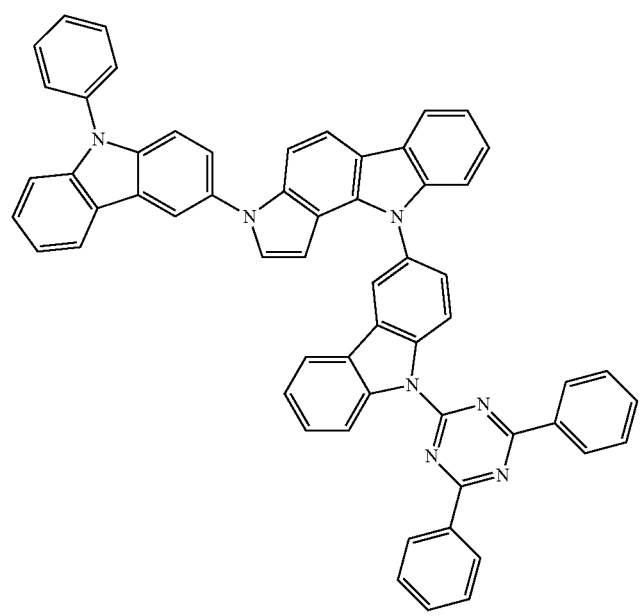
Inv-86

A target compound Inv-86 (2.49 g, 44%) was obtained by performing the same procedure as in Synthesis Example 27, except that IC-21 and 3-bromo-9-(4,6-diphenyl-1,3,5-triazin-2-yl)-9H-carbazole were used instead of IC-1b and 3-bromobiphenyl.

GC-Mass (theoretical value: 843.31 g/mol, measured value: 843 g/mol)

[Synthesis Example 87] Synthesis of Inv-87

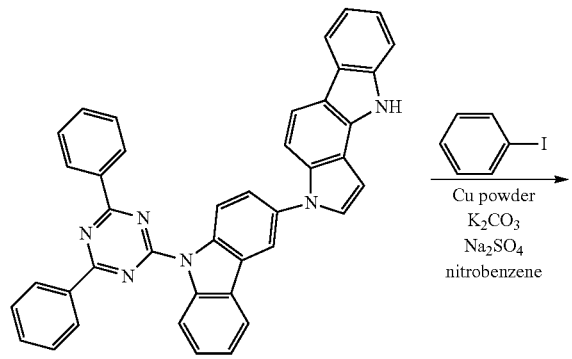

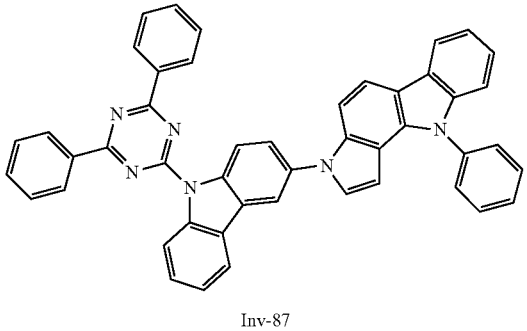

Inv-87

A target compound Inv-87 (1.62 g, 48%) was obtained by performing the same procedure as in Synthesis Example 27, except that IC-22 and iodobenzene were used instead of IC-1b and 3-bromobiphenyl.

GC-Mass (theoretical value: 678.25 g/mol, measured value: 678 g/mol)

[Synthesis Example 88] Synthesis of Inv-88

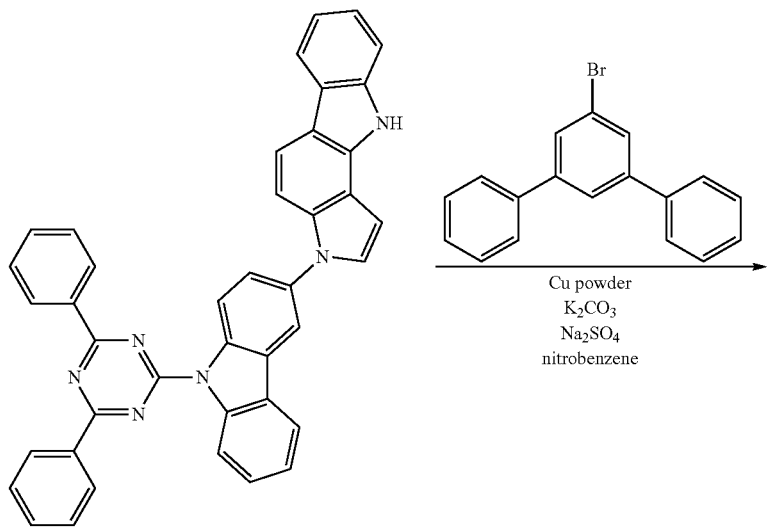

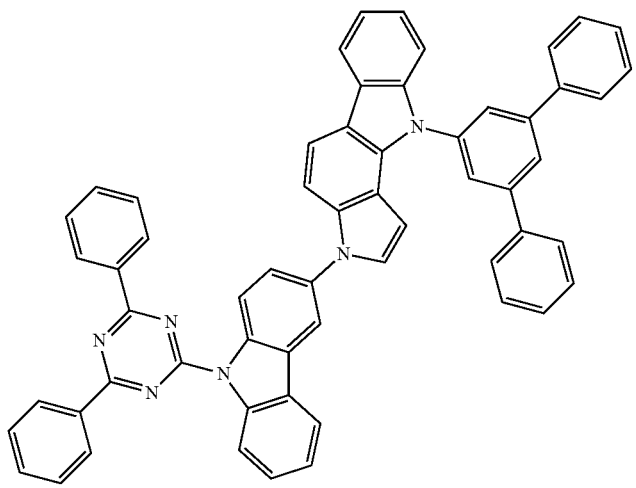

Inv-88

A target compound Inv-88 (1.94 g, 47%) was obtained by performing the same procedure as in Synthesis Example 27, except that IC-22 and 1-bromo-3,5-diphenyl benzene were used instead of IC-1b and 3-bromobiphenyl.

GC-Mass (theoretical value: 830.32 g/mol, measured value: 830 g/mol)

[Synthesis Example 89] Synthesis of Inv-89

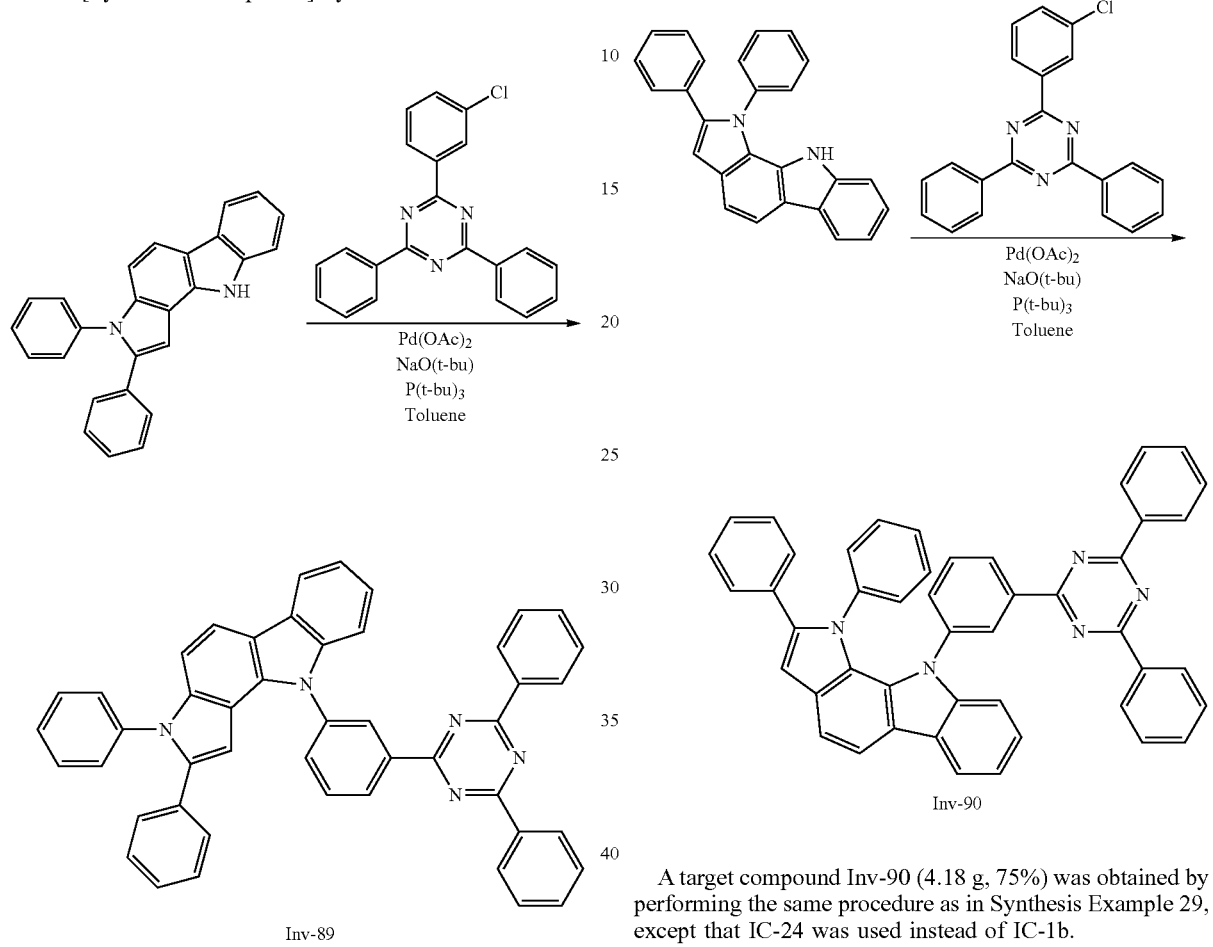

Inv-89

A target compound Inv-89 (3.79 g, 68%) was obtained by performing the same procedure as in Synthesis Example 29, except that IC-23 was used instead of IC-1b.

GC-Mass (theoretical value: 665.26 g/mol, measured value: 665 g/mol)

[Synthesis Example 90] Synthesis of Inv-90

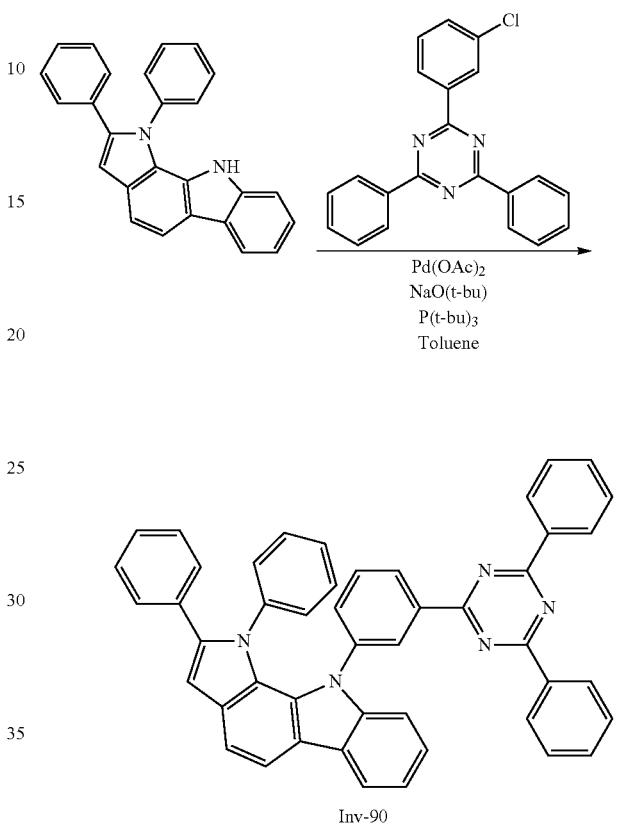

Inv-90

A target compound Inv-90 (4.18 g, 75%) was obtained by performing the same procedure as in Synthesis Example 29, except that IC-24 was used instead of IC-1b.

GC-Mass (theoretical value: 665.26 g/mol, measured value: 665.26 g/mol)

[Synthesis Example 91] Synthesis of Inv-91

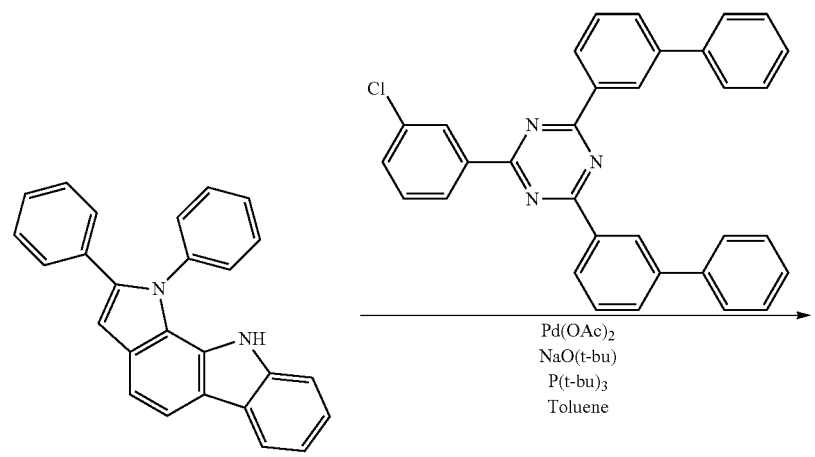

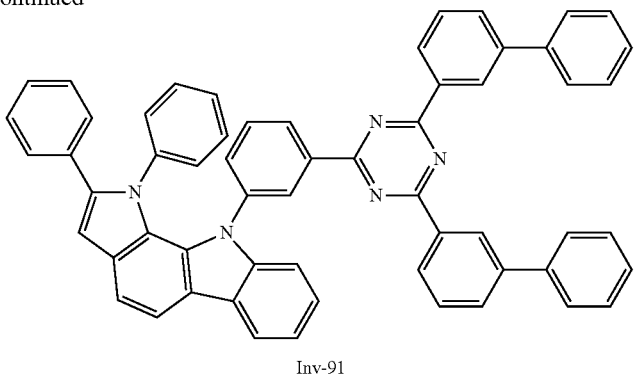
Inv-91

A target compound Inv-91 (5.07 g, 74%) was obtained by performing the same procedure as in Synthesis Example 29, except that IC-24 and 2,4-di(biphenyl-3-yl)-6-(3-chlorophenyl)-1,3,5-triazine were used instead of IC-1b and 2-(3-chlorophenyl)-4,6-diphenyl-1,3,5-triazine.

GC-Mass (theoretical value: 817.32 g/mol, measured value: 817 g/mol)

[Synthesis Example 92] Synthesis of Inv-92

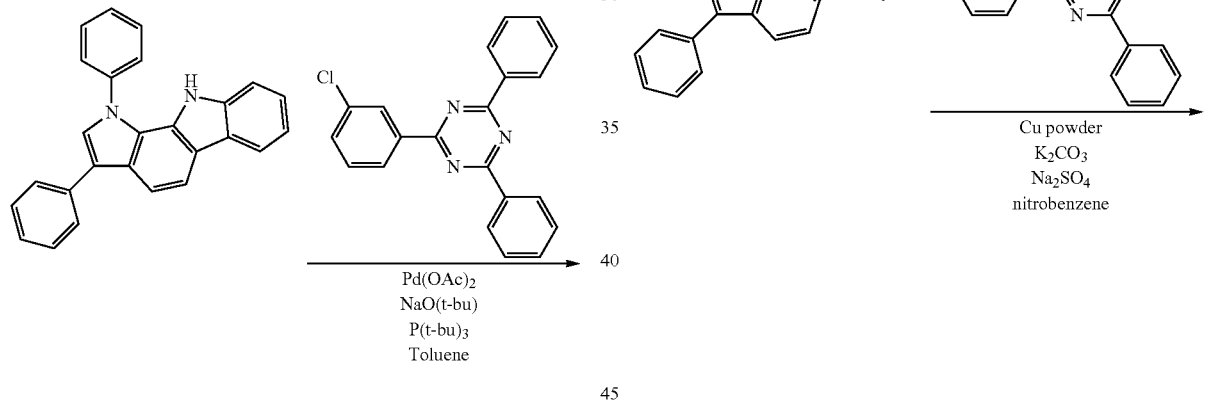
Inv-92

A target compound Inv-92 (4.01 g, 72%) was obtained by performing the same procedure as in Synthesis Example 29, except that IC-25 was used instead of IC-1b.

GC-Mass (theoretical value: 665.26 g/mol, measured value: 665 g/mol)

[Synthesis Example 93] Synthesis of Inv-93

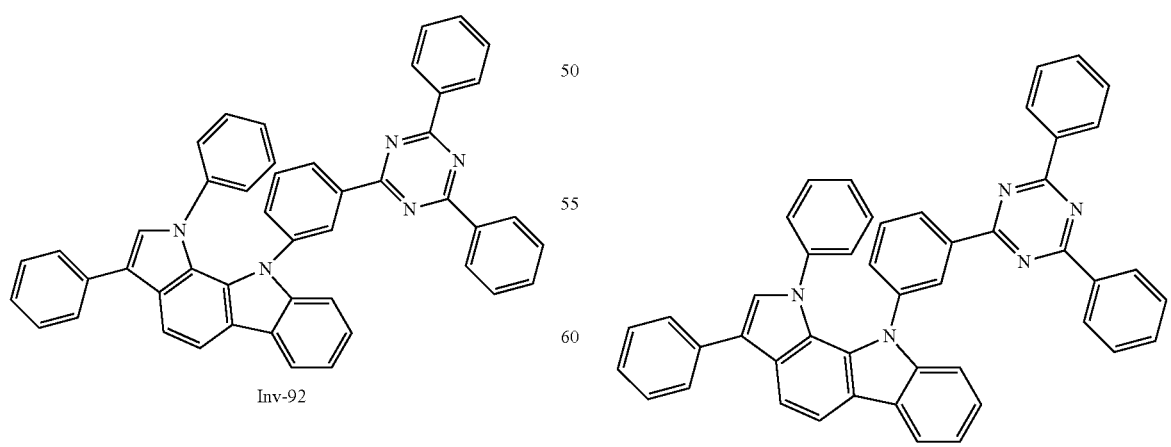
Inv-93

A target compound Inv-93 (2.84 g, 51%) was obtained by performing the same procedure as in Synthesis Example 27, except that IC-25 and 2-(3-bromophenyl)-4,6-diphenylpyrimidine were used instead of IC-1b and 3-bromobiphenyl.

GC-Mass (theoretical value: 664.26 g/mol, measured value: 664 g/mol)

[Synthesis Example 94] Synthesis of Inv-94

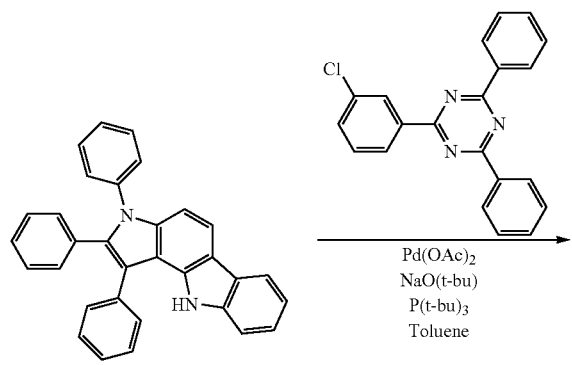

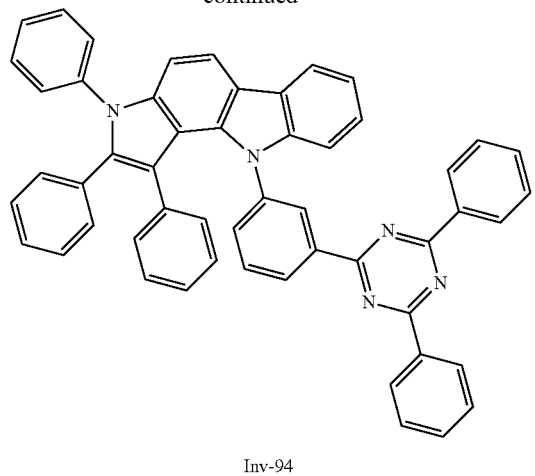

Inv-94

A target compound Inv-94 (3.74 g, 73%) was obtained by performing the same procedure as in Synthesis Example 29, except that IC-26 was used instead of IC-1b.

GC-Mass (theoretical value: 741.29 g/mol, measured value: 741 g/mol)

[Synthesis Example 95] Synthesis of Inv-95

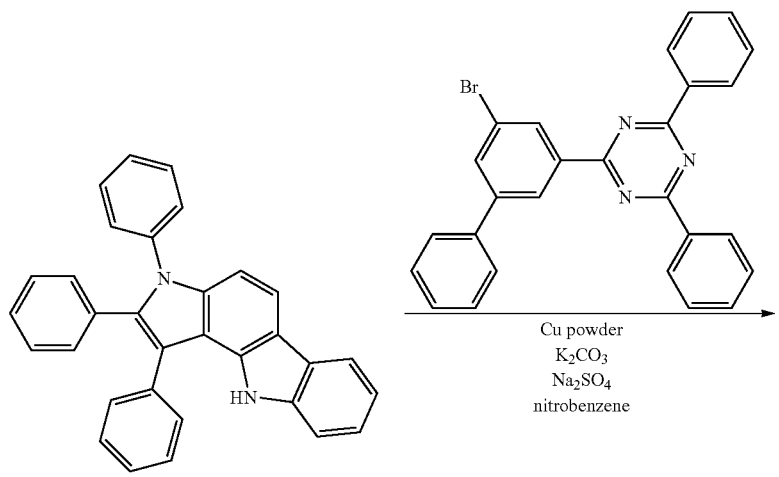

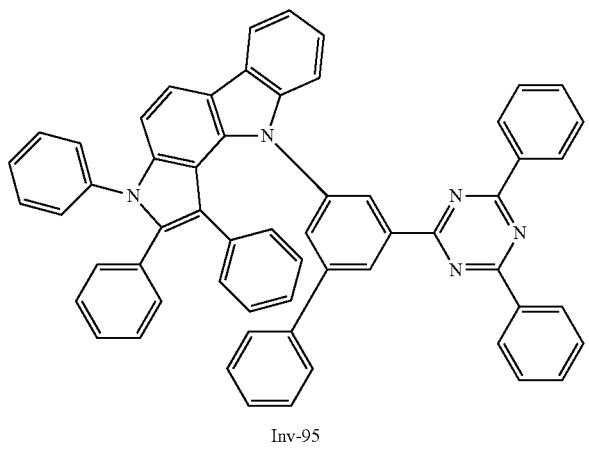

Inv-95

A target compound Inv-95 (2.71 g, 48%) was obtained by performing the same procedure as in Synthesis Example 27, except that IC-26 and 2-(5-bromobiphenyl-3-yl)-4,6-diphenyl-1,3,5-triazine were used instead of IC-1b and 3-bromobiphenyl.

GC-Mass (theoretical value: 817.32 g/mol, measured value: 817 g/mol)

[Synthesis Example 96] Synthesis of Inv-96

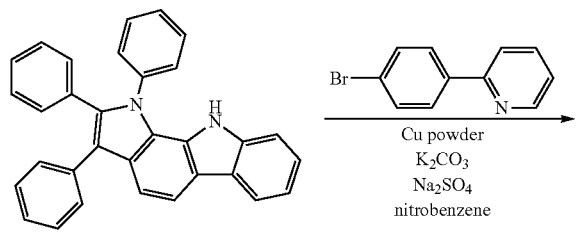

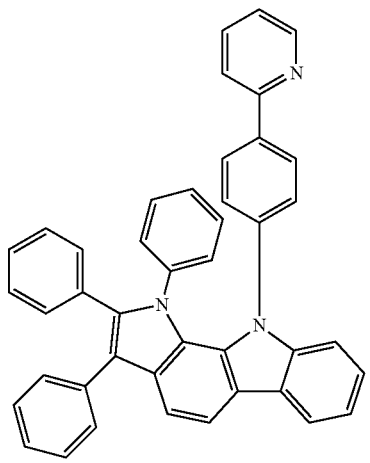

Inv-96

A target compound Inv-96 (2.07 g, 51%) was obtained by performing the same procedure as in Synthesis Example 27, except that IC-27 and 2-(4-bromophenyl)pyridine were used instead of IC-1b and 3-bromobiphenyl.

GC-Mass (theoretical value: 587.24 g/mol, measured value: 587 g/mol)

[Synthesis Example 97] Synthesis of Inv-97

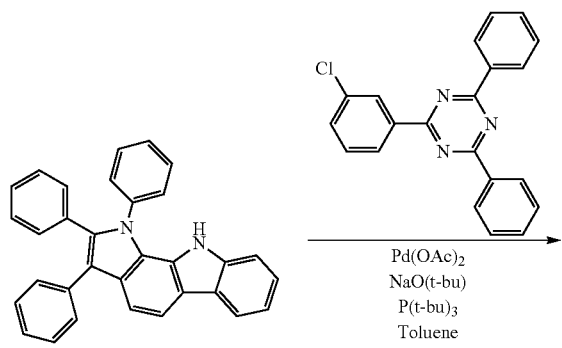

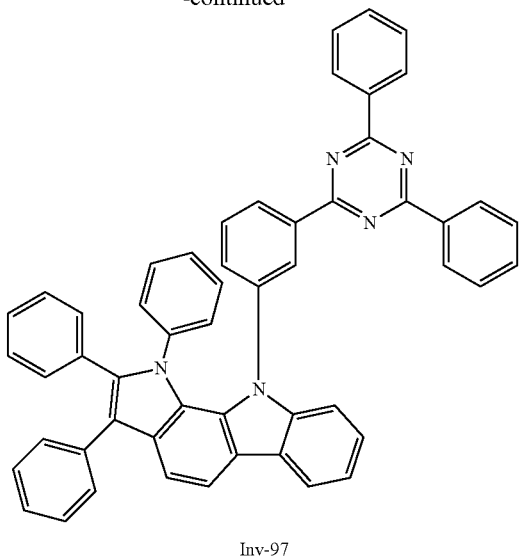

Inv-97

A target compound Inv-97 (4.00 g, 78%) was obtained by performing the same procedure as in Synthesis Example 29, except that IC-27 was used instead of IC-1b.

GC-Mass (theoretical value: 741.29 g/mol, measured value: 741 g/mol)

[Synthesis Example 98] Synthesis of Inv-98

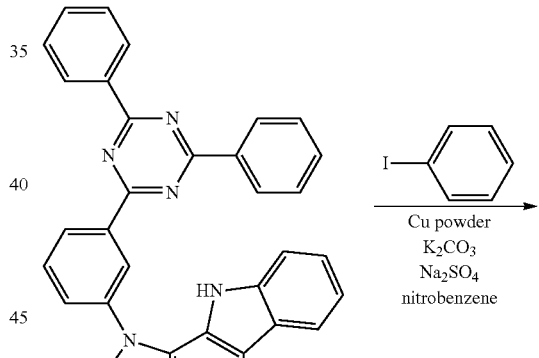

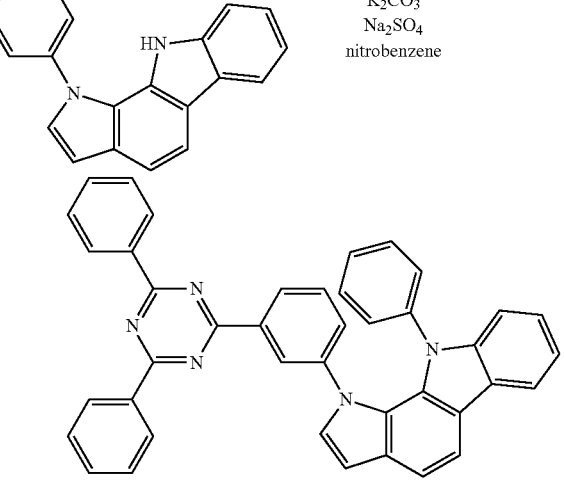

Inv-98

A target compound Inv-98 (1.83 g, 53%) was obtained by performing the same procedure as in Synthesis Example 27, except that IC-28 and iodobenzene were used instead of IC-1b and 3-bromobiphenyl.

GC-Mass (theoretical value: 589.23 g/mol, measured value: 589 g/mol)

[Synthesis Example 99] Synthesis of Inv-99

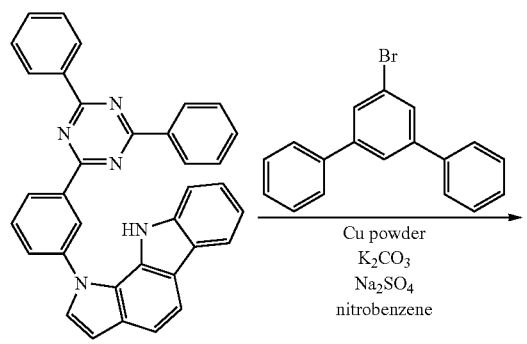

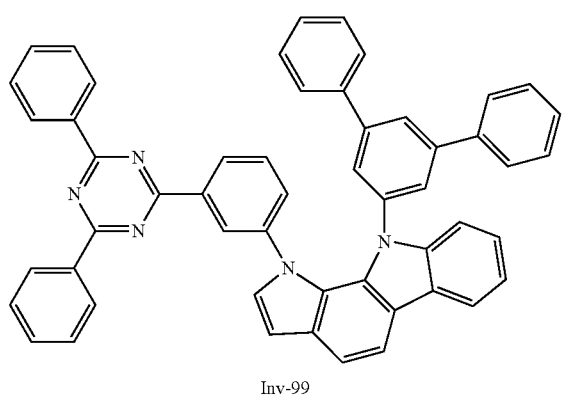

A target compound Inv-99 (2.25 g, 52%) was obtained by performing the same procedure as in Synthesis Example 27, except that IC-28 and 1-bromo-3,5-diphenyl benzene were used instead of IC-1b and 3-bromobiphenyl.

GC-Mass (theoretical value: 741.29 g/mol, measured value: 741 g/mol)

[Synthesis Example 100] Synthesis of Inv-100

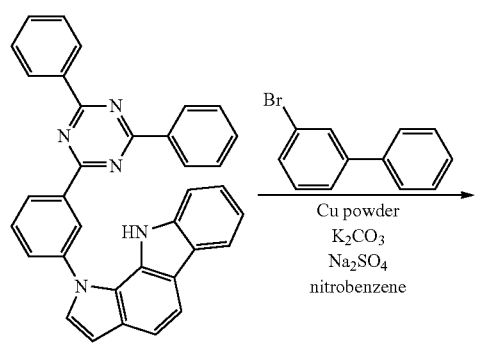

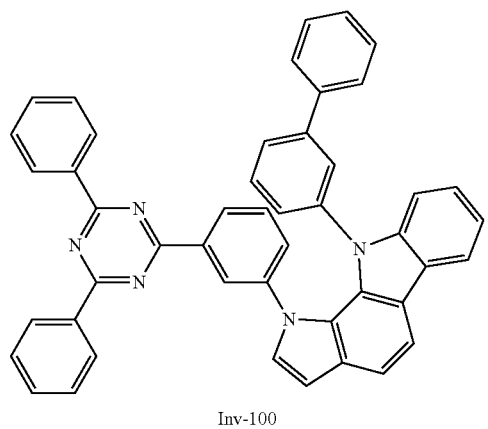

Inv-100

A target compound Inv-100 (1.91 g, 49%) was obtained by performing the same procedure as in Synthesis Example 27, except that IC-28 was used instead of IC-1b.

GC-Mass (theoretical value: 665.26 g/mol, measured value: 665 g/mol)

[Synthesis Example 101] Synthesis of Inv-101

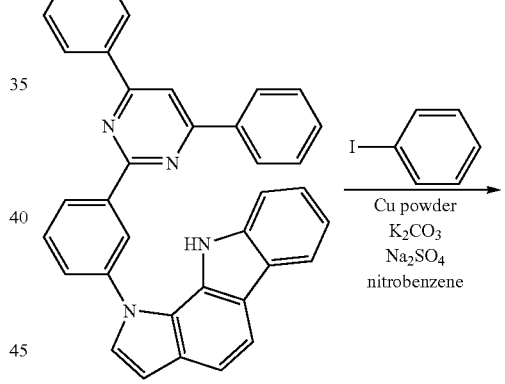

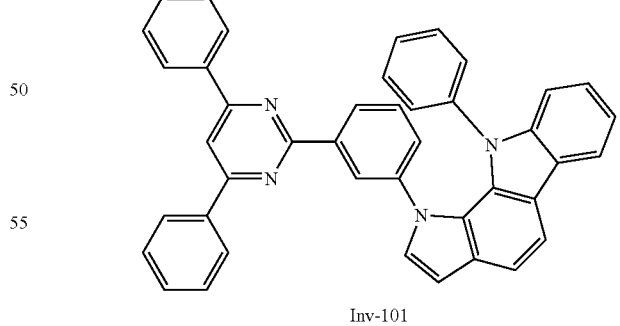

Inv-101

A target compound Inv-101 (1.55 g, 45%) was obtained by performing the same procedure as in Synthesis Example 27, except that IC-29 and iodobenzene were used instead of IC-1b and 3-bromobiphenyl.

GC-Mass (theoretical value: 588.23 g/mol, measured value: 588 g/mol)

[Synthesis Example 102] Synthesis of Inv-102

[Synthesis Example 103] Synthesis of Inv-103

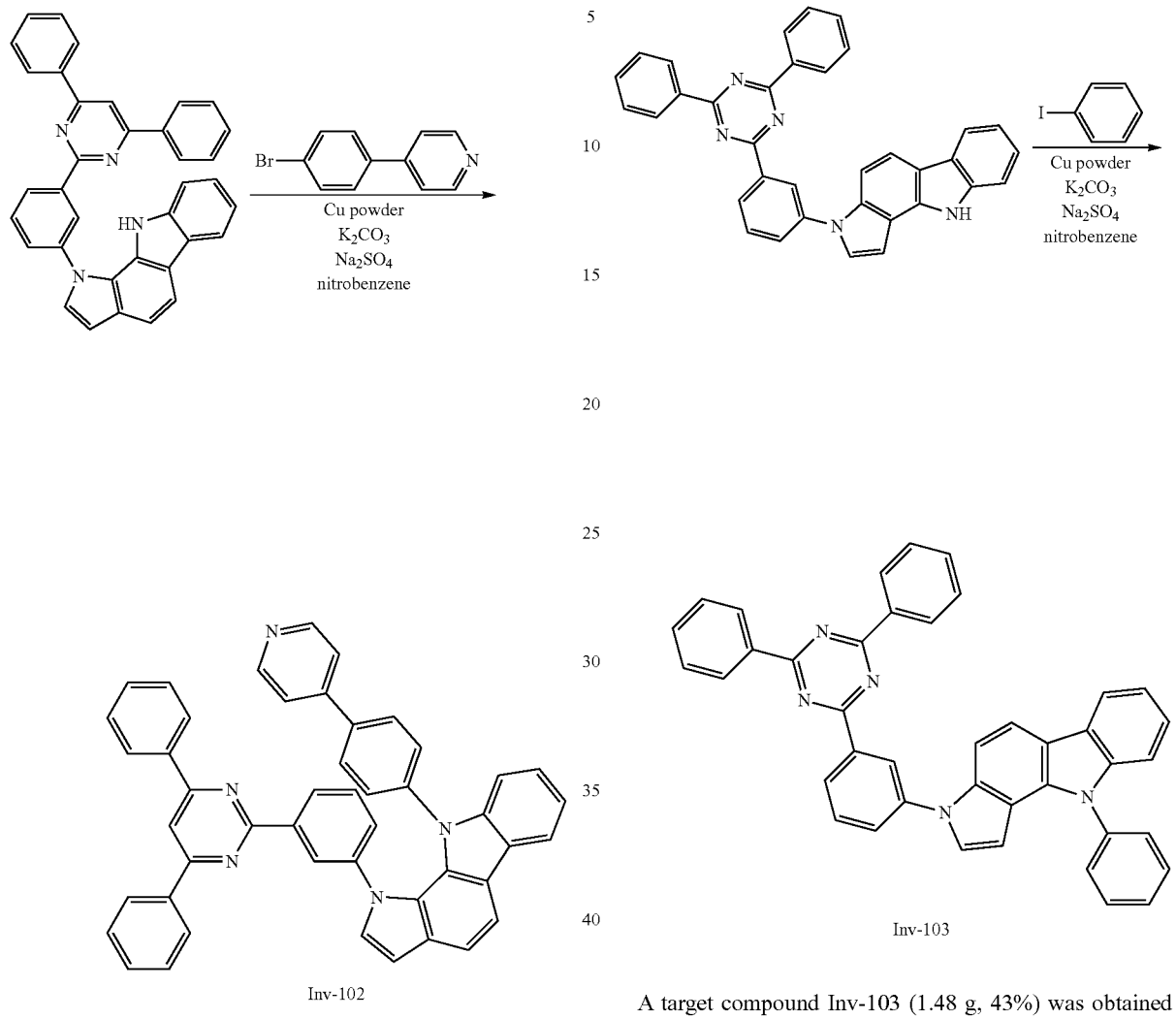

Inv-102

Inv-103

A target compound Inv-102 (1.83 g, 47%) was obtained by performing the same procedure as in Synthesis Example 27, except that IC-29 and 4-(4-bromophenyl)pyridine were used instead of IC-1b and 3-bromobiphenyl.

GC-Mass (theoretical value: 665.26 g/mol, measured value: 665 g/mol)

A target compound Inv-103 (1.48 g, 43%) was obtained by performing the same procedure as in Synthesis Example 27, except that IC-30 and iodobenzene were used instead of IC-1b and 3-bromobiphenyl.

GC-Mass (theoretical value: 589.23 g/mol, measured value: 589 g/mol)

[Synthesis Example 104] Synthesis of Inv-104

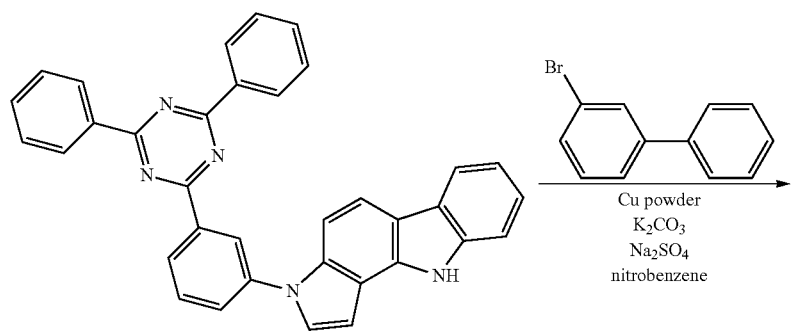

-continued
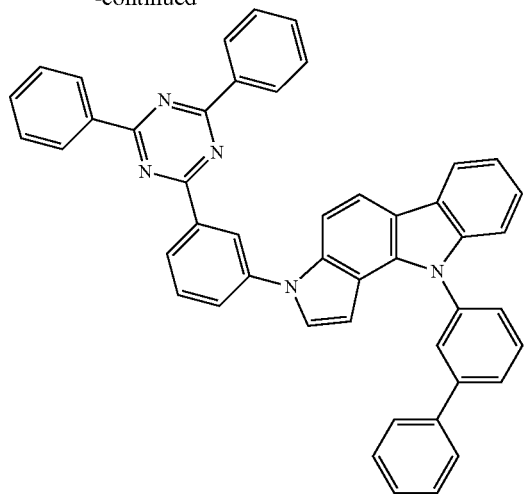
Inv-104
A target compound Inv-104 (1.87 g, 48%) was obtained by performing the same procedure as in Synthesis Example 27, except that IC-30 was used instead of IC-1b.
GC-Mass (theoretical value: 665.26 g/mol, measured value: 665 g/mol)
[Synthesis Example 105] Synthesis of Inv-105
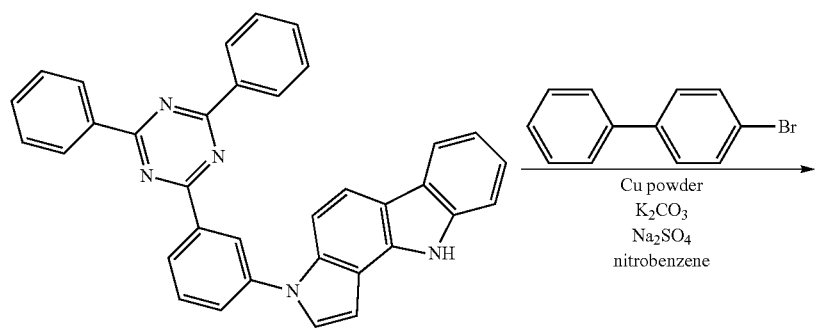
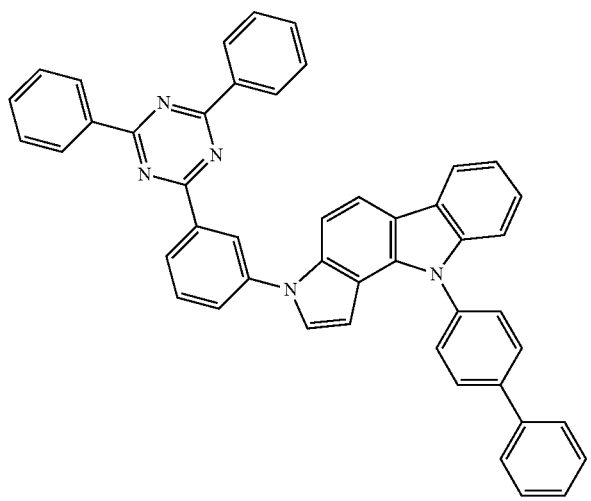
Inv-105

A target compound Inv-105 (1.75 g, 45%) was obtained by performing the same procedure as in Synthesis Example 27, except that IC-30 and 4-bromobiphenyl were used instead of IC-1b and 3-bromobiphenyl.

GC-Mass (theoretical value: 665.26 g/mol, measured value: 665.26 g/mol)

[Synthesis Example 106] Synthesis of Inv-106

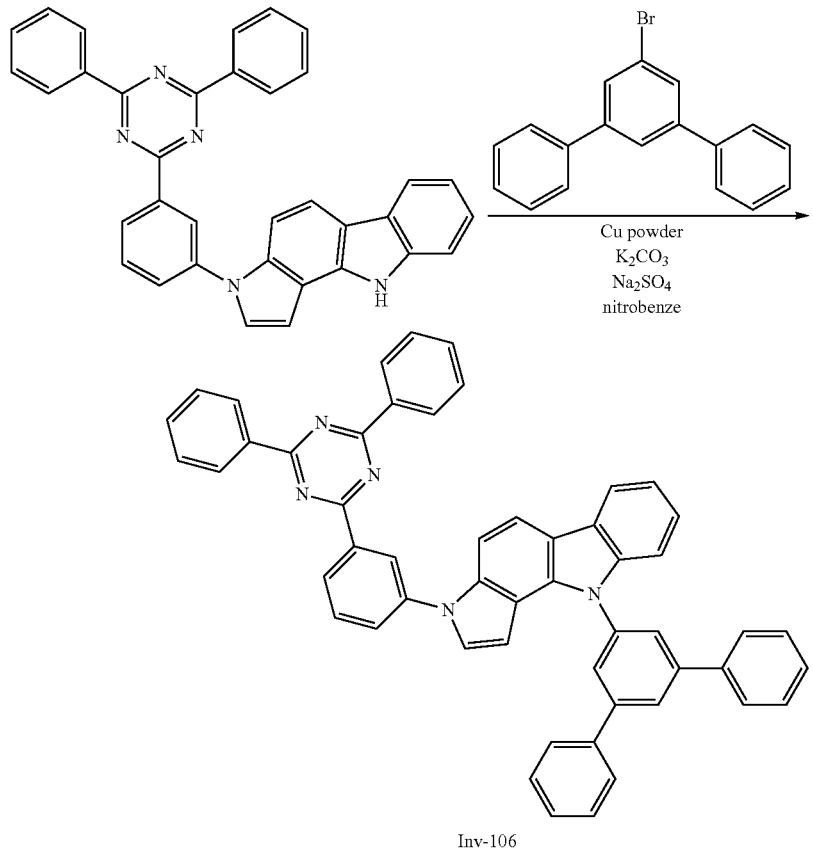

Inv-106

A target compound Inv-106 (2.12 g, 49%) was obtained by performing the same procedure as in Synthesis Example 27, except that IC-30 and 1-bromo-3,5-diphenyl benzene were used instead of IC-1b and 3-bromobiphenyl.

GC-Mass (theoretical value: 741.29 g/mol, measured value: 741 g/mol)

[Synthesis Example 107] Synthesis of Inv-107

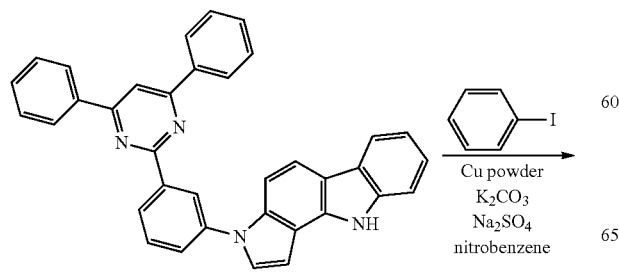

-continued

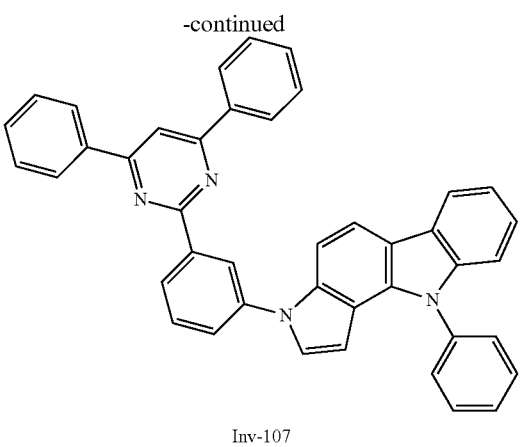

Inv-107

A target compound Inv-107 (1.79 g, 52%) was obtained by performing the same procedure as in Synthesis Example 27, except that IC-31 and iodobenzene were used instead of IC-1b and 3-bromobiphenyl.

GC-Mass (theoretical value: 588.23 g/mol, measured value: 588 g/mol)

[Synthesis Example 108] Synthesis of Inv-108
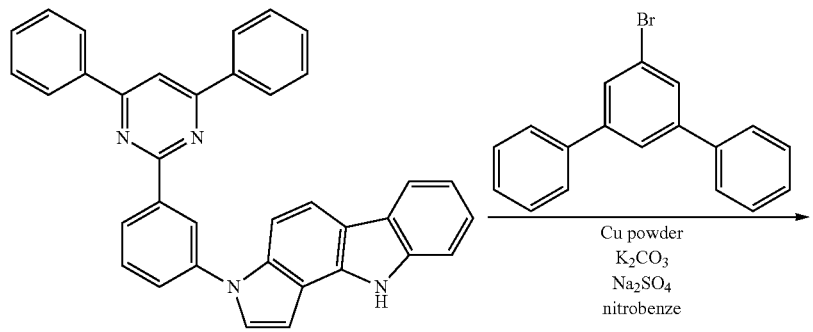
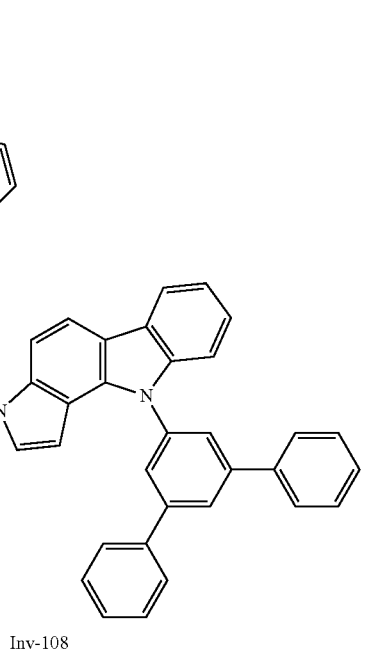
Inv-108
A target compound Inv-108 (1.99 g, 46%) was obtained by performing the same procedure as in Synthesis Example 27, except that IC-31 and 1-bromo-3,5-diphenyl benzene were used instead of IC-1b and 3-bromobiphenyl.
GC-Mass (theoretical value: 740.29 g/mol, measured value: 740 g/mol)
[Synthesis Example 109] Synthesis of Inv-109
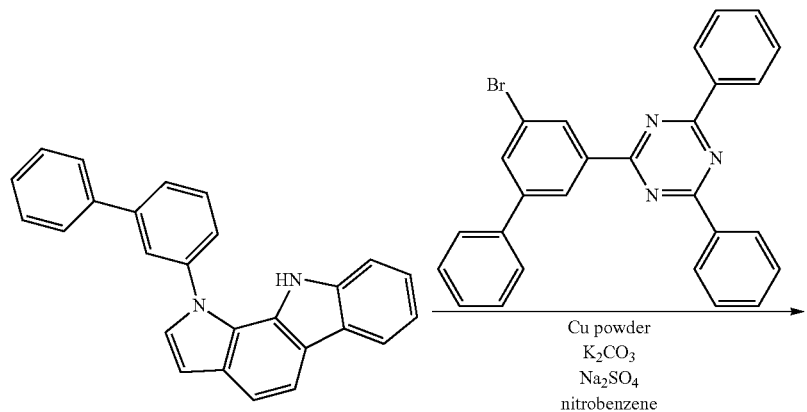

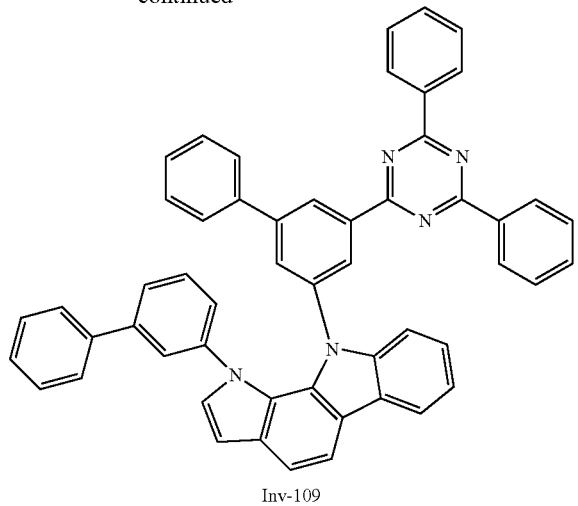

Inv-109

A target compound Inv-109 (3.54 g, 57%) was obtained by performing the same procedure as in Synthesis Example 27, except that IC-17 and 2-(5-bromobiphenyl-3-yl)-4,6-diphenyl-1,3,5-triazine were used instead of IC-1b and 3-bromobiphenyl.

GC-Mass (theoretical value: 741.29 g/mol, measured value: 741 g/mol)

[Synthesis Example 110] Synthesis of Inv-110

A target compound Inv-110 (2.61 g, 53%) was obtained by performing the same procedure as in Synthesis Example 27, except that IC-23 and 2.2'-(5-bromo-1,3-phenylene)dipyridine were used instead of IC-1b and 3-bromobiphenyl.

GC-Mass (theoretical value: 588.23 g/mol, measured value: 588 g/mol)

[Preparation Example 32] Synthesis of IC-32a and IC-32b

<Step 1> Synthesis of 2-(benzo[b]thiophen-5-yl)-4,4,5,5-tetramethyl-1,3,2-dioxaborolane

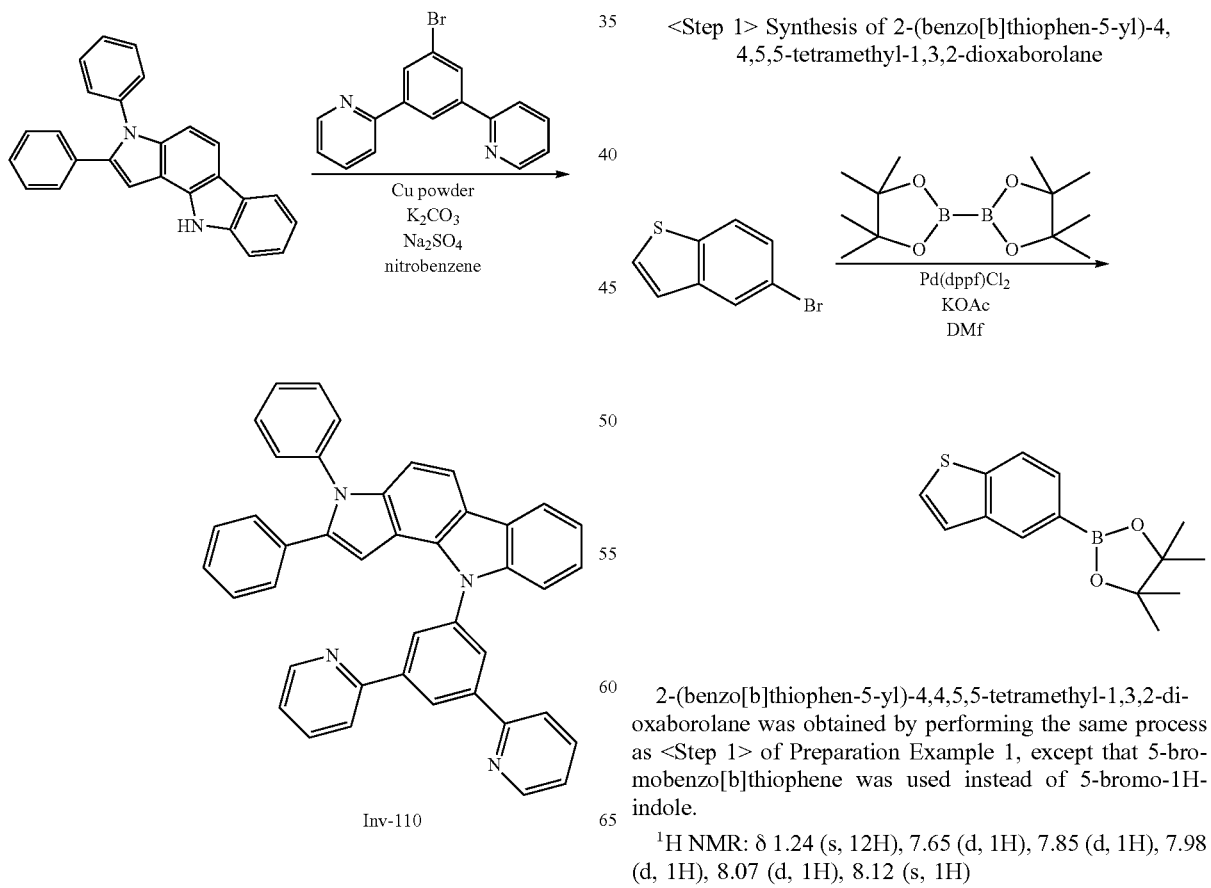

Inv-110

2-(benzo[b]thiophen-5-yl)-4,4,5,5-tetramethyl-1,3,2-dioxaborolane was obtained by performing the same process as <Step 1> of Preparation Example 1, except that 5-bromobenzo[b]thiophene was used instead of 5-bromo-1H-indole.

$^1$H NMR: δ 1.24 (s, 12H), 7.65 (d, 1H), 7.85 (d, 1H), 7.98 (d, 1H), 8.07 (d, 1H), 8.12 (s, 1H)

<Step 2> Synthesis of 5-(2-nitrophenyl)benzo[b]thiophene

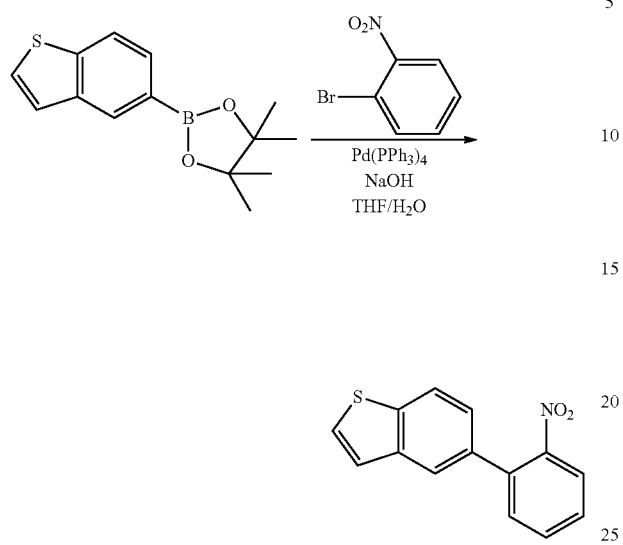

5-(2-nitrophenyl)benzo[b]thiophene was obtained by performing the same procedure as in <Step 2> of Preparation Example 1, except that 2-(benzo[b]thiophen-5-yl)-4,4,5,5-tetramethyl-1,3,2-dioxaborolane obtained in <Step 1> was used instead of 5-(4,4,5,5-tetramethyl-1,3,2-dioxaborolan-2-yl)-1H-indole.

$^1$H NMR: δ 7.67 (m, 2H), 7.88 (m, 2H), 7.98 (d, 1H), 8.00 (d, 1H), 8.07 (m, 2H), 8.13 (s, 1H)

<Step 3> Synthesis of IC-32a and IC-32b

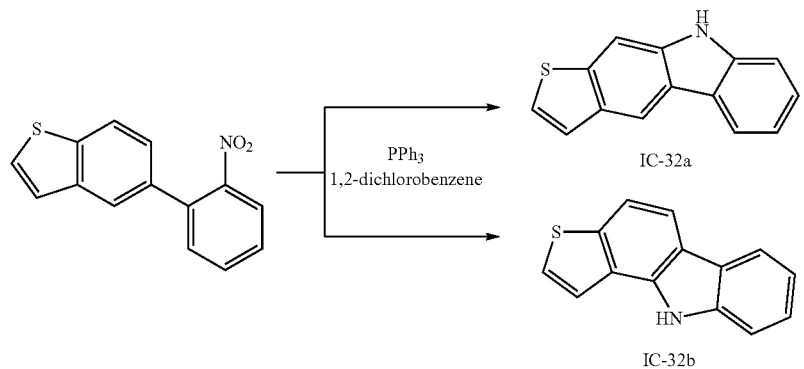 [SMILES: O=[N+]([O-])c1ccccc1-c1ccc2sccc2c1 ; c1ccc2c(c1)[nH]c1cc3sccc3cc12 ; c1ccc2c(c1)[nH]c1c3ccsc3ccc21]

1.70 g (7.60 mmol, yield: 35%) of IC-32a and 1.89 g (8.46 mmol, yield: 39%) of IC-32b were obtained by performing the same procedure as in <Step 4> of Preparation Example 1, except that 5-(2-nitrophenyl)benzo[b]thiophene obtained in <Step 2> was used instead of 5-(2-nitrophenyl)-1-phenyl-1H-indole.

$^1$H-NMR for IC-32a: δ 7.29 (t, 1H), 7.59 (m, 3H), 7.79 (m, 3H), 8.11 (d, 1H), 8.26 (s, 1H)

$^1$H-NMR for IC-32b: δ 7.29 (t, 1H), 7.53 (m, 2H), 7.81 (m, 3H), 8.12 (m, 2H), 8.25 (s, 1H)

[Preparation Example 33] Synthesis of IC-33

<Step 1> Synthesis of 4-(2-isopropylphenyl)-1H-indole

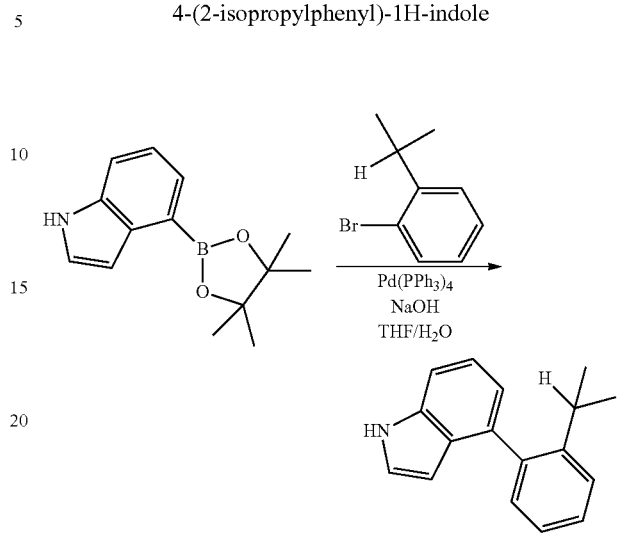

4-(2-isopropylphenyl)-1H-indole was obtained by performing the same procedure as in <Step 1> of Preparation Example 1, except that 4-(4,4,5,5-tetramethyl-1,3,2-dioxaborolan-2-yl)-1H-indole was used instead of 5-(4,4,5,5-tetramethyl-1,3,2-dioxaborolan-2-yl)-1H-indole, and 1-bromo-2-isopropylbenzene was used instead of 1-bromo-2-nitrobenzene.

$^1$H NMR: δ 1.21 (s, 6H), 2.87 (m, 1H), 6.43 (d, 1H), 7.26 (t, 1H), 7.35 (m, 3H), 7.48 (d, 1H), 7.74 (m, 2H), 7.85 (d, 1H), 8.23 (s, 1H)

<Step 2> Synthesis of IC-33

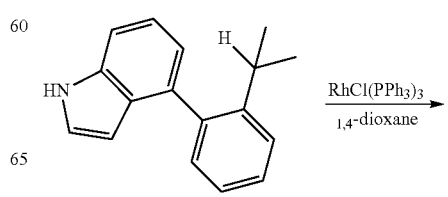

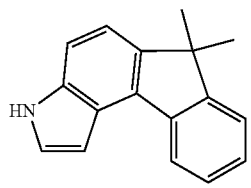

4-(2-isopropylphenyl)-1H-indole (5 g, 21.25 mmol) obtained in <Step 1> and RhCl(PPh$_3$)$_3$ (98.3 mg, 0.5 mol %) were dissolved in 50 ml of 1,4-dioxane under nitrogen flow, and the solution stirred at 135° C. for 1 hour.

After the reaction was completed, the solvent was removed, and the residue was purified by column chromatography (Hexane:MC=3:1 (v/v)), thereby obtaining IC-33 (4 g, yield 81%).

$^1$H NMR: δ 1.20 (s, 6H), 6.45 (d, 1H), 7.25 (d, 1H), 7.37 (m, 3H), 7.49 (d, 1H), 7.75 (d, 1H), 7.86 (d, 1H), 8.22 (s, 1H)

[Preparation Example 34] Synthesis of IC-34

<Step 1> Synthesis of 4-(2-benzhydrylphenyl)-1H-indole

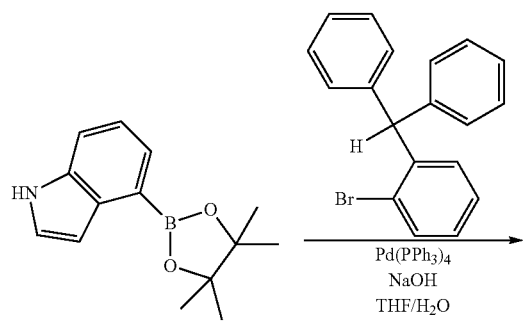

4-(2-benzhydrylphenyl)-1H-indole was obtained by performing the same process as <Step 2> of Preparation Example 1, except that 4-(4,4,5,5-tetramethyl-1,3,2-dioxaborolan-2-yl)-1H-indole was used instead of 5-(4,4,5,5-tetramethyl-1,3,2-dioxaborolan-2-yl)-1H-indole, and (2-bromophenyl)methylene)dibenzene was used instead of 1-bromo-2-nitrobenzene.

$^1$H NMR: δ 2.88 (m, 1H), 6.44 (d, 1H), 7.27 (m, 6H), 7.34 (m, 8H), 7.47 (d, 1H), 7.75 (m, 2H), 7.86 (d, 1H), 8.21 (s, 1H)

<Step 2> Synthesis of IC-34

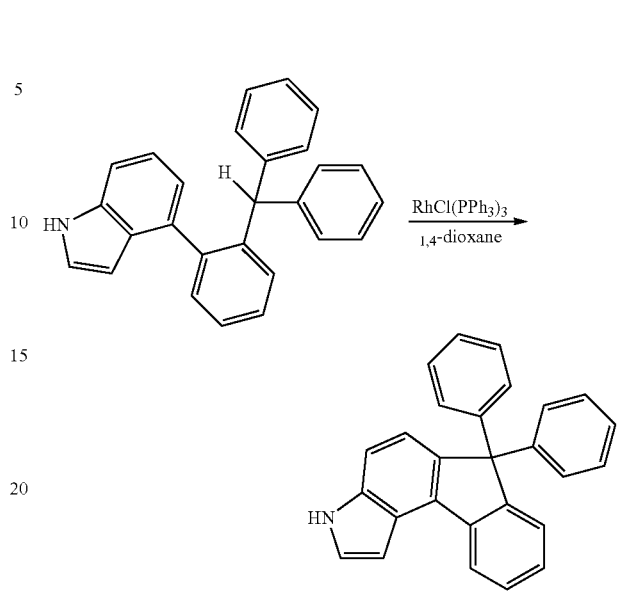

IC-34 was obtained by performing the same procedure as in <Step 2> of Preparation Example 11, except that 4-(2-benzhydrylphenyl)-1H-indole obtained in <Step 1> was used instead of 4-(2-isopropylphenyl)-1H-indole $^1$H NMR: δ 6.43 (d, 1H), 7.26 (m, 5H), 7.34 (m, 8H), 7.46 (d, 1H), 7.76 (m, 2H), 7.85 (d, 1H), 8.20 (s, 1H)

[Preparation Example 35] Synthesis of IC-35

<Step 1> Synthesis of 6-(2-bromophenyl)-7-chloro-1H-indole

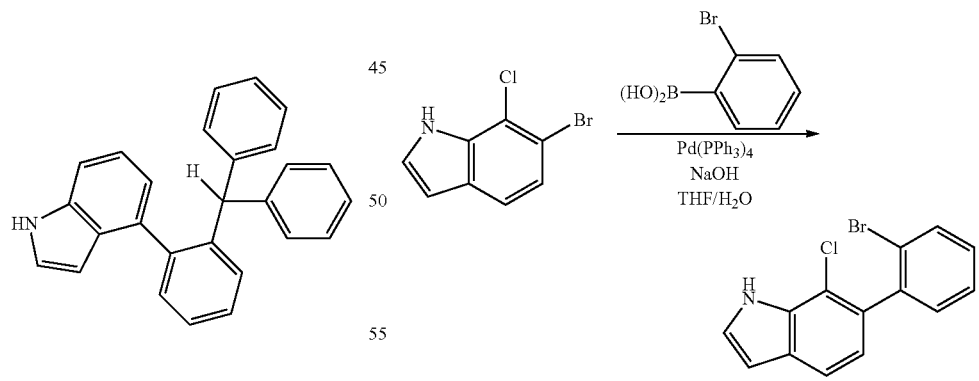

9.13 g (39.6 mmol) of 6-bromo-7-chloro-1H-indole, 9.54 g (47.5 mmol) of 2-bromophenylboronic acid, 4.75 g (118.8 mmol) of NaOH, and 200 ml/100 ml of THF/H$_2$O were mixed under nitrogen flow, and the mixture was stirred. 2.29 g (5 mol %) of Pd(PPh$_3$)$_4$ was added thereto at 40° C., and the resulting mixture was stirred at 80° C. for 12 hours. After the reaction was completed, extraction was performed with methylene chloride, MgSO$_4$ was added thereto, and the mixture was filtered. After the solvent was removed from the filtered organic layer, 8.86 g (28.9 mmol, yield: 73%) of a target compound 6-(2-bromophenyl)-7-chloro-1H-indole was obtained by using column chromatography.

¹H-NMR: δ 6.45 (d, 1H), 7.35 (m, 3H), 7.74 (m, 3H), 8.06 (d, 1H), 8.64 (s, 1H)

<Step 2> Synthesis of Ethyl 3-(2-(7-chloro-1H-indol-6-yl)phenylthio)propanoate

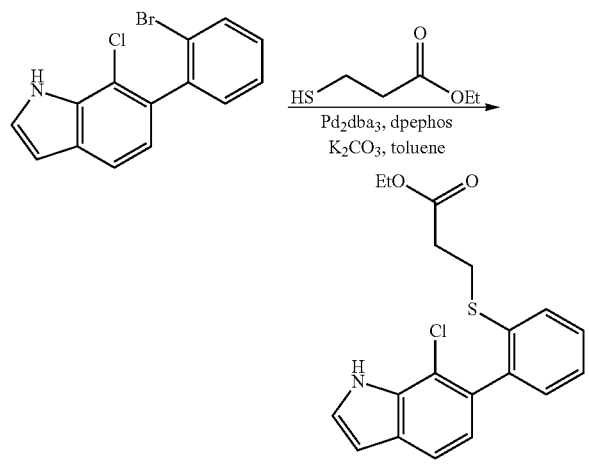

7.45 g (24.3 mmol) of 6-(2-bromophenyl)-7-chloro-1H-indole, 3.59 g (26.77 mmol) of ethyl 3-mercaptopropanoate, 167 mg (0.18 mmol) of Pd₂dba₃, 197 mg (0.37 mmol) of dpephos, and 8.4 g (61 mmol) of K₂CO₃ were added to 100 ml of toluene under nitrogen flow, and the mixture was stirred at 110° C. for 15 hours. After the reaction was completed, extraction was performed with methylene chloride, MgSO₄ was added thereto, and the mixture was filtered. After the solvent was removed from the filtered organic layer, 6.38 g (17.7 mmol, yield: 73%) of a target compound ethyl 3-(2-(7-chloro-1H-indol-6-yl)phenylthio)propanoate was obtained by using column chromatography.

¹H-NMR: δ 1.29 (t, 3H), 2.58 (t, 2H), 3.12 (t, 2H), 4.12 (q, 2H), 6.25 (d, 1H), 7.37 (m, 4H), 7.70 (m, 2H), 8.06 (d, 1H), 8.60 (s, 1H)

<Step 3> Synthesis of IC-35

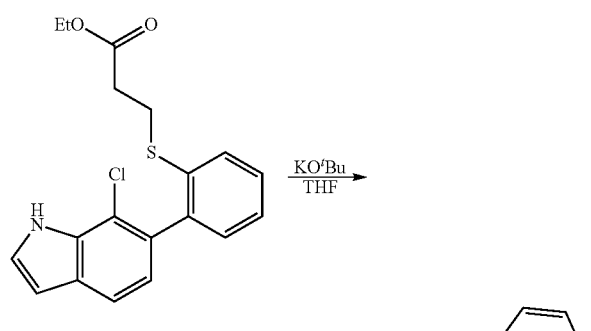

6.34 g (15.4 mmol) of ethyl 3-(2-(7-chloro-1H-indol-6-yl)phenylthio)propanoate and 2.60 g (23.2 mmol) of potassium tert-butoxide were added to 100 ml of THF under nitrogen flow, and the mixture was stirred at 50° C. for 8 hours. After the reaction was completed, extraction was performed with methylene chloride, MgSO₄ was added thereto, and the mixture was filtered. After the solvent was removed from the filtered organic layer, 2.30 g (10.3 mmol, yield: 67%) of IC-35 was obtained by using column chromatography.

¹H-NMR: δ 6.44 (d, 1H), 7.25 (d, 1H), 7.51 (m, 3H), 8.00 (m, 2H), 8.40 (d, 1H), 8.63 (s, 1H)

[Preparation Example 36] Synthesis of IC-36

<Step 1> Synthesis of 5-(2-bromophenyl)-6-chloro-1H-indole

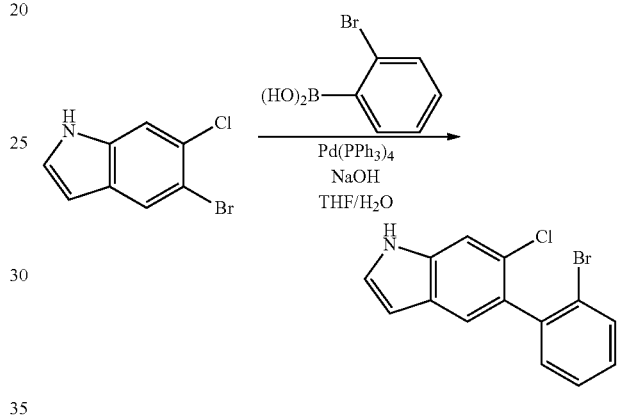

8.62 g (28.1 mmol, yield: 71%) of 5-(2-bromophenyl)-6-chloro-1H-indole was obtained by performing the same procedure as in <Step 1> of Preparation Example 35, except that 9.13 g (39.6 mmol) of 5-bromo-6-chloro-1H-indole was used instead of 6-bromo-7-chloro-1H-indole.

¹H-NMR: δ 6.44 (d, 1H), 7.34 (m, 4H), 7.61 (m, 3H), 8.59 (s, 1H)

<Step 2> Synthesis of Ethyl 3-(2-(6-chloro-1H-indol-5-yl)phenylthio)propanoate

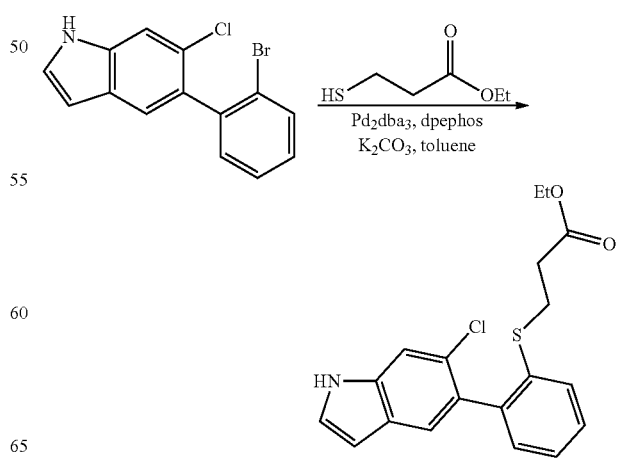

6.73 g (18.71 mmol, yield: 77%) of ethyl 3-(2-(6-chloro-1H-indol-5-yl)phenylthio)propanoate was obtained by performing the same procedure as in <Step 2> of Preparation Example 35, except that 7.45 g (24.3 mmol) of 5-(2-bromophenyl)-6-chloro-1H-indole was used instead of 6-(2-bromophenyl)-7-chloro-1H-indole.

¹H-NMR: δ 1.29 (t, 3H), 2.58 (t, 2H), 3.17 (t, 2H), 4.13 (q, 2H), 6.35 (d, 1H), 7.39 (m, 5H), 7.70 (m, 2H), 8.64 (s, 1H)

<Step 3> Synthesis of IC-36

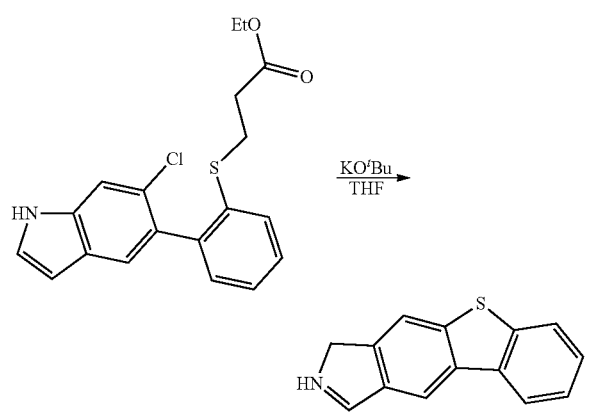

2.44 g (10.9 mmol, yield: 71%) of IC-36 was obtained by performing the same procedure as in <Step 3> of Preparation Example 35, except that 6.34 g (15.4 mmol) of ethyl 3-(2-(6-chloro-1H-indol-5-yl)phenylthio)propanoate was used instead of ethyl 3-(3-(2-chloro-9H-carbazol-3-yl)pyridin-2-ylthio)propanoate.

¹H-NMR: δ 6.50 (d, 1H), 7.51 (m, 3H), 7.71 (d, 1H), 8.01 (m, 2H), 8.45 (d, 1H), 8.68 (s, 1H)

[Preparation Example 37] Synthesis of IC-37

<Step 1> Synthesis of 4-(2-bromophenyl)-5-chloro-1H-indole

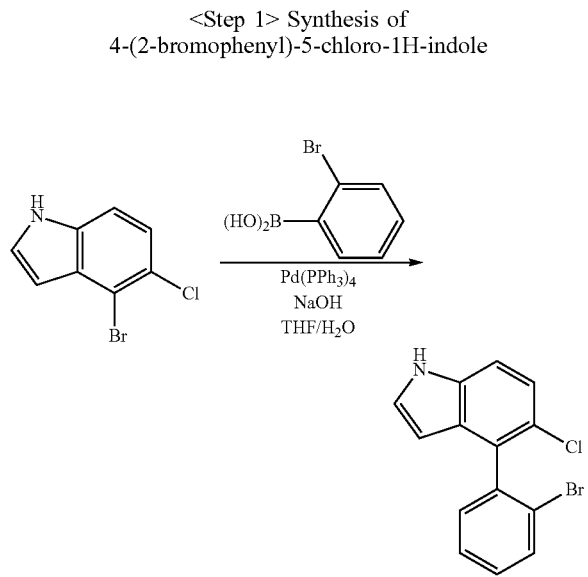

8.50 g (27.7 mmol, yield: 70%) of 4-(2-bromophenyl)-5-chloro-1H-indole was obtained by performing the same procedure as in <Step 1> of Preparation Example 35, except that 9.13 g (39.6 mmol) of 4-bromo-5-chloro-1H-indole was used instead of 6-bromo-7-chloro-1H-indole.

¹H-NMR: δ 6.48 (d, 1H), 7.39 (m, 4H), 7.62 (m, 3H), 8.61 (s, 1H)

<Step 2> Synthesis of Ethyl 3-(2-(5-chloro-1H-indol-4-yl)phenylthio)propanoate

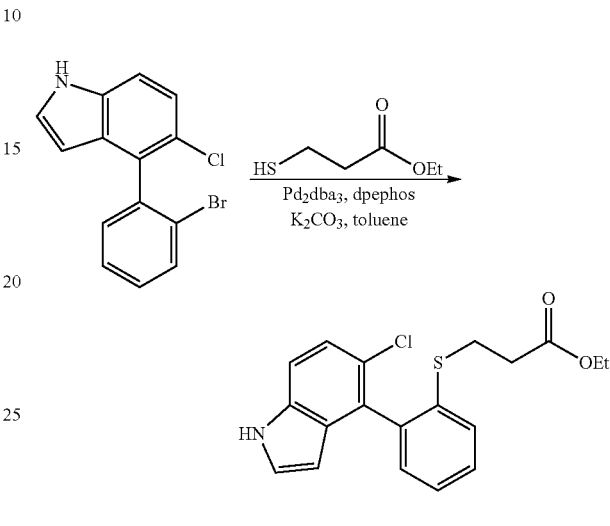

6.56 g (18.2 mmol, yield: 75%) of entyl 3-(2-(5-chloro-1H-indol-4-yl)phenylthio)propanoate was obtained by performing the same procedure as in <Step 2> of Preparation Example 35, except that 7.45 g (24.3 mmol) of 4-(2-bromophenyl)-5-chloro-1H-indole was used instead of 6-(2-bromophenyl)-7-chloro-1H-indole.

¹H-NMR: δ 1.28 (t, 3H), 2.58 (t, 2H), 3.11 (t, 2H), 4.12 (q, 2H), 6.27 (d, 1H), 7.27 (m, 4H), 7.55 (m, 3H), 8.61 (s, 1H)

<Step 3> Synthesis of IC-37

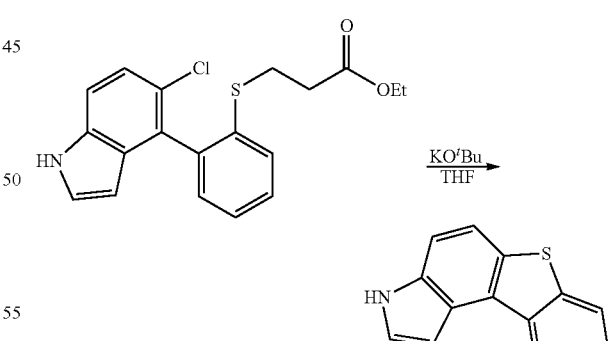

2.68 g (12.0 mmol, yield: 78%) of IC-37 was obtained by performing the same procedure as in <Step 3> of Preparation Example 35, except that 6.34 g (15.4 mmol) of ethyl 3-(2-(5-chloro-1H-indol-4-yl)phenylthio)propanoate was used instead of ethyl 3-(3-(2-chloro-9H-carbazol-3-yl)pyridin-2-ylthio)propanoate.

¹H-NMR: δ 6.50 (d, 1H), 7.31 (m, 2H), 7.51 (m, 2H), 8.01 (m, 2H), 8.44 (d, 1H), 8.58 (s, 1H)

[Preparation Example 38] Synthesis of IC-38

<Step 1> Synthesis of 7-(2-bromophenyl)-6-chloro-1H-indole

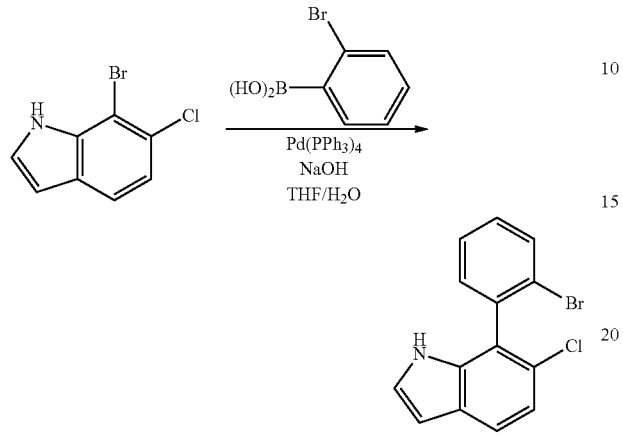

9.59 g (31.3 mmol, yield: 79%) of 7-(2-bromophenyl)-6-chloro-1H-indole was obtained by performing the same procedure as in <Step 1> of Preparation Example 35, except that 9.13 g (39.6 mmol) of 7-bromo-6-chloro-1H-indole was used instead of 6-bromo-7-chloro-1H-indole.

¹H-NMR: δ 6.48 (d, 1H), 7.06 (d, 1H), 7.33 (m, 3H), 7.62 (m, 2H), 8.01 (d, 1H), 8.71 (s, 1H)

<Step 2> Synthesis of Ethyl 3-(2-(6-chloro-1H-indol-7-yl)phenylthio)propanoate

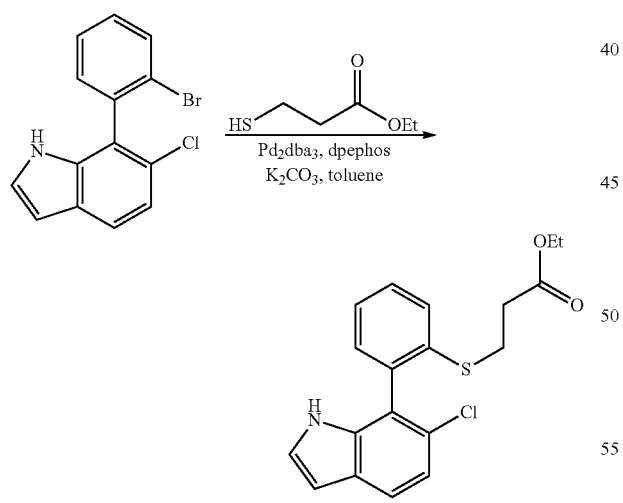

6.47 g (18.0 mmol, yield: 74%) of ethyl 3-(2-(6-chloro-1H-indol-7-yl)phenylthio)propanoate was obtained by performing the same procedure as in <Step 2> of Preparation Example 35, except that 7.45 g (24.3 mmol) of 7-(2-bromophenyl)-6-chloro-1H-indole was used instead of 6-(2-bromophenyl)-7-chloro-1H-indole.

¹H-NMR: δ 1.29 (t, 3H), 2.58 (t, 2H), 3.13 (t, 2H), 4.12 (q, 2H), 6.24 (d, 1H), 7.06 (d, 1H), 7.27 (m, 3H), 7.70 (m, 2H), 8.00 (d, 1H), 8.61 (s, 1H)

<Step 3> Synthesis of IC-38

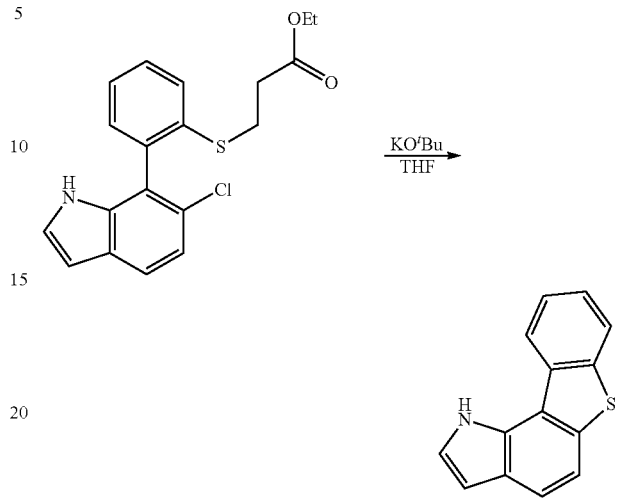

2.48 g (11.1 mmol, yield: 72%) of IC-38 was obtained by performing the same procedure as in <Step 3> of Preparation Example 35, except that 6.34 g (15.4 mmol) of ethyl 3-(2-(6-chloro-1H-indol-7-yl)phenylthio)propanoate was used instead of ethyl 3-(3-(2-chloro-9H-carbazol-3-yl)pyridin-2-ylthio)propanoate.

¹H-NMR: δ 6.44 (d, 1H), 7.51 (m, 4H), 7.89 (m, 2H), 8.48 (d, 1H), 8.68 (s, 1H)

[Preparation Example 39] Synthesis of IC-39

<Step 1> Synthesis of 6-(2-bromophenyl)-5-chloro-1H-indole

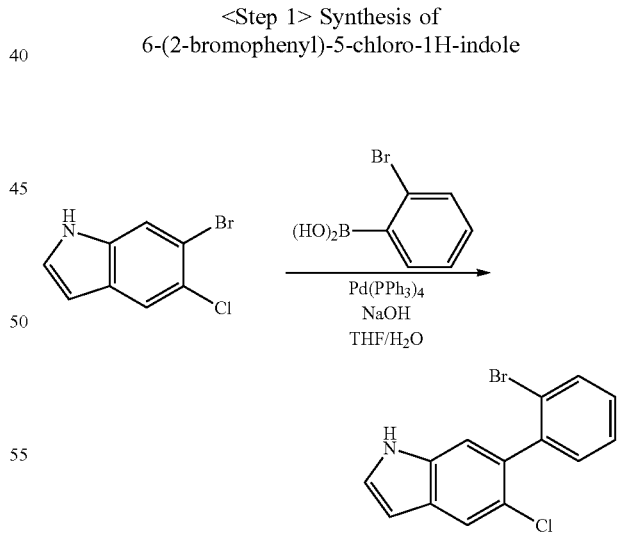

8.13 g (26.5 mmol, yield: 67%) of 6-(2-bromophenyl)-5-chloro-1H-indole was obtained by performing the same procedure as in <Step 1> of Preparation Example 35, except that 9.13 g (39.6 mmol) of 6-bromo-5-chloro-1H-indole was used instead of 6-bromo-7-chloro-1H-indole.

¹H-NMR: δ 6.45 (d, 1H), 7.29 (m, 3H), 7.62 (m, 4H), 8.71 (s, 1H)

<Step 2> Synthesis of Ethyl 3-(2-(5-chloro-1H-indol-6-yl)phenylthio)propanoate

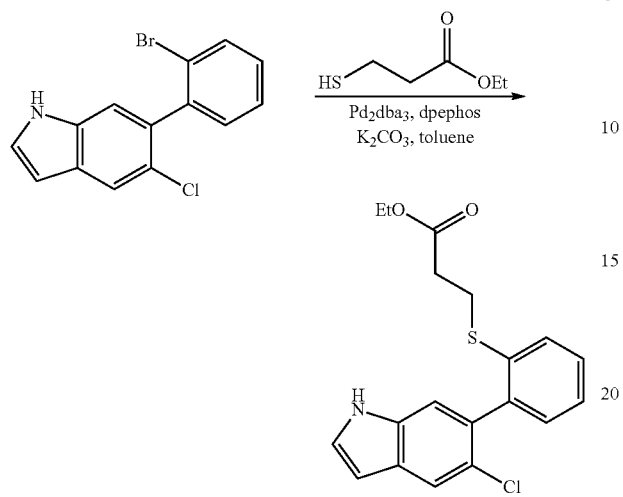

7.00 g (19.4 mmol, yield: 81%) of ethyl 3-(2-(5-chloro-1H-indol-6-yl)phenylthio)propanoate was obtained by performing the same procedure as in <Step 2> of Preparation Example 35, except that 7.45 g (24.3 mmol) of 6-(2-bromophenyl)-5-chloro-1H-indole was used instead of 6-(2-bromophenyl)-7-chloro-1H-indole.

$^1$H-NMR: δ 1.29 (t, 3H), 2.58 (t, 2H), 3.12 (t, 2H), 4.13 (q, 2H), 6.26 (d, 1H), 7.37 (m, 4H), 7.66 (m, 3H), 8.61 (s, 1H)

<Step 3> Synthesis of IC-39

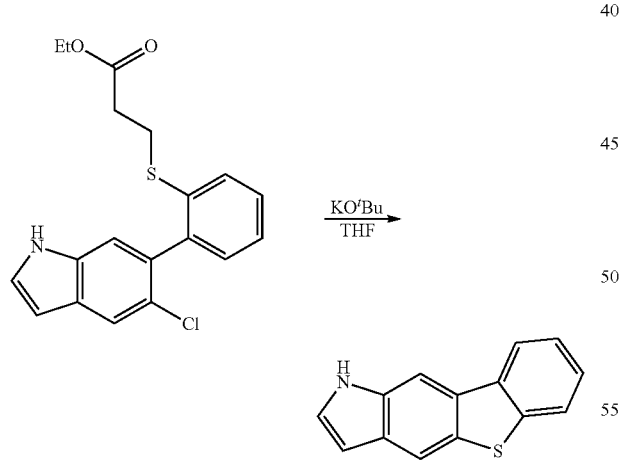

2.58 g (11.5 mmol, yield: 75%) of IC-39 was obtained by performing the same procedure as in <Step 3> of Preparation Example 35, except that 6.34 g (15.4 mmol) of ethyl 3-(2-(5-chloro-1H-indol-6-yl)phenylthio)propanoate was used instead of ethyl 3-(3-(2-chloro-9H-carbazol-3-yl)pyridin-2-ylthio)propanoate.

$^1$H-NMR: δ 6.45 (d, 1H), 7.31 (d, 1H), 7.50 (m, 2H), 7.81 (m, 2H), 8.01 (d, 1H), 8.48 (d, 1H), 8.68 (s, 1H)

[Preparation Example 40] Synthesis of IC-40

<Step 1> Synthesis of 5-(2-bromophenyl)-4-chloro-1H-indole

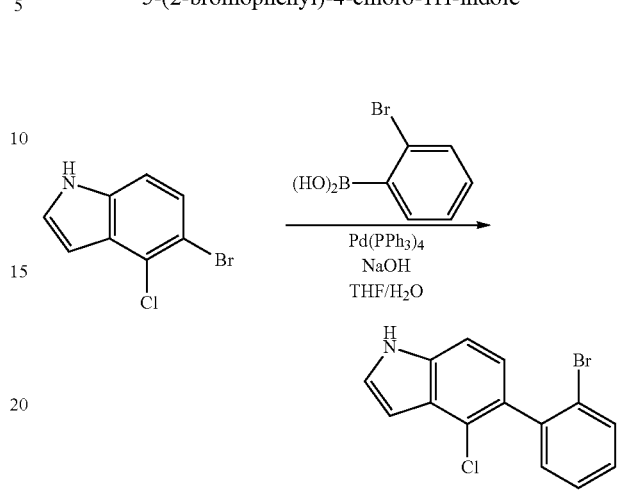

8.98 g (29.3 mmol, yield: 74%) of 5-(2-bromophenyl)-4-chloro-1H-indole was obtained by performing the same procedure as in <Step 1> of Preparation Example 35, except that 9.13 g (39.6 mmol) of 4-bromo-5-chloro-1H-indole was used instead of 5-bromo-4-chloro-1H-indole.

$^1$H-NMR: δ 6.44 (d, 1H), 7.38 (m, 3H), 7.59 (m, 3H), 7.82 (d, 1H), 8.71 (s, 1H)

<Step 2> Synthesis of Ethyl 3-(2-(4-chloro-1H-indol-5-yl)phenylthio)propanoate

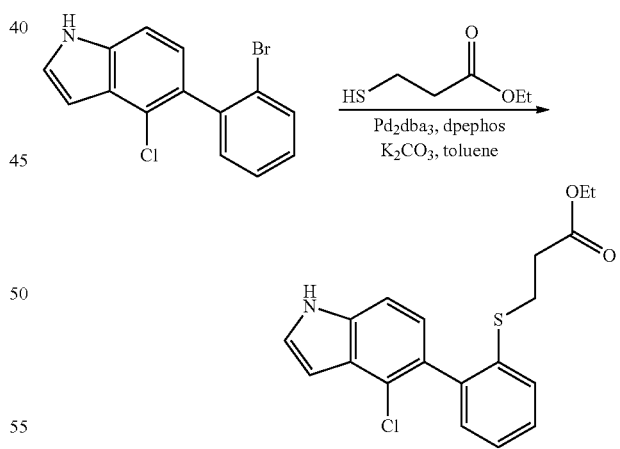

6.82 g (19.0 mmol, yield: 78%) of ethyl 3-(2-(4-chloro-1H-indol-5-yl)phenylthio)propanoate was obtained by performing the same procedure as in <Step 2> of Preparation Example 35, except that 7.45 g (24.3 mmol) of 5-(2-bromophenyl)-4-chloro-1H-indole was used instead of 6-(2-bromophenyl)-7-chloro-1H-indole.

$^1$H-NMR: δ 1.30 (t, 3H), 2.58 (t, 2H), 3.12 (t, 2H), 4.11 (q, 2H), 6.25 (d, 1H), 7.33 (m, 4H), 7.65 (m, 3H), 8.61 (s, 1H)

\<Step 3\> Synthesis of IC-40

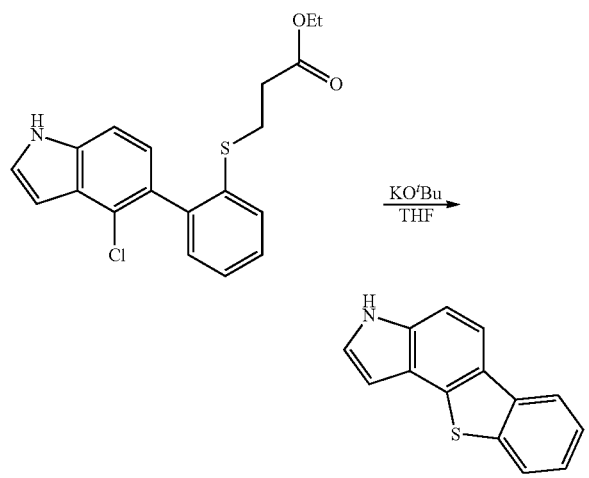

2.58 g (11.6 mmol, yield: 75%) of IC-40 was obtained by performing the same procedure as in \<Step 3\> of Preparation Example 35, except that 6.34 g (15.4 mmol) of ethyl 3-(2-(4-chloro-1H-indol-5-yl)phenylthio)propanoate was used instead of ethyl 3-(3-(2-chloro-9H-carbazol-3-yl)pyridin-2-ylthio)propanoate.

$^1$H-NMR: δ 6.43 (d, 1H), 7.33 (m, 2H), 7.51 (m, 2H), 7.99 (m, 2H), 8.48 (d, 1H), 8.68 (s, 1H)

[Preparation Example 41] Synthesis of IC-41

\<Step 1\> Synthesis of 7-(2-nitrophenyl)benzo[b]thiophene

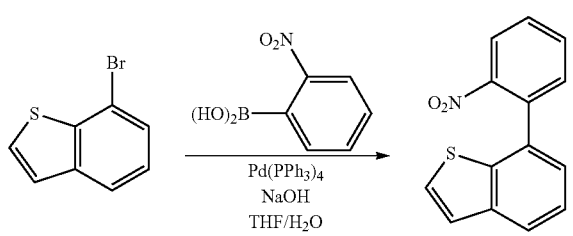 [SMILES: Brc1cccc2ccsc12 ; O=[N+]([O-])c1ccccc1B(O)O ; O=[N+]([O-])c1ccccc1-c1cccc2ccsc12]

12.2 g (35.2 mmol) of 7-bromobenzo[b]thiophene, 6.44 g (38.7 mmol) of 2-nitrophenylboronic acid, 4.22 g (105.6 mmol) of NaOH, and 300 ml/150 ml of THF/H$_2$O were mixed under nitrogen flow, and the mixture was stirred. 2.03 g (5 mol %) of Pd(PPh$_3$)$_4$ was added thereto at 40° C., and the resulting mixture was stirred at 80° C. for 12 hours. After the reaction was completed, extraction was performed with methylene chloride, MgSO$_4$ was added thereto, and the mixture was filtered. After the solvent was removed from the filtered organic layer, 7.38 g (28.9 mmol, yield 82%) of 7-(2-nitrophenyl)benzo[b]thiophene was obtained by using column chromatography.

$^1$H-NMR: δ 7.63 (m, 5H), 7.96 (m, 3H), 8.21 (d, 1H)

\<Step 2\> Synthesis of IC-41

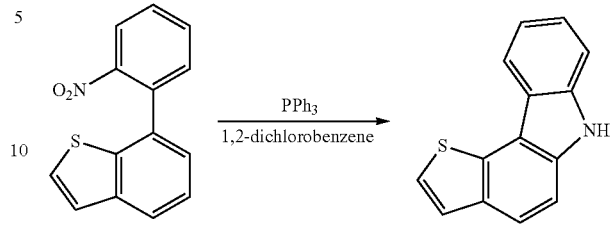

5.53 g (21.7 mmol) of 7-(2-nitrophenyl)benzo[b]thiophene, 14.2 g (54.2 mmol) of triphenylphosphine, and 100 ml of 1,2-dichlorobenzene were mixed under nitrogen flow, and then the mixture was stirred for 12 hours. After the reaction was completed, 1,2-dichlorobenzene was removed, and extraction was performed with dichloromethane. Water was removed from the extracted organic layer by MgSO$_4$, and 3.29 g (14.8 mmol, yield: 68%) of a target compound IC-41 was obtained by using column chromatography.

$^1$H-NMR: δ 7.37 (t, 1H), 7.46 (m, 5H), 7.87 (d, 1H), 8.20 (d, 1H), 8.24 (s, 1H)

[Preparation Example 42] Synthesis of IC-42a and IC-42b

\<Step 1\> Synthesis of 6-(2-nitrophenyl)benzo[b]thiophene

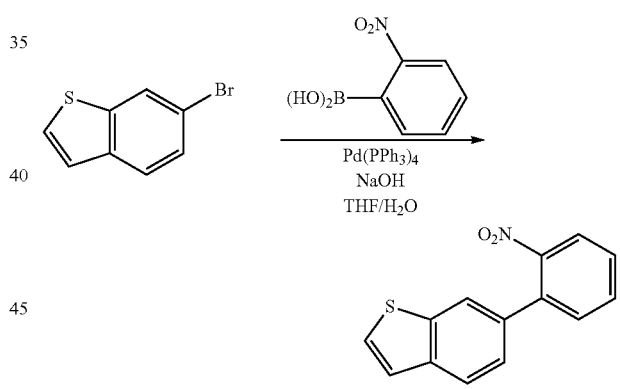

7.01 g (27.5 mmol, yield: 78%) of 6-(2-nitrophenyl)benzo[b]thiophene was obtained by performing the same procedure as in \<Step 1\> of Preparation Example 41, except that 12.2 g (35.2 mmol) of 6-bromobenzo[b]thiophene was used instead of 7-bromobenzo[b]thiophene.

$^1$H-NMR: δ 7.68 (m, 3H), 7.98 (m, 6H)<

\<Step 2\> Synthesis of IC-42a and IC-42b

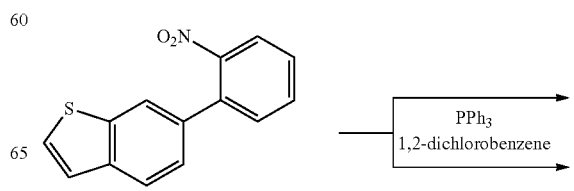

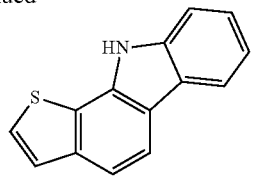

IC-42a

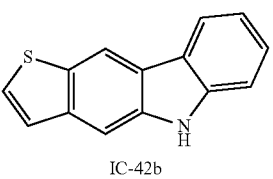

IC-42b 1.60 g (7.16 mmol, yield: 33%) of IC-42a and 1.79 g (8.03 mmol, yield: 37%) of IC-42b were obtained by performing the same procedure as in <Step 2> of Preparation Example 41, except that 5.53 g (21.7 mmol) of 6-(2-nitrophenyl)benzo[b]thiophene was used instead of 7-(2-nitrophenyl)benzo[b]thiophene.

$^1$H-NMR for IC-42a: δ 7.27 (t, 1H), 7.53 (m, 4H), 7.78 (d, 1H), 7.92 (d, 1H), 8.10 (d, 1H), 8.25 (s, 1H)

$^1$H-NMR for IC-42b: δ 7.29 (t, 1H), 7.63 (m, 3H), 7.79 (m, 3H), 8.11 (d, 1H), 8.25 (s, 1H)

[Preparation Example 43] Synthesis of IC-43

<Step 1> Synthesis of 4-(2-nitrophenyl)benzo[b]thiophene

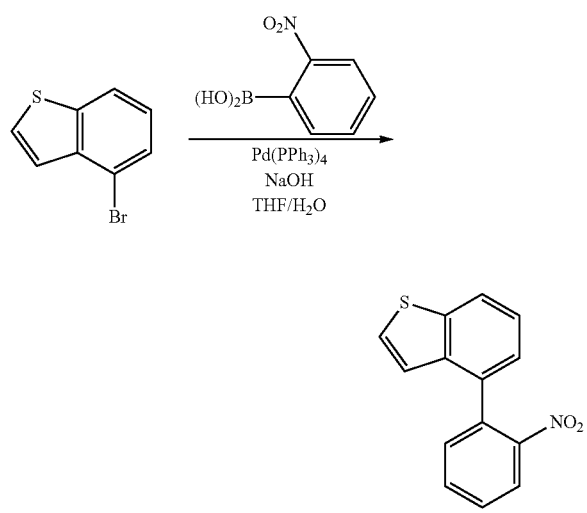 [SMILES: Brc1cccc2sccc12 ; O=[N+]([O-])c1ccccc1B(O)O ; O=[N+]([O-])c1ccccc1-c1cccc2sccc12]

7.28 g (28.5 mmol, yield: 81%) of 4-(2-nitrophenyl)benzo[b]thiophene was obtained by performing the same procedure as in <Step 1> of Preparation Example 41, except that 12.2 g (35.2 mmol) of 4-bromobenzo[b]thiophene was used instead of 7-bromobenzo[b]thiophene.

$^1$H-NMR: δ 7.68 (m, 4H), 7.89 (m, 3H), 8.01 (m, 2H)<Step 2> Synthesis of IC-43

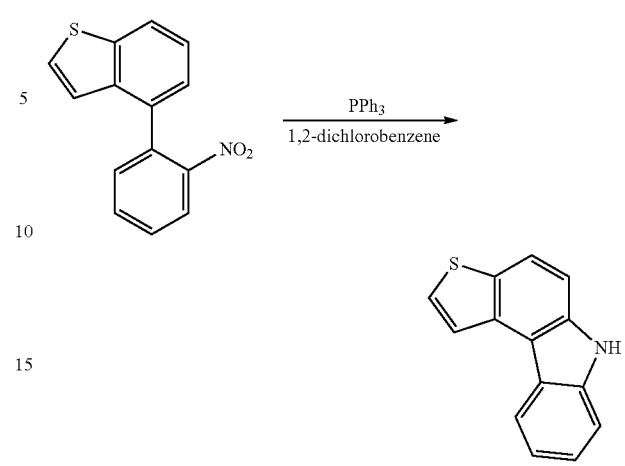

3.05 g (13.7 mmol, yield: 63%) of IC-43 was obtained by performing the same procedure as in <Step 2> of Preparation Example 41, except that 5.53 g (21.7 mmol) of 4-(2-nitrophenyl)benzo[b]thiophene was used instead of 7-(2-nitrophenyl)benzo[b]thiophene.

$^1$H-NMR: δ 7.31 (m, 2H), 7.73 (m, 4H), 7.96 (d, 1H), 8.10 (d, 1H), 8.26 (s, 1H)

[Preparation Example 44] Synthesis of IC-44

<Step 1> Synthesis of (6-bromodibenzo[b,d]thiophen-4-yl)trimethylsilane

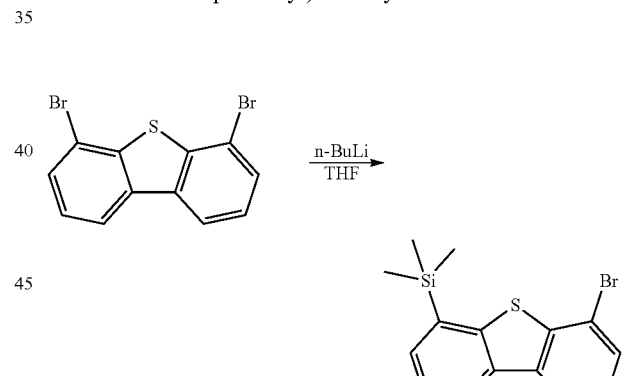

After 17.1 g (50.0 mmol) of 4,6-dibromodibenzo[b,d]thiophene was dissolved in 300 ml of THF under nitrogen flow, 19.6 ml (50.0 mmol) of n-butyllithium (2.5 M in hexane) was slowly added to the solution at −78° C., and after 30 minutes, the mixture was stirred at normal temperature for 1 hour, 5.43 g (50.0 mmol) of chlorotrimethylsilane was added thereto, and the resulting mixture was stirred at normal temperature for 12 hours. After the reaction was completed, extraction was performed with methylene chloride, MgSO$_4$ was added thereto, and the mixture was filtered. After the solvent was removed from the filtered organic layer, 10.2 g (30.5 mmol, yield: 61%) of (6-bromodibenzo[b,d]thiophen-4-yl)trimethylsilane was obtained by using column chromatography.

$^1$H-NMR: δ 0.27 (s, 9H), 7.48 (m, 4H), 8.41 (m, 2H)<

<Step 2> Synthesis of 6-(trimethylsilyl)dibenzo[b,d]thiophen-4-amine

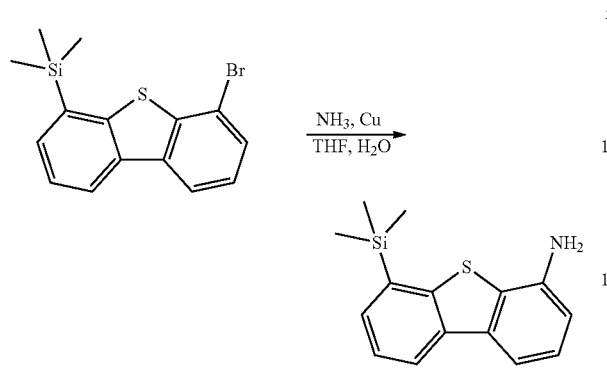

After 10.1 g (30.0 mmol) of (6-bromodibenzo[b,d]thiophen-4-yl)trimethylsilane was dissolved in 100 ml of toluene under nitrogen flow, 10.2 ml (150 mmol) of 28% aqueous ammonia and 0.10 g (5 mol %) of Cu were added to the solution, and the mixture was stirred at 110° C. for 12 hours. After the reaction was completed, extraction was performed with methylene chloride, MgSO$_4$ was added thereto, and the mixture was filtered. After the solvent was removed from the filtered organic layer, 6.60 g (24.3 mmol, yield: 81%) of 6-(trimethylsilyl)dibenzo[b,d]thiophen-4-amine was obtained by using column chromatography.

$^1$H-NMR: δ 0.26 (s, 9H), 5.27 (s, 2H), 6.89 (d, 1H), 7.29 (t, 1H), 7.52 (m, 2H), 7.81 (d, 1H), 8.39 (d, 1H)

<Step 3> Synthesis of IC-44-1

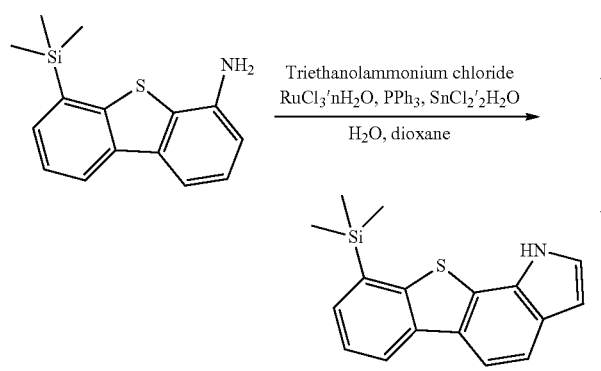

After 5.43 g (20.0 mmol) of 6-(trimethylsilyl)dibenzo[b,d]thiophen-4-amine was dissolved in H$_2$O/dioxane (10 ml/90 ml) under nitrogen flow, 0.372 g (2 mmol) of triethanolammonium chloride, 0.052 g (0.2 mmol) of RuCl$_n$.H$_2$O 0, 0.158 g (0.6 mmol) of PPh$_3$, and 0.452 g (2 mmol) of SnCl$_2$.2H$_2$O were added to the solution, and the resulting mixture was stirred at 180° C. for 20 hours. After the reaction was completed, the reactant was poured into aqueous 5% HCl, extraction was performed with methylene chloride, MgSO$_4$ was added thereto, and the mixture was filtered. After the solvent was removed from the filtered organic layer, 2.60 g (8.8 mmol, yield: 44%) of IC-44-1 was obtained by using column chromatography.

$^1$H-NMR: δ 0.26 (s, 9H), 6.45 (d, 1H), 7.28 (d, 1H), 7.56 (m, 3H), 8.09 (d, 1H), 8.41 (d, 1H), 8.65 (s, 1H)

<Step 4> Synthesis of IC-44

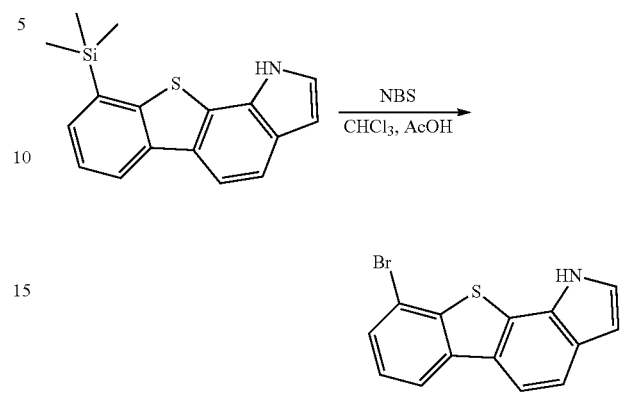

After 2.60 g (8.8 mmol) of IC-44-1 was dissolved in CHCl$_3$/AcOH (50 ml/50 ml) under nitrogen flow, 1.58 g (8.8 mmol) of NBS was slowly added thereto at 0° C., and the mixture was stirred at normal temperature for 1 hour. After the reaction was completed, the reactant was poured into a 5% NaHCO$_3$ aqueous solution, extraction was performed with methylene chloride, MgSO$_4$ was added thereto, and the mixture was filtered. After the solvent was removed from the filtered organic layer, 2.37 g (7.83 mmol, yield: 89%) of IC-44 was obtained by using column chromatography.

$^1$H-NMR: δ 6.45 (d, 1H), 7.27 (d, 1H), 7.54 (m, 3H), 8.05 (d, 1H), 8.40 (d, 1H), 8.65 (s, 1H)

[Preparation Example 45] Synthesis of IC-45a and IC-45b

<Step 1> Synthesis of (8-bromodibenzo[b,d]thiophen-2-yl)trimethylsilane

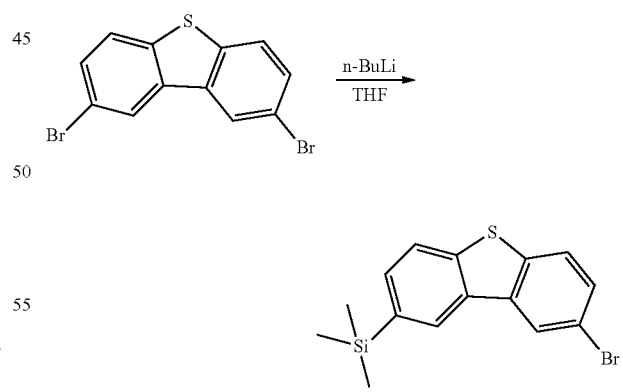

11.6 g (34.5 mmol, yield: 69%) of (8-bromodibenzo[b,d]thiophen-2-yl)trimethylsilane was obtained by performing the same procedure as in <Step 1> of Preparation Example 44, except that 17.1 g (50.0 mmol) of 2,8-dibromodibenzo[b,d]thiophene was used instead of 4,6-dibromodibenzo[b,d]thiophene.

$^1$H-NMR: δ 0.25 (s, 9H), 7.48 (m, 2H), 7.96 (m, 4H)<

<Step 2> Synthesis of 8-(trimethylsilyl)dibenzo[b,d]thiophen-2-amine

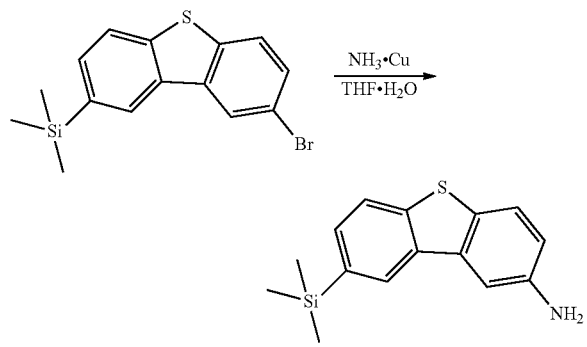

6.35 g (23.4 mmol, yield: 78%) of 8-(trimethylsilyl)dibenzo[b,d]thiophen-2-amine was obtained by performing the same procedure as <Step 2> of Preparation Example 44, except that 10.1 g (30.0 mmol) of (8-bromodibenzo[b,d]thiophen-2-yl)trimethylsilane was used instead of (6-bromodibenzo[b,d]thiophen-4-yl)trimethylsilane.

$^1$H-NMR: δ 0.26 (s, 9H), 5.26 (s, 2H), 7.48 (m, 3H), 7.79 (d, 1H), 7.96 (d, 1H), 8.01 (s, 1H)

<Step 3> Synthesis of IC-45a-1 and IC-45b-1

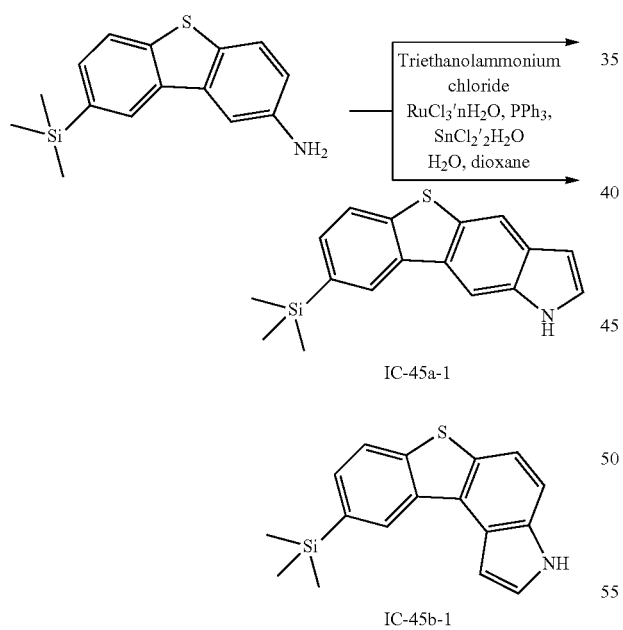

2.07 g (7.00 mmol, yield: 35%) of IC-45a-1 and 1.95 g (6.60 mmol, yield: 33%) of IC-45b-1 were obtained by performing the same procedure as <Step 3> of Preparation Example 44, except that 5.43 g (20.0 mmol) of 8-(trimethylsilyl)dibenzo[b,d]thiophen-2-amine was used instead of 6-(trimethylsilyl)dibenzo[b,d]thiophen-4-amine.

$^1$H-NMR for IC-45a-1: δ 0.26 (s, 9H), 6.45 (d, 1H), 7.27 (d, 1H), 7.56 (d, 1H), 7.82 (m, 2H), 8.02 (m, 2H), 8.65 (s, 1H)

$^1$H-NMR for IC-45b-1: δ 0.26 (s, 9H), 6.44 (d, 1H), 7.29 (m, 2H), 7.53 (d, 1H), 8.01 (m, 3H), 8.65 (s, 1H)

<Step 4> Synthesis of IC-45a

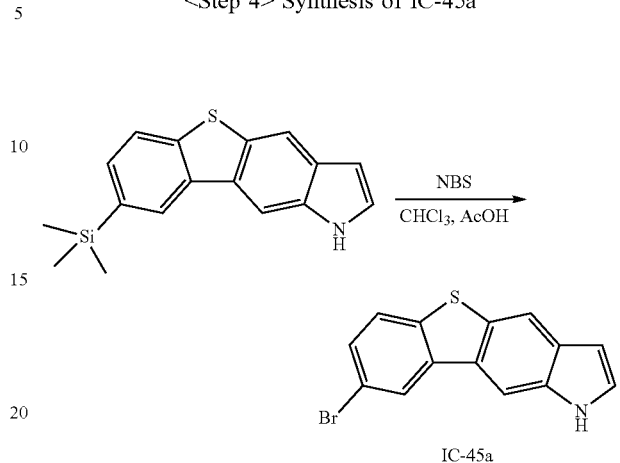

After 1.95 g (6.6 mmol) of IC-45a-1 was dissolved in CHCl$_3$/AcOH (40 ml/40 ml) under nitrogen flow, 1.19 g (6.6 mol) of NBS was slowly added thereto at 0° C., and the mixture was stirred at normal temperature for 1 hour. After the reaction was completed, the reactant was poured into a 5% NaHCO$_3$ aqueous solution, extraction was performed with methylene chloride, MgSO$_4$ was added thereto, and the mixture was filtered. After the solvent was removed from the filtered organic layer, 1.72 g of (5.68 mmol, yield: 86%) of a target compound IC-45a was obtained by using column chromatography.

$^1$H-NMR: δ 6.44 (d, 1H), 7.28 (t, 1H), 7.42 (d, 1H), 7.83 (m, 4H), 8.63 (s, 1H)

<Step 5> Synthesis of IC-45b

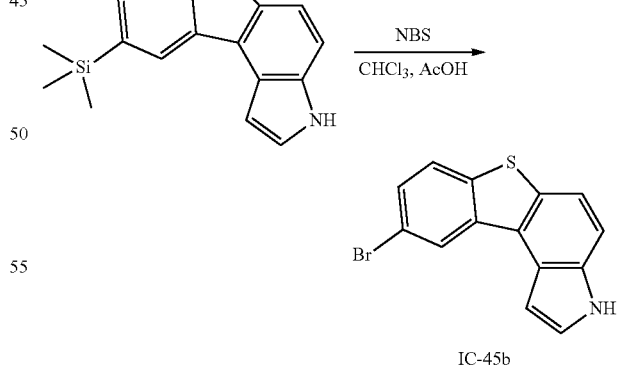

1.76 g (5.81 mmol, yield: 88%) of IC-45b was obtained by performing the same procedure as in <Step 4> in Preparation Example 45, except that 1.95 g (6.60 mmol) of IC-45b-1 was used instead of IC-45a-1.

$^1$H-NMR: δ 6.45 (d, 1H), 7.30 (m, 2H), 7.45 (d, 1H), 7.92 (m, 3H), 8.61 (s, 1H)

[Preparation Example 46] Synthesis of IC-46

<Step 1> Synthesis of 2-(benzofuran-5-yl)-4,4,5,5-tetramethyl-1,3,2-dioxaborolane

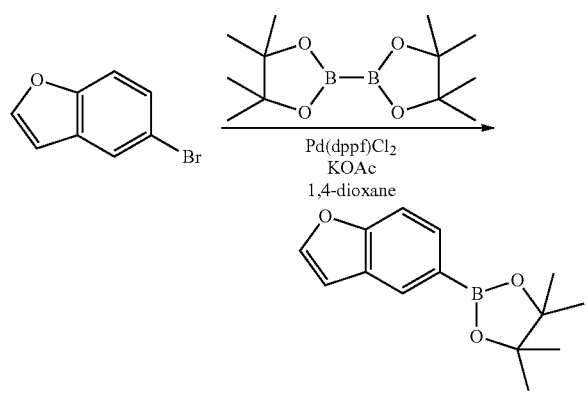

5-bromobenzofuran (25 g, 0.126 mol), 4,4,4',4',5,5,5',5'-octamethyl-2,2'-bi(1,3,2-dioxaborolane) (38.67 g, 0.152 mol), Pd(dppf)Cl$_2$ (3.11 g, 3 mol), KOAc (37.36 g, 0.381 mol) and 1,4-dioxane (500 ml) were mixed under nitrogen flow, and the mixture was stirred at 130° C. for 12 hours.

After the reaction was completed, extraction was performed with ethyl acetate, moisture was removed with MgSO$_4$, and purification was performed by column chromatography (Hexane:EA=10:1 (v/v)), thereby obtaining 2-(benzofuran-5-yl)-4,4,5,5-tetramethyl-1,3,2-dioxaborolane (23.23 g, yield 75%).

$^1$H-NMR: δ 1.25 (s, 12H), 6.46 (d, 1H), 7.28 (d, 1H), 7.43 (d, 1H), 7.53 (d, 1H), 7.98 (s, 1H)

<Step 2> Synthesis of 5-(2-nitrophenyl)-1H-indole

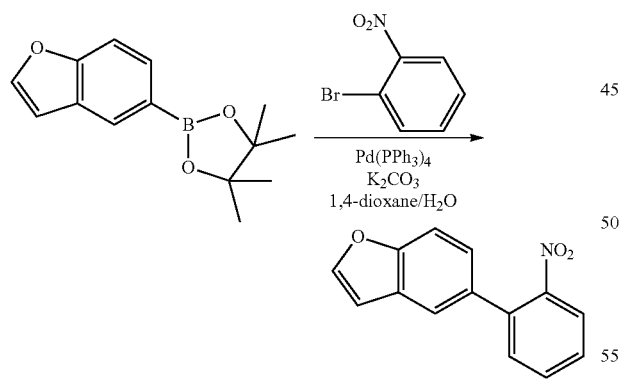

1-bromo-2-nitrobenzene (15.86 g, 78.52 mmol), 2-(benzofuran-5-yl)-4,4,5,5-tetramethyl-1,3,2-dioxaborolane (23 g, 94.23 mmol) obtained in <Step 1>, K$_2$CO$_3$ (32.56 g, 235.57 mmol) and 1,4-dioxane/H$_2$O (400 ml/200 ml) were mixed under nitrogen flow, then Pd(PPh$_3$)$_4$ (4.54 g, 5 mol %) was added to the mixture at 40° C., and the resulting mixture was stirred at 110° C. for 12 hours.

After the reaction was completed, extraction was performed with methylene chloride, MgSO$_4$ was added thereto, and the mixture was filtered. After the solvent was removed from the organic layer obtained, the residue was purified by column chromatography (Hexane:EA=3:1 (v/v)), thereby obtaining 5-(2-nitrophenyl)benzofuran (12.40 g, yield 66%).

$^1$H-NMR: δ 6.45 (d, 1H), 7.26 (d, 1H), 7.42 (d, 1H), 7.52 (d, 1H), 7.66 (t, 1H), 7.85 (t, 1H), 7.96 (s, 1H), 8.01 (d, 1H), 8.06 (t, 1H)

<Step 3> Synthesis of IC-46

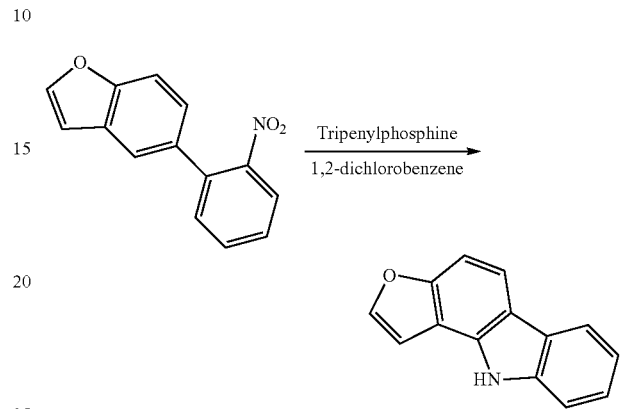

5-(2-nitrophenyl)benzofuran (10 g, 41.80 mmol) obtained in <Step 2>, triphenylphosphine (27.41 g, 104.50 mmol) and 1,2-dichlorobenzene (150 ml) were mixed under nitrogen flow, and the mixture was stirred for 12 hours.

After the reaction was completed, 1,2-dichlorobenzene was removed, and extraction was performed with dichloromethane. For the organic layer obtained, water was removed with MgSO$_4$, and purification was performed by column chromatography (Hexane:MC=3:1 (v/v)), thereby obtaining IC-46 (4.76 g, yield 55%).

$^1$H-NMR: δ 6.51 (d, 1H), 7.27 (d, 1H), 7.43 (d, 1H), 7.54 (d, 1H), 7.68 (t, 1H), 7.86 (t, 1H), 8.00 (d, 1H), 8.05 (t, 1H), 10.58 (s, 1H)

[Preparation Example 47] Synthesis of IC-47

<Step 1> Synthesis of 2-(benzofuran-6-yl)-4,4,5,5-tetramethyl-1,3,2-dioxaborolane

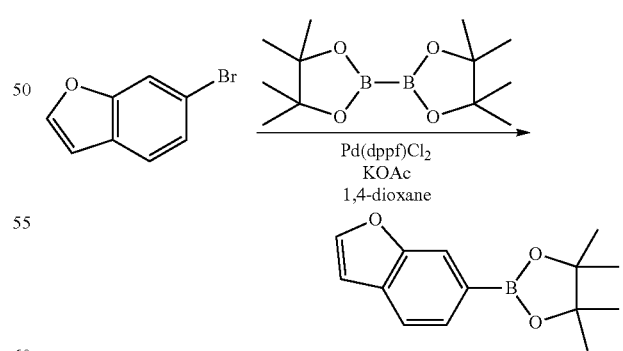

2-(benzofuran-6-yl)-4,4,5,5-tetramethyl-1,3,2-dioxaborolane was obtained by performing the same procedure as in <Step 1> of Preparation Example 46, except that 6-bromobenzofuran was used instead of 5-bromobenzofuran.

$^1$H-NMR: δ 1.25 (s, 12H), 6.46 (d, 1H), 7.28 (d, 1H), 7.43 (d, 1H), 7.53 (d, 1H), 7.98 (s, 1H)

‹Step 2› Synthesis of 6-(2-nitrophenyl)benzofuran

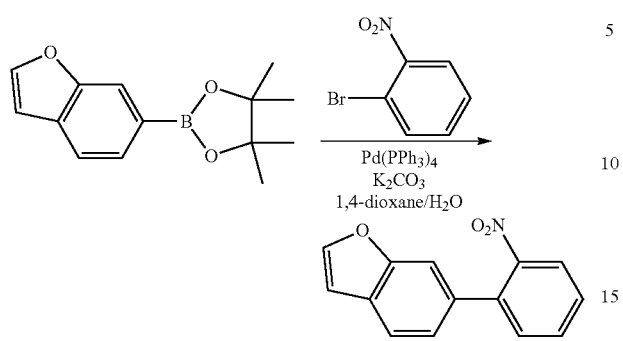

6-(2-nitrophenyl)benzofuran was obtained by performing the same procedure as in ‹Step 2› of Preparation Example 46, except that 2-(benzofuran-6-yl)-4,4,5,5-tetramethyl-1,3,2-dioxaborolane was used instead of 2-(benzofuran-5-yl)-4,4,5,5-tetramethyl-1,3,2-dioxaborolane (23 g, 94.23 mmol).

$^1$H-NMR: δ 6.45 (d, 1H), 7.26 (d, 1H), 7.42 (d, 1H), 7.52 (d, 1H), 7.66 (t, 1H), 7.85 (t, 1H), 7.96 (s, 1H), 8.01 (d, 1H), 8.06 (t, 1H)

‹Step 3› Synthesis of IC-47

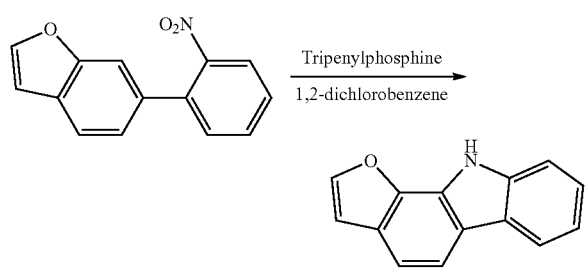

IC-47 was obtained by performing the same procedure as in ‹Step 3› of Preparation Example 46, except that 6-(2-nitrophenyl)benzofuran was used instead of 5-(2-nitrophenyl)benzofuran.

$^1$H-NMR: δ 6.51 (d, 1H), 7.27 (d, 1H), 7.43 (d, 1H), 7.54 (d, 1H), 7.68 (t, 1H), 7.86 (t, 1H), 8.00 (d, 1H), 8.05 (t, 1H), 10.58 (s, 1H)

[Preparation Example 48] Synthesis of IC-48

‹Step 1› Synthesis of Dibenzo[b,d]furan-3-amine

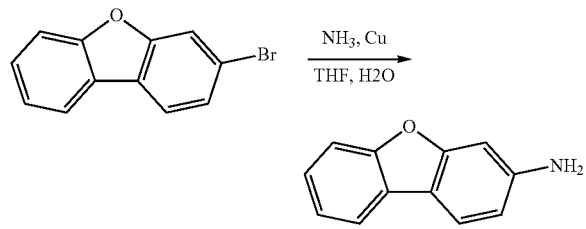

After 3-bromodibenzo[b,d]furan (7.41 g, 30.0 mmol) was dissolved in 100 ml of THF under nitrogen flow, 28% aqueous ammonia (10.2 ml, 150 mmol) and Cu (0.10 g, 5 mol %) were added to the solution, and the mixture was stirred at 110° C. for 12 hours. After the reaction was completed, extraction was performed with methylene chloride, MgSO$_4$ was added thereto, and the mixture was filtered. After the solvent was removed from the filtered organic layer, purification was performed by column chromatography (Hexane:EA=10:1 (v/v)), thereby obtaining 4.45 g (yield: 81%) of dibenzo[b,d]furan-3-amine.

$^1$H-NMR: δ 5.32 (s, 2H), 6.33 (d, 1H), 7.34 (m, 2H), 7.43 (s, 1H), 7.65 (d, 2H), 7.89 (d, 1H)

‹Step 2› Synthesis of IC-48

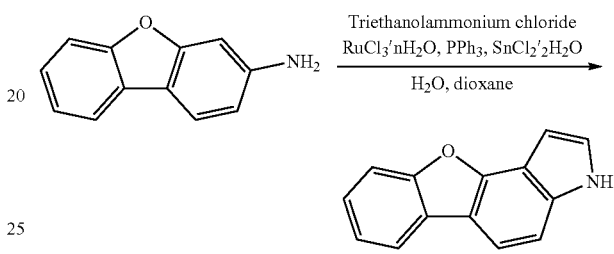

After dibenzo[b,d]furan-3-amine (4.45 g, 24.29 mmol) was dissolved in H$_2$O/dioxane (10 ml/90 ml) under nitrogen flow, triethanolammonium chloride (0.45 g, 2.43 mmol), (0.055 g, 0.2 mmol), PPh$_3$ (0.191 g, 0.7 mmol), and (0.548 g, 2.43 mmol) were added to the solution, and the resulting mixture was stirred at 180° C. for 20 hours. After the reaction was completed, the reactant was poured into aqueous 5% HCl, extraction was performed with methylene chloride, MgSO$_4$ was added thereto, and the mixture was filtered. After the solvent was removed from the filtered organic layer, purification was performed by column chromatography (Hexane:MC=1:1 (v/v)), thereby obtaining 2.7 g (yield: 53%) of IC-48.

$^1$H-NMR: δ 6.45 (d, 1H), 7.13 (d, 1H), 7.27 (d, 1H), 7.35 (m, 2H), 7.66 (d, 1H), 7.88 (d, 2H), 10.46 (s, 1H)

[Preparation Example 49] Synthesis of IC-49

‹Step 1› Synthesis of 5,5-dimethyl-5H-dibenzo[b,d]silol-3-amine

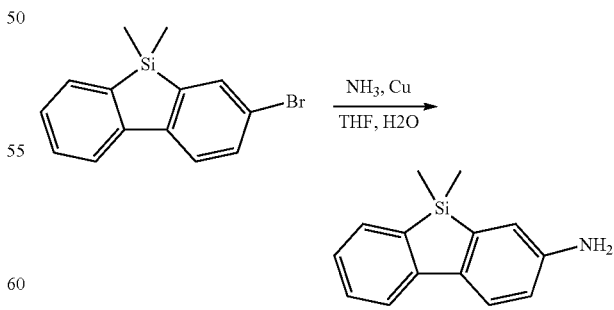

5,5-dimethyl-5H-dibenzo[b,d]silol-3-amine was obtained by performing the same procedure as in ‹Step 1› of Preparation Example 48, except that 3-bromo-5,5-dimethyl-5H-dibenzo[b,d]silole was used instead of 3-bromodibenzo[b,d]furan.

$^1$H-NMR: δ 0.68 (s, 6H), 5.31 (s, 2H), 6.68 (d, 1H), 6.80 (s, 1H), 7.33 (t, 1H), 7.52 (d, 1H), 7.61 (t, 1H), 7.64 (d, 1H), 7.91 (d, 1H)

<Step 2> Synthesis of IC-49

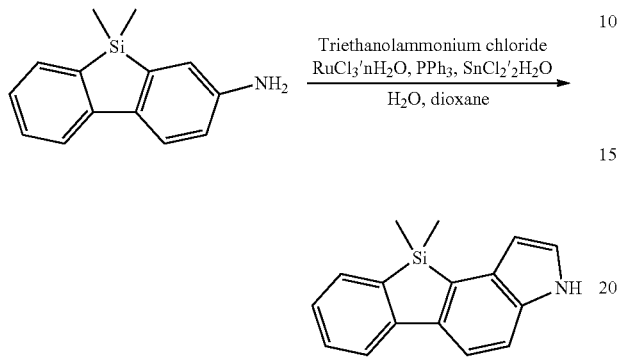

IC-49 was obtained by performing the same procedure as in <Step 2> of Preparation Example 48, except that 5,5-dimethyl-5H-dibenzo[b,d]silol-3-amine obtained in <Step 1> was used instead of dibenzo[b,d]furan-3-amine.

$^1$H-NMR: δ0.66 (s, 6H), 6.45 (d, 1H), 7.27 (d, 1H), 7.33 (t, 1H), 7.52 (d, 1H), 7.61 (t, 1H), 7.79 (d, 1H), 7.89 (d, 1H), 7.97 (d, 1H), 10.42 (s, 1H)

[Preparation Example 50] Synthesis of IC-50

<Step 1> Synthesis of 5,5-diphenyl-5H-dibenzo[b,d]silol-3-amine

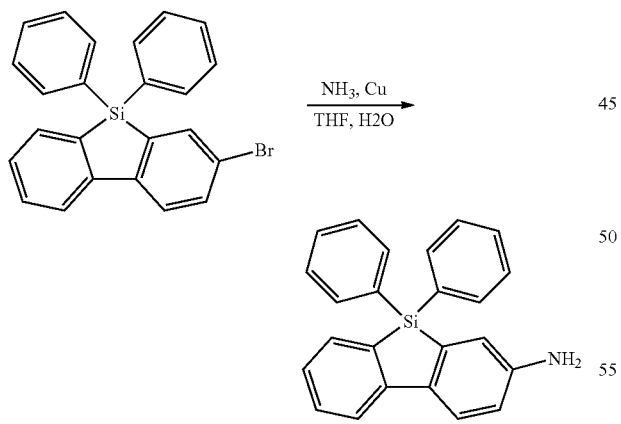

5,5-diphenyl-5H-dibenzo[b,d]silol-3-amine was obtained by performing the same procedure as in <Step 1> of Preparation Example 48, except that 3-bromo-5,5-diphenyl-5H-dibenzo[b,d]silole was used instead of 3-bromodibenzo[b,d]furan.

$^1$H-NMR: δ 5.33 (s, 2H), 6.67 (d, 1H), 6.81 (s, 1H), 7.31 (t, 1H), 7.37 (m, 4H), 7.46 (m, 4H), 7.54 (m, 3H), 7.62 (t, 1H), 7.66 (d, 1H), 7.92 (d, 1H)

<Step 2> Synthesis of IC-50

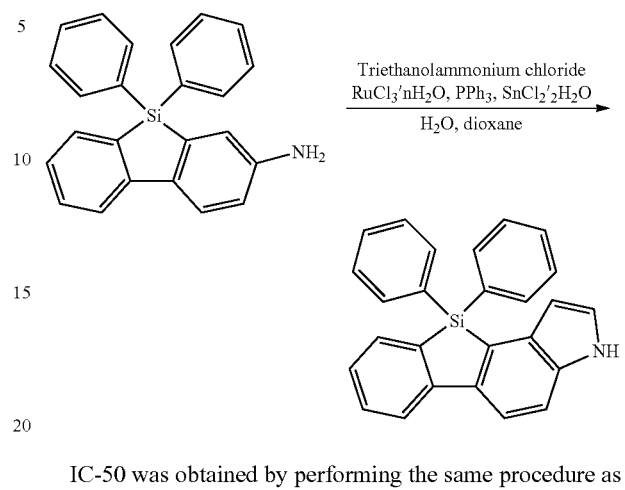

IC-50 was obtained by performing the same procedure as in <Step 2> of Preparation Example 48, except that 5,5-diphenyl-5H-dibenzo[b,d]silol-3-amine obtained in <Step 1> was used instead of dibenzo[b,d]furan-3-amine.

$^1$H-NMR: δ 6.44 (d, 1H), 7.26 (d, 1H), 7.35 (m, 5H), 7.47 (m, 4H), 7.53 (m, 3H), 7.62 (t, 1H), 7.78 (d, 1H), 7.90 (d, 1H), 7.96 (d, 1H), 10.41 (s, 1H)

[Preparation Example 51] Synthesis of IC-51

<Step 1> Synthesis of IC-51

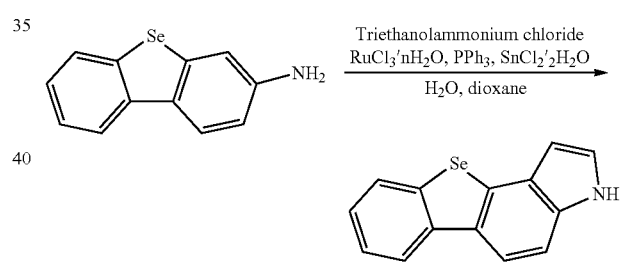

IC-51 was obtained by performing the same procedure as in <Step 2> of Preparation Example 48, except that dibenzo[b,d]selenophen-3-amine was used instead of dibenzo[b,d]furan-3-amine.

$^1$H-NMR: δ 6.47 (d, 1H), 7.15 (d, 1H), 7.26 (d, 1H), 7.36 (m, 2H), 7.67 (d, 1H), 7.89 (d, 2H), 10.45 (s, 1H)

[Preparation Example 52] Synthesis of IC-52

<Step 1> Synthesis of 2-(benzo[b]selenophen-5-yl)-4,4,5,5-tetramethyl-1,3,2-dioxaborolane

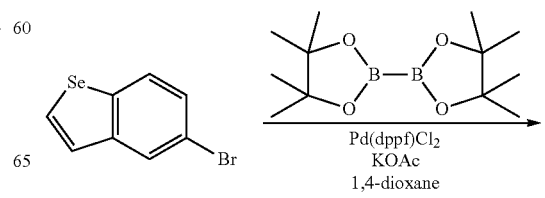

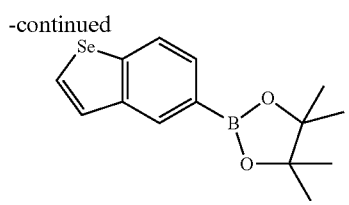

2-(benzo[b]selenophen-5-yl)-4,4,5,5-tetramethyl-1,3,2-dioxaborolane was obtained by performing the same procedure as in <Step 1> of Preparation Example 46, except that 5-bromobenzo[b]selenophene was used instead of 5-bromobenzofuran.

$^1$H-NMR: δ 1.26 (s, 12H), 6.45 (d, 1H), 7.27 (d, 1H), 7.43 (d, 1H), 7.54 (d, 1H), 8.00 (s, 1H)

<Step 2> Synthesis of 5-(2-nitrophenyl)benzo[b]selenophene

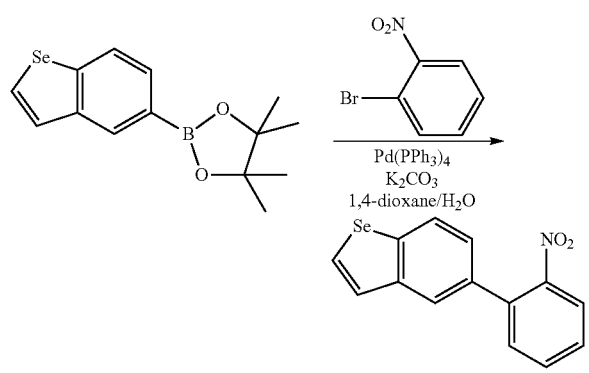

5-(2-nitrophenyl)benzo[b]selenophene was obtained by performing the same procedure as in <Step 2> of Preparation Example 46, except that 2-(benzo[b]selenophen-5-yl)-4,4,5,5-tetramethyl-1,3,2-dioxaborolane was used instead of 2-(benzofuran-5-yl)-4,4,5,5-tetramethyl-1,3,2-dioxaborolane.

$^1$H-NMR: δ 6.44 (d, 1H), 7.27 (d, 1H), 7.43 (d, 1H), 7.51 (d, 1H), 7.65 (t, 1H), 7.84 (t, 1H), 7.94 (s, 1H), 8.00 (d, 1H), 8.05 (t, 1H)

<Step 3> Synthesis of IC-52

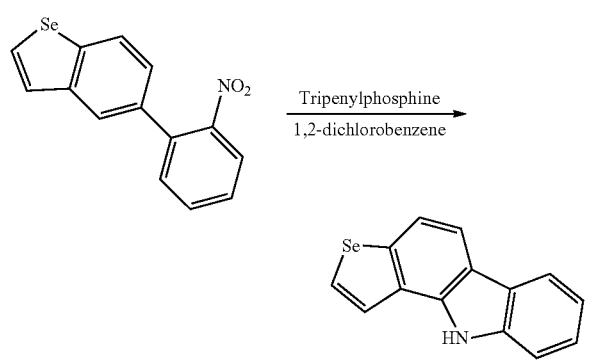

IC-52 was obtained by performing the same procedure as in <Step 3> of Preparation Example 46, except that 5-(2-nitrophenyl)benzo[b]selenophene was used instead of 5-(2-nitrophenyl)benzofuran.

$^1$H-NMR: δ 6.52 (d, 1H), 7.26 (d, 1H), 7.44 (d, 1H), 7.55 (d, 1H), 7.69 (t, 1H), 7.85 (t, 1H), 7.96 (d, 1H), 8.03 (t, 1H), 10.56 (s, 1H)

[Preparation Example 53] Synthesis of IC-53

<Step 1> Synthesis of 2-(benzo[b]selenophen-6-yl)-4,4,5,5-tetramethyl-1,3,2-dioxaborolane

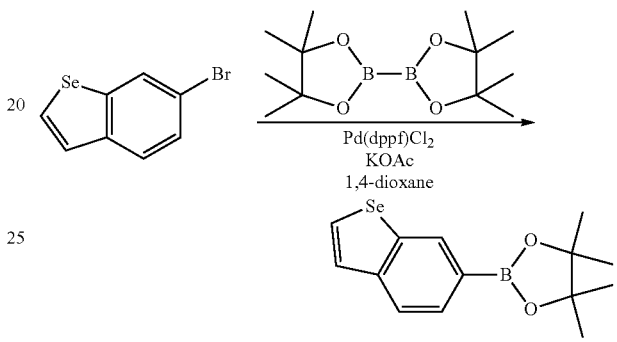

2-(benzo[b]selenophen-6-yl)-4,4,5,5-tetramethyl-1,3,2-dioxaborolane was obtained by performing the same procedure as in <Step 1> of Preparation Example 46, except that 6-bromobenzo[b]selenophene was used instead of 5-bromobenzofuran.

$^1$H-NMR: δ 1.24 (s, 12H), 6.45 (d, 1H), 7.28 (d, 1H), 7.44 (d, 1H), 7.57 (d, 1H), 7.96 (s, 1H)

<Step 2> Synthesis of 6-(2-nitrophenyl)benzo[b]selenophene

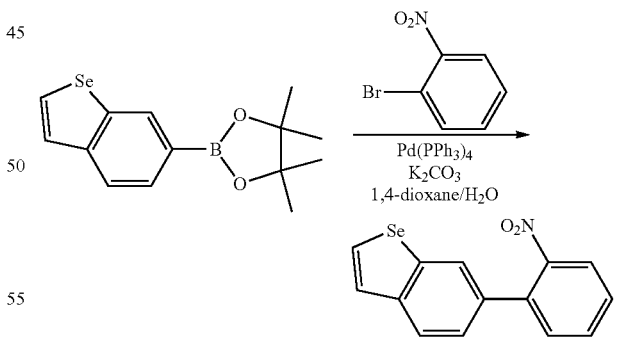

6-(2-nitrophenyl)benzo[b]selenophene was obtained by performing the same procedure as in <Step 2> of Preparation Example 46, except that 2-(benzo[b]selenophen-6-yl)-4,4,5,5-tetramethyl-1,3,2-dioxaborolane was used instead of 2-(benzofuran-5-yl)-4,4,5,5-tetramethyl-1,3,2-dioxaborolane.

$^1$H-NMR: δ 6.46 (d, 1H), 7.26 (d, 1H), 7.43 (d, 1H), 7.54 (d, 1H), 7.67 (t, 1H), 7.86 (t, 1H), 7.93 (s, 1H), 8.02 (d, 1H), 8.08 (t, 1H)

<Step 3> Synthesis of IC-53

IC-53 was obtained by performing the same procedure as in <Step 3> of Preparation Example 46, except that 6-(2-nitrophenyl)benzo[b]selenophene was used instead of 5-(2-nitrophenyl)benzofuran.

$^1$H-NMR: δ 6.52 (d, 1H), 7.27 (d, 1H), 7.43 (d, 1H), 7.52 (d, 1H), 7.67 (t, 1H), 7.85 (t, 1H), 8.01 (d, 1H), 8.09 (t, 1H), 10.55 (s, 1H)

[Synthesis Example 111] Synthesis of Inv-111

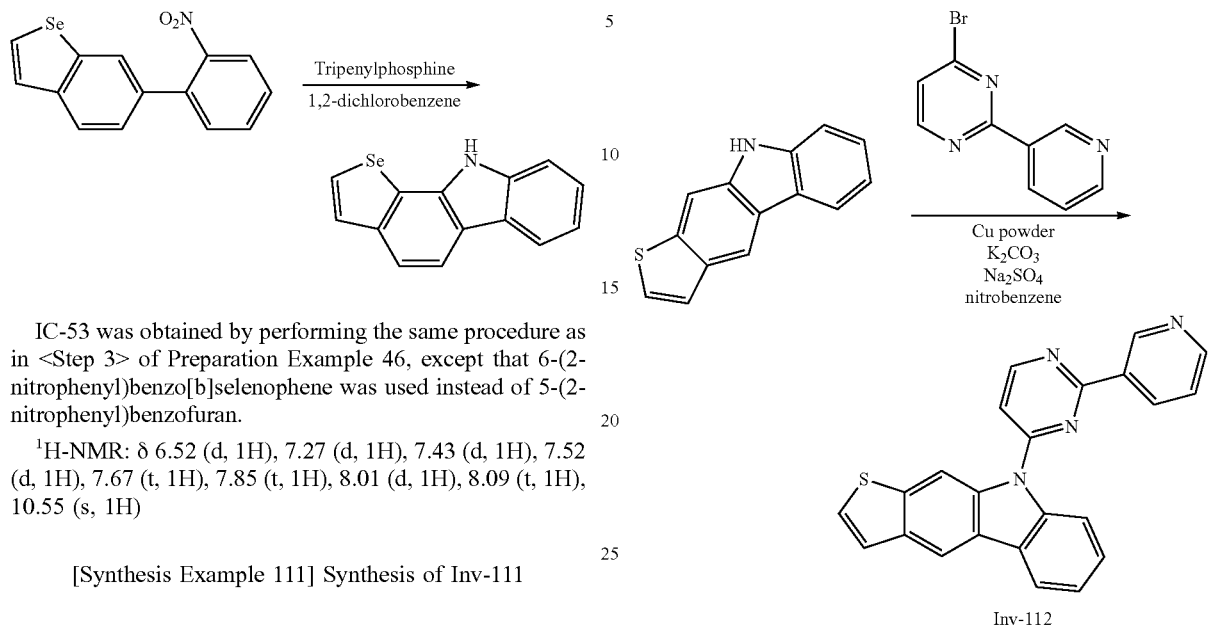

A target compound Inv-111 (3.89 g, yield 64%) was obtained by performing the same procedure as Synthesis Example 1, except that IC-32a prepared in Preparation Example 32 was used instead of IC-1a, and 2-bromo-4,6-diphenylpyridine was used instead of 2-bromo-4,6-diphenylpyridine.

GC-Mass (theoretical value: 452.13 g/mol, measured value: 452 g/mol)

[Synthesis Example 112] Synthesis of Inv-112

A target compound Inv-112 (3 g, yield 59%) was obtained by performing the same procedure as in Synthesis Example 1, except that IC-32a prepared in Preparation Example 32 was used instead of IC-1a, and 4-bromo-2-(pyridin-3-yl)pyrimidine was used instead of 2-bromo-4,6-diphenyl pyridine.

GC-Mass (theoretical value: 378.09 g/mol, measured value: 378 g/mol)

[Synthesis Example 113] Synthesis of Inv-113

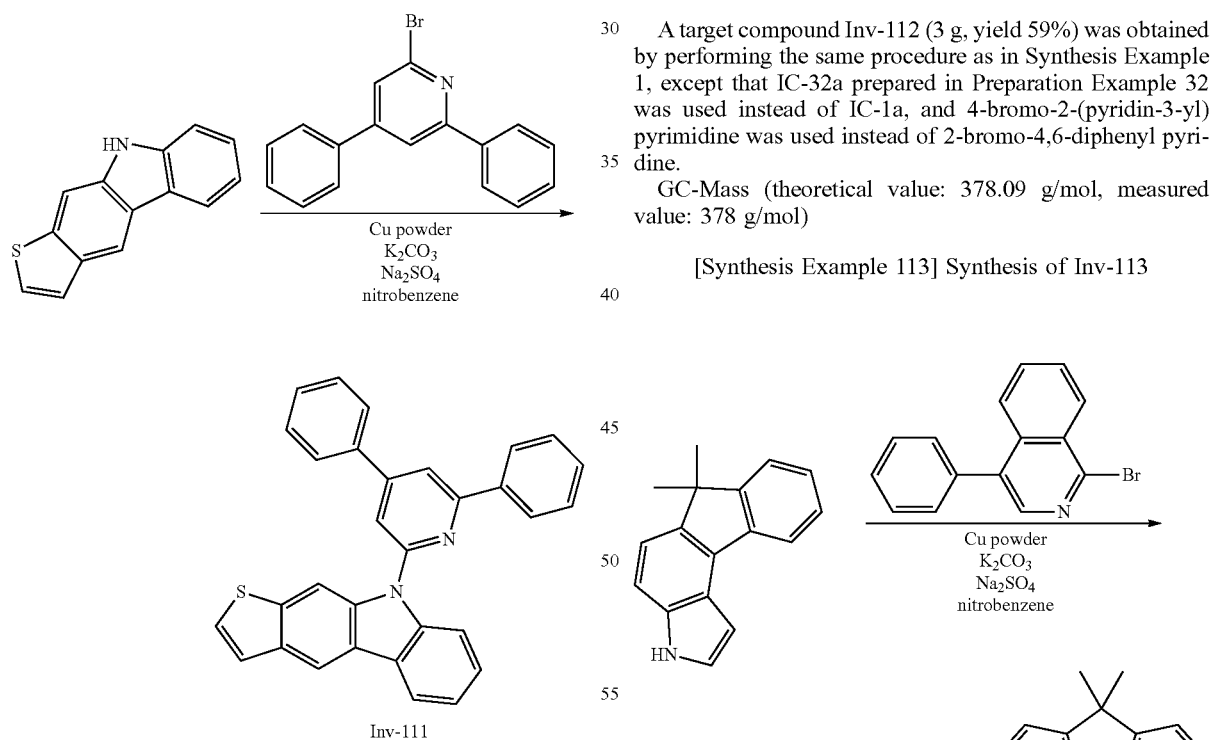

A target compound Inv-113 (3.26 g, yield 58%) was obtained by performing the same procedure as in Synthesis Example 1, except that IC-33 prepared in Preparation Example 33 was used instead of IC-1a, and 1-bromo-4-phenylisoquinoline was used instead of 2-bromo-4,6-diphenylpyridine.

GC-Mass (theoretical value: 436.19 g/mol, measured value: 436 g/mol)

[Synthesis Example 114] Synthesis of Inv-114

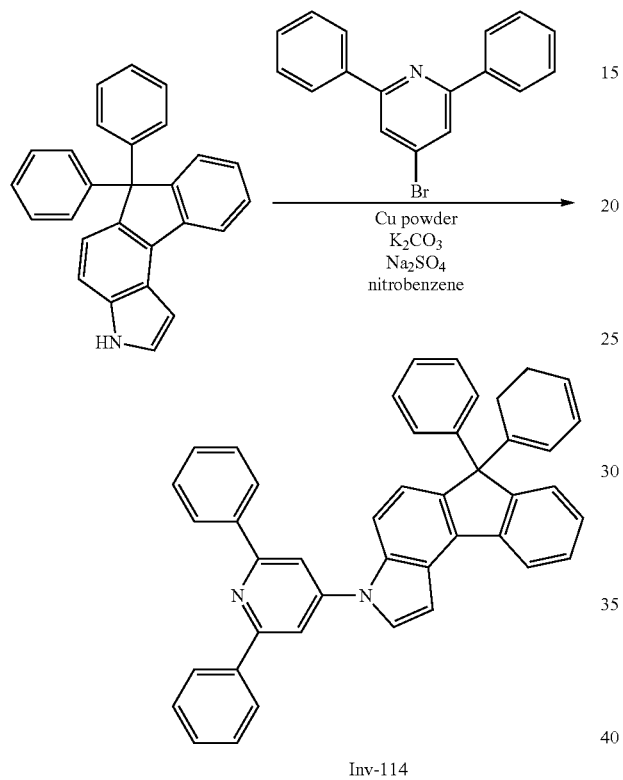

Inv-114

A target compound Inv-114 (3.11 g, yield 63%) was obtained by performing the same procedure as in Synthesis Example 1, except that IC-34 prepared in Preparation Example 34 was used instead of IC-1a, and 4-bromo-2,6-diphenylpyridine was used instead of 2-bromo-4,6-diphenylpyridine.

GC-Mass (theoretical value: 586.24 g/mol, measured value: 586 g/mol)

[Synthesis Example 115] Synthesis of Inv-115

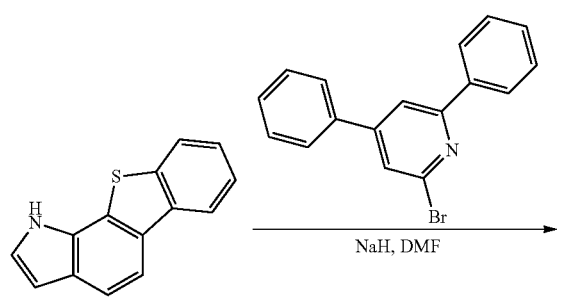

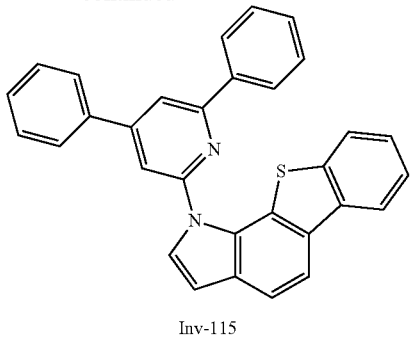

Inv-115

IC-35 (2.23 g, 10.0 mmol), 2-bromo-4,6-diphenylpyridine (3.72 g, 12.0 mmol), NaH (0.29 g, 12.0 mmol) and DMF (30 ml) were mixed under nitrogen flow, and the mixture was stirred at normal temperature for 3 hours. After the reaction was completed, water was added thereto, the solid compound was filtered, and purification was performed by column chromatography, thereby obtaining a target compound Inv-115 (3.85 g, yield: 85%).

GC-Mass (theoretical value: 452.57 g/mol, measured value: 452 g/mol)

[Synthesis Example 116] Synthesis of Inv-116

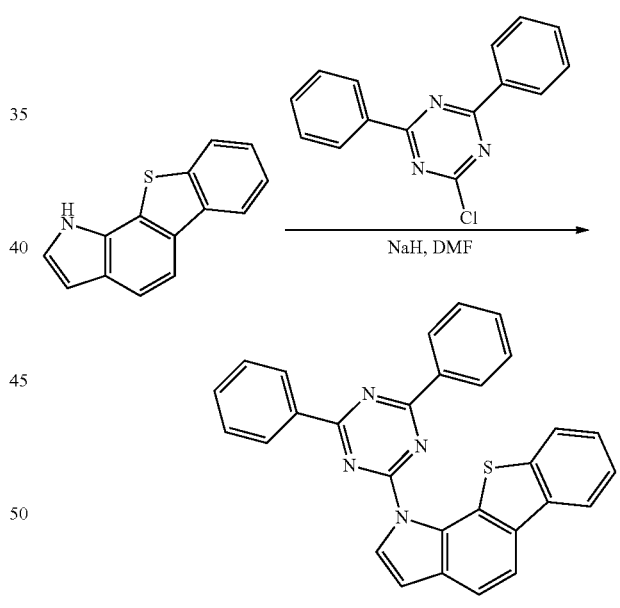

Inv-116

IC-35 (2.23 g, 10.0 mmol), 2-chloro-4,6-diphenyl-1,3,5-triazine (3.21 g, 12.0 mmol), NaH (0.29 g, 12.0 mmol) and DMF (30 ml) were mixed under nitrogen flow, and the mixture was stirred at normal temperature for 3 hours. After the reaction was completed, water was added thereto, the solid compound was filtered, and purification was performed by column chromatography, thereby obtaining a target compound Inv-116 (3.95 g, yield: 87%).

GC-Mass (theoretical value: 454.55 g/mol, measured value: 454 g/mol)

[Synthesis Example 117] Synthesis of Inv-117

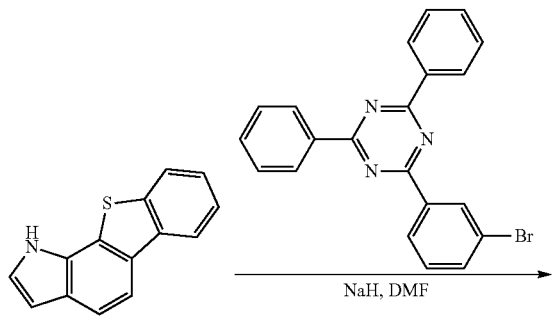

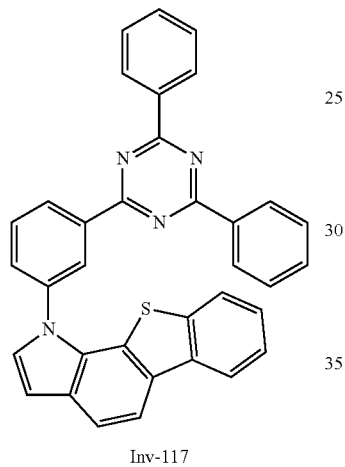
Inv-117

IC-35 (2.23 g, 10.0 mmol), 2-(3-bromophenyl)-4,6-diphenyl-1,3,5-triazine (4.66 g, 12.0 mmol), NaH (0.29 g, 12.0 mmol) and DMF (30 ml) were mixed under nitrogen flow, and the mixture was stirred at normal temperature for 3 hours. After the reaction was completed, water was added thereto, the solid compound was filtered, and purification was performed by column chromatography, thereby obtaining a target compound Inv-117 (3.40 g, yield: 64%).

GC-Mass (theoretical value: 530.64 g/mol, measured value: 530 g/mol)

[Synthesis Example 118] Synthesis of Inv-118

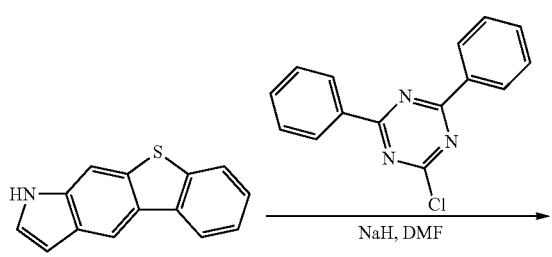

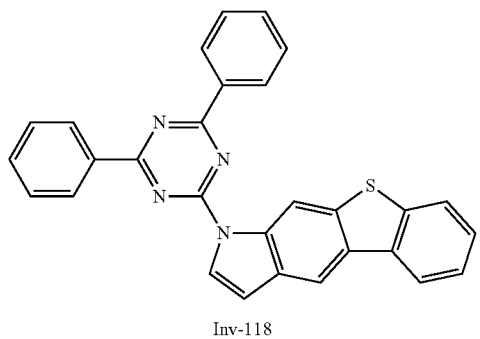
Inv-118

Inv-118 (3.95 g, yield: 87%) was obtained by performing the same procedure as in Synthesis Example 116, except that IC-36 (2.23 g, 10.0 mmol) was used instead of IC-35.

GC-Mass (theoretical value: 454.55 g/mol, measured value: 454 g/mol)

[Synthesis Example 119] Synthesis of Inv-119

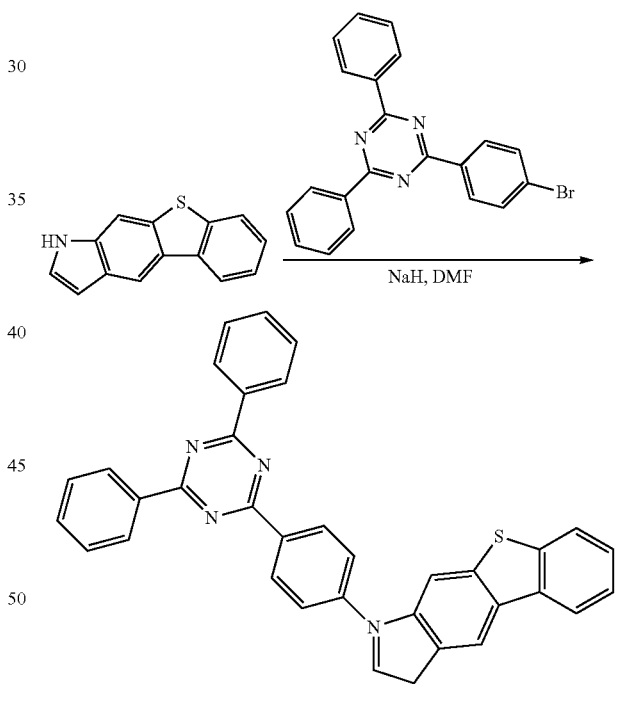
Inv-119

IC-36 (2.23 g, 10.0 mmol), 2-(4-bromophenyl)-4,6-diphenyl-1,3,5-triazine (4.66 g, 12.0 mmol), NaH (0.29 g, 12.0 mmol) and DMF (30 ml) were mixed under nitrogen flow, and the mixture was stirred at normal temperature for 3 hours. After the reaction was completed, water was added thereto, the solid compound was filtered, and purification was performed by column chromatography, thereby obtaining a target compound Inv-119 (3.61 g, yield: 68%).

GC-Mass (theoretical value: 530.64 g/mol, measured value: 530 g/mol)

[Synthesis Example 120] Synthesis of Inv-120

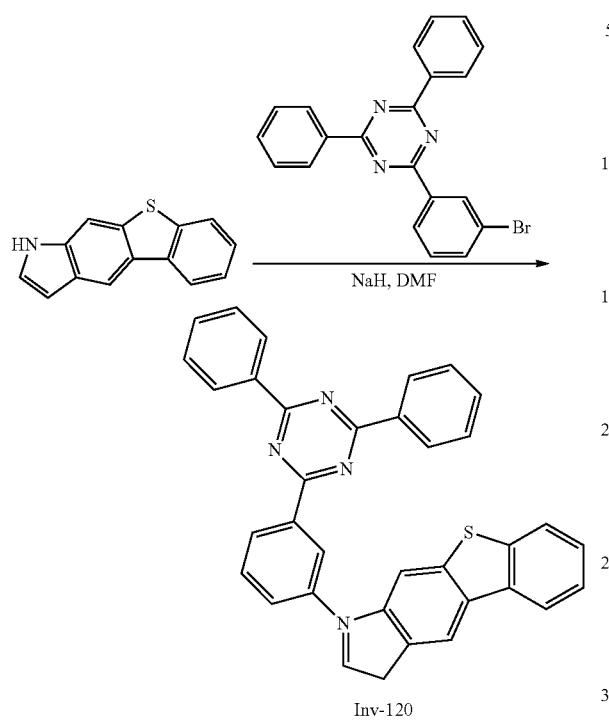

Inv-120 (3.50 g, yield: 66%) was obtained by performing the same procedure as in Synthesis Example 117, except that IC-36 (2.23 g, 10.0 mmol) was used instead of IC-35.

GC-Mass (theoretical value: 530.64 g/mol, measured value: 530 g/mol)

[Synthesis Example 121] Synthesis of Inv-121

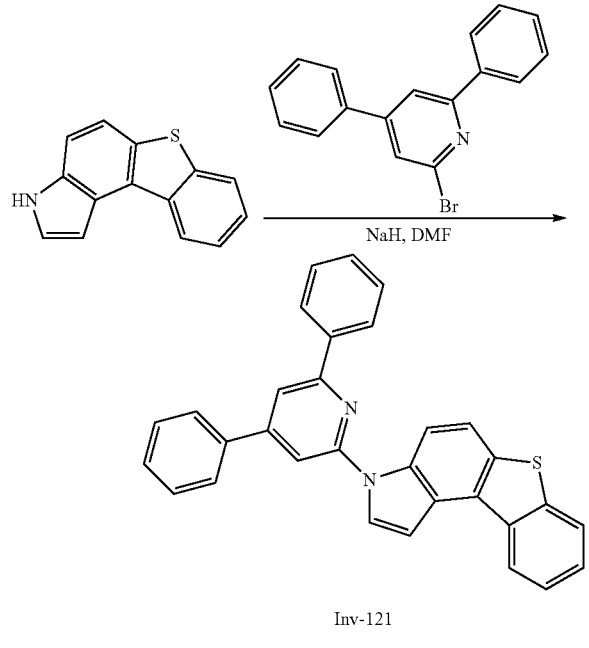

Inv-121 (3.67 g, yield: 81%) was obtained by performing the same procedure as in Synthesis Example 115, except that IC-37 (2.23 g, 10.0 mmol) was used instead of IC-35.

GC-Mass (theoretical value: 452.57 g/mol, measured value: 452 g/mol)

[Synthesis Example 122] Synthesis of Inv-122

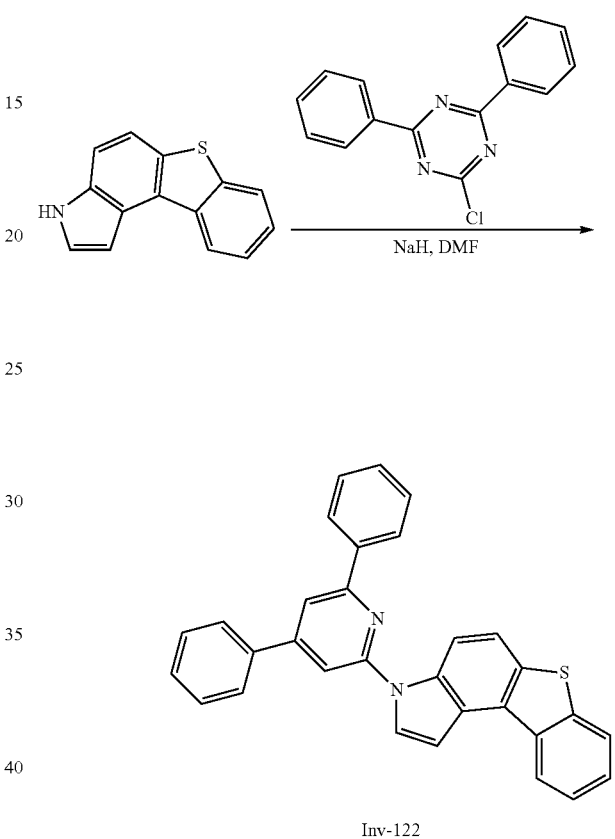

Inv-122 (3.73 g, yield: 82%) was obtained by performing the same procedure as in Synthesis Example 116, except that IC-37 (2.23 g, 10.0 mmol) was used instead of IC-35.

GC-Mass (theoretical value: 454.55 g/mol, measured value: 454 g/mol)

[Synthesis Example 123] Synthesis of Inv-123

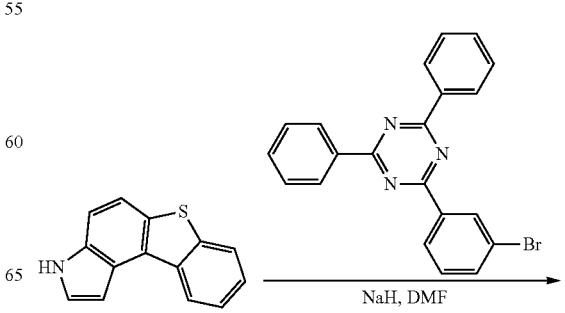

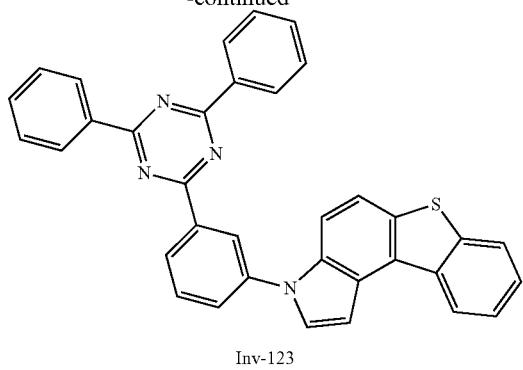

Inv-123

Inv-123 (3.66 g, yield: 69%) was obtained by performing the same procedure as in Synthesis Example 117, except that IC-37 (2.23 g, 10.0 mmol) was used instead of IC-35.

GC-Mass (theoretical value: 530.64 g/mol, measured value: 530 g/mol)

[Synthesis Example 124] Synthesis of Inv-124

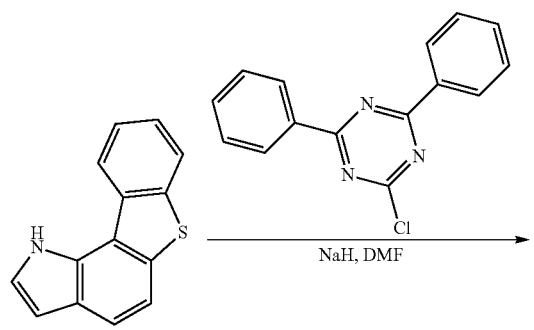

Inv-124

Inv-124 (3.91 g, yield: 86%) was obtained by performing the same procedure as in Synthesis Example 116, except that IC-38 (2.23 g, 10.0 mmol) was used instead of IC-35.

GC-Mass (theoretical value: 454.55 g/mol, measured value: 454 g/mol)

[Synthesis Example 125] Synthesis of Inv-125

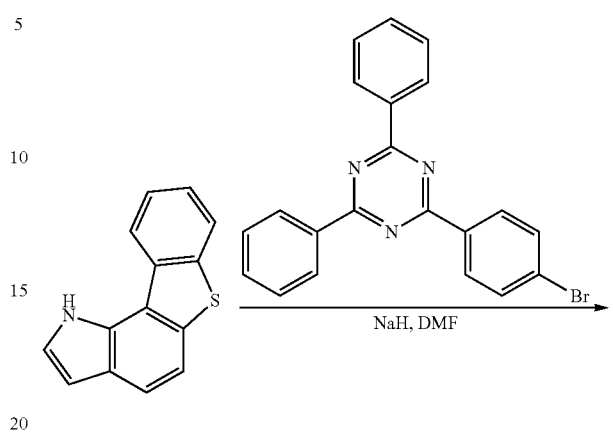

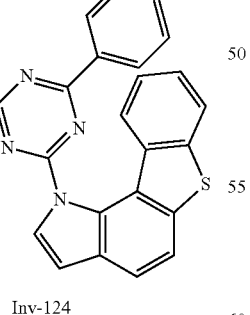

Inv-125

Inv-125 (3.24 g, yield: 61%) was obtained by performing the same procedure as in Synthesis Example 119, except that IC-38 (2.23 g, 10.0 mmol) was used instead of IC-36.

GC-Mass (theoretical value: 530.64 g/mol, measured value: 530 g/mol)

[Synthesis Example 126] Synthesis of Inv-126

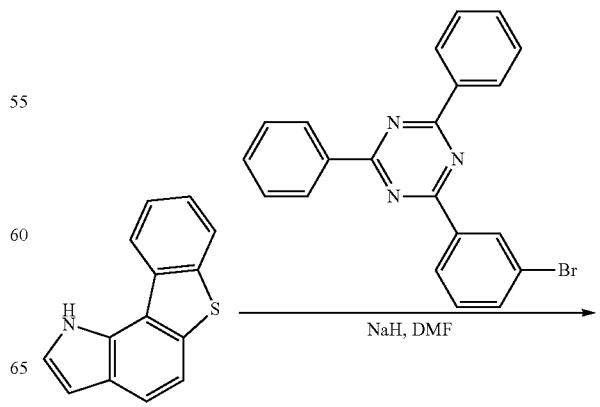

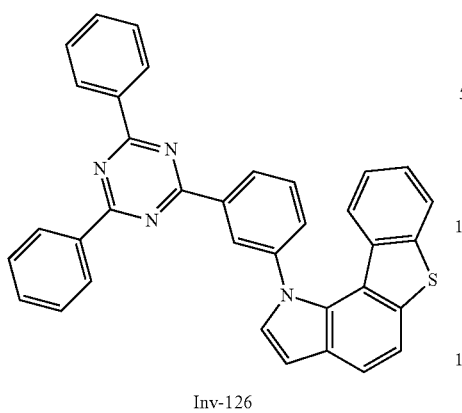

Inv-126

Inv-126 (3.50 g, yield: 66%) was obtained by performing the same procedure as in Synthesis Example 117, except that IC-38 (2.23 g, 10.0 mmol) was used instead of IC-35.

GC-Mass (theoretical value: 530.64 g/mol, measured value: 530 g/mol)

[Synthesis Example 127] Synthesis of Inv-127

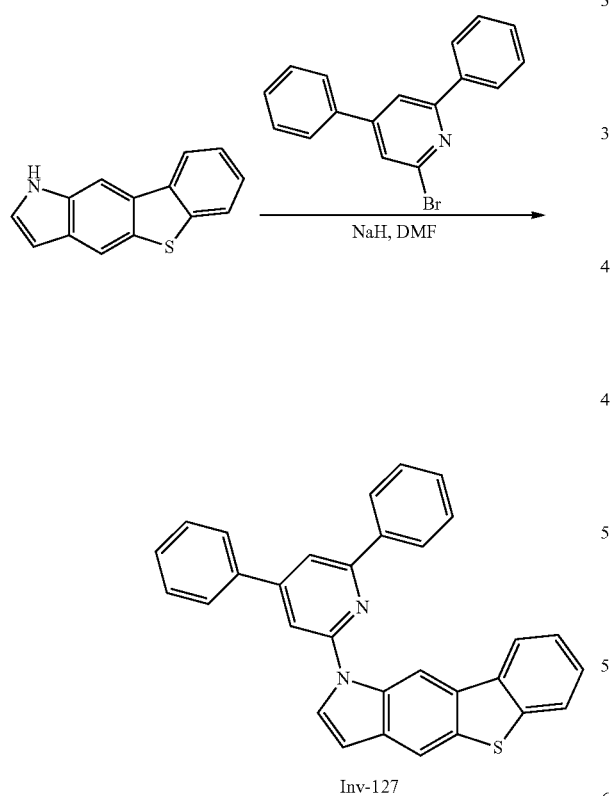

Inv-127

Inv-127 (3.94 g, yield: 87%) was obtained by performing the same procedure as in Synthesis Example 115, except that IC-39 (2.23 g, 10.0 mmol) was used instead of IC-35.

GC-Mass (theoretical value: 452.57 g/mol, measured value: 452 g/mol)

[Synthesis Example 128] Synthesis of Inv-128

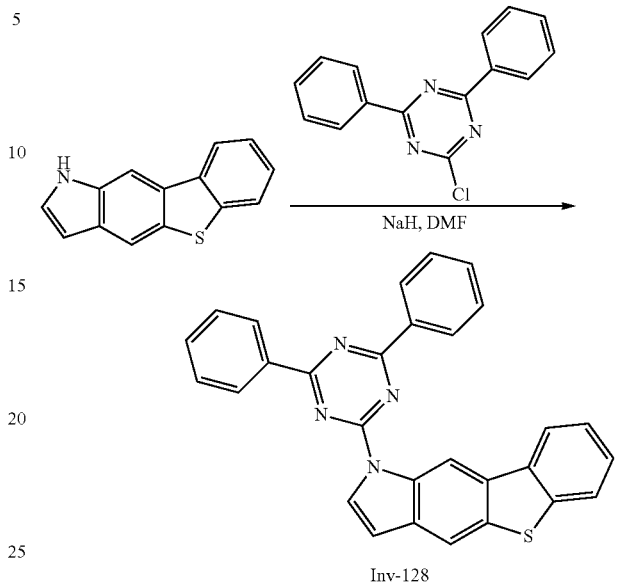

Inv-128

Inv-128 (3.64 g, yield: 80%) was obtained by performing the same procedure as in Synthesis Example 116, except that IC-39 (2.23 g, 10.0 mmol) was used instead of IC-35.

GC-Mass (theoretical value: 454.55 g/mol, measured value: 454 g/mol)

[Synthesis Example 129] Synthesis of Inv-129

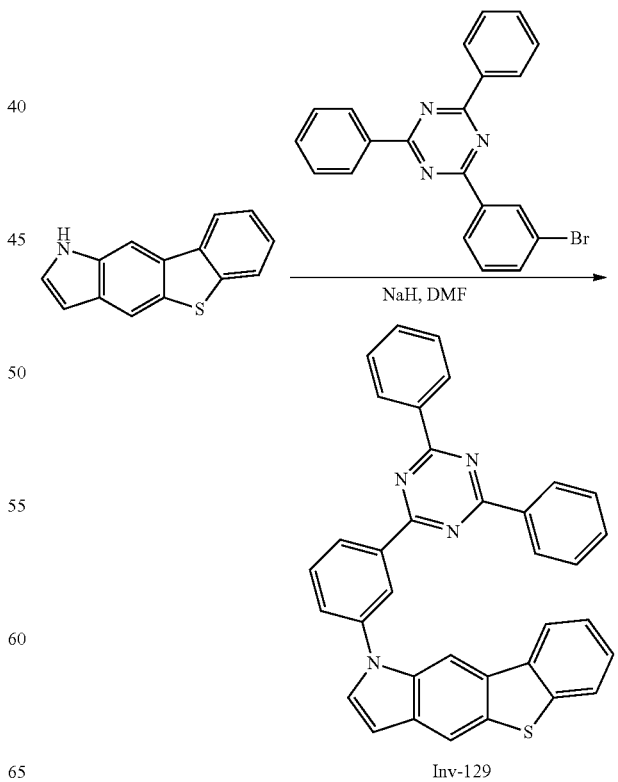

Inv-129

Inv-129 (2.44 g, yield: 46%) was obtained by performing the same procedure as in Synthesis Example 117, except that IC-39 (2.23 g, 10.0 mmol) was used instead of IC-35.

GC-Mass (theoretical value: 530.64 g/mol, measured value: 530 g/mol)

[Synthesis Example 130] Synthesis of Inv-130

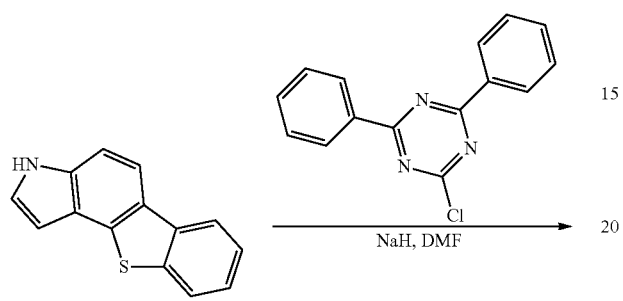

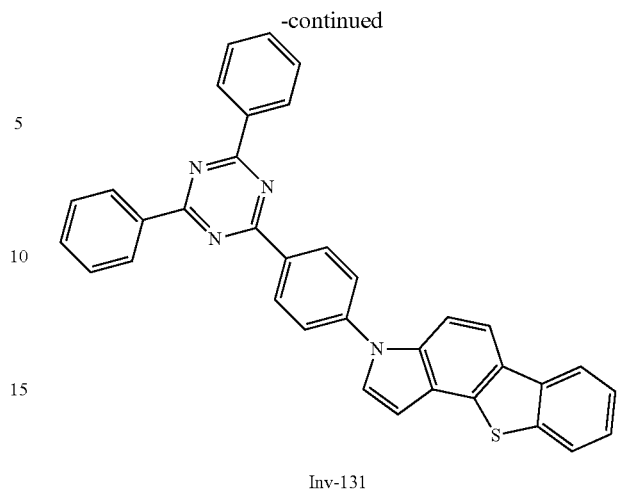

Inv-131

Inv-131 (2.92 g, yield: 55%) was obtained by performing the same procedure as in Synthesis Example 119, except that IC-40 (2.23 g, 10.0 mmol) was used instead of IC-36.

GC-Mass (theoretical value: 530.64 g/mol, measured value: 530 g/mol)

[Synthesis Example 132] Synthesis of Inv-132

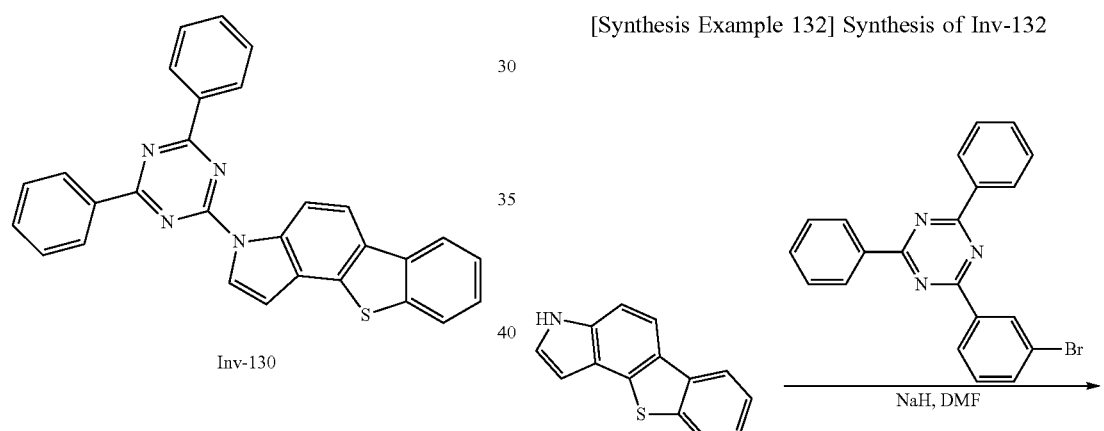

Inv-130

Inv-130 (4.05 g, yield: 89%) was obtained by performing the same procedure as in Synthesis Example 116, except that IC-40 (2.23 g, 10.0 mmol) was used instead of IC-35.

GC-Mass (theoretical value: 454.55 g/mol, measured value: 454 g/mol)

[Synthesis Example 131] Synthesis of Inv-131

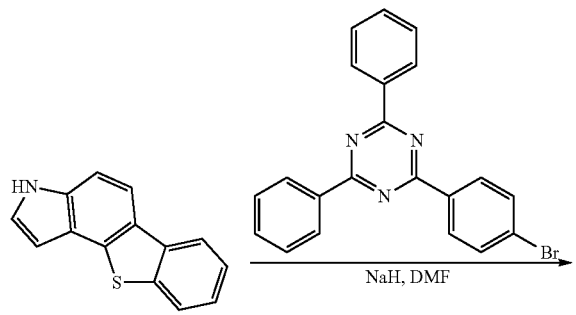

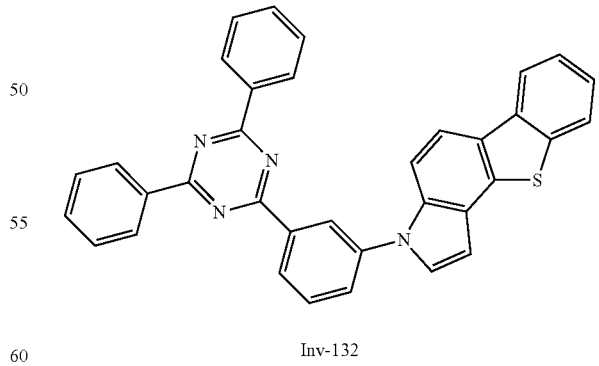

Inv-132

Inv-132 (3.34 g, yield: 63%) was obtained by performing the same procedure as in Synthesis Example 117, except that IC-40 (2.23 g, 10.0 mmol) was used instead of IC-35.

GC-Mass (theoretical value: 530.64 g/mol, measured value: 530 g/mol)

[Synthesis Example 133] Synthesis of Inv-133

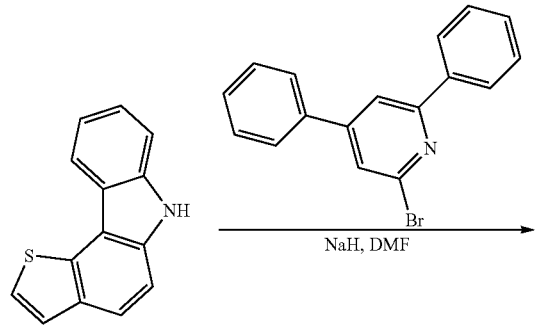

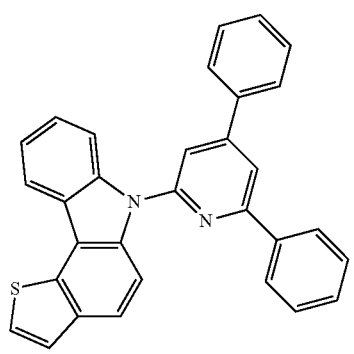

Inv-133

Inv-133 (3.85 g, yield: 85%) was obtained by performing the same procedure as in Synthesis Example 115, except that IC-41 (2.23 g, 10.0 mmol) was used instead of IC-35.

GC-Mass (theoretical value: 452.57 g/mol, measured value: 452 g/mol)

[Synthesis Example 134] Synthesis of Inv-134

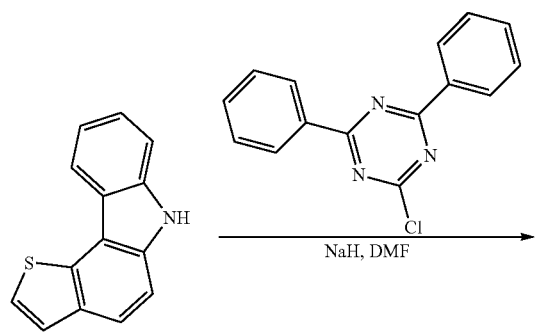

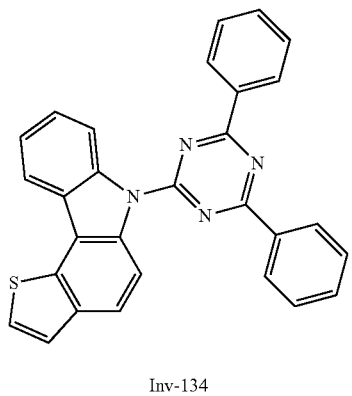

Inv-134

Inv-134 (3.95 g, yield: 87%) was obtained by performing the same procedure as in Synthesis Example 116, except that IC-41 (2.23 g, 10.0 mmol) was used instead of IC-35.

GC-Mass (theoretical value: 454.55 g/mol, measured value: 454 g/mol)

[Synthesis Example 135] Synthesis of Inv-135

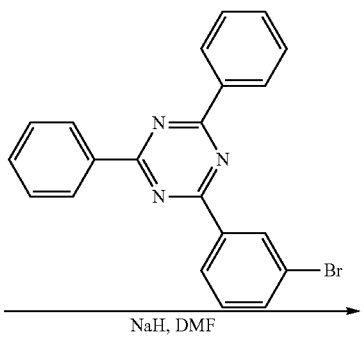

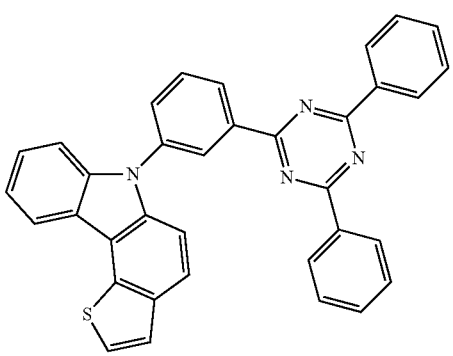

Inv-135

Inv-135 (3.50 g, yield: 66%) was obtained by performing the same procedure as in Synthesis Example 117, except that IC-41 (2.23 g, 10.0 mmol) was used instead of IC-35.

GC-Mass (theoretical value: 530.64 g/mol, measured value: 530 g/mol)

[Synthesis Example 136] Synthesis of Inv-136

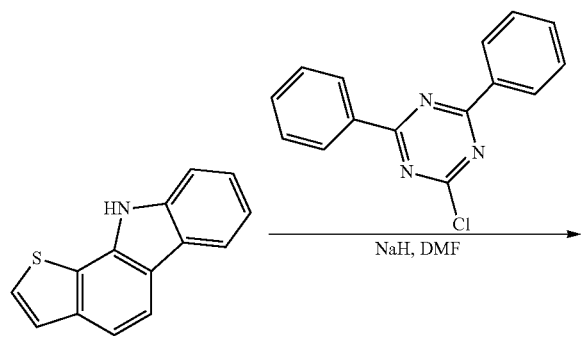

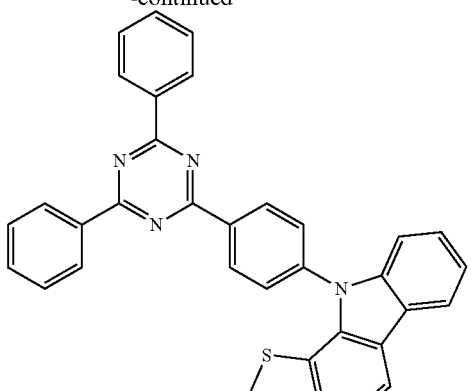
Inv. 137

Inv-137 (3.18 g, yield: 60%) was obtained by performing the same procedure as in Synthesis Example 119, except that IC-42a (2.23 g, 10.0 mmol) was used instead of IC-36.

GC-Mass (theoretical value: 530.64 g/mol, measured value: 530 g/mol)

[Synthesis Example 138] Synthesis of Inv-138

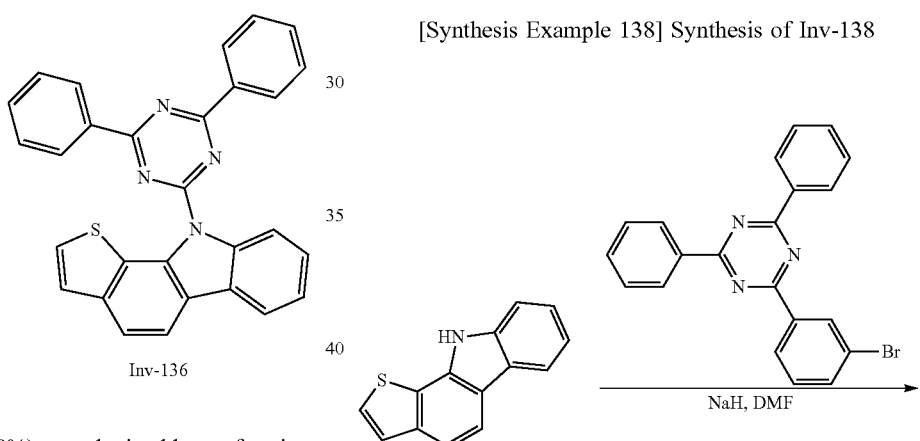
Inv-136

Inv-136 (4.09 g, yield: 90%) was obtained by performing the same procedure as in Synthesis Example 116, except that IC-42a (2.23 g, 10.0 mmol) was used instead of IC-35.

GC-Mass (theoretical value: 454.55 g/mol, measured value: 454 g/mol)

[Synthesis Example 137] Synthesis of Inv-137

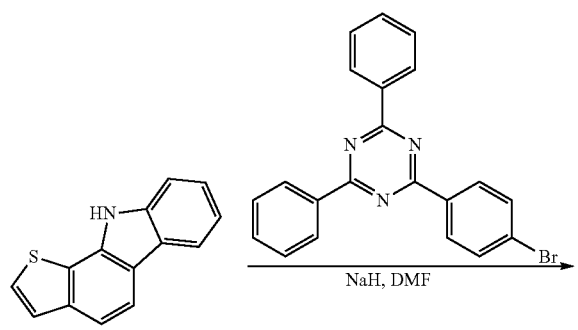

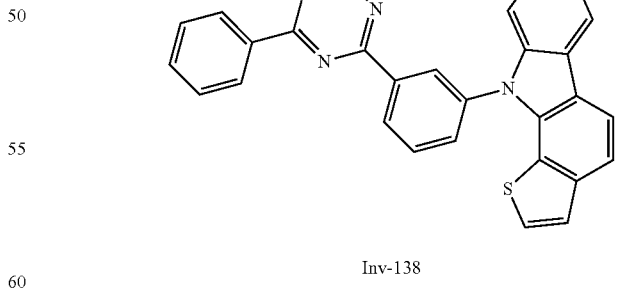
Inv-138

Inv-138 (2.97 g, yield: 56%) was obtained by performing the same procedure as in Synthesis Example 117, except that IC-42a (2.23 g, 10.0 mmol) was used instead of IC-35.

GC-Mass (theoretical value: 530.64 g/mol, measured value: 530 g/mol)

[Synthesis Example 139] Synthesis of Inv-139

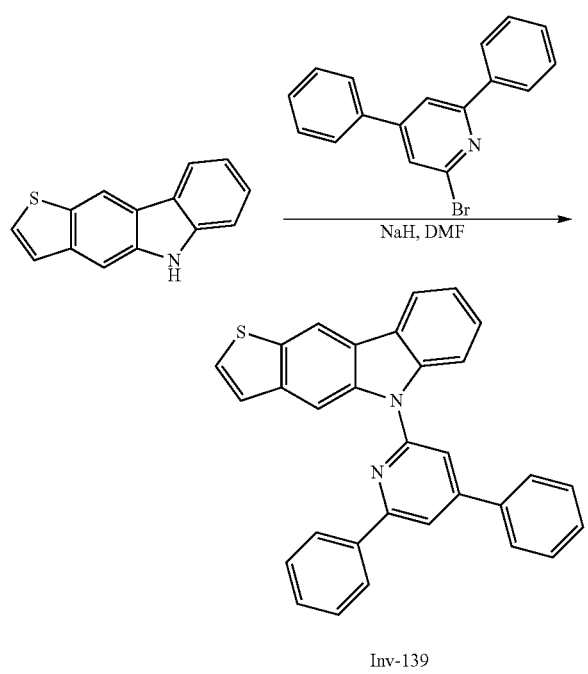

Inv-139

Inv-139 (3.67 g, yield: 81%) was obtained by performing the same procedure as in Synthesis Example 115, except that IC-42b (2.23 g, 10.0 mmol) was used instead of IC-35.

GC-Mass (theoretical value: 452.57 g/mol, measured value: 452 g/mol)

[Synthesis Example 140] Synthesis of Inv-140

Inv-140

Inv-140 (3.95 g, yield: 87%) was obtained by performing the same procedure as in Synthesis Example 116, except that IC-42b (2.23 g, 10.0 mmol) was used instead of IC-35.

GC-Mass (theoretical value: 454.55 g/mol, measured value: 454 g/mol)

[Synthesis Example 141] Synthesis of Inv-141

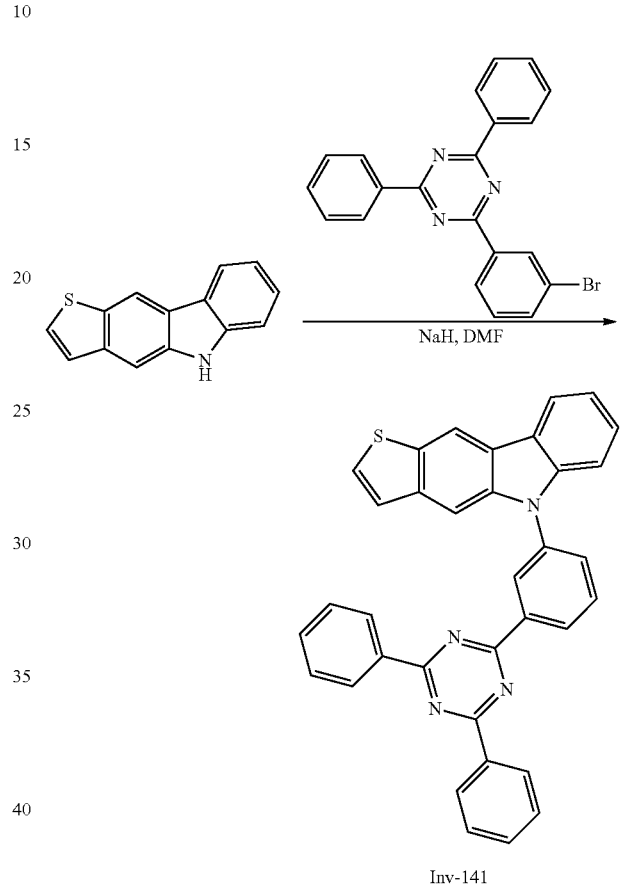

Inv-141

Inv-141 (3.45 g, yield: 65%) was obtained by performing the same procedure as in Synthesis Example 117, except that IC-42b (2.23 g, 10.0 mmol) was used instead of IC-35.

GC-Mass (theoretical value: 530.64 g/mol, measured value: 530 g/mol)

[Synthesis Example 142] Synthesis of Inv-142

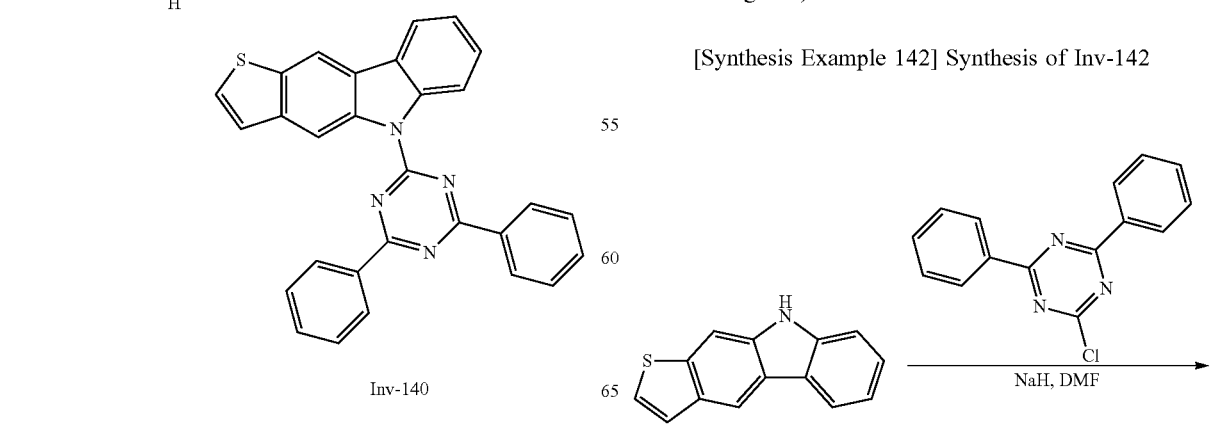

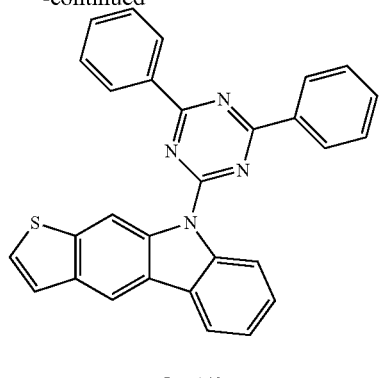

Inv-142

Inv-142 (3.77 g, yield: 83%) was obtained by performing the same procedure as in Synthesis Example 116, except that IC-32a (2.23 g, 10.0 mmol) was used instead of IC-35.

GC-Mass (theoretical value: 454.55 g/mol, measured value: 454 g/mol)

[Synthesis Example 143] Synthesis of Inv-143

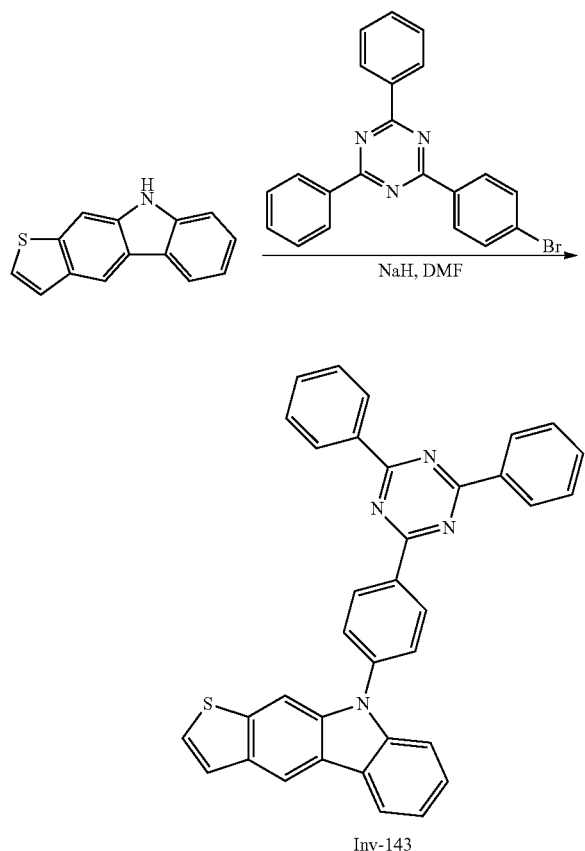

Inv-143

Inv-143 (3.45 g, yield: 65%) was obtained by performing the same procedure as in Synthesis Example 119, except that IC-32a (2.23 g, 10.0 mmol) was used instead of IC-36.

GC-Mass (theoretical value: 530.64 g/mol, measured value: 530 g/mol)

[Synthesis Example 144] Synthesis of Inv-144

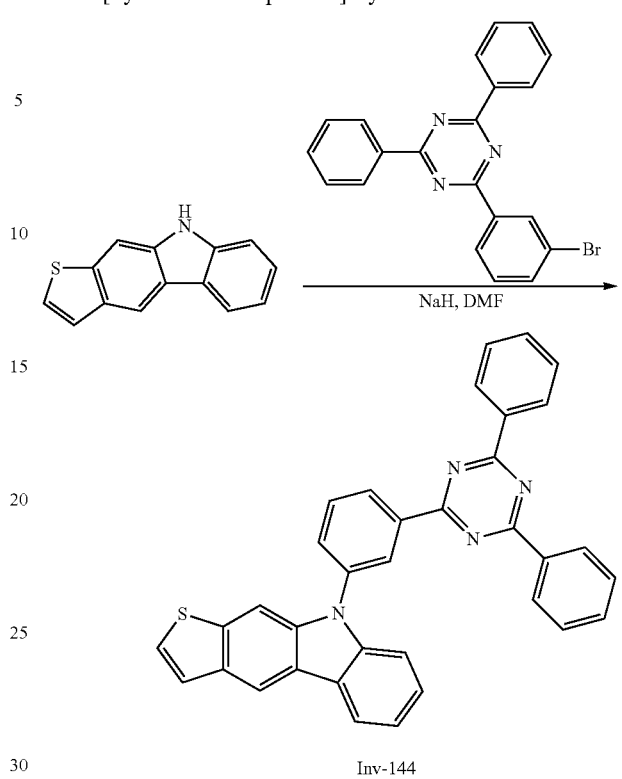

Inv-144

Inv-144 (3.77 g, yield: 71%) was obtained by performing the same procedure as in Synthesis Example 117, except that IC-32a (2.23 g, 10.0 mmol) was used instead of IC-35.

GC-Mass (theoretical value: 530.64 g/mol, measured value: 530 g/mol)

[Synthesis Example 145] Synthesis of Inv-145

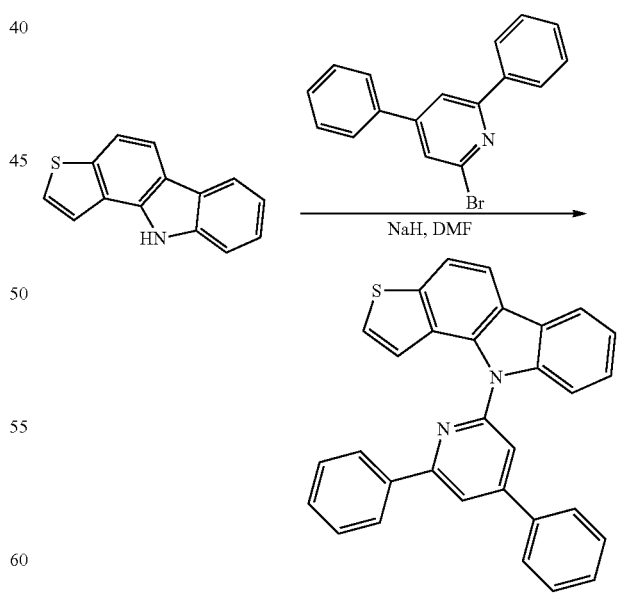

Inv-145

Inv-145 (3.76 g, yield: 83%) was obtained by performing the same procedure as in Synthesis Example 115, except that IC-32b (2.23 g, 10.0 mmol) was used instead of IC-35.

GC-Mass (theoretical value: 452.57 g/mol, measured value: 452 g/mol)

[Synthesis Example 146] Synthesis of Inv-146

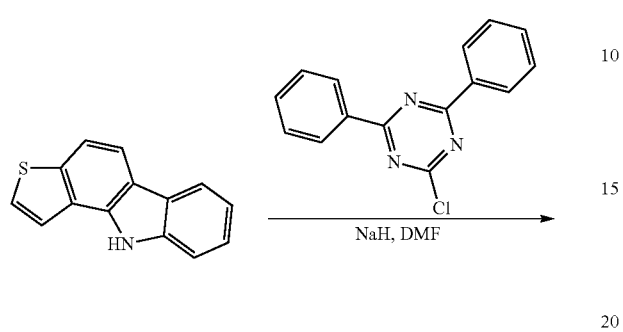

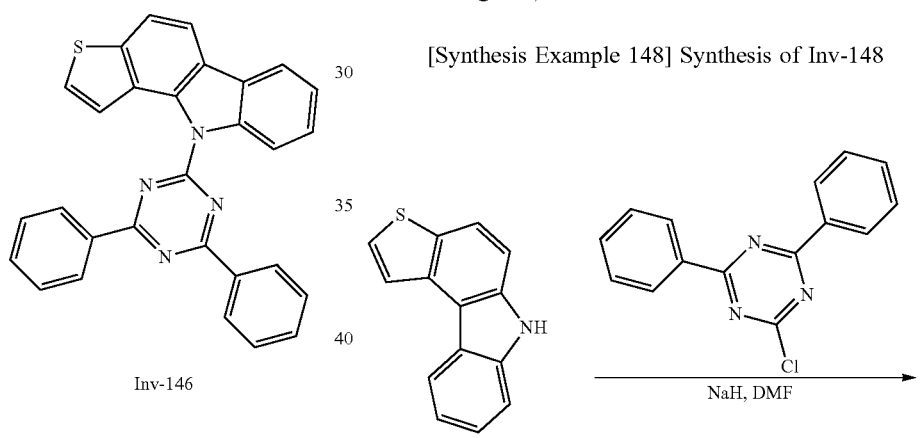

Inv-146

Inv-146 (3.77 g, yield: 83%) was obtained by performing the same procedure as in Synthesis Example 116, except that IC-32b (2.23 g, 10.0 mmol) was used instead of IC-35.

GC-Mass (theoretical value: 454.55 g/mol, measured value: 454 g/mol)

[Synthesis Example 147] Synthesis of Inv-147

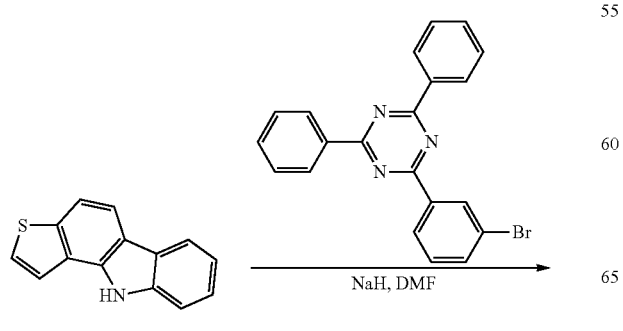

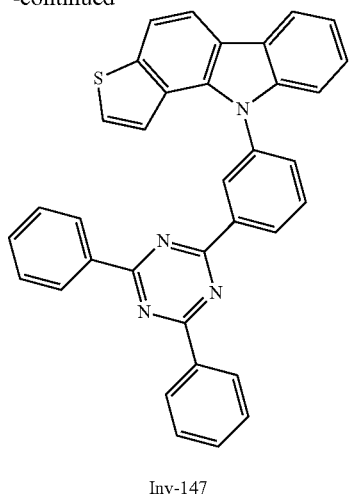

Inv-147

Inv-147 (3.77 g, yield: 71%) was obtained by performing the same procedure as in Synthesis Example 117, except that IC-32b (2.23 g, 10.0 mmol) was used instead of IC-35.

GC-Mass (theoretical value: 530.64 g/mol, measured value: 530 g/mol)

[Synthesis Example 148] Synthesis of Inv-148

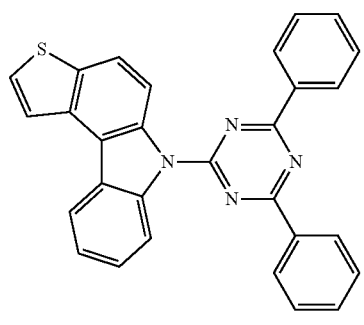

Inv-148

Inv-148 (3.50 g, yield: 77%) was obtained by performing the same procedure as in Synthesis Example 116, except that IC-43 (2.23 g, 10.0 mmol) was used instead of IC-35.

GC-Mass (theoretical value: 454.55 g/mol, measured value: 454 g/mol)

[Synthesis Example 149] Synthesis of Inv-149

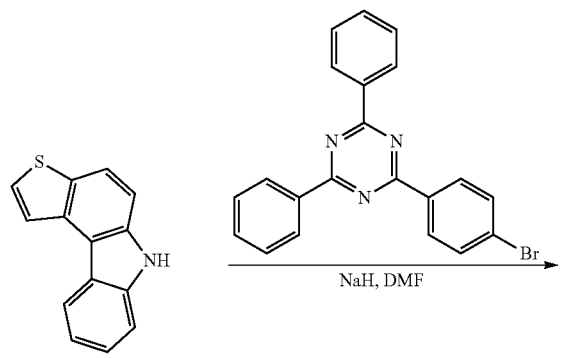

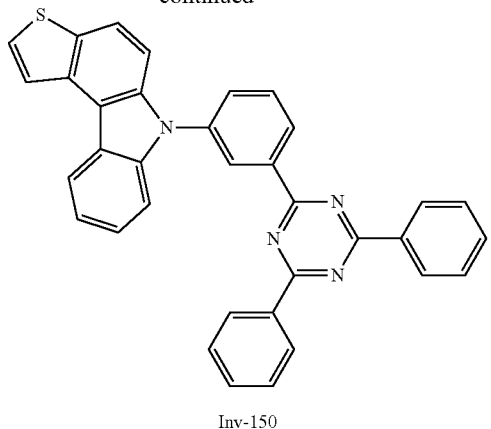

Inv-150

Inv-150 (4.14 g, yield: 78%) was obtained by performing the same procedure as in Synthesis Example 117, except that IC-43 (2.23 g, 10.0 mmol) was used instead of IC-35.

GC-Mass (theoretical value: 530.64 g/mol, measured value: 530 g/mol)

[Synthesis Example 151] Synthesis of Inv-151

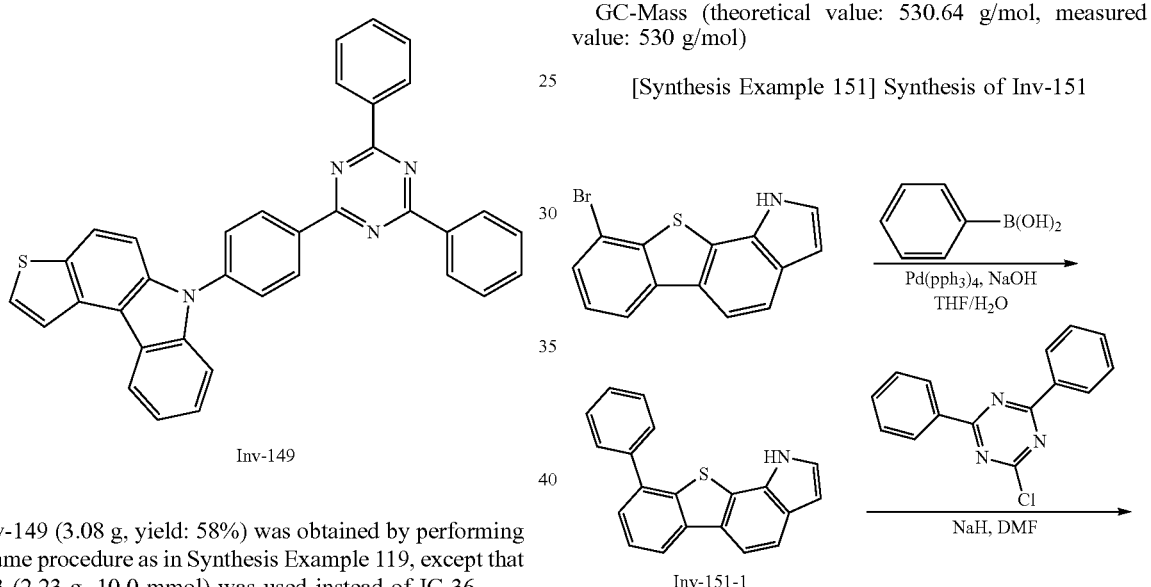

Inv-149

Inv-149 (3.08 g, yield: 58%) was obtained by performing the same procedure as in Synthesis Example 119, except that IC-43 (2.23 g, 10.0 mmol) was used instead of IC-36.

GC-Mass (theoretical value: 530.64 g/mol, measured value: 530 g/mol)

[Synthesis Example 150] Synthesis of Inv-150

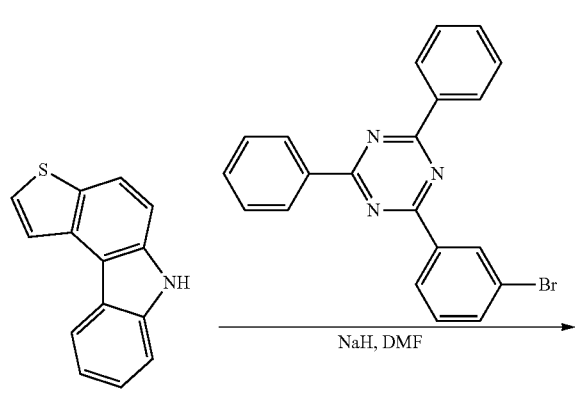

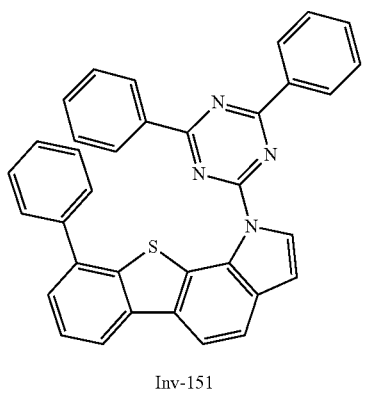

Inv-151

2.42 g (8.0 mmol) of IC-44, 1.07 g (8.8 mmol) of phenylboronic acid, 0.96 g (24.0 mmol) of NaOH, and 40 ml/20 ml of THF/H$_2$O were mixed under nitrogen flow, and the mixture was stirred. 0.46 g (5 mol %) of Pd(PPh$_3$)$_4$ was added thereto at 40° C., and the resulting mixture was stirred at 80° C. for 12 hours. After the reaction was completed, extraction was performed with methylene chloride, MgSO$_4$ was added thereto, and the mixture was filtered. After the solvent was removed from the filtered organic layer, 2.06 g (yield: 86%) of the intermediate compound Inv-151-1 was obtained by using column chromatography.

The intermediate compound Inv-151-1 (2.06 g, 6.88 mmol), 2-chloro-4,6-diphenyl-1,3,5-triazine (2.21 g, 8.26 mmol), NaH (1.98 g, 8.26 mmol) and DMF (40 ml) were mixed under nitrogen flow, and the mixture was stirred at normal temperature for 3 hours. After the reaction was completed, water was added thereto, the solid compound was filtered, and purification was performed by column chromatography, thereby obtaining a target compound Inv-151 (3.10 g, yield: 85%).

GC-Mass (theoretical value: 530.64 g/mol, measured value: 530 g/mol)

[Synthesis Example 152] Synthesis of Inv-152

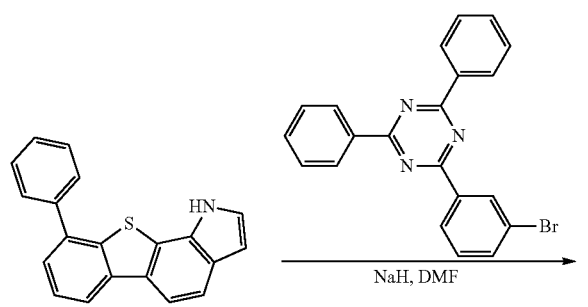

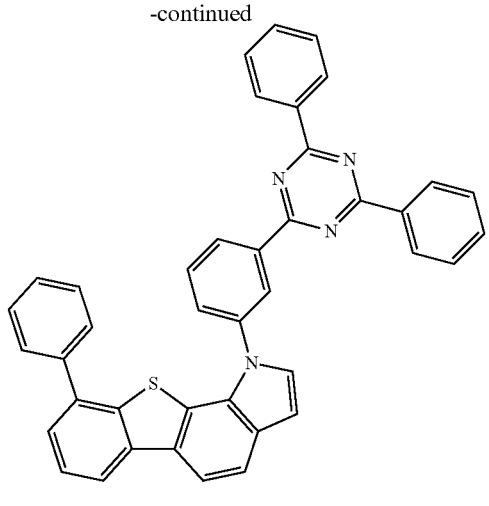

Inv-152

Inv-152 (4.14 g, yield: 78%) was obtained by performing the same procedure as in Synthesis Example 151, except that 2-(3-bromophenyl)-4,6-diphenyl-1,3,5-triazine (3.21 g, 8.26 mmol) was used instead of 2-chloro-4,6-diphenyl-1,3,5-triazine.

GC-Mass (theoretical value: 606.74 g/mol, measured value: 606 g/mol)

[Synthesis Example 153] Synthesis of Inv-153

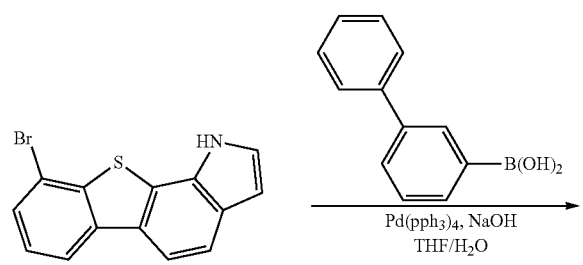

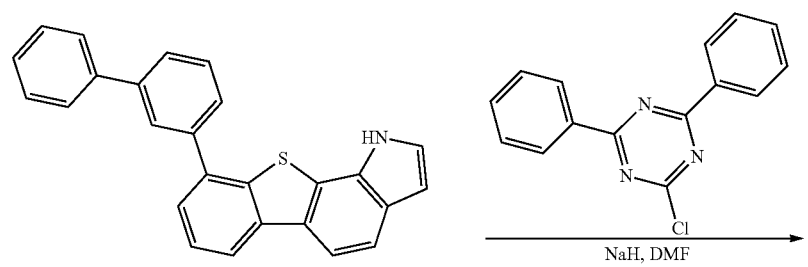

Inv-153-1

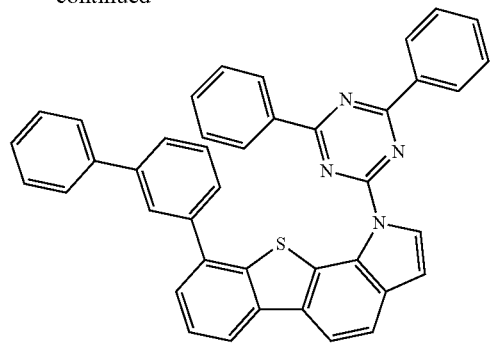

Inv-153

The intermediate compound Inv-153-1 (2.58 g, yield: 86%) was obtained by performing the same procedure as in Synthesis Example 151, except that biphenyl-3-ylboronic acid (1.74 g, 8.8 mmol) was used instead of phenylboronic acid.

A target compound Inv-153 (3.34 g, yield: 80%) was obtained by performing the same procedure as in Synthesis Example 151, except that Inv-153-1 (2.58 g, 6.88 mmol) was used instead of Inv-151-1.

GC-Mass (theoretical value: 606.74 g/mol, measured value: 606 g/mol)

[Synthesis Example 154] Synthesis of Inv-154

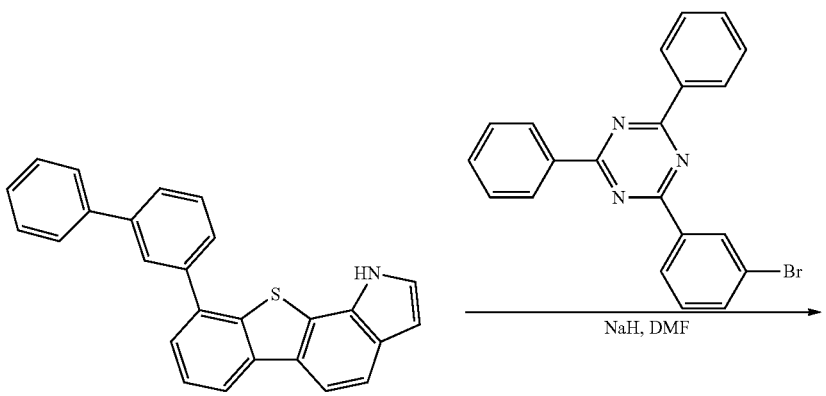

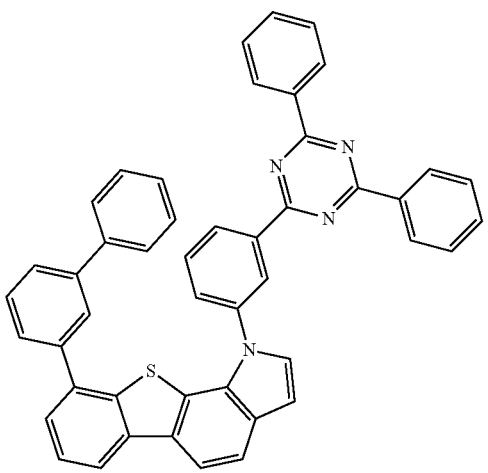

Inv-154

A target compound Inv-154 (3.24 g, yield: 69%) was obtained by performing the same procedure as in Synthesis Example 152, except that Inv-153-1 (2.58 g, 6.88 mmol) was used instead of Inv-151-1.

GC-Mass (theoretical value: 682.83 g/mol, measured value: 682 g/mol)

[Synthesis Example 155] Synthesis of Inv-155

The intermediate compound Inv-155-1 (3.29 g, yield: 91%) was obtained by performing the same procedure as in Synthesis Example 151, except that 3,5-diphenylphenylboronic acid (2.41 g, 8.8 mmol) was used instead of phenylboronic acid.

A target compound Inv-155 (3.99 g, yield: 85%) was obtained by performing the same procedure as in Synthesis Example 151, except that Inv-155-1 (2.58 g, 6.88 mmol) was used instead of Inv-151-1.

GC-Mass (theoretical value: 682.83 g/mol, measured value: 682 g/mol)

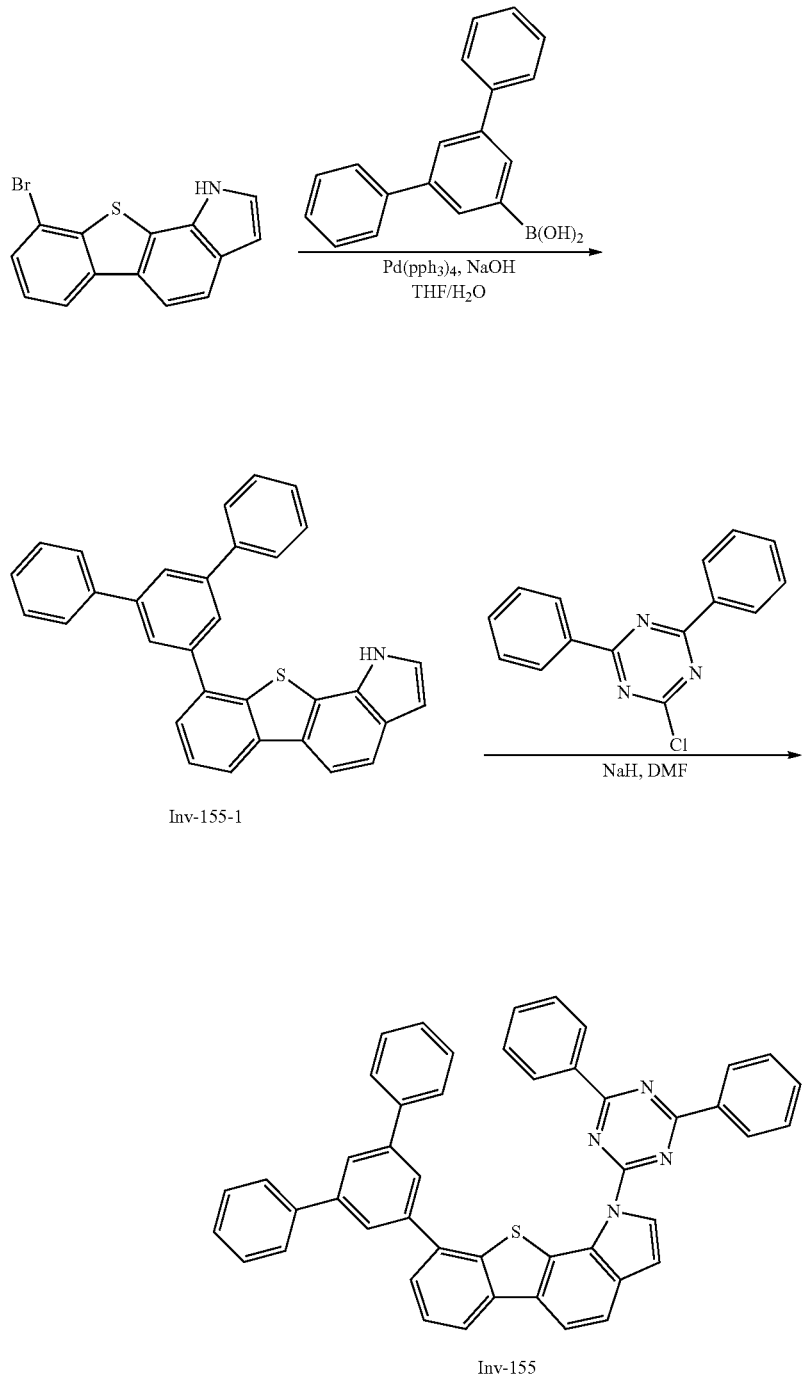

[Synthesis Example 156] Synthesis of Inv-156

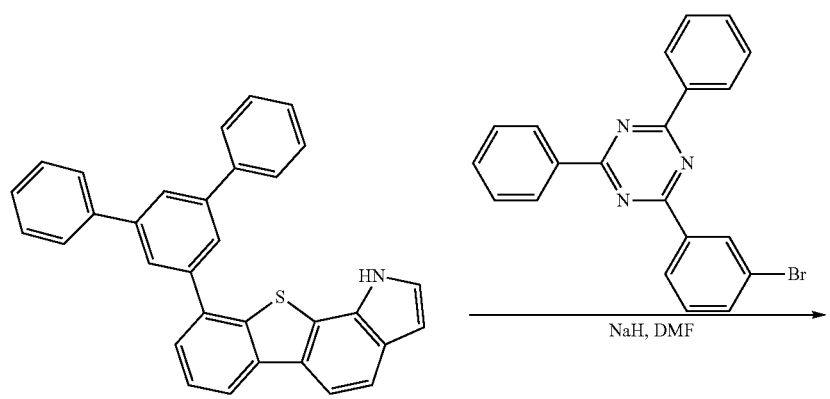

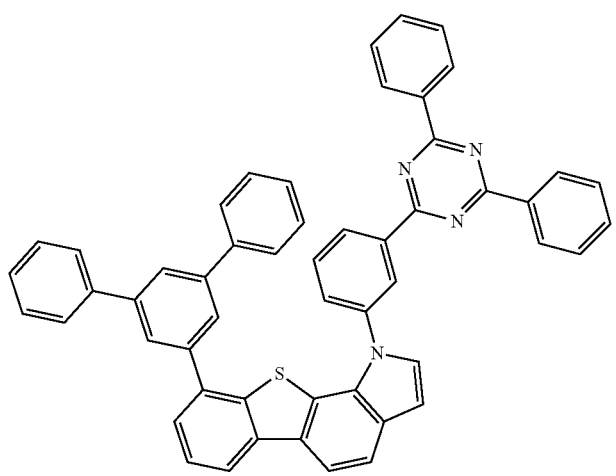

A target compound Inv-156 (3.03 g, yield: 58%) was obtained by performing the same procedure as in Synthesis Example 152, except that Inv-155-1 (2.58 g, 6.88 mmol) was used instead of Inv-151-1.

GC-Mass (theoretical value: 758.93 g/mol, measured value: 758 g/mol)

[Synthesis Example 157] Synthesis of Inv-157

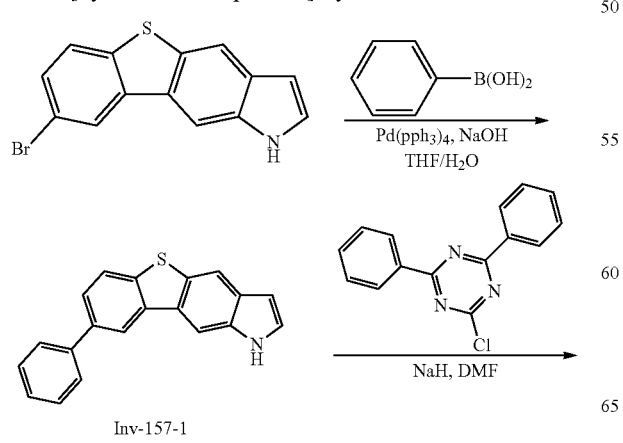

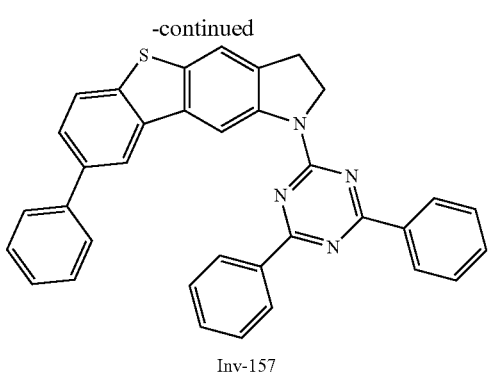

A target compound Inv-157 (2.72 g, yield: 64%) was obtained by performing the same procedure as in Synthesis Example 151, except that IC-45a (2.42 g, 8.0 mmol) was used instead of IC-44.

GC-Mass (theoretical value: 530.64 g/mol, measured value: 530 g/mol)

[Synthesis Example 158] Synthesis of Inv-158

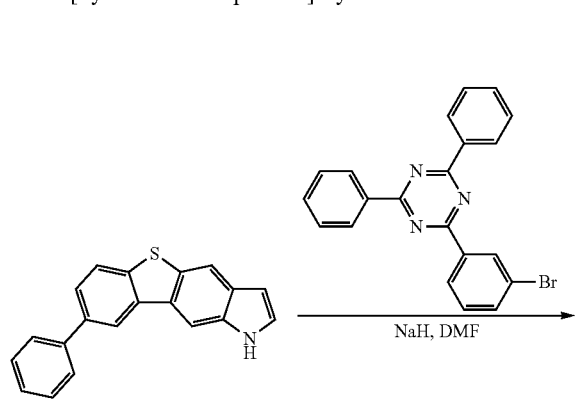

A target compound Inv-158 (2.67 g, yield: 64%) was obtained by performing the same procedure as in Synthesis Example 152, except that Inv-157-1 (2.58 g, 6.88 mmol) was used instead of Inv-151-1.

GC-Mass (theoretical value: 606.74 g/mol, measured value: 606 g/mol)

[Synthesis Example 159] Synthesis of Inv-159

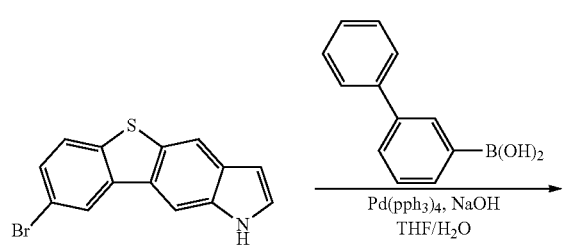

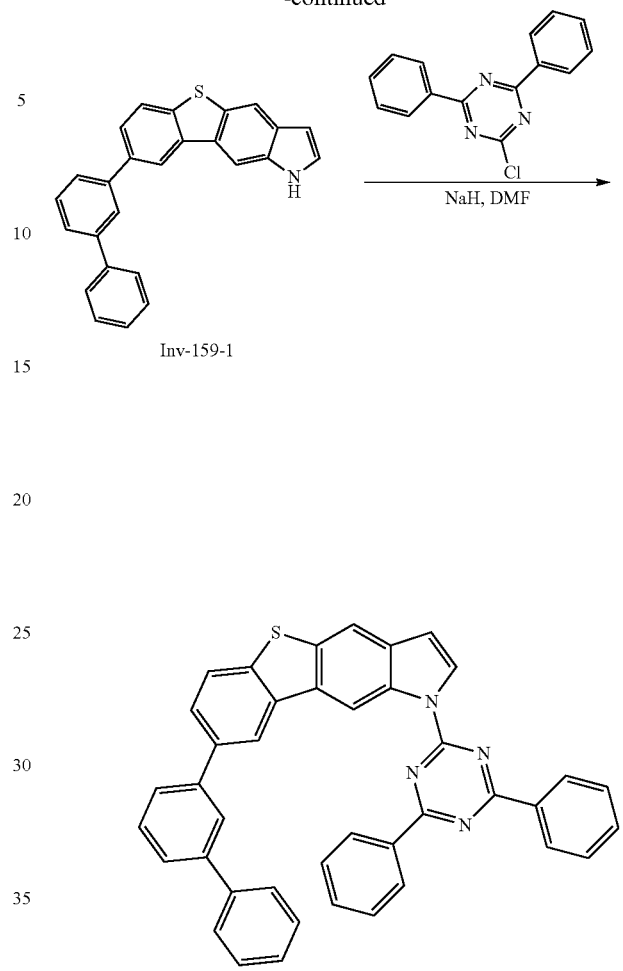

A target compound Inv-159 (2.80 g, yield: 55%) was obtained by performing the same procedure as in Synthesis Example 153, except that IC-45a (2.42 g, 8.0 mmol) was used instead of IC-44.

GC-Mass (theoretical value: 606.74 g/mol, measured value: 606 g/mol)

[Synthesis Example 160] Synthesis of Inv-160

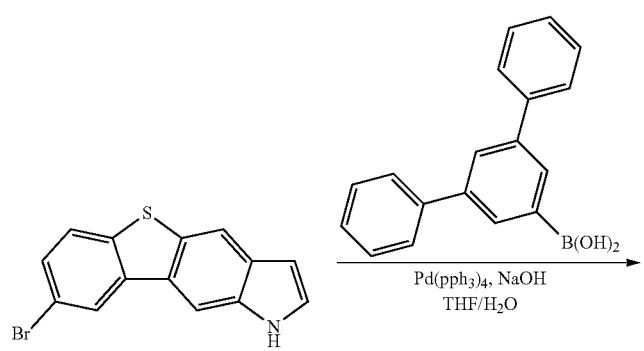

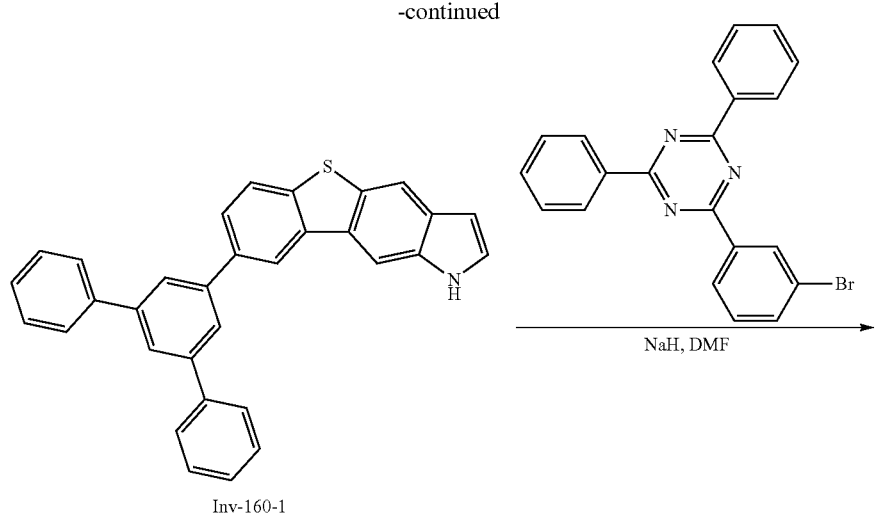
Inv-160
A target compound Inv-160 (2.62 g, yield: 43%) was obtained by performing the same procedure as in Synthesis Example 155, except that IC-45a (2.42 g, 8.0 mmol) was used instead of IC-44.
GC-Mass (theoretical value: 758.93 g/mol, measured value: 758 g/mol)
[Synthesis Example 161] Synthesis of Inv-161
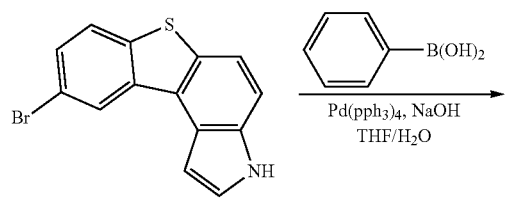
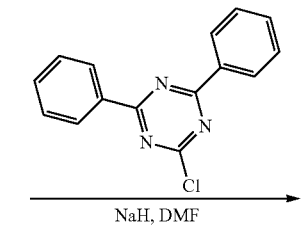
Inv-161-1
Inv-161

A target compound Inv-161 (2.42 g, yield: 57%) was obtained by performing the same procedure as in Synthesis Example 151, except that IC-45b (2.42 g, 8.0 mmol) was used instead of IC-44.

GC-Mass (theoretical value: 530.64 g/mol, measured value: 530 g/mol)

[Synthesis Example 162] Synthesis of Inv-162

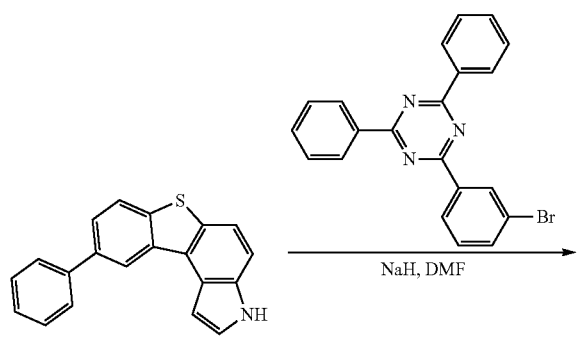

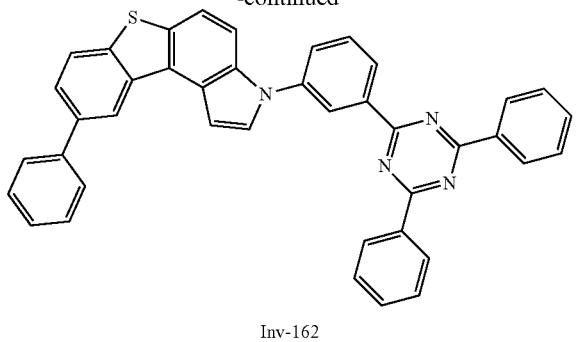

Inv-162

A target compound Inv-162 (2.55 g, yield: 61%) was obtained by performing the same procedure as in Synthesis Example 152, except that Inv-161-1 (2.58 g, 6.88 mmol) was used instead of Inv-151-1.

GC-Mass (theoretical value: 606.74 g/mol, measured value: 606 g/mol)

[Synthesis Example 163] Synthesis of Inv-163

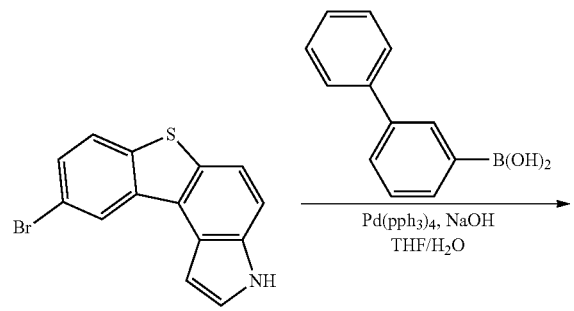

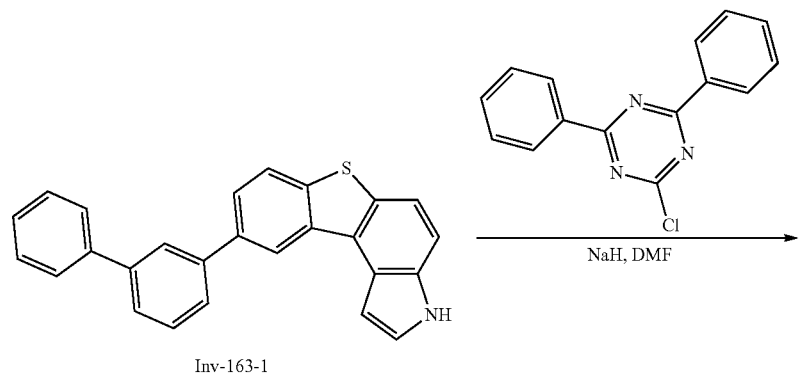

Inv-163-1

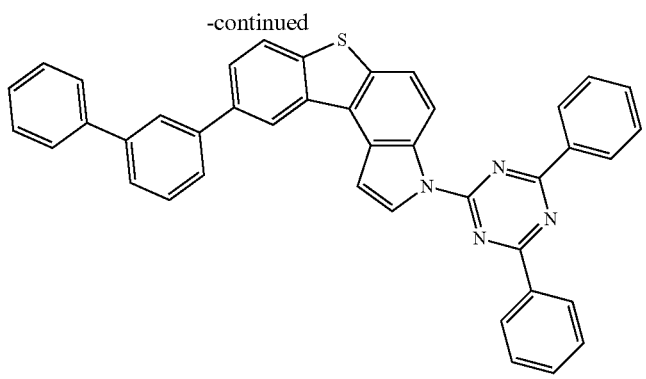
Inv-163
A target compound Inv-163 (2.04 g, yield: 42%) was obtained by performing the same procedure as in Synthesis Example 153, except that IC-45b (2.42 g, 8.0 mmol) was used instead of IC-44.
GC-Mass (theoretical value: 606.74 g/mol, measured value: 606 g/mol)
[Synthesis Example 164] Synthesis of Inv-164
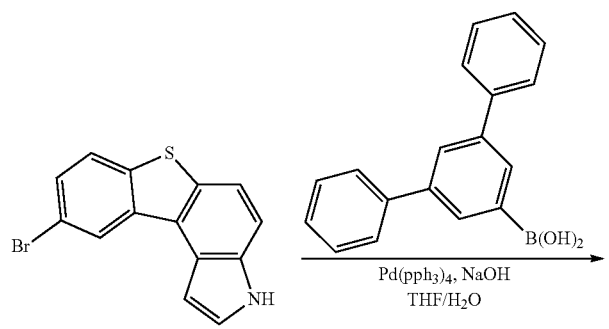
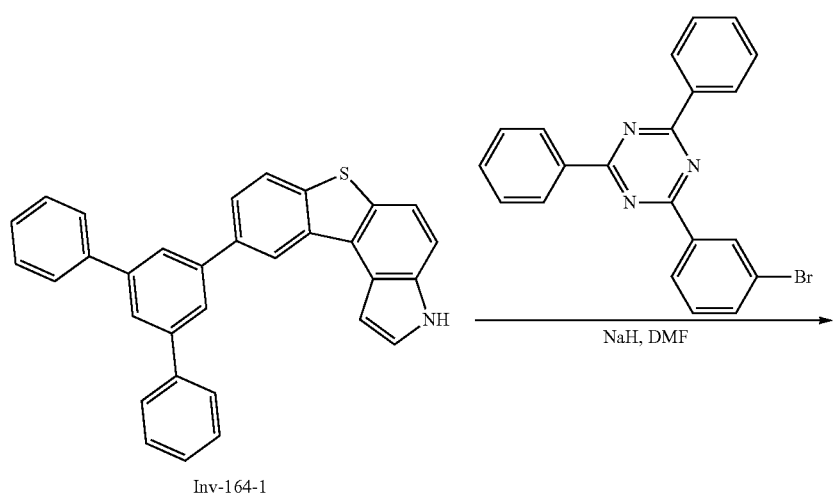
Inv-164-1

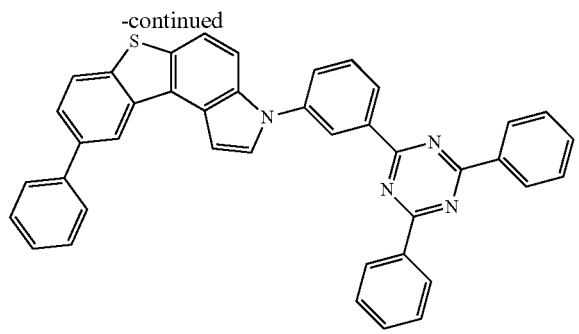

Inv-164

A target compound Inv-164 (2.85 g, yield: 47%) was obtained by performing the same procedure as in Synthesis Example 155, except that IC-45b (2.42 g, 8.0 mmol) was used instead of IC-44.

GC-Mass (theoretical value: 758.93 g/mol, measured value: 758 g/mol)

[Synthesis Example 165] Synthesis of Inv-165

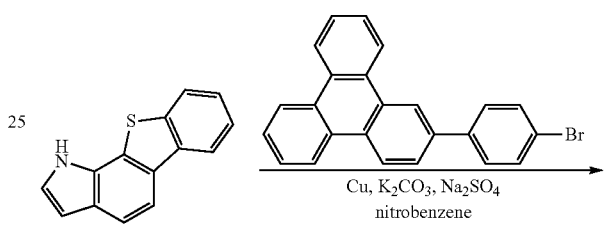

The compound IC-35 (4.47 g, 20.00 mmol), 2-bromotriphenylene (9.22 g, 30.00 mmol), Cu powder (0.38 g, 1.00 mmol), $K_2CO_3$ (5.52 g, 40.00 mmol), $Na_2SO_4$ (5.68 g, 40.00 mmol), and nitrobenzene (100 ml) were mixed under nitrogen flow, and the mixture was stirred at 190° C. for 12 hours. After the reaction was completed, nitrobenzene was removed, the organic layer was separated with methylene chloride, and water was removed by using $MgSO_4$. After the solvent was removed from the organic layer, purification was performed by column chromatography, thereby obtaining a target compound Inv-165 (5.93 g, yield 66%).

GC-Mass (theoretical value: 449.56 g/mol, measured value: 449 g/mol)

[Synthesis Example 166] Synthesis of Inv-166

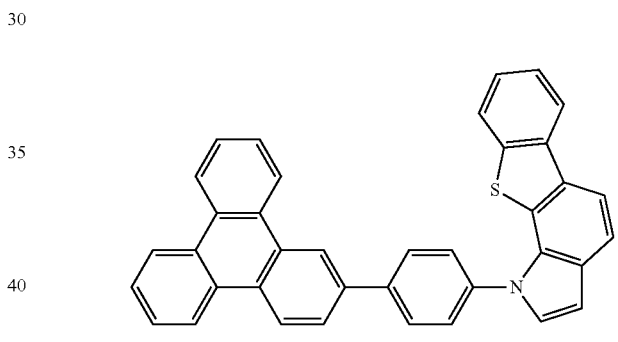

Inv-166

Inv-166 (7.04 g, yield: 67%) was obtained by performing the same procedure as in Synthesis Example 165, except that 2-(4-bromophenyl)triphenylene (11.50 g, 30.0 mmol) was used instead of 2-bromotriphenylene.

GC-Mass (theoretical value: 525.66 g/mol, measured value: 525 g/mol)

[Synthesis Example 167] Synthesis of Inv-167

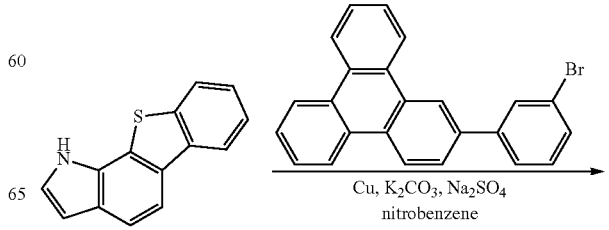

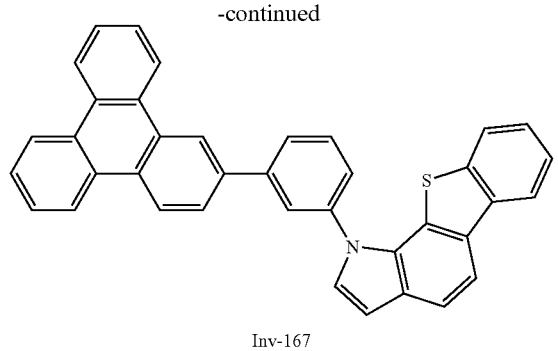

Inv-167

Inv-167 (6.90 g, yield: 61%) was obtained by performing the same procedure as in Synthesis Example 165, except that 2-(3-bromophenyl)triphenylene (11.50 g, 30.0 mmol) was used instead of 2-bromotriphenylene.

GC-Mass (theoretical value: 525.66 g/mol, measured value: 525 g/mol)

[Synthesis Example 168] Synthesis of Inv-168

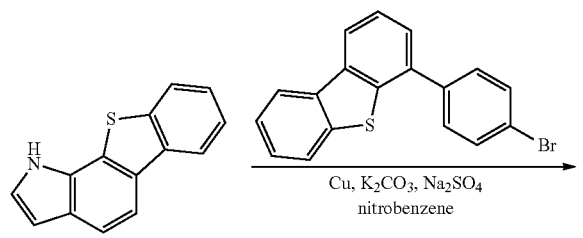

Inv-168

Inv-168 (5.68 g, yield: 59%) was obtained by performing the same procedure as in Synthesis Example 165, except that 4-(4-bromophenyl)dibenzo[b,d]thiophene (10.18 g, 30.0 mmol) was used instead of 2-bromotriphenylene.

GC-Mass (theoretical value: 481.63 g/mol, measured value: 481 g/mol)

[Synthesis Example 169] Synthesis of Inv-169

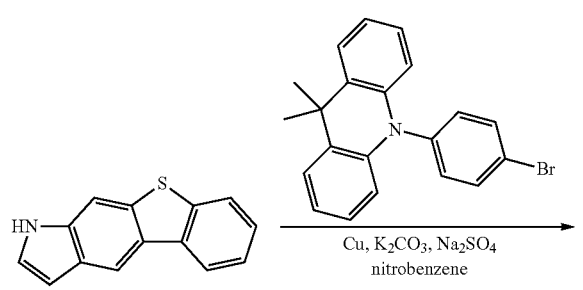

Inv-169

The compound IC-36 (4.47 g, 20.00 mmol), 10-(4-bromophenyl)-9,9-dimethyl-9,10-dihydroacridine (10.93 g, 30.00 mmol), Cu powder (0.38 g, 1.00 mmol), K$_2$CO$_3$ (5.52 g, 40.00 mmol), Na$_2$SO$_4$ (5.68 g, 40.00 mmol) and nitrobenzene (100 ml) were mixed under nitrogen flow, and the mixture was stirred at 190° C. for 12 hours. After the reaction was completed, nitrobenzene was removed, the organic layer was separated with methylene chloride, and water was removed by using MgSO$_4$. After the solvent was removed from the organic layer, purification was performed by column chromatography, thereby obtaining a target compound Inv-169 (6.38 g, yield 63%).

GC-Mass (theoretical value: 506.66 g/mol, measured value: 506 g/mol)

[Synthesis Example 170] Synthesis of Inv-170

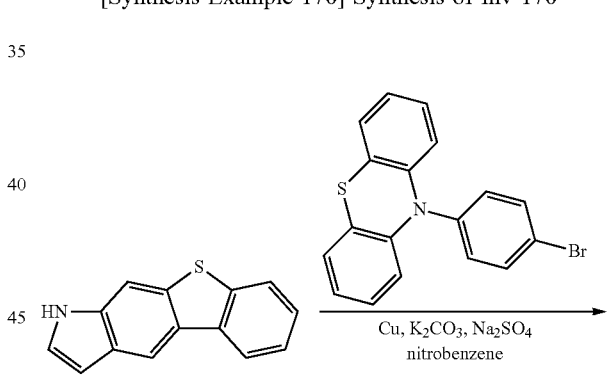

Inv-170

Inv-170 (6.85 g, yield: 69%) was obtained by performing the same procedure as in Synthesis Example 169, except that 10-(4-bromophenyl)-10H-phenothiazine (10.63 g, 30.0 mmol) was used instead of 10-(4-bromophenyl)-9,9-dimethyl-9,10-dihydroacridine.

GC-Mass (theoretical value: 496.64 g/mol, measured value: 496 g/mol)

[Synthesis Example 171] Synthesis of Inv-171

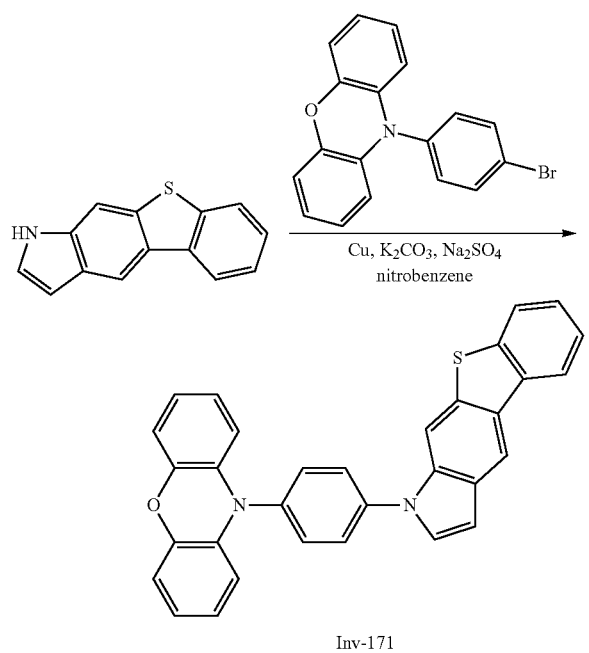

Inv-171

Inv-171 (6.92 g, yield: 72%) was obtained by performing the same procedure as in Synthesis Example 169, except that 10-(4-bromophenyl)-10H-phenothiazine (10.15 g, 30.0 mmol) was used instead of 10-(4-bromophenyl)-9,9-dimethyl-9,10-dihydroacridine.

GC-Mass (theoretical value: 480.58 g/mol, measured value: 480 g/mol)

[Synthesis Example 172] Synthesis of Inv-172

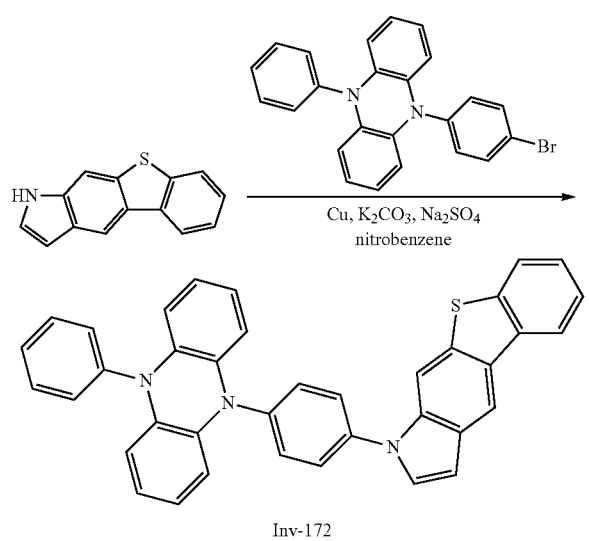

Inv-172

Inv-172 (5.78 g, yield: 52%) was obtained by performing the same procedure as in Synthesis Example 169, except that 5-(4-bromophenyl)-10-phenyl-5,10-dihydrophenazine (12.40 g, 30.0 mmol) was used instead of 10-(4-bromophenyl)-9,9-dimethyl-9,10-dihydroacridine.

GC-Mass (theoretical value: 555.69 g/mol, measured value: 555 g/mol)

[Synthesis Example 173] Synthesis of Inv-173

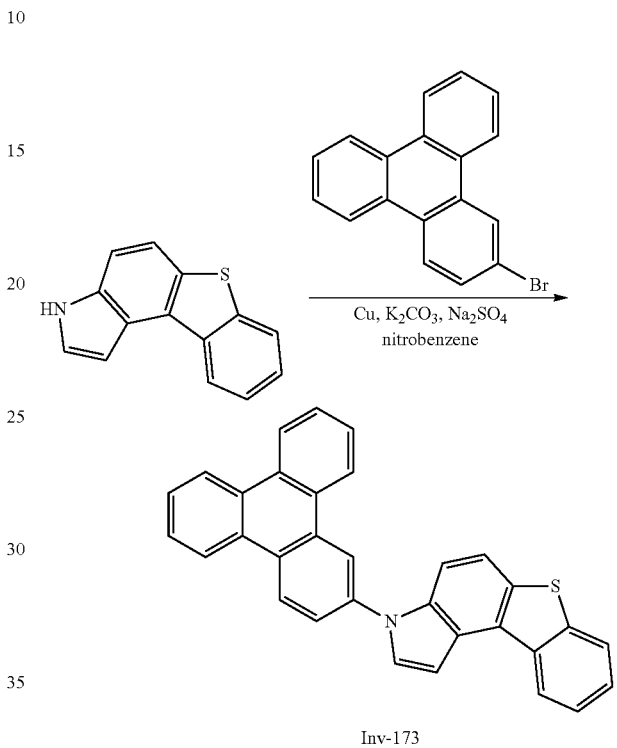

Inv-173

Inv-173 (5.30 g, yield: 59%) was obtained by performing the same procedure as in Synthesis Example 165, except that IC-37 (4.47 g, 20.0 mmol) was used instead of IC-35.

GC-Mass (theoretical value: 449.56 g/mol, measured value: 449 g/mol)

[Synthesis Example 174] Synthesis of Inv-174

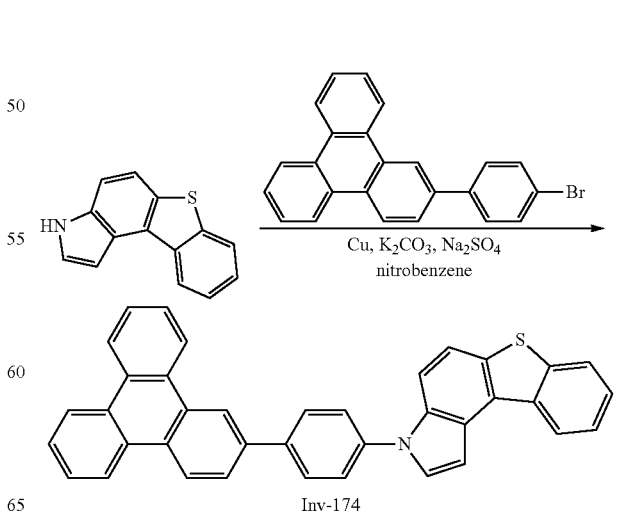

Inv-174

Inv-174 (6.73 g, yield: 64%) was obtained by performing the same procedure as in Synthesis Example 166, except that IC-37 (4.47 g, 20.0 mmol) was used instead of IC-35.

GC-Mass (theoretical value: 525.66 g/mol, measured value: 525 g/mol)

[Synthesis Example 175] Synthesis of Inv-175

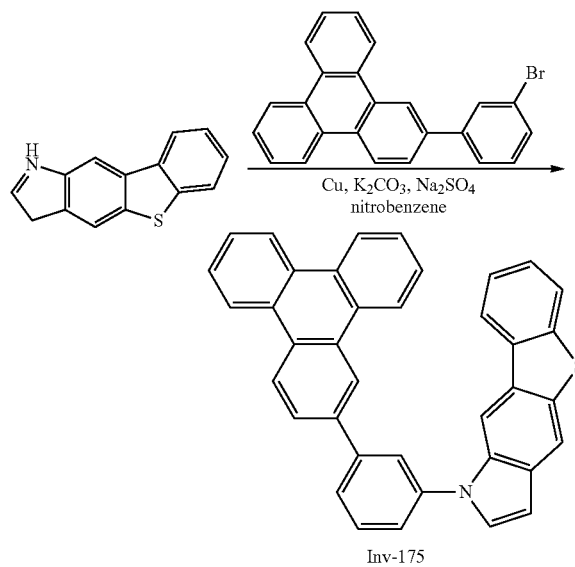

Inv-175

Inv-175 (6.41 g, yield: 61%) was obtained by performing the same procedure as in Synthesis Example 167, except that IC-39 (4.47 g, 20.0 mmol) was used instead of IC-35.

GC-Mass (theoretical value: 525.66 g/mol, measured value: 525 g/mol)

[Synthesis Example 176] Synthesis of Inv-176

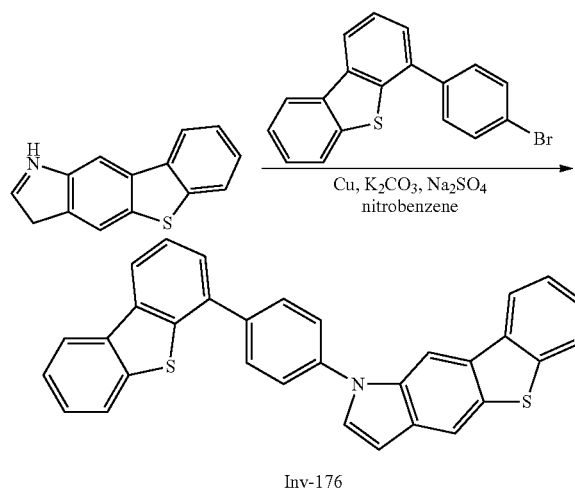

Inv-176

Inv-176 (6.36 g, yield: 66%) was obtained by performing the same procedure as in Synthesis Example 168, except that IC-39 (4.47 g, 20.0 mmol) was used instead of IC-35.

GC-Mass (theoretical value: 481.63 g/mol, measured value: 481 g/mol)

[Synthesis Example 177] Synthesis of Inv-177

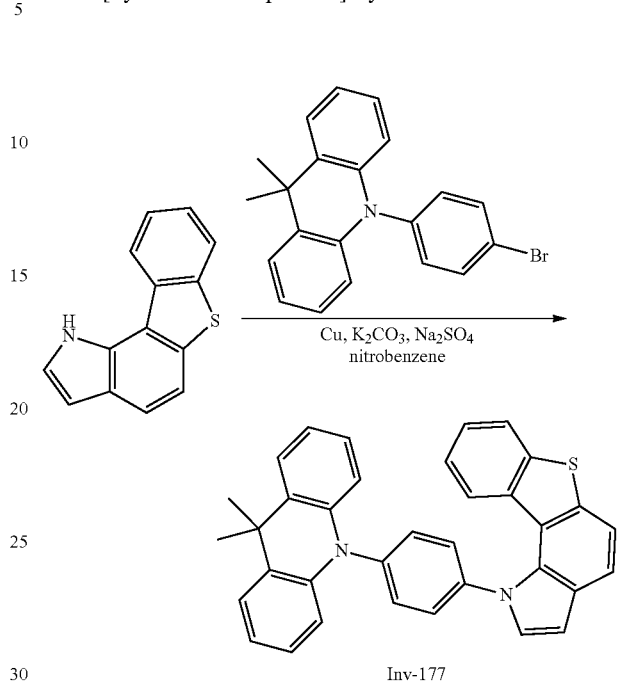

Inv-177

Inv-177 (6.69 g, yield: 66%) was obtained by performing the same procedure as in Synthesis Example 169, except that IC-38 (4.47 g, 20.0 mmol) was used instead of IC-36.

GC-Mass (theoretical value: 506.66 g/mol, measured value: 506 g/mol)

[Synthesis Example 178] Synthesis of Inv-178

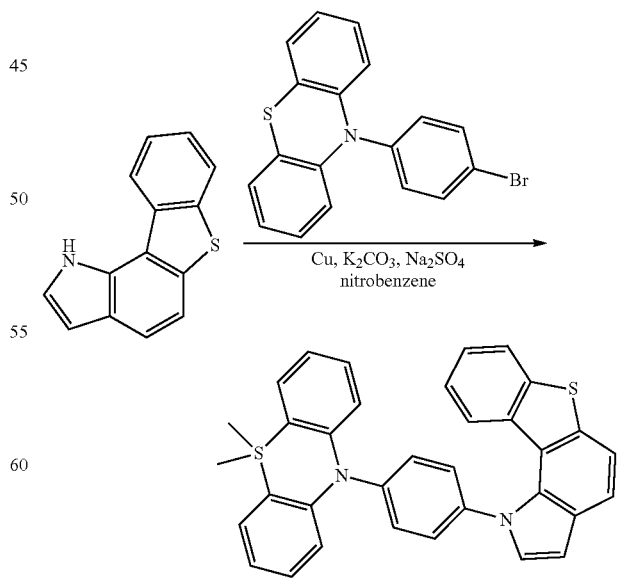

Inv-178

Inv-178 (5.36 g, yield: 54%) was obtained by performing the same procedure as in Synthesis Example 170, except that IC-38 (4.47 g, 20.0 mmol) was used instead of IC-36.

GC-Mass (theoretical value: 496.64 g/mol, measured value: 496 g/mol)

[Synthesis Example 179] Synthesis of Inv-179

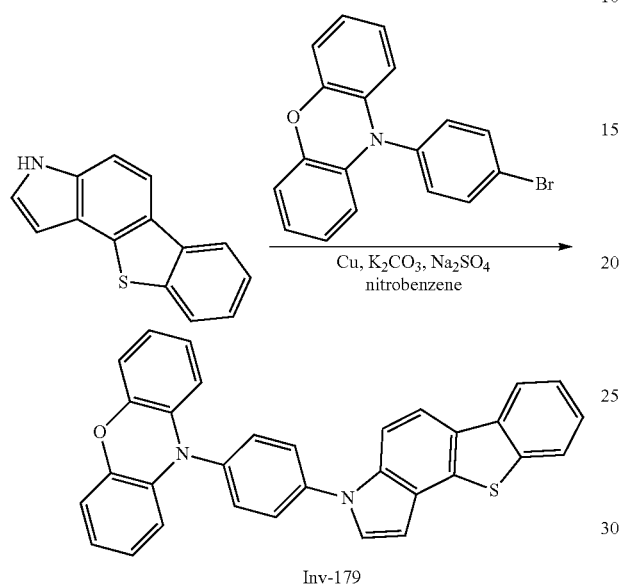

Inv-179

Inv-179 (5.86 g, yield: 61%) was obtained by performing the same procedure as in Synthesis Example 171, except that IC-40 (4.47 g, 20.0 mmol) was used instead of IC-36.

GC-Mass (theoretical value: 480.58 g/mol, measured value: 480 g/mol)

[Synthesis Example 180] Synthesis of Inv-180

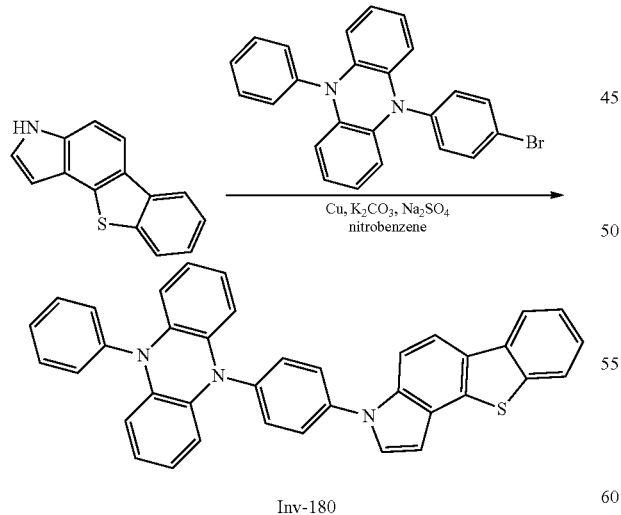

Inv-180

Inv-180 (7.11 g, yield: 64%) was obtained by performing the same procedure as in Synthesis Example 172, except that IC-40 (4.47 g, 20.0 mmol) was used instead of IC-36.

GC-Mass (theoretical value: 555.69 g/mol, measured value: 555 g/mol)

[Synthesis Example 181] Synthesis of Inv-181

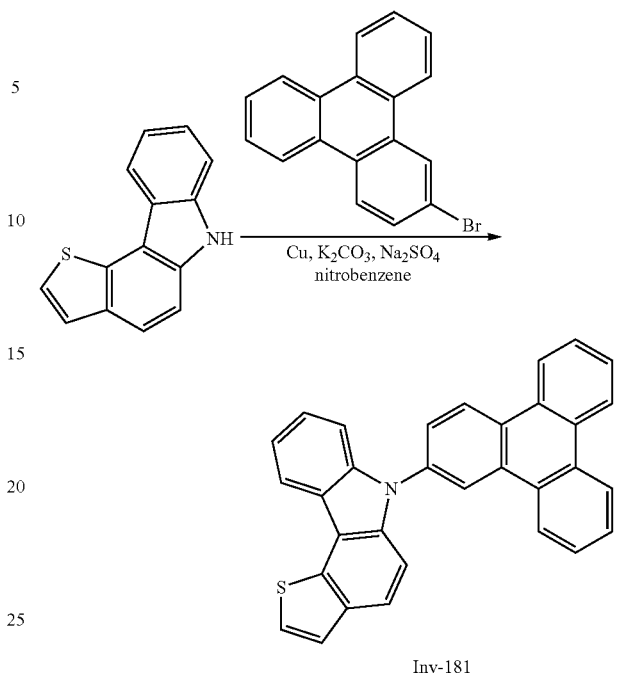

Inv-181

Inv-181 (5.30 g, yield: 59%) was obtained by performing the same procedure as in Synthesis Example 165, except that IC-41 (4.47 g, 20.0 mmol) was used instead of IC-35.

GC-Mass (theoretical value: 449.56 g/mol, measured value: 449 g/mol)

[Synthesis Example 182] Synthesis of Inv-182

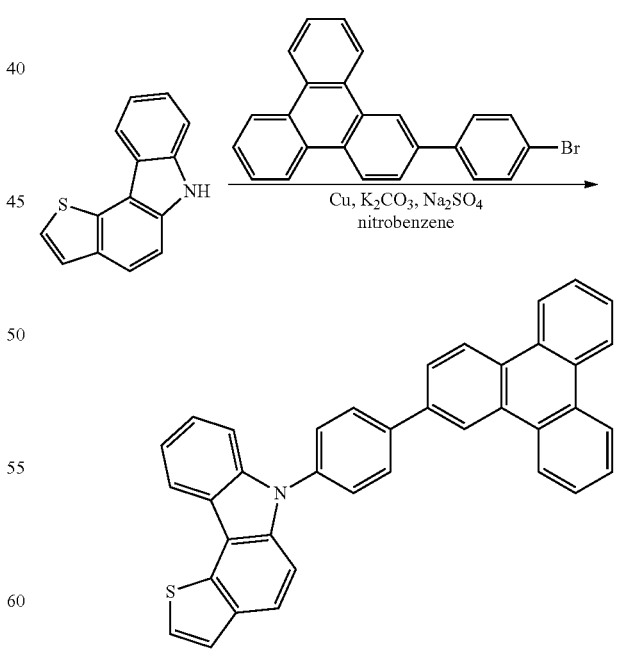

Inv-182

Inv-182 (6.62 g, yield: 65%) was obtained by performing the same procedure as in Synthesis Example 166, except that IC-41 (4.47 g, 20.0 mmol) was used instead of IC-35.

GC-Mass (theoretical value: 525.66 g/mol, measured value: 525 g/mol)

[Synthesis Example 183] Synthesis of Inv-183

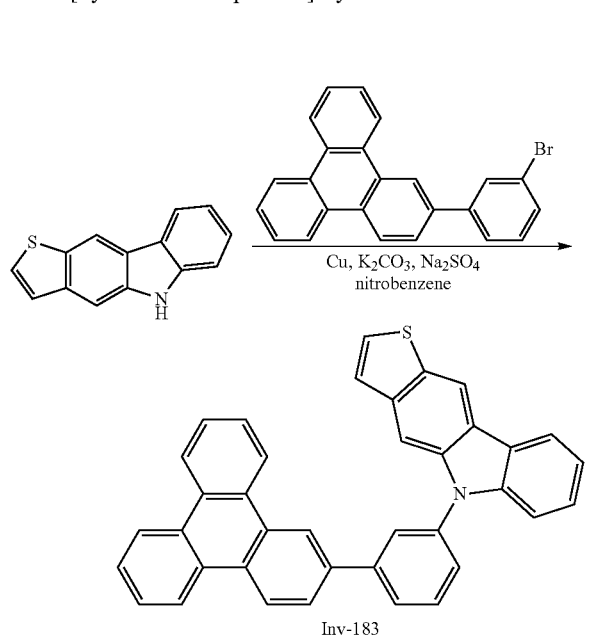

Inv-183

Inv-183 (6.31 g, yield: 64%) was obtained by performing the same procedure as in Synthesis Example 167, except that IC-42b (4.47 g, 20.0 mmol) was used instead of IC-35.

GC-Mass (theoretical value: 525.66 g/mol, measured value: 525 g/mol)

[Synthesis Example 184] Synthesis of Inv-184

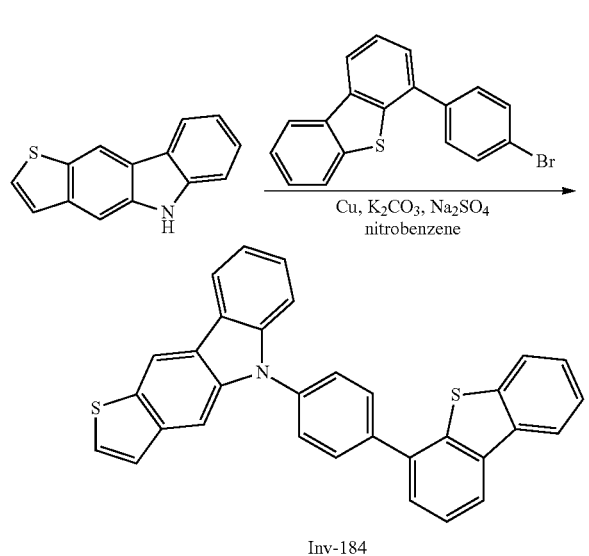

Inv-184

Inv-184 (5.59 g, yield: 58%) was obtained by performing the same procedure as in Synthesis Example 168, except that IC-42b (4.47 g, 20.0 mmol) was used instead of IC-35.

GC-Mass (theoretical value: 481.63 g/mol, measured value: 481 g/mol)

[Synthesis Example 185] Synthesis of Inv-185

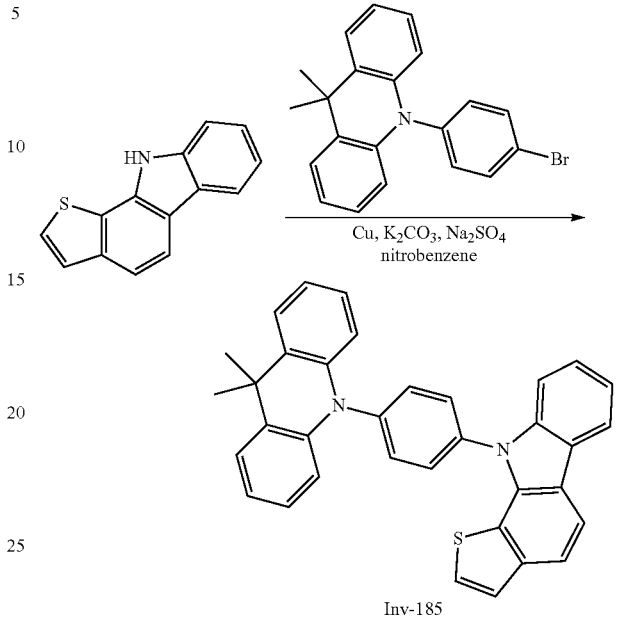

Inv-185

Inv-185 (5.68 g, yield: 56%) was obtained by performing the same procedure as in Synthesis Example 169, except that IC-42a (4.47 g, 20.0 mmol) was used instead of IC-36.

GC-Mass (theoretical value: 506.66 g/mol, measured value: 506 g/mol)

[Synthesis Example 186] Synthesis of Inv-186

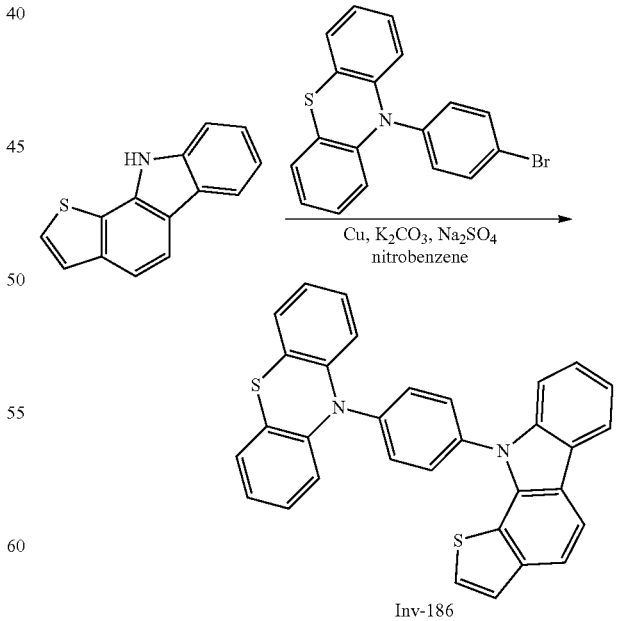

Inv-186

Inv-186 (5.86 g, yield: 59%) was obtained by performing the same procedure as in Synthesis Example 170, except that IC-42a (4.47 g, 20.0 mmol) was used instead of IC-36.

GC-Mass (theoretical value: 496.64 g/mol, measured value: 496 g/mol)

[Synthesis Example 187] Synthesis of Inv-187

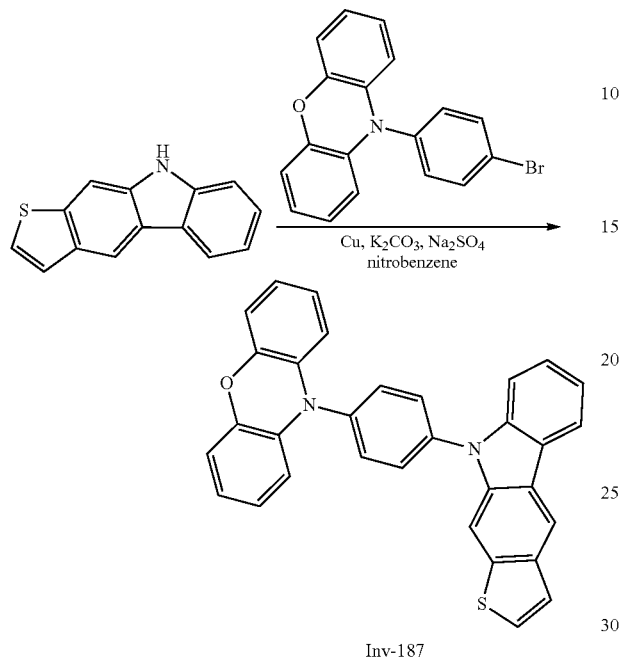

Inv-187

Inv-187 (5.86 g, yield: 61%) was obtained by performing the same procedure as in Synthesis Example 171, except that IC-32a (4.47 g, 20.0 mmol) was used instead of IC-36.

GC-Mass (theoretical value: 480.58 g/mol, measured value: 480 g/mol)

[Synthesis Example 188] Synthesis of Inv-188

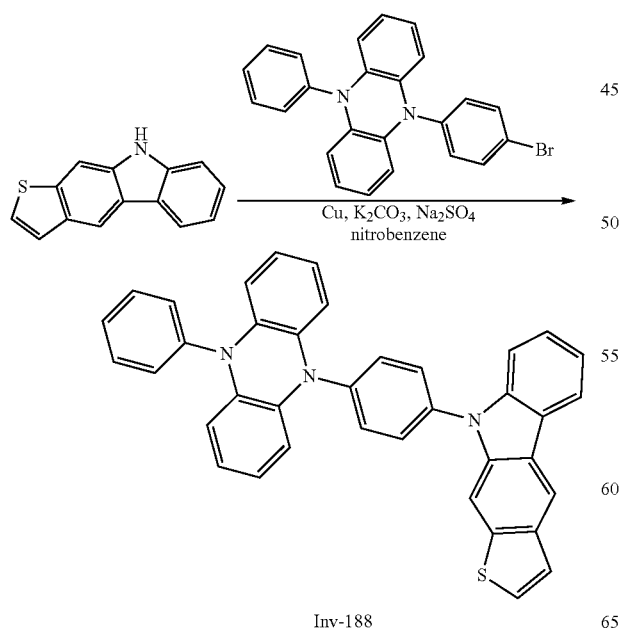

Inv-188

Inv-188 (6.33 g, yield: 57%) was obtained by performing the same procedure as in Synthesis Example 172, except that IC-32a (4.47 g, 20.0 mmol) was used instead of IC-36.

GC-Mass (theoretical value: 555.69 g/mol, measured value: 555 g/mol)

[Synthesis Example 189] Synthesis of Inv-189

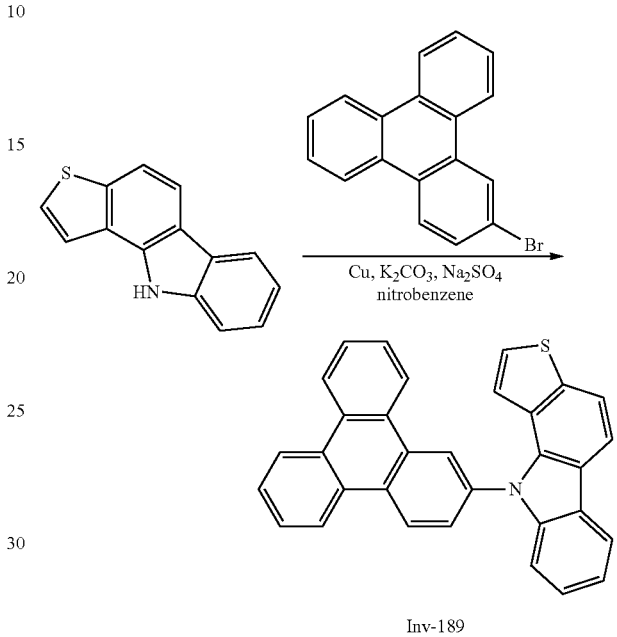

Inv-189

Inv-189 (6.89 g, yield: 69%) was obtained by performing the same procedure as in Synthesis Example 165, except that IC-32b (4.47 g, 20.0 mmol) was used instead of IC-35.

GC-Mass (theoretical value: 449.56 g/mol, measured value: 449 g/mol)

[Synthesis Example 190] Synthesis of Inv-190

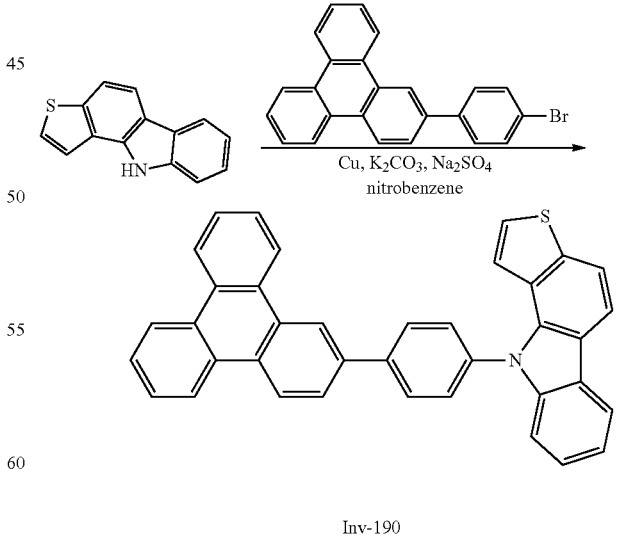

Inv-190

Inv-190 (5.68 g, yield: 54%) was obtained by performing the same procedure as in Synthesis Example 166, except that IC-32b (4.47 g, 20.0 mmol) was used instead of IC-35.

GC-Mass (theoretical value: 525.66 g/mol, measured value: 525 g/mol)

[Synthesis Example 191] Synthesis of Inv-191

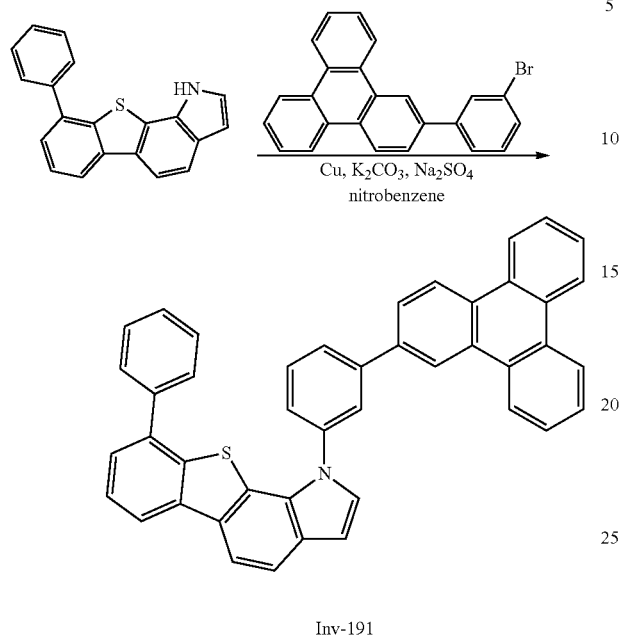

Inv-191

Inv-191 (7.34 g, yield: 61%) was obtained by performing the same procedure as in Synthesis Example 167, except that Inv-151-1 (5.98 g, 20.0 mmol) was used instead of IC-35.

GC-Mass (theoretical value: 601.76 g/mol, measured value: 601 g/mol)

[Synthesis Example 192] Synthesis of Inv-192

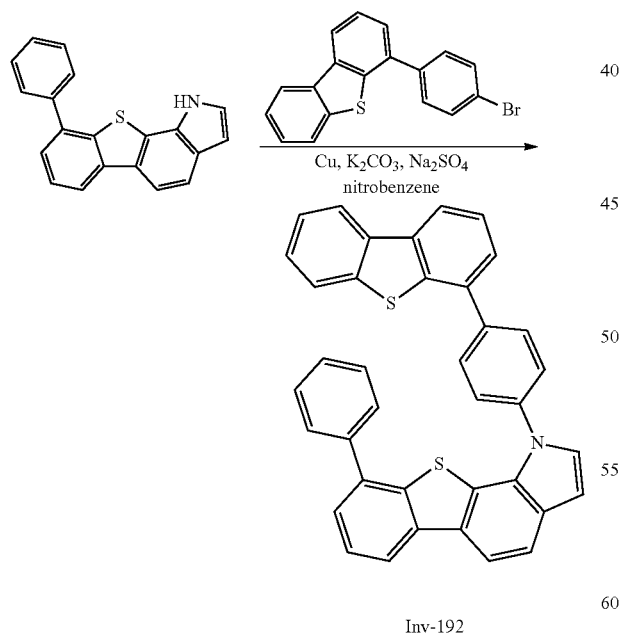

Inv-192

Inv-192 (7.70 g, yield: 69%) was obtained by performing the same procedure as in Synthesis Example 168, except that Inv-151-1 (5.98 g, 20.0 mmol) was used instead of IC-35.

GC-Mass (theoretical value: 557.73 g/mol, measured value: 557 g/mol)

[Synthesis Example 193] Synthesis of Inv-193

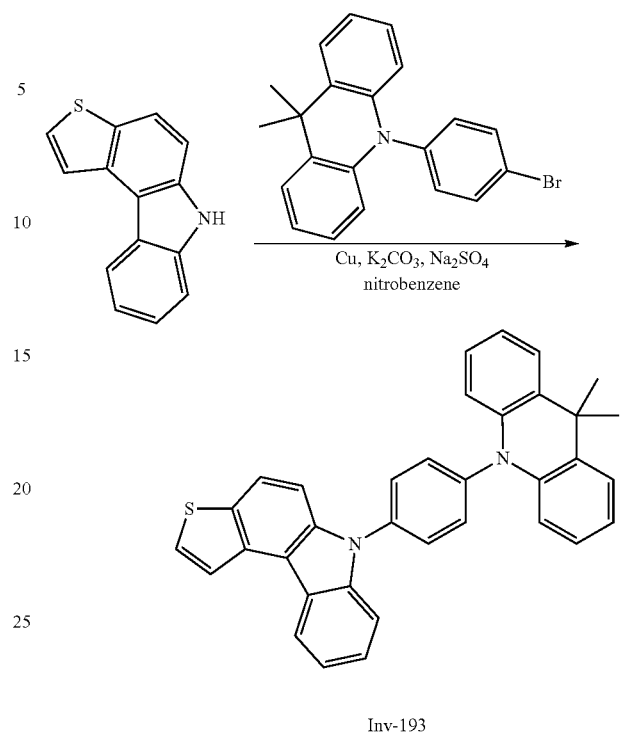

Inv-193

Inv-193 (6.69 g, yield: 66%) was obtained by performing the same procedure as in Synthesis Example 169, except that IC-43 (4.47 g, 20.0 mmol) was used instead of IC-36.

GC-Mass (theoretical value: 506.66 g/mol, measured value: 506 g/mol)

[Synthesis Example 194] Synthesis of Inv-194

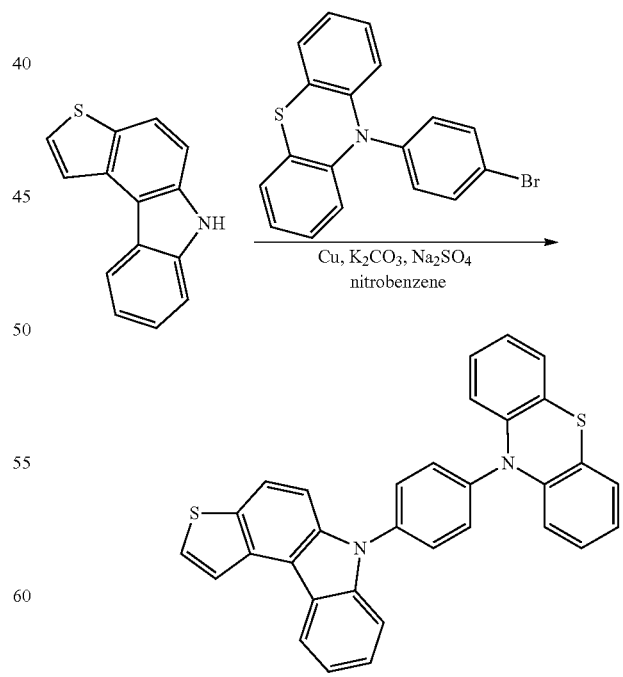

Inv-194

Inv-194 (5.66 g, yield: 57%) was obtained by performing the same procedure as in Synthesis Example 170, except that IC-43 (4.47 g, 20.0 mmol) was used instead of IC-36.

GC-Mass (theoretical value: 496.64 g/mol, measured value: 496 g/mol)

[Synthesis Example 195] Synthesis of Inv-195

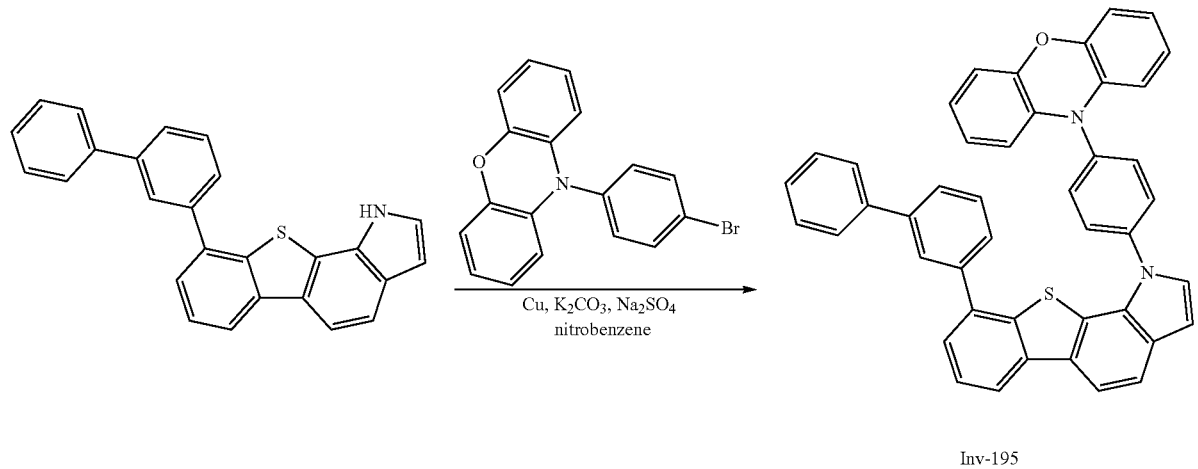

Inv-195

Inv-195 (8.10 g, yield: 64%) was obtained by performing the same procedure as in Synthesis Example 171, except that Inv-153-1 (5.98 g, 20.0 mmol) was used instead of IC-36.

GC-Mass (theoretical value: 632.77 g/mol, measured value: 632 g/mol)

[Synthesis Example 196] Synthesis of Inv-196

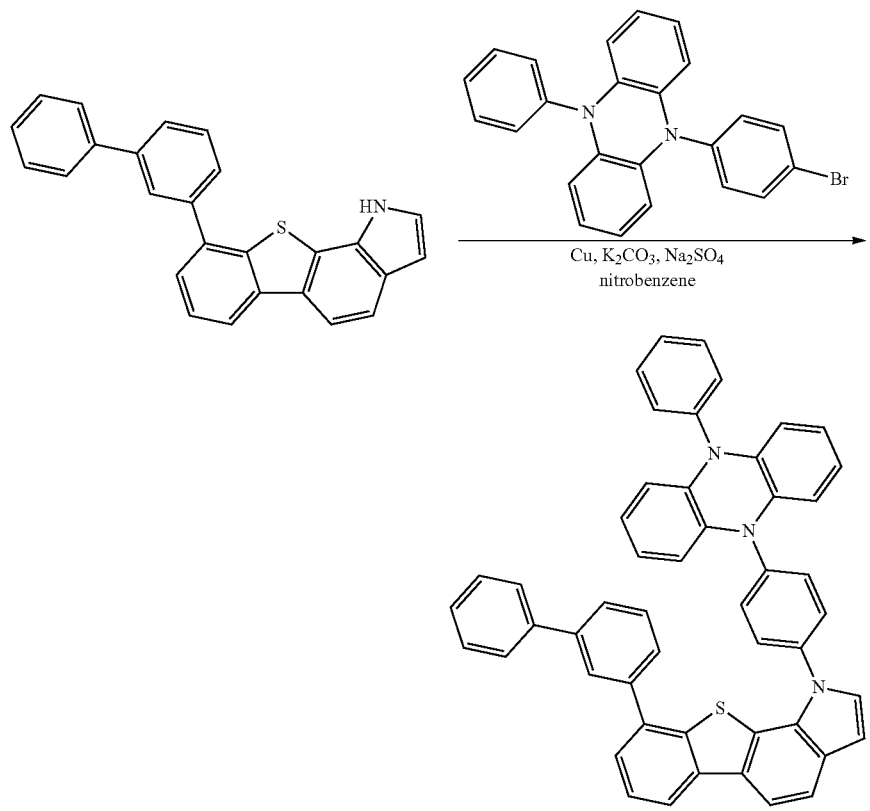

Inv-196

Inv-196 (7.65 g, yield: 54%) was obtained by performing the same procedure as in Synthesis Example 172, except that Inv-153-1 (5.98 g, 20.0 mmol) was used instead of IC-36.

GC-Mass (theoretical value: 707.88 g/mol, measured value: 707 g/mol)

[Synthesis Example 197] Synthesis of Inv-197

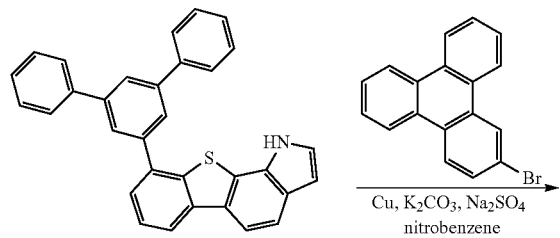

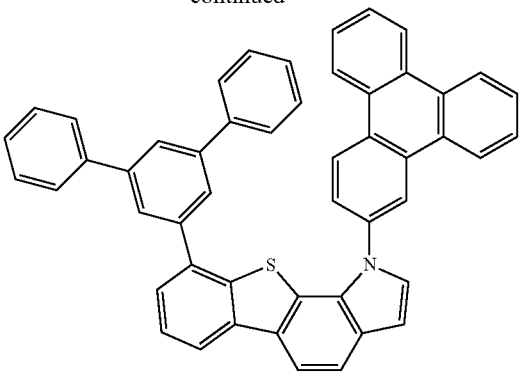

Inv-197

Inv-197 (8.41 g, yield: 62%) was obtained by performing the same procedure as in Synthesis Example 165, except that Inv-155-1 (9.03 g, 20.0 mmol) was used instead of IC-35.

GC-Mass (theoretical value: 677.85 g/mol, measured value: 677 g/mol)

[Synthesis Example 198] Synthesis of Inv-198

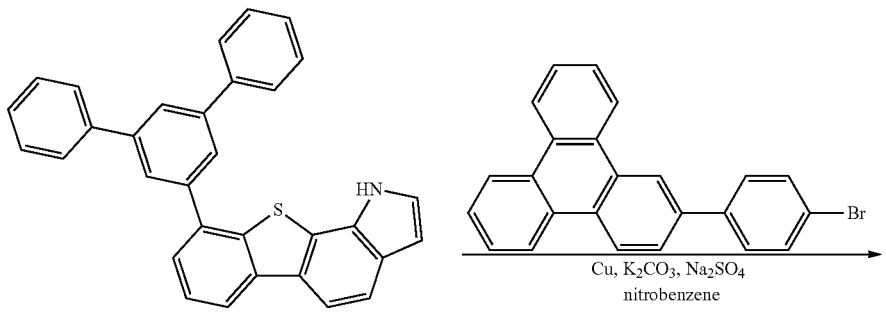

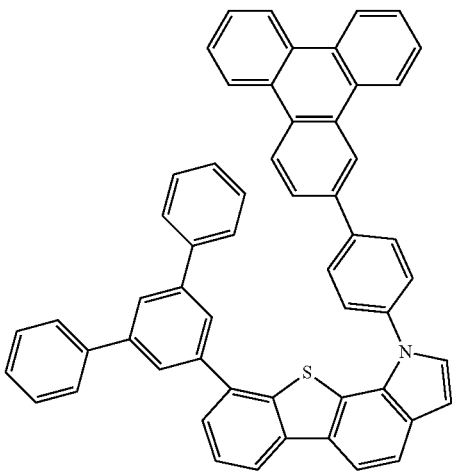

Inv-198

Inv-198 (9.95 g, yield: 66%) was obtained by performing the same procedure as in Synthesis Example 166, except that Inv-155-1 (9.03 g, 20.0 mmol) was used instead of IC-35.

GC-Mass (theoretical value: 753.95 g/mol, measured value: 753 g/mol)

[Synthesis Example 199] Synthesis of Inv-199

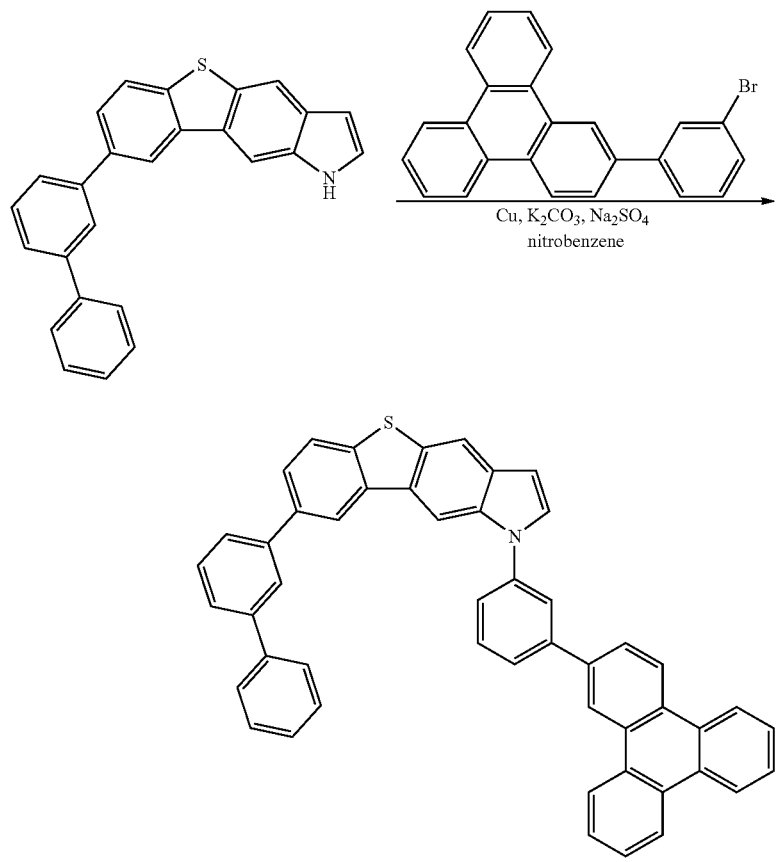

Inv-199

Inv-199 (8.54 g, yield: 63%) was obtained by performing the same procedure as in Synthesis Example 167, except that Inv-159-1 (7.51 g, 20.0 mmol) was used instead of IC-35.

GC-Mass (theoretical value: 677.85 g/mol, measured value: 677 g/mol)

[Synthesis Example 200] Synthesis of Inv-200

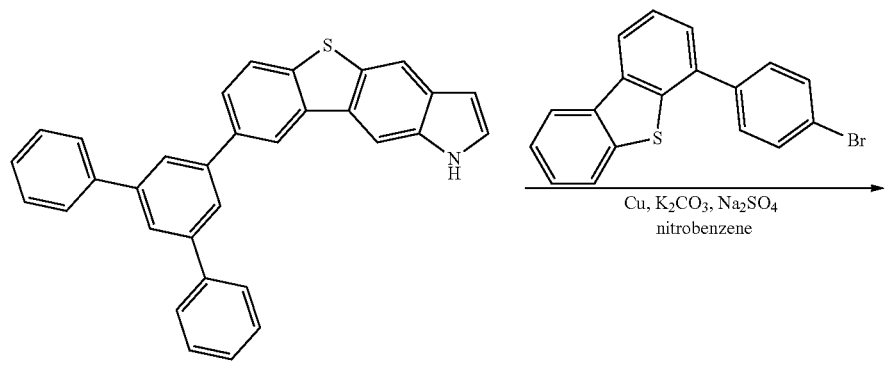

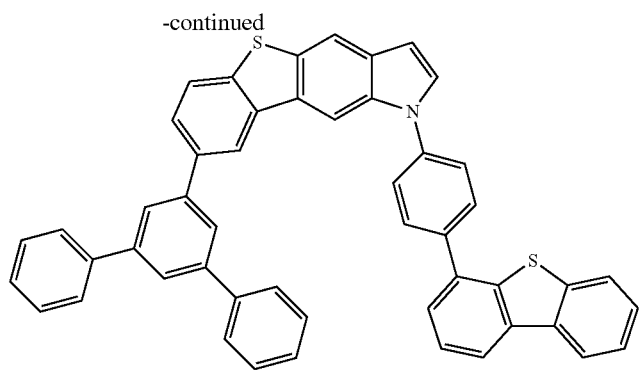

Inv-200

Inv-200 (8.52 g, yield: 60%) was obtained by performing the same procedure as in Synthesis Example 168, except that Inv-159-1 (9.03 g, 20.0 mmol) was used instead of IC-35.

GC-Mass (theoretical value: 709.92 g/mol, measured value: 709 g/mol)

[Synthesis Example 201] Synthesis of Inv-201

GC-Mass (theoretical value: 582.76 g/mol, measured value: 582 g/mol)

[Synthesis Example 202] Synthesis of Inv-202

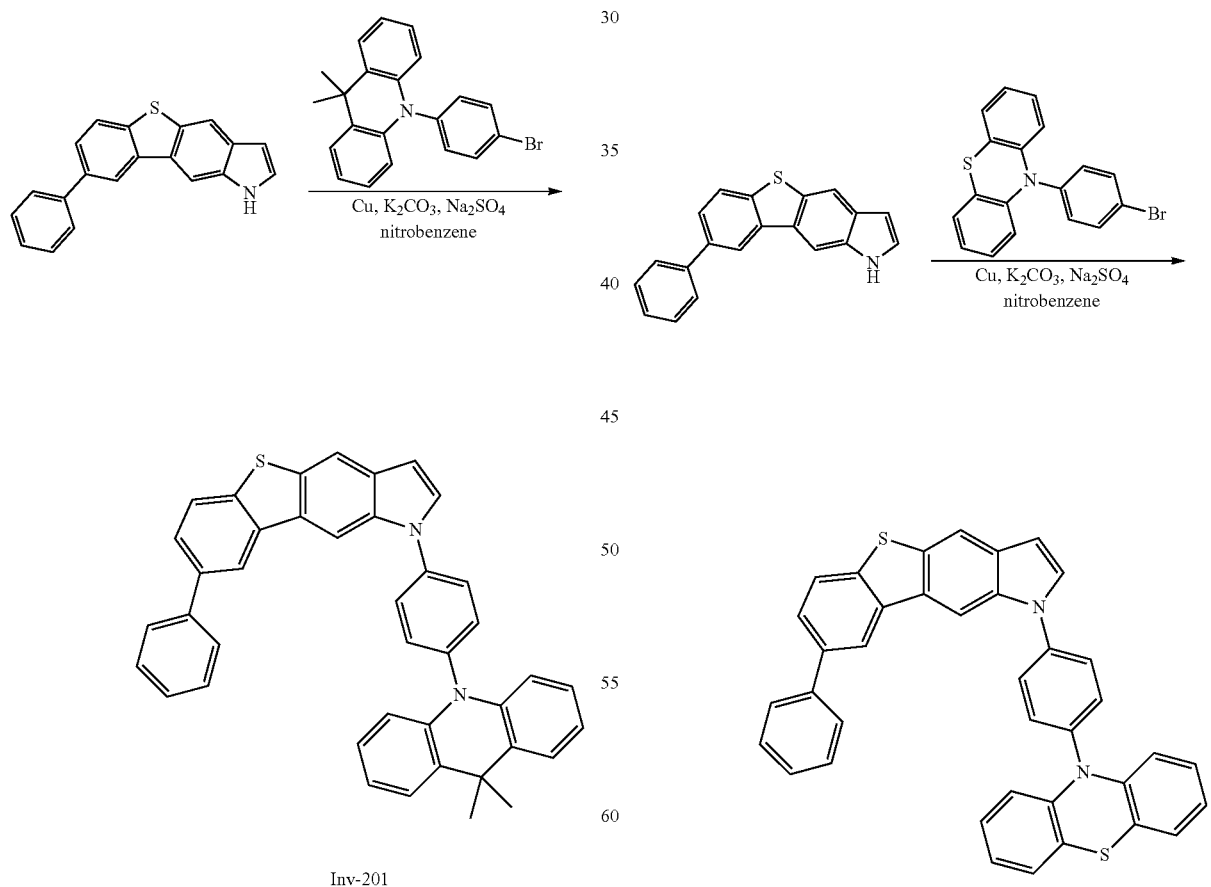

Inv-201

Inv-202

Inv-201 (6.18 g, yield: 53%) was obtained by performing the same procedure as in Synthesis Example 169, except that Inv-157-1 (5.98 g, 20.0 mmol) was used instead of IC-36.

Inv-202 (5.84 g, yield: 51%) was obtained by performing the same procedure as in Synthesis Example 170, except that Inv-157-1 (5.98 g, 20.0 mmol) was used instead of IC-36.

GC-Mass (theoretical value: 572.74 g/mol, measured value: 572 g/mol)

[Synthesis Example 203] Synthesis of Inv-203

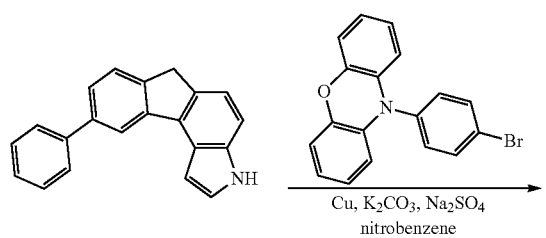

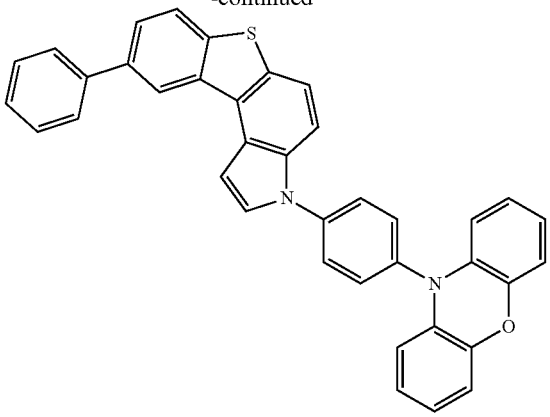

Inv-203

Inv-203 (7.46 g, yield: 67%) was obtained by performing the same procedure as in Synthesis Example 171, except that Inv-161-1 (5.98 g, 20.0 mmol) was used instead of IC-36.

GC-Mass (theoretical value: 556.67 g/mol, measured value: 556 g/mol)

[Synthesis Example 204] Synthesis of Inv-204

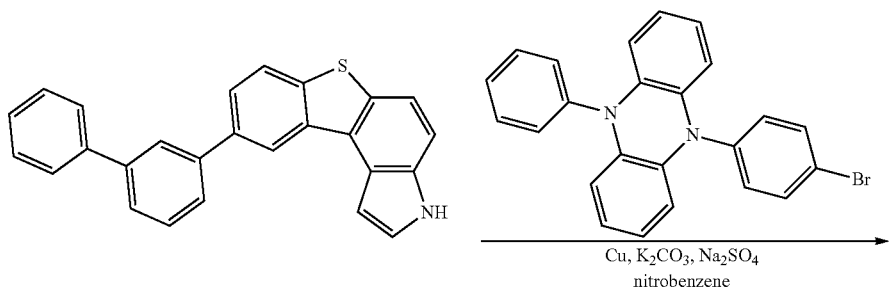

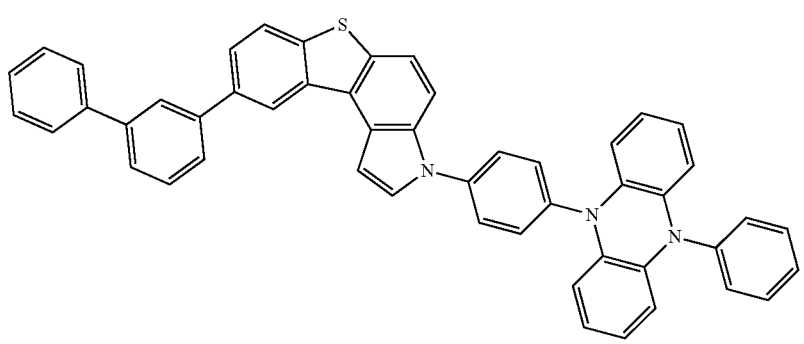

Inv-204

Inv-204 (9.06 g, yield: 64%) was obtained by performing the same procedure as in Synthesis Example 172, except that Inv-163-1 (7.51 g, 20.0 mmol) was used instead of IC-36.

GC-Mass (theoretical value: 707.88 g/mol, measured value: 707 g/mol)

[Synthesis Example 205] Synthesis of Inv-205

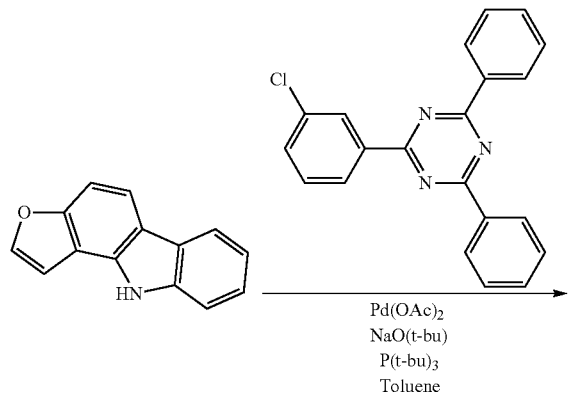

IC-46 (3 g, 14.48 mmol), 2-(3-chlorophenyl)-4,6-diphenyl-1,3,5-triazine (5.97 g, 17.37 mmol), Pd(OAc)$_2$ (0.16 g, 5 mol %), NaO(t-bu) (2.78 g, 28.95 mmol), P(t-bu)$_3$ (0.29 g, 1.45 mmol), and toluene (100 ml) were mixed under nitrogen flow, and the mixture was stirred at 110° C. for 12 hours.

After the reaction was completed, extraction was performed with ethyl acetate, moisture was removed with MgSO$_4$, and purification was performed by column chromatography (Hexane:EA=2:1 (v/v)), thereby obtaining Inv-205 (5.59 g, yield 75%).

GC-Mass (theoretical value: 514.18 g/mol, measured value: 514 g/mol)

[Synthesis Example 206] Synthesis of Inv-206

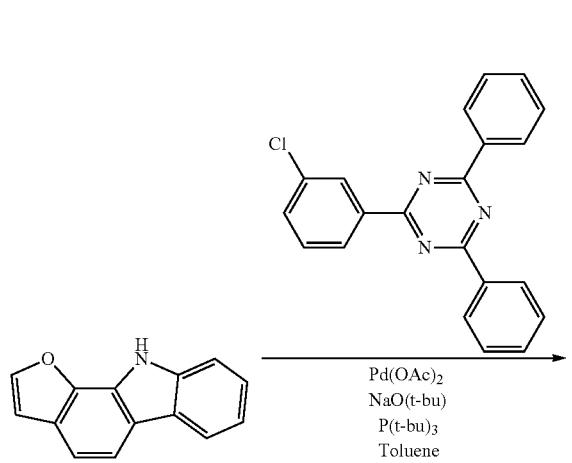

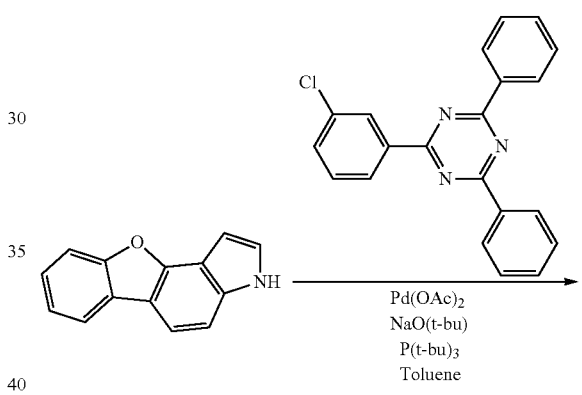

A target compound Inv-206 (5.29 g, 71%) was obtained by performing the same procedure as in Synthesis Example 205, except that IC-47 was used instead of IC-46.

GC-Mass (theoretical value: 514.18 g/mol, measured value: 514 g/mol)

[Synthesis Example 207] Synthesis of Inv-207

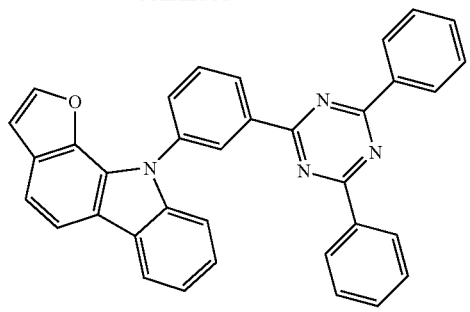

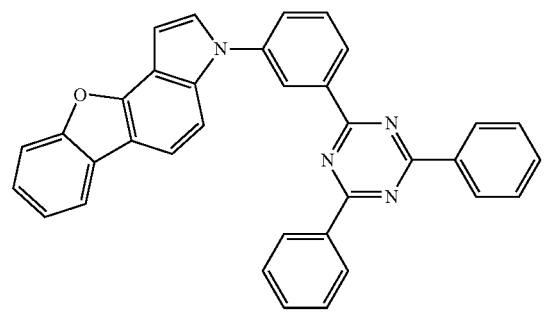

A target compound Inv-207 (5.44 g, 73%) was obtained by performing the same procedure as in Synthesis Example 205, except that IC-48 was used instead of IC-46.

GC-Mass (theoretical value: 514.18 g/mol, measured value: 514 g/mol)

[Synthesis Example 208] Synthesis of Inv-208

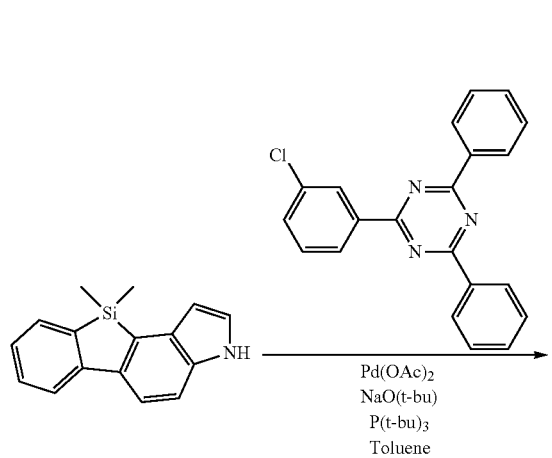

A target compound Inv-208 (4.62 g, 69%) was obtained by performing the same procedure as in Synthesis Example 205, except that IC-49 was used instead of IC-46.

GC-Mass (theoretical value: 556.21 g/mol, measured value: 556 g/mol)

[Synthesis Example 209] Synthesis of Inv-209

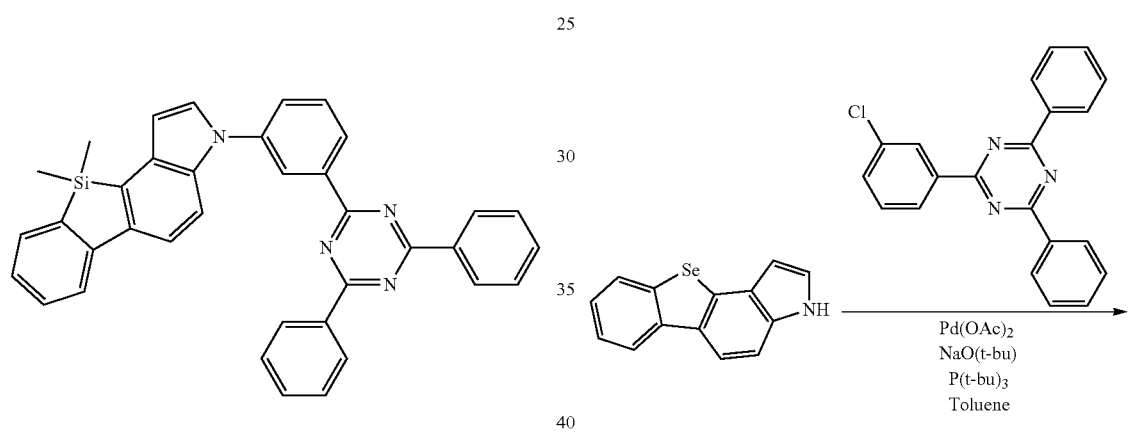

A target compound Inv-209 (3.66 g, 67%) was obtained by performing the same procedure as in Synthesis Example 205, except that IC-50 was used instead of IC-46.

GC-Mass (theoretical value: 680.24 g/mol, measured value: 680 g/mol)

[Synthesis Example 210] Synthesis of Inv-210

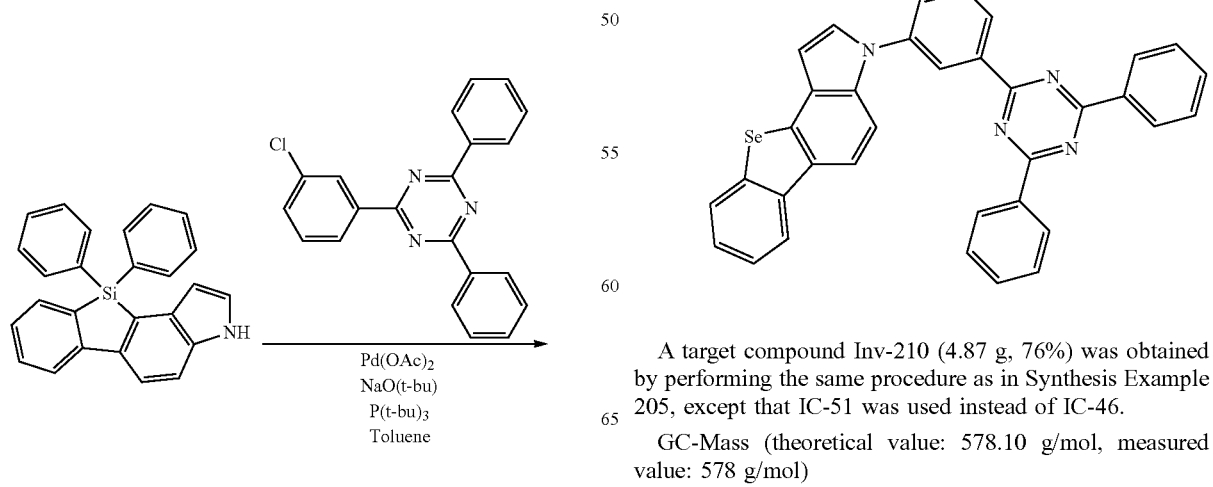

A target compound Inv-210 (4.87 g, 76%) was obtained by performing the same procedure as in Synthesis Example 205, except that IC-51 was used instead of IC-46.

GC-Mass (theoretical value: 578.10 g/mol, measured value: 578 g/mol)

[Synthesis Example 211] Synthesis of Inv-211

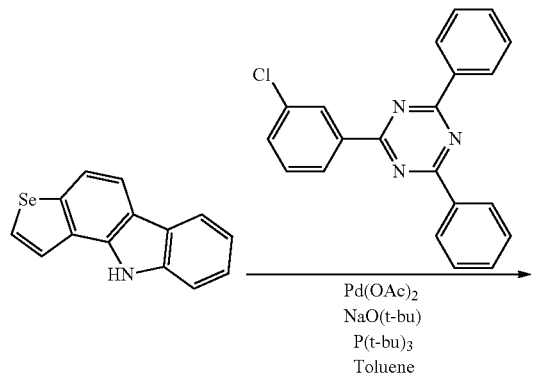

A target compound Inv-211 (4.75 g, 74%) was obtained by performing the same procedure as in Synthesis Example 205, except that IC-52 was used instead of IC-46.

GC-Mass (theoretical value: 578.10 g/mol, measured value: 578 g/mol)

[Synthesis Example 212] Synthesis of Inv-212

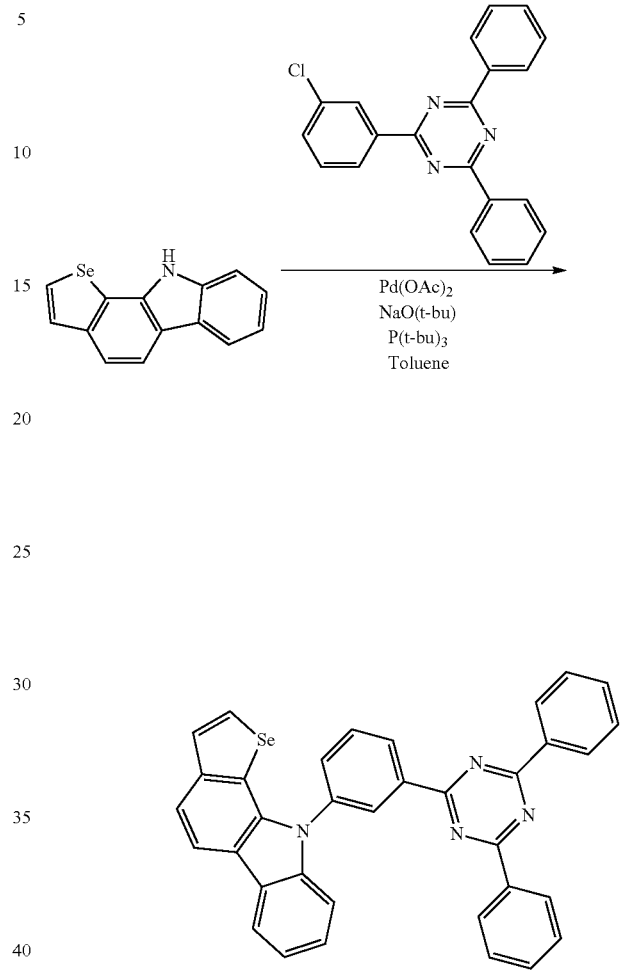

A target compound Inv-212 (4.68 g, 73%) was obtained by performing the same procedure as in Synthesis Example 205, except that IC-53 was used instead of IC-46.

GC-Mass (theoretical value: 578.10 g/mol, measured value: 578 g/mol)

[Synthesis Example 213] Synthesis of Inv-213

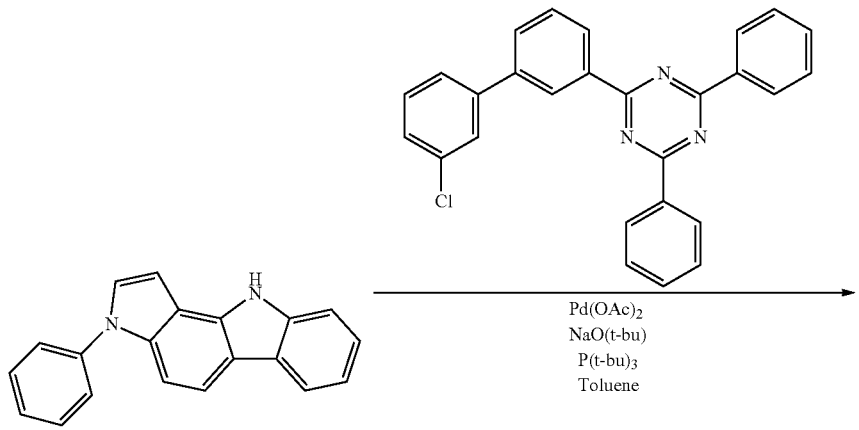

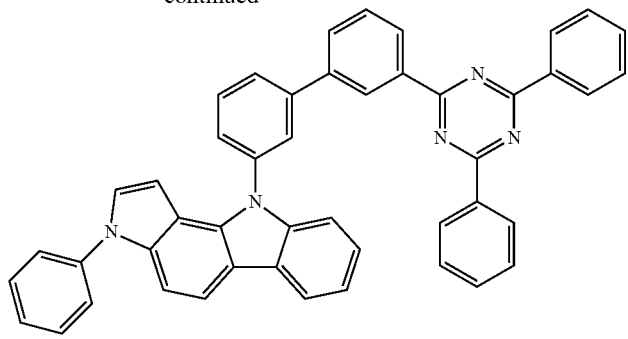
A target compound Inv-213 (4.31 g, yield 61%) was obtained by performing the same procedure as in Synthesis Example 29, except that 2-(3'-chlorobiphenyl-3-yl)-4,6-diphenyl-1,3,5-triazine was used instead of 2-(3-chlorophenyl)-4,6-diphenyl-1,3,5-triazine.
GC-Mass (theoretical value: 665.26 g/mol, measured value: 665 g/mol)
[Synthesis Example 214] Synthesis of Inv-214
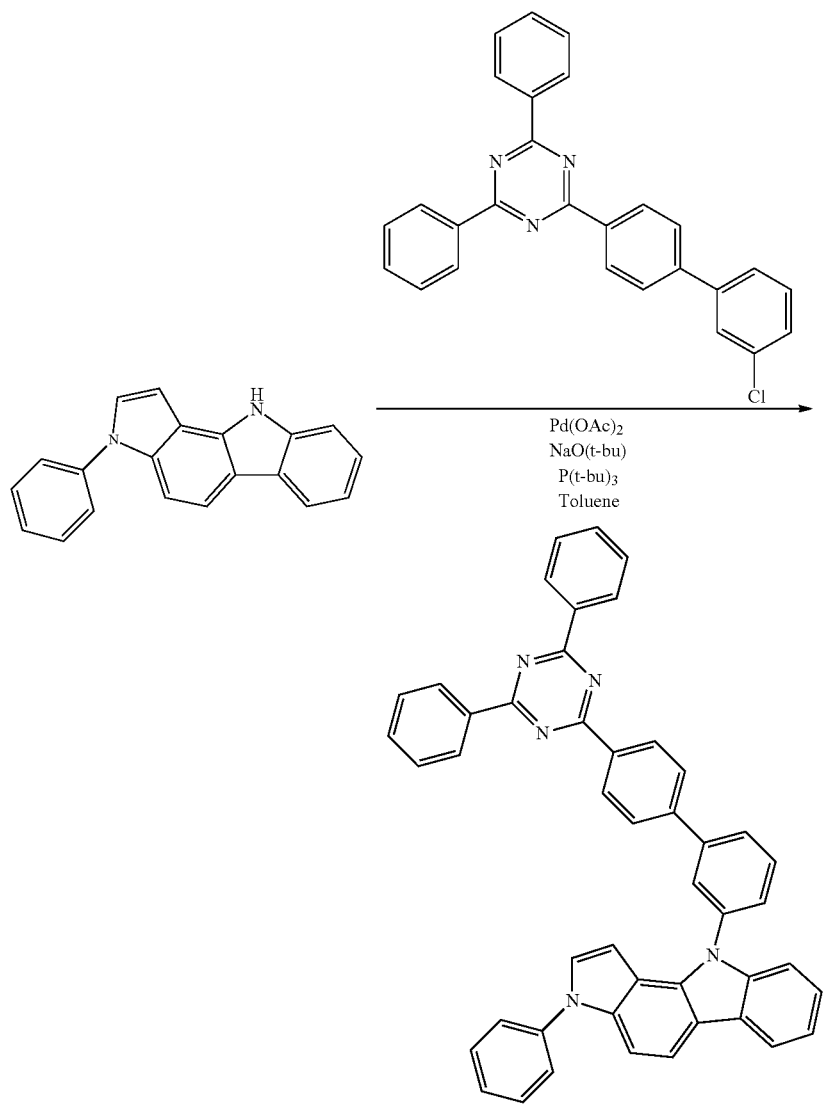

A target compound Inv-214 (4.10 g, yield 58%) was obtained by performing the same procedure as in Synthesis Example 29, except that 2-(3'-chlorobiphenyl-4-yl)-4,6-diphenyl-1,3,5-triazine was used instead of 2-(3-chlorophenyl)-4,6-diphenyl-1,3,5-triazine.

GC-Mass (theoretical value: 665.26 g/mol, measured value: 665 g/mol)

[Synthetic Example 215] Synthesis of Inv-215

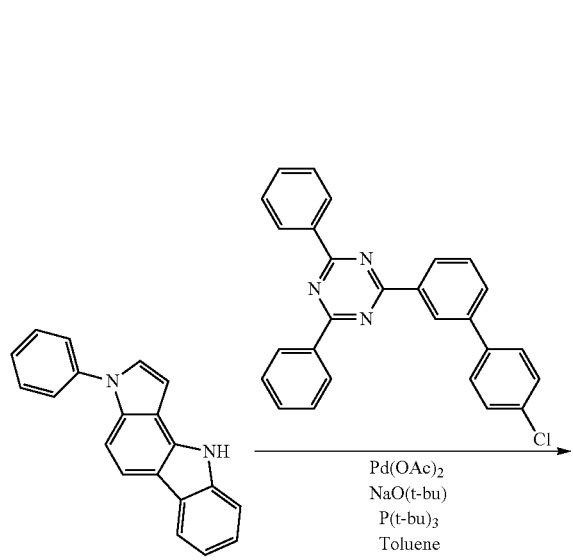

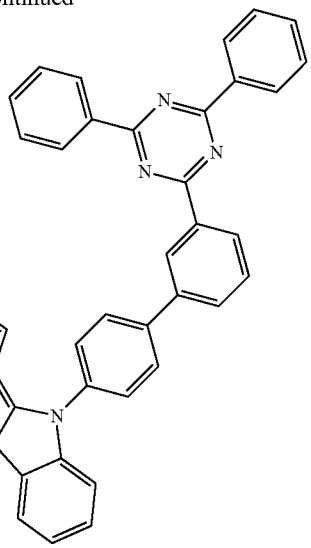

A target compound Inv-215 (4.66 g, yield 66%) was obtained by performing the same procedure as in Synthesis Example 29, except that 2-(4'-chlorobiphenyl-3-yl)-4,6-diphenyl-1,3,5-triazine was used instead of 2-(3-chlorophenyl)-4,6-diphenyl-1,3,5-triazine.

GC-Mass (theoretical value: 665.26 g/mol, measured value: 665 g/mol)

[Synthesis Example 216] Synthesis of Inv-216

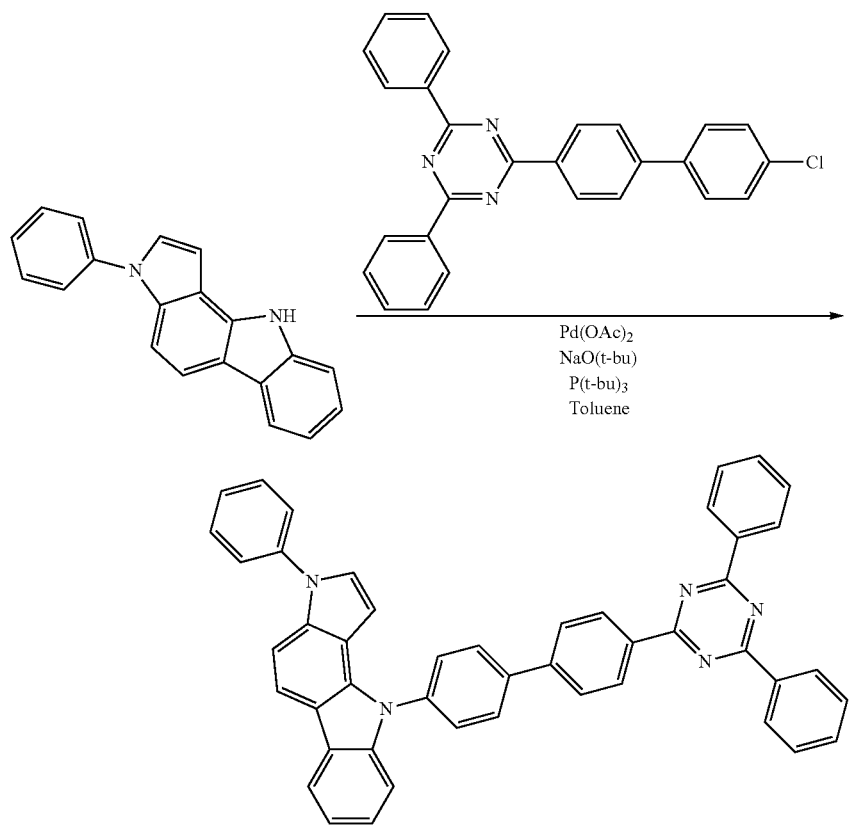

A target compound Inv-216 (4.24 g, yield 60%) was obtained by performing the same procedure as in Synthesis Example 29, except that 2-(4'-chlorobiphenyl-4-yl)-4,6-diphenyl-1,3,5-triazine was used instead of 2-(3-chlorophenyl)-4,6-diphenyl-1,3,5-triazine.

GC-Mass (theoretical value: 665.26 g/mol, measured value: 665 g/mol)

[Synthesis Example 217] Synthesis of Inv-217

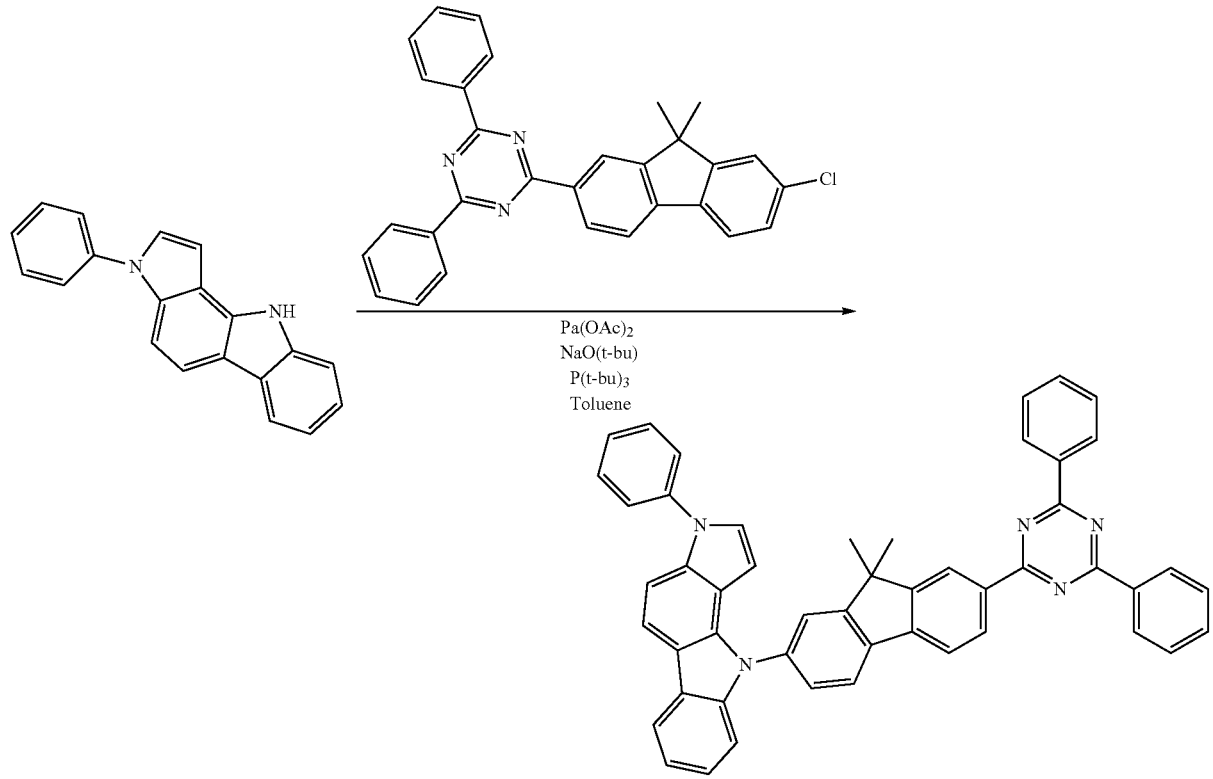

A target compound Inv-217 (4.12 g, 55%) was obtained by performing the same procedure as in Synthesis Example 29, except that 2-(7-chloro-9,9-dimethyl-9H-fluoren-2-yl)-4,6-diphenyl-1,3,5-triazine was used instead of 2-(3-chlorophenyl)-4,6-diphenyl-1,3,5-triazine.

GC-Mass (theoretical value: 705.29 g/mol, measured value: 705 g/mol)

[Synthesis Example 218] Synthesis of Inv-218

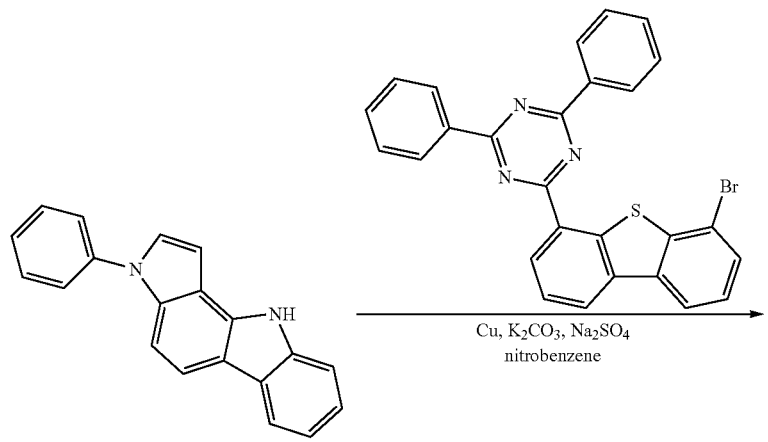

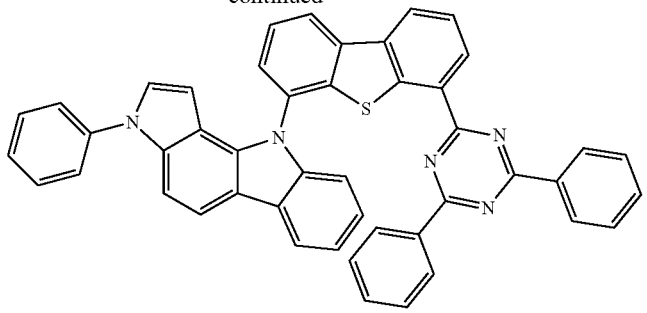

A target compound Inv-218 (4.67 g, yield 38%) was obtained by performing the same procedure as Synthesis Example 1, except that IC-1b as another compound prepared in Preparation Example 1 was used instead of IC-1a, and 2-(6-bromodibenzo[b,c]thiophen-4-yl)-4,6-diphenyl-1,3,5-triazine was used instead of 2-bromo-4,6-diphenylpyridine.

GC-Mass (theoretical value: 695.21 g/mol, measured value: 695 g/mol)

[Synthesis Example 219] Synthesis of Inv-219

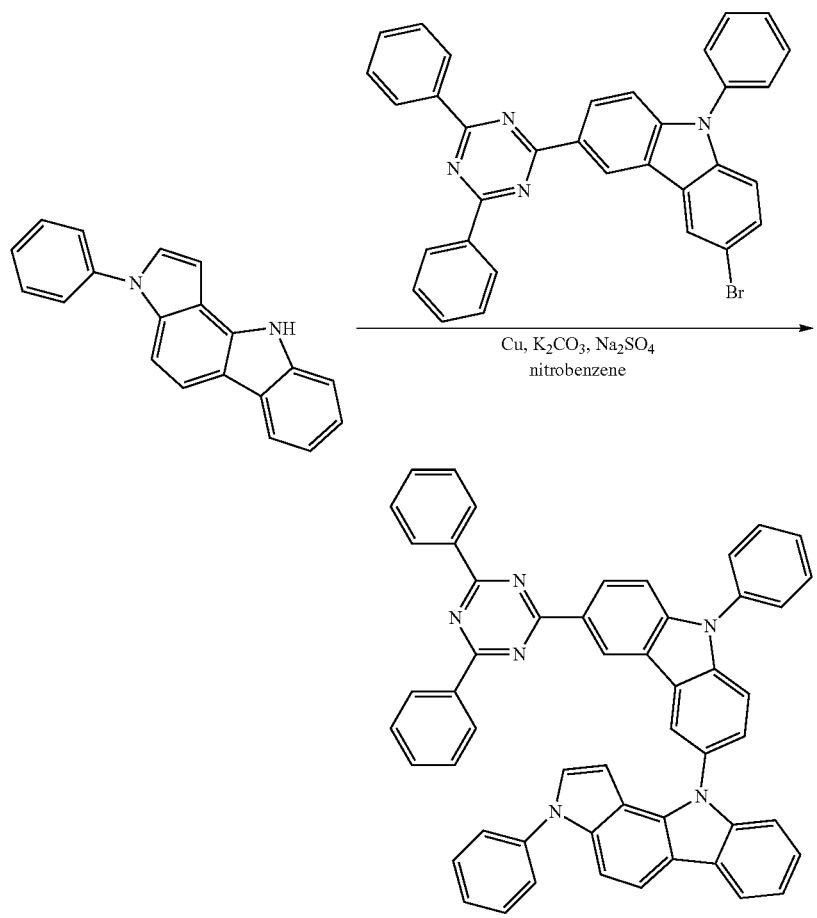

A target compound Inv-219 (5.34 g, yield 40%) was obtained by performing the same procedure as Synthesis Example 1, except that IC-1b as another compound prepared in Preparation Example 1 was used instead of IC-1a, and 3-bromo-6-(4,6-diphenyl-1,3,5-triazin-2-yl)-9-phenyl-9H-carbazole was used instead of 2-bromo-4,6-diphenylpyridine.

GC-Mass (theoretical value: 754.28 g/mol, measured value: 754 g/mol)

[Examples 1 to 30] Manufacture of Organic Electroluminescent Device

Compounds Inv-1 to Inv-26 and Inv-111 to Inv-114 synthesized in Synthesis Examples 1 to 26 and 111 to 114 were subjected to highly-pure sublimation purification by a typically known method, and then a green organic electroluminescent device was manufactured according to the following procedure.

First, a glass substrate on which a thin film of indium tin oxide (ITO) was coated to a thickness of 1500 Å was washed with distilled water under ultrasonic wave. After washed with distilled water, the glass substrate was ultrasonically washed with a solvent such as isopropyl alcohol, acetone and methanol, dried, and transferred to a UV ozone cleaner (Power sonic 405, Hwashin Technology Co., Ltd.), and then the substrate was cleaned for 5 minutes by using UV rays, and transferred to a vacuum deposition system.

An organic electroluminescent device was manufactured by laminating m-MTDATA (60 nm)/TCTA (80 nm)/each compound of Inv-1 to Inv-26 and Inv-111 to Inv-114+10% Ir(ppy)$_3$ (300 nm)/BCP (10 nm)/Alq$_3$ (30 nm)/LiF (1 nm)/Al (200 nm) in this order on the ITO transparent electrode thus-prepared.

[Comparative Example 1] Manufacture of Organic Electroluminescent Device

An organic electroluminescent device was manufactured in the same manner as in Example 1, except that CBP was used instead of Compound Inv-1 as a light-emitting host material when a light-emitting layer is formed.

The structures of m-MTDATA, TCTA, Ir(ppy)$_3$, CBP and BCP used in Examples 1 to 30 and Comparative Example 1 are as follows.

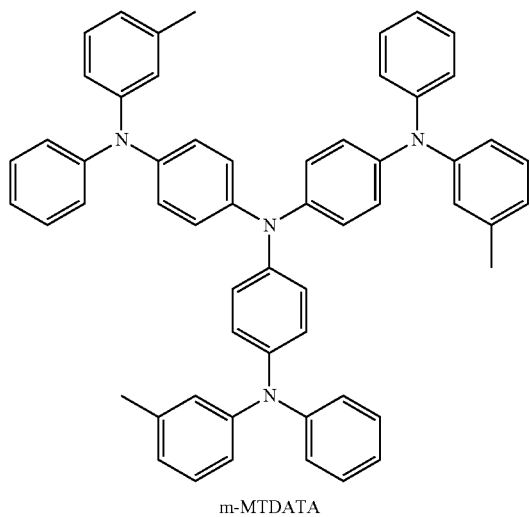

m-MTDATA

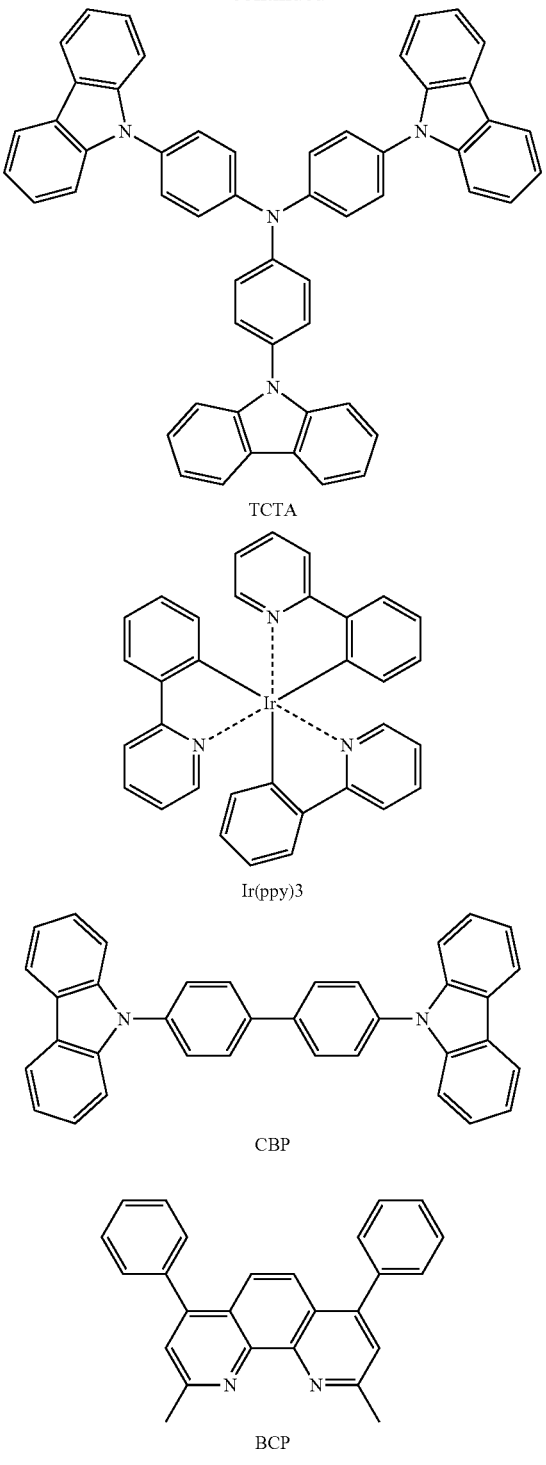

Evaluative Example

For each of the green organic electroluminescent devices manufactured in Examples 1 to 30 and Comparative Example 1, the driving voltage, current efficiency, and light-emitting peak are measured at a current density of 10 mA/cm$^2$, and the results are shown in the following Table 1.

TABLE 1

| Sample | Host | Driving voltage (V) | EL Peak (nm) | Current efficiency (cd/A) |
|---|---|---|---|---|
| Example 1 | Inv-1 | 6.78 | 517 | 42.4 |
| Example 2 | Inv-2 | 6.81 | 516 | 41.1 |
| Example 3 | Inv-3 | 6.83 | 517 | 40.8 |
| Example 4 | Inv-4 | 6.81 | 515 | 41.0 |
| Example 5 | Inv-5 | 6.81 | 517 | 40.4 |
| Example 6 | Inv-6 | 6.77 | 516 | 42.1 |
| Example 7 | Inv-7 | 6.78 | 518 | 41.5 |
| Example 8 | Inv-8 | 6.80 | 516 | 40.2 |
| Example 9 | Inv-9 | 6.79 | 517 | 41.3 |
| Example 10 | Inv-10 | 6.85 | 516 | 40.6 |
| Example 11 | Inv-11 | 6.77 | 515 | 42.0 |
| Example 12 | Inv-12 | 6.79 | 518 | 41.3 |
| Example 13 | Inv-13 | 6.82 | 517 | 40.2 |
| Example 14 | Inv-14 | 6.83 | 518 | 40.9 |
| Example 15 | Inv-15 | 6.81 | 516 | 41.0 |
| Example 16 | Inv-16 | 6.79 | 516 | 41.3 |
| Example 17 | Inv-17 | 6.87 | 517 | 39.4 |
| Example 18 | Inv-18 | 6.86 | 515 | 37.6 |
| Example 19 | Inv-19 | 6.89 | 518 | 38.3 |
| Example 20 | Inv-20 | 6.85 | 517 | 38.8 |
| Example 21 | Inv-21 | 7.06 | 518 | 37.2 |
| Example 22 | Inv-22 | 7.12 | 518 | 37.5 |
| Example 23 | Inv-23 | 7.22 | 519 | 36.2 |
| Example 24 | Inv-24 | 6.83 | 516 | 39.1 |
| Example 25 | Inv-25 | 7.09 | 517 | 37.9 |
| Example 26 | Inv-26 | 7.01 | 515 | 38.1 |
| Example 27 | Inv-111 | 6.98 | 517 | 37.5 |
| Example 28 | Inv-112 | 7.02 | 518 | 37.9 |
| Example 29 | Inv-113 | 6.95 | 517 | 38.1 |
| Example 30 | Inv-114 | 6.86 | 516 | 39.2 |
| Comparative Example 1 | CBP | 6.93 | 516 | 38.2 |

As shown in Table 1, it can be seen that when compared with the green organic electroluminescent device using a CBP in the related art (Comparative Example 1), the green organic electroluminescent devices using the compounds (Inv-1 to Inv-26 and Inv-111 to Inv-114) according to the present invention as a light-emitting layer of the green organic electroluminescent device (Examples 1 to 30) show excellent performances in terms of efficiency and driving voltage.

[Examples 31 to 114] Manufacture of Organic Electroluminescent Device

Compounds Inv-27 to Inv-110 synthesized in Synthesis Examples 27 to 110 were subjected to highly-pure sublimation purification by a typically known method, and then a green organic electroluminescent device was manufactured in the same manner as in Example 1.

Evaluative Example

For each of the green organic electroluminescent devices manufactured in Examples 31 to 114 and Comparative Example 1, the driving voltage, current efficiency, and light-emitting peak are measured at a current density of 10 mA/cm$^2$, and the results are shown in the following Table 2.

TABLE 2

| Sample | Host | Driving voltage (V) | EL Peak (nm) | Current efficiency (cd/A) |
|---|---|---|---|---|
| Example 31 | Inv-27 | 6.88 | 518 | 41.4 |
| Example 32 | Inv-28 | 6.87 | 519 | 40.9 |
| Example 33 | Inv-29 | 6.63 | 516 | 43.2 |
| Example 34 | Inv-30 | 6.65 | 516 | 43.5 |
| Example 35 | Inv-31 | 6.71 | 516 | 41.7 |
| Example 36 | Inv-32 | 6.68 | 516 | 42.1 |
| Example 37 | Inv-33 | 6.66 | 516 | 42.6 |
| Example 38 | Inv-34 | 6.91 | 517 | 40.4 |
| Example 39 | Inv-35 | 6.85 | 518 | 38.8 |
| Example 40 | Inv-36 | 6.86 | 519 | 39.1 |
| Example 41 | Inv-37 | 6.84 | 515 | 40.1 |
| Example 42 | Inv-38 | 6.63 | 517 | 42.8 |
| Example 43 | Inv-39 | 6.75 | 516 | 40.2 |
| Example 44 | Inv-40 | 6.73 | 515 | 40.9 |
| Example 45 | Inv-41 | 6.75 | 515 | 41.2 |
| Example 46 | Inv-42 | 6.89 | 516 | 39.2 |
| Example 47 | Inv-43 | 6.87 | 517 | 39.4 |
| Example 48 | Inv-44 | 6.61 | 516 | 40.6 |
| Example 49 | Inv-45 | 6.69 | 518 | 41.2 |
| Example 50 | Inv-46 | 6.67 | 517 | 40.7 |
| Example 51 | Inv-47 | 6.68 | 516 | 41.3 |
| Example 52 | Inv-48 | 6.67 | 518 | 40.8 |
| Example 53 | Inv-49 | 6.91 | 516 | 39.1 |
| Example 54 | Inv-50 | 6.83 | 516 | 39.5 |
| Example 55 | Inv-51 | 6.89 | 517 | 41.9 |
| Example 56 | Inv-52 | 6.81 | 515 | 40.3 |
| Example 57 | Inv-53 | 6.64 | 517 | 42.0 |
| Example 58 | Inv-54 | 6.66 | 518 | 41.1 |
| Example 59 | Inv-55 | 6.69 | 517 | 40.9 |
| Example 60 | Inv-56 | 6.70 | 516 | 41.8 |
| Example 61 | Inv-57 | 6.65 | 518 | 41.3 |
| Example 62 | Inv-58 | 6.66 | 519 | 42.2 |
| Example 63 | Inv-59 | 6.64 | 516 | 41.3 |
| Example 64 | Inv-60 | 6.88 | 516 | 41.8 |
| Example 65 | Inv-61 | 6.72 | 517 | 40.5 |
| Example 66 | Inv-62 | 6.69 | 516 | 42.9 |
| Example 67 | Inv-63 | 6.65 | 517 | 41.3 |
| Example 68 | Inv-64 | 6.68 | 517 | 41.7 |
| Example 69 | Inv-65 | 6.61 | 518 | 41.6 |
| Example 70 | Inv-66 | 6.73 | 516 | 40.4 |
| Example 71 | Inv-67 | 6.68 | 516 | 40.9 |
| Example 72 | Inv-68 | 6.62 | 518 | 41.2 |
| Example 73 | Inv-69 | 6.61 | 516 | 41.8 |
| Example 74 | Inv-70 | 6.83 | 516 | 39.1 |
| Example 75 | Inv-71 | 6.85 | 517 | 38.5 |
| Example 76 | Inv-72 | 6.63 | 516 | 42.0 |
| Example 77 | Inv-73 | 6.68 | 517 | 41.3 |
| Example 78 | Inv-74 | 6.91 | 518 | 42.8 |
| Example 79 | Inv-75 | 6.73 | 516 | 40.6 |
| Example 80 | Inv-76 | 6.62 | 516 | 41.1 |
| Example 81 | Inv-77 | 6.77 | 517 | 40.5 |
| Example 82 | Inv-78 | 6.65 | 516 | 41.0 |
| Example 83 | Inv-79 | 6.66 | 518 | 41.2 |
| Example 84 | Inv-80 | 6.67 | 516 | 40.8 |
| Example 85 | Inv-81 | 6.90 | 517 | 41.9 |
| Example 86 | Inv-82 | 6.75 | 516 | 40.3 |
| Example 87 | Inv-83 | 6.83 | 517 | 40.3 |
| Example 88 | Inv-84 | 6.63 | 516 | 41.2 |
| Example 89 | Inv-85 | 6.69 | 517 | 40.9 |
| Example 90 | Inv-86 | 6.67 | 516 | 41.3 |
| Example 91 | Inv-87 | 6.89 | 518 | 41.5 |
| Example 92 | Inv-88 | 6.73 | 518 | 40.8 |
| Example 93 | Inv-89 | 6.72 | 516 | 40.3 |
| Example 94 | Inv-90 | 6.68 | 516 | 41.0 |
| Example 95 | Inv-91 | 6.69 | 517 | 40.8 |
| Example 96 | Inv-92 | 6.70 | 516 | 40.5 |
| Example 97 | Inv-93 | 6.65 | 517 | 41.3 |
| Example 98 | Inv-94 | 6.67 | 518 | 41.1 |
| Example 99 | Inv-95 | 6.60 | 517 | 42.1 |
| Example 100 | Inv-96 | 6.65 | 518 | 41.9 |
| Example 101 | Inv-97 | 6.85 | 518 | 41.1 |
| Example 102 | Inv-98 | 6.73 | 518 | 40.3 |
| Example 103 | Inv-99 | 6.71 | 517 | 40.2 |
| Example 104 | Inv-100 | 6.68 | 516 | 41.2 |
| Example 105 | Inv-101 | 6.74 | 517 | 40.7 |
| Example 106 | Inv-102 | 6.69 | 517 | 41.3 |
| Example 107 | Inv-103 | 6.85 | 517 | 40.5 |
| Example 108 | Inv-104 | 6.65 | 518 | 41.1 |
| Example 109 | Inv-105 | 6.68 | 517 | 40.8 |
| Example 110 | Inv-106 | 6.70 | 517 | 40.9 |
| Example 111 | Inv-107 | 6.73 | 517 | 41.5 |

TABLE 2-continued

| Sample | Host | Driving voltage (V) | EL Peak (nm) | Current efficiency (cd/A) |
|---|---|---|---|---|
| Example 112 | Inv-108 | 6.75 | 516 | 40.8 |
| Example 113 | Inv-109 | 6.74 | 518 | 41.8 |
| Example 114 | Inv-110 | 6.88 | 516 | 41.3 |
| Comparative Example 1 | CBP | 6.93 | 516 | 38.2 |

As shown in Table 2, it can be seen that when compared with the green organic electroluminescent device using a CBP in the related art (Comparative Example 1), the green organic electroluminescent devices using the compounds (Inv-27 to Inv-110) according to the present invention as a light-emitting layer of the green organic electroluminescent device (Examples 31 to 114) show excellent performances in terms of efficiency and driving voltage.

[Examples 115 to 212] Manufacture of Organic Electroluminescent Device

Compounds Inv-115 to Inv-212 synthesized in Synthesis Examples 115 to 212 were subjected to highly-pure sublimation purification by a typically known method, and then a red organic electroluminescent device was manufactured according to the following procedure.

First, a glass substrate on which a thin film of indium tin oxide (ITO) was coated to a thickness of 1500 Å was washed with distilled water under ultrasonic wave. After washed with distilled water, the glass substrate was ultrasonically washed with a solvent such as isopropyl alcohol, acetone and methanol, dried, and transferred to a UV ozone cleaner (Power sonic 405, Hwashin Technology Co., Ltd.), and then the substrate was cleaned for 5 minutes by using UV rays, and transferred to a vacuum deposition system.

An organic electroluminescent device was manufactured by laminating m-MTDATA (60 nm)/NPB (20 nm)/each compound of Inv-115 to Inv-212+10% (piq)$_2$Ir(acac) (30 nm)/BCP (10 nm)/Alq$_3$ (30 nm)/LiF (1 nm)/Al (200 nm) in this order on the ITO transparent electrode thus-prepared.

[Comparative Example 2] Manufacture of Organic Electroluminescent Device

A red organic electroluminescent device was manufactured in the same manner as in Example 115, except that CBP was used instead of Compound Inv-115 as a light-emitting host material when a light-emitting layer is formed.

The structures of m-MTDATA, NPB, (piq)$_2$Ir(acac) and CBP used in Examples 115 to 212 and Comparative Example 2 are as follows.

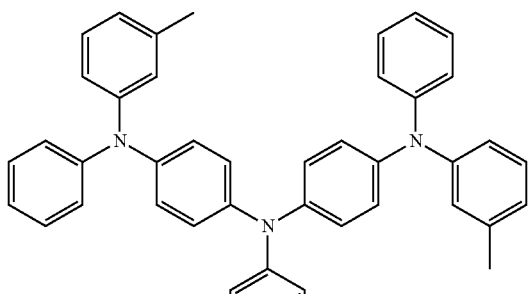

m-MTDATA

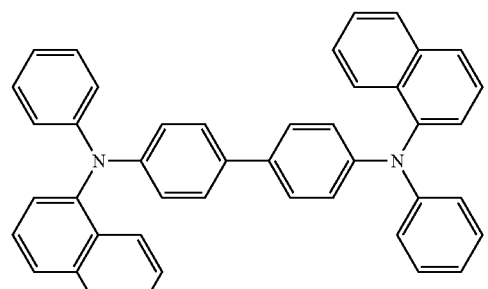

NPB

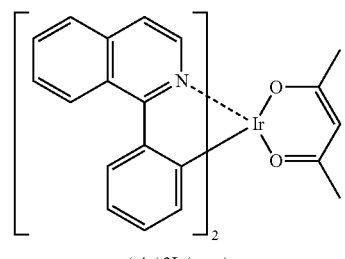

(piq)2Ir(acac)

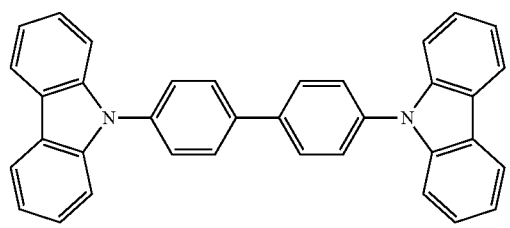

CBP

Evaluative Example

For each of the red organic electroluminescent devices manufactured in Examples 115 to 212 and Comparative Example 2, the driving voltage, current efficiency, and light-emitting peak are measured at a current density of 10 mA/cm$^2$, and the results are shown in the following Table 3.

TABLE 3

| Sample | Host | Driving voltage (V) | Electric current efficiency (cd/A) |
|---|---|---|---|
| Example 115 | Inv-115 | 4.75 | 12.4 |
| Example 116 | Inv-116 | 4.51 | 12.3 |
| Example 117 | Inv-117 | 4.53 | 12.5 |
| Example 118 | Inv-118 | 4.61 | 12.0 |
| Example 119 | Inv-119 | 4.71 | 12.6 |
| Example 120 | Inv-120 | 4.75 | 12.0 |
| Example 121 | Inv-121 | 4.70 | 12.5 |
| Example 122 | Inv-122 | 4.68 | 12.2 |
| Example 123 | Inv-123 | 4.74 | 12.3 |
| Example 124 | Inv-124 | 4.65 | 14.2 |
| Example 125 | Inv-125 | 4.77 | 12.1 |
| Example 126 | Inv-126 | 4.80 | 12.3 |
| Example 127 | Inv-127 | 4.66 | 14.2 |
| Example 128 | Inv-128 | 4.71 | 12.5 |
| Example 129 | Inv-129 | 4.81 | 12.2 |
| Example 130 | Inv-130 | 4.79 | 14.3 |
| Example 131 | Inv-131 | 4.67 | 12.5 |
| Example 132 | Inv-132 | 4.54 | 12.6 |
| Example 133 | Inv-133 | 4.59 | 12.3 |
| Example 134 | Inv-134 | 4.65 | 12.8 |
| Example 135 | Inv-135 | 4.54 | 14.2 |
| Example 136 | Inv-136 | 4.72 | 12.5 |
| Example 137 | Inv-137 | 4.70 | 12.2 |
| Example 138 | Inv-138 | 4.63 | 14.1 |
| Example 139 | Inv-139 | 4.59 | 12.9 |
| Example 140 | Inv-140 | 4.71 | 12.1 |
| Example 141 | Inv-141 | 4.69 | 12.5 |
| Example 142 | Inv-142 | 4.59 | 12.9 |
| Example 143 | Inv-143 | 4.70 | 12.1 |
| Example 144 | Inv-144 | 4.64 | 12.2 |
| Example 145 | Inv-145 | 4.75 | 12.0 |
| Example 146 | Inv-146 | 4.70 | 14.3 |
| Example 147 | Inv-147 | 4.62 | 12.2 |
| Example 148 | Inv-148 | 4.73 | 12.3 |
| Example 149 | Inv-149 | 4.71 | 12.7 |
| Example 150 | Inv-150 | 4.77 | 14.3 |
| Example 151 | Inv-151 | 4.69 | 12.9 |
| Example 152 | Inv-152 | 4.56 | 14.1 |
| Example 153 | Inv-153 | 4.59 | 12.5 |
| Example 154 | Inv-154 | 4.60 | 12.9 |
| Example 155 | Inv-155 | 4.70 | 12.1 |
| Example 156 | Inv-156 | 4.84 | 12.2 |
| Example 157 | Inv-157 | 4.75 | 14.0 |
| Example 158 | Inv-158 | 4.78 | 12.3 |
| Example 159 | Inv-159 | 4.62 | 12.2 |
| Example 160 | Inv-160 | 4.80 | 12.4 |
| Example 161 | Inv-161 | 4.66 | 13.4 |
| Example 162 | Inv-162 | 4.70 | 12.9 |
| Example 163 | Inv-163 | 4.75 | 14.0 |
| Comparative Example 2 | CBP | 5.25 | 8.2 |

| Sample | Host | Driving voltage (V) | Current efficiency |
|---|---|---|---|
| Example 164 | Inv-164 | 4.78 | 12.5 |
| Example 165 | Inv-165 | 4.75 | 13.3 |
| Example 166 | Inv-166 | 4.70 | 14.1 |
| Example 167 | Inv-167 | 4.73 | 13.6 |
| Example 168 | Inv-168 | 4.74 | 12.9 |
| Example 169 | Inv-169 | 4.60 | 12.9 |
| Example 170 | Inv-170 | 4.70 | 13.8 |
| Example 171 | Inv-171 | 4.83 | 13.3 |
| Example 172 | Inv-172 | 4.79 | 14.0 |
| Example 173 | Inv-173 | 4.75 | 13.5 |
| Example 174 | Inv-174 | 4.80 | 13.0 |
| Example 175 | Inv-175 | 4.69 | 14.0 |
| Example 176 | Inv-176 | 4.73 | 13.5 |
| Example 177 | Inv-177 | 4.60 | 12.8 |
| Example 178 | Inv-178 | 4.66 | 12.9 |
| Example 179 | Inv-179 | 4.69 | 13.8 |
| Example 180 | Inv-180 | 4.70 | 12.9 |
| Example 181 | Inv-181 | 4.75 | 13.3 |
| Example 182 | Inv-182 | 4.70 | 12.6 |
| Example 183 | Inv-183 | 4.80 | 13.1 |
| Example 184 | Inv-184 | 4.81 | 13.7 |
| Example 185 | Inv-185 | 4.79 | 12.5 |
| Example 186 | Inv-186 | 4.69 | 13.5 |
| Example 187 | Inv-187 | 4.70 | 12.7 |

TABLE 3-continued

| | | | |
|---|---|---|---|
| Example 188 | Inv-188 | 4.74 | 12.9 |
| Example 189 | Inv-189 | 4.67 | 12.8 |
| Example 190 | Inv-190 | 4.75 | 13.0 |
| Example 191 | Inv-191 | 4.77 | 13.1 |
| Example 192 | Inv-192 | 4.66 | 12.9 |
| Example 193 | Inv-193 | 4.75 | 13.3 |
| Example 194 | Inv-194 | 4.70 | 12.9 |
| Example 195 | Inv-195 | 4.75 | 13.2 |
| Example 196 | Inv-196 | 4.79 | 13.8 |
| Example 197 | Inv-197 | 4.70 | 14.3 |
| Example 198 | Inv-198 | 4.79 | 13.5 |
| Example 199 | Inv-199 | 4.76 | 12.8 |
| Example 200 | Inv-200 | 4.80 | 14.1 |
| Example 201 | Inv-201 | 4.81 | 12.2 |
| Example 202 | Inv-202 | 4.80 | 14.1 |
| Example 203 | Inv-203 | 4.75 | 12.5 |
| Example 204 | Inv-204 | 4.72 | 12.8 |
| Example 205 | Inv-205 | 4.90 | 12.5 |
| Example 206 | Inv-206 | 4.86 | 12.0 |
| Example 207 | Inv-207 | 4.91 | 12.7 |
| Example 208 | Inv-208 | 4.88 | 13.0 |
| Example 209 | Inv-209 | 4.80 | 13.5 |
| Example 210 | Inv-210 | 4.90 | 12.9 |
| Example 211 | Inv-211 | 4.88 | 12.5 |
| Example 212 | Inv-212 | 4.92 | 12.8 |

[Examples 213 to 317] Manufacture of Organic Electroluminescent Device

Compounds Inv-115 to Inv-219 synthesized in Synthesis Examples 115 to 219 were subjected to highly-pure sublimation purification by a typically known method, and then a green organic electroluminescent device was manufactured in the same manner as in Example 1.

Evaluative Example

For each of the green organic electroluminescent devices manufactured in Examples 213 to 317 and Comparative Example 1, the driving voltage, current efficiency, and light-emitting peak are measured at a current density of 10 mA/cm$^2$, and the results are shown in the following Table 4.

TABLE 4

| Sample | Host | Driving voltage (V) | Current efficiency (cd/A) |
|---|---|---|---|
| Example 213 | Inv-115 | 6.78 | 41.5 |
| Example 214 | Inv-116 | 6.61 | 41.0 |
| Example 215 | Inv-117 | 6.63 | 41.2 |
| Example 216 | Inv-118 | 6.61 | 41.0 |
| Example 217 | Inv-119 | 6.61 | 40.9 |
| Example 218 | Inv-120 | 6.77 | 41.5 |
| Example 219 | Inv-121 | 6.78 | 41.4 |
| Example 220 | Inv-122 | 6.60 | 41.0 |
| Example 221 | Inv-123 | 6.79 | 41.3 |
| Example 222 | Inv-124 | 6.65 | 41.2 |
| Example 223 | Inv-125 | 6.77 | 40.5 |
| Example 224 | Inv-126 | 6.79 | 41.0 |
| Example 225 | Inv-127 | 6.62 | 40.7 |
| Example 226 | Inv-128 | 6.63 | 40.8 |
| Example 227 | Inv-129 | 6.61 | 41.0 |
| Example 228 | Inv-130 | 6.79 | 41.6 |
| Example 229 | Inv-131 | 6.67 | 40.5 |
| Example 230 | Inv-132 | 6.66 | 40.3 |
| Example 231 | Inv-133 | 6.69 | 39.9 |
| Example 232 | Inv-134 | 6.65 | 40.0 |
| Example 233 | Inv-135 | 6.66 | 40.1 |
| Example 234 | Inv-136 | 6.72 | 39.9 |
| Example 235 | Inv-137 | 6.60 | 39.5 |
| Example 236 | Inv-138 | 6.63 | 39.8 |
| Example 237 | Inv-139 | 6.69 | 40.9 |
| Example 238 | Inv-140 | 6.51 | 40.3 |
| Example 239 | Inv-141 | 6.59 | 39.9 |
| Example 240 | Inv-142 | 6.51 | 40.4 |
| Example 241 | Inv-143 | 6.72 | 41.1 |
| Example 242 | Inv-144 | 6.66 | 40.4 |
| Example 243 | Inv-145 | 6.77 | 40.9 |
| Example 244 | Inv-146 | 6.78 | 40.5 |
| Example 245 | Inv-147 | 6.62 | 41.1 |
| Example 246 | Inv-148 | 6.63 | 42.3 |
| Example 247 | Inv-149 | 6.61 | 40.7 |
| Example 248 | Inv-150 | 6.70 | 41.3 |
| Example 249 | Inv-151 | 6.69 | 40.8 |
| Example 250 | Inv-152 | 6.51 | 40.6 |

TABLE 4-continued

| Sample | Host | Driving voltage (V) | Current efficiency (cd/A) |
|---|---|---|---|
| Example 251 | Inv-153 | 6.59 | 41.1 |
| Example 252 | Inv-154 | 6.51 | 40.9 |
| Example 253 | Inv-155 | 6.72 | 40.1 |
| Example 254 | Inv-156 | 6.66 | 40.2 |
| Example 255 | Inv-157 | 6.77 | 40.9 |
| Example 256 | Inv-158 | 6.78 | 41.1 |
| Example 257 | Inv-159 | 6.62 | 41.0 |
| Example 258 | Inv-160 | 6.78 | 41.2 |
| Example 259 | Inv-161 | 6.61 | 41.0 |
| Example 260 | Inv-162 | 6.63 | 40.9 |
| Example 261 | Inv-163 | 6.61 | 41.0 |
| Example 262 | Inv-164 | 6.61 | 40.7 |
| Example 263 | Inv-165 | 6.77 | 42.1 |
| Example 264 | Inv-166 | 6.78 | 40.4 |
| Example 265 | Inv-167 | 6.60 | 41.0 |
| Example 266 | Inv-168 | 6.79 | 41.1 |
| Example 267 | Inv-169 | 6.65 | 40.2 |
| Example 268 | Inv-170 | 6.77 | 40.2 |
| Example 269 | Inv-171 | 6.79 | 41.0 |
| Example 270 | Inv-172 | 6.62 | 41.2 |
| Example 271 | Inv-173 | 6.63 | 40.6 |
| Example 272 | Inv-174 | 6.61 | 41.0 |
| Example 273 | Inv-175 | 6.79 | 41.1 |
| Example 274 | Inv-176 | 6.67 | 39.9 |
| Example 275 | Inv-177 | 6.66 | 40.6 |
| Example 276 | Inv-178 | 6.69 | 39.8 |
| Example 277 | Inv-179 | 6.65 | 40.8 |
| Example 278 | Inv-180 | 6.66 | 40.5 |
| Example 279 | Inv-181 | 6.72 | 39.9 |
| Example 280 | Inv-182 | 6.60 | 40.2 |
| Example 281 | Inv-183 | 6.63 | 39.9 |
| Example 282 | Inv-184 | 6.69 | 40.4 |
| Example 283 | Inv-185 | 6.51 | 40.1 |
| Example 284 | Inv-186 | 6.59 | 39.9 |
| Example 285 | Inv-187 | 6.51 | 40.3 |
| Example 286 | Inv-188 | 6.72 | 39.8 |
| Example 287 | Inv-189 | 6.66 | 40.3 |
| Example 288 | Inv-190 | 6.77 | 40.5 |
| Example 289 | Inv-191 | 6.78 | 40.1 |
| Example 290 | Inv-192 | 6.62 | 41.0 |
| Example 291 | Inv-193 | 6.63 | 42.1 |
| Example 292 | Inv-194 | 6.61 | 40.8 |
| Example 293 | Inv-195 | 6.70 | 41.0 |
| Example 294 | Inv-196 | 6.69 | 39.9 |
| Example 295 | Inv-197 | 6.51 | 40.2 |
| Example 296 | Inv-198 | 6.59 | 40.5 |
| Example 297 | Inv-199 | 6.51 | 39.9 |
| Example 298 | Inv-200 | 6.72 | 39.1 |
| Example 299 | Inv-201 | 6.66 | 40.2 |
| Example 300 | Inv-202 | 6.77 | 40.7 |
| Example 301 | Inv-203 | 6.78 | 40.3 |
| Example 302 | Inv-204 | 6.62 | 41.5 |
| Example 303 | Inv-205 | 6.70 | 40.1 |
| Example 304 | Inv-206 | 6.65 | 40.2 |
| Example 305 | Inv-207 | 6.79 | 40.5 |
| Example 306 | Inv-208 | 6.70 | 40.8 |
| Example 307 | Inv-209 | 6.75 | 40.4 |
| Example 308 | Inv-210 | 6.69 | 40.8 |
| Example 309 | Inv-211 | 6.70 | 40.7 |
| Example 310 | Inv-212 | 6.71 | 40.5 |
| Example 311 | Inv-213 | 6.55 | 41.2 |
| Example 312 | Inv-214 | 6.59 | 42.5 |
| Example 313 | Inv-215 | 6.50 | 41.8 |
| Example 314 | Inv-216 | 6.55 | 41.4 |
| Example 315 | Inv-217 | 6.59 | 42.2 |
| Example 316 | Inv-218 | 6.50 | 41.7 |
| Example 317 | Inv-219 | 6.51 | 41.6 |
| Comparative Example 2 | CBP | 6.93 | 38.2 |

As shown in Table 3 and Table 4, it can be seen that when compared with the red or green organic electroluminescent device using a CBP in the related art (Comparative Examples 1 and 2), the red or green organic electroluminescent devices using the compounds (Inv-115 to Inv-219) according to the present invention as a light-emitting layer of the red or green organic electroluminescent device (Examples 115 to 317) show excellent performances in terms of efficiency and driving voltage.

INDUSTRIAL APPLICABILITY

Since the indole-based compound represented by Formula 1 according to the present invention has superior thermal resistance, hole injection and transport capabilities, electron injection and transport capabilities, light-emitting capabilities, and the like, an organic electroluminescent device including the compound as a hole injection/transporting layer, an electron injection/transporting layer, or a phosphorescent/fluorescent-host/dopant of a light-emitting layer and the like may be significantly enhanced in terms of light-emitting performance, driving voltage, lifespan, efficiency, and the like, and thus may be effectively applied to a full-color display panel and the like.

The invention claimed is:
1. A compound of the following Formulae 1a to 1f:

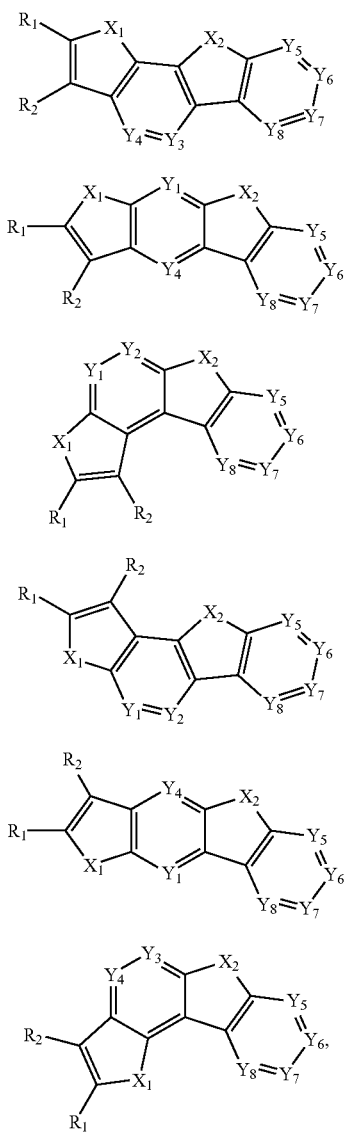

wherein $R_1$ and $R_2$ are each independently selected from the group consisting of hydrogen, deuterium, halogen, a cyano group, a nitro group, a $C_1$ to $C_{40}$ alkyl group, a $C_6$ to $C_{60}$ aryl group, a heteroaryl group having 5 to 60 nuclear atoms and a $C_6$ to $C_{60}$ arylamine group, $Y_1$ to $Y_4$ are each independently N or $CR_3$, $Y_5$ to $Y_8$ are each independently N or $CR_4$, $X_1$ and $X_2$ are each independently selected from the group consisting of Se, $N(Ar_1)$, $C(Ar_2)(Ar_3)$ and $Si(Ar_4)(Ar_5)$, and at least one of $X_1$ and $X_2$ is $N(Ar_1)$, $R_3$ and $R_4$ are each independently selected from the group consisting of hydrogen, deuterium, halogen, a cyano group, a nitro group, a $C_1$ to $C_{40}$ alkyl group, a $C_6$ to $C_{60}$ aryl group, a heteroaryl group having 5 to 60 nuclear atoms, a $C_6$ to $C_{60}$ aryloxy group, a $C_6$ to $C_{60}$ arylsilyl group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group, or an adjacent group forming a part of the fused ring, $Ar_1$ to $Ar_5$ are each independently selected from the group consisting of a $C_6$ to $C_{60}$ aryl group, a heteroaryl group having 5 to 60 nuclear atoms, a $C_6$ to $C_{60}$ aryloxy group, a $C_6$ to $C_{60}$ arylsilyl group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group, and the $C_1$ to $C_{40}$ alkyl group, the $C_6$ to $C_{60}$ aryl group, the heteroaryl group having 5 to 60 nuclear atoms, the $C_6$ to $C_{60}$ aryloxy group, the $C_6$ to $C_{60}$ arylsilyl group, the $C_6$ to $C_{60}$ arylboron group, the $C_6$ to $C_{60}$ arylphosphine group, the $C_6$ to $C_{60}$ arylphosphine oxide group and the $C_6$ to $C_{60}$ arylamine group of $R_1$ to $R_4$ and $Ar_1$ to $Ar_5$ are optionally each independently unsubstituted or substituted with one or more substituents selected from the group consisting of deuterium, halogen, a cyano group, a nitro group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_2$ to $C_{40}$ alkylboron group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group.

2. The compound of claim 1, wherein $Ar_1$ to $Ar_5$ are each independently selected from the group consisting of a $C_6$ to $C_{60}$ aryl group, a heteroaryl group having 5 to 60 nuclear atoms, and a $C_6$ to $C_{60}$ arylamine group.

3. The compound of claim 1, wherein $R_1$ to $R_4$ are each independently selected from the group consisting of a $C_6$ to $C_{60}$ aryl group, a heteroaryl group having 5 to 60 nuclear atoms, and a $C_6$ to $C_{60}$ arylamine group.

4. The compound of claim 1, wherein both $X_1$ and $X_2$ are $N(Ar_1)$.

5. The compound of claim 1, wherein the compound of Formulae 1a to 1f is selected from the group consisting of compounds of the following Formulae 5a to 5f:

Formula 5a
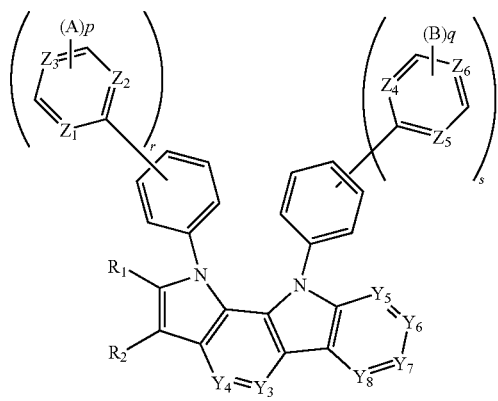

Formula 5b
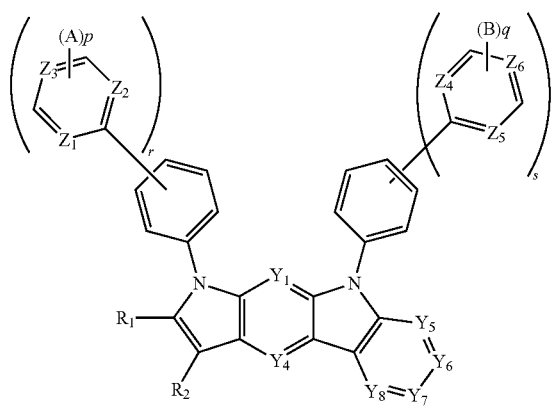

Formula 5c
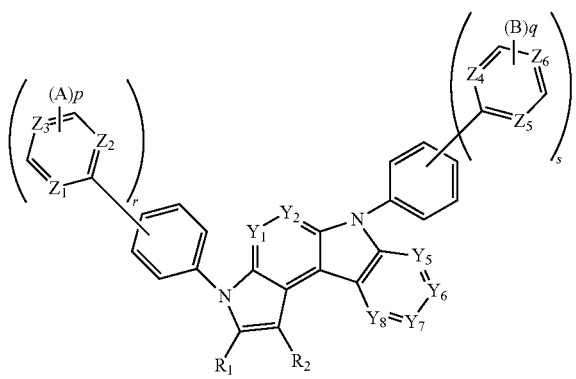

Formula 5d
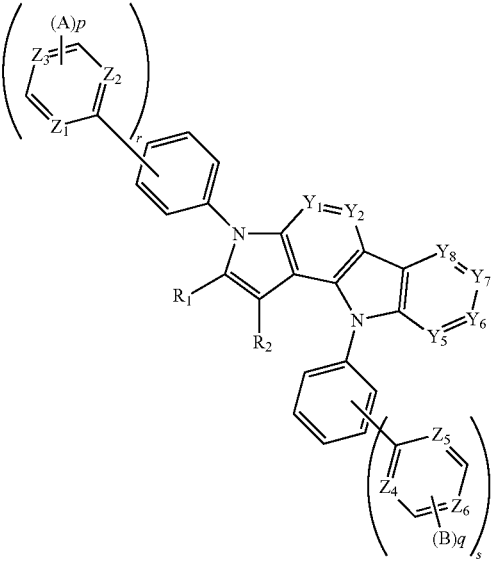

Formula 5e
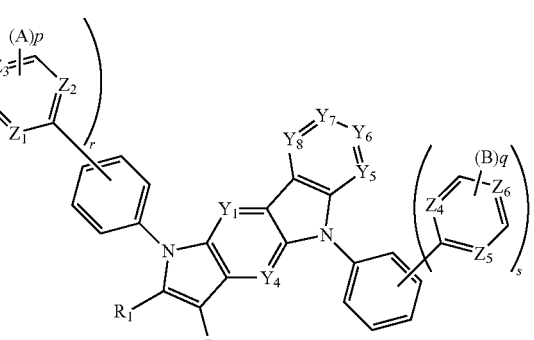

Formula 5f in the formulae, $R_1$, $R_2$ and $Y_1$ to $Y_8$ are the same as those defined in claim 1, $Z_1$ to $Z_5$ are each independently N or $CAr_6$, $Ar_6$, A and B are each independently selected from the group consisting of a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_2$ to $C_{40}$ alkylboron group, a $C_6$ to $C_{60}$ aryl boron group, a $C_6$ to $C_{60}$ arylphosphine group, a $C_6$ to $C_{60}$ arylphosphine oxide group and a $C_6$ to $C_{60}$ arylamine group, r and s are each an integer of 0 to 6, provided that r+s is at least 1 or more, and p and q are each an integer of 0 to 3.

6. The compound of claim 5, wherein $Ar_6$, A and B are each independently selected from the group consisting of a $C_6$ to $C_{60}$ aryl group, a heteroaryl group having 5 to 60 nuclear atoms, and a $C_6$ to $C_{60}$ arylamine group.

7. An organic elecroluminescent device comprising:
(i) an anode;
(ii) a cathode; and
(iii) an organic layer having one or more layers interposed between the anode and the cathode,
wherein at least one in the organic layer comprises the compound of claim 1.

8. The organic electroluminescent device of claim 7, wherein the organic layer comprising the compound is selected from the group consisting of a hole injection layer, a hole transporting layer, an electron injection layer, an electron transporting layer and a light-emitting layer.

9. The organic electroluminescent device of claim 6, wherein the compound is a phosphorescent host of a light-emitting layer.

* * * * *